(12) United States Patent
Appari et al.

(10) Patent No.: US 8,399,433 B2
(45) Date of Patent: Mar. 19, 2013

(54) AMINO PYRIMIDINE ANTICANCER COMPOUNDS

(75) Inventors: Rama Devi Appari, Port Jefferson Station, NY (US); Xin Chen, Commack, NY (US); Ramesh Chilukuri, Port Jefferson Station, NY (US); Andrew P. Crew, N. Babylon, NY (US); Hanqing Dong, Syosset, NY (US); Caterina Ferraro, Fresh Meadows, NY (US); Kenneth Foreman, Syosset, NY (US); Ramesh C. Gupta, Port Jefferson Station, NY (US); An-Hu Li, Commack, NY (US); Dan Sherman, New York, NY (US); Kathryn M. Stolz, Williston Park, NY (US); Brian Volk, Sayville, NY (US); Robert Zahler, Pennington, NJ (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 365 days.

(21) Appl. No.: 12/791,047

(22) Filed: Jun. 1, 2010

(65) Prior Publication Data

US 2011/0136764 A1    Jun. 9, 2011

Related U.S. Application Data

(60) Provisional application No. 61/298,349, filed on Jan. 26, 2010, provisional application No. 61/182,898, filed on Jun. 1, 2009.

(51) Int. Cl.
| | |
|---|---|
| *A61K 31/675* | (2006.01) |
| *C07D 279/10* | (2006.01) |
| *C07D 413/12* | (2006.01) |
| *C07F 9/08* | (2006.01) |

(52) U.S. Cl. ............... 514/80; 514/81; 514/85; 514/86; 544/57; 544/122; 544/243

(58) Field of Classification Search .............. 514/80, 514/81, 85, 86; 544/57, 122, 243
See application file for complete search history.

(56) References Cited

U.S. PATENT DOCUMENTS

| | | | |
|---|---|---|---|
| 6,649,608 | B2 | 11/2003 | Pease |
| 6,878,697 | B2 | 4/2005 | Metcalf |
| 7,109,335 | B2 | 9/2006 | Kath |
| 7,109,337 | B2 | 9/2006 | Kath |
| 7,122,670 | B2 | 10/2006 | Kath |
| 7,230,098 | B2 | 6/2007 | Cui |
| 7,351,712 | B2 | 4/2008 | Kath |
| 7,514,446 | B2 | 4/2009 | Ward |
| 7,521,457 | B2 | 4/2009 | Stadtmueller |
| 2004/0220177 | A1 | 11/2004 | Kath |
| 2005/0124637 | A1 | 6/2005 | Cheng |
| 2005/0203114 | A1 | 9/2005 | Armistead |
| 2005/0256144 | A1 | 11/2005 | Kath |
| 2005/0256145 | A1 | 11/2005 | Kath |
| 2006/0247241 | A1 | 11/2006 | Garcia-Echeverria |
| 2006/0252748 | A1 | 11/2006 | Lindenthal |
| 2007/0015207 | A1 | 1/2007 | Ludovici |
| 2007/0203161 | A1 | 8/2007 | Argade |
| 2008/0039447 | A1 | 2/2008 | Brumby |
| 2008/0132504 | A1 | 6/2008 | Garcia-Echeverria |
| 2008/0176881 | A1 | 7/2008 | Michellys |
| 2008/0182840 | A1 | 7/2008 | Kath |
| 2008/0293708 | A1 | 11/2008 | Kawahara |
| 2009/0054395 | A1 | 2/2009 | Luzzio |
| 2009/0149438 | A1 | 6/2009 | Stadtmueller |
| 2009/0221555 | A1 | 9/2009 | Ahmed |
| 2012/0202776 | A1* | 8/2012 | Wang et al. ................ 514/81 |

FOREIGN PATENT DOCUMENTS

| | | |
|---|---|---|
| WO | 0012485 A1 | 3/2000 |
| WO | 0164655 A1 | 9/2001 |
| WO | 0170741 A1 | 9/2001 |
| WO | 02096888 A1 | 12/2002 |
| WO | 2006021454 A2 | 3/2006 |
| WO | 2007021937 A2 | 2/2007 |
| WO | 2008094602 A2 | 8/2008 |
| WO | 2008094737 A2 | 8/2008 |
| WO | 2008129380 A1 | 10/2008 |
| WO | 2009020990 A1 | 2/2009 |
| WO | 2009071535 A1 | 6/2009 |
| WO | 2009105498 A1 | 8/2009 |
| WO | 2009132202 A2 | 10/2009 |
| WO | 2009143389 A1 | 11/2009 |
| WO | 2010028116 A1 | 3/2010 |
| WO | 2012074951 A1 | 6/2012 |

OTHER PUBLICATIONS

Maung, K. et al., (1999) Oncogene, 18:6824-28.
Owens, L.V. et al., (1995) Cancer Res., 55:2752-55.
Roberts, W.G. et al., (2008) Cancer Res., vol. 68(6), pp. 935-1944.
Wang, D. et al., (2000) J. Cell Sci., 113:4221-30.
Weiner, T.M. et al., (1993) Lancet, 342(8878):1024-25.
U.S. Appl. No. 61/417,601, filed Nov. 29, 2010 Crew.
International Search Report and Written Opinion of the International Search Authority in PCT/US2010/036808, Mailed Feb. 28, 2011.
Cary, L.A. et al., J. Cell Sci., (1996) 109:1787-94.

(Continued)

*Primary Examiner* — James O. Wilson
*Assistant Examiner* — Ebenezer O Sackey

(57) ABSTRACT

Compounds of Formula 1, as shown below and defined herein:

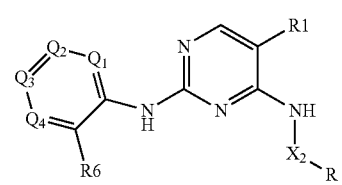

and pharmaceutically acceptable salts, synthesis, intermediates, formulations, and methods of disease treatment therewith, including cancers mediated at least in part by FAK.

25 Claims, No Drawings

OTHER PUBLICATIONS

Chamberlain, S.D. et al., (2009) Bioorganic & Medical Chemistry Letters 19:373-377.
Chamberlain, S.D. et al., (2008) J. Org. Chem. 73:9511-9514.
Cicchini, C. et al., (2008) Exp. Cell Res., vol. 314, pp. 43-52.
International Search Report and Written Opinion of the International Search Authority in PCT/US2011/062290 mailed Mar. 5, 2012.

* cited by examiner

AMINO PYRIMIDINE ANTICANCER COMPOUNDS

This application claims priority of U.S. Appl. Nos. 61/182,898 (1 Jun. 2009) and 61/298,349 (26 Jan. 2010), the contents of which are incorporated herein in their entireties by this reference.

FIELD AND BACKGROUND

The present invention pertains in large part to cancer treatment, targeted therapies, certain chemical compounds, preparations, and methods of treating tumors and cancers with the compounds.

Focal adhesion kinase (FAK) is a cytoplasmic tyrosine kinase which plays a major role in the transduction of the signal transmitted by integrins, a family of heterodimeric receptors for cell adhesion. FAK and integrins are colocalized in perimembrane structures called adhesion plaques.

FAK signaling through ERK, PI3K, and p130cas is important in cancer cell proliferation, survival, and migration. pFAK and/or FAK overexpression has been reported in many cancer tumors. An increase in the proliferation of tumor cells in vivo has been observed after induction of the expression of FAK in human astrocytoma cells. Cary et al., *J. Cell Sci.*, 109:1787-94 (1996). FAK is overexpressed in prostate, breast, thyroid, colon, melanoma, brain and lung cancers, the level of FAK expression being directly correlated with tumors exhibiting the most aggressive phenotype. Weiner et al., *Lancet*, 342(8878):1024-25 (1993); Owens et al., *Cancer Res.*, 55:2752-55 (1995); Maung et al., *Oncogene*, 18:6824-28 (1999); Wang et al., *J. Cell Sci.*, 113:4221-30 (2000). FAK is highly active in human epithelial and mesenchymal tumors such as melanoma, lymphoma, and multiple myeloma. Increased FAK correlates with increased invasiveness and increased ability of cancer to metastasize.

Inhibition of FAK signaling in vitro induces cell growth arrest, reduces motility, and can cause cell death. KD-FAK and DN-FAK have been shown to inhibit tumor growth in vivo. FAK is also known as PTK2.

In hepatocytes, TGFβ induces a Src-dependent activation of FAK; and there is evidence that FAK signaling is required for transcriptional up-regulation of mesenchymal and invasiveness markers and for delocalization of membrane-bound E-cadherin. *Exp. Cell Res.*, 314, 143-52 (2008).

A number of publications disclose compounds said to possess FAK or other kinase inhibiting activity, e.g., Cancer Res., 68(6), 1935-1944 (2008), U.S. Pat. No. 6,649,608, U.S. Pat. No. 6,878,697, U.S. Pat. No. 7,109,335, U.S. Pat. No. 7,109,337, U.S. Pat. No. 7,122,670, U.S. Pat. No. 7,230,098, U.S. Pat. No. 7,351,712, U.S. Pat. No. 7,514,446, U.S. Pat. No. 7,521,457, US2004/0220177, US2005/0124637, US2005/0203114, US2005/0256144, US2005/0256145, US2006/0252748, US2007/0015207, US2007/0203161, US2008/0039447, US2008/0132504, US2008/0176881, US2008/0182840, US2008/0293708, US2009/0054395, US2009/0149438, WO2001/64655, WO2001/070741, WO02/096888, WO2006/021454, WO2007/021937, WO2008/051547, WO2008/094602, WO2008/094737, WO2008/129380, WO2009/020990, WO2009/071535, WO2009/105498, WO2009/143389.

There remains a need for FAK inhibitors having the potential to reach the clinic and regulatory approval for treating disease such as cancer.

SUMMARY

In some aspects, the present invention concerns compounds of Formula 1, as shown below:

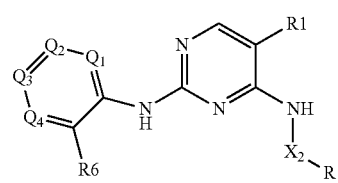

wherein R is an optionally substituted aryl or heteroaryl; R1 is halogen, $CF_3$, CCH, or other suitable substituent; R6 is an optional substituent; $Q_1$ to $Q_4$ are independently >CH, >CF, >N, or >N-oxide; except that at least one of $Q_2$ to $Q_4$ includes a substituent that includes a phosphinate, phosphonate, or phosphine oxide.

In some aspects, compounds of the invention are inhibitors of kinases, including FAK. In some aspects, compounds of the invention are selective inhibitors of FAK.

In some aspects, the invention includes methods treating proliferative disease, particularly cancers, including cancers mediated at least in part by FAK, alone or in combination regimens with other agents.

The invention includes the compounds and salts thereof, any physical forms thereof including solvates and hydrates, preparation of the compounds, intermediates, and pharmaceutical compositions and formulations thereof.

DETAILED DESCRIPTION

Compounds

In some aspects, the invention includes the compounds of Formula 1, above, wherein (Subgenus 1):

R1 is halogen, —$CF_3$, or —CCH;

at least one of $Q_2$ to $Q_4$ is >C—$X_1$—R2;

$Q_1$ and the remaining $Q_2$ to $Q_4$ are independently >CH, >CF, >N, or >N-oxide;

$X_1$ and $X_2$ are independently —$(CR^7R^8)_{0-2}$—;

each $R^7$ and $R^8$ is independently halogen, $C_{0-3}$aliphatic, or —$OC_{0-3}$aliphatic, either of which is optionally halogen substituted, except that in the case of $X_2$, $R^7$ and $R^8$ are not halogen or —$OC_{0-3}$aliphatic;

R6 is halogen, —$OC_{0-3}$aliphatic, or $C_{0-3}$aliphatic, either optionally substituted by one or more halogen or by —$OCF_3$;

R2 is —$P(O)R^9R^{10}$;

$R^9$ and $R^{10}$ are independently $C_{0-3}$aliphatic, either of which can be taken together at any of their atoms to form a ring, wherein any of the foregoing can be further substituted by one or more halogen, $C_{0-6}$aliphatic, or $_{3-6}$cyclic;

R is

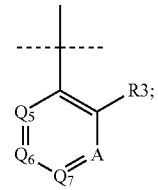

one of $Q_6$, $Q_7$, or A is >CR4;

$Q_5$ and the remaining $Q_6$ to $Q_7$ and A are independently >CH, >CF, >N, or >N-oxide;

R3 is $C_{0-6}$aliphatic, $-S(O)_2R^{11}$, $-S(O)_2NR^{11}R^{12}$, $-C(O)NR^{11}R^{12}$, $-C(O)OR^{11}$; $-NR^{11}S(O)_2R^{12}$, or $-NR^{11}R^{12}$;

$R^{11}$ and $R^{12}$ are independently $C_{0-6}$aliphatic, which can be taken together at any of their atoms to form a ring containing 1-3 heteroatoms;

or alternatively R3 and A define any optionally substituted $_{5-6}$cyclic containing one or more heteroatoms;

R4 is $_{4-6}$cyclic, $-OC_{0-6}$aliphatic, or $C_{0-6}$aliphatic, each optionally substituted, or halogen;

or a pharmaceutically acceptable salt thereof.

In some embodiments of Formula 1 or Subgenus 1 (Subgenus 2):

$Q_3$ is >C—CH$_2$—R2; and $R^9$ and $R^{10}$ are independently $C_{0-3}$alkoxy.

In some embodiments of Formula 1 or Subgenus 1 or 2 (Subgenus 3): R4 is optionally substituted cyclohexyl.

In some embodiments of Formula 1 or Subgenus 1 the compound or salt has the Formula 1a (Subgenus 4):

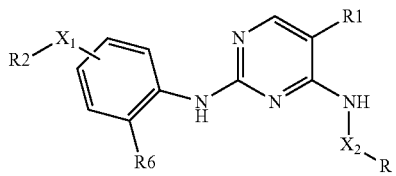

1a
wherein:
$X_1$ and $X_2$ are independently $-(CR^7R^8)_{0-1}-$;
R is

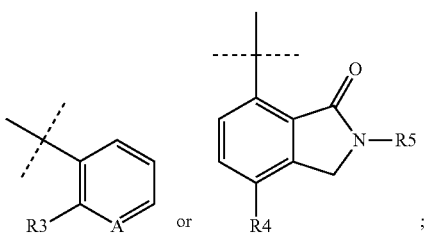

A is CH or N;
R1 is halogen, $-CF_3$, or $-CCH$;
R2 is $-P(O)R^9R^{10}$;
R3 is $-S(O)_2R^{11}$, $-S(O)_2NR^{11}R^{12}$, $-C(O)NR^{11}R^{12}$, $-C(O)OR^{11}$; $-NR^{11}S(O)_2R^{12}$, or $-NR^{11}R^{12}$;
R4 is -x-y-z, wherein:
x is $_{4-6}$cyclic; y is absent or $_{4-6}$heterocyclic; and z is absent or $C_{1-3}$alkyl optionally substituted by 1-2 hydroxy or $C_{1-6}$alkoxy groups, or z is hydroxy or $-C(O)O-C_{0-3}$alkyl; or
-x-y-z is $C_{0-6}$alkoxy, $C_{2-6}$alkenyl, $C_{2-6}$alkynyl, or $C_{0-6}$alkyl, each optionally substituted by 1-2 hydroxy groups;
R5 is $C_{0-2}$alkyl optionally substituted by 1-3 independent hydroxy or halogen groups;
R6 is halo, $-C_{0-3}$alkoxy, $-C_{0-3}$alkyl optionally substituted by halo, or $-OCF_3$;
each $R^7$ and $R^9$ is independently H or $-CH_3$;
$R^9$ and $R^{10}$ are independently hydroxy, $C_{1-6}$alkoxy, or $C_{0-6}$alkyl, any of which can be taken together at any of their atoms to form a ring, or aryl, $-O$-aryl, or $_{4-6}$heterocyclic, wherein any of the foregoing can be further substituted by $_{3-6}$cyclic;

$R^{11}$ and $R^{12}$ are independently $C_{0-6}$alkyl, which can be taken together at any of their atoms to form a ring containing 1-3 heteroatoms; $R^{11}$ or $R^{12}$ can independently be taken at any of their atoms with the ring to which R3 is attached to form a ring.

In some embodiments thereof, one or more H atoms of R are replaced with deuterium (D)).

In some embodiments of Formula 1 or Subgenera 1-4 (Subgenus 5):

$X_1$ and $X_2$ are independently a bond or methylene and $X_1$ is meta or para to the position of nitrogen attachment;

R is

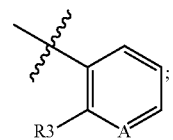

A is CH or N;
R1 is Cl, Br, or $-CF_3$;
R3 is $-N(CH_3)S(O)_2CH_3$ or $-C(O)NHCH_3$; and
R6 is H or methoxy.

In some embodiments of Formula 1 or Subgenus 4 or 5 (Subgenus 6): $R^9$ and $R^{10}$ are independently $C_{0-4}$alkoxy.

In some embodiments of Formula 1 or Subgenera 4-6 (Subgenus 7): $X_1$ is a methylene group positioned meta to R6.

In some embodiments of Formula 1 or Subgenera 4-7 (Subgenus 8):
A is CH;
$X_2$ is a bond;
R1 is $-CF_3$; and
R3 is $-C(O)NHCH_3$.

In some embodiments of Formula 1 or Subgenus 1 (Subgenus 9), the compound or salt of Claim 1, has the formula (Subgenus 9):

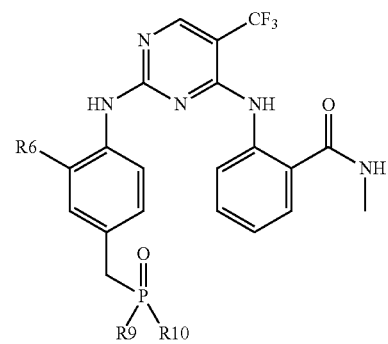

wherein R6 is H or methoxy; and
R9 and R10 are independently $C_{0-3}$alkoxy.

In some embodiments of Formula 1 or Subgenus 4 (Subgenus 10):

$X_1$ and $X_2$ are independently a bond or methylene and $X_1$ is meta or para to the position of nitrogen attachment;

R is

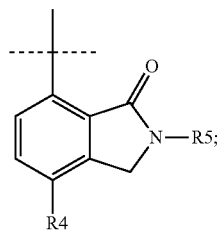

R1 is Br, Cl, or —CF$_3$;
R4 is -x-y-z, wherein
  x is C$_{4-6}$cycloalkyl, phenyl, pyrazolyl, pyrrolidinyl, piperidinyl, or piperazinyl; y is absent, piperidinyl, or piperazinyl; and z is absent, C$_{1-3}$alkyl optionally substituted by 1-2 hydroxy groups, or z is hydroxy or —C(O)O—C$_{0-3}$alkyl; or
  -x-y-z is C$_{0-6}$alkoxy, C$_{2-6}$alkenyl, C$_{2-6}$alkynyl, or C$_{0-6}$alkyl, each optionally substituted by 1-2 hydroxy;
R5 is methyl; and
R6 is H or methoxy.

In some embodiments of Formula 1 or Subgenus 10 (Subgenus 11): R$^9$ and R$^{10}$ are independently C$_{0-3}$alkoxy.

In some embodiments of Formula 1 or Subgenus 10 or 11 (Subgenus 12):
R4 is C$_{4-6}$cycloalkyl which is optionally substituted by hydroxy, piperazinyl that is optionally N-methyl substituted, —C(O)O—C$_{0-3}$alkyl, or C$_{1-3}$alkyl optionally substituted by 1-2 hydroxy groups.

In some embodiments of Formula 1 or Subgenus 10 or 11 (Subgenus 13):
  X$_1$ is a methylene group positioned meta to R6;
  X$_2$ is a bond;
  R1 is —CF$_3$; and
  R4 is -x-y-z, wherein
    x is C$_{4-6}$cycloalkyl, phenyl, pyrazolyl, pyrrolidinyl, piperidinyl, or piperazinyl;
    y is absent; and
    z is absent, C$_{1-3}$alkyl optionally substituted by 1-2 hydroxy groups, hydroxy, or —C(O)O—C$_{0-3}$alkyl.

In some embodiments of Formula 1 or any subgenus thereof, the compound is present as a material in substantially pure form.

In some embodiments, the compound is selected from any one of the Examples herein or a pharmaceutically acceptable salt thereof.

Each variable definition above includes any subset thereof and the compounds of Formula I include any combination of such variables or variable subsets.

In some aspects, the invention includes any of the compound examples herein and pharmaceutically acceptable salts thereof.

The invention includes the compounds and salts thereof, and their physical forms, preparation of the compounds, useful intermediates, and pharmaceutical compositions and formulations thereof.

The compounds of the invention and term "compound" in the claims include any pharmaceutically acceptable salts or solvates, and any amorphous or crystal forms, or tautomers, whether or not specifically recited in context.

The invention includes the isomers of the compounds. Compounds may have one or more asymmetric carbon atoms can exist as two or more stereoisomers. Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

The present invention includes any stereoisomers, even if not specifically shown, individually as well as mixtures, geometric isomers, and pharmaceutically acceptable salts thereof. Where a compound or stereocenter is described or shown without definitive stereochemistry, it is to be taken to embrace all possible individual isomers, configurations, and mixtures thereof. Thus, a material sample containing a mixture of stereoisomers would be embraced by a recitation of either of the stereoisomers or a recitation without definitive stereochemistry. Also contemplated are any cis/trans isomers or tautomers of the compounds described.

Included within the scope of the invention are all stereoisomers, geometric isomers and tautomeric forms of the inventive compounds, including compounds exhibiting more than one type of isomerism, and mixtures of one or more thereof.

When a tautomer of the compound of Formula (I) exists, the compound of formula (I) of the present invention includes any possible tautomers and pharmaceutically acceptable salts thereof, and mixtures thereof, except where specifically stated otherwise.

The compounds of the invention are not limited to those containing all of their atoms in their natural isotopic abundance. The present invention includes compounds wherein one or more hydrogen, carbon or other atoms are replaced by different isotopes thereof. Such compounds can be useful as research and diagnostic tools in metabolism pharmacokinetic studies and in binding assays. A recitation of a compound or an atom within a compound includes isotopologs, i.e., species wherein an atom or compound varies only with respect to isotopic enrichment and/or in the position of isotopic enrichment. For nonlimiting example, in some cases it may be desirable to enrich one or more hydrogen atoms with deuterium (D) or to enrich carbon with $^{13}$C. Other examples of isotopes suitable for inclusion in the compounds of the invention include isotopes of hydrogen, chlorine, fluorine, iodine, nitrogen, oxygen, phosphorus, and sulfur. Certain isotopically-labeled compounds of the invention may be useful in drug and/or substrate tissue distribution studies. Substitution with heavier isotopes such as deuterium may afford certain therapeutic advantages resulting from greater metabolic stability, for example, increased in vivo half-life or reduced dosage requirements, and hence may be preferred in some circumstances. Substitution with positron emitting isotopes may be useful in Positron Emission Topography (PET) studies for examining substrate receptor occupancy.

Further, the compounds may be amorphous or may exist or be prepared in various crystal forms or polymorphs, including solvates and hydrates. The invention includes any such forms provided herein, at any purity level. A recitation of a compound per se means the compound regardless of any unspecified stereochemistry, physical form and whether or not associated with solvent or water.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g., D$_2$O, d6-acetone, d6-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized.

The invention includes prodrugs of compounds of the invention which may, when administered to a patient, be converted into the inventive compounds, for example, by hydrolytic cleavage. Prodrugs in accordance with the invention can, for example, be produced by replacing appropriate functionalities present in the inventive compounds with certain moieties known to those skilled in the art as 'pro-moieties' as known in the art. Particularly favored derivatives and prodrugs of the invention are those that increase the bioavailability of the compounds when such compounds are administered to a patient, enhance delivery of the parent compound to a given biological compartment, increase solubility to allow administration by injection, alter metabolism or alter rate of excretion.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

Compounds that are basic are capable of forming a wide variety of salts with various inorganic and organic acids. The acids that can be used to prepare pharmaceutically acceptable acid addition salts of such basic compounds are those that form acceptable acid addition salts. When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Other salts are aspartate, besylate, bicarbonate/carbonate, bisulphate/sulfate, borate, camsylate, edisylate, gluceptate, glucuronate, hexafluorophosphate, hibenzate, hydrobromide/bromide, hydroiodide/iodide, malonate, methylsulfate, naphthylate, 2-napsylate, nicotinate, orotate, oxalate, palmitate, phosphate/hydrogen, phosphate/dihydrogen, phosphate, saccharate, stearate, tartrate, tosylate, and trifluoroacetate.

When the compound of the present invention is acidic, its corresponding salt can be conveniently prepared from pharmaceutically acceptable bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic bases include salts of primary, secondary, and tertiary amines, as well as cyclic amines and substituted amines such as naturally occurring and synthesized substituted amines. Other pharmaceutically acceptable organic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Other examples include benzathine, diolamine, glycine, meglumine, and olamine.

Synthesis

The invention includes the compounds, intermediates, examples, and synthetic methods described herein.

Phosphonates:

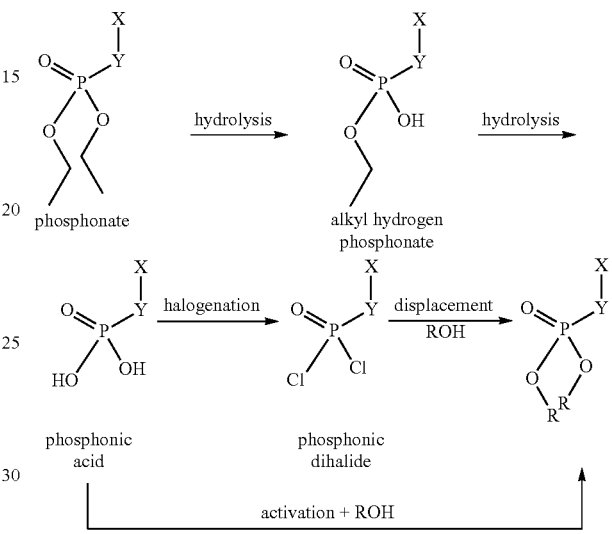

Scheme 1

Preparation of dialkylphosphonates may be achieved via multiple approaches. For example, one dialkyl phosphonate may be converted into another, different dialkyl phosphonate as shown in Scheme 1. Hydrolysis of a dialkylphosphonate under acidic conditions such as concentrated hydrochloric acid affords the corresponding phosphonic acid. Other acid reagents may be used to effect this transformation including, but not limited to, HBr and HBr/HOAc. The transformation may also be achieved using basic conditions, e.g., by treatment with NaOH/MeOH or through the use of reagents such as, but not limited to, TMSI, TMSBr, TMSCl/NaI and NaI in solvents such as acetone, acetonitrile, DCM, chloroform and dioxane. In the schemes, X—Y represents an appropriate aryl, aralkyl, or other moiety, as described herein, bearing the specified phosphorus group. In particular, Y corresponds to $X_1$ in Formula 1. Each R, Rw, Rv represents a phosphorus substituent as described and defined herein such as R9, R10 in Formula 1.

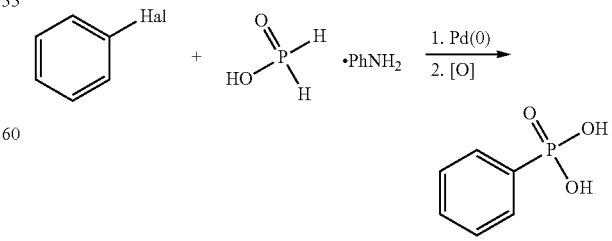

Scheme 2

Aryl phosphonic acids may be prepared from aryl halides/triflates under transition metal catalysis through reaction with phosphinic acid adducts followed by oxidation with reagents such as perchlorate or hydrogen peroxide (Scheme 2).

The hydrolysis of a dialkylphosphonate to a phosphonic acid usually proceeds via an intermediate alkyl hydrogen phosphonate (Scheme 1) which may be isolated if the reaction is stopped before full conversion has occurred. Use of basic hydrolysis conditions in particular lends itself to effective isolation of the intermediate alkyl hydrogen phosphonate.

The phosphonic acids and alkyl hydrogen phosphonates thus obtained may be activated through a number of methods prior to reaction with alcohols to afford the desired dialkyl phosphonates, or alkyl alkylphosphinates, respectively. One method of activation includes halogenation, e.g., using reagents such as oxalyl chloride, thionyl chloride, phosphorus oxychloride and phosphorus oxybromide either neat or in appropriate solvents such as DCM and DCE. Catalytic DMF may also be added to the mixture if desired. Treatment of the phosphonic dihalides thus produced, with alcohols affords the desired dialkyl phosphonates. Another method of activation involves formation of an 'active ester' through reaction with reagents such as DCC and PyBOP. Those skilled in the art will appreciate the large number of other coupling reagents available for activation of phosphonic acids in an analogous manner. Use of Mitsunobu conditions, e.g., $PPh_3$/DEAD or equivalent reagents, is a further method of activation of the phosphonic acid/alkyl hydrogen phosphonate system, which upon treatment with an appropriate alcohol affords desired dialkyl phosphonates or alkyl alkylphosphinates, respectively. Phosphonic acids may also be converted to dialkyl phosphonates through acid catalysis, e.g., TsOH, in the presence of an alkyl alcohol.

Scheme 3

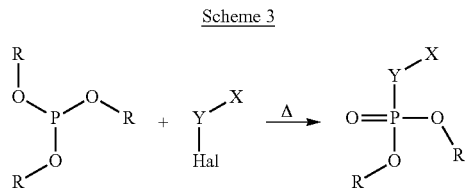

Dialkylphosphonates may also be prepared according to the method of Michaelis-Arbuzov as shown in Scheme 3 whereby alkyl halides or sulphonates (e.g., Hal=Br, I, Cl, OMs; $Y=CR^7R^8$) are heated with trialkylphosphites.

Scheme 4

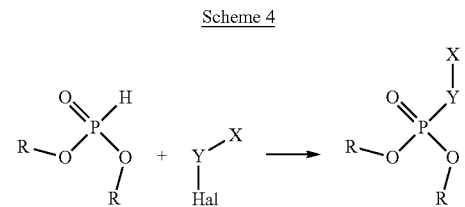

Phosphonates bearing a P-hydrogen may be reacted with alkyl halides or sulphonates (e.g., Hal=Cl, Br, I, OMs; $Y=CR^7R^8$) in the presence of bases, including but not limited to $Na_2CO_3$, $K_2CO_3$, NaOH, $Cs_2CO_3$, $Et_3N$, DIPEA and DBU, and in suitable solvents, e.g., acetonitrile, DMF, dioxane, DMA to afford P-substituted products via SN2-type chemistries (Scheme 4). Additionally, the phosphonates bearing a P-hydrogen may be reacted with aryl halides or triflates (e.g., Hal=Cl, Br, I, OTf; Y=bond) under transition metal catalysis conditions. Examples of such conditions include but are not limited to $Pd_2(dba)_3$/XantPhos/$Cs_2CO_3$/dioxane. As with many Pd(0) or other transition metal catalyzed reactions, the choice of catalyst, catalyst ligand, base, solvent and temperature may be important variables to explore when optimizing such reactions.

Phosphinates:

Scheme 5

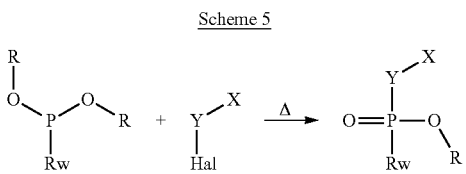

Alkyl phosphinates may be prepared through many of the methods described above for alkyl phosphonates. For example, using Michaelis-Arbuzov conditions whereby an alkyl dialkoxyphosphine is reacted with an alkyl halide or sulphonate (e.g., Hal=Br, I, Cl, OMs; $Y=CR^7R^8$.)

Scheme 6

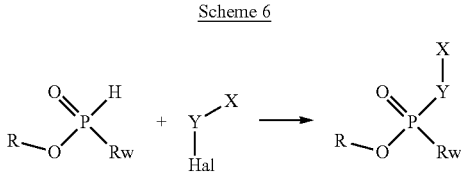

Similarly as for phosphonates, transition metal catalyzed reactions of phosphinates bearing a P-hydrogen also afford derivatized phosphinates when reacted with aryl halides or triflates (e.g., Hal=Br, I, Cl, OMs; Y=bond). The reaction of phosphinates bearing a P-hydrogen with alkyl halides or sulphonates (e.g., Hal=Cl, Br, I, OTf; $Y=Y=CR^7R^8$) in the presence of base also proceeds via SN2 chemistry as with phosphonates (Scheme 6).

Phosphine Oxides:

Scheme 7

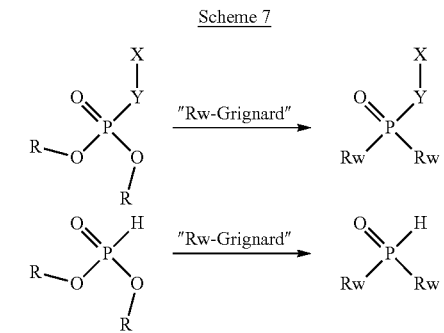

Phosphine oxides may be prepared via a number of methods including through the reaction of dialkyl phosphonates with carbon nucleophiles including, but not limited to, Grignard reagents (Scheme 7).

Scheme 8

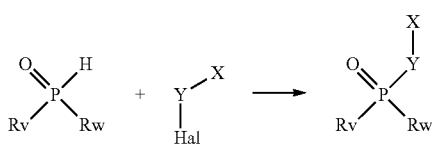

As in the case of phosphonates and phosphinates, dialkyl phosphine oxides bearing a P-hydrogen may be reacted with alkyl halides or sulphonates (e.g., Hal=Br, I, Cl, OMs; Y=$CR^7R^8$) under basic conditions or aryl halides (e.g., Hal=Br, I, Cl, OTf; Y=bond) under transition metal catalysis to form the P-substituted derivatives (Scheme 8).

Scheme 9

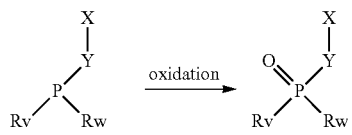

Other methods to access phosphine oxides include the oxidation of phosphines with oxidants such as, but not limited to, hydrogen peroxide (Scheme 9).

Scheme 10

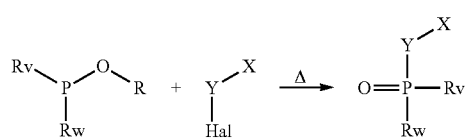

Additionally, dialkyl alkoxyphosphines may be reacted with alkyl halides or sulphonates (e.g., Hal=Br, I, Cl, OMs; Y=$CR^7R^8$) to form phosphine oxides via Michaelis-Arbuzov chemistry (Scheme 10).

Scheme 11

Phosphonates may be alkylated on an alpha carbon by deprotonation with strong base of which tBuOK, nBuLi, NaH and LDA are non-limiting examples, then treatment with carbon electrophiles, e.g., MeI, DMF and chloroformates (Scheme 11) ($R^m$ and/or $R^n$ may be methyl). Control of the stoichiometry of the reaction components may afford mono- or di-alkylated products. Additionally, sequential use of base, electrophile #1, base and electrophile #2 is another means to effectively control dialkylation.

5-Substituted 2,4-diaminopyrimidine Derivatives 2,4-Di-aminopyrimidines may be synthesized through a number of approaches to afford target molecules of pharmacological interest. Below are non-limiting examples of the various approaches that one skilled in the art could utilize to realize target molecules and examples of the type disclosed in this document.

Scheme 12

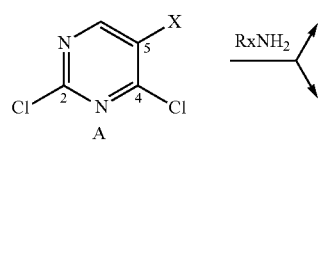
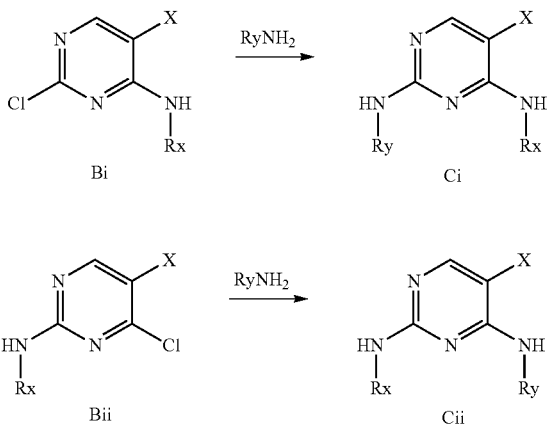

Commercially available 5-substituted-2,4-dichloropyrimidines (A) may be reacted directly with anilines or amines in SNAr reactions to afford mixtures of mono-substitution products Bi and Bii (Scheme 12). Depending on the conditions used and the nature of the aniline/amine and X group, a predominant isomer may be formed. In these situations or under conditions of minimal regioselectivity, the isomers may be separated (fully or partially) through the use of chromatography and/or crystallization. Assignment of structure to each pure isomer may be made through NMR experiments, in particular through the use of HMBC experiments which may disclose a 3 bond H—C correlation between the C4-NH and the C5-C in the case of the 4-substituted product, which is not evident in the C2-NH isomer. Alternatively, a mixture of regioisomers (Bi/Bii) may be reacted with a second aniline/amine to afford a mixture of products Ci/Cii, which may be separated using techniques such as preparative HPLC (MDP) to afford the pure isomers. Assignment of structure may be made by comparison of spectral data to those isomers made by the previous method described above or directly through NMR experimentation.

In addition to the SNAr displacements of the 2- and 4-chloro groups as indicated above, those skilled in the art will recognize that other groups may also serve as good leaving groups that may be displaced by amines and anilines under the appropriate conditions. Examples of displaceable groups include, but are not limited to alkylthio, alkylsulphonyl, bromo, trichloromethyl, fluoro, sulphonyloxy and N-benzotriazolyloxy, and in each case the 2- and 4-leaving groups may the same or different. Indeed in certain circumstances it may be preferred that the 2- and 4-displaceable groups are different as this offers the opportunity to take advantage of different leaving group potentials and so control the regiochemistry of the SNAr reaction.

Scheme 13

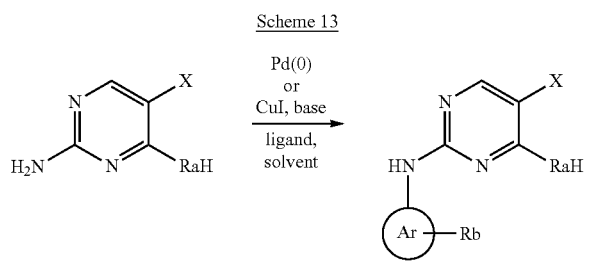

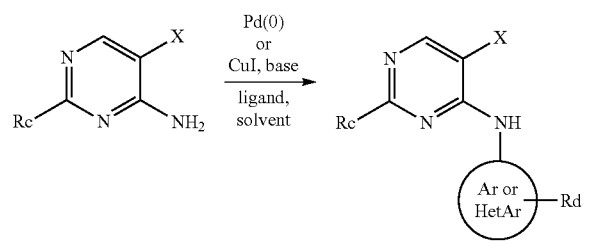

Another approach to access 2-anilino, 4-anilino or 2,4-dianilino-pyrimidines involves transition metal catalyzed arylation of an aminopyrimidine. In a typical procedure, the 2- or 4-aminopyrimidine is heated with an aryl or heteroaryl bromide or iodide in the presence of copper (I) iodide, ethylenediamine ligand and potassium carbonate base in dioxane. Other commonly used reagents are Ph$_2$-pentadienone-Pd, NaOPh and XantPhos. Depending on the nature of the X group at the 5-position (corresponding to R1 in Formula 1) such reactions may be conducted on 2,4-diaminopyrimidines and some preference for one or other amino group observed. Ra may correspond to an amino group NH—X$_2$R of Formula 1 or precursor; Ar-Rb may correspond to a substituted phenyl group of Formula 1; Rc may correspond to an amino group of Formula 1 or precursor; Ar-Rd or HetAr-Rd may correspond to NH—X$_2$R of Formula 1 or precursor.

In addition to refunctionalizing an activated pyrimidine system, one may also access desired derivatives through construction of the pyrimidine ring itself.

Scheme 14

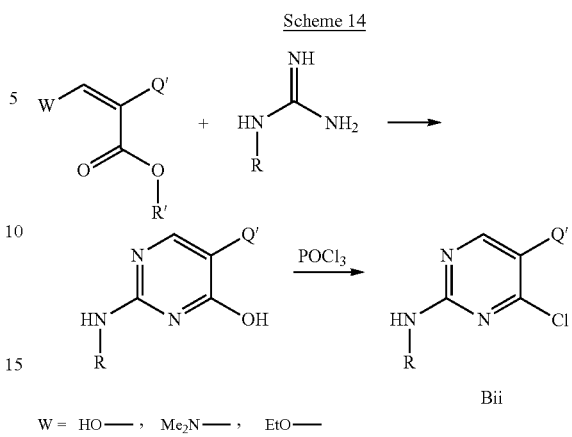

For example, reaction of an appropriately substituted guanidine with an appropriately substituted β-formyl ester, β-(dimethylamino)propenoate or β-(alkoxy)propenoate yields a hydroxy pyrimidine as indicated in the above scheme. Such hydroxypyrimidines may be chlorinated using reagents such as POCl$_3$ to form intermediates analogous to those described in scheme 17 (Bii). The Q' substitution in the reactants could be the same as the final R1 group of Formula 1 (Q), or different as necessary to allow for the cyclization and/or halogenation chemistry to be successful. Where Q' is different from R1, the interconversion of Q' to R1 may be undertaken by the multiple methods known to the skilled artisan, a non-limiting list of which are described later in this document.

Scheme 15

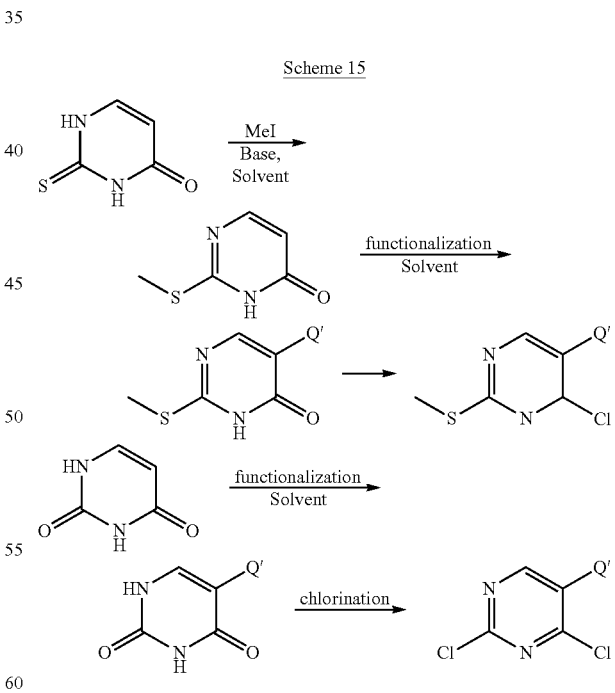

Other methods of accessing suitably functionalized pyrimidine derivatives includes modification of commercially available uracil or thiouracil. For example, S-methylation of thiouracil using iodomethane and base affords an intermediate that may be functionalized at the C5 position to introduce Q, or the precursor to Q, Q'. An example of such C5-functionalisation is halogenation using bromine in acetic acid, N-iodosuccinimide in DMF or N-chlorosuccinimide in acetic acid, which introduces a C5 bromo-, iodo or chloro group, respectively. Groups such as $CF_3$ may be introduced through reaction with $CF_3I$ in the presence of $FeSO_4$, $H_2O_2$ and DMSO.

Similar C5 chemistries may also be used on uracil itself and the derivatives converted to the 4-chloro (for the thiouracil derivative) or 2,4-dichloropyrimidine derivatives through reaction with reagents such as $POCl_3$.

Functional Group Interconversion:

The various functionalities appearing in target molecules and examples (e.g., X at the 5-position of the pyrimidine system, or on the pendant N-aryl or N-benzyl groups), may be introduced through appropriate choice of starting materials, or where the final functionality is not available directly through this process, or where such functionality may be compromised during the subsequent chemistry to build the final molecule, alternative functionalities may be used and subsequently transformed into the final desired functionality by methods, and at points in the sequence, readily determined by one skilled in the art.

For example, a non-exhaustive list of such transformations includes the conversions: Ar/HetAr—OMe→Ar/HetAr—OH ($BBr_3$), Ar/HetAr—$NH_2$→Ar/HetAr—Cl ($NaNO_2$, CuCl), Ar/HetAr—Br→Ar/HetAr—CN ($Pd_2(dba)_3$, $Zn(CN)_2$, DPPF), Me→$CO_2H$ ($KMnO_4$), $CO_2H$→$CO_2Me$ (MeOH, $H_2SO_4$), OH→OAlkyl (Alkyl halide, base), $CO_2H$→CONR'R" (EDC, HOAt, DIPEA, HNR'R"), Ar/HetAr—Br→Ar/HetAr—$CO_2Me$ ($Pd_2(dba)_3$, DPPF, CO(g), MeOH), Br→$CO_2H$ ($^tBuLi$, $CO_2$), Ar/HetAr—H→Ar/HetAr—Br (NBS), CN→$CO_2H$ (conc. $H_2SO_4$), Ar/HetAr—Br→Ar/HetAr—NR'R" ($Pd_2(dba)_3$, DPPF, HNR'R"), Ar/HetAr—I/Br→Ar/HetAr—$CF_3$ ($CF_3CO_2Na$, CuI, NMP). Other functional group interconversion (FGI) examples relating to the generation of aniline and benzylamine synthons used for SNAr chemistry with 2,4-dichloropyrimidines, or pyrimidines with other displaceable leaving groups, are shown below.

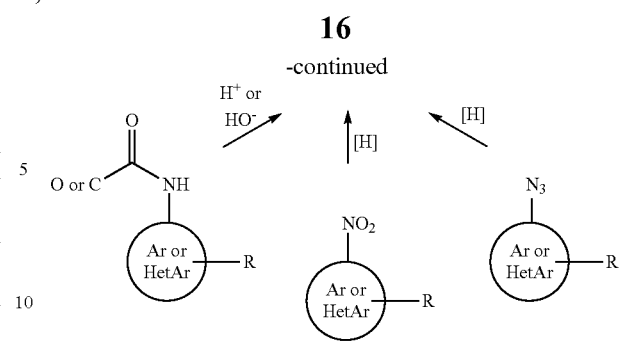

As shown in Scheme 16, nitro- or azidobenzenes may be reduced to the desired aniline compound under a range of conditions. Typically hydrogenation in the presence of a Pd/C catalyst in solvents such as methanol, ethanol, ethyl acetate will yield the desired product. In the case of the azide reduction, Staudinger conditions with $Ph_3P$ may be effectively used. Many aniline precursors are commercially available for conversion to the aniline itself. N-acyl derivatives such as amides may be hydrolyzed under acidic or basic conditions to provide the aniline. In the case of carbamates, e.g., tert-butoxycarbonyl (BOC) protected anilines, the acyl group may be removed with HCl in solvents such as dioxane or through use of TFA in DCM. FMOC protected anilines require basic conditions, typically piperidine in DMF to remove the acyl moiety.

When R is an electron withdrawing group and/or when the aromatic system is a π-deficient heterocycle, a fluoro (or other halogen or triflate), ideally conjugated to said fluoro, may be displaced under SNAr conditions with ammonia itself or an ammonia equivalent or precursor.

Aryl or heteroaryl halides and triflates may also be reacted under transition metal catalysis with ammonia equivalents or precursors to allow the introduction of nitrogen functionality. One skilled in the art will appreciate the large number of catalysts, ligands, bases and solvents cited in the extensive literature and which are commercially available for this conversion.

Scheme 16

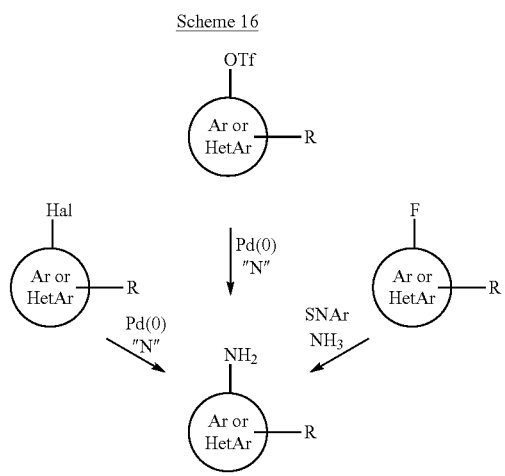

Scheme 17

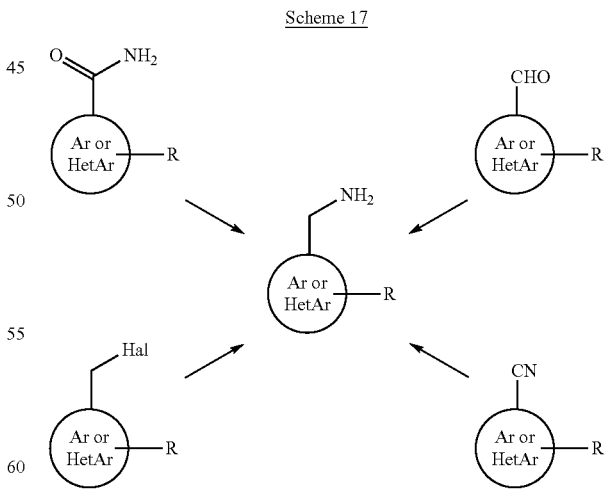

Benzylamines as synthons in the SNAr reaction with 2,4-dichloropyrimidines or pyrimidines with other displaceable 2- and 4-leaving groups, may also be prepared via a number of different approaches. Indicated in scheme 22 are some representative examples of some of the more common routes used. Primary amides may be reduced to the target benzylamines with reducing agents such as LiAlH$_4$ and borane complexes; aldehydes undergo reductive amination with ammonia equivalents in the presence of reducing agents such as NaCN(BH$_3$) and Na(OAc)$_3$BH; benzyl halides undergo typical SN2 displacements with ammonia equivalents or precursors, and benzonitriles may be reduced with a number of reducing agents of which Raney nickel and LiAlH$_4$ are non limiting examples.

Example Synthesis of dialkyl(4-aminobenzyl)phosphonates from other dialkyl phosphonates Scheme 18

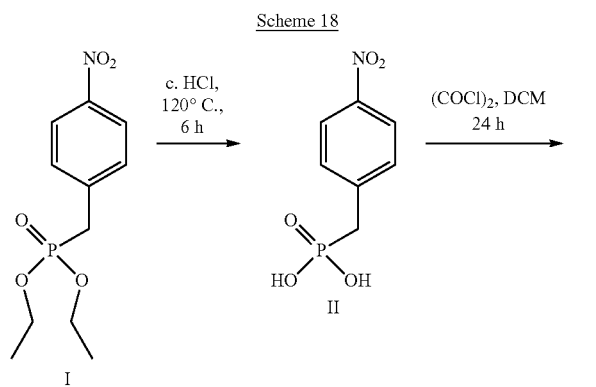

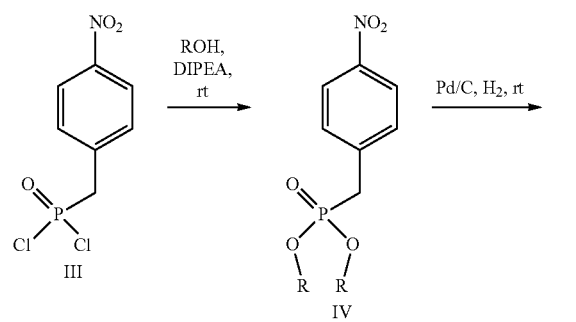

Examples of dialkyl (4-aminobenzyl)phosphonates may be made according to Scheme 18. For example, commercially available diethyl(4-nitrobenzyl)phosphonate I may be hydrolyzed to the corresponding phosphonic acid II using concentrated hydrochloric acid. This acid may be converted to the phosphonic dichloride III with oxalyl chloride and reacted with alkyl alcohols to afford dialkyl phosphonates IV. The nitro group may be reduced by multiple methods including hydrogenation in the presence of a palladium catalyst to afford dialkyl(4-aminobenzyl)phosphonates V.

Example Synthesis of dialkyl(3-aminobenzyl)phosphonates via Michaelis-Arbuzov chemistry Scheme 19

Dialkyl benzylphosphonates may also be made according to Michaelis-Arbuzov chemistry, through heating of trialkylphosphites VI with 1-bromomethyl-3- or 4-nitrobenzene VII to afford dialkyl(3- or 4-nitrobenzyl)phosphonates VIII directly (Scheme 19). The nitro group may be reduced under various conditions known to the skilled artisan including but not limited to catalytic hydrogenation in the presence of palladium on charcoal, to yield dialkyl(3- or 4-aminobenzyl) phosphonates IX.

Example Synthesis of dialkyl(3- and 4-aminophenyl)phosphonates via Pd(0) Coupling Chemistry Scheme 20

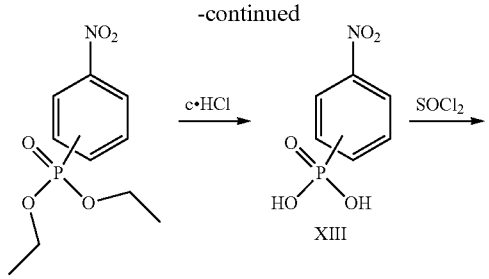

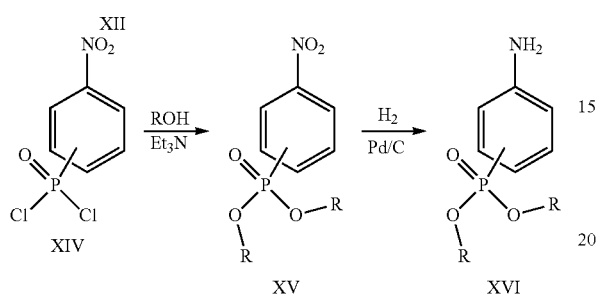

Dialkyl 3- or 4-aminophenylphosphonates may be prepared as shown in Scheme 20. Palladium-catalyzed reactions of p- or m-bromonitrobenzene XI with diethyl phosphonate X affords diethyl 3- or 4-nitrophenylphosphonates XII. These phosphonates may be hydrolyzed into the corresponding phosphonic acids XIII with concentrated hydrochloric acid and then treated with thionyl chloride to yield phosphonic dichlorides XIV. Reaction of these dichlorides with alcohols affords dialkyl 3- or 4-nitrophenyl phosphonate esters XV which maybe reduced into the corresponding anilines XVI by hydrogenation.

Example Synthesis of alkyl(3- and 4-aminobenzyl)alkylphosphinates via Michaelis-Arbuzov Chemistry

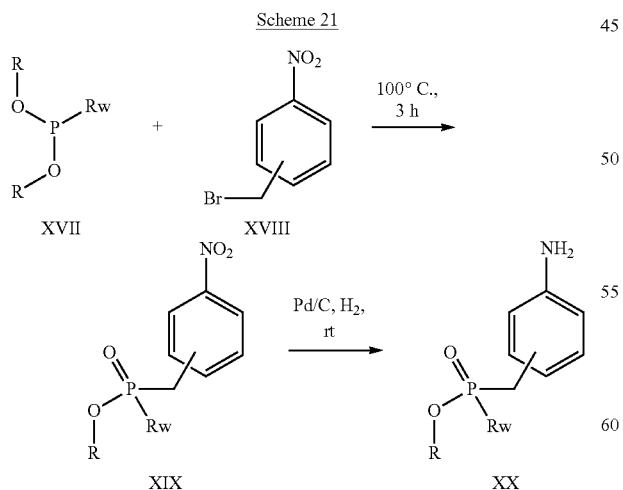

Examples of alkyl phosphinate intermediates may be made according to Scheme 21 using Michaelis-Arbuzov chemistry. For example, p- or m-nitrobenzylbromides XVIII may be heated with neat diethoxymethylphosphine XVII (i.e. R=Et, $R_w$=Me) to afford ethyl methyl(4- or 3-nitrobenzyl)phosphinate XIX. The resulting nitro materials may be reduced by a variety of methods including hydrogenation in the presence of a palladium catalyst to afford the appropriate aminobenzylphosphinates XX, in this case ethyl (3- or 4-aminobenzyl) methylphosphinate.

Example Synthesis of alkyl hydrogen phosphonates and phosphonic acids via hydrolysis of dialkyl phosphonates

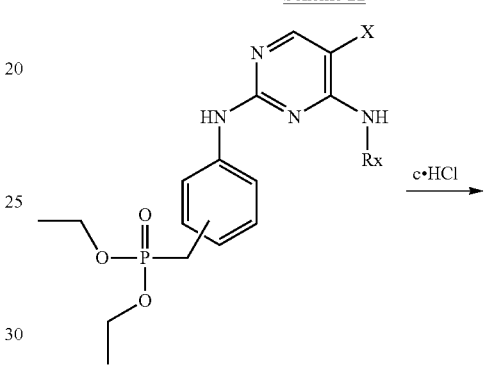

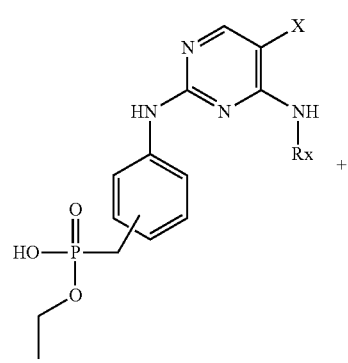

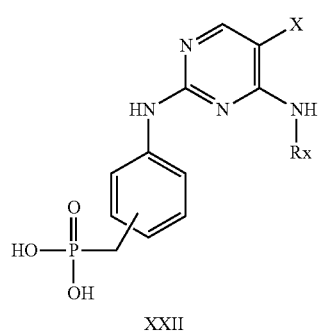

As shown in Scheme 22, alkyl hydrogen phosphonates XXI and phosphonic acids XXII may be synthesized from the corresponding diethyl phosphonates by hydrolysis with concentrated hydrochloric acid. Stopping the reaction before complete hydrolysis occurs allows the isolation of both the alkyl hydrogen phosphonate and the phosphonic acid through chromatographic techniques such as preparative HPLC.

Example Synthesis of dialkyl(3- and 4-aminobenzyl)phosphine oxides via Michaelis-Arbuzov Chemistry

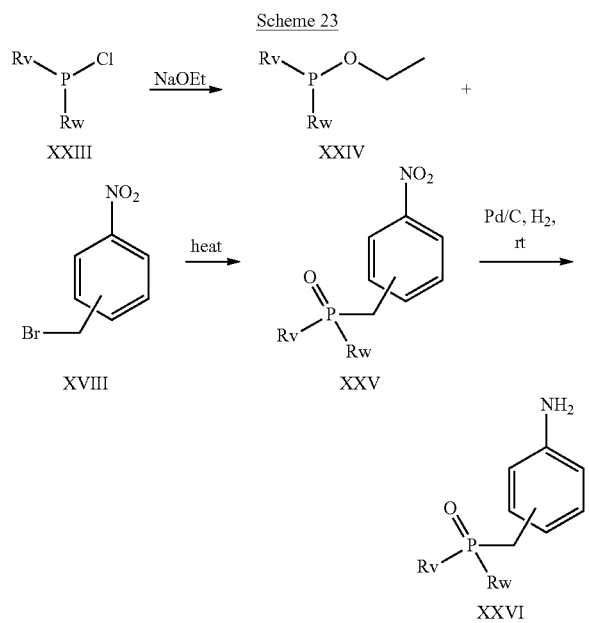

Dialkyl benzylphosphine oxides may be prepared according to Scheme 23 by reaction of a dialkylphosphinous chloride XXIII, e.g., chlorodimethylphosphine with an alkoxide, e.g., sodium ethoxide, to form an intermediate alkyl dialkylphosphinite XXIV, in this example ethyl dimethylphosphinite. This intermediate phosphinite may be reacted without isolation or purification with a benzyl halide e.g. 3- or 4-nitrobenzylbromide XVIII under elevated temperatures utilizing Michaelis-Arbuzov chemistry to afford the desired dialkyl benzylphosphine oxides XXV, in this case dimethyl (3- or 4-nitrobenzyl)phosphine oxide. The nitro group of this example may be reduced using a variety of conditions, for example hydrogenation in the presence of a palladium on charcoal catalyst to afford dialkyl (3- and 4-aminobenzyl) phosphine oxides XXVI.

Example Synthesis of dialkyl(3- and 4-aminophenyl)phosphine oxides via Pd(0) Mediated Coupling Chemistry

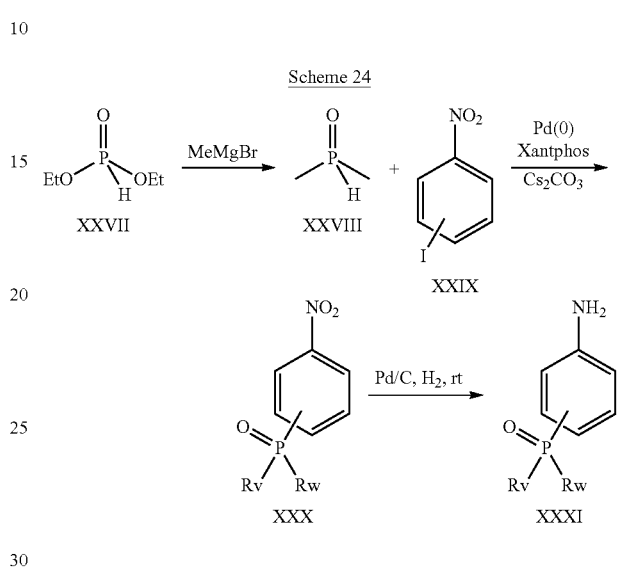

Dialkyl(3- and 4-aminophenyl)phosphine oxides may be prepared as indicated in Scheme 24. Reaction of diethyl phosphonate XXVII with an alkyl magnesium bromide (e.g., methyl magnesium bromide) at 0° C. to rt affords a dialkylphosphine oxide XXVIII (e.g., dimethylphosphine oxide) which may undergo palladium-catalyzed coupling with 3- or 4-nitroiodobenzene XXIX to yield dialkyl 3- or 4-nitrophenylphosphine oxide XXX (e.g. dimethyl 3- or 4-nitrophenylphosphine oxide). The nitro group may be reduced by multiple methods including catalytic hydrogenation to afford the desired aniline intermediates XXXI.

Example Synthesis of the dialkylation of dialkyl benzylphosphonates

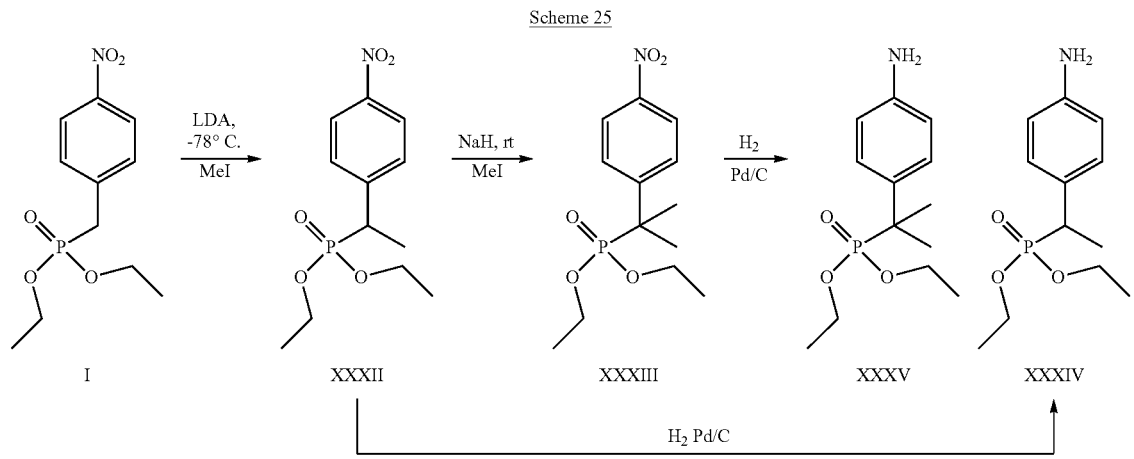

Dialkyl benzylphosphonates such as diethyl(4-nitrobenzyl)phosphonate I, may be monoalkylated at the benzylic carbon by reaction with strong base, of which LDA is a non-limiting example, followed by introduction of a suitable alkyl halide such as iodomethane. The monoalkylated product thus formed XXXII may be alkylated a second time at the benzylic carbon through deprotonation with sodium hydride and reaction with an alkyl halide such as iodomethane to yield derivatives XXXIII. In the instance shown in the scheme, the nitro-derived products may be reduced to the corresponding anilines XXXIV and XXXV via methods such as catalytic hydrogenation.

Example Synthesis of 2,3-dihydro-1H-isoindol-1-one derivatives

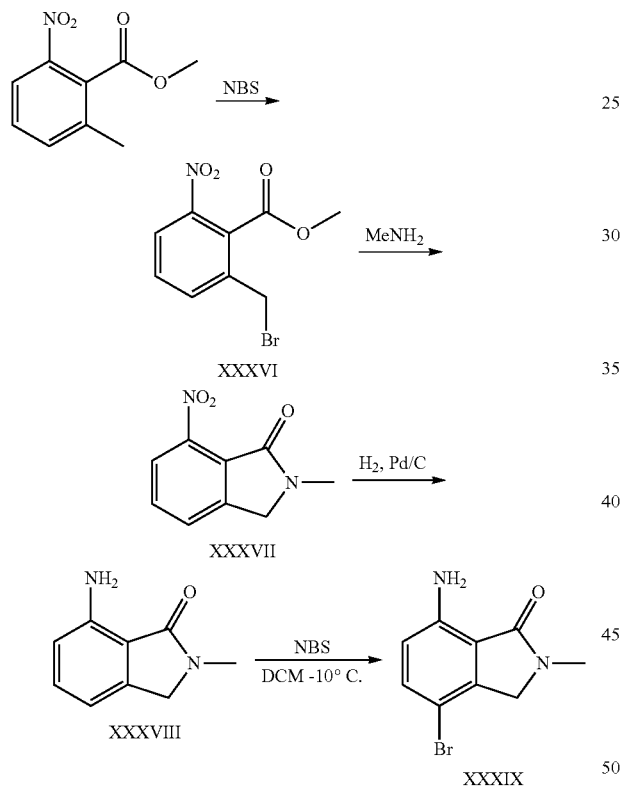

Amino lactam derivatives may be prepared according to Scheme 26. Methyl 2-methyl-6-nitrobenzoate may be brominated at the benzylic position with NBS to afford derivative XXXVI. This ester may be cyclized with methylamine to yield the nitro lactam XXXVII which may be reduced to the aniline derivative XXXVIII. Bromination of XXXVIII at low temperature affords 7-amino-4-bromo-2-methyl-2,3-dihydro-1H-isoindol-1-one XXXIX. This material may be reacted with 4-chloropyrimidine derivatives and then subjected to chemistries known to those skilled in the art that convert the bromo functionality into other groups of utility of which alkoxy, alkyl, aryl, hetaryl, heterocyclyl and cycloalkyl are non-limiting examples.

Example Procedure for the Synthesis of 2-substituted N-methyl-N-[3-({[5-(trifluoromethyl)pyrimidin-4-yl]amino}methyl)pyridin-2-yl]methanesulfonamides e.g. N-[3-({[2-({4-[(diethylphosphoryl)methyl]phenyl}amino)-5-(trifluoromethyl)pyrimidin-4-yl]amino}methyl)pyridin-2-yl]-N-methylmethanesulfonamide

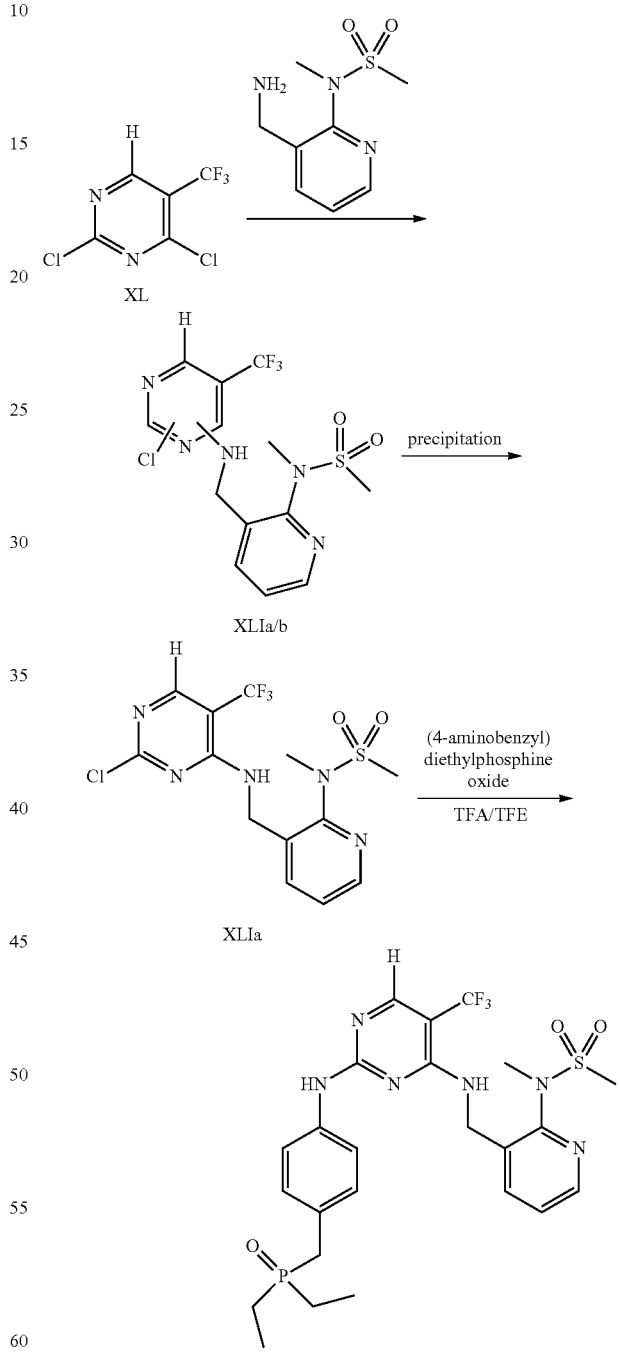

Ex. 10

Reaction of 2,4-dichloro-5-(trifluoromethyl)pyrimidine XL with N-[3-(aminomethyl)pyridin-2-yl]-N-methylmethanesulfonamide (WO2007/072158, WO2008/115369) in the presence of diisopropylethylamine affords a solution of N-[3-({[2-chloro-5-(trifluoromethyl)pyrimidin-4-yl]amino}methyl)pyridin-2-yl]-N-methylmethanesulfonamide XLIa and its regioisomer N-[3-({[4-chloro-5-(trifluoromethyl)pyrimidin-2-yl]amino}methyl)pyridin-2-yl]-N-methylmethanesulfonamide XLIb. On larger scales stirring at 0° C., precipitation of the pure 4-substituted isomer XLIa occurs. Reaction of a sample of the pure mixture of N-[3-({[2-chloro-5-(trifluoromethyl)pyrimidin-4-yl]amino}methyl)pyridin-2-yl]-N-methylmethanesulfonamide with anilines such as 4-[(diethylphosphoryl)methyl]aniline in the presence of TFA and TFE under microwave irradiation yields 2-substituted N-methyl-N-[3-({[5-(trifluoromethyl)pyrimidin-4-yl]amino}methyl)pyridin-2-yl]methanesulfonamides (e.g. N-[3-({[2-({4-[(diethylphosphoryl)methyl]phenyl}amino)-5-(trifluoromethyl)pyrimidin-4-yl]amino}methyl)pyridin-2-yl]-N-methylmethanesulfonamide, Example 10).

e.g. diethyl[4-({4-[({2-[methyl(methylsulfonyl)amino]pyridin-3-yl}methyl)amino]-5-(trifluoromethyl)pyrimidin-2-yl}amino)benzyl]phosphonate (Ex. 1)

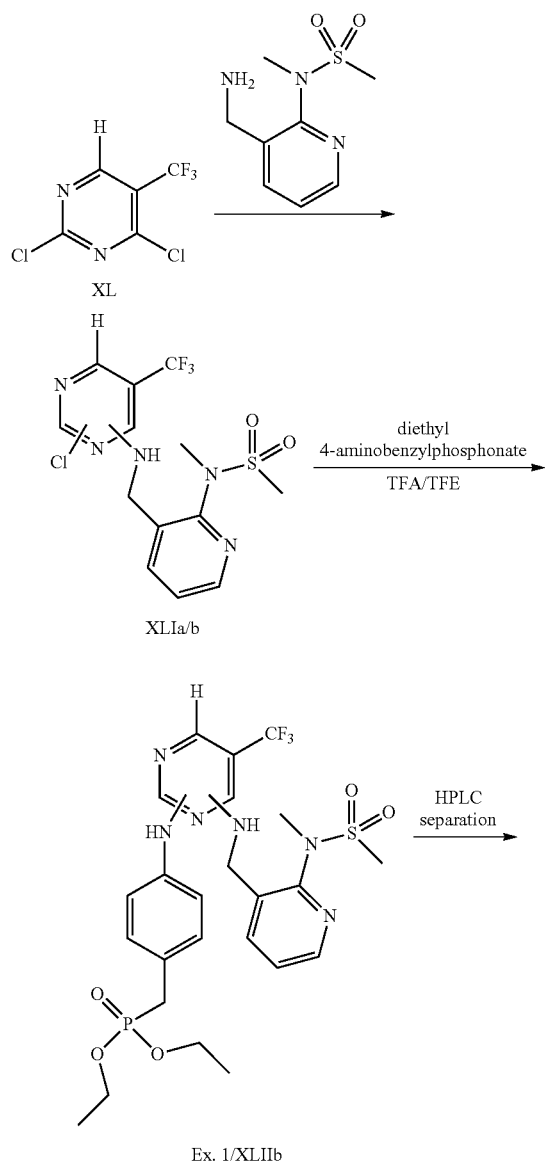

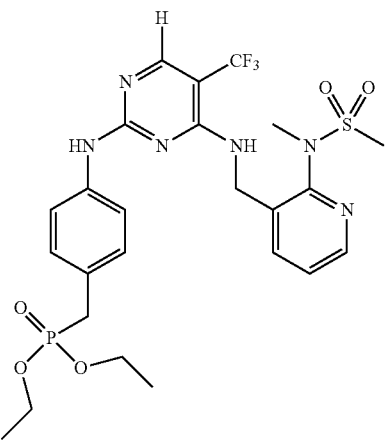

Ex. 1

Reaction of 2,4-dichloro-5-(trifluoromethyl)pyrimidine XL with N-[3-(aminomethyl)pyridin-2-yl]-N-methylmethanesulfonamide (WO2007/072158, WO2008/115369) in the presence of diisopropylethylamine affords a mixture of N-[3-({[2-chloro-5-(trifluoromethyl)pyrimidin-4-yl]amino}methyl)pyridin-2-yl]-N-methylmethanesulfonamide and its regioisomer N-[3-({[4-chloro-5-(trifluoromethyl)pyrimidin-2-yl]amino}methyl)pyridin-2-yl]-N-methylmethanesulfonamide XLIa/XLIb. Reaction of this mixture with anilines such as the commercially available diethyl(4-aminobenzyl)phosphonate in the presence of TFA and TFE under microwave conditions, yields 2-substituted N-methyl-N-[3-({[5-(trifluoromethyl)pyrimidin-4-yl]amino}methyl)pyridin-2-yl]methanesulfonamides and the regioisomers which may be separated by preparative HPLC to afford e.g. diethyl[4-({4-[({2-[methyl(methylsulfonyl)amino]pyridin-3-yl}methyl)amino]-5-(trifluoromethyl)pyrimidin-2-yl}amino)benzyl]phosphonate Ex. 1.

Example Procedure for the Synthesis of 2-substituted N-methyl-2-{[5-(trifluoromethyl)pyrimidin-4-yl]amino}benzamides e.g. diethyl(4-{[4-{[2-(methylcarbamoyl)phenyl]amino}-5-(trifluoromethyl)pyrimidin-2-yl]amino}benzyl)phosphonate (Ex. 20)

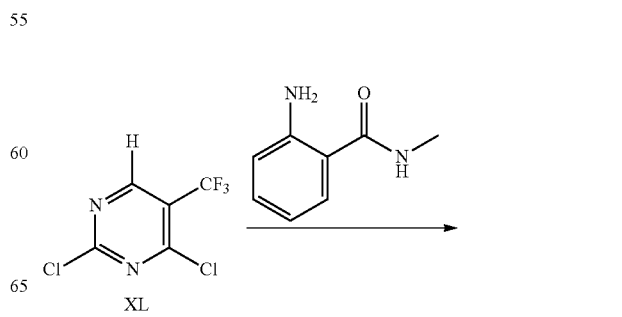

-continued

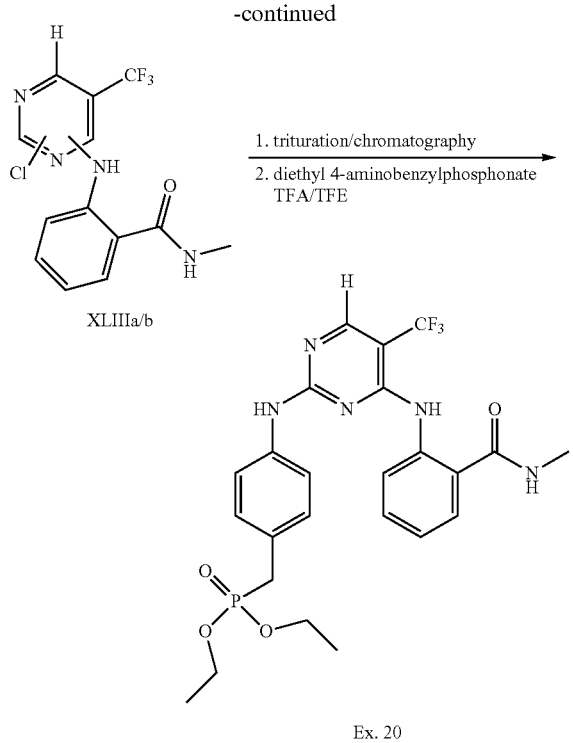

Ex. 20

Reaction of 2,4-dichloro-5-(trifluoromethyl)pyrimidine XL with commercially available 2-amino-N-methyl-benzamide and diisopropylethylamine at room temperature overnight affords a mixture of 2-{[2-chloro-5-(trifluoromethyl)pyrimidin-4-yl]amino}-N-methylbenzamide and 2-{[4-chloro-5-(trifluoromethyl)pyrimidin-2-yl]amino}-N-methylbenzamide (XLIIIa/XLIIIb). Trituration of the mixture with methylene chloride affords a pure sample of the desired 4-substituted product XLIIIa. Concentration of the mother liquors and purification of the residue by chromatography over silica gel using 5% EtOAc in methylene chloride as eluent isolating the less polar material affords further pure 4-substituted isomer plus a mixture of isomers which may be subjected to further chromatography if desired. Reaction of pure 2-{[2-chloro-5-(trifluoromethyl)pyrimidin-4-yl]amino}-N-methylbenzamide XLIIIa with anilines such as diethyl(4-aminobenzyl)phosphonate in the presence of TFA and TFE under microwave irradiation yields the desired products (e.g. diethyl(4-{[4-{[2-(methylcarbamoyl)phenyl]amino}-5-(trifluoromethyl)pyrimidin-2-yl]amino}benzyl)phosphonate, Ex. 20)

Example Procedure for the Synthesis of 2-substituted N-[3-(methylsulfonyl)benzyl]-5-(trifluoromethyl)pyrimidin-4-amines e.g. diethyl(4-{[4-{[3-(methylsulfonyl)benzyl]amino}-5-(trifluoromethyl)pyrimidin-2-yl]amino}benzyl)phosphonate, Ex. 25

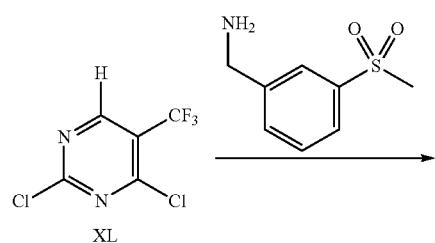

-continued

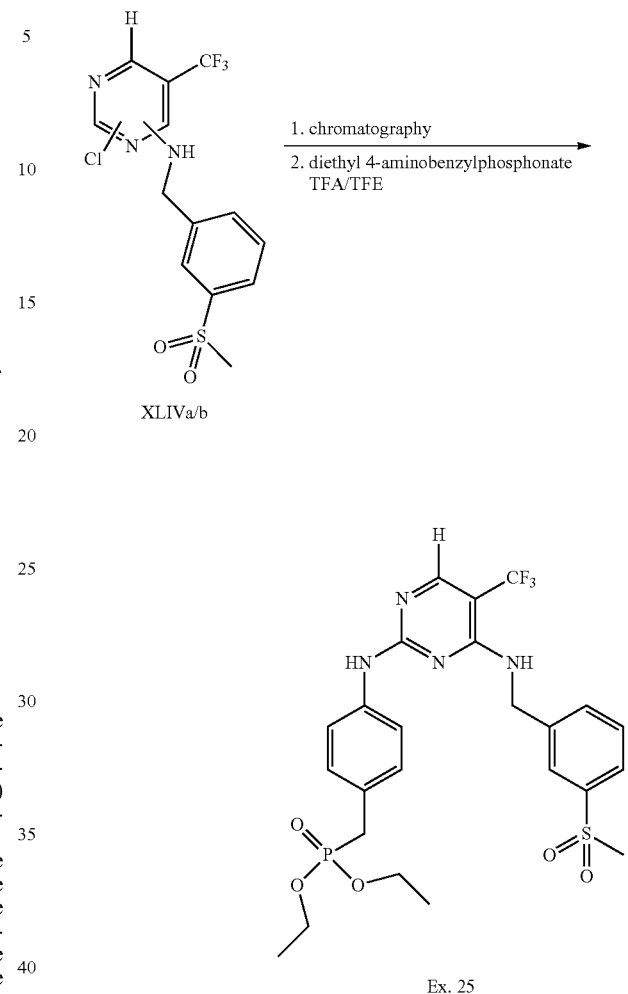

Ex. 25

Reaction of 2,4-dichloro-5-(trifluoromethyl)pyrimidine XL with commercially available 1-[3-(methylsulfonyl)phenyl]methanamine and diisopropylethylamine at 0° C. overnight affords a mixture of 2-chloro-N-[3-(methylsulfonyl)benzyl]-5-(trifluoromethyl)pyrimidin-4-amine and 4-chloro-N-[3-(methylsulfonyl)benzyl]-5-(trifluoromethyl)pyrimidin-2-amine XLIVa/XLIVb. The crude mixture was crystallized from methylene chloride to afford a sample of the pure, undesired 2-substituted isomer XLIVb. The mother liquors were chromatographed over silica gel eluting with 1:1 hexane:ethyl acetate to yield a further pure sample of the 2-substituted isomer plus a sample of the desired 2-chloro-N-[3-(methylsulfonyl)benzyl]-5-(trifluoromethyl)pyrimidin-4-amine XLIVa. Reaction of this latter isomer with anilines such as diethyl(4-aminobenzyl)phosphonate in the presence of TFA and TFE under microwave irradiation yields the desired product (e.g. diethyl(4-{[4-{[3-(methylsulfonyl)benzyl]amino}-5-(trifluoromethyl)pyrimidin-2-yl]amino}benzyl)phosphonate, Ex. 25).

Example Procedure for the Synthesis of 2-substituted N-[3-(methylsulfinyl)benzyl]-5-(trifluoromethyl) pyrimidin-4-amines e.g. diethyl(4-{[4-{[3-(methylsulfinyl)benzyl]amino}-5-(trifluoromethyl)pyrimidin-2-yl]amino}benzyl)phosphonate, Ex. 47

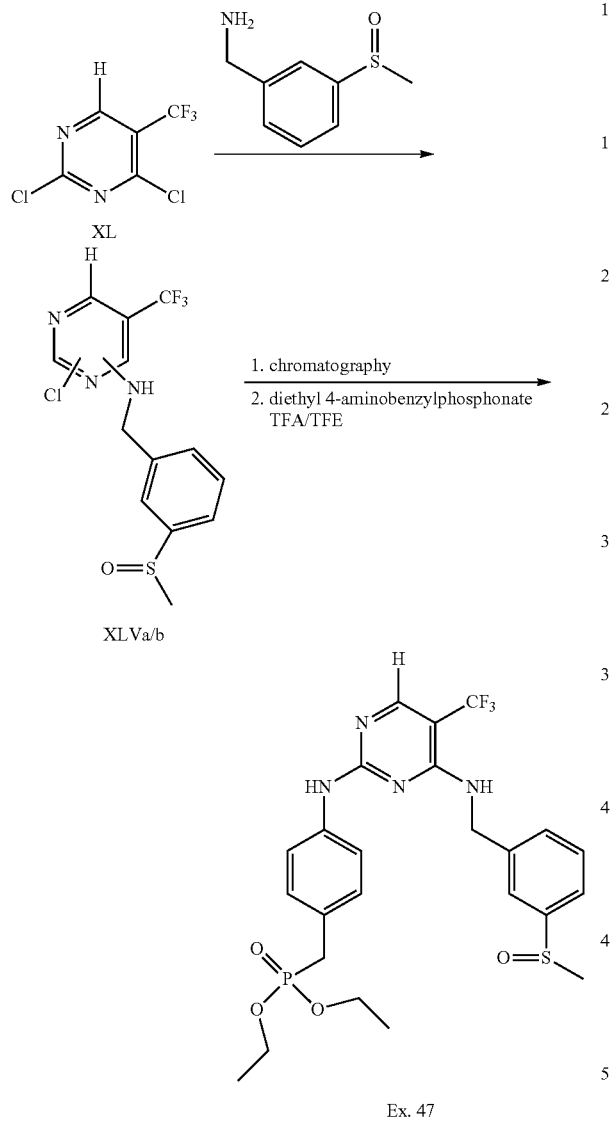

Ex. 47

2,4-dichloro-5-(trifluoromethyl)pyrimidine XL was reacted with 1-[3-(methylsulfinyl)phenyl]methanamine hydrochloride (*Bioorg. Med. Chem. Lett.* 2005, 15, 4136-4142) and diisopropylethylamine at 0° C. overnight to afford a mixture of 2-chloro-N-[3-(methylsulfinyl)benzyl]-5-(trifluoromethyl)pyrimidin-4-amine and 4-chloro-N-[3-(methylsulfinyl)benzyl]-5-(trifluoromethyl)pyrimidin-2-amine XLVa/XLVb. A sample of the pure, desired 4-substituted isomer XLVa was isolated as the non-polar component mixture by chromatography over silica gel eluting with 1:3 hexane:ethyl acetate. Reaction of this latter isomer with anilines such as diethyl(4-aminobenzyl)phosphonate in the presence of TFA and TFE under microwave conditions yields the desired product (e.g. diethyl(4-{[4-{[3-(methylsulfinyl)benzyl]amino}-5-(trifluoromethyl)pyrimidin-2-yl]amino}benzyl)phosphonate, Ex. 47).

Example Procedure for the Synthesis of 2-{[5-chloro/bromo-2-(arylamino)pyrimidin-4-yl]amino}-N-methylbenzamides

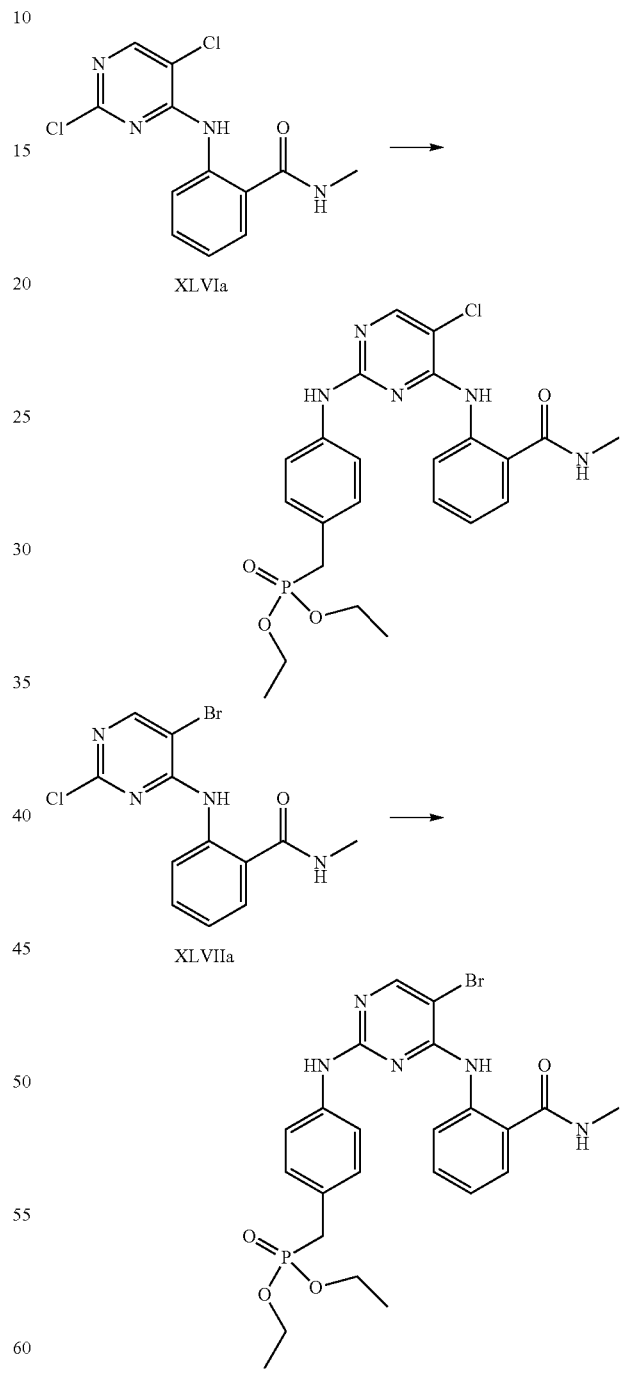

5-Chloro and 5-bromo-2,4-diamino-derived pyrimidines may be prepared by chemistries related to those previously described for the 5-trifluoromethyl variants e.g. as shown in scheme 12 using the 5-chloro or 5-bromo variant of XLIIIa, namely XLVIa and XLVIIa, respectively.

Scheme 27

Access to diverse compounds of the invention, via precursors corresponding to R of Formula 1 can be according to the methods shown below, wherein non-limiting instances of R can be:

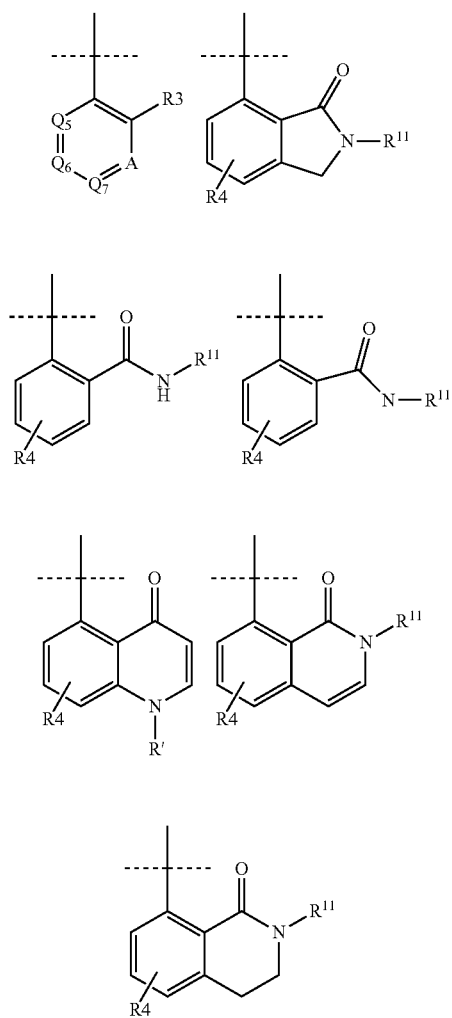

The starting intermediate can be any bromo aryl or heteroaryl precursor of R which can be attached to a pyrimidine core at any stage as described herein via an amine. The generic fused ring represents an optional optionally substituted ring or other substituent as described above for R.

Reaction 1 of Scheme 27 depicts a palladium cross coupling to any aryl or heteroaryl group ($Ar_1$) under Suzuki conditions with and appropriate borane or boronate, such as described in Example 63 and other examples herein, or any suitable variation thereof.

Reactions 2, 3, and 10 also depict Pd couplings used to achieve further diversity in different cyclic substituents. The starting bromo compound can be treated as in reaction 2 with an appropriately functionalized cyclic boronate as in Cpd. 232F. In appropriate cases, the resulting compound can be reduced such as by hydrogenation, as in Cpd. 232E. Alternatively, the functionality of the reagents can be reversed as in reactions 3 and 10, exemplified in Cpd. 205E. R' and R" represent any substituents as contemplated herein.

The boronate product of reaction 3 can be functionalized as in reaction 4, under conditions such as in Ex. 205 by treating with $KHF_2$, followed by and alkylation.

According to reactions 5-7, amino alkyl and amide functionality can be introduced into the group R. As described in Cpd. 109E, an appropriate aryl bromide can be coupled with phenethyl boronic acid, followed by reductive amination or amide coupling, as in Exs. 116 and 117.

Modification such as according to reaction 8 can be used to introduce an unsaturated alkyne spacer for a functional group, as in Exs. 75-77, via Pd mediated coupling with an alkyne.

Further, the bromine can be replaced with an amine as in, e.g., Exs. 199 and 208. Of course, the skilled artisan will understand that the chemistry is general and that examples are not limiting.

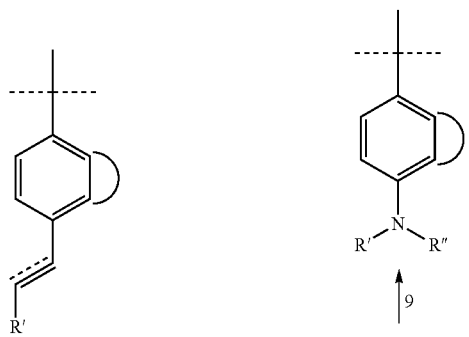

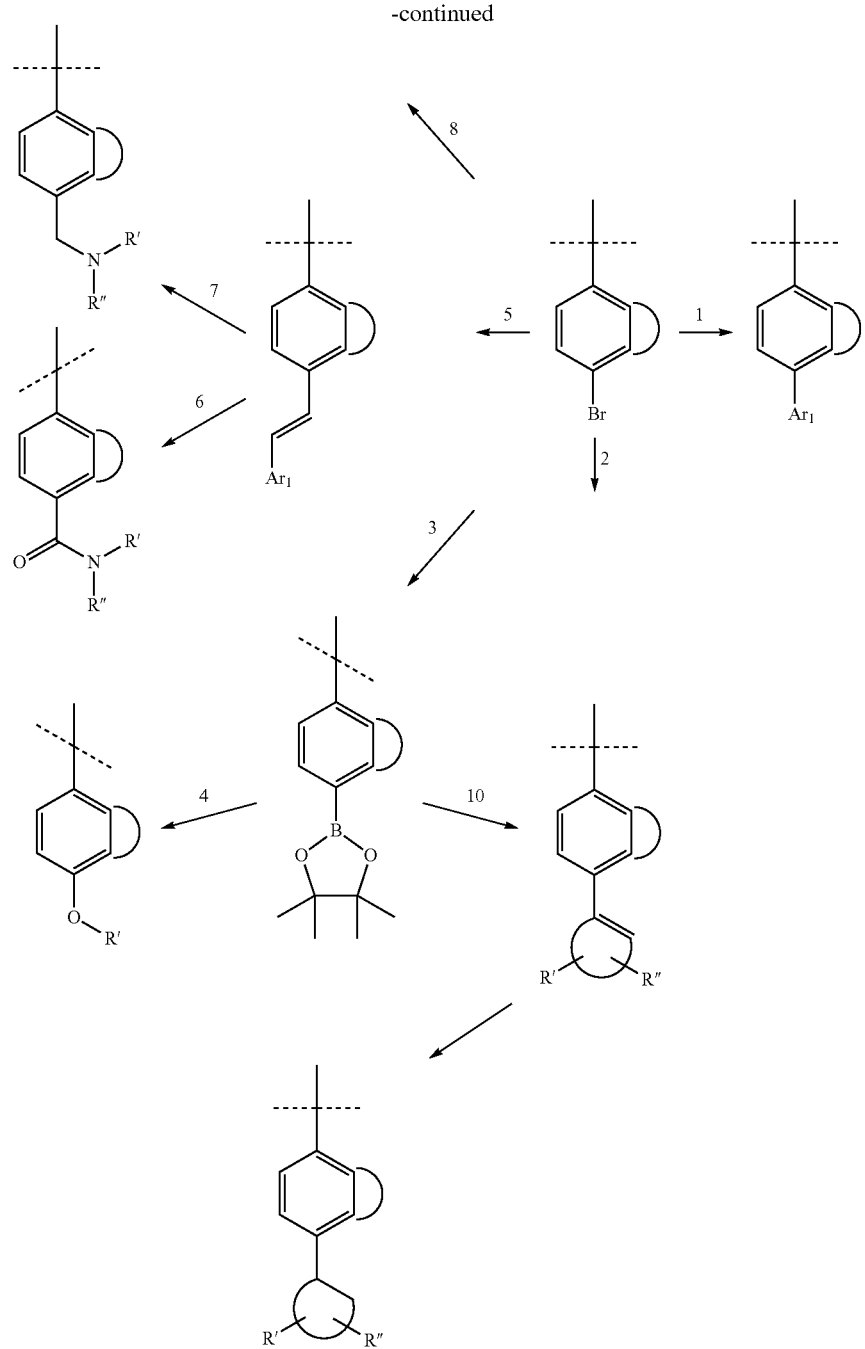

Preparations

Diethyl(3-aminobenzyl)phosphonate

A mixture of 3-nitrobenzyl bromide (648 mg, 3.00 mmol) and triethyl phosphite (0.669 mL, 3.90 mmol) was stirred at 140° C. under nitrogen for 16 h. The excess triethyl phosphite was removed under reduced pressure and the residue purified by chromatography over silica gel eluting with 2% MeOH in dichloromethane to afford diethyl(3-nitrobenzyl)phosphonate, 0.80 g (yield: 98%). $^1$H-NMR (CD$_3$OD, 400 MHz): δ=1.27 (t, J=6.8 Hz, 6H), 3.43 (d, J=22.0 Hz, 2H), 4.08 (q, J=6.8 Hz, 4H), 7.58 (t, J=8.0 Hz, 1H), 7.72 (d, J=7.6 Hz, 1H), 8.15 (d, J=8.4 Hz, 1H), 8.22 (d, J=2.4 Hz, 1H). MS (ES$^+$): m/z 273.99 (MH$^+$). HPLC: t$_R$=2.92 min (ZQ3, polar_5 min).

A solution of the diethyl(3-nitrobenzyl)phosphonate prepared as described above, in MeOH (5 mL) was hydrogenated in the presence of 10% Pd/C (100 mg) overnight. The reaction mixture was filtered and the filtrate concentrated in vacuo to afford the desired product diethyl(3-aminobenzyl)phosphonate (0.690 g; yield: 95%), which was used directly in further chemistries without purification. $^1$H-NMR (CDCl$_3$, 400 MHz): δ=1.24 (t, J=7.2 Hz, 6H), 3.04 (d, J=21.6 Hz, 2H), 3.66 (s, br, 2H), 4.01 (q, J=7.2 Hz, 4H), 6.57 (d, J=8.8 Hz, 1H), 6.67-6.68 (m, 2H), 7.08 (t, J=7.6 Hz, 1H). MS (ES$^+$): m/z 244.00 (MH$^+$). HPLC: t$_R$=2.24 min (ZQ3, polar_5 min).

Diethyl(2-aminobenzyl)phosphonate

Prepared according to the procedure described for diethyl (3-aminobenzyl)phosphonate. The intermediate diethyl(3-nitrobenzyl)phosphonate was obtained in 97% yield as an brownish oil. $^1$H-NMR (CD$_3$OD, 400 MHz): δ=1.23 (t, J=7.2 Hz, 6H), 3.79 (d, J=22.8 Hz, 2H), 4.01 (q, J=7.2 Hz, 4H), 7.48-7.53 (m, 2H), 7.64 (t, J=8.0 Hz, 1H), 7.99 (d, J=8.0 Hz, 1H). MS (ES$^+$): m/z 273.99 (MH$^+$). HPLC: $t_R$=2.89 min (ZQ3, polar__5 min).

The diethyl(2-aminobenzyl)phosphonate was obtained in 94% yield, as was used directly in further chemistries without purification. $^1$H-NMR (CDCl$_3$, 400 MHz): δ=1.24 (t, J=7.2 Hz, 6H), 3.12 (d, J=20.8 Hz, 2H), 3.98 (q, J=7.2 Hz, 4H), 4.25 (s, br, 2H), 6.70-6.75 (m, 2H), 7.01-7.08 (m, 2H). MS (ES$^+$): m/z 244.00 (MH$^+$). HPLC: $t_R$=2.63 min (ZQ3, polar__5 min).

Diethyl[1-(4-aminophenyl)ethyl]phosphonate

2M LDA in THF (1.83 mL, 3.66 mmol) was added dropwise under N$_2$, to a stirred solution of diethyl(4-nitrobenzyl) phosphonate (1.00 g, 3.66 mmol) in THF (10 mL) at −78° C. After 1 hour, iodomethane (0.456 mL, 7.32 mmol) was added dropwise and the mixture stirred at −78° C. for 30 min then allowed to warm to room temperature during 3-4 h. Water (10 mL) was then added slowly followed by EtOAc (20 mL). The layers were separated and the aqueous phase was extracted with EtOAc (3×20 mL). The organic phases were combined, dried (MgSO$_4$), concentrated in vacuo, and the residue purified by chromatography over silica gel eluting with 10% EtOAc in hexanes to afford 180 mg of pure diethyl[1-(4-nitrophenyl)ethyl]phosphonate (yield: 17%) and 680 mg of a mixture of diethyl(4-nitrobenzyl)phosphonate and diethyl[2-(4-nitrophenyl)propan-2-yl]phosphonate.

Diethyl[1-(4-nitrophenyl)ethyl]phosphonate: $^1$H-NMR (CD$_3$OD, 400 MHz): δ=1.19 (t, J=7.2 Hz, 3H), 1.29 (t, J=7.2 Hz, 3H), 1.57 (d, J=7.2 Hz, 1.5H), 1.61 (d, J=7.2 Hz, 1.5H), 3.52 (q, J=7.6 Hz, 0.5H), 3.57 (q, J=7.6 Hz, 0.5H), 3.93-4.00 (m, 2H), 4.06-4.10 (m, 2H), 7.60 (dd, J=2.4, 8.8 Hz, 2H), 8.20 (dd, J=1.2, 8.8 Hz, 2H). MS (ES$^+$): m/z 288.09 (MH$^+$). HPLC: $t_R$=1.36 min (UPLC TOF, polar).

A solution of diethyl[1-(4-nitrophenyl)ethyl]phosphonate (180 mg) in MeOH (5 mL) was hydrogenated in the presence of 10% Pd/C (50 mg) for 4 h. The reaction mixture was filtered and the filtrate concentrated in vacuo to afford 150 mg of the desired diethyl[1-(4-aminophenyl)ethyl]phosphonate (yield: 94%). which was used directly in further chemistries without purification. $^1$H-NMR (CDCl$_3$, 400 MHz): δ=1.16 (t, J=7.2 Hz, 3H), 1.27 (t, J=7.2 Hz, 3H), 1.50 (d, J=7.6 Hz, 1.5H), 1.53 (d, J=7.6 Hz, 1.5H), 3.01-3.10 (m, 1H), 3.76-3.82 (m, 1H), 3.89-3.93 (m, 1H), 3.97-4.03 (m, 2H), 6.66-6.68 (m, 2H), 7.12-7.15 (m, 2H). MS (ES$^+$): m/z 258.04 (MH$^+$). HPLC: $t_R$=2.20 min (ZQ3, polar__5 min).

Diethyl[2-(4-aminophenyl)propan-2-yl]phosphonate

A solution of diethyl[1-(4-nitrophenyl)ethyl]phosphonate (206 mg, 0.717 mmol) in THF (5 mL) at room temperature under N$_2$, was treated portionwise with NaH (60% in mineral oil, 143 mg, 3.58 mmol). The resulting mixture was stirred for 5 min then iodomethane (0.268 mL, 4.30 mmol) was added dropwise and the mixture stirred for a further 5 h. Water (10 mL) was added slowly followed by EtOAc (20 mL). The layers were separated and the aqueous phase extracted with EtOAc (3×20 mL). The organic phases were combined, dried (MgSO$_4$), concentrated in vacuo, and the residue purified by chromatography over silica gel eluting with 5% MeOH in dichloromethane to afford 103 mg of desired diethyl[2-(4-nitrophenyl)propan-2-yl]phosphonate (yield: 48%). $^1$H-NMR (CD$_3$OD, 400 MHz): δ=1.22 (t, J=7.2 Hz, 6H), 1.64 (s, 3H), 1.69 (s, 3H), 3.94-4.01 (m, 4H), 7.78 (dd, J=2.4, 9.2 Hz, 2H), 8.21 (dd, J=0.8, 8.8 Hz, 2H). MS (ES$^+$): m/z 302.11 (MH$^+$). HPLC: $t_R$=1.44 min (UPLC TOF, polar).

The diethyl[2-(4-nitrophenyl)propan-2-yl]phosphonate (103 mg) prepared as described above, was hydrogenated in the presence of 10% Pd/C (50 mg) in MeOH (5 mL) for 4 h. The mixture was filtered and the filtrate concentrated in vacuo to afford 92.5 mg of the desired diethyl[2-(4-aminophenyl) propan-2-yl]phosphonate (yield: 99%), which was used in further chemistries without purification. $^1$H-NMR (CDCl$_3$, 400 MHz): δ=1.20 (t, J=7.2 Hz, 6H), 1.54 (s, 3H), 1.59 (s, 3H), 3.65 (s, br, 2H), 3.80-3.94 (m, 2H), 6.66 (d, J=8.8 Hz, 2H), 7.32 (dd, J=2.4, 8.8 Hz, 2H). MS (ES$^+$): m/z 272.02 (MH$^+$). HPLC: $t_R$=2.45 min (ZQ3, polar__5 min).

3-[(Dimethylphosphoryl)methyl]aniline

A solution of chlorodimethylphosphine (250 mg, 2.60 mmol) in THF (0.7 mL) was added dropwise to a stirred suspension of sodium ethoxide (194 mg, 2.85 mmol) in THF (0.8 mL) at 0° C. The resulting mixture was stirred at room temperature for 30 min. then treated with 1-(bromomethyl)-3-nitrobenzene (560 mg, 2.59 mmol). The mixture was then stirred under nitrogen at 100° C. in a sealed tube for 2 h., concentrated in vacuo and the residue purified by chromatography over silica gel eluting with 5% MeOH in dichloromethane to afford 153 mg of dimethyl(3-nitrobenzyl)phosphane oxide (yield: 28%). $^1$H-NMR (CDCl$_3$, 400 MHz): δ=1.53 (d, J=12.4 Hz, 6H), 3.27 (d, J=14.0 Hz, 2H), 7.55 (t, J=7.6 Hz, 1H), 7.71 (d, J=7.6 Hz, 1H), 8.11 (d, J=2.0 Hz, 1H), 8.16 (dd, J=0.8, 7.2 Hz, 1H). MS (ES$^+$): m/z 214.00 (MH$^+$). HPLC: $t_R$=2.16 min (ZQ3, polar__5 min).

The dimethyl(3-nitrobenzyl)phosphane oxide (153 mg) produced as described above was hydrogenated in the presence of 10% Pd/C (100 mg) in MeOH (5 mL) overnight. The mixture was filtered and the filtrate concentrated in vacuo to afford 128 mg of the desired 3-[(dimethylphosphoryl)methyl]aniline (yield: 96%), which was used in further chemistries without purification. $^1$H-NMR (CDCl$_3$, 400 MHz): δ=1.44 (d, J=12.8 Hz, 6H), 3.06 (d, J=15.6 Hz, 2H), 3.81 (s, br, 2H), 6.55-6.58 (m, 3H), 7.08 (t, J=7.6 Hz, 1H). MS (ES$^+$): m/z 184.02 (MH$^+$). HPLC: $t_R$=0.58 and 0.90 min (ZQ3, polar__5 min).

4-[(Dimethylphosphoryl)methyl]aniline

Prepared according to the procedure described above for 3-[(dimethylphosphoryl)methyl]aniline using 1-(bromomethyl)-4-nitrobenzene. The nitro intermediate dimethyl(4-nitrobenzyl)phosphane oxide, was obtained in 21% yield.

$^1$H-NMR (CDCl$_3$, 400 MHz): δ=1.51 (d, J=12.8 Hz, 6H), 3.27 (d, J=14.4 Hz, 2H), 7.47 (dd, J=2.4, 8.8 Hz, 2H), 8.22 (d, J=8.4 Hz, 2H). MS (ES$^+$): m/z 214.00 (MH$^+$). HPLC: $t_R$=2.17 min (ZQ3, polar__5 min).

The 4-[(dimethylphosphoryl)methyl]aniline was obtained in 95% yield, and was used directly in further chemistries without purification. $^1$H-NMR (CDCl$_3$, 400 MHz): δ=1.41 (d, J=12.4 Hz, 6H), 3.05 (d, J=15.2 Hz, 2H), 3.74 (s, br, 2H), 6.65 (d, J=7.2 Hz, 2H), 6.99 (dd, J=2.0, 8.0 Hz, 2H). MS (ES$^+$): m/z 184.01 (MH$^+$). HPLC: $t_R$=0.56 and 0.75 min (ZQ3, polar__5 min).

3-[(Diethylphosphoryl)methyl]aniline

Prepared according to the procedure described above for 3-[(dimethylphosphoryl)methyl]aniline using chlorodiethylphosphine. The nitro intermediate diethyl(3-nitrobenzyl)phosphane oxide was obtained in 80% yield.

$^1$H-NMR (CD$_3$OD, 400 MHz): δ=1.13 (t, J=7.6 Hz, 3H), 1.17 (t, J=8.0 Hz, 3H), 1.73-1.85 (m, 4H), 3.40 (d, J=13.2 Hz, 2H), 7.60 (t, J=7.6 Hz, 1H), 7.12 (d, J=7.6 Hz, 1H), 8.16 (d, J=8.0 Hz, 1H), 8.23 (dd, J=1.6, 7.6 Hz, 1H). MS (ES$^+$): m/z 242.01 (MH$^+$). HPLC: $t_R$=2.45 min (ZQ3, polar__5 min).

The aniline derivative 3-[(diethylphosphoryl)methyl]aniline was obtained in 97% yield, and was used directly in further chemistries without purification. $^1$H-NMR (CDCl$_3$, 400 MHz): δ=1.12-1.20 (m, 6H), 1.62-1.71 (m, 4H), 3.03 (d, J=14.4 Hz, 2H), 3.72 (s, br, 2H), 6.56-6.62 (m, 3H), 7.08 (t, J=7.6 Hz, 1H). MS (ES$^+$): m/z 212.02 (MH$^+$). HPLC: $t_R$=1.62 min (ZQ3, polar__5 min).

3-[(Diethylphosphoryl)methyl]aniline

Prepared according to the procedure described above for 3-[(dimethylphosphoryl)methyl]aniline using chlorodiethylphosphine and 1-(bromomethyl)-4-nitrobenzene. The nitro intermediate diethyl(4-nitrobenzyl)phosphane oxide was obtained in 70% yield.

$^1$H-NMR (CD$_3$OD, 400 MHz): δ=1.13 (t, J=7.6 Hz, 3H), 1.17 (t, J=8.0 Hz, 3H), 1.74-1.84 (m, 4H), 3.40 (d, J=13.6 Hz, 2H), 7.55 (dd, J=1.6, 8.8 Hz, 2H), 8.21 (d, J=8.4 Hz, 2H). MS (ES$^+$): m/z 241.99 (MH$^+$). HPLC: $t_R$=2.45 min (ZQ3, polar__5 min).

The aniline derivative 4-[(diethylphosphoryl)methyl]aniline was obtained in 97% yield, and was used directly in further chemistries without purification. $^1$H-NMR (CDCl$_3$, 400 MHz): δ=1.12-1.20 (m, 6H), 1.59-1.68 (m, 4H), 3.02 (d, J=14.4 Hz, 2H), 6.64 (d, J=8.8 Hz, 2H), 7.02 (dd, J=1.6, 8.0 Hz, 2H). MS (ES$^+$): m/z 212.02 (MH$^+$). HPLC: $t_R$=1.14 min (ZQ3, polar__5 min).

3-[(dipropan-2-ylphosphoryl)methyl]aniline

Prepared according to the procedure described above for 3-[(dimethylphosphoryl)methyl]aniline using dipropan-2-ylphosphinous chloride. The nitro intermediate (3-nitrobenzyl)(dipropan-2-yl)phosphane oxide was obtained in 75% yield.

$^1$H-NMR (CD$_3$OD, 400 MHz): δ=1.13-1.21 (m, 12H), 2.08-2.18 (m, 2H), 3.42 (d, J=11.6 Hz, 2H), 7.58 (t, J=8.0 Hz, 1H), 7.78 (d, J=7.2 Hz, 1H), 8.14 (d, J=8.0 Hz, 1H), 8.29 (d, J=1.6 Hz, 1H). MS (ES$^+$): m/z 270.04 (MH$^+$). HPLC: $t_R$=2.74 min (ZQ3, polar__5 min).

The aniline derivative 3-[(dipropan-2-ylphosphoryl)methyl]aniline was obtained in 91% yield, and was used directly in further chemistries without purification. $^1$H-NMR (CD$_3$OD, 400 MHz): δ=1.12-1.19 (m, 12H), 2.05-2.13 (m, 2H), 3.12 (d, J=12.8 Hz, 2H), 6.60-6.70 (m, 3H), 7.03 (t, J=7.6 Hz, 1H). MS (ES$^+$): m/z 240.04 (MH$^+$). HPLC: $t_R$=2.07 min (ZQ3, polar__5 min).

4-[(dipropan-2-ylphosphoryl)methyl]aniline

Prepared according to the procedure described above for 3-[(dimethylphosphoryl)methyl]aniline using dipropan-2-ylphosphinous chloride and 1-(bromomethyl)-4-nitrobenzene. The nitro intermediate (4-nitrobenzyl)(dipropan-2-yl)phosphane oxide was obtained in 85% yield.

$^1$H-NMR (CD$_3$OD, 400 MHz): δ=1.14-1.21 (m, 12H), 2.08-2.18 (m, 2H), 3.41 (d, J=12.8 Hz, 2H), 7.61 (dd, J=2.0, 8.8 Hz, 2H), 8.19 (d, J=8.8 Hz, 2H). MS (ES$^+$): m/z 270.04 (MH$^+$). HPLC: $t_R$=2.74 min (ZQ3, polar__5 min).

The aniline derivative 4-[(dipropan-2-ylphosphoryl)methyl]aniline was obtained in 92% yield, and was used directly in further chemistries without purification. $^1$H-NMR (CD$_3$OD, 400 MHz): δ=1.10-1.17 (m, 12H), 2.02-2.10 (m, 2H), 3.10 (d, J=12.4 Hz, 2H), 6.69 (d, J=8.4 Hz, 2H), 7.07 (dd, J=2.0, 8.0 Hz, 2H). MS (ES$^+$): m/z 240.04 (MH$^+$). HPLC: $t_R$=1.91 min (ZQ3, polar__5 min).

Dimethylphosphane oxide

Diethyl phosphite (1.29 mL, 10 mmol) was added slowly dropwise to a solution of methyl magnesium bromide in THF (1.4 M, 21.4 mL, 30 mmol) at 0° C. After stirring at room temperature for 5 h. saturated aqueous sodium bicarbonate (10 mL) was added cautiously, followed by MeOH (10 mL). The white solids produced were removed by filtration and the filtrate concentrated in vacuo to afford the desired dimethylphosphane oxide as a clear oil (0.45 g, yield: 58%). This material was further dried by azeotropic removal of water using toluene before use in subsequent chemistries.

$^1$H-NMR (D$_2$O, 400 MHz): δ=1.68 (dd, J=4.0, 14.4 Hz, 6H), 7.09 (dq, J=4.0, 489.2 Hz, 1H).

4-(Dimethylphosphoryl)aniline

A degassed suspension of 1-iodo-4-nitrobenzene (90 mg, 0.36 mmol), dimethylphosphane oxide (29.2 mg, 0.38 mmol), bis(dibenzylideneacetone)palladium (3.31 mg, 0.0036 mmol), XantPhos (6.27 mg, 0.0108 mmol), and Cs$_2$CO$_3$ (165 mg, 0.506 mmol) in dry dioxane (0.4 mL) was heated in a sealed tube at 90° C. for 4 h. The cooled mixture was filtered, the filtrate concentrated in vacuo, and the residue chromatographed over silica gel eluting with 5% MeOH in dichloromethane to afford 26 mg of dimethyl(4-nitrophenyl)phosphane oxide (yield: 36%).

$^1$H-NMR (CD$_3$OD, 400 MHz): δ=1.86 (d, J=13.6 Hz, 6H), 8.06 (dd, J=8.8, 10.8 Hz, 2H), 8.38 (dd, J=1.6, 8.8 Hz, 2H). MS (ES$^+$): m/z 199.96 (MH$^+$). HPLC: $t_R$=1.96 min (ZQ3, polar__5 min).

The dimethyl(4-nitrophenyl)phosphane oxide) produced as described above was hydrogenated in the presence of 10% Pd/C (15 mg) in MeOH (5 mL) for 2 h. The mixture was then filtered and the filtrate concentrated in vacuo to yield 19 mg of the desired 4-(dimethylphosphoryl)aniline (yield: 86%) which was used directly in further chemistries without purification. $^1$H-NMR (CDCl$_3$, 400 MHz): δ=1.67 (d, J=12.8 Hz, 6H), 4.11 (s, br, 2H), 6.73 (dd, J=2.0, 8.4 Hz, 2H), 7.48 (dd, J=8.4, 11.2 Hz, 2H). MS (ES$^+$): m/z 170.04 (MH$^+$). HPLC: $t_R$=1.23 min (ZQ3, polar__5 min).

3-(Dimethylphosphoryl)aniline

Prepared according to the procedure described above for 4-(dimethylphosphoryl)aniline using 1-iodo-3-nitrobenzene. The nitro intermediate dimethyl(3-nitrophenyl)phosphane oxide) was obtained in 27% yield.

$^1$H-NMR (CD$_3$OD, 400 MHz): δ=1.87 (d, J=13.6 Hz, 6H), 7.83 (dt, J=2.4, 7.6 Hz, 1H), 8.19 (t, J=8.8 Hz, 1H), 8.45 (d, J=8.0 Hz, 1H), 8.66 (dt, J=1.6, 12.0 Hz, 1H). MS (ES$^+$): m/z 199.96 (MH$^+$). HPLC: $t_R$=2.06 min (ZQ3, polar__5 min).

The aniline derivative 3-(dimethylphosphoryl)aniline was obtained in 96% yield, and was used directly in further chemistries without purification. $^1$H-NMR (CDCl$_3$, 400 MHz): δ=1.69 (d, J=12.8 Hz, 6H), 3.91 (s, br, 2H), 6.81 (dt, J=1.2, 8.0 Hz, 1H), 6.97 (dd, J=7.6, 11.6 Hz, 1H), 7.12 (dt, J=2.0, 13.2

Hz, 1H), 7.23-7.28 (m, 1H). MS (ES$^+$): m/z 170.02 (MH$^+$). HPLC: $t_R$=1.27 min (ZQ3, polar_5 min).

Diethyl(4-aminophenyl)phosphonate

A mixture of Pd(PPh$_3$)$_4$ (3.0 g, 25 mmol), p-bromonitrobenzene (50 g, 250 mmol), diethyl phosphonate (51.5 g, 370 mmol) and triethylamine (50 g, 500 mmol) in EtOH (1.5 L) was degassed 3 times then stirred at reflux overnight.

The resulting mixture was filtered, the filtrate concentrated in vacuo, and the residue chromatographed over silica gel eluting with petroleum ether:EtOAc 5:1 to afford 60 g of diethyl(4-nitrophenyl)phosphonate (yield: 94%).

A mixture of diethyl(4-nitrophenyl)phosphonate (150 mg, 0.58 mmol), EtOH (40 ml) and 10% Pd/C (30 mg) was hydrogenated under 50 psi of hydrogen pressure at 40° C. for 6 h. After cooling to room temperature, the reaction mixture was filtered and the filtrate concentrated in vacuo to afford 130 mg of desired diethyl(4-aminophenyl)phosphonate (yield: 98%), which was used directly in further chemistries without purification.

$^1$H-NMR (CDCl$_3$, 400 MHz): δ=1.17-1.27 (m, 6H), 3.91-4.07 (m, 4H), 6.62 (dd, J=3.6, 8.4 Hz, 2H), 7.51 (dd, J=8.4, 12.8 Hz, 2H). MS: m/z 230.05 [MH$^+$].

Diethyl(3-aminophenyl)phosphonate

Diethyl(3-nitrophenyl)phosphonate was prepared according to the procedure described above for diethyl(4-nitrophenyl)phosphonate using m-bromonitrobenzene (yield: 49%). $^1$H-NMR (CDCl$_3$, 400 MHz): δ=1.35 (t, J=6.8 Hz, 6H), 4.10-4.23 (m, 4H), 7.68 (m, 1H), 8.15 (m, 1H), 8.39 (m, 1H), 8.76-8.75 (d, 1H).

A solution of diethyl(3-nitrophenyl)phosphonate (520 mg, 2.0 mmol) and SnCl$_2$ (1.8 g, 8 mmol) in EtOH (50 mL) was heated at reflux for 12 h. The mixture was then filtered and the filtrate concentrated in vacuo to yield a crude product, which was purified by preparative HPLC to afford 320 mg of desired diethyl(3-aminophenyl)phosphonate (yield: 69%).

$^1$H-NMR (DMSO-d$_6$, 400 MHz): δ=1.20 (m, 6H), 3.91-4.00 (m, 4H), 5.39 (s, br, 2H), 6.73-6.81 (m, 2H), 6.91 (dd, J=1.6, 16.4 Hz, 1H), 7.11-7.16 (m, 1H). MS: m/z 230.10 [MH$^+$].

(4-Nitrophenyl)phosphonic acid

A solution of diethyl(4-nitrophenyl)phosphonate (60 g, 230 mmol) in 250 mL of concentrated HCl (aq) was stirred at reflux overnight. The excess HCl was removed under reduced pressure and the product used in further chemistries without purification (46.8 g, yield: 100%).

(3-Nitrophenyl)phosphonic acid

Prepared according to the procedure described for (4-nitrophenyl)phosphonic acid using diethyl(3-nitrophenyl)phosphonate (yield: 76%).

(4-Nitrophenyl)phosphonic dichloride

A solution of (4-nitrophenyl)phosphonic acid (1.0 g, 5 mmol) in SOCl$_2$ (30 ml) was stirred at reflux for 5 h. The reaction mixture was concentrated under reduced pressure to dryness and the crude (4-nitrophenyl)phosphonic dichloride isolated used directly in further chemistries without purification.

(3-Nitrophenyl)phosphonic dichloride

Prepared according to the procedure described for (4-nitrophenyl)phosphonic dichloride using (3-nitrophenyl)phosphonic acid.

Dipropan-2-yl(4-nitrophenyl)phosphonate

A solution of distilled dry propan-2-ol (20 ml) and triethylamine (1.0 g, 10 mmol) was added dropwise to (4-nitrophenyl)phosphonic dichloride (1.2 g, 5 mmol) at 0° C. The resulting mixture was stirred at reflux overnight, the mixture filtered and the filtrate concentrated under reduced pressure to yield a crude product, which was purified by chromatography over silica gel eluting with petroleum ether:EtOAc: 5:1 to afford 360 mg of desired dipropan-2-yl(4-nitrophenyl)phosphonate (yield: 25%). $^1$H-NMR (CDCl$_3$, 400 MHz): δ=1.18 (d, J=6.0 Hz, 6H), 1.33 (d, J=6.4 Hz, 6H), 4.65-4.73 (m, 2H), 7.93 (dd, J=8.8, 12.8 Hz, 2H), 8.22 (dd, J=3.2, 8.8 Hz, 2H).

Dipropan-2-yl(3-nitrophenyl)phosphonate

Prepared according to the procedure described for dipropan-2-yl(4-nitrophenyl)phosphonate using (3-nitrophenyl)phosphonic dichloride (yield: 41%). $^1$H-NMR (CDCl$_3$, 400 MHz): δ=1.19 (d, J=6.0 Hz, 6H), 1.34 (d, J=6.4 Hz, 6H), 4.68-4.73 (m, 2H), 7.60 (m, 1H), 8.08 (dd, J=7.6, 12.8 Hz, 1H), 8.32 (d, J=8.4 Hz, 1H), 8.57 (d, J=14.0 Hz, 1H).

The following two phosphonate esters were prepared according to the procedures described above for dipropan-2-yl(4-nitrophenyl)phosphonate and dipropan-2-yl(3-nitrophenyl)phosphonate using the appropriate phosphonic dichloride and alcohol.

5,5-Dimethyl-2-(4-nitrophenyl)-1,3,2-dioxaphosphinane 2-oxide

Yield: 75%. $^1$H-NMR (CDCl$_3$, 400 MHz): δ=1.07 (s, 3H), 1.10 (s, 3H), 3.84 (dd, J=11.2, 13.6 Hz, 2H), 4.28 (dd, J=9.6, 10.8 Hz, 2H), 7.95-8.00 (m, 2H), 8.26-8.29 (m, 2H).

5,5-Dimethyl-2-(3-nitrophenyl)-1,3,2-dioxaphosphinane 2-oxide

Yield: 76%. $^1$H-NMR (CDCl$_3$, 400 MHz): δ=1.07 (s, 3H), 1.13 (s, 3H), 3.86 (dd, J=11.2, 13.6 Hz, 2H), 4.31 (dd, J=9.6, 10.8 Hz, 2H), 7.66 (d, J=4.0 Hz, 1H), 8.12 (d, J=12.8 Hz, 1H), 8.38 (m, 1H), 8.61 (d, J=14.4 Hz, 1H).

Dipropan-2-yl(4-aminophenyl)phosphonate

A mixture of dipropan-2-yl(4-nitrophenyl)phosphonate (287 mg, 1.0 mmol), i-PrOH (30 ml) and 10% Pd/C (30 mg) was hydrogenated under 50 psi of hydrogen pressure at 40° C. for 6 h. The reaction mixture was then filtered and the filtrate concentrated in vacuo to afford 238 mg of desired dipropan-2-yl(4-aminophenyl)phosphonate (yield: 92%), which used directly in further chemistries without purification. $^1$H-NMR (DMSO-d$_6$, 400 MHz): δ=1.11 (d, J=6.0 Hz, 6H), 1.21 (d, J=6.4 Hz, 6H), 4.38-4.43 (m, 2H), 5.74 (s, br, 2H), 6.56-6.59 (m, 2H), 7.27-7.32 (m, 2H). MS: m/z 257.90 [MH$^+$].

Dipropan-2-yl(3-aminophenyl)phosphonate

Prepared according to the procedure described for dipropan-2-yl(4-aminophenyl)phosphonate using dipropan-2-yl(3-nitrophenyl)phosphonate. Yield: 45%. $^1$H-NMR (DMSO-d₆, 400 MHz): δ=1.15 (d, J=6.4 Hz, 6H), 1.24 (d, J=6.4 Hz, 6H), 4.45-4.50 (m, 2H), 5.35 (s, br, 2H), 6.70-6.77 (m, 2H), 6.58 (d, J=8.0 Hz, 1H), 7.10-7.25 (m, 1H). MS: m/z 257.97 [MH⁺].

4-(5,5-Dimethyl-2-oxido-1,3,2-dioxaphosphinan-2-yl)aniline

Prepared according to the procedure described for dipropan-2-yl(4-aminophenyl)phosphonate using 5,5-dimethyl-2-(4-nitrophenyl)-1,3,2-dioxaphosphinane 2-oxide. Yield: 41%. ¹H-NMR (DMSO-d₆, 400 MHz): δ=0.97 (s, 3H), 1.02 (s, 3H), 3.78 (m, 2H), 4.08 (m, 2H), 5.91 (s, br, 2H), 6.61 (dd, J=3.6, 8.4 Hz, 2H), 7.34 (m, 2H). MS: m/z 242.10 [MH⁺].

3-(5,5-Dimethyl-2-oxido-1,3,2-dioxaphosphinan-2-yl)aniline

Prepared according to the procedure described for dipropan-2-yl(4-aminophenyl)phosphonate using 5,5-dimethyl-2-(3-nitrophenyl)-1,3,2-dioxaphosphinane 2-oxide. Yield: 63%. ¹H-NMR (DMSO-d₆, 400 MHz): δ=0.94 (s, 3H), 1.07 (s, 3H), 3.84 (dd, J=9.6, 10.8 Hz, 2H), 4.07 (dd, J=11.2, 14.0 Hz, 2H), 5.43 (s, br, 2H), 6.75-6.78 (m, 2H), 6.88 (d, 1H), 7.16 (m, 1H). MS: m/z 242.11 [MH⁺].

Ethyl(4-amino-3-methoxybenzyl)methylphosphinate

A mixture of (3-methoxy-4-nitrophenyl)methanol (0.5 g, 2.73 mmol) and thionyl chloride (0.3 mL, 4.09 mmol) was heated at reflux for 12 h. then the mixture concentrated in vacuo to afford 0.55 g of 4-(chloromethyl)-2-methoxy-1-nitrobenzene, (yield: 100% yield) which was used in further chemistries without purification.

¹H NMR (CD₃OD, 400 MHz): δ=4.00 (s, 3H), 4.60 (s, 2H), 7.05 (dd, J=8.34, 1.77 Hz, 1H), 7.14 (d, J=1.52 Hz, 1H), 7.86 (d, J=8.34 Hz, 1H). MS (ES⁺): m/z 202.0264 [MH⁺] (TOF, polar).

A mixture of 4-(chloromethyl)-2-methoxy-1-nitrobenzene (1.1 g, 5.46 mmol) and diethyl methylphosphonite (0.89 g, 1.2 mmol) were heated at 100° C. for 16 h in a sealed tube. The reaction mixture was concentrated in vacuo and the residue crude purified using an Isco Combiflash system eluting with 0→5% MeOH in DCM as eluent to afford 0.641 g of ethyl (3-methoxy-4-nitrobenzyl)methylphosphinate (yield: 43% yield). MS (ES⁺): m/z 273.99 [MH⁺] (ZQ3, polar 5 min).

A solution of ethyl(3-methoxy-4-nitrobenzyl)methylphosphinate (0.64 g, 2.34 mmol) in ethanol (5.0 mL) was charged with palladium 10% wt on activated carbon (0.25 g). The reaction mixture was evacuated and purged with hydrogen gas (3×) and allowed to stir under hydrogen for 16 h. The reaction mixture was filtered through a pad of celite and the filtrate concentrated in vacuo to afford 0.54 g of ethyl(4-amino-3-methoxybenzyl)methylphosphinate (yield: 95% yield). This material was used in successive reactions without further purification. MS (ES⁺): m/z 244.01 [MH⁺] (ZQ3, polar 5 min).

Diethyl(4-amino-3-methoxybenzyl)phosphonate

This material was prepared according to the procedure described above for ethyl(4-amino-3-methoxybenzyl)methylphosphinate using triethylphosphite in the first step. MS (ES⁺): m/z 274.01 [MH⁺] (ZQ3, polar 5 min).

Methyl 2-(bromomethyl)-6-nitrobenzoate (XXXVI)

A solution of methyl 2-methyl-6-nitrobenzoate (TL (1996) 37 5425, 15.6 g, 80 mmol), NBS (21.4 g, 120 mmol) and benzoyl peroxide (200 mg, 0.82 mmol) in 1,2-dichloroethane (250 mL) was heated at reflux for 8 h. The reaction mixture was concentrated to dryness and the crude mixture purified by chromatography over silica gel eluting with 2% ethyl acetate/hexanes to afford 10.5 g of methyl 2-(bromomethyl)-6-nitrobenzoate (XXXVI, yield: 65%). ¹H NMR (CDCl3, 400 MHz): δ 3.98 (s, 3H), 4.57 (s, 2H), 7.59 (dd, 1H, J=7.8, 8.4 Hz), 7.78 (d, 1H, J=7.8 Hz), 8.1 (d, 1H, J=8.4 Hz).

2-Methyl-7-nitro-2,3-dihydro-1H-isoindol-1-one (XXXVII)

A solution of methylamine in ethanol (10 mL, 80 mmol, 8M solution in ethanol) was added to a solution of methyl 2-(bromomethyl)-6-nitrobenzoate (8.1 g, 29.6 mmol) in THF (30 mL). After stirring for 2 h the reaction mixture was concentrated to dryness and water (30 mL) was added with rapid stirring. The solids produced were isolated by filtration and dried to give 4.35 g of 2-methyl-7-nitro-2,3-dihydro-1H-isoindol-1-one (XXXVII, yield: 78%).

¹H NMR (CDCl₃, 400 MHz): δ 3.21 (s, 3H), 4.44 (s, 2H), 7.64 (m, 2H), 7.73-7.74 (m, 1H).

7-Amino-2-methyl-2,3-dihydro-1H-isoindol-1-one (XXXVIII)

A solution of 2-methyl-7-nitro-2,3-dihydro-1H-isoindol-1-one (6.09 g, 31 mmol) in DCM:ethanol (8:2) was hydrogenated under 40 psi of H₂ in the presence of 5% Pd/C (500 mg) until cessation of H₂ uptake. The reaction mixture was filtered, and the filtrate dried (Na₂SO₄) and concentrated in vacuo to afford 4.45 g of 7-amino-2-methyl-2,3-dihydro-1H-isoindol-1-one (XXXVIII, yield: 73%). ¹H NMR (CDCl₃, 400 MHz): δ 3.11 (s, 3H), 4.27 (s, 2H), 5.19 (bs, 2H), 5.5 (d, 1H, J=7.8 Hz), 6.71 (d, 1H, J=7.2 Hz).

7-Amino-4-bromo-2-methyl-2,3-dihydro-1H-isoindol-1-one (XXXIX)

NBS (2.3 g, 12.96) was added to a cold (−8° C. to −10° C.) solution of 7-amino-2-methyl-2,3-dihydro-1H-isoindol-1-one (2 g, 12.4 mmol) in DCM (40 mL) and the mixture stirred at −8° C. to −10° C. for 1 h. A solution of 10% aq. sodium thiosulfate (30 mL) was then added to the reaction mixture and stirring was continued for another 20 minutes. The layers were separated and the aqueous layer was extracted with DCM (2×20 mL). The combined organic extracts were washed with water (3×40 mL) and brine (30 mL), and the organic layer was dried (Na₂SO₄) and concentrated in vacuo to yield 3.2 g of crude product. This material was triturated with ethyl acetate (10 mL) to give 2.2 g of pure 7-amino-4-bromo-2-methyl-2,3-dihydro-1H-isoindol-1-one (XXXIX, yield: 74%).

¹H NMR (CDCl₃, 400 MHz): δ 3.14 (s, 3H), 4.20 (s, 2H), 5.20 (bs, 2H), 5.49 (d, 1H, J=8.4 Hz), 5.79 (d, 1H, J=8.4 Hz).

2-Chloro-N-[3-(methylsulfonyl)benzyl]-5-(trifluoromethyl)pyrimidin-4-amine (XLIVa)

Diisopropylethylamine (31.5 mL, 180 mmol) was added to a suspension of 2,4-dichloro-5-trifluoromethylpyrimidine (XL, 15.0 g, 69.4 mmol) and 1-[3-(methylsulfonyl)phenyl]methanamine hydrochloride (13.3 g, 60 mmol) in THF (300 mL) at 0° C., and the resulting mixture stirred at room temperature overnight. The mixture was then evaporated to dryness, the residue taken up in methylene chloride (100 mL) and the resulting solution washed with water (100 mL), dried over anhydrous sodium sulfate, filtered and concentrated in vacuo. The crude residue obtained was taken up in hot methylene chloride (35 mL) then left to stir overnight at room temperature. The separated solid was isolated by filtration (9.4 g) and determined to be a pure sample of the more polar component of the product mixture (4-chloro-N-[3-(methylsulfonyl)benzyl]-5-(trifluoromethyl)pyrimidin-2-amine XLIVb). The mother liquors were adsorbed onto silica gel and chromatographed over silica gel eluting with hexane:ethyl acetate 50:50 to afford 8.5 g of pure non-polar material (2-chloro-N-[3-(methylsulfonyl)benzyl]-5-(trifluoromethyl)pyrimidin-4-amine XLIVa) and a further 0.7 g of the polar component.

XLIVa: $^1$H NMR (DMSO-d$_6$) δ: 8.63 (t, J=5.9 Hz, 1H), 8.46 (s, 1H), 7.92 (s, 1H), 7.83 (dt, J=7.1, 1.8 Hz, 1H), 7.66 (dt, J=7.7, 1.8 Hz, 1H), 7.63 (t, J=7.3 Hz, 1H), 4.72 (d, J=6.0 Hz, 2H), 3.20 (s, 3H). $^{13}$C NMR (DMSO-d$_6$) δ: 162.58, 158.33, 155.80 (q, J=5 Hz), 140.89, 139.87, 132.40, 129.56, 125.86, 125.67, 123.42 (q, J=272 Hz), 105.24 (q, J=32 Hz), 43.65, 43.51. A HMBC 3-bond correlation is observed between the C$^4$—N-proton at 8.63 ppm and the C$^5$-carbon at ~105 ppm.

2-Chloro-N-[3-(methylsulfinyl)benzyl]-5-(trifluoromethyl)pyrimidin-4-amine (XLVa)

Prepared according to the procedure described above for 2-chloro-N-[3-(methylsulfonyl)benzyl]-5-(trifluoromethyl)pyrimidin-4-amine (XLIVa) using 2,4-dichloro-5-trifluoromethylpyrimidine (XL, 324 mg, 1.5 mmol), 1-[3-(methylsulfinyl)phenyl]methanamine hydrochloride (249 mg, 1.2 mmol) and diisopropylethylamine (0.65 mL, 3.75 mmol) in THF (10 mL). Pure desired 2-chloro-N-[3-(methylsulfinyl)benzyl]-5-(trifluoromethyl)pyrimidin-4-amine (XLVa, 162 mg) was isolated as the non-polar component by chromatography eluting with hexane:ethyl acetate 25:75. $^1$H NMR (DMSO-d$_6$) δ: 8.61 (t, J=5.7 Hz, 1H), 8.44 (s, 1H), 7.67 (s, 1H), 7.49-7.58 (m, 2H), 7.45 (dt, J=6.6, 2.0 Hz, 1H), 4.70 (d, J=5.9 Hz, 2H), 2.72 (s, 3H). $^{13}$C NMR (DMSO-d$_6$) δ: 162.59, 158.35, 155.74 (q, J=5 Hz), 146.49, 139.73, 129.47, 129.24, 123.43 (q, J=272 Hz), 122.40, 122.36, 105.16 (q, J=32 Hz), 43.84, 43.23. A HMBC 3-bond correlation is observed between the C$^4$—N-proton at 8.61 ppm and the C$^5$-carbon at ~105 ppm.

2-{[2-Chloro-5-(trifluoromethyl)pyrimidin-4-yl]amino}-N-methylbenzamide (XLIIIa)

A solution of 2,4-dichloro-5-trifluoromethylpyrimidine (XL, 9.5 g, 44.0 mmol) and 2-amino-N-methylbenzamide (6.0 g, 40 mmol) in THF (50 mL) was treated with DIPEA (15 mL, 8.6 mmol) and the resulting mixture stirred at room temperature overnight.
The product mixture was concentrated in vacuo and the residue triturated with methylene chloride to afford a white solid that was a pure sample of the non-polar component of the mixture (2-{[2-chloro-5-(trifluoromethyl)pyrimidin-4-yl]amino}-N-methylbenzamide XLIIIa). The methylene mother liquors were concentrated and the residue chromatographed over silica gel eluting with 5% EtOAc in methylene chloride to give a further sample of pure non-polar isomer (0.6 g), a sample containing 90% non-polar plus 10% polar isomer (XLIIIb, 0.7 g) and a 1:1 mixture of both isomers (3 g). Total yield of both isomers: 9.3 g (70%).

XLIIIa: $^1$H NMR (DMSO-d$_6$) δ: 12.06 (s, 1H), 8.86 (q, J=4.3 Hz, 1H), 8.68 (s, 1H), 8.38 (d, J=8.2 Hz, 1H), 7.78 (dd, J=7.8, 1.2 Hz, 1H), 7.59 (td, J=7.9, 1.3 Hz, 1H), 7.26 (td, J=7.6, 0.9 Hz, 1H), 2.80 (d, J=4.5 Hz, 3H). $^{13}$C NMR (DMSO-d$_6$) δ: 168.60, 162.19, 156.78 (q, J=5 Hz), 156.42, 137.52, 131.57, 128.02, 123.14 (q, J=272 Hz), 123.87, 122.31, 107.25 (q, J=32 Hz), 26.24. In HMBC experiments, a 3-bond correlation is observed between the C$^4$—N-proton at 12.06 ppm and the C$^5$-carbon at ~107 ppm.

Diethyl(4-{[4-chloro-5-(trifluoromethyl)pyrimidin-2-yl]amino}-3-methoxybenzyl)phosphonate 1.0 M Zinc dichloride in ether (4.07 mL, 4.07 mmol) was added to a solution of 2,4-dichloro-5-trifluoromethylpyrimidine (0.803 g, 3.70 mmol) in 1,2-dichloroethane (6.7 mL) and t-BuOH (6.7 mL). After 30 minutes diethyl(4-amino-3-methoxybenzyl)phosphonate (1.01 g, 3.70 mmol) was added followed by triethylamine (0.567 mL, 4.07 mmol) while keeping the temperature at ~25° C. The reaction mixture was allowed to stir at rt overnight before quenching with sat. aq. NaHCO$_3$ (10 mL). The resulting mixture was extracted with EtOAc (15 mL) and the organic layer was washed with brine (10 mL), dried over anhydrous NaSO$_4$, filtered, and concentrated under reduced pressure to afford a yellow oil. This crude material was initially purified using an Isco Combiflash system eluting with 0→5% MeOH in DCM as eluent followed by preparative HPLC (MDP) to afford diethyl(4-{[4-chloro-5-(trifluoromethyl)pyrimidin-2-yl]amino}-3-methoxybenzyl)phosphonate, 1.09 g (70% yield). $^1$H NMR (CD$_3$OD, 400 MHz): δ=1.28 (t, J=7.07 Hz, 6H), 3.23-3.29 (m, 2H), 3.90-3.95 (m, 3H), 4.01-4.13 (m, 4H), 6.90-6.96 (m, 1H), 7.03 (m, J=2.00 Hz, 1H), 8.02 (d, J=8.34 Hz, 1H), 8.62 (s, 1H). MS (ES$^+$).

Ethyl(4-aminobenzyl)methylphosphinate

A solution of p-nitrobenzylbromide (2.4 g, 11 mmol) in diethoxymethylphosphine (2.0 g, 15 mmol) was stirred at 140° C. in a sealed tube under nitrogen for 16 h. The reaction mixture was concentrated in vacuo and the residue was purified by chromatography over silica eluting with 25% EtOAc in hexane to afford 2.4 g, 87% yield, of ethyl methyl(4-nitrobenzyl)phosphinate. $^1$H NMR (400 MHz, chloroform-d) δ ppm 1.29 (t, J=7.1 Hz, 3H), 1.44 (d, J=13.9 Hz, 3H), 3.25 (d, J=17.7 Hz, 2H), 3.96-4.18 (m, 2H), 7.47 (dd, J=9.0, 2.4 Hz, 2H), 8.20 (d, J=8.1 Hz, 2H). MS (ES+): m/z: 244.0745 [MH+]. HPLC: t$_R$=1.13 min (TOF MS: polar_3 min).

A solution of this material (2.4 g, 9.9 mmol) in MeOH (10 mL) was charged with palladium on activated carbon (10% wt) (0.52 g, 0.49 mmol) and evacuated and purged with hydrogen (3×). The mixture was stirred under an atmosphere of hydrogen for 16 h at rt then filtered through a pad of celite and concentrated in vacuo to afford 2.0 g (95% yield) of the title compound. $^1$H NMR (400 MHz, chloroform-d) δ ppm 1.29 (t, J=7.1 Hz, 3H), 1.34 (d, J=13.6 Hz, 3H), 3.04 (d, J=17.4 Hz, 2H), 3.97-4.12 (m, 2H), 6.65 (d, J=7.8 Hz, 2H), 7.04 (dd, J=8.6, 2.5 Hz, 2H). MS (ES+): m/z: 214.0976 [MH+]. HPLC: t$_R$=0.76 min (TOF MS: polar_3 min).

Ethyl(4-{[4-chloro-5-(trifluoromethyl)pyrimidin-2-yl]amino}benzyl)methylphosphinate Prepared as described above for diethyl(4-{[4-chloro-5-(trifluoromethyl)pyrimidin-2-yl]amino}-3-methoxybenzyl)phosphonate using ethyl(4-aminobenzyl)methylphosphinate in place of diethyl(4-amino-3-methoxybenzyl)phosphonate. Following chromatography, the semi-pure product was crystallized from ethyl acetate to afford 1.1 g (61% yield) of the title compound. $^1$H NMR (400 MHz, DMSO-d$_6$) δ ppm 10.64 (s, 1H), 8.79 (d, J=0.51 Hz, 1H), 7.62 (d, J=8.34 Hz, 2H), 7.25

(dd, J=2.27, 8.59 Hz, 2H), 3.86-4.01 (m, 2H), 3.15 (d, J=17.68 Hz, 2H), 1.31 (d, J=13.64 Hz, 3H), 1.19 (t, J=6.95 Hz, 3H); MS (ES+): m/z: 396.0708 [MH+]. HPLC: $t_R$=1.41 min (UPLC TOF MS: polar_3 min).

Diethyl(4-{[4-chloro-5-(trifluoromethyl)pyrimidin-2-yl]amino}-3-methoxybenzyl)phosphonate 1.0 M Zinc dichloride in ether (4.07 mL, 4.07 mmol) was added to a solution of the commercially available 2,4-dichloro-5-trifluoromethylpyrimidine (0.803 g, 3.70 mmol) in 1,2-dichloroethane (6.7 mL) and t-BuOH (6.7 mL). After 30 minutes diethyl(4-amino-3-methoxybenzyl)phosphonate (1.01 g, 3.70 mmol) was added followed by triethylamine (0.567 mL, 4.07 mmol) while keeping the temperature at ~25° C. The reaction mixture was allowed to stir at rt overnight before quenching with sat. aq. NaHCO$_3$ (10 mL). The resulting mixture was extracted with EtOAc (15 mL) and the organic layer was washed with brine (10 mL), dried over anhydrous NaSO$_4$, filtered, and concentrated under reduced pressure to afford a yellow oil. This crude material was initially purified using an Isco Combiflash system eluting with 0→5% MeOH in DCM as eluent followed by preparative HPLC (MDP) to afford diethyl(4-{[4-chloro-5-(trifluoromethyl)pyrimidin-2-yl]amino}-3-methoxybenzyl)phosphonate, 1.09 g (70% yield). $^1$H NMR (CD$_3$OD, 400 MHz): δ=1.28 (t, J=7.07 Hz, 6H), 3.23-3.29 (m, 2H), 3.90-3.95 (m, 3H), 4.01-4.13 (m, 4H), 6.90-6.96 (m, 1H), 7.03 (m, J=2.00 Hz, 1H), 8.02 (d, J=8.34 Hz, 1H), 8.62 (s, 1H).

Ethyl cis-4-(7-amino-2-methyl-1-oxo-2,3-dihydro-1H-isoindol-4-yl)cyclohexanecarboxylate (cis isomer)

Ethyl trans-4-(7-amino-2-methyl-1-oxo-2,3-dihydro-1H-isoindol-4-yl)cyclohexanecarboxylate (trans isomer)

A solution of ethyl 4-(2-methyl-7-nitro-1-oxo-2,3-dihydro-1H-isoindol-4-yl)cyclohex-3-ene-1-carboxylate (1.03 g, 2.99 mmol) in EtOH (2.6 mL, 45 mmol) was charged with palladium 10% wt on activated carbon (0.1:0.9, Palladium:Carbon, 0.11 g, 0.10 mmol). The reaction mixture was evacuated and purged with hydrogen gas (3×). The reaction mixture was allowed to stir under hydrogen gas at rt for 16 h. The reaction mixture was filtered through a pad of celite. The filtrate was collected and then concentrated in vacuo to oil. The two isomers were resolved by SFC purification to afford 544 mg (58% yield) of the cis and 232 mg (25% yield) of the trans title compounds. Cis: $^1$H NMR (400 MHz, Methanol-d) δ ppm 7.06 (d, J=8.34 Hz, 1H), 6.61 (d, J=8.34 Hz, 1H), 4.37 (s, 2H), 4.20 (q, J=7.07 Hz, 2H), 3.11 (s, 3H), 2.72 (d, J=2.53 Hz, 1H), 2.46-2.56 (m, 1H), 2.22-2.29 (m, 2H), 1.60-1.75 (m, 6H), 1.29 (t, 3H). MS (ES+): m/z 317.14/319.18 (100/15) [MH+]. HPLC: $t_R$=1.41 min (Micromass TOF: polar_3 min). Trans: $^1$H NMR (400 MHz, Methanol-d) δ ppm 7.15 (d, J=8.34 Hz, 1H), 6.62 (d, J=8.34 Hz, 1H), 4.38 (s, 2H), 4.13 (q, J=7.16 Hz, 2H), 3.11 (s, 3H), 2.34-2.54 (m, 2H), 2.04-2.11 (m, 2H), 1.82-1.92 (m, 2H), 1.48-1.64 (m, 4H), 1.26 (t, 3H). MS (ES+): m/z 317.15/319.16 (100/7) [MH+]. HPLC: $t_R$=1.38 min (UPLC TOF, polar_3 min).

Ethyl 4-(2-methyl-7-nitro-1-oxo-2,3-dihydro-1H-isoindol-4-yl)cyclohex-3-ene-1-carboxylate A mixture of 2-methyl-7-nitro-4-(4,4,5,5-tetramethyl-1,3,2-dioxaborolan-2-yl)-2,3-dihydro-1H-isoindol-1-one (1.50 g, 4.72 mmol), ethyl 4-{[(trifluoromethyl)sulfonyl]oxy}cyclohex-3-ene-1-carboxylate (1.57 g, 5.19 mmol), potassium carbonate (1.95 g, 14.1 mmol) and [1,1'-bis(diphenylphosphino)ferrocene]dichloropalladium(II), complex with dichloromethane (1:1) (0.385 g, 0.472 mmol) in 1,4-dioxane (12.0 mL, 154 mmol) and H$_2$O (3.00 mL, 166 mmol) was evacuated and refilled with Ar$_{(g)}$((3×) and irradiated in the microwave at 100° C. for 30 min. The crude mixture was concentrated in vacuo to a solid and purified by CombiFlash® Rf 4x Organic Purification System [120 g RediSep® Normal-phase GOLD Silica Flash Column, dried loaded, elution gradient: 0→40% EtOAc in DCM] to afford 1.03 g (63% yield) of the desired product. $^1$H NMR (400 MHz, Chloroform-d) δ ppm 7.71 (d, J=8.08 Hz, 1H), 7.45 (d, 1H), 5.93-5.99 (m, 1H), 4.20 (q, J=7.07 Hz, 2H), 2.65-2.75 (m, 1H), 2.49-2.56 (m, 2H), 2.36-2.49 (m, 2H), 2.16-2.24 (m, 1H), 1.87-2.00 (m, 1H), 1.54 (br. s., 3H), 1.31 (t, J=7.20 Hz, 3H). MS (ES+): m/z 346.15/347.15 (100/15) [MH+]. HPLC: $t_R$=1.43 min (UPLC TOF, polar_3 min).

2-Methyl-7-nitro-4-(4,4,5,5-tetramethyl-1,3,2-dioxaborolan-2-yl)-2,3-dihydro-1H-isoindol-1-one To a nitrogen degassed solution of dioxane (375 mL) was added Pd$_2$(dba)$_3$ (2.02 g, 2.21 mmol) and tricyclohexylphosphine (2.48 g, 8.85 mmol) and stirred for 30 minutes. To this mixture, 4-bromo-2-methyl-7-nitro-2,3-dihydro-isoindol-1-one, 20.0 g, 73.8 mmol), bis(pinacolato)diboron (24.4 g, 96 mmol) and KOAc (11.58 g, 118.1 mmol) were added and heated at reflux for 6 h. Cooled to RT and the precipitated solid was filtered off. The filtrate was evaporated to dryness and the residue was triturated with diisopropyl ether (100 mL) and filtered to give 2-methyl-7-nitro-4-(4,4,5,5-tetramethyl-[1,3,2]dioxaborolan-2-yl)-2,3-dihydro-isoindol-1-one as a yellow solid (16.0 g, 68%). $^1$H NMR (CDCl$_3$, 500 MHz) δ 1.34 (s, 12H), 3.24 (s, 3H), 4.58 (s, 2H), 7.68 (d, J=7.5 Hz, 1H), 8.06 (d, J=7.5 Hz, 1H).

4-Bromo-2-methyl-7-nitro-2,3-dihydro-1H-isoindol-1-one

To a cold suspension of 4-bromo-2-methyl-2,3-dihydroisoindol-1-one (60 g, 265 mmol) in concentrated sulfuric acid (60 mL) was added pre-cooled mixture of conc. nitric acid (12.5 mL, 265 mmol) and conc. sulfuric acid (60 mL) over 20 min. The reaction mixture was stirred for 30 min at 0° C. and 2 h at room temperature. The reaction mixture was poured over ice-water mixture (300 mL). The precipitate was filtered, washed with water (3×100 mL) and suspended in isopropanol (200 mL). The slurry was heated on steam bath and cooled. The solid was filtered and dried in air to give 53 g (74%) of the title compound. $^1$H NMR (CDCl$_3$, 300 MHz) δ 3.22 (s, 3H), 4.36 (s, 2H), 7.67 (d, J=8.4 Hz, 1H), 7.78 (d, J=8.4 Hz, 1H).

4-Bromo-2-methyl-2,3-dihydro-1H-isoindol-1-one

A solution of methylamine in ethanol (10 mL, 80 mmol, 8M solution in ethanol) was added to a solution of Methyl 3-Bromo-2-(bromomethyl)benzoate in THF (30 mL). After stirring for 2 h the reaction mixture was concentrated to dryness and water (30 mL) was added with rapid stirring. The solids produced were isolated by filtration and dried to give the desired product

Methyl 3-Bromo-2-(bromomethyl)benzoate

This material was prepared from the commercial 3-bromo-2-methyl benzoic acid by first making the methyl ester, then NBS bromination.

Ethyl 4-{[(trifluoromethyl)sulfonyl]oxy}cyclohex-3-ene-1-carboxylate 1.50 M of lithium diisopropylamide mono(tetrahydrofuran) in cyclohexane (2.15 mL, 3.23 mmol) was added to a solution of 4-(ethoxycarbonyl)cyclohexanone (0.500 g, 2.94 mmol) in THF (19.1 mL, 235 mmol) at −78° C. and left to stir for 1 hour, after which, trifluoromethanesulfonic anhydride (0.912 g, 3.23 mmol) added. The reaction mixture was allowed to stir while warming to rt. The reaction was quenched with water. The organic layer was diluted with EtOAc and washed with water (2×) and brine (1×), dried over sodium sulfate, filtered and then concentrated in vacuo. The crude mixture was purified by CombiFlash®Rf 4× Organic Purification System [12 g RediSep® Normal-phase Silica Flash Column, dried loaded, elution gradient: 0→15% EtOAc in Heptane] to afford 0.30 g (33% yield) of the desired product. The product was carried onto the next step without any further purification. MS (ES+): m/z 304.05/305.05 (100/65) [MH+]. HPLC: $t_R$=1.37 min (UPLC TOF, polar_3 min).

7-amino-4-(trans-4-hydroxycyclohexyl)-2-methyl-2,3-dihydro-1H-isoindol-1-one (trans isomer)

7-amino-4-(cis-4-hydroxycyclohexyl)-2-methyl-2,3-dihydro-1H-isoindol-1-one (cis isomer)

A solution of 7-amino-2-methyl-4-(4-oxocyclohexyl)-2,3-dihydro-1H-isoindol-1-one (1.35 g, 5.23 mmol) was dissolved in MeOH (30 mL), and cooled to 0° C., followed by addition of sodium borohydride (0.198 g, 5.23 mmol). The reaction mixture was stirred at 0° C. for 1 h. The reaction was quenched with sat. aq. NH$_4$Cl, diluted with EtOAc, washed with brine, and dried over anhydrous sodium sulfate. The compound was purified on an Isco Combiflash eluting with 0 to 4% MeOH in EtOAc to afford the trans isomer and the cis isomer. Trans-isomer: $^1$H NMR (400 MHz, DMSO-d$_6$) δ 7.05 (d, J=8.34 Hz, 1H), 6.51 (d, J=8.34 Hz, 1H), 5.83 (s, 2H), 4.53 (d, J=4.29 Hz, 1H), 4.33 (s, 2H), 3.38-3.48 (m, 1H), 2.98 (s, 3H), 2.28-2.38 (m, 1H), 1.90 (d, J=9.35 Hz, 2H), 1.68 (d, J=12.38 Hz, 2H), 1.38-1.51 (m, 2H), 1.19-1.32 (m, 2H); MS (ES$^+$): m/z: 262.1674 [MH$^+$]. HPLC: $t_R$=0.98 min (UPLC TOF MS: polar_3 min). Cis-isomer: $^1$H NMR (400 MHz, DMSO-d$_6$) δ 7.07 (d, J=8.34 Hz, 1H), 6.54 (d, J=8.34 Hz, 1H), 5.83 (s, 2H), 4.33 (s, 3H), 2.99 (s, 3H), 2.34-2.43 (m, 1H), 1.70-1.87 (m, 4H), 1.38-1.57 (m, 4H); MS (ES$^+$): m/z: 262.1693 [MH$^+$]. HPLC: $t_R$=1.04 min (UPLC TOF MS: polar_3 min).

7-amino-2-methyl-4-(4-oxocyclohexyl)-2,3-dihydro-1H-isoindol-1-one

To a solution of 7-amino-4-(1,4-dioxaspiro[4.5]dec-8-yl)-2-methyl-2,3-dihydro-1H-isoindol-1-one (1.64 g, 5.42 mmol) in THF (60 mL) was added aqueous 3.0 M HCl (1.81 mL), the resulting mixture was stirred at rt overnight. The mixture to 0° C., diluted with water and basified to pH ~10 with 1M NaOH. The aqueous mixture was extracted with EtOAc (3×) and the combined organic fractions were washed with brine, dried over sodium sulfate, filtered, and concentrated to afford the title compound. $^1$H NMR (400 MHz, DMSO-d$_6$) δ 7.11 (d, J=8.34 Hz, 1H), 6.53 (d, J=8.34 Hz, 1H), 5.88 (s, 2H), 4.41 (s, 2H), 3.00 (s, 3H), 2.56 (dt, J=6.06, 14.15 Hz, 2H), 2.21-2.30 (m, 2H), 1.96-2.04 (m, 2H), 1.78-1.91 (m, 2H); MS (ES$^+$): m/z: 260.1517 [MH$^+$]. HPLC: $t_R$=1.06 min (UPLC TOF MS: polar_3 min).

7-amino-4-(1,4-dioxaspiro[4.5]dec-8-yl)-2-methyl-2,3-dihydro-1H-isoindol-1-one To a solution of 7-amino-4-(1,4-dioxaspiro[4.5]dec-7-en-8-yl)-2-methyl-2,3-dihydro-1H-isoindol-1-one (1.7 g, 5.7 mmol) in EtOH (100 mL) was added palladium 10% wt on activated carbon (0.60 g, 0.57 mmol). The reaction mixture was evacuated and purged with hydrogen (3×) and stirred over night at rt. The reaction mixture was filtered through a pad of celite and concentrated in vacuo to afford the title compound. $^1$H NMR (400 MHz, DMSO-d$_6$) δ 7.04 (d, J=8.34 Hz, 1H), 6.52 (d, J=8.08 Hz, 1H), 5.85 (s, 2H), 4.34 (s, 2H), 3.86-3.89 (m, 4H), 2.98 (s, 3H), 2.42-2.48 (m, 1H), 1.52-1.80 (m, 8H); MS (ES$^+$): m/z: 303.1516 [MH$^+$]. HPLC: $t_R$=1.21 min (UPLC TOF MS: polar_3 min).

7-amino-4-(1,4-dioxaspiro[4.5]dec-7-en-8-yl)-2-methyl-2,3-dihydro-1H-isoindol-1-one A mixture of 7-amino-4-bromo-2-methyl-2,3-dihydro-1H-isoindol-1-one (1.7 g, 7.0 mmol), 1,4-dioxa-spiro[4,5]dec-7-en-8-boronic acid pinacol ester (2.2 g, 8.5 mmol) (preparation: WO 2007/141517), potassium carbonate (2.9 g, 21 mmol) and [1,1'-bis(diphenylphosphino)ferrocene]dichloropalladium(II), complex with dichloromethane (1:1) (0.57 g, 0.69 mmol) in 1,4-dioxane (40 mL) and H$_2$O (10 mL) was evacuated and refilled with nitrogen (3×) and irradiated in the microwave at 100° C. for 30 min. The reaction mixture was partitioned between EtOAc and brine and separated. The aqueous layer was extracted with EtOAc (3×) and the combined organic fractions were dried over sodium sulfate, filtered, and concentrated. The compound was purified on an Isco Combiflash eluting with 30 to 100% EtOAc in heptane to afford the title compound. $^1$H NMR (400 MHz, DMSO-d$_6$) δ 7.14 (d, J=8.34 Hz, 1H), 6.55 (d, J=8.59 Hz, 1H), 6.08 (s, 2H), 5.60-5.66 (m, 1H), 4.39 (s, 2H), 3.91 (s, 4H), 2.98 (s, 3H), 2.50 (td, J=1.86, 3.60 Hz, 1H), 2.42-2.48 (m, 2H), 2.31-2.37 (m, 2H), 1.77 (t, J=6.44 Hz, 2H); MS (ES$^+$): m/z: 302.1621 [MH$^+$]. HPLC: $t_R$=1.21 min (UPLC TOF MS: polar_3 min).

Diethyl(4-{[4-chloro-5-(trifluoromethyl)pyrimidin-2-yl]amino}benzyl)phosphonate Prepared in a manner analogous to that for diethyl(4-{[4-chloro-5-(trifluoromethyl)pyrimidin-2-yl]amino}-3-methoxybenzyl)phosphonate using commercially available diethyl(4-aminobenzyl)phosphonate in place of diethyl(4-amino-3-methoxybenzyl)phosphonate. Following chromatography, the semi-pure product was crystallized from ethyl acetate to afford the title compound. 1H NMR (400 MHz, METHANOL-d4) d ppm 1.22-1.32 (m, 6H), 3.17-3.28 (m, 2H), 3.98-4.10 (m, 4H), 7.30 (dd, J=8.72, 2.65 Hz, 2H), 7.65 (d, J=7.83 Hz, 2H), 8.63 (s, 1H).

7-Amino-2-methyl-4-[cis-4-(4-methylpiperazin-1-yl)cyclohexyl]-2,3-dihydro-1H-isoindol-1-one (cis isomer)

7-amino-2-methyl-4-[trans-4-(4-methylpiperazin-1-yl)cyclohexyl]-2,3-dihydro-1H-isoindol-1-one (trans isomer)

A solution of 7-amino-2-methyl-4-(4-oxocyclohexyl)-2,3-dihydro-1H-isoindol-1-one (100.0 mg, 0.3871 mmol) in 1,2-dichloroethane (2.0 mL) was charged with 1-methylpiperazine (58.16 mg, 0.5807 mmol) and sodium triacetoxyborohydride (164.1 mg, 0.7743 mmol). The reaction mixture was stirred at rt for 24 hours. The reaction mixture was quenched with NaHCO$_3$ (10 mL) and extracted with EtOAc (20 mL). The organic layer was washed with brine (10 mL), dried over Na$_2$SO$_4$, filtered and concentrated under reduced pressure to yield a light yellow oil. The crude material was purified and by silica gel chromatography on the combi-flash Rf system using DCM/7M NH$_3$ in MeOH (100:0→90:10) as eluent to afford the cis isomer (76.5 mg, 58%, first eluting product) and the trans isomer (30.0 mg, 23%, second eluting product). Cis isomer: $^1$H NMR (CDCl$_3$, 400 MHz): δ=1.42-1.56 (m, 4H), 1.82-1.96 (m, 2H), 2.06 (d, J=11.87 Hz, 2H), 2.27 (br. s., 1H), 2.34 (s, 3H), 2.38-2.78 (m, 9H), 3.14 (s, 3H), 4.31 (s, 2H), 5.08 (s, 2H), 6.58 (d, J=8.34 Hz, 1H), 7.18 (d, J=8.34 Hz, 1H). MS (ES$^+$): m/z 343.25 [MH$^+$]. Trans isomer: $^1$H NMR (CDCl$_3$, 400 MHz): δ=1.35-1.75 (m, 7H), 1.91 (d, J=12.13 Hz, 2H), 2.03-2.13 (m, 2H), 2.34 (s, 3H), 2.47-2.82 (m, 7H), 3.14 (s, 3H), 4.28 (s, 2H), 5.09 (s, 2H), 6.56 (d, J=8.34 Hz, 1H), 7.09 (d, J=8.34 Hz, 1H). MS (ES$^+$): m/z 343.26 [MH$^+$].

4-Chloro-N-(2-methoxyphenyl)-5-(trifluoromethyl)pyrimidin-2-amine

This material was prepared in a manner analogous to diethyl(4-{[4-chloro-5-(trifluoromethyl)pyrimidin-2-yl]amino}-3-methoxybenzyl)phosphonate using commercially available starting materials (2,4-dichloro-5-(trifluoromethyl)pyrimidine and 2-Methoxyaniline). The crude product from this reaction was recrystallized using MeCN to afford a white solid, 610 mg, 46% yield. $^1$H NMR (CDCl$_3$): 3.93 (s, 3H), 6.94 (dd, J=8.1 Hz, 1.5 Hz, 1H), 7.03 (td, J=7.8 Hz, 1.5 Hz, 1H), 7.10 (td, J=7.6 Hz, 1.8 Hz, 1H), 8.14 (br s, 1H), 8.41 (dd, J=8.1 Hz, 1.8 Hz, 1H), 8.56 (s, 1H). MS (ES+): m/z=304.00 [MH$^+$]. HPLC: t$_R$=3.89 min (ZQ3, polar_5 min).

EXAMPLES

Example 1

Diethyl[4-({4-[({2-[methyl(methylsulfonyl)amino]pyridin-3-yl}methyl)amino]-5-(trifluoromethyl)pyrimidin-2-yl}amino)benzyl]phosphonate

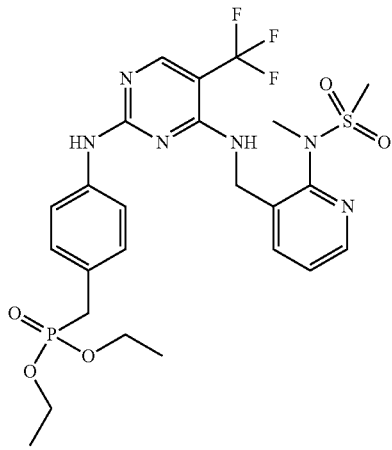 [SMILES: CCOP(=O)(Cc1ccc(Nc2ncc(C(F)(F)F)c(NCc3cccnc3N(C)S(C)(=O)=O)n2)cc1)OCC]

N-[3-({[(2-Chloro-5-(trifluoromethyl)pyrimidin-4-yl]amino}methyl)pyridin-2-yl]-N-methylmethanesulfonamide (XLIa). N-[3-(aminomethyl)pyridin-2-yl]-N-methylmethanesulfonamide (5 g, 23.25 mmol) was added dropwise to a solution of 2,4-dichloro-5-trifluoromethylpyrimidine (XL, 6.5 g, 30 mmol) in MeOH (80 mL) at 0° C. After 30 min DIPEA (8.25 mL, 47.5 mmol) was added through a syringe and stirring continued for 1 h at 0° C. The precipitated solids (3 g) were collected by filtration and shown by TLC to be the pure non-polar component of the initial mixture (XLIa). The filtrate was evaporated and the residue chromatographed over silica gel eluting with 5% EtOAc in DCM to yield another batch of pure non-polar isomer (0.3 g), a mixture of the two isomers (1.7 g), and pure polar isomer (XLIb, 1.3 g). XLIa: $^1$H NMR (DMSO-d$_6$) δ: 8.54 (t, J=5.7 Hz, 1H), 8.46 (dd, J=5.2, 1.6 Hz, 1H), 8.45 (s, 1H), 7.77 (dd, J=7.8, 1.6 Hz, 1H), 7.44 (dd, J=7.7, 4.8 Hz, 1H), 4.74 (d, J=5.2 Hz, 2H), 3.28 (s, 3H), 3.12 (s, 3H). Unassigned peaks: δ: 1.29 (m).

HMBC experiments indicate a 3-bond H—C correlation between the C$^4$—N-proton at 8.54 ppm and the C$^5$-carbon, which is only observable for the regioisomer as shown above.

A solution of a 1:1 mixture of N-[3-({[(2-chloro-5-(trifluoromethyl)pyrimidin-4-yl]amino}methyl)pyridin-2-yl]-N-methylmethanesulfonamide (XLIa) and N-[3-({[(4-chloro-5-(trifluoromethyl)pyrimidin-2-yl]amino}methyl)pyridin-2-yl]-N-methylmethanesulfonamide (XLIb) (30 mg, 0.08 mmol) and commercially available diethyl(4-aminobenzyl)phosphonate (22.1 mg, 0.091 mmol) in a mixture of trifluoroacetic acid (6.8 μL, 0.1 mmol) and trifluoroethanol (0.5 mL) under N$_2$, was stirred at 105° C. for 75 min in a Biotage microwave reactor. The solvents were removed in vacuo and the resulting mixture separated using preparative HPLC (MDP) to afford 14.2 mg of diethyl[4-({4-[({2-[methyl(methylsulfonyl)amino]pyridin-3-yl}methyl)amino]-5-(trifluoromethyl)pyrimidin-2-yl}amino)benzyl]phosphonate (Ex. 1) (yield: 31%) and 9.5 mg of the regioisomer XLIIb (yield: 21%). $^1$H-NMR (DMSO-d$_6$, 400 MHz): δ=1.14 (t, J=7.2 Hz, 6H), 3.08 (d, J=21.2 Hz, 2H), 3.16 (s, 3H), 3.17 (s, 3H), 3.88-3.94 (m, 4H), 4.81 (s, d, J=6.0 Hz, 2H), 7.01 (d, J=6.8 Hz, 2H), 7.36-7.38 (m, 2H), 7.41 (dd, J=4.8, 7.6 Hz, 1H), 7.66 (d, J=6.4 Hz, 2H), 8.26 (d, J=0.8 Hz, 1H), 8.43 (dd, J=1.6, 4.4 Hz, 1H), 9.60 (s, br, 1H). MS (ES$^+$): m/z 603.43 (MH$^+$). HPLC: t$_R$=3.18 min (ZQ3, polar_5 min). XLIIb: $^1$H-NMR (DMSO-d$_6$, 400 MHz): δ=1.14 (t, J=6.8 Hz, 6H), 2.96 (s, 3H), 3.17 (d, J=8.4 Hz, 3H), 3.89-3.98 (m, 4H), 4.46 (d, J=5.2 Hz, 3H), 4.59 (s, 2H), 7.06 (d, J=6.8 Hz, 1H), 7.21 (d, J=8.0 Hz, 2H), 7.38 (m, 1H), 7.56 (m, 1H), 8.21 (m, 1H), 8.32 (s, 1H), 8.42 (m, 1H), 8.82 (s, 1H). MS (ES$^+$): m/z 603.03 (MH$^+$). HPLC: t$_R$=3.06 min (ZQ3, polar_5 min).

Example 2

Diethyl[4-({4-[({2-methyl(methylsulfonyl)amino]pyridin-3-yl}methyl)amino]-5-(trifluoromethyl)pyrimidin-2-yl}amino)phenyl]phosphonate

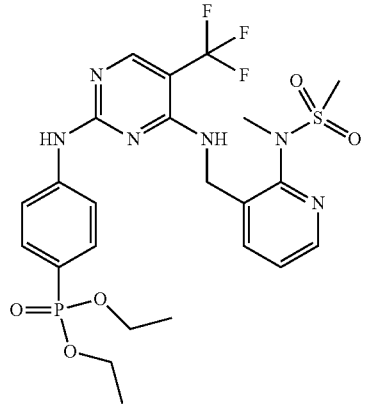 [SMILES: CCOP(=O)(OCC)c1ccc(Nc2ncc(C(F)(F)F)c(NCc3cccnc3N(C)S(C)(=O)=O)n2)cc1]

Prepared according to the procedure and purification technique described for Example 1, utilizing diethyl(4-aminophenyl)phosphonate (yield 2.5%). ¹H-NMR (CD₃OD, 400 MHz, 400 MHz): δ=1.31 (dt, J=0.8, 7.2 Hz, 6H), 3.31 (s, 3H), 3.32 (s, 3H), 4.07 (m, 4H), 4.96 (s, 2H), 7.36 (dd, J=4.4, 7.6 Hz, 1H), 7.53-7.58 (m, 2H), 7.65-7.68 (m, 2H), 7.78 (dd, J=2.0, 8.0 Hz, 1H), 8.24 (d, J=0.4 Hz, 1H), 8.43 (dd, J=2.0, 4.8 Hz, 1H), 8.56 (s, 2H). MS (ES⁺): m/z 589.06 (MH⁺). HPLC: $t_R$=3.22 min (ZQ3, polar_5 min). Undesired polar isomer (yield: 13.5%): ¹H-NMR (CD₃OD, 400 MHz): δ=1.32 (dt, J=0.4, 7.2 Hz, 6H), 3.06 (s, br, 6H), 4.11 (m, 4H), 4.71 (s, 2H), 7.33 (dd, J=4.8, 7.2 Hz, 1H), 7.49-7.58 (m, 3H), 7.71 (m, 1H), 7.84 (m, 1H), 8.24 (s, 1H), 8.41 (d, J=3.2 Hz, 1H), 8.55 (s, 1H). MS (ES⁺): m/z 589.06 (MH⁺). HPLC: $t_R$=3.12 min (ZQ3, polar_5 min).

Example 3

Diethyl[2-({4-[({2-[methyl(methylsulfonyl)amino]pyridin-3-yl}methyl)amino]-5-(trifluoromethyl)pyrimidin-2-yl}amino)benzyl]phosphonate

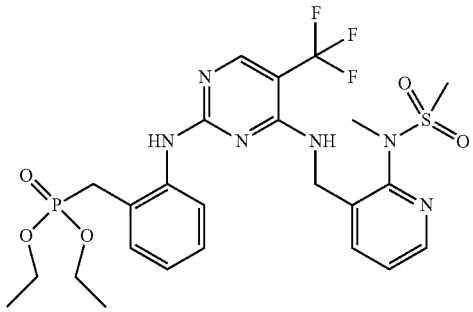 [SMILES: CCOP(=O)(Cc1ccccc1Nc1ncc(C(F)(F)F)c(NCc2cccnc2N(C)S(C)(=O)=O)n1)OCC]

Prepared according to the procedure and purification technique described for Example 1, utilizing diethyl(2-aminobenzyl)phosphonate (yield: 18%). ¹H-NMR (CD₃OD, 400 MHz, 400 MHz): δ=1.20 (t, J=7.2 Hz, 6H), 3.04 (s, 3H), 3.07 (s, 3H), 3.25 (d, J=21.6 Hz, 2H), 3.94-4.04 (m, 4H), 4.75 (s, 2H), 7.09-7.15 (m, 2H), 7.29-7.34 (m, 3H), 7.63 (d, J=6.0 Hz, 1H), 8.12 (s, 1H), 8.41 (dd, J=2.0, 4.8 Hz, 1H). MS (ES⁺): m/z 602.95 (MH⁺). HPLC: $t_R$=3.28 min (ZQ3, polar_5 min). Undesired polar isomer (yield: 14%): ¹H-NMR (CD₃OD, 400 MHz): δ=1.23 (t, J=7.2 Hz, 6H), 2.93 (s, 3H), 3.06 (s, 3H), 3.24 (d, J=21.2 Hz, 2H), 3.99-4.05 (m, 4H), 4.50 (s, 2H), 7.17 (d, J=6.8 Hz, 1H), 7.23-7.31 (m, 3H), 7.38 (d, J=7.2 Hz, 1H), 7.43 (d, J=7.2 Hz, 1H), 8.27 (s, 1H), 8.40 (dd, J=1.2, 4.4 Hz, 1H). MS (ES⁺): m/z 602.95 (MH⁺). HPLC: $t_R$=3.16 min (ZQ3, polar_5 min).

Example 4

Diethyl[3-({4-[({2-[methyl(methylsulfonyl)amino]pyridin-3-yl}methyl)amino]-5-(trifluoromethyl)pyrimidin-2-yl}amino)benzyl]phosphonate

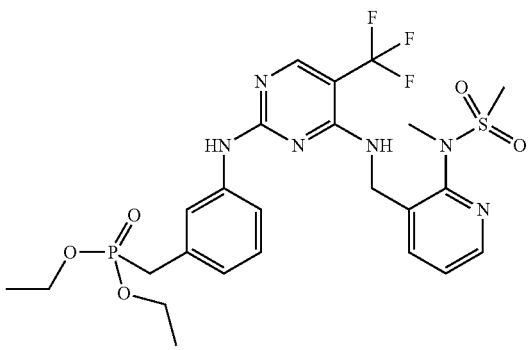 [SMILES: CCOP(=O)(Cc1cccc(Nc2ncc(C(F)(F)F)c(NCc3cccnc3N(C)S(C)(=O)=O)n2)c1)OCC]

Prepared according to the procedure and purification technique described for Example 1, utilizing diethyl(3-aminobenzyl)phosphonate (yield: 24%). ¹H-NMR (CD₃OD, 400 MHz, 400 MHz): δ=1.23 (t, J=7.2 Hz, 6H), 3.08 (s, 1.5H), 3.11 (s, 3H), 3.14 (s, 1.5H), 3.20 (s, 2H), 3.95-4.03 (m, 4H), 4.91 (s, 2H), 6.92 (d, J=7.6 Hz, 1H), 7.11 (t, J=7.6 Hz, 1H), 7.33-7.38 (m, 2H), 7.48 (s, 1H), 7.79 (dd, J=2.0, 8.4 Hz, 1H), 8.17 (s, 1H), 8.41 (dd, J=2.0, 4.8 Hz, 1H). MS (ES⁺): m/z 602.98 (MH⁺). HPLC: $t_R$=3.21 min (ZQ3, polar_5 min). Undesired polar isomer (yield: 19%): ¹H-NMR (CD₃OD, 400 MHz): δ=1.23 (t, J=7.2 Hz, 6H), 3.05 (s, 3H), 3.07 (s, 3H), 3.11 (d, J=21.2 Hz, 2H), 3.99-4.02 (m, 4H), 4.61 (s, 2H), 7.07 (m, 1H), 7.13-7.17 (m, 2H), 7.27-7.32 (m, 2H), 7.62 (m, 1H), 8.16 (s, 1H), 8.39 (dd, J=2.0, 4.8 Hz, 1H). MS (ES⁺): m/z 602.73 (MH⁺). HPLC: $t_R$=3.07 min (ZQ3, polar_5 min).

Example 5

Diethyl{1-[4-({4-[({2-[methyl(methylsulfonyl)amino]pyridin-3-yl}methyl)amino]-5-(trifluoromethyl)pyrimidin-2-yl}amino)phenyl]ethyl}phosphonate

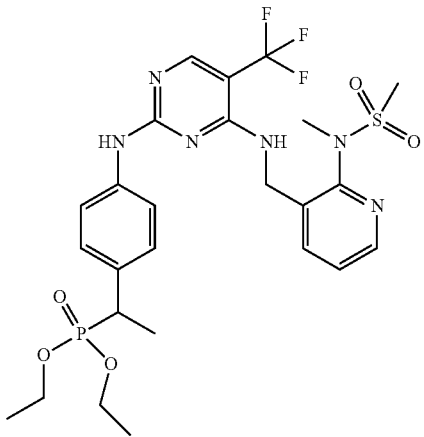 [SMILES: CCOP(=O)(OCC)C(C)c1ccc(Nc2ncc(C(F)(F)F)c(NCc3cccnc3N(C)S(C)(=O)=O)n2)cc1]

Prepared according to the procedure and purification technique described for Example 1, utilizing diethyl[1-(4-aminophenyl)ethyl]phosphonate (yield: 5%). ¹H-NMR (CD₃OD, 400 MHz, 400 MHz): δ=1.14 (t, J=7.2 Hz, 3H), 1.27 (t, J=7.2 Hz, 3H), 1.49 (d, J=7.2 Hz, 1.5H), 1.54 (d, J=7.2 Hz, 1.5H), 3.10 (s, 3H), 3.17 (s, 3H), 3.25 (q, J=7.2 Hz, 1H), 3.82-3.96 (m, 2H), 4.00-4.07 (m, 2H), 4.96 (s, 2H), 7.29 (dd, J=1.6, 8.4 Hz, 2H), 7.35-7.40 (m, 3H), 7.72 (d, J=7.2 Hz, 1H), 8.24 (s, 1H), 8.45 (dd, J=2.0, 4.8 Hz, 1H). MS (ES⁺): m/z 616.97 (MH⁺). HPLC: $t_R$=3.27 min (ZQ3, polar_5 min). Undesired polar isomer (yield: 5%): ¹H-NMR (CD₃OD, 400 MHz): δ=1.12 (t, J=7.2 Hz, 3H), 1.25 (t, J=7.2 Hz, 3H), 1.52 (d, J=7.6 Hz, 1.5H), 1.57 (d, J=7.6 Hz, 1.5H), 3.06 (s, 3H), 3.07 (s, 3H), 3.38 (q, J=7.2 Hz, 1H), 3.84-3.93 (m, 2H), 4.01-4.05 (m, 2H), 4.61 (s, 2H), 7.29 (dd, J=3.6, 7.2 Hz, 1H), 7.36-7.41 (m, 4H), 7.45 (d, J=6.0 Hz, 1H), 8.30 (s, 1H), 8.43 (dd, J=1.6, 4.4 Hz, 1H). MS (ES⁺): m/z 616.97 (MH⁺). HPLC: $t_R$=3.16 min (ZQ3, polar_5 min).

Example 6

[4-({4-[({2-[Methyl(methylsulfonyl)amino]pyridin-3-yl}methyl)amino]-5-(trifluoromethyl)pyrimidin-2-yl}amino)phenyl]phosphonic acid

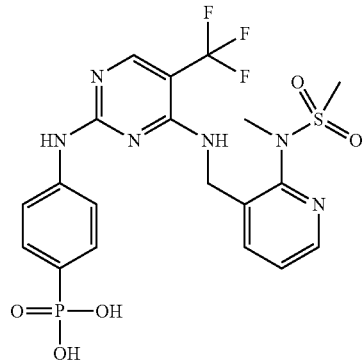 [SMILES: CN(c1ncccc1CNc1nc(Nc2ccc(P(=O)(O)O)cc2)ncc1C(F)(F)F)S(C)(=O)=O]

Prepared according to the procedure and purification technique described for Example 1, utilizing P-(4-aminophenyl)-N,N'-dipropylphosphonic diamide. The phosphonic diamide moiety hydrolyzed during the reaction to afford the corresponding phosphonic acid (yield: 2.7%). $^1$H-NMR (CD$_3$OD, 400 MHz): δ=3.11 (s, 3H), 3.18 (s, 3H), 4.91 (s, 2H), 7.16-7.35 (m, 3H), 7.51 (m, 1H), 7.62 (m, 1H), 7.73 (m, 1H), 8.23 (s, 1H), 8.40 (m, 1H). MS (ES$^+$): m/z 532.84 (MH$^+$). HPLC: t$_R$=2.75 min (ZQ3, polar_5 min). Undesired polar isomer (yield: 3.2%): $^1$H-NMR (CD$_3$OD, 400 MHz): δ=3.03 (s, 3H), 3.08 (s, 3H), 4.61 (s, 2H), 7.23-7.35 (m, 3H), 7.53-7.67 (m, 3H), 8.18-8.23 (m, 1H), 8.35-8.40 (m, 1H). MS (ES$^+$): m/z 532.43 (MH$^+$). HPLC: t$_R$=2.42 min (ZQ3, polar_5 min).

Also prepared by heating diethyl[4-({4-[({2-[methyl(methylsulfonyl)amino]pyridin-3-yl}methyl)amino]-5-(trifluoromethyl)pyrimidin-2-yl}amino)phenyl]phosphonate (Example 2) at 100° C. with an excess of concentrated hydrochloric acid for 6 h. The reaction mixture was concentrated in vacuo and the residue purified by preparative HPLC (MDP) afford the title compound.

Example 7

Diethyl{2-[4-({4-[({2-[Diethyl(methylsulfonyl)amino]pyridin-3-yl}methyl)amino]-5-(trifluoromethyl)pyrimidin-2-yl}amino)phenyl]propan-2-yl}phosphonate

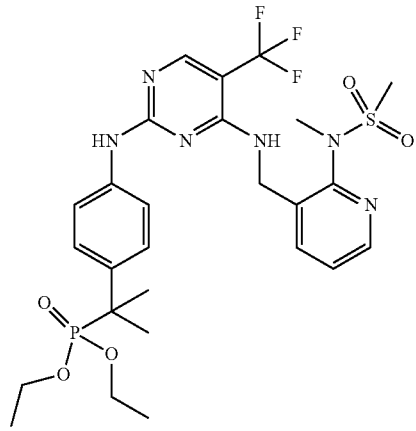 [SMILES: CCOP(=O)(OCC)C(C)(C)c1ccc(Nc2ncc(C(F)(F)F)c(NCc3cccnc3N(C)S(C)(=O)=O)n2)cc1]

A solution of N-[3-({[(2-chloro-5-(trifluoromethyl)pyrimidin-4-yl]amino}methyl)pyridin-2-yl]-N-methylmethanesulfonamide (XLIa 30 mg, 0.08 mmol) and diethyl[2-(4-aminophenyl)propan-2-yl]phosphonate (XXXV, 24.7 mg, 0.091 mmol) in a mixture of trifluoroacetic acid (17.5 μL, 0.227 mmol) and trifluoroethanol (0.5 mL) was stirred under N$_2$ at 105° C. for 75 min in a Biotage microwave reactor. The mixture was concentrated in vacuo and the residue purified by preparative HPLC (MDP) to afford 4.6 mg of Example 7 (yield: 10%). $^1$H-NMR (CD$_3$OD, 400 MHz): δ=1.18 (t, J=7.2 Hz, 6H), 1.56 (s, 3H), 1.60 (s, 3H), 3.11 (s, 3H), 3.18 (s, 3H), 3.85-3.94 (m, 4H), 4.97 (s, 2H), 7.36 (dd, J=4.8, 8.0 Hz, 1H), 7.40-7.46 (m, 4H), 7.73 (d, J=6.8 Hz, 1H), 8.22 (s, 1H), 8.45 (dd, J=1.6, 4.4 Hz, 1H). MS (ES$^+$): m/z 631.02 (MH$^+$). HPLC: t$_R$=3.40 min (ZQ3, polar_5 min).

Example 8

N-[3-({[2-({4-[(Dipropan-2-ylphosphoryl)methyl]phenyl}amino)-5-(trifluoromethyl)pyrimidin-4-yl]amino}methyl)pyridin-2-yl]-N-methylmethanesulfonamide

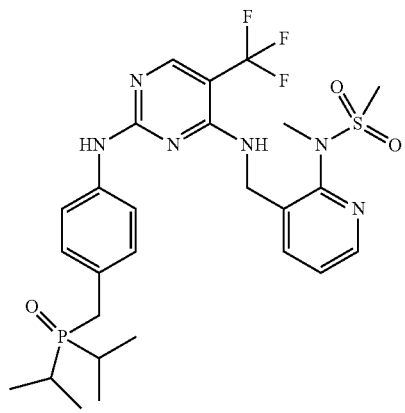 [SMILES: CC(C)P(=O)(Cc1ccc(Nc2ncc(C(F)(F)F)c(NCc3cccnc3N(C)S(C)(=O)=O)n2)cc1)C(C)C]

A solution of N-[3-({[(2-chloro-5-(trifluoromethyl)pyrimidin-4-yl]amino}methyl)pyridin-2-yl]-N-methylmethanesulfonamide (XLIa 30 mg, 0.08 mmol) and 4-[(dipropan-2-ylphosphoryl)methyl]aniline (21.8 mg, 0.091 mmol) in a mixture of trifluoroacetic acid (17.5 μL, 0.227 mmol) and trifluoroethanol (0.5 mL) was stirred under N$_2$ at 105° C. for 45 min in a Biotage microwave reactor. The mixture was concentrated in vacuo and the residue portioned between DCM (5 mL) and a saturated aqueous sodium bicarbonate solution (2 mL). The organic phase was removed and the aqueous phase extracted with DCM (3×5 mL). The combined organic phases were dried over magnesium sulfate and concentrated in vacuo to afford crude product which was purified by chromatography over silica gel eluting with 5% 7N ammonia in methanol in DCM to yield 38.6 mg of Example 8 (yield: 80%). $^1$H-NMR (CDCl$_3$, 400 MHz): δ=1.11-1.19 (m, 12H), 1.96-2.06 (m, 2H), 3.07 (d, J=12.4 Hz, 2H), 3.07 (s, 3H), 3.29 (s, 3H), 4.94 (d, J=5.2 Hz, 2H), 6.10 (s, br, 1H), 7.24-7.29 (m, 3H), 7.51 (d, J=8.4 Hz, 2H), 7.61 (s, br, 1H), 7.81 (dd, J=2.0, 8.0 Hz, 1H), 8.18 (s, 1H), 8.41 (dd, J=1.6, 4.8 Hz, 1H). MS (ES+): m/z 598.98 (MH+). HPLC: t_R=3.10 min (ZQ3, polar_5 min).

Example 9

N-[3-({[2-({3-[(Dipropan-2-ylphosphoryl)methyl]phenyl}amino)-5-(trifluoromethyl)pyrimidin-4-yl]amino}methyl)pyridin-2-yl]-N-methylmethanesulfonamide

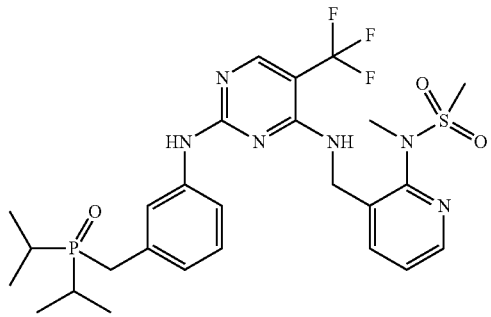 [SMILES: CC(C)P(=O)(Cc1cccc(Nc2ncc(C(F)(F)F)c(NCc3cccnc3N(C)S(C)(=O)=O)n2)c1)C(C)C]

Prepared according to the procedure and purification technique described for Example 8, utilizing 3-[(dipropan-2-ylphosphoryl)methyl]aniline (yield: 89%). $^1$H-NMR (CDCl$_3$, 400 MHz): δ=1.12-1.18 (m, 12H), 1.99-2.05 (m, 2H), 3.07 (d, J=12.4 Hz, 2H), 3.07 (s, 3H), 3.28 (s, 3H), 4.95 (d, J=4.8 Hz, 2H), 6.06 (s, br, 1H), 7.00 (d, J=7.2 Hz, 1H), 7.21 (t, J=8.0 Hz, 1H), 7.27 (dd, J=4.8, 7.6 Hz, 1H), 7.41 (s, br, 1H), 7.48 (s, 1H), 7.57 (d, J=8.0 Hz, 1H), 7.85 (dd, J=1.6, 7.6 Hz, 1H), 8.19 (s, 1H), 8.41 (dd, J=1.6, 8.8 Hz, 1H). MS (ES+): m/z 598.89 (MH+). HPLC: t_R=3.14 min (ZQ3, polar_5 min).

Example 10

N-[3-({[2-({4-[(Diethylphosphoryl)methyl]phenyl}amino)-5-(trifluoromethyl)pyrimidin-4-yl]amino}methyl)pyridin-2-yl]-N-methylmethanesulfonamide

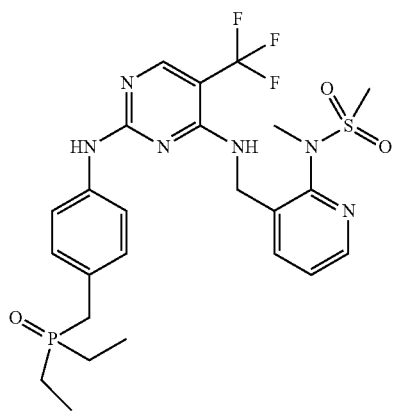 [SMILES: CCP(=O)(CC)Cc1ccc(Nc2ncc(C(F)(F)F)c(NCc3cccnc3N(C)S(C)(=O)=O)n2)cc1]

Prepared according to the procedure and purification technique described for Example 8, utilizing 4-[(diethylphosphoryl)methyl]aniline (yield: 70%). $^1$H-NMR (CDCl$_3$, 400 MHz): δ=1.12-1.20 (m, 6H), 1.61-1.70 (m, 4H), 3.08 (d, J=14.0 Hz, 2H), 3.08 (s, 3H), 3.29 (s, 3H), 4.95 (d, J=5.6 Hz, 2H), 6.08 (s, br, 1H), 7.19 (dd, J=1.6, 8.4 Hz, 2H), 7.27 (dd, J=4.8, 8.0 Hz, 1H), 7.46 (s, br, 1H), 7.52 (d, J=8.4 Hz, 2H), 7.80 (dd, J=1.2, 7.6 Hz, 1H), 8.19 (s, 1H), 8.42 (dd, J=2.0, 4.8 Hz, 1H). MS (ES+): m/z 570.98 (MH+). HPLC: t_R=2.91 min (ZQ3, polar_5 min).

Example 11

N-[3-({[2-({3-[(Diethylphosphoryl)methyl]phenyl}amino)-5-(trifluoromethyl)pyrimidin-4-yl]amino}methyl)pyridin-2-yl]-N-methylmethanesulfonamide

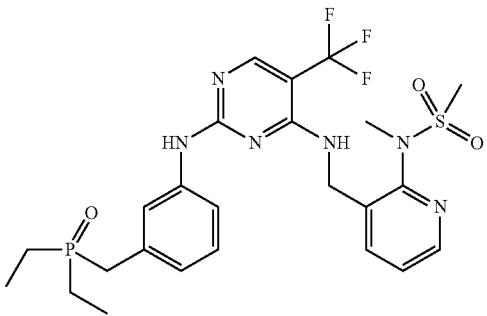 [SMILES: CCP(=O)(CC)Cc1cccc(Nc2ncc(C(F)(F)F)c(NCc3cccnc3N(C)S(C)(=O)=O)n2)c1]

Prepared according to the procedure and purification technique described for Example 8, utilizing 3-[(diethylphosphoryl)methyl]aniline (yield: 90%). $^1$H-NMR (CDCl$_3$, 400 MHz): δ=1.11-1.19 (m, 6H), 1.63-1.71 (m, 4H), 3.10 (d, J=14.0 Hz, 2H), 3.08 (s, 3H), 3.28 (s, 3H), 4.94 (d, J=5.2 Hz, 2H), 6.06 (br, t, J=2.4 Hz, 1H), 6.92 (d, J=7.2 Hz, 1H), 7.22 (t, J=8.0 Hz, 1H), 7.28 (dd, J=4.8, 8.0 Hz, 1H), 7.43 (s, br, 1H), 7.48 (s, 1H), 7.53 (d, J=8.4 Hz, 1H), 7.83 (dd, J=1.6, 7.6 Hz, 1H), 8.19 (s, 1H), 8.42 (dd, J=2.0, 8.8 Hz, 1H). MS (ES+): m/z 570.86 (MH+). HPLC: t_R=2.94 min (ZQ3, polar_5 min).

Example 12

N-[3-({[2-({4-[(Dimethylphosphoryl)methyl]phenyl}amino)-5-(trifluoromethyl)pyrimidin-4-yl]amino}methyl)pyridin-2-yl]-N-methylmethanesulfonamide

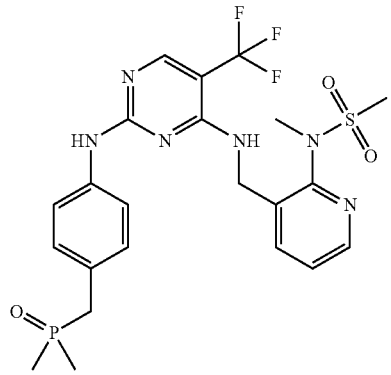 [SMILES: CN(c1ncccc1CNc1nc(Nc2ccc(CP(C)(C)=O)cc2)ncc1C(F)(F)F)S(C)(=O)=O]

Prepared according to the procedure and purification technique described for Example 8, utilizing 4-[(dimethylphosphoryl)methyl]aniline (yield: 81%). $^1$H-NMR (CDCl$_3$, 400 MHz): δ=1.43 (d, J=12.8 Hz, 6H), 3.08 (s, 3H), 3.12 (d, J=14.8 Hz, 2H), 3.28 (s, 3H), 4.95 (d, J=5.2 Hz, 2H), 6.06 (s, br, 1H), 7.16 (d, J=8.4 Hz, 2H), 7.27 (dd, J=4.8, 7.6 Hz, 1H), 7.51 (s, br, 1H), 7.52 (d, J=7.6 Hz, 2H), 7.80 (d, J=8.0 Hz, 1H), 8.19 (s, 1H), 8.42 (dd, J=2.0, 4.8 Hz, 1H). MS (ES$^+$): m/z 543.01 (MH$^+$). HPLC: t$_R$=2.74 min (ZQ3, polar_5 min).

Example 13

N-[3-({[2-({3-[(Dimethylphosphoryl)methyl]phenyl}amino)-5-(trifluoromethyl)pyrimidin-4-yl]amino}methyl)pyridin-2-yl]-N-methylmethanesulfonamide

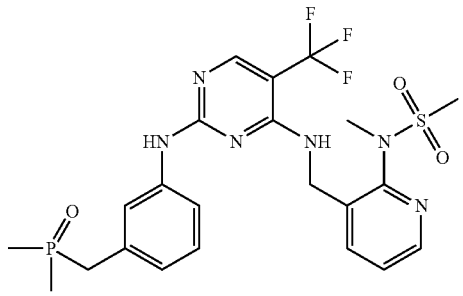

Prepared according to the procedure and purification technique described for Example 8, utilizing 3-[(dimethylphosphoryl)methyl]aniline (yield: 78%). $^1$H-NMR (CDCl$_3$, 400 MHz): δ=1.45 (d, J=12.8 Hz, 6H), 3.08 (s, 3H), 3.12 (d, J=15.2 Hz, 2H), 3.28 (s, 3H), 4.94 (d, J=5.6 Hz, 2H), 6.03 (s, br, 1H), 6.91 (d, J=7.2 Hz, 1H), 7.22-7.29 (m, 2H), 7.45 (d, J=6.0 Hz, 1H), 7.52 (d, J=8.0 Hz, 1H), 7.83 (d, J=7.6 Hz, 1H), 8.19 (s, 1H), 8.42 (d, J=4.4 Hz, 1H). MS (ES$^+$): m/z 543.01 (MH$^+$). HPLC: t$_R$=2.77 min (ZQ3, polar_5 min).

Example 14

N-[3-({[2-{[4-(Dimethylphosphoryl)phenyl]amino}-5-(trifluoromethyl)pyrimidin-4-yl]amino}methyl)pyridin-2-yl]-N-methylmethanesulfonamide

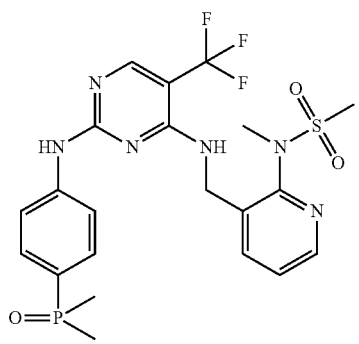 [SMILES: CN(c1ncccc1CNc1nc(Nc2ccc(P(C)(C)=O)cc2)ncc1C(F)(F)F)S(C)(=O)=O]

Prepared according to the procedure and purification technique described for Example 8, utilizing 4-(dimethylphosphoryl)aniline (yield: 43%). $^1$H-NMR (CD$_3$OD, 400 MHz): δ=1.73 (d, J=13.2 Hz, 6H), 3.14 (s, 3H), 3.23 (s, 3H), 4.95 (s, 2H), 7.35 (dd, J=4.8, 7.2 Hz, 1H), 7.55-7.60 (m, 2H), 7.69-7.71 (m, 2H), 7.78 (dd, J=0.8, 7.6 Hz, 1H), 8.23 (s, 1H), 8.42 (dd, J=0.8, 7.6 Hz, 1H). MS (ES$^+$): m/z 528.97 (MH$^+$). HPLC: t$_R$=2.80 min (ZQ3, polar_5 min).

Example 15

N-[3-({[2-{[3-(Dimethylphosphoryl)phenyl]amino}-5-(trifluoromethyl)pyrimidin-4-yl]amino}methyl)pyridin-2-yl]-N-methylmethanesulfonamide

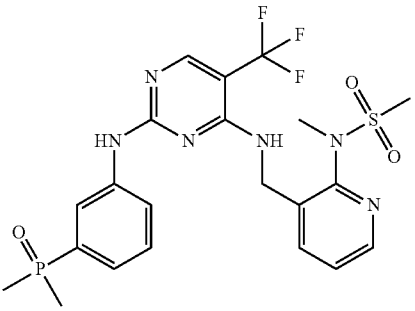

Prepared according to the procedure and purification technique described for Example 8, utilizing 4-(dimethylphosphoryl)aniline (yield: 41%). $^1$H-NMR (CD$_3$OD, 400 MHz): δ=1.74 (d, J=13.2 Hz, 6H), 3.12 (s, 3H), 3.22 (s, 3H), 4.93 (s, 2H), 7.33-7.37 (m, 3H), 7.79-7.83 (m, 2H), 7.90 (d, J=13.6 Hz, 1H), 8.21 (s, 1H), 8.41 (dd, J=2.4, 4.8 Hz, 1H). MS (ES$^+$): m/z 528.95 (MH$^+$). HPLC: t$_R$=2.80 min (ZQ3, polar_5 min).

Example 16

2-{[2-({4-[(Dimethylphosphoryl)methyl]phenyl}amino)-5-(trifluoromethyl)pyrimidin-4-yl]amino}-N-methylbenzamide

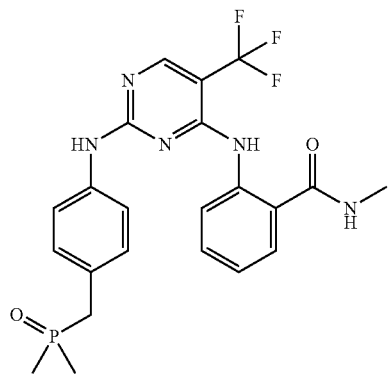 [SMILES: CNC(=O)c1ccccc1Nc1nc(Nc2ccc(CP(C)(C)=O)cc2)ncc1C(F)(F)F]

A solution of 2-{[2-chloro-5-(trifluoromethyl)pyrimidin-4-yl]amino}-N-methylbenzamide (XLIIIa, 35 mg, 0.106 mmol) and 4-dimethylphosphinoylmethyl)phenylamine (23.3 mg, 0.127 mmol) in a mixture of trifluoroacetic acid (24.5 µL, 0.318 mmol) and trifluoroethanol (0.5 mL) was stirred under N$_2$ at 105° C. for 45 min in a Biotage microwave reactor. The mixture was concentrated in vacuo and the residue portioned between DCM (5 mL) and a saturated aqueous sodium bicarbonate solution (2 mL). The organic phase was removed and the aqueous phase extracted with DCM (3×5 mL). The combined organic phases were dried over magnesium sulfate and concentrated in vacuo to afford crude product which was purified by chromatography over silica gel eluting with 5% 7N ammonia in methanol in DCM to yield 34.6 mg of Example 16 (yield: 68%). $^1$H-NMR (CDCl$_3$, 400 MHz): δ=1.44 (d, J=12.8 Hz, 6H), 2.97 (d, J=4.8 Hz, 3H), 3.10 (d, J=14.8 Hz, 2H), 6.65 (d, J=8.4 Hz, 1H), 6.75 (d, J=4.4 Hz, 1H), 6.99 (dd, J=2.0, 8.4 Hz, 1H), 7.03 (t, J=7.2 Hz, 1H), 7.12 (dd, J=2.4, 8.4 Hz, 1H), 7.41 (dt, J=0.8, 8.4 Hz, 1H), 7.49 (dd, J=1.6, 7.6 Hz, 1H), 7.52 (d, J=8.4 Hz, 1H), 7.63 (s, br, 1H), 8.34 (s, 1H), 8.38 (d, J=8.4 Hz, 1H), 10.90 (s, br, 1H). MS (ES$^+$): m/z 478.00 (MH$^+$). HPLC: t$_R$=2.84 min (ZQ3, polar_5 min).

Example 17

2-{2-[3-(Dimethylphosphinoylmethyl)phenylamino]-5-trifluoromethylpyrimidin-4-ylamino}-N-methyl-benzamide

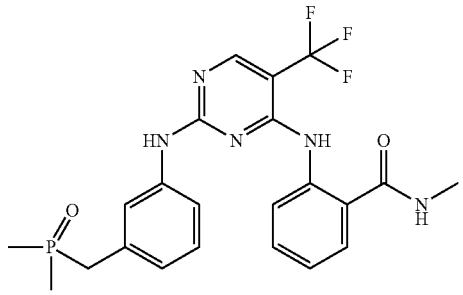

This compound was prepared according to the procedure and purification technique described for Example 16, utilizing 3-[(dimethylphosphoryl)methyl]aniline (yield: 53%). $^1$H-NMR (CDCl$_3$/CD$_3$OD (5:1), 400 MHz): δ=1.27 (d, J=12.8 Hz, 6H), 2.96 (s, J=16.4 Hz, 2H), 6.83 (d, J=6.8 Hz, 1H), 7.17-7.25 (m, 2H), 7.29-7.33 (m, 1H), 7.44 (t, J=8.4 Hz, 1H), 7.59 (d, J=7.2 Hz, 1H), 7.71 (s, 1H), 8.21 (d, J=8.4 Hz, 1H), 8.32 (s, 1H). MS (ES$^+$): m/z 477.74 (MH$^+$). HPLC: t$_R$=2.89 min (ZQ3, polar_5 min).

Example 18

2-{[2-{[4-(Dimethylphosphoryl)phenyl]amino}-5-(trifluoromethyl)pyrimidin-4-yl]amino}-N-methyl-benzamide

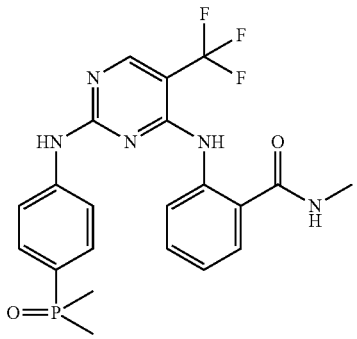 [SMILES: CNC(=O)c1ccccc1Nc1nc(Nc2ccc(P(C)(C)=O)cc2)ncc1C(F)(F)F]

Prepared according to the procedure and purification technique described for Example 16, utilizing 4-(dimethylphosphoryl)aniline (yield: 44%). $^1$H-NMR (CD$_3$OD, 400 MHz): δ=1.76 (d, J=13.2 Hz, 6H), 2.90 (s, 3H), 7.20 (dd, J=1.2, 7.6 Hz, 1H), 7.51 (dt, J=1.6, 7.2 Hz, 1H), 7.61-7.66 (m, 3H), 7.84 (dd, J=2.8, 8.8 Hz, 2H), 8.39 (s, 1H), 8.42 (d, J=8.0 Hz, 1H). MS (ES$^+$): m/z 463.97 (MH$^+$). HPLC: t$_R$=2.87 min (ZQ3, polar_5 min).

Example 19

2-{[2-{[4-(Dimethylphosphoryl)phenyl]amino}-5-(trifluoromethyl)pyrimidin-4-yl]amino}-N-methyl-benzamide

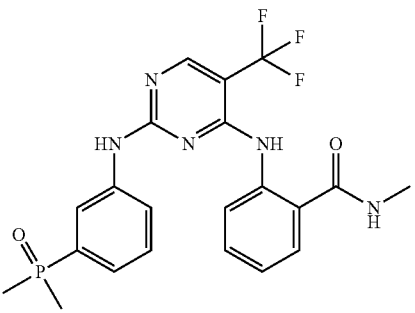

Prepared according to the procedure and purification technique described for Example 16, utilizing 3-(dimethylphosphoryl)aniline (yield: 46%). $^1$H-NMR (CD$_3$OD, 400 MHz): δ=1.72 (d, J=13.6 Hz, 6H), 2.90 (s, 3H), 7.16 (dt, J=1.2, 7.2 Hz, 1H), 7.42-7.45 (m, 3H), 7.63 (dd, J=1.6, 8.0 Hz, 1H), 7.89-7.97 (m, 2H), 8.38 (s, 1H), 8.41 (m, 1H). MS (ES$^+$): m/z 463.92 (MH$^+$). HPLC: t$_R$=2.89 min (ZQ3, polar_5 min).

Example 20

Diethyl(4-{[4-{[2-(methylcarbamoyl)phenyl]amino}-5-(trifluoromethyl)pyrimidin-2-yl]amino}benzyl)phosphonate

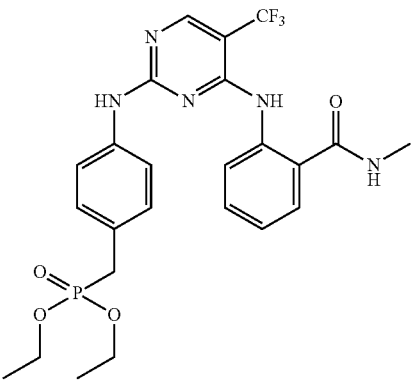 [SMILES: CCOP(=O)(Cc1ccc(Nc2ncc(C(F)(F)F)c(Nc3ccccc3C(=O)NC)n2)cc1)OCC]

A solution of 2-(2-chloro-5-trifluoromethyl-pyrimidin-4-ylamino)-N-methyl-benzamide (33 mg, 0.10 mmol) and diethyl(4-aminobenzyl)phosphonate (29 mg, 0.12 mmol) in TFA (34 mg, 0.30 mmol) and TFE (1 mL) was heated at 100° C. for 30 min in a CEM microwave. The reaction mixture was concentrated in vacuo and the residue purified by preparative HPLC (MDP; 0.1% formic acid use as eluent buffer) to afford 30 mg of Example 20 (yield: 56%). $^1$H NMR (DMSO-$d_6$): 1.17 (t, J=7.1 Hz, 6H), 2.78 (d, J=4.5 Hz, 3H), 3.17 (d, J=21.4 Hz, 2H), 3.94 (m, 4H), 7.15-7.19 (m, 3H), 7.49 (t, J=7.6 Hz, 1H), 7.57 (d, J=8.1 Hz, 2H), 7.72 (dd, J=8.1 Hz, 1.5 Hz, 2H), 8.44 (s, 1H), 8.50 (br s, 1H), 8.73 (d, J=4.5 Hz, 1H), 9.82 (s, 1H), 11.33 (s, 1H). LC-MS (ZQ3, polar-5 min, $t_R$=3.29 min): 537.97 (MH$^+$).

Example 21

Diethyl[2-(4-{[4-{[2-(methylcarbamoyl)phenyl]amino}-5-(trifluoromethyl)pyrimidin-2-yl]amino}phenyl)propan-2-yl]phosphonate

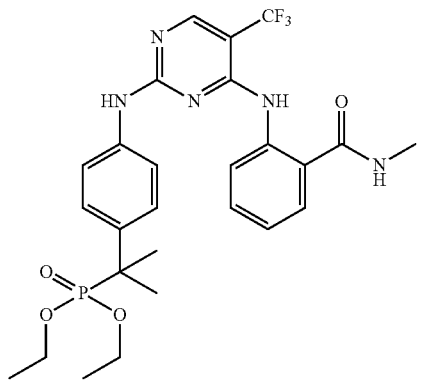 [SMILES: CCOP(=O)(OCC)C(C)(C)c1ccc(Nc2ncc(C(F)(F)F)c(Nc3ccccc3C(=O)NC)n2)cc1]

Prepared according to the procedure and purification technique described for Example 20, utilizing diethyl[2-(4-aminophenyl)propan-2-yl]phosphonate. $^1$H NMR (DMSO-$d_6$): 1.13 (t, J=7.1 Hz, 6H), 1.49 (s, 3H), 1.53 (s, 3H), 2.79 (d, J=4.5 Hz, 3H), 3.84 (m, 4H), 7.19 (td, J=7.6 Hz, 1.2 Hz, 1H), 7.37 (dd, J=8.8 Hz, 2.0 Hz, 2H), 7.50 (t, J=7.6 Hz, 1H), 7.60 (d, J=8.1 Hz, 2H), 7.73 (dd, J=7.8 Hz, 1.5 Hz, 2H), 8.45 (s, 1H), 8.50 (br s, 1H), 8.74 (d, J=4.5 Hz, 1H), 9.84 (s, 1H), 11.38 (s, 1H). LC-MS (ZQ3, polar-5 min, $t_R$=3.53 min): 566.00 (MH$^+$).

Example 22

Ethyl methyl(4-{[4-{[2-(methylcarbamoyl)phenyl]amino}-5-(trifluoromethyl)pyrimidin-2-yl]amino}benzyl)phosphinate

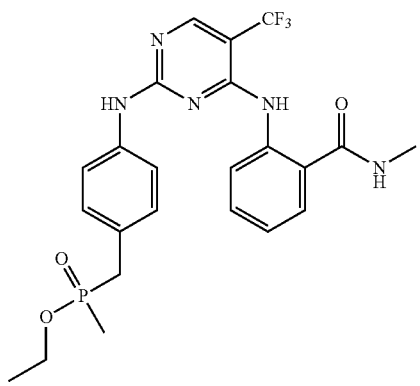 [SMILES: CCOP(C)(=O)Cc1ccc(Nc2ncc(C(F)(F)F)c(Nc3ccccc3C(=O)NC)n2)cc1]

Prepared according to the procedure and purification technique described for Example 20, utilizing ethyl(4-aminobenzyl)methylphosphinate. $^1$H NMR (DMSO-$d_6$): 1.20 (t, J=7.1 Hz, 3H), 1.30 (d, J=13.9 Hz, 3H), 2.78 (d, J=4.5 Hz, 3H), 3.12 (d, J=17.7 Hz, 2H), 3.94 (m, 2H), 7.15-7.18 (m, 3H), 7.48 (t, J=7.6 Hz, 1H), 7.57 (d, J=7.6 Hz, 2H), 7.71 (dd, J=8.1 Hz, 1.5 Hz, 2H), 8.43 (s, 1H), 8.50 (br s, 1H), 8.73 (d, J=4.5 Hz, 1H), 9.82 (s, 1H), 11.32 (s, 1H). LC-MS (ZQ3, polar-5 min, $t_R$=3.06 min): 507.97 (MH$^+$).

Example 23

2-{[2-({3-[(Diethylphosphoryl)methyl]phenyl}amino)-5-(trifluoromethyl)pyrimidin-4-yl]amino}-N-methylbenzamide

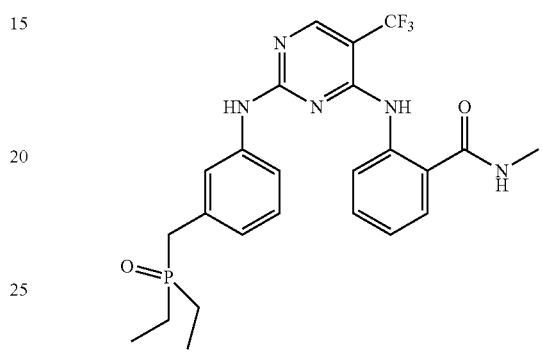

Prepared according to the procedure and purification technique described for Example 20, utilizing 3-[(diethylphosphoryl)methyl]aniline. $^1$H NMR (CD$_3$OD): 1.08 (t, J=7.8 Hz, 3H), 1.12 (t, J=7.8 Hz, 3H), 1.65-1.74 (m, 4H), 2.90 (s, 3H), 3.14 (d, J=14.4 Hz, 2H), 6.98 (d, J=7.6 Hz, 1H), 7.18 (td, J=7.6 Hz, 1.0 Hz, 1H), 7.24 (t, J=7.6 Hz, 1H), 7.45 (t, J=7.6 Hz, 1H), 7.51 (d, J=8.1 Hz, 1H), 7.57 (s, 1H), 7.64 (dd, J=7.8 Hz, 1.5 Hz, 1H), 8.34 (s, 1H), 8.44 (m, 1H). LC-MS (ZQ3, polar-5 min, $t_R$=3.05 min): 506.02 (MH$^+$).

Example 24

2-{[2-({4-[(Diethylphosphoryl)methyl]phenyl}amino)-5-(trifluoromethyl)pyrimidin-4-yl]amino}-N-methylbenzamide

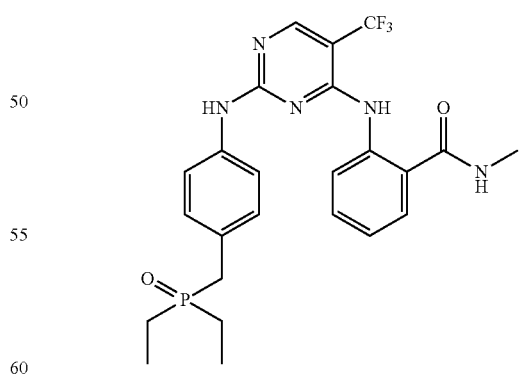

Prepared according to the procedure and purification technique described for Example 20, utilizing 4-[(diethylphosphoryl)methyl]aniline. $^1$H NMR (CD$_3$OD): 1.13 (t, J=7.4 Hz, 3H), 1.24 (t, J=7.4 Hz, 3H), 1.70-1.79 (m, 4H), 2.90 (s, 3H), 3.20 (d, J=13.9 Hz, 2H), 7.15-7.22 (m, 3H), 7.48 (td, J=7.8 Hz, 1.5 Hz, 1H), 7.58 (d, J=8.6 Hz, 2H), 7.64 (dd, J=7.8 Hz, 1.2 Hz, 1H), 8.32 (s, 1H), 8.43 (m, 1H). LC-MS (ZQ3, polar-5 min, $t_R$=3.02 min): 506.02 (MH+).

Example 25

Diethyl(4-{[4-{[3-(methylsulfonyl)benzyl]amino}-5-(trifluoromethyl)pyrimidin-2-yl]amino}benzyl)phosphonate

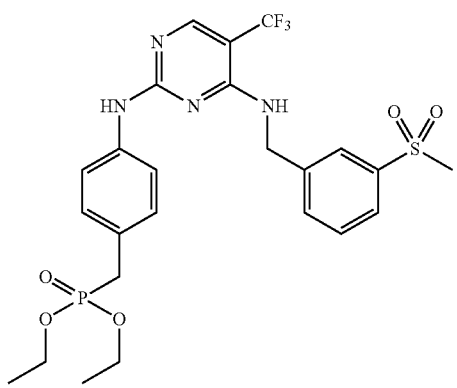 [SMILES: CCOP(=O)(Cc1ccc(Nc2ncc(C(F)(F)F)c(NCc3cccc(S(C)(=O)=O)c3)n2)cc1)OCC]

Prepared according to the procedure described above for Example 20 using 2-chloro-N-[3-(methylsulfonyl)benzyl]-5-(trifluoromethyl)pyrimidin-4-amine (XLIVa). $^1$H NMR (CD$_3$OD): 1.25 (t, J=7.1 Hz, 6H), 3.02 (s, 3H), 3.17 (d, J=21.4 Hz, 2H), 4.02 (m, 4H), 4.80 (s, 2H), 7.15 (dd, J=8.6 Hz, 2.5 Hz, 2H), 7.39 (d, J=8.4 Hz, 2H), 7.56-7.66 (m, 2H), 7.81 (d, J=7.8 Hz, 1H), 7.93 (s, 1H), 8.15 (s, 1H). LC-MS (ZQ3, polar-5 min, $t_R$=3.11 min): 572.96 (MH+).

Example 26

Dibutyl[4-({4-[({2-[methyl(methylsulfonyl)amino]pyridin-3-yl}methyl)amino]-5-(trifluoromethyl)pyrimidin-2-yl}amino)benzyl]phosphonate

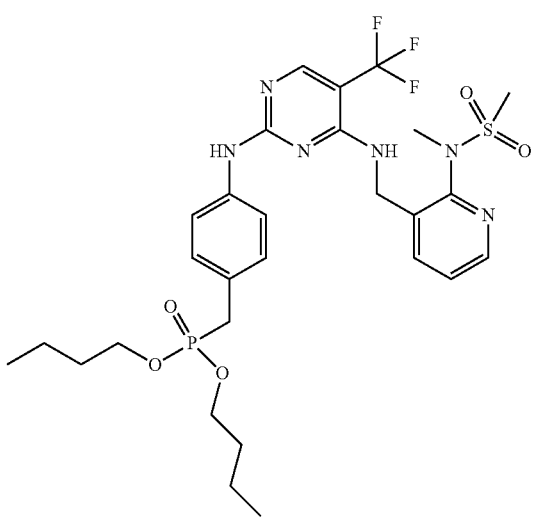 [SMILES: CCCCOP(=O)(Cc1ccc(Nc2ncc(C(F)(F)F)c(NCc3cccnc3N(C)S(C)(=O)=O)n2)cc1)OCCCC]

A mixture of diethyl(4-nitrobenzyl)phosphonate (I, 700 mg, 2.56 mmol) and 5 mL concentrated HCl was heated at 120° C. for 6 hours. The cooled mixture was then diluted with water, the suspended solid isolated by filtration, washed with water and dried in vacuo to afford 500 mg of (4-nitrobenzyl)phosphonic acid (II) which was used without further purification. This material was mixed with oxalyl chloride (5 mL) and heated at 65° C. under nitrogen for 12 hr after which time the mixture was concentrated in vacuo to afford crude (4-nitrobenzyl)phosphonic dichloride (III). This dichloride was dissolved in dry methylene chloride (5 mL), cooled in ice under nitrogen and treated with n-butanol (1.05 mL, 11.5 mmol) and DIPEA (0.88 mL, 5.07 mmol). After 1 hr at room temperature the mixture was concentrated in vacuo and chromatographed over silica gel eluting with EtOAc:hexane 30-70% to yield 498 mg of dibutyl(4-nitrobenzyl)phosphonate (IV, R=nBu) yield: 66%). A solution of this phosphonate ester in methanol (5 mL) was hydrogenated in the presence of 5% Pd/C (32 mg) for 2 h. The suspension was filtered and the filtrate concentrated in vacuo to afford 368 mg of dibutyl(4-aminobenzyl)phosphonate (yield: 82%).

A mixture of dibutyl(4-aminobenzyl)phosphonate (18 mg, 0.06 mmol), N-[3-({[2-chloro-5-(trifluoromethyl)pyrimidin-4-yl]amino}methyl)pyridin-2-yl]-N-methylmethanesulfonamide XLIa (20 mg, 0.05 mmol), TFA (12 uL, 0.15 mmol) and TFE (0.5 mL) was heated at 105° C. under nitrogen in a microwave reactor for 40 minutes. The resulting mixture was concentrated in vacuo and the residue purified by preparative HPLC (MDP) to afford 24 mg of dibutyl[4-({4-[({2-[methyl(methylsulfonyl)amino]pyridin-3-yl}methyl)amino]-5-(trifluoromethyl)pyrimidin-2-yl}amino)benzyl] phosphonate trifluoroacetate (Example 26, yield 73%).

$^1$H NMR (400 MHz, CD$_3$OD) δ=0.91 (t, J=7.5 Hz, 6H), 1.30-1.42 (m, 4H), 1.53-1.65 (m, 4H), 3.11 (s, 3H), 3.17 (s, 3H), 3.22 (d, J=21.7 Hz, 2H), 3.91-4.02 (m, 4H), 4.94 (s, 2H), 7.25 (dd, J=8.5, 2.4 Hz, 2H), 7.33-7.41 (m, 3H), 7.73 (d, J=7.3 Hz, 1H), 8.20 (s, 1H), 8.45 (dd, J=4.7, 1.9 Hz, 1H). MS (ES+): m/z 659.30 (100) [MH+]; HPLC: $t_R$=1.16 min (UPLC, purity).

The following compounds were prepared in a manner analogous to that described for Example 26 using the appropriate alcohol.

| Example | Compound Name | HPLC Retention time (min.) | MS Data (M + H) |
|---|---|---|---|
| 27 | dipropan-2-yl [4-({4-[({2-[methyl(methylsulfonyl)amino]pyridin-3-yl}methyl)amino]-5-(trifluoromethyl)pyrimidin-2-yl}amino)benzyl]phosphonate | 1.01 | 631.24 |
| 28 | dipropyl [4-({4-[({2-[methyl(methylsulfonyl)amino]pyridin-3-yl}methyl)amino]-5-(trifluoromethyl)pyrimidin-2-yl}amino)benzyl]phosphonate | 1.04 | 631.25 |
| 29 | dibutan-2-yl [4-({4-[({2-[methyl(methylsulfonyl)amino]pyridin-3-yl}methyl)amino]-5-(trifluoromethyl)pyrimidin-2-yl}amino)benzyl]phosphonate | 1.14 | 659.31 |
| 30 | bis(2-methylpropyl) [4-({4-[({2-[methyl(methylsulfonyl)amino]pyridin-3-yl}methyl)amino]-5-(trifluoromethyl)pyrimidin-2-yl}amino)benzyl]phosphonate | 1.15 | 659.26 |
| 31 | N-methyl-N-[3-({[2-({4-[(2-oxido-1,3,2-dioxaphosphinan-2-yl)methyl]phenyl}amino)-5-(trifluoromethyl)pyrimidin-4-yl]amino}methyl)pyridin-2-yl]methanesulfonamide | 0.77 | 587.19 |

-continued

| Example | Compound Name | HPLC Retention time (min.) | MS Data (M + H) |
|---|---|---|---|
| 32 | N-[3-({[2-({4-[(5,5-dimethyl-2-oxido-1,3,2-dioxaphosphinan-2-yl)methyl]phenyl}amino)-5-(trifluoromethyl)pyrimidin-4-yl]amino}methyl)pyridin-2-yl]-N-methylmethanesulfonamide | 0.86 | 615.21 |
| 33 | bis[2-(thiophen-3-yl)ethyl] [4-({4-[({2-[methyl(methylsulfonyl)amino]pyridin-3-yl}methyl)amino]-5-(trifluoromethyl)pyrimidin-2-yl}amino)benzyl]phosphonate | 1.16 | 767.21 |
| 34 | bis(cyclobutylmethyl) [4-({4-[({2-[methyl(methylsulfonyl)amino]pyridin-3-yl}methyl)amino]-5-(trifluoromethyl)pyrimidin-2-yl}amino)benzyl]phosphonate | 1.20 | 683.34 |

Example 35

Dipropan-2-yl[3-({4-[({2-[methyl(methylsulfonyl)amino]pyridin-3-yl}methyl)amino]-5-(trifluoromethyl)pyrimidin-2-yl}amino)benzyl]phosphonate

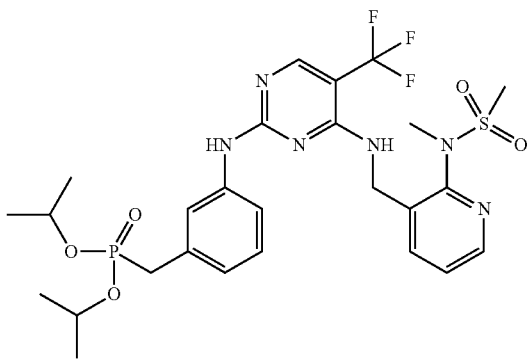 [SMILES: CC(C)OP(=O)(Cc1cccc(Nc2ncc(C(F)(F)F)c(NCc3cccnc3N(C)S(C)(=O)=O)n2)c1)OC(C)C]

A mixture of triisopropyl phosphite (500 mg, 2.31 mmol) and 1-bromomethyl-3-nitrobenzene (506 mg, 2.43 mmol) was heated at 100° C. under nitrogen for 3 h. The crude dipropan-2-yl(3-nitrobenzyl)phosphonate thus formed was dissolved in MeOH (5 mL) and hydrogenated in the presence of 5% Pd/C (49 mg) for 2 h. The mixture was filtered and concentrated in vacuo and the dipropan-2-yl(3-aminobenzyl) phosphonate residue heated in a microwave reactor at 105° C. under nitrogen for 40 minutes with N-[3-({[2-chloro-5-(trifluoromethyl)pyrimidin-4-yl]amino}methyl)pyridin-2-yl]-N-methylmethanesulfonamide XLIa (20 mg, 0.051 mmol), TFA (12 uL, 0.15 mmol) and 0.5 mL TFE. The mixture was evaporated to dryness and purified by preparative HPLC to afford 11 mg of dipropan-2-yl[3-({4-[({2-[methyl(methylsulfonyl)amino]pyridin-3-yl}methyl)amino]-5-(trifluoromethyl)pyrimidin-2-yl}amino)benzyl]phosphonate trifluoroacetate (Example 35, yield: 34%). $^1$H NMR (400 MHz, CD$_3$OD) δ=1.19 (d, J=6.1 Hz, 6H), 1.28 (d, J=6.1 Hz, 6H), 3.06-3.12 (m, 4H), 3.12-3.19 (m, 4H), 4.51-4.63 (m, 2H), 4.96 (s, 2H), 7.14 (d, J=7.3 Hz, 1H), 7.21-7.28 (m, 1H), 7.29-7.33 (m, 1H), 7.35-7.43 (m, 2H), 7.76 (d, J=7.6 Hz, 1H), 8.21 (s, 1H), 8.45 (dd, J=4.8, 1.8 Hz, 1H). MS (ES+): m/z 631.27 (100) [MH+]; HPLC: t$_R$=1.03 min (UPLC, purity).

The following compounds were prepared in a manner analogous to that described for Example 35 using the appropriate trialkyl phosphite.

| Example | Compound Name | HPLC Retention time (min.) | MS Data (M + H) |
|---|---|---|---|
| 54 | dibutyl [3-({4-[({2-[methyl(methylsulfonyl)amino]pyridin-3-yl}methyl)amino]-5-(trifluoromethyl)pyrimidin-2-yl}amino)benzyl]phosphonate | 1.16 | 659.28 |
| 55 | bis(2,2-dimethylpropyl) [3-({4-[({2-[methyl(methylsulfonyl)amino]pyridin-3-yl}methyl)amino]-5-(trifluoromethyl)pyrimidin-2-yl}amino)benzyl]phosphonate | 1.25 | 687.32 |
| 56 | dimethyl [3-({4-[({2-[methyl(methylsulfonyl)amino]pyridin-3-yl}methyl)amino]-5-(trifluoromethyl)pyrimidin-2-yl}amino)benzyl]phosphonate | 1.81 | 575.13 |

Example 36

Dimethyl[4-({4-[({2-[methyl(methylsulfonyl)amino]pyridin-3-yl}methyl)amino]-5-(trifluoromethyl)pyrimidin-2-yl}amino)phenyl]phosphonate

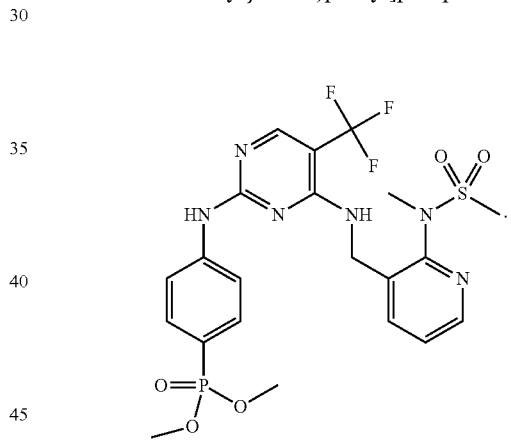

A solution of N-[3-({[(2-chloro-5-(trifluoromethyl)pyrimidin-4-yl]amino}methyl)pyridin-2-yl]-N-methylmethanesulfonamide (XLIa, 20 mg, 0.051 mmol) and dimethyl(4-aminophenyl)phosphonate (12.2 mg, 0.061 mmol) in a mixture of trifluoroacetic acid (12 μL, 0.15 mmol) and trifluoroethanol (0.5 mL) was stirred under N$_2$ at 105° C. for 40 min in a Biotage microwave reactor. The mixture was concentrated in vacuo and the residue purified by preparative HPLC (MDP) to afford 9 mg of dimethyl[4-({4-[({2-[methyl(methylsulfonyl)amino]pyridin-3-yl}methyl)amino]-5-(trifluoromethyl)pyrimidin-2-yl}amino)phenyl]phosphonate trifluoroacetate (Example 36, yield: 30%). $^1$H NMR (400 MHz, CD$_3$OD) δ=3.13 (s, 3H), 3.21 (s, 3H), 3.72 (s, 3H), 3.74 (s, 3H), 4.98 (s, 2H), 7.37 (dd, J=7.7, 4.7 Hz, 1H), 7.55-7.67 (m, 4H), 7.76 (dd, J=7.8, 1.8 Hz, 1H), 8.28 (s, 1H), 8.45 (dd, J=4.8, 1.8 Hz, 1H). MS (ES+): m/z 561.16 (100) [MH+]; HPLC: t$_R$=0.86 min (UPLC, purity).

The following compounds were prepared in a manner analogous to that described for Example 36 using the appropriate dialkyl(3- or 4-aminophenyl)phosphonate ester.

| Example | Compound Name | HPLC Retention time (min.) | MS Data (M + H) |
|---|---|---|---|
| 37 | dipropyl [4-({4-[({2-[methyl(methylsulfonyl)amino]pyridin-3-yl}methyl)amino]-5-(trifluoromethyl)pyrimidin-2-yl}amino)phenyl]phosphonate | 1.09 | 617.26 |
| 38 | dipropan-2-yl [4-({4-[({2-[methyl(methylsulfonyl)amino]pyridin-3-yl}methyl)amino]-5-(trifluoromethyl)pyrimidin-2-yl}amino)phenyl]phosphonate | 1.06 | 617.26 |
| 39 | diethyl [3-({4-[({2-[methyl(methylsulfonyl)amino]pyridin-3-yl}methyl)amino]-5-(trifluoromethyl)pyrimidin-2-yl}amino)phenyl]phosphonate | 0.96 | 589.24 |
| 57 | dipropyl [3-({4-[({2-[methyl(methylsulfonyl)amino]pyridin-3-yl}methyl)amino]-5-(trifluoromethyl)pyrimidin-2-yl}amino)phenyl]phosphonate | 1.09 | 617.22 |
| 58 | dipropan-2-yl [3-({4-[({2-[methyl(methylsulfonyl)amino]pyridin-3-yl}methyl)amino]-5-(trifluoromethyl)pyrimidin-2-yl}amino)phenyl]phosphonate | 1.07 | 617.23 |
| 59 | N-[3-({[2-{[3-(5,5-dimethyl-2-oxido-1,3,2-dioxaphosphinan-2-yl)phenyl]amino}-5-(trifluoromethyl)pyrimidin-4-yl]amino}methyl)pyridin-2-yl]-N-methylmethanesulfonamide | 0.92 | 601.17 |
| 60 | N-[3-({[2-{[4-(5,5-dimethyl-2-oxido-1,3,2-dioxaphosphinan-2-yl)phenyl]amino}-5-(trifluoromethyl)pyrimidin-4-yl]amino}methyl)pyridin-2-yl]-N-methylmethanesulfonamide | 0.93 | 601.20 |

Example 40

Ethyl hydrogen[4-({4-[({2-[methyl(methylsulfonyl)amino]pyridin-3-yl}methyl)amino]-5-(trifluoromethyl)pyrimidin-2-yl}amino)phenyl]phosphonate

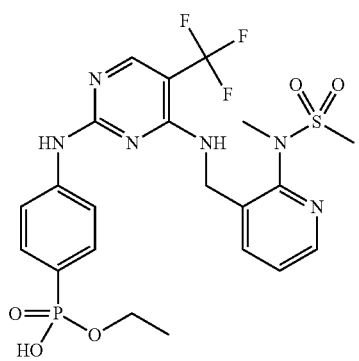 [SMILES: CCOP(=O)(O)c1ccc(Nc2ncc(C(F)(F)F)c(NCc3cccnc3N(C)S(C)(=O)=O)n2)cc1]

Diethyl[4-({4-[({2-[methyl(methylsulfonyl)amino]pyridin-3-yl}methyl)amino]-5-(trifluoromethyl)pyrimidin-2-yl}amino)phenyl]phosphonate (Example 2) in an excess of concentrated HCl (37%) and heated at 80° C. for 5 h. The reaction mixture was concentrated in vacuo and the residue purified by preparative HPLC (MDP) to afford the title compound (Example 40). $^1$H NMR (400 MHz, DMSO-d6) δ ppm 1.15 (t, J=6.9 Hz, 3H), 3.16 (s, 6H), 3.81 (ddd, J=14.7, 7.3, 7.1 Hz, 2H), 4.83 (d, J=5.6 Hz, 2H), 7.34-7.45 (m, 3H), 7.55 (dd, J=8.2, 3.2 Hz, 2H), 7.64-7.73 (m, 2H), 8.31 (d, J=0.8 Hz, 1H), 8.45 (dd, J=4.7, 1.9 Hz, 1H), 9.86 (s, 1H); MS (UPLC TOF): m/z 562.14 [MH+]; HPLC: tR=1.15 min (polar-3).

Example 41

[4-({4-[({2-[Methyl(methylsulfonyl)amino]pyridin-3-yl}methyl)amino]-5-(trifluoromethyl)pyrimidin-2-yl}amino)benzyl]phosphonic acid

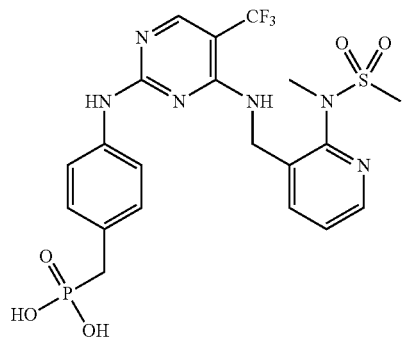 [SMILES: CN(c1ncccc1CNc1nc(Nc2ccc(CP(=O)(O)O)cc2)ncc1C(F)(F)F)S(C)(=O)=O]

Synthesized using the method described above for Example 40 heating at 100° C. and using diethyl[4-({4-[({2-[methyl(methylsulfonyl)amino]pyridin-3-yl}methyl)amino]-5-(trifluoromethyl)pyrimidin-2-yl}amino)benzyl]phosphonate (Ex. 1). $^1$H NMR (400 MHz, DMSO-d6) δ ppm 2.84 (d, J=21.2 Hz, 2H), 3.12 (s, 3H), 3.15 (s, 3H), 4.81 (d, J=5.6 Hz, 2H), 7.00 (d, J=7.6 Hz, 2H), 7.26 (d, J=7.6 Hz, 2H), 7.42 (dd, J=7.6, 4.8 Hz, 1H), 7.66 (d, J=7.3 Hz, 1H), 8.04 (br. s., 1H), 8.33 (s, 1H), 8.45 (dd, J=4.7, 1.6 Hz, 1H), 9.93 (br. s., 1H); MS (ES$^+$): m/z 546.95 (MH$^+$). HPLC: t$_R$=2.58 min (ZQ3; polar__5 min).

Example 42

Ethyl hydrogen[4-({4-[({2-[methyl(methylsulfonyl)amino]pyridin-3-yl}methyl)amino]-5-(trifluoromethyl)pyrimidin-2-yl}amino)benzyl]phosphonate

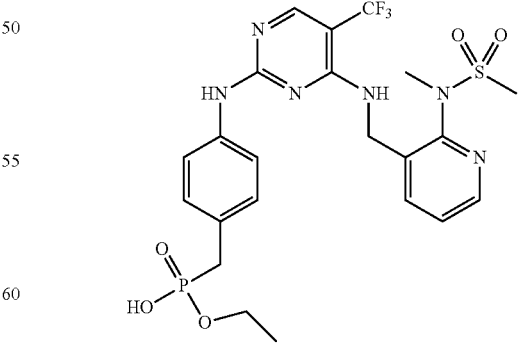

Synthesized using the method described above for Example 40 heating at 100° C. using diethyl[4-({4-[({2-[methyl(methylsulfonyl)amino]pyridin-3-yl}methyl)amino]-5-(trifluoromethyl)pyrimidin-2-yl}amino)benzyl]phosphonate. ¹H NMR (400 MHz, DMSO-d6) δ ppm 1.14 (t, J=6.9 Hz, 3H), 2.93 (d, J=21.0 Hz, 2H), 3.15 (s, 3H), 3.16 (s, 3H), 3.85 (qd, J=7.3, 7.1 Hz, 2H), 4.81 (d, J=5.8 Hz, 2H), 6.99 (d, J=8.3 Hz, 2H), 7.33 (d, J=6.1 Hz, 2H), 7.42 (dd, J=7.8, 4.8 Hz, 1H), 7.60-7.68 (m, 2H), 8.25 (s, 1H), 8.44 (dd, J=4.8, 1.8 Hz, 1H), 9.55 (br. s., 1H); UPLC TOF: polar_3 t$_R$=1.11 min; m/z 576.15 [MH+].

Example 43

[3-({4-[({2-[Methyl(methylsulfonyl)amino]pyridin-3-yl}methyl)amino]-5-(trifluoromethyl)pyrimidin-2-yl}amino)benzyl]phosphonic acid

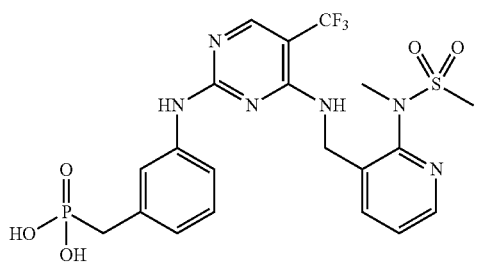 [SMILES: CN(c1ncccc1CNc1nc(Nc2cccc(CP(=O)(O)O)c2)ncc1C(F)(F)F)S(C)(=O)=O]

Synthesized using the method described above for Example 40 heating at 100° C. and using diethyl[3-({4-[({2-[methyl(methylsulfonyl)amino]pyridin-3-yl}methyl)amino]-5-(trifluoromethyl)pyrimidin-2-yl}amino)benzyl]phosphonate (Ex. 4). ¹H NMR (400 MHz, DMSO-d6) δ ppm 2.75-2.85 (m, 2H), 3.12 (s, 3H), 3.15 (s, 3H), 4.80 (d, J=5.6 Hz, 2H), 6.83 (d, J=7.3 Hz, 1H), 6.92-7.00 (m, 1H), 7.27 (br. s., 1H), 7.37 (d, J=7.8 Hz, 1H), 7.41 (dd, J=7.7, 4.7 Hz, 1H), 7.61-7.72 (m, 2H), 8.27 (s, 1H), 8.43 (dd, J=4.5, 1.8 Hz, 1H), 9.59 (br. s., 1H); UPLC TOF: polar_3 t$_R$=1.05 min; m/z 548.12 [MH+].

Example 44

Ethyl hydrogen[3-({4-[({2-[methyl(methylsulfonyl)amino]pyridin-3-yl}methyl)amino]-5-(trifluoromethyl)pyrimidin-2-yl}amino)benzyl]phosphonate

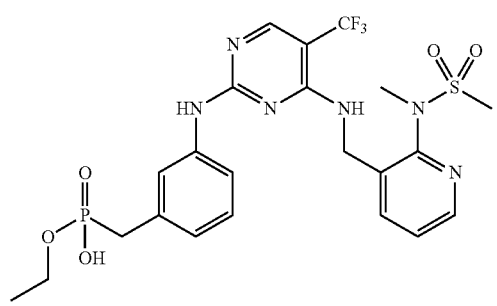 [SMILES: CCOP(=O)(O)Cc1cccc(Nc2ncc(C(F)(F)F)c(NCc3cccnc3N(C)S(C)(=O)=O)n2)c1]

Synthesized using the method described above for Example 40 heating using diethyl[3-({4-[({2-[methyl(methylsulfonyl)amino]pyridin-3-yl}methyl)amino]-5-(trifluoromethyl)pyrimidin-2-yl}amino)benzyl]phosphonate. ¹H NMR (400 MHz, DMSO-d6) δ ppm 1.14 (t, J=7.1 Hz, 3H), 2.84-2.94 (m, 2H), 3.12 (s, 3H), 3.15 (s, 3H), 3.85 (ddd, J=14.9, 7.3, 7.1 Hz, 2H), 4.80 (d, J=5.6 Hz, 2H), 6.83 (d, J=7.8 Hz, 1H), 6.98 (t, J=8.3 Hz, 1H), 7.32-7.39 (m, 2H), 7.41 (dd, J=7.8, 4.8 Hz, 1H), 7.60 (t, J=5.4 Hz, 1H), 7.69 (d, J=6.8 Hz, 1H), 8.26 (s, 1H), 8.43 (dd, J=4.5, 1.8 Hz, 1H), 9.58 (br. s., 1H); UPLC TOF: polar_3 t$_R$=1.12 min; m/z 576.16 [MH+].

Example 45

Ethyl methyl[4-({4-[({2-[methyl(methylsulfonyl)amino]pyridin-3-yl}methyl)amino]-5-(trifluoromethyl)pyrimidin-2-yl}amino)benzyl]phosphinate

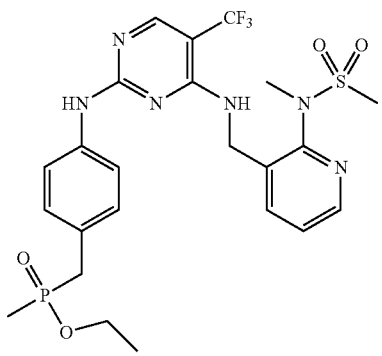

A solution of p-nitrobenzylbromide (11 mmol) in diethoxymethylphosphine (15 mmol) and was stirred at 120° C. under nitrogen in a sealed tube for 16 h. The reaction mixture was concentrated in vacuo to afford crude ethyl methyl(4-nitrobenzyl)phosphinate. A 0.1M solution of this material in methanol was hydrogenated over 10% palladium on carbon (0.50 mmol) overnight, then filtered and the filtrate concentrated in vacuo. The residue was purified using an Isco Combiflash system eluting with 0→10% MeOH in DCM to afford ethyl(4-aminobenzyl)methylphosphinate. A solution of N-[3-({[(2-chloro-5-(trifluoromethyl)pyrimidin-4-yl]amino}methyl)pyridin-2-yl}-N-methylmethanesulfonamide (XLIa, 0.13 mmol), ethyl(4-aminobenzyl)methylphosphinate (0.152 mmol) and TFA (0.379 mmol) in TFE (0.15 M) was heated at 100° C. for 30 min in a microwave reactor. The reaction mixture was partitioned between EtOAc and water, the layers separated and the aqueous phase extracted with EtOAc (3×). The combined organic extracts were washed with brine, dried over sodium sulfate, filtered, and concentrated in vacuo. The residue was purified using an Isco Combiflash system eluting with 0→5% MeOH in DCM to afford ethyl methyl[4-({4-[({2-[methyl(methylsulfonyl)amino]pyridin-3-yl}methyl)amino]-5-(trifluoromethyl)pyrimidin-2-yl}amino)benzyl]phosphinate. ¹H NMR (400 MHz, DMSO-d6) δ ppm 1.17 (t, J=6.9 Hz, 3H), 1.25 (d, J=13.9 Hz, 3H), 3.04 (d, J=17.4 Hz, 2H), 3.16 (s, 6H), 3.89 (dd, J=13.1, 7.3 Hz, 2H), 4.81 (d, J=5.6 Hz, 2H), 6.99 (d, J=7.3 Hz, 2H), 7.34-7.44 (m, 3H), 7.58 (t, J=5.6 Hz, 1H), 7.66 (d, J=7.8 Hz, 1H), 8.25 (s, 1H), 8.43 (dd, J=4.7, 1.6 Hz, 1H), 9.54 (br. s., 1H); UPLC TOF: polar_3 t$_R$=1.30 min; m/z 573.13 [MH+].

Example 46

Ethyl methyl[3-({4-[({2-[methyl(methylsulfonyl)amino]pyridin-3-yl}methyl)amino]-5-(trifluoromethyl)pyrimidin-2-yl}amino)benzyl]phosphinate

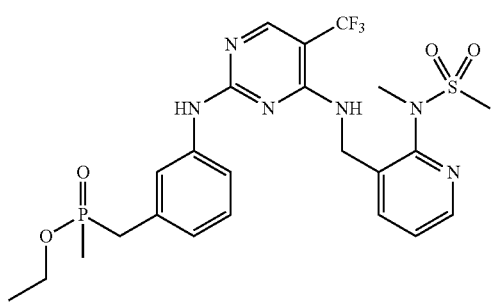 [SMILES: CCOP(C)(=O)Cc1cccc(Nc2ncc(C(F)(F)F)c(NCc3cccnc3N(C)S(C)(=O)=O)n2)c1]

Prepared as described above for Example 45 using m-nitrobenzylbromide. $^1$H NMR (400 MHz, DMSO-d6) δ ppm 1.16 (t, J=6.9 Hz, 3H), 1.26 (d, J=13.9 Hz, 3H), 3.00 (d, J=17.7 Hz, 2H), 3.13 (s, 3H), 3.15 (s, 3H), 3.83-3.94 (m, 2H), 4.81 (d, J=5.8 Hz, 2H), 6.84 (d, J=7.3 Hz, 1H), 7.02 (t, J=8.0 Hz, 1H), 7.34-7.39 (m, 2H), 7.42 (dd, J=7.7, 4.7 Hz, 1H), 7.62 (t, J=5.1 Hz, 1H), 7.70 (d, J=6.3 Hz, 1H), 8.26 (s, 1H), 8.44 (dd, J=4.7, 1.9 Hz, 1H), 9.60 (br. s., 1H); UPLC TOF: polar_3 t$_R$=1.31 min; m/z 574.18 [MH+].

Example 47

Diethyl(4-{[4-{[3-(methylsulfinyl)benzyl]amino}-5-(trifluoromethyl)pyrimidin-2-yl]amino}benzyl)phosphonate

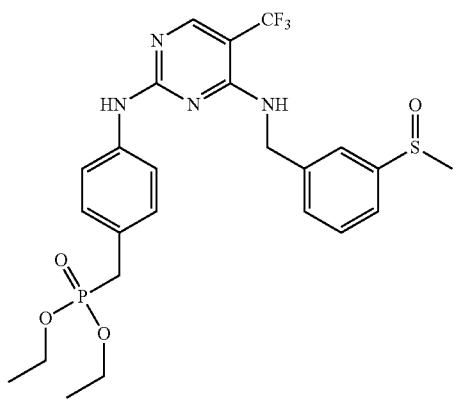 [SMILES: CCOP(=O)(Cc1ccc(Nc2ncc(C(F)(F)F)c(NCc3cccc(S(C)=O)c3)n2)cc1)OCC]

Prepared according to the procedure described for Example 20 using 2-chloro-N-[3-(methylsulfinyl)benzyl]-5-(trifluoromethyl)pyrimidin-4-amine (XLVa). $^1$H NMR (CD$_3$OD): 1.25 (t, J=7.1 Hz, 6H), 2.70 (s, 3H), 3.18 (d, J=21.5 Hz, 2H), 4.02 (m, 4H), 4.79 (s, 2H), 7.15 (dd, J=8.6 Hz, 2.5 Hz, 2H), 7.42 (d, J=8.3 Hz, 2H), 7.52-7.56 (m, 3H), 7.69 (s, 1H), 8.14 (s, 1H). LC-MS (ZQ3, polar-5 min, retention time=2.87 min): 556.94 (MH$^+$).

Example 48

Diethyl{4-[(5-chloro-4-{[2-(methylcarbamoyl)phenyl]amino}pyrimidin-2-yl)amino]benzyl}phosphonate

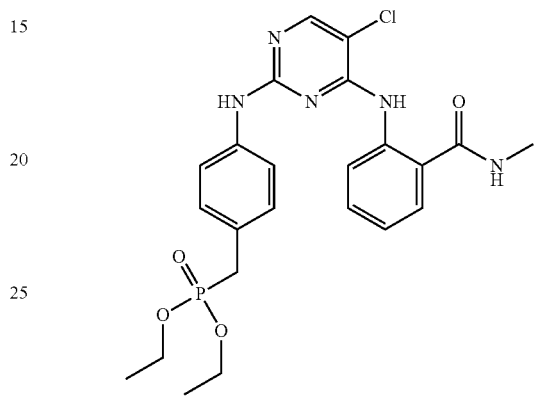

A solution of 2,4,5-trichloropyrimidine (1.0 g, 5.4 mmol) and 2-amino-N-methylbenzamide (0.98 g, 6.5 mmol) in THF (5.0 mL) was charged with DIPEA (1.42 mL, 8.18 mmol) and the mixture allowed to stir at rt for 16 h. The reaction was quenched with NaHCO$_3$ (10 mL) and extracted with EtOAc (15 mL). The organic layer was washed with brine (10 mL), dried over NaSO$_4$, filtered, and concentrated in vacuo to yield a yellow solid which was recrystallized from EtOAc to afford 422 mg of 2-[(2,5-dichloropyrimidin-4-yl)amino]-N-methylbenzamide (yield: 26% yield*). Further material could be recovered from the mother liquors if desired.

$^1$H NMR (CD$_3$OD, 400 MHz): δ=2.93 (s, 3H), 7.21 (td, J=7.64, 1.14 Hz, 1H), 7.56 (ddd, J=8.53, 7.26, 1.64 Hz, 1H), 7.71 (dd, J=7.83, 1.26 Hz, 1H), 8.30 (s, 1H) 8.63 (dd, J=8.59, 0.76 Hz, 1H). MS (ES$^+$): m/z 296.90 [MH$^+$] (ZQ3, polar_5 min).

A solution of 2-[(2,5-dichloropyrimidin-4-yl)amino]-N-methylbenzamide (29.7 mg, 0.100 mmol), diethyl(4-aminobenzyl)phosphonate (29.2 mg, 0.120 mmol), TFA (23 uL, 0.30 mmol) and TFE (1.0 mL) was heated at 100° C. for 30 minutes in a microwave reactor. The reaction mixture was then quenched with saturated aqueous sodium bicarbonate (15 mL) and extracted with EtOAc (20 mL). The organic layer was washed with brine (15 mL), dried over anhydrous NaSO$_4$, filtered, and concentrated in vacuo to yield a yellow solid. This material was purified by preparative HPLC (MDP) to afford 12 mg of diethyl{4-[(5-chloro-4-{[2-(methylcarbamoyl)phenyl]amino}pyrimidin-2-yl)amino]benzyl}phosphonate (yield: 24%). $^1$H NMR (CD$_3$OD, 400 MHz): δ=1.26 (t, J=7.07 Hz, 6H), 2.92 (s, 3H), 3.15-3.24 (m, 2H), 3.99-4.08 (m, 4H), 7.12 (td, J=7.64, 1.14 Hz, 1H), 7.21 (dd, J=8.59, 2.53 Hz, 2H), 7.48 (ddd, J=8.53, 7.26, 1.64 Hz, 1H), 7.55 (d, J=8.08 Hz, 2H), 7.65 (dd, J=7.83, 1.52 Hz, 1H), 8.06 (s, 1H), 8.70 (d, J=8.34 Hz, 1H). MS (ES+): m/z 506.15 [MH+] (TOF, polar).

Example 49

Diethyl{4-[(5-bromo-4-{[2-(methylcarbamoyl)phenyl]amino}pyrimidin-2-yl)amino]benzyl}phosphonate

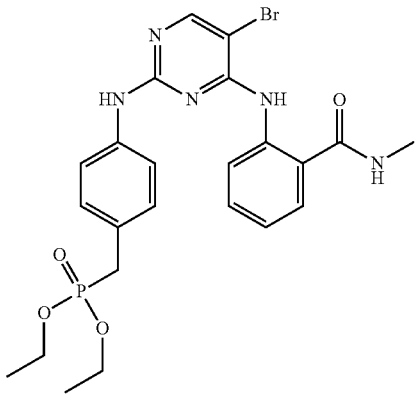 [SMILES: CCOP(=O)(Cc1ccc(Nc2ncc(Br)c(Nc3ccccc3C(=O)NC)n2)cc1)OCC]

Prepared according to the procedure described above for Example 48 using 2-[(5-bromo-2-chloropyrimidin-4-yl)amino]-N-methylbenzamide. $^1$H NMR (CD$_3$OD, 400 MHz): δ=2.93 (s, 1H), 7.21 (td, J=7.64, 1.14 Hz, 1H), 7.70 (dd, J=7.83, 1.26 Hz, 1H), 8.40 (s, 1H), 8.58 (dd, J=8.59, 0.76 Hz, 1H). MS (ES+): m/z 342.80 [MH+] (ZQ3, polar 5 min).

Example 49: $^1$H NMR (CD$_3$OD, 400 MHz): δ=1.26 (t, J=7.07 Hz, 6H), 2.92 (s, 3H), 3.16-3.24 (m, 2H), 3.99-4.08 (m, 4H), 7.13 (td, J=7.58, 1.26 Hz, 1H), 7.21 (dd, J=8.59, 2.53 Hz, 2H), 7.49 (ddd, J=8.53, 7.26, 1.64 Hz, 1H), 7.55 (d, J=8.59 Hz, 2H), 7.64 (dd, J=7.83, 1.52 Hz, 1H), 8.16 (s, 1H), 8.63 (d, J=8.34 Hz, 1H). MS (ES+): m/z 550.09 [MH+] (TOF, polar).

Example 50

Ethyl[4-({4-[({2-[methyl(methylsulfonyl)amino]pyridin-3-yl}methyl)amino]-5-(trifluoromethyl)pyrimidin-2-yl}amino)benzyl]phenylphosphinate

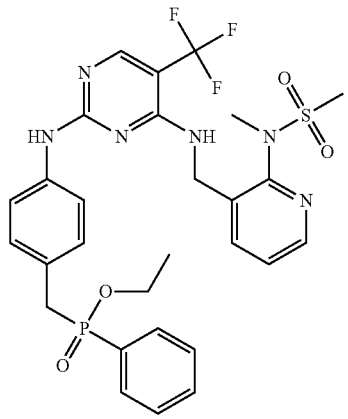 [SMILES: CCOP(=O)(Cc1ccc(Nc2ncc(C(F)(F)F)c(NCc3cccnc3N(C)S(C)(=O)=O)n2)cc1)c1ccccc1]

This compound was prepared according to the procedure described for Example 45 using diethoxyphenylphosphine in place of diethoxymethylphosphine. $^1$H NMR (400 MHz, DMSO-d$_6$) δ ppm 1.15 (t, J=7.1 Hz, 3H), 3.13 (s, 3H), 3.17 (s, 3H), 3.28 (d, J=17.4 Hz, 2H), 3.71-3.81 (m, 1H), 3.83-3.94 (m, 1H), 4.78 (d, J=5.6 Hz, 2H), 6.82 (d, J=7.1 Hz, 2H), 7.26 (br. s., 2H), 7.40 (dd, J=7.7, 4.7 Hz, 1H), 7.43-7.51 (m, 2H), 7.54-7.68 (m, 5H), 8.24 (s, 1H), 8.42 (dd, J=4.7, 1.9 Hz, 1H), 9.48 (br. s., 1H); UPLC TOF: polar_3 t$_R$=1.41 min; m/z 636.18 [MH+].

Example 51

Ethyl[3-({4-[({2-[methyl(methylsulfonyl)amino]pyridin-3-yl}methyl)amino]-5-(trifluoromethyl)pyrimidin-2-yl}amino)benzyl]phenylphosphinate

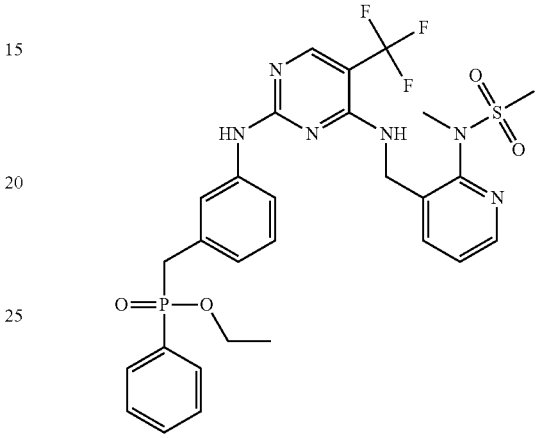

Same procedure as Example 45 except using diethoxyphenylphosphine and using m-nitrobenzylbromide. $^1$H NMR (400 MHz, DMSO-d$_6$) δ ppm 1.14 (t, J=7.1 Hz, 3H), 3.10 (s, 3H), 3.12 (s, 3H), 3.24 (dd, J=5.6, 2.3 Hz, 2H), 3.69-3.81 (m, 1H), 3.82-3.93 (m, 1H), 4.79 (d, J=5.8 Hz, 2H), 6.63 (d, J=7.6 Hz, 1H), 6.86-6.93 (m, 1H), 7.26-7.35 (m, 2H), 7.41 (dd, J=7.7, 4.7 Hz, 1H), 7.43-7.50 (m, 2H), 7.50-7.64 (m, 4H), 7.66-7.71 (m, 1H), 8.23 (s, 1H), 8.42 (dd, J=4.5, 1.8 Hz, 1H), 9.51 (br. s., 1H); UPLC TOF: polar_3 t$_R$=1.44 min; m/z 636.18 [MH+].

Example 52

Ethyl(3-methoxy-4-{[4-{[2-(methylcarbamoyl)phenyl]amino}-5-(trifluoromethyl)pyrimidin-2-yl]amino}benzyl)methylphosphinate

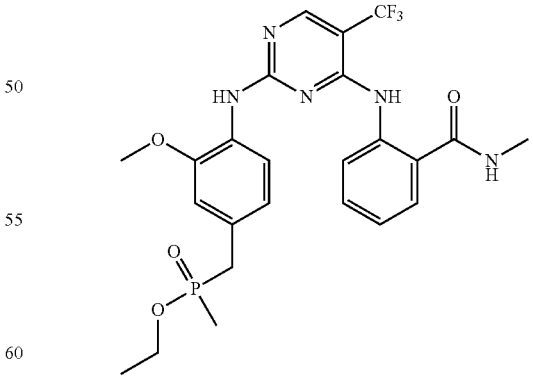

Prepared according to the procedure described for Example 48 using (2-{[2-chloro-5-(trifluoromethyl)pyrimidin-4-yl]amino}-N-methylbenzamide and ethyl(4-amino-3-methoxybenzyl)methylphosphinate (yield: 57%). $^1$H NMR (CD$_3$OD, 400 MHz): δ=1.32 (t, J=7.07 Hz, 3H), 1.44 (d, J=13.89 Hz, 3H), 2.90 (s, 3H), 3.24 (d, J=17.68 Hz, 2H), 3.91 (s, 3H), 4.07 (m, J=7.20, 7.20, 7.20, 7.20, 1.52 Hz, 2H), 6.79 (dt, J=8.21, 2.08 Hz, 1H), 6.99 (t, J=2.02 Hz, 1H), 7.18 (td, J=7.58, 1.01 Hz, 1H), 7.47 (td, J=7.96, 1.52 Hz, 1H), 7.63 (dd, J=7.83, 1.52 Hz, 1H), 7.97 (d, J=8.08 Hz, 1H), 8.29-8.35 (m, 2H). MS (ES+): m/z 538.1789 [MH+] (TOF, polar).

Example 53

Diethyl(3-methoxy-4-{[4-{[2-(methylcarbamoyl)phenyl]amino}-5-(trifluoromethyl)pyrimidin-2-yl]amino}benzyl)phosphonate

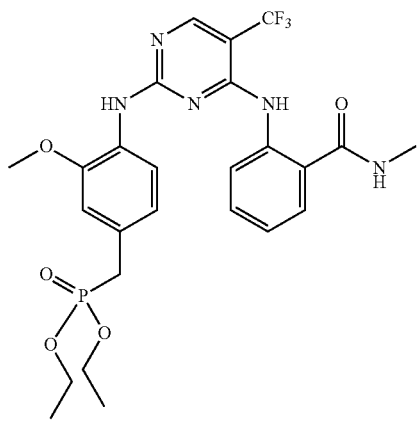

Prepared according to the procedure described for Example 48 using (2-{[2-chloro-5-(trifluoromethyl)pyrimidin-4-yl]amino}-N-methylbenzamide and diethyl(4-amino-3-methoxybenzyl)phosphonate. $^1$H NMR (CD$_3$OD, 400 MHz): δ=1.27 (t, J=7.07 Hz, 6H), 2.90 (s, 3H), 3.20-3.28 (m, 2H), 3.91 (s, 3H), 4.01-4.11 (m, 4H), 6.80 (dt, J=8.21, 2.21 Hz, 1H), 6.99 (t, J=2.15 Hz, 1H), 7.19 (td, J=7.58, 1.26 Hz, 1H), 7.48 (ddd, J=8.46, 7.20, 1.52 Hz, 1H), 7.64 (dd, J=7.83, 1.52 Hz, 1H), 7.96 (d, J=8.08 Hz, 1H), 8.30-8.36 (m, 2H). MS (ES+): m/z 568.1542 [MH+] (TOF, polar).

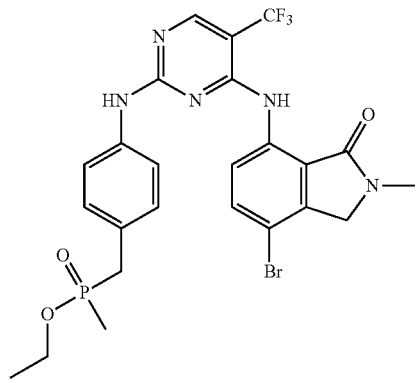 [SMILES: CCOP(C)(=O)Cc1ccc(Nc2ncc(C(F)(F)F)c(Nc3ccc(Br)c4c3C(=O)N(C)C4)n2)cc1]

Example 61

Ethyl[4-({4-[(7-bromo-2-methyl-3-oxo-2,3-dihydro-1H-isoindol-4-yl)amino]-5-(trifluoromethyl)pyrimidin-2-yl}amino)benzyl]methylphosphinate A solution of ethyl(4-{[4-chloro-5-(trifluoromethyl)pyrimidin-2-yl]amino}benzyl)methylphosphinate (230 mg, 584 mmol) and 7-amino-4-bromo-2-methyl-2,3-dihydro-1H-isoindol-1-one (169 mg, 701 mmol) in TFE (2.0 mL) was charged with TFA (200 mg, 1.75 mmol) and the reaction mixture irradiated in a microwave reactor at 105° C. for 1 hour. The resulting mixture was concentrated under reduced pressure and the residue purified using an Isco Combiflash system eluting with 0→5% MeOH in DCM as eluent to afford the title compound, 337.5 mg (96.6% yield). $^1$H NMR (CDCl$_3$, 400 MHz): δ=1.33 (t, J=6.95 Hz, 3H), 1.45 (d, J=13.64 Hz, 3H), 3.22 (s, 1H), 3.24 (s, 3H), 3.26 (s, 1H), 4.03-4.15 (m, 2H), 4.34 (s, 2H), 7.36-7.41 (m, 2H), 7.50 (d, J=8.08 Hz, 4H), 7.54 (d, J=8.84 Hz, 1H), 8.20 (s, 1H), 8.30 (d, J=9.35 Hz, 1H). MS (ES+): m/z 600.0844 [MH+] (TOF, polar).

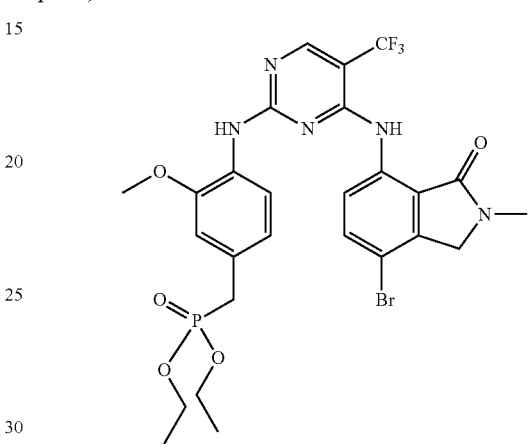

Example 62

Diethyl[4-({4-[(7-bromo-2-methyl-3-oxo-2,3-dihydro-1H-isoindol-4-yl)amino]-5-(trifluoromethyl)pyrimidin-2-yl}amino)-3-methoxybenzyl]phosphonate This example was prepared according to the procedure described above for Example using diethyl(4-{[4-chloro-5-(trifluoromethyl)pyrimidin-2-yl]amino}-3-methoxybenzyl)phosphonate. $^1$H NMR (DMSO-d6, 400 MHz): δ=1.21 (t, J=6.95 Hz, 6H), 3.08 (s, 3H), 3.27-3.37 (m, 2H), 3.74 (s, 3H), 3.97-4.08 (m, 4H), 4.40 (s, 2H), 6.94 (d, J=8.08 Hz, 1H), 7.08 (s, 1H), 7.55 (d, J=8.59 Hz, 1H), 8.42 (s, 1H), 9.21 (s, 1H), 10.53 (s, 1H). MS (ES+): m/z 660.1093 [MH+] (TOF, polar).

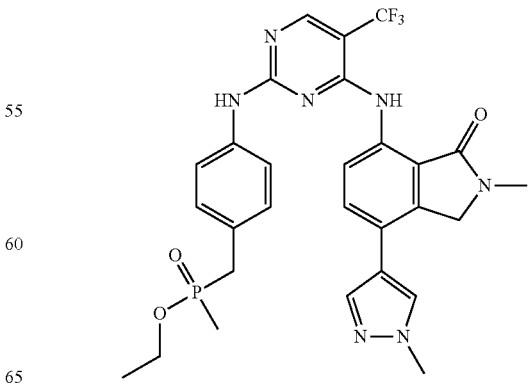

Example 63

Ethyl methyl(4-{[4-{[2-methyl-7-(1-methyl-1H-pyrazol-4-yl)-3-oxo-2,3-dihydro-1H-isoindol-4-yl]amino}-5-(trifluoromethyl)pyrimidin-2-yl]amino}benzyl)phosphinate Ethyl[4-({4-[(7-bromo-2-methyl-3-oxo-2,3-dihydro-1H-isoindol-4-yl)amino]-5-(trifluoromethyl)pyrimidin-2-yl}amino)benzyl]methylphosphinate (Ex. 61, 10 mg, 0.017 mmol) was mixed with 1-methyl-4-(4,4,5,5-tetramethyl-1,3,2-dioxaborolan-2-yl)1H-pyrazole (6.9 mg, 0.034 mmol), potassium carbonate (6.9 mg, 0.050 mmol), dioxane (0.6 mL), water (0.1 mL) and [1,1'-bis(diphenylphosphino)ferrocene]dichloropalladium(II), complex with dichloromethane (1:1) (1.4 mg, 0.0017 mmol) and the mixture irradiated under nitrogen in a microwave reactor at 100° C. for 30 minutes. The crude mixture was passed through a thiol-SPE cartridge to remove Pd residues and then purified by preparative HPLC (MDP) to afford ethyl methyl(4-{[4-{[2-methyl-7-(1-methyl-1H-pyrazol-4-yl)-3-oxo-2,3-dihydro-1H-isoindol-4-yl]amino}-5-(trifluoromethyl)pyrimidin-2-yl]amino}benzyl)phosphinate TFA salt (5.2 mg, 52% yield).

$^1$H NMR (400 MHz, CD$_3$OD) δ=1.29 (t, J=6.9 Hz, 3H), 1.47 (d, J=13.9 Hz, 3H), 3.20 (s, 3H), 3.30 (d, J=17.5 Hz, 2H), 3.97 (s, 3H), 4.02-4.13 (m, 2H), 4.59 (s, 2H), 7.37 (dd, J=8.6, 2.3 Hz, 2H), 7.58 (d, J=8.1 Hz, 2H), 7.68 (d, J=8.6 Hz, 1H), 7.89 (s, 1H), 8.02 (s, 1H), 8.36 (s, 1H), 8.66 (br. s., 1H). MS (ES+): m/z 600.23 (100) [MH+]; HPLC: tR=0.92 min (UPLC, purity).

The following compounds were prepared in an analogous manner utilizing either Example 61 as a precursor (as in the example above) or Example 62.

| Pre-Ex. | cursor | Compound Name | HPLC Retention time (min.) | MS Data (M + H) |
|---|---|---|---|---|
| 64 | Ex. 61 | Ethyl (4-{[4-({7-[1-(2-hydroxyethyl)-1H-pyrazol-4-yl]-2-methyl-3-oxo-2,3-dihydro-1H-isoindol-4-yl}amino)-5-(trifluoromethyl)pyrimidin-2-yl]amino}benzyl)methylphosphinate | 0.86 | 630.23 |
| 65 | Ex. 61 | Ethyl [4-({4-[(7-{1-[(2R)-2,3-dihydroxypropyl]-1H-pyrazol-4-yl}-2-methyl-3-oxo-2,3-dihydro-1H-isoindol-4-yl)amino]-5-(trifluoromethyl)pyrimidin-2-yl}amino)benzyl]methylphosphinate | 0.82 | 660.30 |
| 66 | Ex. 61 | Ethyl methyl[4-({4-[(2-methyl-3-oxo-7-phenyl-2,3-dihydro-1H-isoindol-4-yl)amino]-5-(trifluoromethyl)pyrimidin-2-yl}amino)benzyl]phosphinate | 1.13 | 596.20 |
| 67 | Ex. 61 | Ethyl methyl(4-{[4-{[2-methyl-3-oxo-7-(1H-pyrazol-4-yl)-2,3-dihydro-1H-isoindol-4-yl]amino}-5-(trifluoromethyl)pyrimidin-2-yl]amino}benzyl)phosphinate | 0.87 | 586.22 |
| 68 | Ex. 61 | Ethyl methyl(4-{[4-{[2-methyl-3-oxo-7-(prop-1-en-2-yl)-2,3-dihydro-1H-isoindol-4-yl]amino}-5-(trifluoromethyl)pyrimidin-2-yl]amino}benzyl)phosphinate | 1.08 | 560.25 |
| 69 | Ex. 62 | Diethyl (4-{[4-({7-[1-(2-hydroxyethyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate | 0.96 | 690.41 |
| 70 | Ex. 62 | Diethyl [4-({4-[(7-{1-[(2S)-2,3-dihydroxypropyl]-1H-pyrazol-4-yl}-2-methyl-3-oxo-2,3-dihydro-1H-isoindol-4-yl)amino]-5-(trifluoromethyl)pyrimidin-2-yl}amino)-3-methoxybenzyl]phosphonate | 0.92 | 720.49 |
| 71 | Ex. 62 | Diethyl (3-methoxy-4-{[4-{[2-methyl-7-(1-methyl-1H-pyrazol-4-yl)-3-oxo-2,3-dihydro-1H-isoindol-4-yl]amino}-5-(trifluoromethyl)pyrimidin-2-yl]amino}benzyl)phosphonate | 1.04 | 660.43 |
| 72 | Ex. 62 | Diethyl (4-{[4-({7-[1-(2-hydroxy-2-methylpropyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate | 1.04 | 718.56 |
| 73 | Ex. 62 | Diethyl (4-{[4-{[7-(1-carbamoyl-1,2,3,6-tetrahydropyridin-4-yl)-2-methyl-3-oxo-2,3-dihydro-1H-isoindol-4-yl]amino}-5-(trifluoromethyl)pyrimidin-2-yl]amino}-3-methoxybenzyl)phosphonate | 0.96 | 704.45 |
| 74 | Ex. 62 | Diethyl (4-{[4-({7-[1-(3-hydroxycyclobutyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate | 1.00 | 716.56 |

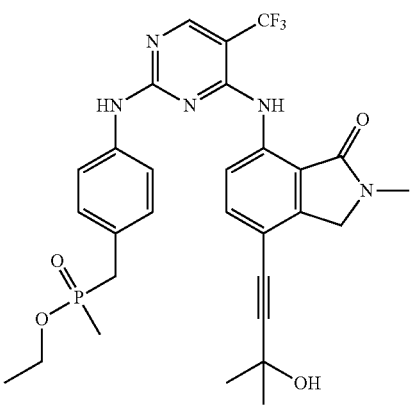 [SMILES: CCOP(C)(=O)Cc1ccc(Nc2ncc(C(F)(F)F)c(Nc3ccc(C#CC(C)(C)O)c4c3C(=O)N(C)C4)n2)cc1]

Example 75

Ethyl (4-{[4-{[7-(3-hydroxy-3-methylbut-1-yn-1-yl)-2-methyl-3-oxo-2,3-dihydro-1H-isoindol-4-yl]amino}-5-(trifluoromethyl)pyrimidin-2-yl]amino}benzyl)methylphosphinate Ethyl[4-({4-[(7-bromo-2-methyl-3-oxo-2,3-dihydro-1H-isoindol-4-yl)amino]-5-(trifluoromethyl)pyrimidin-2-yl}amino)benzyl]methylphosphinate (Ex. 61, 10 mg, 0.017 mmol) was mixed with 2-methyl-3-butyn-2-ol (8.2 µL, 0.084 mmol), triphenylphosphine (1.3 mg, 0.0050 mmol), DIPEA (58 µL, 0.334 mmol), dioxane (1.0 mL), CuI (0.3 mg, 0.00017 mmol) and [1,1'-bis(diphenylphosphino)ferrocene]dichloropalladium(II), complex with dichloromethane(1:1) (1.4 mg, 0.0017 mmol). The mixture was irradiated in a microwave reactor under nitrogen at 105° C. for 1 hour. The crude mixture was passed through a thiol-SPE cartridge to remove Pd residues and then purified by preparative HPLC (MDP) to afford ethyl (4-{[4-{[7-(3-hydroxy-3-methylbut-1-yn-1-yl)-2-methyl-3-oxo-2,3-dihydro-1H-isoindol-4-yl]amino}-5-(trifluoromethyl)pyrimidin-2-yl]amino}benzyl)methylphosphinate TFA salt (3.8 mg, 38% yield).

1H NMR (400 MHz, DMSO-d6) δ=1.22 (t, J=6.9 Hz, 3H), 1.34 (d, J=13.9 Hz, 3H), 1.50 (s, 6H), 3.10 (s, 3H), 3.19 (d, J=17.7 Hz, 2H), 3.93-4.02 (m, 2H), 4.47 (s, 2H), 7.27 (d, J=6.8 Hz, 2H), 7.44 (br. s., 1H), 7.57 (br. s., 2H), 8.50 (s, 1H), 8.70 (br. s., 1H), 9.96 (s, 1H). MS (ES+): m/z 602.24 (100) [MH+]; HPLC: tR=0.99 min (UPLC, purity).

The following compounds were prepared in an analogous manner.

| Ex. | Compound Name | HPLC Retention Time (min.) | MS Data (M + H) |
|---|---|---|---|
| 76 | Ethyl (4-{[4-{[7-(3-hydroxybut-1-yn-1-yl)-2-methyl-3-oxo-2,3-dihydro-1H-isoindol-4-yl]amino}-5-(trifluoromethyl)pyrimidin-2-yl]amino}benzyl)methylphosphinate | 0.95 | 588.27 |
| 77 | Ethyl (4-{[4-{[7-(3-hydroxyprop-1-yn-1-yl)-2-methyl-3-oxo-2,3-dihydro-1H-isoindol-4-yl]amino}-5-(trifluoromethyl)pyrimidin-2-yl]amino}benzyl)methylphosphinate | 0.91 | 574.22 |

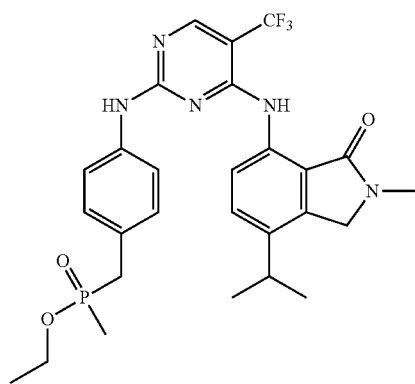 [SMILES: CCOP(C)(=O)Cc1ccc(Nc2ncc(C(F)(F)F)c(Nc3ccc(C(C)C)c4c3C(=O)N(C)C4)n2)cc1]

Example 78

Ethyl methyl(4-{[4-{[2-methyl-3-oxo-7-(propan-2-yl)-2,3-dihydro-1H-isoindol-4-yl]amino}-5-(trifluoromethyl)pyrimidin-2-yl]amino}benzyl)phosphinate A mixture of ethyl methyl(4-{[4-{[2-methyl-3-oxo-7-(prop-1-en-2-yl)-2,3-dihydro-1H-isoindol-4-yl]amino}-5-(trifluoromethyl)pyrimidin-2-yl]amino}benzyl)phosphinate (Ex. 68, 5 mg, 0.009 mmol) and 1.0 mg of Pd/C in 1 mL methanol was stirred under an atmosphere of hydrogen overnight. The mixture then was filtered and purified by preparative HPLC (MDP) to afford and ethyl methyl(4-{[4-{[2-methyl-3-oxo-7-(propan-2-yl)-2,3-dihydro-1H-isoindol-4-yl]amino}-5-(trifluoromethyl)pyrimidin-2-yl]amino}benzyl)phosphinate TFA salt 21 (1.2 mg, 24% yield).

1H NMR (400 MHz, DMSO-d6) δ=1.20 (t, J=7.1 Hz, 3H), 1.25 (d, J=6.8 Hz, 6H), 1.34 (d, J=13.6 Hz, 3H), 2.95 (ddd, J=13.8, 6.8, 6.7 Hz, 1H), 3.18 (d, J=17.9 Hz, 2H), 3.89-4.02 (m, 2H), 4.52 (s, 2H), 7.19-7.29 (m, 2H), 7.37 (d, J=8.1 Hz, 1H), 7.58 (br. s., 2 H), 8.42-8.54 (m, 2H), 9.88 (s, 1H), 10.58 (br. s., 1H). MS (ES+): m/z 562.29 (100) [MH+]; HPLC: tR=1.08 min (UPLC, purity).

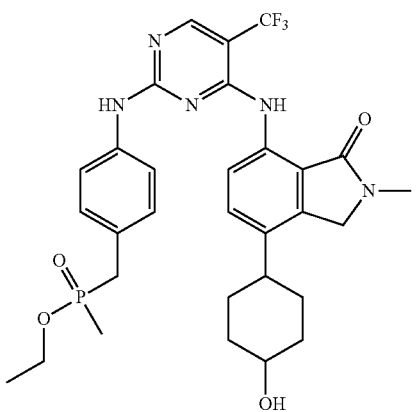 [SMILES: CCOP(C)(=O)Cc1ccc(Nc2ncc(C(F)(F)F)c(Nc3ccc(C4CCC(O)CC4)c4c3C(=O)N(C)C4)n2)cc1]

Example 79

Ethyl (4-{[4-{[7-(4-hydroxycyclohexyl)-2-methyl-3-oxo-2,3-dihydro-1H-isoindol-4-yl]amino}-5-(trifluoromethyl)pyrimidin-2-yl]amino}benzyl)methylphosphinate A mixture of ethyl[4-({4-[(7-bromo-2-methyl-3-oxo-2,3-dihydro-1H-isoindol-4-yl)amino]-5-(trifluoromethyl)pyrimidin-2-yl}amino)benzyl]methylphosphinate (Ex. 61, 15 mg, 0.025 mmol), 4-hydropiperidine (127 mg, 1.25 mmol), Pd(dba)2 (2.9 mg, 0.0050 mmol), BINAP (15.6 mg, 0.025 mmol), cesium carbonate (24.5 mg, 0.075 mmol) and dioxane (1.0 mL) was heated at 100° C. under nitrogen for 16 hr. The crude reaction mixture was passed through a thiol-SPE cartridge to remove Pd residues and then purified by preparative HPLC (MDP) to afford ethyl (4-{[4-{[7-(4-hydroxycyclohexyl)-2-methyl-3-oxo-2,3-dihydro-1H-isoindol-4-yl]amino}-5-(trifluoromethyl)pyrimidin-2-yl]amino}benzyl)methylphosphinate TFA salt (1.2 mg, 7.7% yield). 1H NMR (400 MHz, CD3OD) δ=1.32 (t, J=6.9 Hz, 3H), 1.49 (d, J=13.9 Hz, 3H), 1.69-1.83 (m, 2H), 2.01-2.12 (m, 2H), 3.05 (t, J=9.9 Hz, 2H), 3.19 (s, 3H), 3.31 (d, J=17.2 Hz, 2H), 3.39-3.48 (m, 2H), 3.85 (dt, J=8.4, 4.3 Hz, 1H), 4.03-4.15 (m, 2H), 4.56 (s, 2H), 7.22 (d, J=8.6 Hz, 1H), 7.37 (dd, J=8.6, 2.3 Hz, 2H), 7.55 (d, J=8.3 Hz, 2H), 8.34 (s, 1H), 8.58 (br. s., 1H). MS (ES+): m/z 619.41 (100) [MH+]; HPLC: tR=0.84 min (UPLC, purity).

The following compounds were prepared in an analogous manner utilizing either Example 61 as a precursor (as in the example above) or Example 62.

| Ex. | Precursor | Compound Name | HPLC Retention time (min.) | MS Data (M + H) |
|---|---|---|---|---|
| 80 | Ex. 61 | Ethyl methyl(4-{[4-{[2-methyl-3-oxo-7-(pyrrolidin-1-yl)-2,3-dihydro-1H-isoindol-4-yl]amino}-5-(trifluoromethyl)pyrimidin-2-yl]amino}benzyl)phosphinate | 1.01 | 589.37 |
| 81 | Ex. 61 | Ethyl (4-{[4-{[7-(3-hydroxypyrrolidin-1-yl)-2-methyl-3-oxo-2,3-dihydro-1H-isoindol-4-yl]amino}-5-(trifluoromethyl)pyrimidin-2-yl]amino}benzyl)methylphosphinate | 0.83 | 605.36 |
| 82 | Ex. 61 | Ethyl methyl(4-{[4-{[2-methyl-3-oxo-7-(piperidin-1-yl)-2,3-dihydro-1H-isoindol-4-yl]amino}-5-(trifluoromethyl)pyrimidin-2-yl]amino}benzyl)phosphinate | 1.04 | 603.35 |
| 83 | Ex. 62 | Diethyl (3-methoxy-4-{[4-{[2-methyl-3-oxo-7-(pyrrolidin-1-yl)-2,3-dihydro-1H-isoindol-4-yl]amino}-5-(trifluoromethyl)pyrimidin-2-yl]amino}benzyl)phosphonate | 1.14 | 649.35 |
| 84 | Ex. 62 | Diethyl (4-({7-[(3S)-3-hydroxypyrrolidin-1-yl]-2-methyl-3-oxo-2,3-dihydro-1H-isoindol-4-yl}amino)-5-(trifluoromethyl)pyrimidin-2-yl]amino}-3-methoxybenzyl)phosphonate | 0.94 | 665.42 |
| 85 | Ex. 62 | Diethyl (4-{[4-{[7-(4-hydroxypiperidin-1-yl)-2-methyl-3-oxo-2,3-dihydro-1H-isoindol-4-yl]amino}-5-(trifluoromethyl)pyrimidin-2-yl]amino}-3-methoxybenzyl)phosphonate | 0.96 | 679.41 |
| 86 | Ex. 62 | Diethyl (4-{[4-{[7-(3-hydroxypiperidin-1-yl)-2-methyl-3-oxo-2,3-dihydro-1H-isoindol-4-yl]amino}-5-(trifluoromethyl)pyrimidin-2-yl]amino}-3-methoxybenzyl)phosphonate | 1.02 | 679.49 |

Example 87

Ethyl cis-4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexanecarboxylate A solution of diethyl (4-{[4-chloro-5-(trifluoromethyl)pyrimidin-2-yl]amino}-3-methoxybenzyl)phosphonate (119.5 mg, 0.26 mmol) and ethyl cis-4-(7-amino-2-methyl-1-oxo-2,3-dihydro-1H-isoindol-4-yl)cyclohexanecarboxylate (100 mg, 0.32 mmol) in TFE (2.39 mL, 32.8 mmol) was treated with TFA (90.1 mg, 0.790 mmol) and irradiated on the microwave at 105° C. for 30 minutes. The reaction mixture was concentrated under reduced pressure to a solid. The material was purified on a CombiFlash®Rf 4X Organic Purification System [24 g RediSep® Normal-phase GOLD Silica Flash Column, dry loaded, elution gradient: 0→5% MeOH in 1:1 DCM/EtOAc] to afford 74 mg (38%) of the desired product. $^1$H NMR (400 MHz, MeOD) δ ppm 8.46 (br. s., 1H), 8.35 (s, 1H), 7.89 (d, J=8.08 Hz, 1H), 7.26 (d, J=8.84 Hz, 1H), 7.08 (t, J=2.02 Hz, 1H), 6.94 (dt, 1H), 4.52 (s, 2H), 4.26 (q, J=7.07 Hz, 2H), 4.11 (quin, J=7.26 Hz, 4H), 3.92 (s, 3H), 3.36 (br. s., 1H), 3.30 (br. s., 1H), 3.20 (s, 3H), 2.79 (br. s., 1H), 2.68 (br. s., 1H), 2.28-2.33 (m, 2H), 2.30 (d, J=6.82 Hz, 2H), 1.77 (d, J=5.81 Hz, 6H), 1.27-1.37 (m, 9H). MS (ES+): m/z=734.23 [MH+]. HPLC: $t_R$=1.77 min (UPLC TOF, polar_3 min).

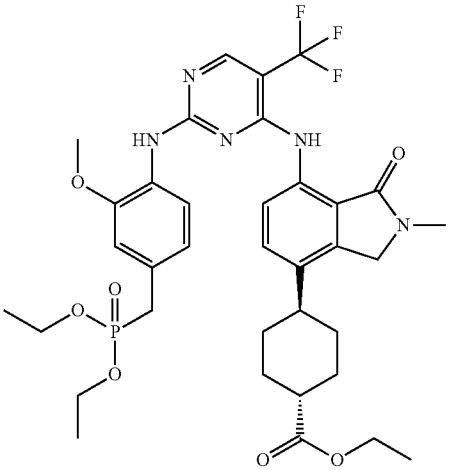

Example 88

Ethyl trans-4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexanecarboxylate This compound was prepared in a manner analogous to Example 87 using diethyl (4-{[4-chloro-5-(trifluoromethyl)pyrimidin-2-yl]amino}-3-methoxybenzyl)phosphonate and ethyl trans-4-(7-amino-2-methyl-1-oxo-2,3-dihydro-1H-isoindol-4-yl)cyclohexanecarboxylate. $^1$H NMR (400 MHz, MeOD) δ ppm 8.51 (d, J=8.84 Hz, 1H), 8.36 (s, 1H), 7.89 (d, J=8.08 Hz, 1H), 7.40 (d, J=8.84 Hz, 1H), 7.08 (t, J=2.02 Hz, 1H), 6.97 (dt, 1H), 4.53 (s, 2H), 4.06-4.20 (m, 6H), 3.92 (s, 3H), 3.35-3.36 (m, 1H), 3.29-3.31 (m, 1H), 3.20 (s, 3H), 2.44-2.68 (m, 2H), 2.14 (d, J=10.61 Hz, 2H), 1.91-1.98 (m,

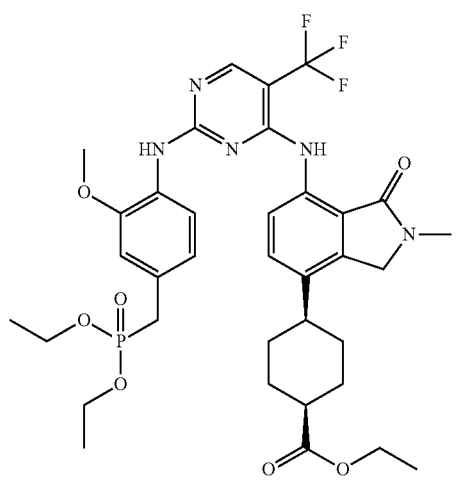 [SMILES: CCOC(=O)[C@H]1CC[C@@H](c2ccc(Nc3nc(Nc4ccc(CP(=O)(OCC)OCC)cc4OC)ncc3C(F)(F)F)c3c2CN(C)C3=O)CC1]

2H), 1.57-1.77 (m, 4H), 1.30 (q, 9H). MS (ES+): m/z=734.84 [MH+]. HPLC: $t_R$=1.74 min (UPLC TOF, polar_3 min).

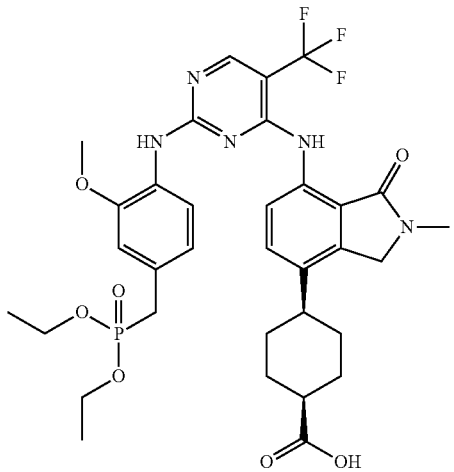 [SMILES: CCOP(=O)(Cc1ccc(Nc2ncc(C(F)(F)F)c(Nc3ccc([C@H]4CC[C@@H](C(=O)O)CC4)c4c3C(=O)N(C)C4)n2)c(OC)c1)OCC]

Example 89

Cis-4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexanecarboxylic acid Ethyl cis-4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexanecarboxylate (Example 87, 64.0 mg, 0.087 mmol) was taken up in THF (0.50 mL, 6.2 mmol) and MeOH (0.50 mL, 12 mmol). This was treated with a solution of Lithium hydroxide, monohydrate (18.3 mg, 0.44 mmol) in H$_2$O (0.50 mL, 28 mmol) and allowed to stir at rt for 30 hours, during which, the reaction mixture transformed from a thick slurry to a homogenous solution. The reaction was concentrated in vacuo to a solid. The crude product was purified by CombiFlash®Rf 4X Organic Purification System [12 g RediSep® Normal-phase GOLD Silica Flash Column, dried loaded, elution gradient: 0→7.5% MeOH in 1:1 EtOAc/DCM] to afford 4.0 mg (6% yield) of the desired product. $^1$H NMR (400 MHz, DMSO-d6) δ ppm 8.95 (s, 1H), 8.38 (s, 1H), 7.52 (br. s., 1H), 7.19 (br. s., 1H), 7.05 (s, 1H), 6.90 (d, J=8.59 Hz, 1H), 4.50 (s, 2H), 3.95-4.06 (m, 4H), 3.77 (s, 3H), 3.21-3.29 (m, 2H), 3.08 (s, 3H), 2.67 (br. s., 1H), 2.60 (br. s., 1H), 2.15 (d, J=7.83 Hz, 2H), 1.55-1.69 (m, 6H), 1.21 (t, 6H). MS (ES+): m/z=706.81 [MH+]. HPLC: $t_R$=1.55 min (UPLC TOF, polar_3 min). Example 89 may be further prepared as a salt. Non-limiting examples include the sodium, potassium, ammonium, 1,3-dihydroxy-2-(hydroxymethyl)propan-2-aminium [tromethamine], lysine and choline salts. This can be achieved by combining the compound with sodium hydroxide, potassium hydroxide, ammonium hydroxide, or 2-amino-2-(hydroxymethyl)propane-1,3-diol [tromethamine], lysine or choline by mixing of solids where appropriate or by combining solutions of known concentrations of either or both components. Known techniques include filtration of a suspension (if the salt precipitates) or concentration or lyophilization of the salt solution. The compound may be formulated as a solution using, for example, a combination of water, a cyclodextrin such as hydroxypropyl-β-cyclodextrin (HPBCD), a surfactant such as sodium lauryl sulfate (SLS), a PEG ether such as PEG-400, propylene glycol (PG) and a buffer to modulate the pH such as a bicarbonate, carbonate or hydroxide salt (or combination thereof). Some non-limiting examples of this are aqueous mixtures containing 5-10% SLS buffered to pH 9.5, 10% SLS+30% PEG400+15% PG, 40% HPBCD, and 20-40% HPBCD buffered to pH 9.5. The skilled artisan will realize there are other excipients and combinations including solid, suspension and other solution forms.

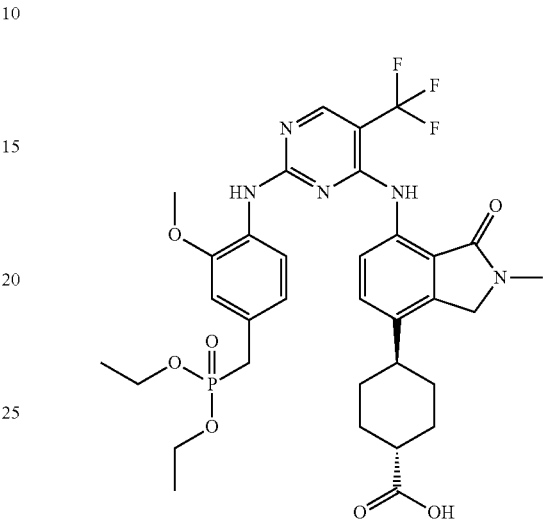

Example 90

Trans-4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexanecarboxylic acid Ethyl trans-4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexanecarboxylate (Example 88, 40.0 mg, 0.055 mmol) was taken up in THF (0.073 mL, 0.90 mmol) and MeOH (0.073 mL, 1.8 mmol). This was treated with a solution of Lithium hydroxide, monohydrate (11.4 mg, 0.27 mmol) in H$_2$O (0.073 mL, 4.1 mmol) and allowed to stir at rt for 30 hrs during which, the reaction mixture transformed from a thick slurry to a homogenous solution. The reaction was concentrated in vacuo to a solid. The product was purified by CombiFlash®Rf 4X Organic Purification System [24 g RediSep® Normal-phase GOLD Silica Flash Column, dried loaded, elution gradient: 0→5% MeOH in DCM] to afford 38.7 mg (100% yield) of the desired product. $^1$H NMR (400 MHz, DMSO-d6) δ ppm 8.95 (s, 1H), 8.38 (s, 1H), 7.52 (br. s., 1H), 7.19 (br. s., 1H), 7.05 (s, 1H), 6.90 (d, J=8.59 Hz, 1H), 4.50 (s, 2H), 3.95-4.06 (m, 4H), 3.77 (s, 3H), 3.21-3.29 (m, 2H), 3.08 (s, 3H), 2.67 (br. s., 1H), 2.60 (br. s., 1H), 2.15 (d, J=7.83 Hz, 2H), 1.55-1.69 (m, 6H), 1.21 (t, 6H). MS (ES+): m/z 706.22 [MH+]. HPLC: $t_R$=1.55 min (UPLC TOF, polar_3 min). Example 90 may be further prepared as a salt. Non-limiting examples include the sodium, potassium, ammonium, and 1,3-dihydroxy-2-(hydroxymethyl)propan-2-aminium salts. This can be achieved by dissolving the compound in methanol or ethanol with a suitable co-solvent such as DCM or THF and treating the resulting solution with the necessary amount of an aqueous stock solution of known concentration of sodium hydroxide, potassium hydroxide, or 2-amino-2-(hydroxymethyl)propane-1,3-diol. The resulting mixture can be thoroughly stirred or sonicated to ensure dissolution and mixing. The solvents can then be removed under reduced pressure to afford the appropriate salt.

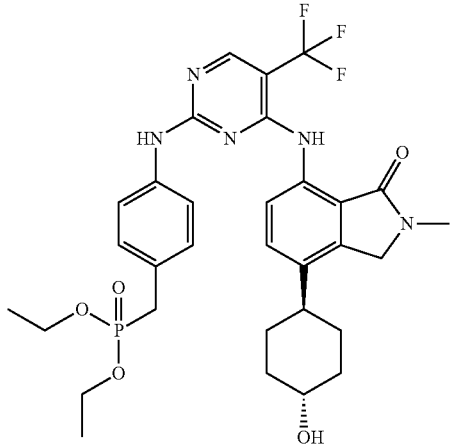 [SMILES: CCOP(=O)(Cc1ccc(Nc2ncc(C(F)(F)F)c(Nc3ccc([C@H]4CC[C@H](O)CC4)c4c3C(=O)N(C)C4)n2)cc1)OCC]

Example 91

Diethyl (4-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}benzyl) phosphonate This compound was prepared in a manner analogous to Example 87 using diethyl (4-{[4-chloro-5-(trifluoromethyl)pyrimidin-2-yl]amino}-3-methoxybenzyl)phosphonate and 7-amino-4-(trans-4-hydroxycyclohexyl)-2-methyl-2,3-dihydro-1H-isoindol-1-one. Purification: ISCO Combi-flash Rf system, eluting with 0 to 5% MeOH in EtOAc. $^1$H NMR (400 MHz, DMSO-$d_6$) δ 10.57 (s, 1H), 9.87 (s, 1H), 8.45 (s, 1H), 7.56 (br. s., 1H), 7.38 (d, J=8.59 Hz, 1H), 7.26 (dd, J=2.15, 8.46 Hz, 2H), 4.58 (d, J=4.55 Hz, 1H), 4.52 (s, 2H), 3.91-4.01 (m, 4H), 3.46-3.54 (m, 1H), 3.17-3.27 (m, 2H), 3.08 (s, 3H), 1.94 (d, J=9.85 Hz, 2H), 1.76 (d, J=12.13 Hz, 2H), 1.53-1.65 (m, 2H), 1.23-1.36 (m, 2H), 1.18 (t, J=7.07 Hz, 6H). MS (ES$^+$): m/z: 648.1830 [MH$^+$]. HPLC: $t_R$=1.44 min (UPLC TOF MS: polar_3 min).

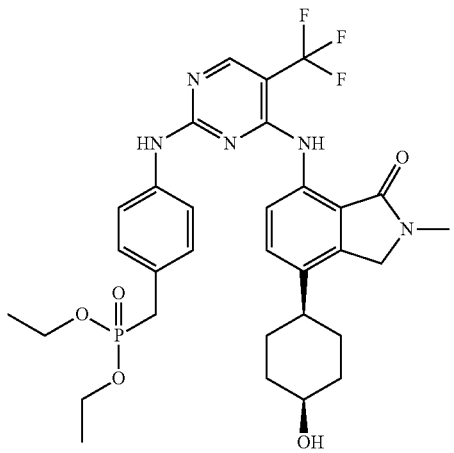 [SMILES: CCOP(=O)(Cc1ccc(Nc2ncc(C(F)(F)F)c(Nc3ccc([C@H]4CC[C@@H](O)CC4)c4c3C(=O)N(C)C4)n2)cc1)OCC]

Example 92

Diethyl (4-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}benzyl) phosphonate This compound was prepared in a manner analogous to Example 87 using diethyl (4-{[4-chloro-5-(trifluoromethyl)pyrimidin-2-yl]amino}-3-methoxybenzyl)phosphonate and 7-amino-4-(cis-4-hydroxycyclohexyl)-2-methyl-2,3-dihydro-1H-isoindol-1-one. Purification: ISCO Combi-flash Rf system, eluting with 0 to 5% MeOH in EtOAc. $^1$H NMR (400 MHz, DMSO-$d_6$) δ 10.58 (br. s., 1H), 9.87 (s, 1H), 8.46 (s, 1H), 7.37 (d, J=8.34 Hz, 1H), 7.25 (dd, J=2.53, 8.59 Hz, 3H), 4.52 (s, 3H), 4.40 (d, J=4.04 Hz, 2H), 3.89-4.02 (m, 5H), 3.17-3.26 (m, 2H), 3.08 (s, 3H), 1.91 (q, J=12.80 Hz, 1H), 1.78 (d, J=13.64 Hz, 2H), 1.48-1.62 (m, 4H), 1.18 (t, J=7.07 Hz, 6H). MS (ES$^+$): m/z: 648.22 [MH$^+$]. HPLC: $t_R$=3.46 min (Micromass ZQ3: polar_5 min).

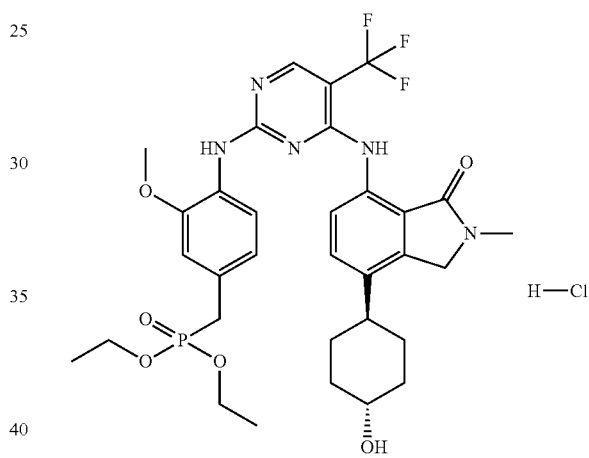

Example 93

Diethyl (4-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}-3-methoxybenzyl)phosphonate hydrochloride This compound was prepared in a manner analogous to Example 87 using diethyl (4-{[4-chloro-5-(trifluoromethyl)pyrimidin-2-yl]amino}-3-methoxybenzyl)phosphonate and 7-amino-4-(trans-4-hydroxycyclohexyl)-2-methyl-2,3-dihydro-1H-isoindol-1-one. Purification: ISCO Combi-flash RF system eluting with 0 to 5% MeOH in EtOAc. The pure product was dissolved in 1 mL of 12M HCl then concentrated in vacuo to afford the title compound as the HCl Salt: $^1$H NMR (400 MHz, DMSO-$d_6$) δ10.60 (s, 1H), 9.10 (br. s., 1H), 8.37 (s, 1H), 7.43 (br. s., 1H), 7.31 (d, J=8.59 Hz, 1H), 7.07 (s, 1H), 6.92 (d, J=7.83 Hz, 1H), 4.48 (s, 2H), 3.92-4.05 (m, 7H), 3.44-3.56 (m, 1H), 3.23-3.35 (m, 2H), 3.06 (s, 3H), 1.92 (d, J=10.36 Hz, 2H), 1.54-1.75 (m, 4H), 1.23-1.33 (m, 2H), 1.19 (t, J=7.07 Hz, 6H). MS (ES$^+$): m/z: 678.24 [MH$^+$]. HPLC: $t_R$=3.37 min (Micromass ZQ3: polar_5 min).

Example 94

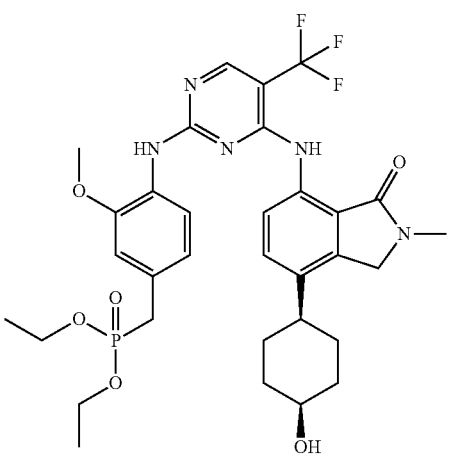 [SMILES: CCOP(=O)(Cc1ccc(Nc2ncc(C(F)(F)F)c(Nc3ccc([C@H]4CC[C@@H](O)CC4)c4c3C(=O)N(C)C4)n2)c(OC)c1)OCC]

Diethyl (4-{[4-{[7-(cis-4-hydroxycyclohexyl)-2-methyl-3-oxo-2,3-dihydro-1H-isoindol-4-yl]amino}-5-(trifluoromethyl)pyrimidin-2-yl]amino}-3-methoxybenzyl)phosphonate This compound was prepared in a manner analogous to Example 87 using diethyl (4-{[4-chloro-5-(trifluoromethyl)pyrimidin-2-yl]amino}-3-methoxybenzyl)phosphonate and 7-amino-4-(cis-4-hydroxycyclohexyl)-2-methyl-2,3-dihydro-1H-isoindol-1-one. Purification: ISCO Combi-flash Rf system, eluting with 0 to 5% MeOH in EtOAc. $^1$H NMR (400 MHz, DMSO-$d_6$) δ10.56 (s, 1H), 9.00 (s, 1H), 8.37 (s, 1H), 7.47 (br. s., 1H), 7.29 (d, J=8.34 Hz, 1H), 7.06 (s, 1H), 6.91 (d, J=8.08 Hz, 1H), 4.49 (s, 2H), 4.40 (d, J=4.80 Hz, 1H), 3.95-4.07 (m, 4H), 3.91 (br. s., 1H), 3.75 (s, 3H), 3.07 (s, 3H), 1.84-1.97 (m, 2H), 1.77 (d, J=12.38 Hz, 2H), 1.43-1.61 (m, 4H), 1.20 (t, J=6.95 Hz, 6H); MS (ES$^+$): m/z: 678.24 [MH$^+$]. HPLC: $t_R$=3.52 min (ZQ3: polar_5 min).

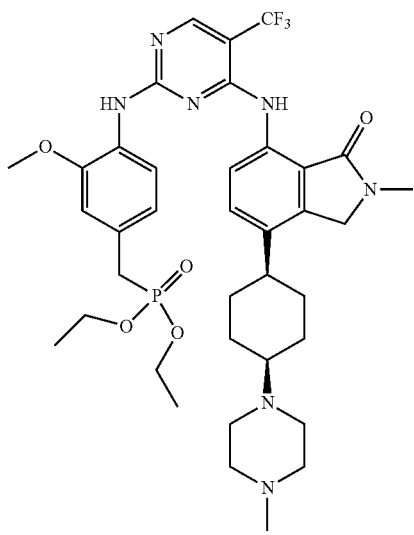

Example 95

Diethyl (3-methoxy-4-{[4-({2-methyl-7-[cis-4-(4-methylpiperazin-1-yl)cyclohexyl]-3-oxo-2,3-dihydro-1H-isoindol-4-yl}amino)-5-(trifluoromethyl)pyrimidin-2-yl]amino}benzyl)phosphonate This compound was prepared in a manner analogous to Example 87 using diethyl (4-{[4-chloro-5-(trifluoromethyl)pyrimidin-2-yl]amino}-3-methoxybenzyl)phosphonate and 7-amino-2-methyl-4-[cis-4-(4-methylpiperazin-1-yl)cyclohexyl]-2,3-dihydro-1H-isoindol-1-one.
$^1$H NMR (CD$_3$OD, 400 MHz): δ=1.29 (t, J=7.07 Hz, 6H), 1.72 (dd, J=12.76, 3.66 Hz, 2H), 1.77-1.89 (m, 2H), 1.92-2.04 (m, 2H), 2.21 (d, J=12.13 Hz, 2H), 2.81-2.91 (m, 2H), 2.93 (s, 3H), 3.19 (s, 3H), 3.33-3.41 (m, 2H), 3.45 (br. s., 3H), 3.91 (s, 3H), 4.05-4.15 (m, 4H), 4.55 (s, 2H), 6.99 (ddd, J=7.96, 2.40, 2.27 Hz, 1H), 7.13 (t, J=2.02 Hz, 1H), 7.45 (d, J=8.59 Hz, 1H), 7.70 (d, J=8.08 Hz, 1H), 8.36 (s, 1H), 8.41 (br. s., 1H). MS (ES$^+$): m/z 760.30 [MH$^+$]; HPLC: tR=1.18 minutes (UPLC TOF MS: polar_3 min).

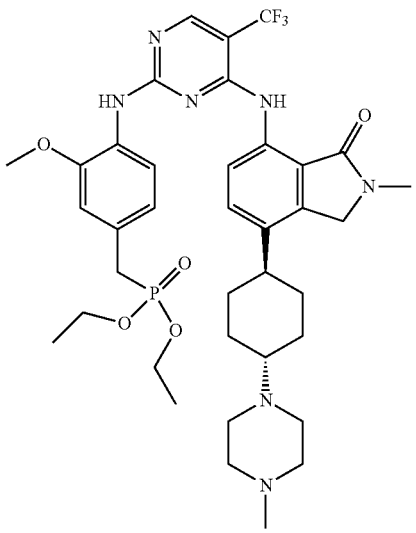

Example 96

Diethyl (3-methoxy-4-{[4-({2-methyl-7-[trans-4-(4-methylpiperazin-1-yl)cyclohexyl]-3-oxo-2,3-dihydro-1H-isoindol-4-yl}amino)-5-(trifluoromethyl)pyrimidin-2-yl]amino}benzyl)phosphonate This compound was prepared in a manner analogous to Example 87 using diethyl (4-{[4-chloro-5-(trifluoromethyl)pyrimidin-2-yl]amino}-3-methoxybenzyl)phosphonate and 7-amino-2-methyl-4-[trans-4-(4-methylpiperazin-1-yl)cyclohexyl]-2,3-dihydro-1H-isoindol-1-one.
$^1$H NMR (CDCl$_3$, 400 MHz): δ=1.25-1.30 (m, 6H), 1.40-1.55 (m, 2H), 1.62 (q, J=12.80 Hz, 2H), 1.97 (d, J=12.63 Hz, 2H), 2.13 (d, J=11.87 Hz, 2H), 2.37 (s, 3H), 2.50 (d, J=12.13 Hz, 2H), 2.61 (br. s., 2H), 2.77 (br. s., 3H), 3.14-3.20 (m, 2H), 3.22 (s, 3H), 3.93 (s, 3H), 4.00-4.10 (m, 4H), 4.38 (s, 2H), 6.89 (dt, J=8.15, 2.24 Hz, 1H), 6.94 (t, J=2.02 Hz, 1H), 7.34 (d, J=8.59 Hz, 1H), 7.63 (d, J=8.59 Hz, 1H), 8.29 (d, J=8.59 Hz, 1H), 8.39 (s, 1H), 8.63 (d, J=8.59 Hz, 1H), 10.50 (s, 1H). MS (ES$^+$): m/z 760.32 [MH$^+$]; HPLC: $t_R$=1.20 min (UPLC TOF MS: polar_3 min).

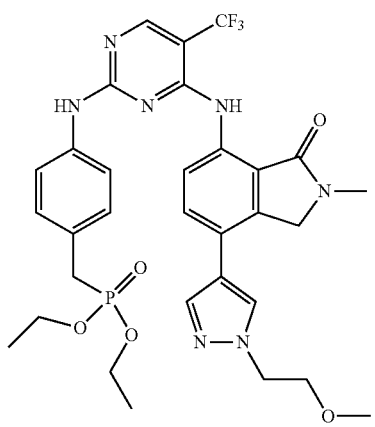 [SMILES: CCOP(=O)(Cc1ccc(Nc2ncc(C(F)(F)F)c(Nc3ccc(-c4cnn(CCOC)c4)c4c3C(=O)N(C)C4)n2)cc1)OCC]

Example 97

Diethyl (4-{[4-({7-[1-(2-methoxyethyl)-1H-pyrazol-4-yl]-2-methyl-3-oxo-2,3-dihydro-1H-isoindol-4-yl}amino)-5-(trifluoromethyl)pyrimidin-2-yl]amino}benzyl)phosphonate A mixture of diethyl[4-({4-[(7-bromo-2-methyl-3-oxo-2,3-dihydro-1H-isoindol-4-yl)amino]-5-(trifluoromethyl)pyrimidin-2-yl}amino)benzyl]phosphonate (10.0 mg, 0.0159 mmol), 1-(2-methoxyethyl)-4-(4,4,5,5-tetramethyl-1,3,2-dioxaborolan-2-yl)-1H-pyrazole (8.02 mg, 0.0318 mmol), potassium carbonate (6.60 mg, 0.0477 mmol), 1,4-dioxane (0.4 mL), H$_2$O (0.1 mL) and [1,1'-bis(diphenylphosphino)ferrocene]dichloropalladium(II), complex with dichloromethane (1:1) (1.30 mg, 0.00159 mmol) was evacuated and purged with N$_2$. The mixture was irradiated in a microwave reactor at 100° C. for 30 minutes. The crude mixture was passed through a Thiol-SPE column to remove Pd and purified by MDP to obtain the title compound (2.1 mg, 19.6% yield). $^1$H NMR (400 MHz, CD$_3$OD) δ=1.25 (t, J=7.1 Hz, 6H), 3.21 (s, 3H), 3.30 (d, J=22.7 Hz), 3.35 (s, 3H), 3.79 (t, J=5.2 Hz, 2H), 4.01-4.13 (m, 4H), 4.37 (t, J=5.2 Hz, 2H), 4.60 (s, 2H), 7.37 (dd, J=8.6, 2.3 Hz, 2H), 7.57 (d, J=8.6 Hz, 2H), 7.72 (d, J=8.8 Hz, 1H), 7.94 (s, 1H), 8.08 (s, 1H), 8.36 (s, 1H), 8.68 (br. s., 1H). MS (ES+): m/z 674.34 (100) [MH+]; HPLC: tR=1.05 min (UPLC, purity).

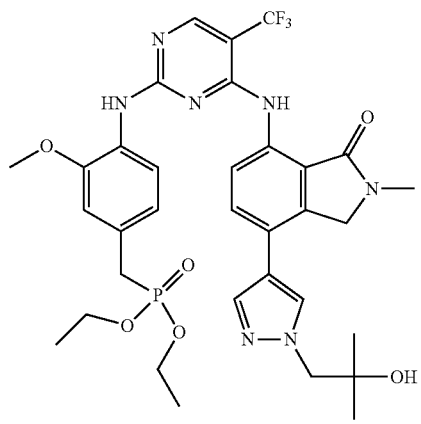

Example 98

Diethyl (4-{[4-({7-[1-(2-hydroxy-2-methylpropyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate The title compound was prepared using the procedure from Example 97 using diethyl[4-({4-[(7-bromo-2-methyl-3-oxo-2,3-dihydro-1H-isoindol-4-yl)amino]-5-(trifluoromethyl)pyrimidin-2-yl}amino)-3-methoxybenzyl]phosphonate and Compound 98A. MS (ES+): m/z 718.56 (100) [MH$^+$]; HPLC: t$_R$=1.04 min (UPLC, purity).

Compound 98A: 2-Methyl-1-[4-(4,4,5,5-tetramethyl-1,3,2-dioxaborolan-2-yl)-1H-pyrazol-1-yl]propan-2-ol Sodium hydride (58.74 mg, 0.002448 mol) was added to solution of 4-(4,4,5,5-tetramethyl[1,3,2]dioxaborolan-2-yl)-1H-pyrazole (500.0 mg, 0.002577 mol) in DMF (5 mL) at room temperature. After gas evolution ceased, 2,2-dimethyloxirane, (0.46 mL, 0.0052 mol) was added. The mixture was heated to 100° C. for 1 hour. The material was extracted with EtOAc, and washed with water (3×). The organic layer was concentrated in vacuo to afford the title compound as a tan solid. $^1$H NMR (400 MHz, DMSO-d6) δ=1.04 (s, 6H), 1.25 (s, 12H), 4.03 (s, 2H), 4.68 (s, 1H), 7.56 (s, 1H), 7.84 (s, 1H).

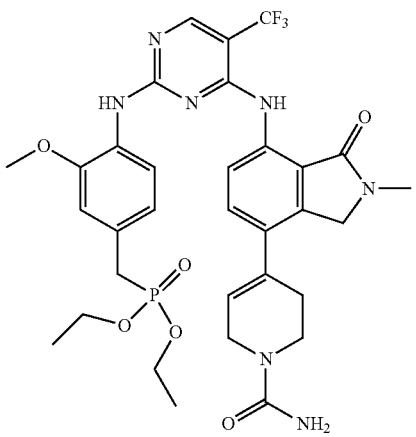

Example 99

Diethyl (4-{[4-{[7-(1-carbamoyl-1,2,3,6-tetrahydropyridin-4-yl)-2-methyl-3-oxo-2,3-dihydro-1H-isoindol-4-yl]amino}-5-(trifluoromethyl)pyrimidin-2-yl]amino}-3-methoxybenzyl)phosphonate The title compound was prepared using the procedure from Example 97 using diethyl[4-({4-[(7-bromo-2-methyl-3-oxo-2,3-dihydro-1H-isoindol-4-yl)amino]-5-(trifluoromethyl)pyrimidin-2-yl}amino)-3-methoxybenzyl]phosphonate and Compound 99A. MS (ES+): m/z 704.45 (100) [MH$^+$]; HPLC: t$_R$=0.96 min (UPLC, purity).

Compound 99A: 4-(4,4,5,5-Tetramethyl-1,3,2-dioxaborolan-2-yl)-3,6-dihydropyridine-1(2H)-carboxamide Trimethylsilyl isocyanate (0.2205 mL, 1.629 mmol) was added to a room temperature solution of 4-(4,4,5,5-tetramethyl-1,3,2-dioxaborolan-2-yl)-1,2,3,6-tetrahydropyridine (200.0 mg, 0.8145 mmol) and DIPEA (0.5675 mL, 3.258 mmol) in DCM (10 mL). The mixture was stirred for 3 hours, after which, it was partioned between DCM and sat. NaHCO$_3$. The organic layer was concentrated in vacuo to afford the title compound as a tan solid.

MS (ES+): m/z 253.07 (100) [MH$^+$]; HPLC: t$_R$=2.61 min (ZQ3, polar_5 min).

Compound 99B: 4-(4,4,5,5-Tetramethyl-1,3,2-dioxaborolan-2-yl)-1,2,3,6-tetrahydropyridine 4-(4,4,5,5-tetramethyl-[1,3,2]dioxaborolan-2-yl)-3,6-dihydro-2H-pyridine-1-carboxylic acid tert-butyl ester (Tetrahedron Letters, 2000, 44, pp 3705-3708, 500 mg, 1.617 mmol) was added 2 mL DCM and 2 mL TFA. The mixture was stirred at room temperature for 3 hours. The solvents were evaporated in vacuo to afford the title compound (323 mg, 96% yield). The product was not further purified for next step. MS (ES$^+$): m/z 210.19 (100) [MH$^+$]; HPLC: t$_R$=0.55 min (UPLC, Analytical).

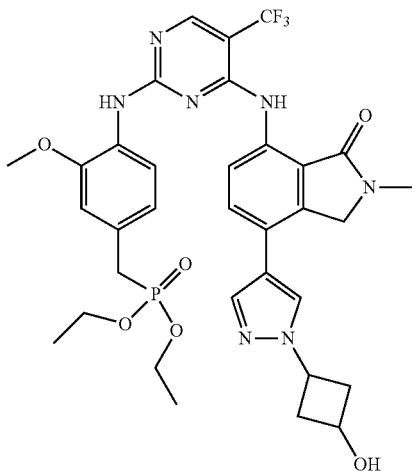

Example 100

Diethyl (4-{[4-({7-[1-(3-hydroxycyclobutyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate The title compound was prepared using the procedure from Example 97 using diethyl[4-({4-[(7-bromo-2-methyl-3-oxo-2,3-dihydro-1H-isoindol-4-yl)amino]-5-(trifluoromethyl)pyrimidin-2-yl}amino)-3-methoxybenzyl]phosphonate and Compound 100A. After the Suzuki reaction and SPE prepurification, dried material was dissolved in DCM and 1.0 M HCl in ether. The mixture was stirred at room temperature for half an hour. The crude material was purified using MDP. MS (ES+): m/z 716.56 (100) [MH$^+$]; HPLC: t$_R$=1.00 min (UPLC, purity).

Compound 100A: 1-(3-{[tert-butyl(dimethyl)silyl]oxy}cyclobutyl)-4-(4,4,5,5-tetramethyl-1,3,2-dioxaborolan-2-yl)-1H-pyrazole Over the course of 5 minutes, a 2.00 M solution of isopropylmagnesium chloride in THF (0.13084 mL, 0.26168 mmol) was added dropwise to an ice cooled solution of 1-[3-(tert-butyl-dimethyl-silanyloxy)-cyclobutyl]-4-iodo-1H-pyrazole (Compound 100B, 30.00 mg, 0.07930 mmol) in THF (0.33 mL). The reaction mixture was stirred at 0° C. for another hour. 2-Methoxy-4,4,5,5-tetramethyl-1,3,2-dioxaborolane (0.057933 mL, 0.33939 mmol) was added at 0° C. and then the mixture was stirred at rt for another hour. The reaction mixture was cooled back down to 0° C., quenched with saturated aqueous NH$_4$Cl, and extracted with EtOAc. The combined organic layers were washed with brine, dried over anhydrous Na$_2$SO$_4$, filtered, and concentrated in vacuo to dryness, giving the title compound as a colorless oil. Compound was taken on for the next step without further purification. MS (ES+): m/z 379.04 (100) [MH$^+$]; HPLC: t$_R$=3.85 min (ZQ3, polar_5 min).

Compound 100B: 1-[3-(tert-Butyl-dimethyl-silanyloxy)-cyclobutyl]-4-iodo-1H-pyrazole A mixture of 3-(4-Iodo-pyrazol-1-yl)-cyclobutanol (Compound 100C, 75.00 mg, 0.2840 mmol), 4-dimethylaminopyridine (6.940 mg, 0.05680 mmol), 1H-imidazole (58.01 mg, 0.8521 mmol), tert-butyldimethylsilyl chloride (0.08562 g, 0.5680 mmol) and DCM (4 mL) were stirred at room temperature for 20 minutes. The material was transferred to a separatory funnel extracting with DCM washing with aqueous saturated NaHCO$_3$. The organic layer was dry-loaded on silica for column chromatography eluting with 3% EtOAc in hexanes to afford 59 mg (55% yield) of the title compound as colorless oil. MS (ES$^+$): m/z 378.94 (100) [MH$^+$]; HPLC: t$_R$=4.35 min (Polar_5 min, ZQ3).

Compound 100C: 3-(4-Iodo-1H-pyrazol-1-yl)cyclobutanol 3-(4-Iodo-pyrazol-1-yl)cyclobutanone (Compound 100D, 1.000 g, 3.816 mmol), sodium borohydride (145.8 mg, 3.854 mmol) and ethanol (22.28 mL, 381.6 mmol) were added to a round bottom flask and the reaction mixture was stirred at 0° C. for 3 h. Reaction mixture was concentrated in vacuo and washed with water extracting with DCM. The organic layer was dried over anhydrous Na$_2$SO$_4$ and concentrated in vacuo to afford 956 mg of the final compound as colorless oil. Compound was taken on to the next step without further purification. MS (ES$^+$): m/z 264.86 (100) [MH$^+$]; HPLC: t$_R$=2.50 min (Polar_5 min, ZQ3).

Compound 100D: 3-(4-Iodo-pyrazol-1-yl)cyclobutanone

A solution of 1-(5,8-dioxa-spiro[3.4]oct-2-yl)-4-iodo-1H-pyrazole (Compound 100E, 8.8 g, 29 mmol) and pyridinium p-toluenesulfonate (21 g, 87 mmol) in dioxane-water (140 mL of 1:1 mixture) was stirred at 85° C. for 12 h. The reaction mixture was concentrated and diluted with ethyl acetate (100 mL), the organic layer was washed with water (2×50 mL), dried (Na$_2$SO$_4$) and concentrated to give 6.5 g (yield: 86%) of 3-(4-iodo-1H-pyrazol-1-yl)cyclobutanone. $^1$H NMR (CDCl$_3$, 300 MHz): δ=3.53-3.57 (m, 2H), 3.73-3.77 (m, 2H), 5.0-5.02 (m, 1H), 7.56 (s, 1H), 7.58 (s, 1H).

Compound 100E: 1-(5,8-dioxa-spiro[3.4]oct-2-yl)-4-iodo-1H-pyrazole

To a solution of 2-bromo-5,8-dioxa-spiro[3.4]octane (Compound 100F, 19 g, 100 mmol) and 4-iodopyrazole (38.6 g, 200 mmol) in DMF (100 mL) was added powdered $K_2CO_3$ (41.4 g, 300 mmol) and 18-crown-6 ether (5.3 g, 20 mmol). The reaction mixture was stirred at 85-90° C. for 2 days. The reaction mixture was diluted with ethyl acetate (400 mL) and washed with water (4×100 mL). The combined organic layers were washed with brine and concentrated, the residue was purified by column chromatography (ethyl acetate/DCM: 5:95) to give 8.8 g (29%) of 1-(5,8-dioxa-spiro[3.4]oct-2-yl)-4-iodo-1H-pyrazole. $^1$H NMR (CDCl$_3$, 300 MHz): δ=2.87-2.89 (m, 4H), 3.92-3.96 (m, 4H), 4.64-4.68 (m, 1H), 7.53 (s, 2H).

Compound 100F: 2-bromo-5,8-dioxa-spiro[3.4]octane

A mixture of 3-bromocyclobutanone (Compound 100F, 5.9 g, 39.6 mmol), 1,2-ethanediol (8.6 mL, 158.4 mmol) and PPTS (1.9 g, 7.92 mmol) in benzene (40 mL) was heated to reflux in a Dean-Stark apparatus. After 12 h, the reaction mixture was allowed to cool and washed with water (2×30 mL). The organic phase was dried (Na$_2$SO$_4$) and concentrated and the residue was purified by column chromatography (ethyl acetate/hexanes: 1:5) to give 984 mg of 2-bromo-5,8-dioxa-spiro[3.4]octane. $^1$H NMR (CDCl$_3$, 300 MHz): δ=2.77-2.82 (m, 2H), 2.95-3.00 (m, 2H), 4.19-4.23 (m, 1H).

Compound 100F: 3-bromocyclobutanone

A solution of bromine (0.51 mL, 10 mmol) in CCl$_4$ (20 mL) was heated to 70° C., then a mixture of 3-oxocyclobutanecarboxylic acid (1.14 g, 10 mmol) and red mercuric oxide (1.56 g, 7.9 mmol) was added over 30 min. After 1 h, the reaction mixture became colorless. The solids were filtered off and solvent was removed at 30° C. using rotary evaporator (product is volatile, 22° C./0.5 mmHg). The residue was dissolved in hexanes and filtered through a silica gel pad and concentrated to give 3-bromocyclobutane, which contains CCl$_4$. $^1$H NMR (CDCl$_3$, 300 MHz): δ=3.44-3.50 (m, 2H), 3.72-3.80 (m, 2H), 4.51-4.55 (m, 1H).

Example 101

Diethyl[4-({4-[(7-{1-[(2S)-2,3-dihydroxypropyl]-1H-pyrazol-4-yl}-2-methyl-3-oxo-2,3-dihydro-1H-isoindol-4-yl)amino]-5-(trifluoromethyl)pyrimidin-2-yl}amino)benzyl]phosphonate The title compound was prepared using the procedure from Example 97 using [4-({4-[(7-bromo-2-methyl-3-oxo-2,3-dihydro-1H-isoindol-4-yl)amino]-5-(trifluoromethyl)pyrimidin-2-yl}amino)benzyl]phosphonate and 1-{[(4S)-2,2-dimethyl-1,3-dioxolan-4-yl]methyl}-4-(4,4,5,5-tetramethyl-1,3,2-dioxaborolan-2-yl)-1H-pyrazole. After the Suzuki reaction and SPE pre-purification, the dried material was dissolved in DCM and 1.0 M HCl in ether. The mixture was stirred at room temperature for half an hour. The crude material was purified using MDP. 1H NMR (DMSO-d6) δ ppm: 10.74 (s, 1H), 9.91 (s, 1H), 8.70 (br s, 1H), 8.47 (s, 1H), 8.18 (s, 1H), 7.97 (s, 1H), 7.77 (d, J=8.6 Hz, 1H), 7.55 (br s, 2H), 7.30 (d, J=6.8 Hz, 2H), 5.00 (d, J=5.3 Hz, 1H), 4.76 (t, J=5.6 Hz, 1H), 4.64 (s, 2H), 4.27 (dd, J=13.8, 4.2 Hz, 1H), 4.02-4.07 (m, 1H), 3.93-4.02 (m, 4H), 3.84-3.92 (m, 1H), 3.35-3.43 (m, 2H), 3.20-3.29 (m, 2H), 3.13 (s, 3H), 1.17 (td, J=7.0, 1.9 Hz, 6H). MS (ES+): m/z 690.11 [MH$^+$]; HPLC: t$_R$=3.04 min (ZQ3, polar_5 min).

Compound 101A: 1-{[(4S)-2,2-dimethyl-1,3-dioxolan-4-yl]methyl}-4-(4,4,5,5-tetramethyl-1,3,2-dioxaborolan-2-yl)-1H-pyrazole A solution of 4-(4,4,5,5-Tetramethyl[1,3,2]dioxaborolan-2-yl)-1H-pyrazole (9.24 g, 47.6 mmol), (R)-(−)-(2,2-Dimethyl-1,3-dioxolan-4-yl)methyl p-toluenesulfonate (15.00 g, 52.38 mmol) and CsHCO$_3$ (23.3 g, 71.4 mmol) in anhydrous DMF (236 mL) was heated to 100° C. for 16 h. The reaction mixture was cooled to rt and partitioned between EtOAc and H$_2$O. The aqueous layer was re-extracted with EtOAc (3×) and the combined organic fractions were washed with H$_2$O (2×) and brine (2×), dried over Na$_2$SO$_4$, filtered and concentrated in vacuo resulting in the title compound as an orange oil which was used in the next step without further purification.

$^1$H NMR (400 MHz, CDCl$_3$): δ=1.31 (s, 12H), 1.33 (s, 3H), 1.39 (s, 3H), 3.78 (dd, J=8.8, 5.9 Hz, 1H), 4.07 (dd, J=8.8, 6.2 Hz, 1H), 4.23-4.35 (m, 2H), 4.47 (quint, J=5.8 Hz, 1H), 7.78 (s, 1H), 7.81 (s, 1H).

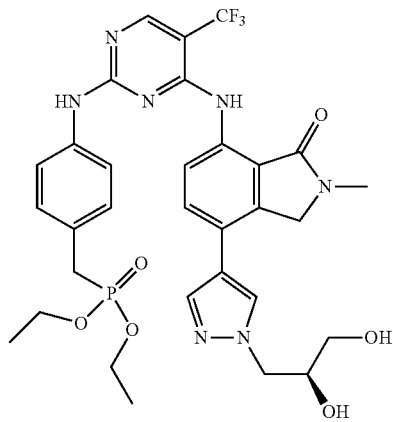 [SMILES: CCOP(=O)(Cc1ccc(Nc2ncc(C(F)(F)F)c(Nc3ccc(-c4cnn(C[C@H](O)CO)c4)c4c3C(=O)N(C)C4)n2)cc1)OCC]

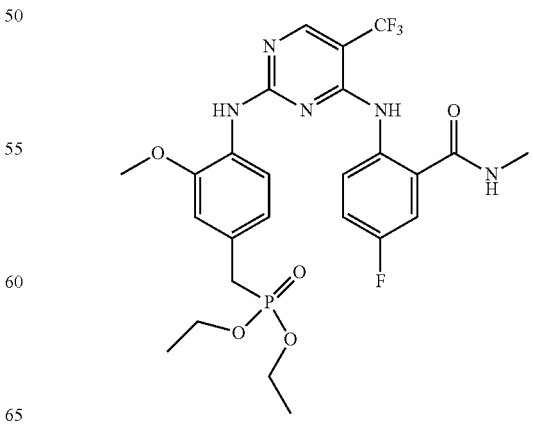

Example 102

Diethyl (4-{[4-{[4-fluoro-2-(methylcarbamoyl)phenyl]amino}-5-(trifluoromethyl)pyrimidin-2-yl]amino}-3-methoxybenzyl)phosphonate A solution of diethyl (4-{[4-chloro-5-(trifluoromethyl)pyrimidin-2-yl]amino}-3-methoxybenzyl)phosphonate (50.0 mg, 0.110 mmol) and 2-amino-5-fluoro-N-methylbenzamide (Compound 102A, 22.24 mg, 0.1322 mmol) in TFE (1.00 mL) was charged with TFA (37.7 mg, 0.330 mmol). The reaction mixture was irradiated on the microwave at 105° C. for 1 hour. The reaction mixture was concentrated under reduced pressure to yield a yellow oil. The material was purified by silica gel chromatography on an ISCO Combiflash Rf system using DCM/MeOH (100:0->95:5) as eluent. The fractions containing product were combined and concentrated under reduced pressure to yield a white solid, 21.4 mg (33% yield). The material still contained impurities, therefore was submitted for mass directed purification. The fractions containing product were combined and dried on the freeze dryer to yield a white solid, 10.9 mg (17% yield). $^1$H NMR (DMSO-d6, 400 MHz): δ=1.19 (t, J=7.07 Hz, 6H), 2.76 (d, J=4.55 Hz, 3H), 3.21-3.28 (m, 2H), 3.76 (s, 3H), 3.92-4.04 (m, 4H), 6.84 (d, J=6.57 Hz, 1H), 7.01 (br. s., 1H), 7.24 (br. s., 1H), 7.38-7.65 (m, 2H), 8.24-8.55 (m, 2H), 8.79 (br. s., 2H), 11.25 (br. s., 1H). MS (ES$^+$): m/z 586.19 [MH$^+$] (TOF, polar)

Compound 102A:
2-Amino-5-fluoro-N-methylbenzamide

A solution of 5-fluoro-N-methyl-2-nitrobenzamide (Compound 102B) in EtOH (10.0 mL) was charged with Palladium 10% wt on activated carbon (0.316 g, 0.297 mmol). The reaction mixture was evacuated and purged with hydrogen gas (3 times). The reaction mixture was allowed to stir under hydrogen at rt for 16 h. The reaction mixture was filtered through a pad of celite. The filtrate was concentrated under reduced pressure to yield a light yellow semi-solid. The material was purified by silica gel chromatography using DCM/MeOH (100:0→95:5) as eluent. The fractions containing product were combined and concentrated under reduced pressure to yield a white solid, 0.500 g (100% yield). $^1$H NMR (CDCl$_3$, 400 MHz): δ=2.98 (d, J=4.80 Hz, 3H), 5.30 (d, J=5.31 Hz, 1H), 6.64 (dd, J=8.84, 4.80 Hz, 1H), 6.96 (ddd, J=8.91, 7.89, 2.91 Hz, 1H), 7.02 (dd, J=9.22, 2.91 Hz, 1H). MS (ES$^+$): m/z 169.08 [MH$^+$] (TOF, polar).

Compound 102B:
5-fluoro-N-methyl-2-nitrobenzamide

A solution of 5-fluoro-2-nitrobenzoic acid (0.550 g, 2.97 mmol), methylamine hydrochloride (0.241 g, 3.56 mmol), TBTU (0.954 g, 2.97 mmol), and DIPEA (1.15 g, 8.91 mmol) in DCM (10.0 mL) was stirred at rt for 30 minutes. The reaction was quenched with saturated NaHCO$_3$ (10 mL) and extracted with DCM (15 mL). The organic layer was washed with brine (10 mL), dried over anhydrous Na$_2$SO$_4$, filtered, and concentrated under reduced pressure to yield a yellow semi-solid. $^1$H NMR (CDCl$_3$, 400 MHz): δ=3.06 (d, J=5.05 Hz, 3H), 7.20-7.26 (m, 1H), 8.16 (dd, J=8.84, 4.55 Hz, 1H). MS (ES$^+$): m/z 199.05 [MH$^+$] (TOF, polar).

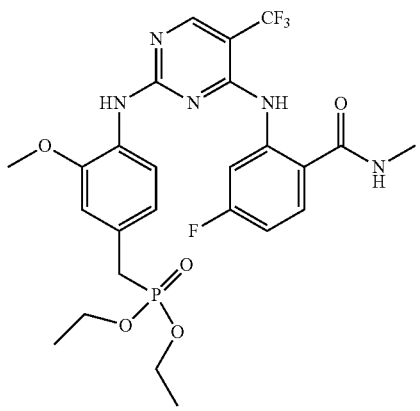

Example 103

Diethyl (4-{[4-{[5-fluoro-2-(methylcarbamoyl)phenyl]amino}-5-(trifluoromethyl)pyrimidin-2-yl]amino}-3-methoxybenzyl)phosphonate The title compound was prepared using the procedure from Example 102 using diethyl (4-{[4-chloro-5-(trifluoromethyl)pyrimidin-2-yl]amino}-3-methoxybenzyl)phosphonate and 2-Amino-4-fluoro-N-methylbenzamide. $^1$H NMR (DMSO-d6, 400 MHz): δ=1.19 (t, J=7.07 Hz, 6H), 2.77 (d, J=4.55 Hz, 3H), 3.16-3.24 (m, 2H), 3.78 (s, 3H), 3.92-4.01 (m, 4H), 6.83 (d, J=7.83 Hz, 1H), 6.93 (br. s., 1H), 6.99 (s, 1H), 7.53 (br. s., 1H), 7.78 (t, J=7.33 Hz, 1H), 8.25-8.48 (m, 2H), 8.62-9.04 (m, 2H), 11.86 (br. s., 1H). MS (ES$^+$): m/z 586.18 [MH$^+$] (TOF, polar).

Compound 103A:
2-Amino-4-fluoro-N-methylbenzamide

The title compound was prepared using the procedure from Compound 102A with 4-Fluoro-N-methyl-2-nitrobenzamide (Compound 103B). MS (ES$^+$): m/z 169.07 [MH$^+$] (TOF, polar).

Compound 103B:
4-Fluoro-N-methyl-2-nitrobenzamide

The title compound was prepared using the procedure from 5-fluoro-N-methyl-2-nitrobenzamide (Compound 102B) with the commercially available 4-fluoro-2-nitrobenzoic acid. $^1$H NMR (CDCl$_3$, 400 MHz): δ=3.04 (d, J=4.80 Hz, 3H), 5.88 (br. s., 1H), 7.39 (ddd, J=8.46, 7.45, 2.53 Hz, 1H), 7.55 (dd, J=8.59, 5.31 Hz, 1H), 7.78 (dd, J=8.34, 2.53 Hz, 1H). MS (ES$^+$): m/z 199.05 [MH$^+$] (TOF, polar).

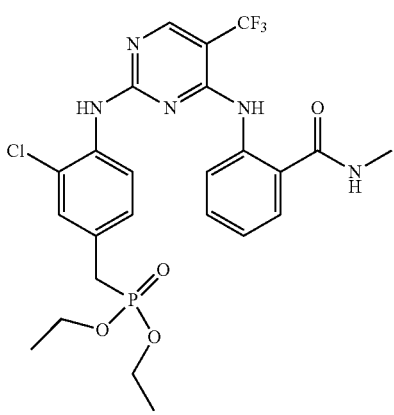 [SMILES: CCOP(=O)(Cc1ccc(Nc2ncc(C(F)(F)F)c(Nc3ccccc3C(=O)NC)n2)c(Cl)c1)OCC]

Example 104

Diethyl (3-chloro-4-{[4-{[2-(methylcarbamoyl)phenyl]amino}-5-(trifluoromethyl)pyrimidin-2-yl]amino}benzyl)phosphonate The title compound was prepared using the procedure from Example 102 with 2-{[2-chloro-5-(trifluoromethyl)pyrimidin-4-yl]amino}-N-methylbenzamide (0.060 g, 0.18 mmol) and diethyl (4-amino-3-chlorobenzyl)phosphonate (Compound 104A, 0.101 g, 0.363 mmol). $^1$H NMR (400 MHz, DMSO-$d_6$) δ11.56 (s, 1H), 9.40 (s, 1H), 8.70 (d, J=4.55 Hz, 1H), 8.38 (s, 1H), 7.66 (dd, J=1.39, 7.96 Hz, 1H), 7.50 (d, J=8.08 Hz, 1H), 7.46 (t, J=2.27 Hz, 1H), 7.29-7.34 (m, 1H), 7.24-7.29 (m, 2H), 7.04 (t, J=7.20 Hz, 1H), 3.94-4.05 (m, 4H), 2.77 (d, J=4.55 Hz, 3H), 1.19 (t, J=6.95 Hz, 6H); MS (ES$^+$): m/z: 572.08 [MH$^+$]. HPLC: $t_R$=3.42 min (Micromass ZQ3: polar_5 min).

Compound 104A: 2-{[2-chloro-5-(trifluoromethyl)pyrimidin-4-yl]amino}-N-methylbenzamide To a solution of 2,4-dichloro-5-trifluoromethylpyrimidine (500 mg, 2.3 mmol) in dry CH$_3$CN (40 mL) was added 2-amino-N-methylbenzamide (350 mg, 2.3 mmol) at room temperature. The reaction mixture was cooled to −30° C. using dry ice. Powdered KOH (1.0 g, 17.8 mmol) was added and the reaction mixture was stirred at −30° C. for 1 h, and then warmed to −10° C. to −5° C. and stirred for another 2 h, then quenched with water (200 mL). The mixture was extracted with EtOAc (3×100 mL), the combined organic layer was dried over MgSO$_4$, concentrated, and residue was purified by column chromatography to give 213 mg of the title compound (yield: 28%). $^1$H NMR (DMSO, 400 MHz): δ=2.75 (d, J=4.4 Hz, 3H), 7.20-7.24 (m, 1H), 7.53-7.58 (m, 1H), 7.74 (dd, J=2.0, 8.0 Hz, 1H), 8.33 (dd, J=1.2, 8.4 Hz, 1H), 8.85 (s, br, 1H), 12.0 (s, br, 1H).

Compound 104B: Diethyl (4-amino-3-chlorobenzyl)phosphonate

A solution of diethyl (3-chloro-4-nitrobenzyl)phosphonate (Compound 104C, 0.500 g, 1.62 mmol) in EtOH (10 mL) was charged with iron (0.454 g, 8.12 mmol) and heated to reflux. When the reaction mixture reached reflux, it was charged with 0.1 N aq HCl (0.500 mL, 0.0812 mmol) and stirred for 10 min. The reaction mixture was filtered through a pad of celite and the filtrate was concentrated in vacuo. The compound was purified on an Isco Combiflash eluting with 40 to 90% EtOAc in heptane to afford the title compound. $^1$H NMR (400 MHz, chloroform-d) δ 7.19 (t, J=2.40 Hz, 1H), 7.01 (td, J=2.27, 8.08 Hz, 1H), 6.71 (dd, J=0.63, 8.21 Hz, 1H), 3.96-4.08 (m, 4H), 2.96-3.06 (m, 2H), 1.26 (t, J=7.07 Hz, 6H); MS (ES$^+$): m/z: 278.0633 [MH$^+$]. HPLC: $t_R$=1.18 min (UPLC TOF MS: polar_3 min).

Compound 104C: Diethyl (3-chloro-4-nitrobenzyl)phosphonate

A solution of 4-(bromomethyl)-2-chloro-1-nitrobenzene (Compound 104D, 2.9 g, 12 mmol) in triethyl phosphite (2.6 mL, 15 mmol) was stirred at 120° C. for 16 h under nitrogen. The reaction mixture was concentrated in vacuo and the residue was purified on an Isco Combiflash eluting with 50 to 90% EtOAc in heptane to afford the title compound. MS (ES$^+$): m/z: 308.0416 [MH$^+$]. HPLC: $t_R$=1.33 min (UPLC TOF MS: polar_3 min).

Compound 104D: 4-(bromomethyl)-2-chloro-1-nitrobenzene

A solution of 3-chloro-4-nitrotoluene (2.0 g, 12 mmol), NBS (2.62 g, 14.6 mmol) and 2,2'-azo-bis-isobutyronitrile (0.195 g, 1.16 mmol) in α,α,α-trifluorotoluene (200 mL) was heated at 80° C. under an atmosphere of nitrogen for 3 h. Solvent was removed in vacuo and the residue was partitioned between EtOAc and water and separated. The aqueous layer was extracted with EtOAc (3×) and the combined organic fractions were washed with brine, dried over sodium sulfate, filtered, and concentrated. The crude product was taken to the next step without purification.

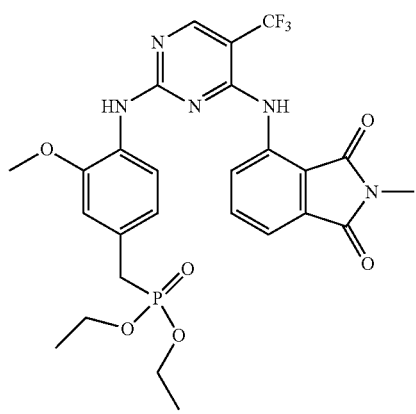

Example 105

Diethyl[3-methoxy-4-({4-[(2-methyl-1,3-dioxo-2,3-dihydro-1H-isoindol-4-yl)amino]-5-(trifluoromethyl)pyrimidin-2-yl}amino)benzyl]phosphonate The title compound was prepared using the procedure for Example 102 with diethyl (4-{[4-chloro-5-(trifluoromethyl)

pyrimidin-2-yl]amino}-3-methoxybenzyl)phosphonate and the commercially available 4-amino-2-methyl-1H-isoindole-1,3(2H)-dione. MS (ES+): m/z 594.34 (100) [MH+]; HPLC: $t_R$=1.17 min (UPLC, purity).

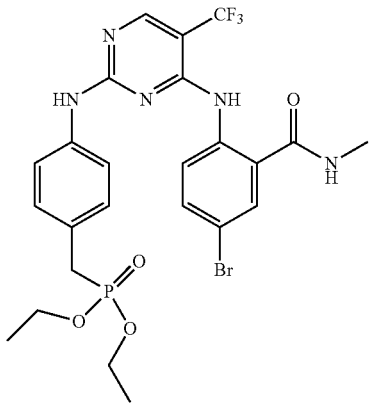 [SMILES: CCOP(=O)(Cc1ccc(Nc2ncc(C(F)(F)F)c(Nc3ccc(Br)cc3C(=O)NC)n2)cc1)OCC]

Example 106

Diethyl (4-{[4-{[4-bromo-2-(methylcarbamoyl)phenyl]amino}-5-(trifluoromethyl)pyrimidin-2-yl]amino}benzyl)phosphonate The title compound was prepared using the procedure for Example 102 with diethyl[4-({4-[(7-bromo-2-methyl-3-oxo-2,3-dihydro-1H-isoindol-4-yl)amino]-5-(trifluoromethyl)pyrimidin-2-yl}amino)benzyl]phosphonate and Compound 106A. MS (ES+): m/z 618.23 (100) [MH+]; HPLC: $t_R$=1.11 min (UPLC, purity).

Compound 106A:
2-Amino-5-bromo-N-methylbenzamide

A mixture of methyl 2-amino-5-bromobenzoate (Compound 106B, 65 g) and CH₃NH₂·H₂O (1000 mL) was stirred at 80° C. overnight in a pressure tube. The mixture was diluted with H₂O (1000 mL) and extracted with EtOAc (3×500 mL). The combined organic layers were dried over MgSO₄, concentrated to afford the title compound (55 g, yield: 87%) as a gray solid. ¹H NMR (CDCl₃, 400 MHz): δ=2.93 (d, J=5.2 Hz, 3H), 5.48 (s, br, 2H), 6.04 (s, br, 1H), 6.54 (d, J=8.4 Hz, 1H), 7.24 (dd, J=2.0, 8.4 Hz, 1H), 7.38 (d, J=2.0 Hz, 1H).

Compound 106B: Methyl-2-amino-5-bromobenzoate

2-Amino-5-bromobenzoic acid (80 g, 0.37 mmol) was dissolved in MeOH (600 mL) and a solution of H₂SO₄ (50 mL) was slowly added. The reaction mixture was refluxed for 72 h, then concentrated. NaOH solution was added to adjust the pH to 10-11. The mixture was extracted with EtOAc (3×500 mL). The combined organic layer was dried over MgSO₄, concentrated to afford the desired compound (65 g, yield: 76%) as a colorless oil, which is used directly in the next step without purification.

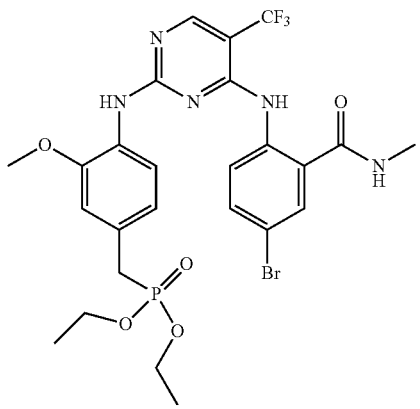

Example 107

Diethyl (4-{[4-{[4-bromo-2-(methylcarbamoyl)phenyl]amino}-5-(trifluoromethyl)pyrimidin-2-yl]amino}-3-methoxybenzyl)phosphonate The title compound was prepared using the procedure for Example 102 with diethyl (4-{[4-chloro-5-(trifluoromethyl)pyrimidin-2-yl]amino}-3-methoxybenzyl)phosphonate and Compound 106A. MS (ES+): m/z 646.31 (100) [MH+]; HPLC: $t_R$=1.14 min (UPLC, purity).

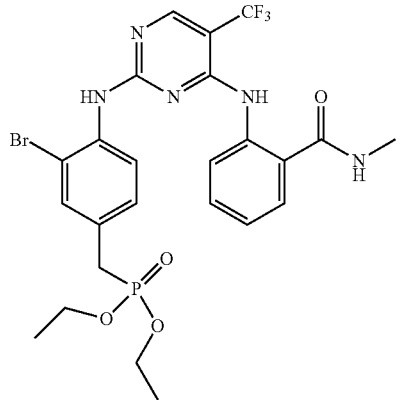

Example 108

Diethyl (3-bromo-4-{[4-{[2-(methylcarbamoyl)phenyl]amino}-5-(trifluoromethyl) pyrimidin-2-yl]amino}benzyl) phosphonate The title compound was prepared using the procedure for Example 102 with 2-{[2-chloro-5-(trifluoromethyl)pyrimidin-4-yl]amino}-N-methylbenzamide (0.300 g, 0.907 mmol) and Compound 108A to afford the title compound. ¹H NMR (400 MHz, DMSO-d₆) δ 11.56 (s, 1H), 9.38 (s, 1H), 8.69 (d, J=4.55 Hz, 1H), 8.37 (s, 1H), 7.65 (dd, J=1.39, 7.96 Hz, 1H), 7.63 (t, J=2.15 Hz, 1H), 7.47 (d, J=8.08 Hz, 1H), 7.31 (td, J=2.24, 8.15 Hz, 1H), 7.25-7.29 (m, 1H), 7.03 (t, J=7.71 Hz, 1H), 3.95-4.04 (m, 4H), 2.76 (d, J=4.55 Hz, 3H), 1.19 (t, J=7.07 Hz, 6H); MS (ES+): m/z: 616.08, 618.06 [MH+]. HPLC: $t_R$=3.46 min (Micromass ZQ3: polar_5 min).

Compound 108A: Diethyl (4-amino-3-bromobenzyl)phosphonate

Di-tert-butyl[2-bromo-4-(bromomethyl)phenyl]imidodicarbonate (Compound 108B, 6.0 g, 13 mmol) was taken up in triethyl phosphite (5.0 mL, 29 mmol) and stirred at 120° C. for 16 h. The reaction mixture was transferred to a microwave vial and was irradiated in the microwave for 4 h at 190° C. The reaction mixture was concentrated in vacuo. The compound was purified on an Isco Combiflash eluting with 10 to 100% EtOAc in heptane. The product was partitioned between EtOAc and water and separated. The aqueous was extracted with EtOAc (3×) and the combined organic fractions were washed with brine, dried over sodium sulfate, filtered, and concentrated to afford the title compound. $^1$H NMR (400 MHz, chloroform-d) δ 7.33 (t, J=2.27 Hz, 1H), 7.04 (ddd, J=2.27, 2.40, 8.21 Hz, 1H), 6.71 (dd, J=0.76, 8.08 Hz, 1H), 3.97-4.06 (m, 4H), 2.96-3.04 (m, 2H), 1.26 (t, J=7.07 Hz, 6H); MS (ES+): m/z: 322.00, 323.96 [MH+]. HPLC: $t_R$=2.83 min (UPLC TOF MS: polar_3 min).

Compound 108B: Di-tert-butyl[2-bromo-4-(bromomethyl)phenyl]imidodicarbonate

A solution of di-tert-butyl (2-bromo-4-methylphenyl)imidodicarbonate (Compound 108C, 5.0 g, 13 mmol), NBS (2.56 g, 14.2 mmol) and 2,2'-Azo-bis-isobutyronitrile (0.217 g, 1.29 mmol) in α,α,α-trifluorotoluene (16 mL) was heated at 80° C. under an atmosphere of nitrogen for 3 h. Solvent was removed in vacuo and the residue was partitioned between EtOAc and water and separated. The aqueous was extracted with EtOAc (3×) and the combined organic fractions were washed with brine, dried over sodium sulfate, filtered, and concentrated to afford the title compound. $^1$H NMR (400 MHz, chloroform-d) δ 7.64 (d, J=1.77 Hz, 1H), 7.34 (dd, J=2.02, 8.08 Hz, 1H), 7.19 (d, J=8.08 Hz, 1H), 4.44 (s, 2H), 1.41 (s, 18H); MS (ES+): m/z: N/A [MH+]. HPLC: $t_R$=1.83 min (UPLC TOF MS: polar_3 min).

Compound 108C: Di-tert-butyl (2-bromo-4-methylphenyl)imidodicarbonate

A solution of 3-Bromo-4-aminotoluene (4.0 g, 21 mmol) in THF (50 mL) was charged with di-tert-butyldicarbonate (4.7 g, 21 mmol) and stirred at reflux for 24 h. The reaction mixture was partitioned between EtOAc and water and separated. The aqueous layer was extracted with EtOAc (3×) and the combined organic fractions were washed with brine, dried over sodium sulfate, filtered, and concentrated. The compound was purified in two batches on an Isco Combiflash eluting with 0 to 10% EtOAc in heptane to afford the title compound. $^1$H NMR (400 MHz, chloroform-d) δ 7.40-7.44 (m, 1H), 7.08-7.10 (m, 2H), 2.35 (s, 3H), 1.41 (s, 18H).

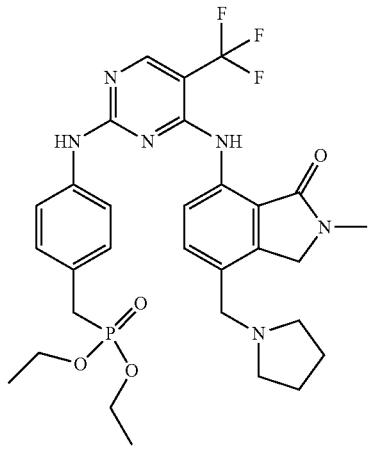 [SMILES: CCOP(=O)(Cc1ccc(Nc2ncc(C(F)(F)F)c(Nc3ccc(CN4CCCC4)c4c3C(=O)N(C)C4)n2)cc1)OCC]

Example 109

Diethyl (4-{[4-{[2-methyl-3-oxo-7-(pyrrolidin-1-ylmethyl)-2,3-dihydro-1H-isoindol-4-yl]amino}-5-(trifluoromethyl)pyrimidin-2-yl]amino}benzyl)phosphonate The title compound was prepared using the procedure for Example 102 with diethyl (4-{[4-chloro-5-(trifluoromethyl)pyrimidin-2-yl]amino}benzyl)phosphonate and Compound 109A. MS (ES+): m/z 633.45 (100) [MH+]; HPLC: $t_R$=0.72 min (UPLC, purity).

Compound 109A: 7-Amino-2-methyl-4-(pyrrolidin-1-ylmethyl)-2,3-dihydro-1H-isoindol-1-one To tert-butyl[2-methyl-3-oxo-7-(pyrrolidin-1-ylmethyl)-2,3-dihydro-1H-isoindol-4-yl]carbamate (Compound 109B) was added DCM (0.5 mL) and TFA (0.5 mL, 6 mmol). The solution was stirred at room temperature for 20 minutes. The crude product was dried in vacuo and used directly in next step without further purification. MS (ES+): m/z 246.31 (100) [MH+]; HPLC: $t_R$=0.29 min (UPLC, Analytical).

Compound 109B: tert-Butyl[2-methyl-3-oxo-7-(pyrrolidin-1-ylmethyl)-2,3-dihydro-1H-isoindol-4-yl]carbamate A mixture of tert-Butyl (7-formyl-2-methyl-3-oxo-2,3-dihydro-1H-isoindol-4-yl)carbamate (Compound 109C, 23.0 mg, 0.0792 mmol) and sodium triacetoxyborohydride (101 mg, 0.475 mmol) in THF (0.5 mL) was stirred at room temperature for 20 minutes. Pyrrolidine (39.7 uL, 0.475 mmol) was added and the resulting mixture was stirred at room temperature overnight. The THF was removed in vacuo and the crude product was partitioned between EtOAc and brine. The organic layer was dried over MgSO$_4$ and concentrated in vacuo to deliver the desired product. MS (ES+): m/z 346.32 (100) [MH+] HPLC: $t_R$=0.76 min (UPLC, Analytical).

Compound 109C: tert-Butyl (7-formyl-2-methyl-3-oxo-2,3-dihydro-1H-isoindol-4-yl)carbamate tert-Butyl {2-methyl-3-oxo-7-[(E)-2-phenylethenyl]-2,3-dihydro-1H-isoindol-4-yl}carbamate (Compound 109D, 1.0E2 mg, 0.27 mmol) was added in one portion to a pre-stirred mixture (room temperature, 45 min) of potassium osmate dihydrate (1.0 mg, 0.0027 mmol) and potassium monopersulfate (170 mg, 1.1 mmol) in DMF (1.35 mL). After stirring overnight at room temperature, the reaction mixture was treated with 1.35 mL of saturated aqueous $Na_2SO_3$. The resulting slurry was extracted with EtOAc (3×) and the combined organic layers were washed with 1N HCl (3×) and brine and concentrated in vacuo. The desired product was obtained after chromatography using an ISCO Combiflash unit (0-15% EtOAc in Heptane) as 23 mg of a tan solid (29% yield). $^1$H NMR (400 MHz, DMSO-$d_6$) δ=1.51 (s, 9H), 3.08 (s, 3H), 4.74 (s, 2H), 8.12 (d, J=8.6 Hz, 1H), 8.21 (d, J=8.6 Hz, 1H), 9.95 (s, 1H), 10.01 (s, 1H). MS (ES+): m/z 291.28 (100) [MH$^+$]; HPLC: $t_R$=1.27 min (UPLC, Analytical).

Compound 109D: tert-Butyl {2-methyl-3-oxo-7-[(E)-2-phenylethenyl]-2,3-dihydro-1H-isoindol-4-yl}carbamate 7-Amino-2-methyl-4-[(E)-2-phenylethenyl]-2,3-dihydro-1H-isoindol-1-one (Compound 109E, 1.3 g, 4.9 mmol), di-tert-butyldicarbonate (5.4 g, 24 mmol), 4-dimethylaminopyridine (60 mg, 0.49 mmol) and acetonitrile (20 mL) were mixed and heated at 50° C. until the reaction mixture became clear (~5 minutes). The mixture was then stirred at room temperature for 18 hours. The reaction mixture was concentrated and the desired product was isolated after column chromatography (yield for two steps: 47%). $^1$H NMR (400 MHz, DMSO-d6) δ=1.50 (s, 9H), 3.10 (s, 3H), 4.69 (s, 2H), 7.11-7.26 (m, 2H), 7.26-7.32 (m, 1H), 7.39 (t, J=7.6 Hz, 2H), 7.61-7.67 (m, 2H), 7.84 (d, J=8.8 Hz, 1H), 8.05 (d, J=8.6 Hz, 1H), 9.71 (s, 1H). MS (ES+): m/z 365.31 (100) [MH$^+$]; HPLC: $t_R$=1.37 min (UPLC, Analytical).

Compound 109E: 7-amino-2-methyl-4-[(E)-2-phenylethenyl]-2,3-dihydro-1H-isoindol-1-one A mixture of 7-amino-4-bromo-2-methyl-2,3-dihydro-1H-isoindol-1-one (1.0 g, 4.1 mmol), E-phenylethenylboronic acid (921 mg, 6.22 mmol), potassium carbonate (1.72 g, 12.4 mmol), [1,1'-bis(diphenylphosphino)ferrocene]dichloropalladium(II), complex with dichloromethane (1:1) (169 mg, 0.207 mmol) in 10 mL 1,4-Dioxane and 2.5 mL $H_2O$ was irradiated in a microwave reactor at 100° C. for 30 minutes. The crude mixture was partitioned between EtOAc and sat. $NaHCO_3$. The combined organic layers were washed with brine, dried over $Na_2SO_4$, filtered and concentrated. The crude product was used in the next step without further purification. MS (ES+): m/z 265.31 (100) [MH$^+$]; HPLC: $t_R$=1.24 min (UPLC, Analytical).

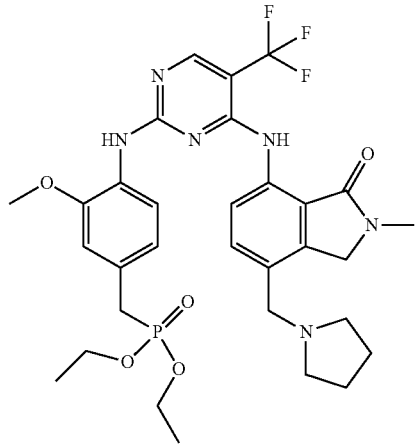

Example 110

Diethyl (3-methoxy-4-{[4-{[2-methyl-3-oxo-7-(pyrrolidin-1-ylmethyl)-2,3-dihydro-1H-isoindol-4-yl]amino}-5-(trifluoromethyl)pyrimidin-2-yl]amino}benzyl)phosphonate The title compound was prepared using the procedure for Example 102 with diethyl (4-{[4-chloro-5-(trifluoromethyl)pyrimidin-2-yl]amino}-3-methoxybenzyl)phosphonate and Compound 109A. MS (ES+): m/z 663.51 (100) [MH$^+$]; HPLC: $t_R$=0.74 min (UPLC, purity).

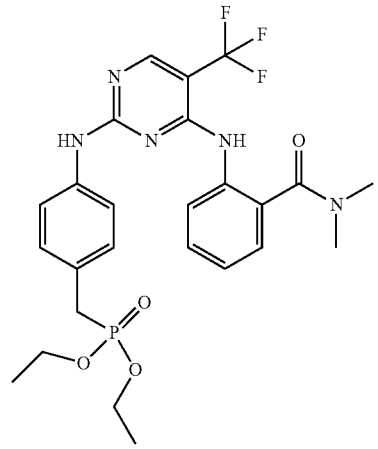 [SMILES: CCOP(=O)(Cc1ccc(Nc2ncc(C(F)(F)F)c(Nc3ccccc3C(=O)N(C)C)n2)cc1)OCC]

Example 111

Diethyl (4-{[4-{[2-(dimethylcarbamoyl)phenyl]amino}-5-(trifluoromethyl)pyrimidin-2-yl]amino}benzyl)phosphonate The title compound was prepared using the procedure for Example 102 with diethyl (4-{[4-chloro-5-(trifluoromethyl)pyrimidin-2-yl]amino}benzyl)phosphonate and the commercially available 2-amino-N,N-dimethylbenzamide. MS (ES+): m/z 552.38 (100) [MH$^+$]; HPLC: $t_R$=0.96 min (UPLC, purity).

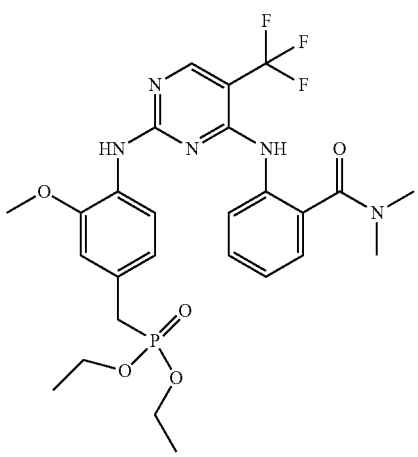

Example 112

Diethyl (4-{[4-{[2-(dimethylcarbamoyl)phenyl]amino}-5-(trifluoromethyl)pyrimidin-2-yl]amino}-3-methoxybenzyl)phosphonate The title compound was prepared using the procedure for Example 102 with diethyl (4-{[4-chloro-5-(trifluoromethyl)pyrimidin-2-yl]amino}-3-methoxybenzyl)phosphonate and the commercially available 2-amino-N,N-dimethylbenzamide. MS (ES+): m/z 582.40 (100) [MH$^+$]; HPLC: $t_R$=1.01 min (UPLC, purity).

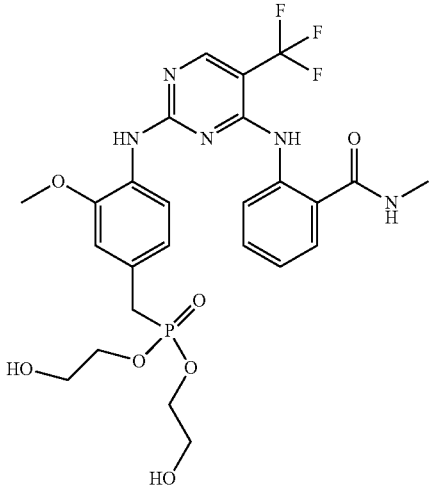

Example 113

Bis(2-hydroxyethyl)(3-methoxy-4-{[4-{[2-(methylcarbamoyl)phenyl]amino}-5-(trifluoromethyl)pyrimidin-2-yl]amino}benzyl)phosphonate The title compound was prepared according to the procedure for Example 102 using bis(2-hydroxyethyl)(4-amino-3-methoxybenzyl)phosphonate (Compound 113A, 30 mg, 0.1 mmol) and 2-(2-chloro-5-(trifluoromethyl)pyrimidin-4-ylamino)-N-methylbenzamide (Compound 104A, 33 mg, 0.1 mmol). The reaction mixture was concentrated in vacuo and the residue was purified by HPLC to afford the title compound. $^1$H-NMR (DMSO-d6, 400 MHz): δ=2.83 (s, 3H), 3.35 (d, J=21.6 Hz, 2H), 3.60 (dd, J=5.2, 10.4 Hz, 4H), 3.84 (s, 3H), 3.99-4.03 (m, 4H), 4.95 (t, J=5.2 Hz, 2H), 6.92 (d, J=7.6 Hz, 1H), 7.11 (s, 1H), 7.16 (t, J=7.6 Hz, 1H), 7.45 (m, 1H), 7.61 (d, J=8.0 Hz, 1H), 7.73 (dd, J=1.2, 8.0 Hz, 1H), 8.43 (s, 1H), 8.48 (m, 1H), 8.80 (m, 2H), 11.49 (s, 1H). MS (ES+): m/z 600.11 [MH$^+$]; HPLC: $t_R$=2.80 min (ZQ3, polar_5 min).

Compound 113A: Bis(2-hydroxyethyl)(4-amino-3-methoxybenzyl)phosphonate

A mixture of bis(2-hydroxyethyl)(3-methoxy-4-nitrobenzyl)phosphonate (Compound 133B, 1.2 g, 3.58 mmol) and 5% Pd/C (0.2 g) in EtOH (80 mL) was hydrogenated under 50 psi hydrogen pressure at 40° C. for 6 h. The reaction mixture was filtered and the filtrate was concentrated to give the desired product (0.9 g, 82%).

Compound 113B: Bis(2-hydroxyethyl)(3-methoxy-4-nitrobenzyl)phosphonate

At 0° C., to a solution of ethylene glycol (1.5 g, 24 mmol) and TEA (2.4 g, 24 mmol) was added a solution of 3-methoxy-4-nitrobenzylphosphonic dichloride (1.72 g, 6.07 mmol) in THF (300 mL) dropwise. The reaction mixture was warmed to room temperature and stirred at 70° C. for 12 h. Solvent was removed and residue was purified by column chromatography to give 1.2 g of the desired product (yield: 59%).

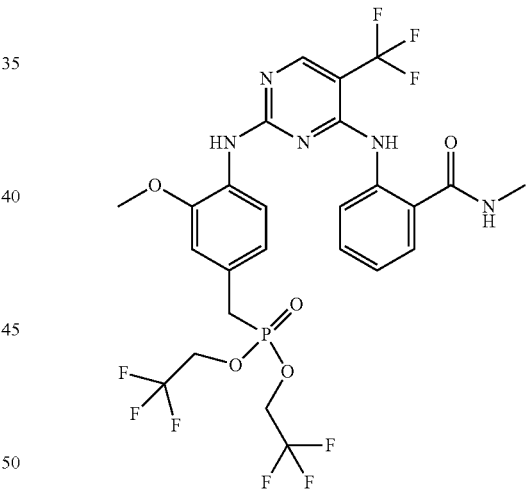

Example 114

Bis(2,2,2-trifluoroethyl)(3-methoxy-4-{[4-{[2-(methylcarbamoyl)phenyl]amino}-5-(trifluoromethyl)pyrimidin-2-yl]amino}benzyl)phosphonate The title compound was prepared according to the procedure for Example 102 bis(2,2,2-trifluoroethyl)(4-amino-3-methoxybenzyl)phosphonate (Compound 114A, 38 mg, 0.1 mmol) and 2-(2-chloro-5-(trifluoromethyl)pyrimidin-4-ylamino)-N-methylbenzamide (33 mg, 0.1 mmol). The reaction mixture was concentrated in vacuo and the residue was purified by HPLC to afford the title compound. $^1$H-NMR (DMSO-d6, 400 MHz): δ=2.73 (s, 3H), 3.52 (d, J=21.6 Hz, 2H), 3.73 (s, 3H), 4.60-4.65 (m, 4H), 6.81 (d, J=7.6 Hz, 1H), 6.98 (s, 1H), 7.05 (t, J=7.6 Hz, 1H), 7.34 (t, J=7.2 Hz, 1H), 7.57 (d, J=8.0 Hz, 1H), 7.65 (dd, J=1.2, 7.6 Hz, 1H), 8.34 (s, 1H), 8.38 (s, 1H), 8.68 (d, J=4.4 Hz, 1H), 8.71 (s, 1H), 11.42 (s, 1H). MS (ES+): m/z 676.05 [MH$^+$]; HPLC: $t_R$=3.69 min (ZQ3, polar__5 min).

Compound 114A: Bis(2,2,2-trifluoroethyl)(4-amino-3-methoxybenzyl)phosphonate The title compound was prepared according to the procedure for Compound 113A using bis(2,2,2-trifluoroethyl)(3-methoxy-4-nitrobenzyl)phosphonate (Compound 114B, 2.8 g, 6.81 mmol). The reaction mixture was filtered and the filtrate was concentrated to give the desired product (2 g, 77%). $^1$H NMR (DMSO-d$_6$, 400 MHz): δ=3.29 (d, J=21.2 Hz, 2H), 3.68 (s, 3H), 4.50-4.61 (m, 4H), 4.64 (s, br, 2H), 6.50-6.60 (m, 2H), 6.67 (s, 1H).

Compound 114B: Bis(2,2,2-trifluoroethyl)(3-methoxy-4-nitrobenzyl)phosphonate At 0° C., to a solution of 2,2,2-trifluoroethanol (5.7 g, 57 mmol) and TEA (5.7 g, 57 mmol) in THF (30 mL) was added a solution of 3-methoxy-4-nitrobenzylphosphonic dichloride (Compound 114C, 4.0 g, 14.2 mmol) in THF (30 mL) dropwise. The reaction mixture was warmed to room temperature and stirred at 70° C. for 12 h. Solvent was removed and residue was purified by column chromatography to give 2.8 g of the desired product (yield: 52%).). $^1$H NMR (400 MHz, CDCl$_3$) δ ppm 7.85 (dd, J=8.3, 1.0 Hz, 1H), 7.04 (t, J=2.0 Hz, 1H), 6.95 (dq, J=8.3, 1.8 Hz, 1H), 4.29-4.41 (m, 4H), 3.97 (s, 3H), 3.39 (d, J=22.7 Hz, 2H). MS (ES$^+$): m/z 411.96 (100) [MH$^+$]; HPLC: $t_R$=3.31 min (ZQ3, polar__5 min).

Compound 114C: (3-Methoxy-4-nitrobenzyl)phosphonic dichloride

A solution of (3-methoxy-4-nitrobenzyl)phosphonic acid (Compound 114D, 30 g, 66 mmol) in thionyl chloride (100 mL) was refluxed for 18 h. The excess amount of thionyl chloride was removed under reduced pressure to leave a residue (20 g, 82%), which was used in the next step without purification.

Compound 114D: (3-methoxy-4-nitrobenzyl)phosphonic acid

A suspension of diethyl (3-methoxy-4-nitrobenzyl)phosphonate (Compound 114E, 5.04 g, 16.6 mmol) in concentrated HCl (50.0 mL, 1630 mmol) was heated at 120° C. for a total of 16 h. After cooling to ambient temperature, the reaction mixture was concentrated in vacuo. After drying under vacuum for several hours, a solid had precipitated upon standing, giving the title material as a yellow solid, 4.1398 g (96%, 15.913 mmol). $^1$H NMR (DMSO-d$_6$) δ ppm 7.81 (dd, J=8.3, 0.8 Hz, 1H), 7.23 (t, J=1.9 Hz, 1H), 6.99 (dt, J=8.3, 1.9 Hz, 1H), 5.75 (br s, 3H), 3.89 (s, 5H), 3.10 (d, J=22.0 Hz, 2H). MS (ES$^+$): m/z 248.02 (100) [MH$^+$]; HPLC: $t_R$=1.68 min (ZQ3, polar__5 min).

Compound 114E: Diethyl (3-methoxy-4-nitrobenzyl)phosphonate

In a sealed tube, a mixture of 4-(bromomethyl)-2-methoxy-1-nitrobenzene (4.22 g, 17.2 mmol) and triethyl phosphite (3.5 g, 21 mmol) was heated to 100° C. for 16 h. The reaction was cooled to ambient temperature, transferred to a round bottom flask, and concentrated in vacuo. The crude oil was adsorbed onto a pre-filled solid loading cartridge [RediSepRf 25 gram] and purified using the Teledyne/ISCO system [RediSepRf Silica 40 gram], eluting with 0-5% MeOH:CH$_2$Cl$_2$. The desired fractions were combined and concentrated in vacuo, affording the title material as a yellow oil, 5.0439 g (87%, 14.970 mmol). $^1$H NMR (CDCl$_3$) δ ppm 7.83 (dd, J=8.2, 0.9 Hz, 1H), 7.08 (t, J=1.9 Hz, 1H), 6.94 (dt, J=8.3, 2.0 Hz, 1H), 4.07 (ddd, J=8.3, 7.1, 1.3 Hz, 4H), 3.97 (s, 3H), 3.14-3.25 (m, 2H), 1.29 (t, J=7.1 Hz, 6H). MS (ES$^+$): m/z 304.00 (100) [MH$^+$]; HPLC: $t_R$=2.89 min (ZQ3, polar__5 min).

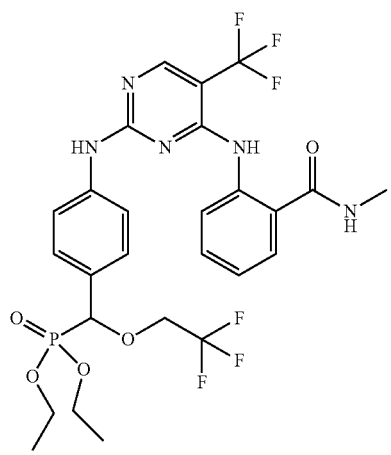 [SMILES: CCOP(=O)(OCC)C(OCC(F)(F)F)c1ccc(Nc2ncc(C(F)(F)F)c(Nc3ccccc3C(=O)NC)n2)cc1]

Example 115

Diethyl[(4-{[4-{[2-(methylcarbamoyl)phenyl]amino}-5-(trifluoromethylpyrimidin-2-yl]amino}phenyl)(2,2,2-trifluoroethoxy)methyl]phosphonate The title compound was prepared using the procedure for Example 102 with 2-{[2-chloro-5-(trifluoromethyl)pyrimidin-4-yl]amino}-N-methylbenzamide (40 mg, 0.12 mmol) and diethyl[(4-aminophenyl)(hydroxy)methyl]-phosphonate (37.6 mg, 0.15 mmol). The crude product was purified by prep TLC (5% 7 N ammonia in MeOH in DCM) to give 13.8 mg of the desired product (yield: 18%). $^1$H NMR (CD$_3$OD, 400 MHz): δ=1.22 (t, J=7.6 Hz, 3H), 1.31 (t, J=7.2 Hz, 3H), 2.90 (s, 3H), 3.91-4.08 (m, 4H), 4.12-4.18 (m, 2H), 4.95 (d, J=14.8 Hz, 1H), 7.18 (t, J=7.2 Hz, 1H), 7.36 (d, J=8.4 Hz, 2H), 7.49 (dt, J=2.4, 7.6 Hz, 1H), 7.64 (dd, J=1.6, 7.6 Hz, 1H), 7.68 (d, J=7.6 Hz, 2H), 8.35 (s, 1H), 8.43 (m, 1H). MS (ES$^+$): m/z 636.14 [MH$^+$]. HPLC: $t_R$=1.59 min (UPLC TOF, polar__3 min).

Compound 115A: Diethyl[(4-aminophenyl)(hydroxy)methyl]phosphonate

A mixture of p-nitrobenzaldehyde (3.022 g, 20 mmol), diethyl phosphite (2.762 g, 20 mmol), and MgO (2.0 g, 49.6 mmol) in THF (30 mL) was stirred at room temperature for 5 days. The reaction mixture was filtered, the filtrate was concentrated, and residue was purified by silica gel chromatography (EtOAc/hexanes: 1:4) to give 4.53 g of diethyl[(4-nitrophenyl)(hydroxy)methyl]phosphonate (yield: 78%). $^1$H NMR (CDCl$_3$, 400 MHz): δ=1.27 (m, 6H), 4.08-4.18 (m, 4H), 5.18 (d, J=12.0 Hz, 1H), 7.67-7.70 (m, 2H), 8.24 (dd, J=0.8, 8.8 Hz, 2H). MS (ES+): m/z 290.07 [MH+]. HPLC: t$_R$=1.15 min (UPLC TOF, polar_3 min). This material (4.53 g) was hydrogenated in the presence of 10% Pd/C (200 mg) in MeOH (20 mL) under 1 atmosphere for 4 h. The catalyst was filtered off, filtrate was concentrated, and the residue was purified by silica gel chromatography (2% MeOH in DCM) to afford 3.93 g of the title compound (yield: 72%). MS (ES+): m/z 242.08 [MH+—H$_2$O]. HPLC: t$_R$=0.8 min (UPLC TOF, polar_3 min).

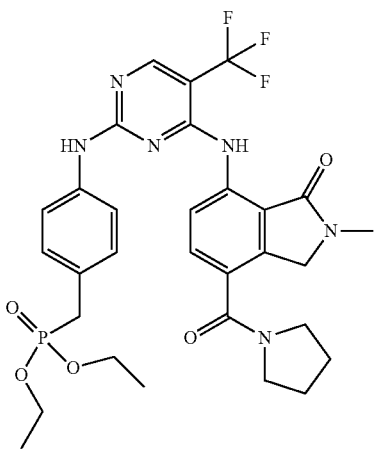 [SMILES: CCOP(=O)(Cc1ccc(Nc2ncc(C(F)(F)F)c(Nc3ccc(C(=O)N4CCCC4)c4c3C(=O)N(C)C4)n2)cc1)OCC]

Example 116

Diethyl (4-{[4-{[2-methyl-3-oxo-7-(pyrrolidin-1-ylcarbonyl)-2,3-dihydro-1H-isoindol-4-yl]amino}-5-(trifluoromethyl)pyrimidin-2-yl]amino}benzyl)phosphonate The title compound was prepared using the procedure for Example 102 with diethyl (4-{[4-chloro-5-(trifluoromethyl)pyrimidin-2-yl]amino}benzyl)phosphonate and Compound 116A. MS (ES+): m/z 647.49 (100) [MH+]; HPLC: t$_R$=0.97 min (UPLC, purity).

Compound 116A: 7-amino-2-methyl-4-(pyrrolidin-1-ylcarbonyl)-2,3-dihydro-1H-isoindol-1-one To tert-butyl[2-methyl-3-oxo-7-(pyrrolidin-1-ylcarbonyl)-2,3-dihydro-1H-isoindol-4-yl]carbamate (Compound 116B) was added DCM (0.5 mL) and TFA (0.5 mL). The reaction mixture was stirred at room temperature for 30 minutes, after which it was concentrated to dryness an used without further purification. MS (ES+): m/z 260.30 (100) [MH+]; HPLC: t$_R$=0.69 min (UPLC, Analytical).

Compound 116B: tert-Butyl[2-methyl-3-oxo-7-(pyrrolidin-1-ylcarbonyl)-2,3-dihydro-1H-isoindol-4-yl]carbamate 7-[(Tert-butoxycarbonyl)amino]-2-methyl-1-oxo-2,3-dihydro-1H-isoindole-4-carboxylic acid (Compound 116C, 45 mg, 0.15 mmol), pyrrolidine (123 uL, 1.47 mmol), TBTU (236 mg, 0.734 mmol), DIPEA (128 uL, 0.734 mmol) and DMF (1 mL) were mixed and stirred at room temperature for 2 hours. The reaction mixture was diluted with EtOAc and washed with water (2×) and brine. The crude product was purified by column chromatography. MS (ES+): m/z 360.34 (100) [MH+]; HPLC: t$_R$=1.20 min (UPLC, Analytical).

Compound 116C: 7-[(tert-butoxycarbonyl)amino]-2-methyl-1-oxo-2,3-dihydro-1H-isoindole-4-carboxylic acid Potassium osmate, dihydrate (10.1 mg, 0.0274 mmol) and potassium monopersulfate (270 mg, 1.8 mmol) were added to DMF (1.35 mL) and the mixture was stirred together for 45 minutes at room temperature. Tert-butyl {2-methyl-3-oxo-7-[(E)-2-phenylethenyl]-2,3-dihydro-1H-isoindol-4-yl}carbamate (100 mg, 0.27 mmol) was added in one portion and the resulting mixture was stirred at room temperature overnight. Another portion of potassium osmate and potassium monopersulfate were added and the resulting mixture was stirred at room temperature over the weekend. Sat. aqueous Na$_2$SO$_3$ (1.35 mL) was added to the crude mixture and the slurry was extracted by EtOAc (3×). The combined organic layers were washed with 1N HCl (3×) and brine. The crude product was used directly in the next step. MS (ES+): m/z 307.26 (100) [MH+]; HPLC: t$_R$=1.14 min (UPLC, Analytical).

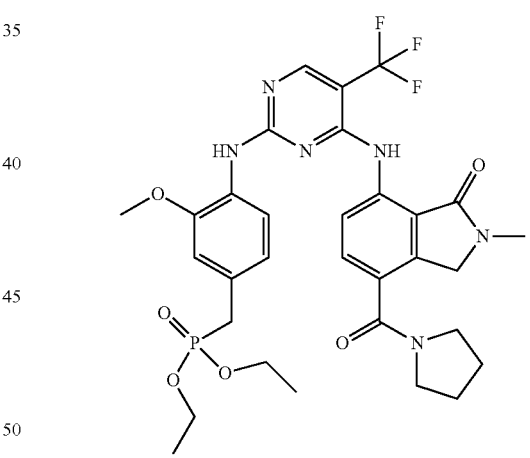

Example 117

Diethyl (3-methoxy-4-{[4-{[2-methyl-3-oxo-7-(pyrrolidin-1-ylcarbonyl)-2,3-dihydro-1H-isoindol-4-yl]amino}-5-(trifluoromethyl)pyrimidin-2-yl]amino}benzyl)phosphonate The title compound was prepared using the procedure for Example 102 with diethyl (4-{[4-chloro-5-(trifluoromethyl)pyrimidin-2-yl]amino}-3-methoxybenzyl)phosphonate and Compound 116A. MS (ES+): m/z 677.46 (100) [MH+]; HPLC: t$_R$=0.98 min (UPLC, purity).

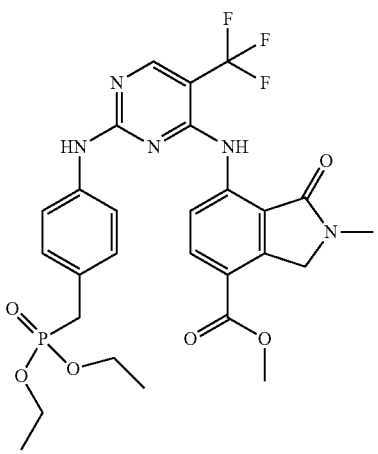 [SMILES: CCOP(=O)(Cc1ccc(Nc2ncc(C(F)(F)F)c(Nc3ccc(C(=O)OC)c4c3C(=O)N(C)C4)n2)cc1)OCC]

Example 118

Methyl 7-{[2-({4-[(diethoxyphosphoryl)methyl]phenyl}amino)-5-(trifluoromethyl)pyrimidin-4-yl]amino}-2-methyl-1-oxo-2,3-dihydro-1H-isoindole-4-carboxylate The title compound was prepared using the procedure for Example 102 with diethyl (4-{[4-chloro-5-(trifluoromethyl)pyrimidin-2-yl]amino}benzyl)phosphonate and Compound 118A. MS (ES+): m/z 608.32 (100) [MH$^+$]; HPLC: t$_R$=1.08 min (UPLC, purity).

Compound 118A: Methyl 7-amino-2-methyl-1-oxo-2,3-dihydro-1H-isoindole-4-carboxylate Methyl 7-[bis(tert-butoxycarbonyl)amino]-2-methyl-1-oxo-2,3-dihydro-1H-isoindole-4-carboxylate (Compound 118B, 40.0 mg, 0.0951 mmol), DCM (0.4 mL) and TFA (0.4 mL) were mixed and stirred at room temperature for 30 minutes. The solvents were evaporated and the crude product was used directly in the next step. MS (ES+): m/z 221.26 (100) [MH$^+$]; HPLC: t$_R$=0.77 min (UPLC, Analytical).

Compound 118B: Methyl 7-[bis(tert-butoxycarbonyl)amino]-2-methyl-1-oxo-2,3-dihydro-1H-isoindole-4-carboxylate A mixture of di-tert-butyl (7-bromo-2-methyl-3-oxo-2,3-dihydro-1H-isoindol-4-yl)imidodicarbonate (Compound 118C, 500 mg, 1.13 mmol), Pd(PPh$_3$)$_4$ (131 mg, 0.113 mmol), in MeOH (5 mL) and THF (10 mL) was evacuated and refilled with carbon monoxide (3×), then heated at 65° C. overnight. The solvent was removed in vacuo and the crude product was taken up in EtOAc and washed successively with water then brine. The desired product was purified by column chromatography. MS (ES+): m/z 321.28 (100) [(M-Boc)H$^+$]; HPLC: t$_R$=1.32 min (UPLC, Analytical).

Compound 118C: Di-tert-butyl (7-bromo-2-methyl-3-oxo-2,3-dihydro-1H-isoindol-4-yl)imidodicarbonate A mixture of 7-Amino-4-bromo-2-methyl-2,3-dihydro-1H-isoindol-1-one (1.0 g, 4.1 mmol), di-tert-butyldicarbonate (5.43 g, 24.9 mmol), 4-dimethylaminopyridine (507 mg, 4.15 mmol) in MeCN (20.0 mL) was heated at 50° C. for 10 minutes and then stirred at room temperature for 2 hours. The product was purified by chromatography the desired product (1.2 g, 66% yield). $^1$H NMR (400 MHz, DMSO-d$_6$) δ=1.34 (s, 18H), 3.05 (s, 3H), 4.40 (s, 2H), 7.23 (d, J=8.3 Hz, 1H), 7.77 (d, J=8.3 Hz, 1H). MS (ES+): m/z 341.17, 343.18 (100) [(M-Boc)H$^+$]; HPLC: t$_R$=1.16 min (UPLC, Analytical).

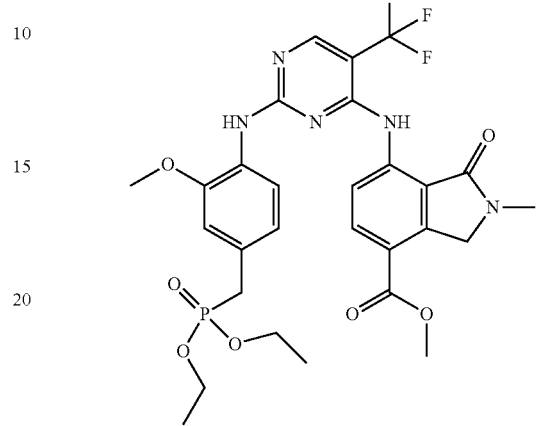

Example 119

Methyl 7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindole-4-carboxylate The title compound was prepared using the procedure for Example 102 with diethyl (4-{[4-chloro-5-(trifluoromethyl)pyrimidin-2-yl]amino}-3-methoxybenzyl)phosphonate and Compound 118A. MS (ES+): m/z 638.24 (100) [MH$^+$]; HPLC: t$_R$=1.09 min (UPLC, purity).

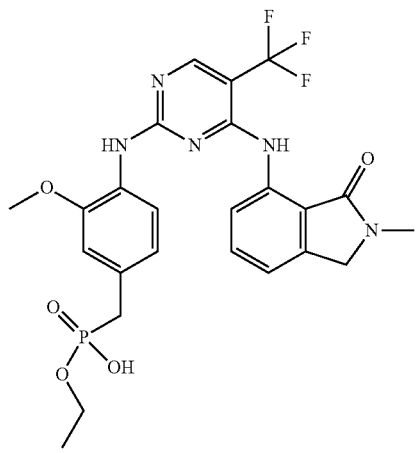

Example 120

Ethyl hydrogen[3-methoxy-4-({4-[(2-methyl-3-oxo-2,3-dihydro-1H-isoindol-4-yl)amino]-5-(trifluoromethyl)pyrimidin-2-yl}amino)benzyl]phosphonate A solution of diethyl[3-methoxy-4-({4-[(2-methyl-3-oxo-2,3-dihydro-1H-isoindol-4-yl)amino]-5-(trifluoromethyl)

pyrimidin-2-yl}amino)benzyl]phosphonate (14.7 mg, 0.0254 mmol) in 37% HCl (1 mL) was heated at 80° C. for 3.5 h. The reaction mixture was concentrated in vacuo. The residue was dissolved in DMSO and submitted for mass-directed purification (under basic conditions; ammonium bicarbonate buffer, pH 9). The fractions containing product were combined and concentrated in vacuo, yielding the title material as a white solid, 4.5 mg (32%). $^1$H NMR (400 MHz, MeOD) δ ppm: 8.50 (br s, 1H), 8.32 (s, 1H), 7.71 (d, J=8.1 Hz, 1H), 7.47 (t, J=8.0 Hz, 1H), 7.16 (d, J=7.3 Hz, 1H), 7.12 (t, J=1.6 Hz, 1H), 6.94 (dt, J=8.1, 1.9 Hz, 1H), 4.45 (s, 2H), 3.89 (s, 3H), 3.88 (quin, J=6.9 Hz, 2H), 3.16 (s, 3H), 3.02 (d, J=20.2 Hz, 2H), 1.20 (t, J=7.1 Hz, 3H). MS (ES+): m/z 552.15 [MH$^+$]; HPLC: $t_R$=2.81 min (ZQ3, polar_5 min).

Compound 121D: Octahydropyrazino[2,1-c][1,4]oxazine bis-hydrochloride

Prepared according to WO2006/120478. $^1$H NMR (CD$_3$OD, 400 MHz): δ=3.09-3.26 (m, 2H), 3.32-3.42 (m, 3H), 3.52-3.56 (m, 2H), 3.62-3.74 (m, 4H), 3.95-3.98 (m, 2H).

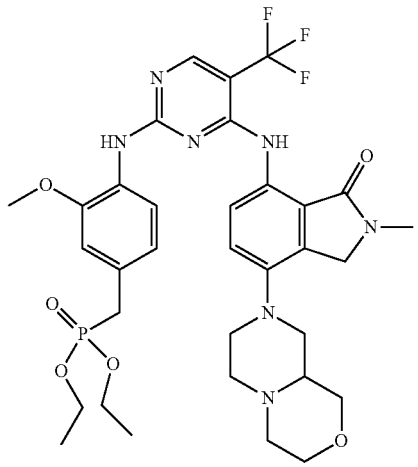

Example 122

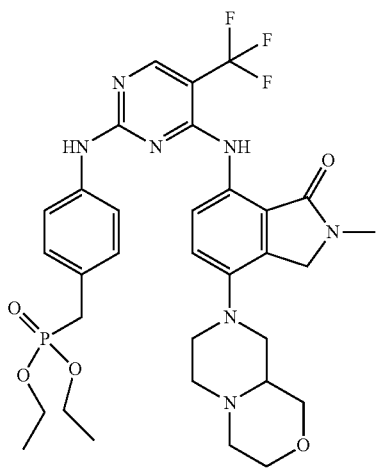 [SMILES: CCOP(=O)(Cc1ccc(Nc2ncc(C(F)(F)F)c(Nc3ccc(N4CCN5CCOCC5C4)c4c3C(=O)N(C)C4)n2)cc1)OCC]

Example 121

Diethyl (4-{[4-{[7-(hexahydropyrazino[2,1-c][1,4]oxazin-8(1H)-yl)-2-methyl-3-oxo-2,3-dihydro-1H-isoindol-4-yl]amino}-5-(trifluoromethyl)pyrimidin-2-yl]amino}benzyl)phosphonate The title compound was prepared using the procedure for Example 102 with diethyl (4-{[4-chloro-5-(trifluoromethyl)pyrimidin-2-yl]amino}benzyl)phosphonate and Compound 121A. MS (ES+): m/z 690.38 (100) [MH$^+$]; HPLC: $t_R$=0.78 min (UPLC, purity).

Compound 121B: 7-Amino-4-(hexahydropyrazino[2,1-c][1,4]oxazin-8(1H)-yl)-2-methyl-2,3-dihydro-1H-isoindol-1-one The title compound was prepared using the procedure from Compound 210A with Compound 121B.
MS (ES+): m/z 303.35 (100) [MH$^+$]; HPLC: $t_R$=0.29 min (UPLC, Analytical).

Compound 121C: 4-(Hexahydropyrazino[2,1-c][1,4]oxazin-8(1H)-yl)-2-methyl-7-nitro-2,3-dihydro-1H-isoindol-1-one The title compound was prepared using the procedure from Compound 210B with Compound 121D MS (ES+): m/z 333.31 (100) [MH$^+$]; HPLC: $t_R$=0.15 min (UPLC, Analytical).

Example 122

Diethyl (4-{[4-{[7-(hexahydropyrazino[2,1-c][1,4]oxazin-8(1H)-yl)-2-methyl-3-oxo-2,3-dihydro-1H-isoindol-4-yl]amino}-5-(trifluoromethyl)pyrimidin-2-yl]amino}-3-methoxybenzyl)phosphonate The title compound was prepared using the procedure for Example 102 with diethyl (4-{[4-chloro-5-(trifluoromethyl)pyrimidin-2-yl]amino}-3-methoxybenzyl)phosphonate and Compound 121A. MS (ES+): m/z 720.47 (100) [MH$^+$]; HPLC: $t_R$=0.79 min (UPLC, purity).

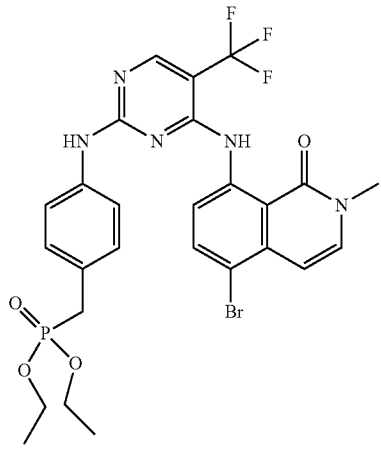 [SMILES: CCOP(=O)(Cc1ccc(Nc2ncc(C(F)(F)F)c(Nc3ccc(Br)c4ccn(C)c(=O)c34)n2)cc1)OCC]

Example 123

Diethyl[4-({4-[(5-bromo-2-methyl-1-oxo-1,2-dihydroisoquinolin-8-yl)amino]-5-(trifluoromethyl)pyrimidin-2-yl}amino)benzyl]phosphonate The title compound was prepared according to the procedure for Example 102 using diethyl (4-{[4-chloro-5-(trifluoromethyl)pyrimidin-2-yl]amino}benzyl)phosphonate (166.9 mg, 0.3939 mmol) and 8-amino-5-bromo-2-methylisoquinolin-1(2H)-one (Compound 123A, 120 mg, 0.47 mmol). The crude material was adsorbed onto a pre-filled silica gel loading cartridge and purified using an ISCO Combiflash system eluting first with 0-100% EtOAc:$CH_2Cl_2$ and then 15% MeOH:EtOAc. The desired fractions were pooled together and concentrated in vacuo. The material was further purified by trituration in $CH_2Cl_2$ and heptane to afford the title product (158.3 mg 62%). $^1$H NMR (400 MHz, DMSO-$d_6$) δ ppm 13.28 (br s, 1H), 9.90 (s, 1H), 8.82 (br s, 1H), 8.50 (s, 1H), 7.86 (d, J=8.8 Hz, 1H), 7.70 (d, J=7.6 Hz, 1H), 7.58 (br d, J=5.6 Hz, 2H), 7.25 (dd, J=8.6, 2.3 Hz, 2H), 6.82 (d, J=7.6 Hz, 1H), 3.90-4.03 (m, 4H), 3.55 (s, 3H), 3.21 (d, J=21.2 Hz, 2H), 1.19 (t, J=6.9 Hz, 6H). MS (ES$^+$): m/z 640.03/642.05 (96/100) [MH$^+$]. HPLC: $t_R$=3.90 min (ZQ3, polar_5 min).

Compound 123A: 8-Amino-5-bromo-2-methylisoquinolin-1(2H)-one

To a solution of 5-bromo-8-nitro-2-methylisoquinolin-1(2H)-one (Compound 123B, 0.350 g, 1.2 mmol) in ethanol (15 mL) was added iron powder (0.5 g) and 2 N HCl (3 mL). The resulting mixture was heated at reflux for 2 h. TLC (EtOAc/$CH_2Cl_2$: 1:9) showed the reaction was complete. After cooled to room temperature, the reaction mixture was filtered, solids washed with ethanol/$CH_2Cl_2$ mixture. The combined filtrate was evaporated to dryness, neutralized with aq. $Na_2CO_3$ (20 mL), and extracted with EtOAc (3×50 mL). The combined organic layer was washed with water (20 mL), dried and evaporated to give a residue, which was purified by column chromatography on silica gel (EtOAc/$CH_2Cl_2$: 1:9)) to afford the desired product as a solid (0.120 g, 39%). $^1$H NMR (CDCl$_3$, 300 MHz): δ=3.51 (s, 3H), 6.44 (d, J=7.8 Hz, 1H), 6.53 (br, 2H), 6.71 (d, J=7.8 Hz, 1H), 7.03 (d, J=7.5 Hz, 1H), 7.49 (d, J=8.7 Hz, 1H).

Compound 123B: 5-Bromo-8-nitro-2-methylisoquinolin-1(2H)-one

To a solution of 5-bromo-2-methyl-8-nitroisoquinolinium tosylate (20.0 g) in $CH_2Cl_2$ (400 mL) was added aq. $Na_2CO_3$ (5%, 400 mL) and hydrogen peroxide (30%, 20 mL). The resulting mixture was stirred at room temperature for 16 h, the organic layer was separated and the aqueous layer was extracted with $CH_2Cl_2$ (5×100 mL). The combined organic layer was washed with water (100 mL), dried over sodium sulfate and evaporated to give the crude product, which was purified by column chromatography on silica gel (EtOAc/$CH_2Cl_2$ (1:9)) to give 2.2 g of the desired product (yield: 8%). $^1$H NMR (CDCl$_3$, 300 MHz): δ=3.60 (s, 3H), 6.90 (d, J=7.8 Hz, 1H), 7.28 (d, J=7.2 Hz, 1H), 7.30 (d, J=7.2 Hz, 1H), 7.92 (d, J=7.8 Hz, 1H).

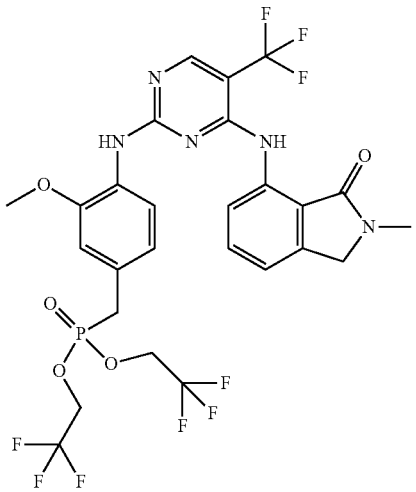

Example 124

Bis(2,2,2-trifluoroethyl) [3-methoxy-4-({4-[(2-methyl-3-oxo-2,3-dihydro-1H-isoindol-4-yl)amino]-5-(trifluoromethyl)pyrimidin-2-yl}amino)benzyl]phosphonate The title compound was prepared according to the procedure for Example 102 using bis(2,2,2-trifluoroethyl) (4-{[4-chloro-5-(trifluoromethyl)pyrimidin-2-yl]amino}-3-methoxybenzyl)phosphonate (Compound 124A, 67.0 mg, 0.119 mmol) and 7-amino-2-methyl-2,3-dihydro-1H-isoindol-1-one (Preparation XXXVIII, 26.9 mg, 0.166 mmol). The crude product was adsorbed onto a pre-filled solid loading cartridge and purified using the Teledyne/ISCO Combiflash system eluting with 0-5% MeOH:$CH_2Cl_2$. The desired fractions were pooled together and concentrated in vacuo. The material was further purified by MDP (under basic conditions; ammonium bicarbonate buffer, pH 9), which afforded the title material as an off-white solid, 54.8 mg (64%). $^1$H NMR (400 MHz, DMSO-$d_6$) δ ppm 10.60 (s, 1H), 9.13 (s, 1H), 8.40 (s, 1H), 8.37 (br s, 1H), 7.49 (br d, J=7.1 Hz, 1H), 7.37 (br t, J=7.1 Hz, 1H), 7.15 (d, J=7.6 Hz, 1H), 7.06 (s, 1H), 6.92 (d, J=8.1 Hz, 1H), 4.60-4.74 (m, 4H), 4.45 (s, 2H), 3.74 (s, 3H), 3.61 (d, J=22.2 Hz, 2H), 3.06 (s, 3H). MS (ES$^+$): m/z 688.08 (100) [MH$^+$]. HPLC: $t_R$=3.72 min (ZQ3, polar_5 min).

Compound 124A: Bis(2,2,2-trifluoroethyl) (4-{[4-chloro-5-(trifluoromethyl)pyrimidin-2-yl]amino}-3-methoxybenzyl)phosphonate This compound was prepared using the procedure for diethyl (4-{[4-chloro-5-(trifluoromethyl) pyrimidin-2-yl]amino}-3-methoxybenzyl)phosphonate with Bis(2,2,2-trifluoroethyl) (4-amino-3-methoxybenzyl)phosphonate (Compound 114A) and 2,4-dichloro-5-(trifluoromethyl)pyrimidine. Purified using an ISCO Combiflash system eluting w/20-100% EtOAc in heptane and then MDP (ammonium bicarbonate basic buffer pH9). $^1$H NMR (DMSO-$d_6$) δ ppm 9.73 (s, 1H), 8.69 (s, 1H), 7.47 (d, J=8.0 Hz, 1H), 7.03 (s, 1H), 6.90 (d, J=7.9 Hz, 1H), 4.67 (quin, J=8.5 Hz, 4H), 3.76 (s, 3H), 3.56 (d, J=22.1 Hz, 2H). MS (ES$^+$): m/z 562.00/564.02 (100/38) [MH$^+$]. HPLC: $t_R$=3.86 min (ZQ3, polar_5 min).

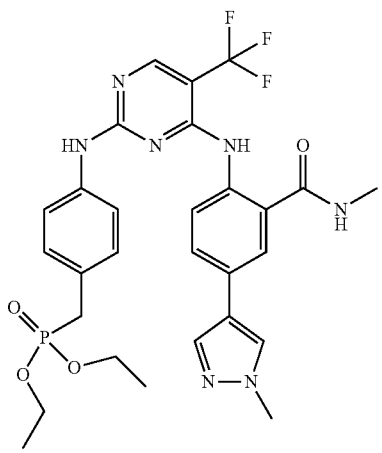 [SMILES: CCOP(=O)(Cc1ccc(Nc2ncc(C(F)(F)F)c(Nc3ccc(-c4cnn(C)c4)cc3C(=O)NC)n2)cc1)OCC]

Example 125

Diethyl (4-{[4-{[2-(methylcarbamoyl)-4-(1-methyl-1H-pyrazol-4-yl)phenyl]amino}-5-(trifluoromethyl)pyrimidin-2-yl]amino}benzyl)phosphonate The title compound was prepared using the procedure from Example 97 with Example 106 and the commercially available 1-methyl-4-(4,4,5,5-tetramethyl-1,3,2-dioxaborolan-2-yl)-1H-pyrazole. MS (ES+): m/z 618.24 (100) [MH+]; HPLC: $t_R$=0.93 min (UPLC, purity).

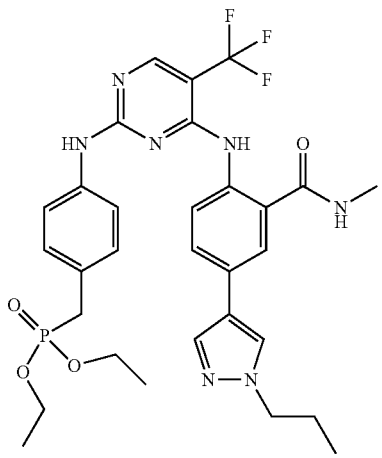 [SMILES: CCCn1cc(-c2ccc(Nc3nc(Nc4ccc(CP(=O)(OCC)OCC)cc4)ncc3C(F)(F)F)c(C(=O)NC)c2)cn1]

Example 126

Diethyl (4-{[4-{[2-(methylcarbamoyl)-4-(1-propyl-1H-pyrazol-4-yl)phenyl]amino}-5-(trifluoromethyl)pyrimidin-2-yl]amino}benzyl)phosphonate The title compound was prepared using the procedure from Example 97 with Example 106 and the commercially available pinacol ester of 1-propyl-1H-pyrazole-4-boronic acid. MS (ES+): m/z 646.29 (100) [MH+]; HPLC: $t_R$=1.14 min (UPLC, purity

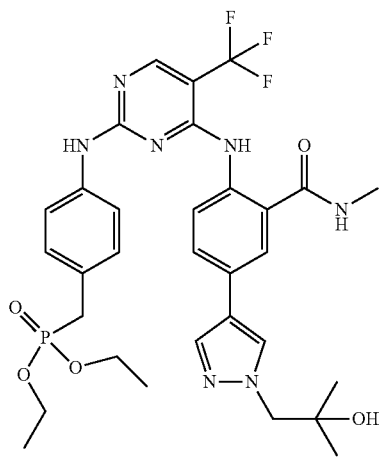 [SMILES: CCOP(=O)(Cc1ccc(Nc2ncc(C(F)(F)F)c(Nc3ccc(-c4cnn(CC(C)(C)O)c4)cc3C(=O)NC)n2)cc1)OCC]

Example 127

Diethyl (4-{[4-({4-[1-(2-hydroxy-2-methylpropyl)-1H-pyrazol-4-yl]-2-(methylcarbamoyl)phenyl}amino)-5-(trifluoromethyl)pyrimidin-2-yl]amino}benzyl)phosphonate The title compound was prepared using the procedure from Example 97 with Example 106 and Compound 98A. MS (ES+): m/z 676.34 (100) [MH+]; HPLC: $t_R$=1.04 min (UPLC, purity).

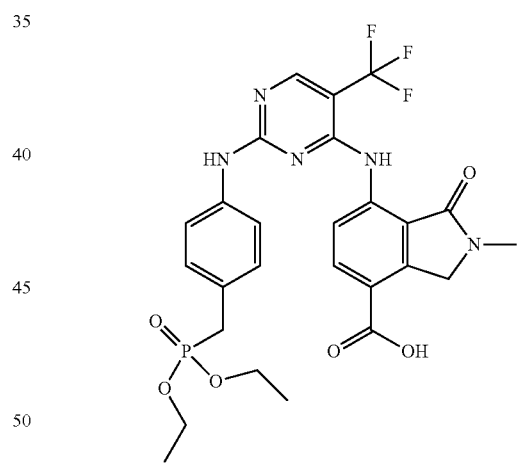

Example 128

7-{[2-({4-[(Diethoxyphosphoryl)methyl]phenyl}amino)-5-(trifluoromethyl)pyrimidin-4-yl]amino}-2-methyl-1-oxo-2,3-dihydro-1H-isoindole-4-carboxylic acid The title compound was prepared using the procedure from Example 102 using diethyl (4-{[4-chloro-5-(trifluoromethyl)pyrimidin-2-yl]amino}benzyl)phosphonate and Compound 128A. MS (ES+): m/z 594.19 (100) [MH+]; HPLC: $t_R$=1.05 min (UPLC, purity).

Compound 128A: 7-amino-2-methyl-1-oxo-2,3-dihydro-1H-isoindole-4-carboxylic acid The title compound was prepared by deprotecting Compound 116C with TFA. The crude product was taken on to the next step without purification.

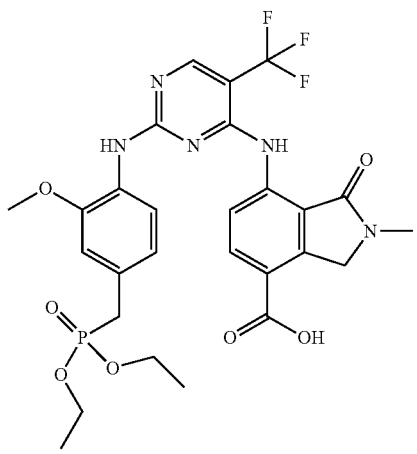

Example 129

7-{[2-({4-[(Diethoxyphosphoryl)methyl]-2-methoxyphenyl}amino)-5-(trifluoromethyl)pyrimidin-4-yl]amino}-2-methyl-1-oxo-2,3-dihydro-1H-isoindole-4-carboxylic acid The title compound was prepared using the procedure from Example 102 using diethyl (4-{[4-chloro-5-(trifluoromethyl)pyrimidin-2-yl]amino}-3-methoxybenzyl)phosphonate and Compound 128A. MS (ES+): m/z 624.19 (100) [MH+]; HPLC: $t_R$=1.07 min (UPLC, purity).

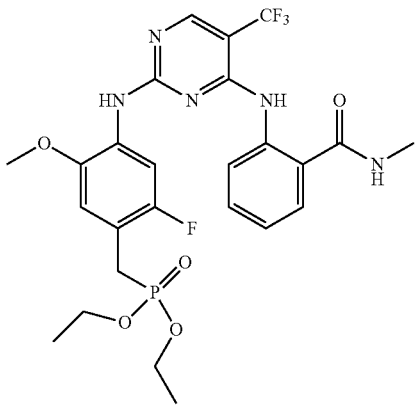

Example 130

Diethyl (2-fluoro-5-methoxy-4-{[4-{[2-(methylcarbamoyl)phenyl]amino}-5-(trifluoromethyl)pyrimidin-2-yl]amino}benzyl)phosphonate A solution of 2-{[2-chloro-5-(trifluoromethyl)pyrimidin-4-yl]amino}-N-methylbenzamide (Compound 104A, 75.0 mg, 0.227 mmol) and diethyl (4-amino-2-fluoro-5-methoxybenzyl)phosphonate (Compound 130A, 79.0 mg, 0.271 mmol) in TFE (1.1 mL) was charged with TFA (77.3 mg, 0.678 mmol). The reaction mixture was irradiated on the microwave at 105° C. for 30 min. The reaction mixture was concentrated under reduced pressure to yield a yellow oil. The reaction was purified by silica gel chromatography on the combi-flash Rf system using EtOAc/MeOH (100:0→95:5) as eluent. The fractions containing product were combined and concentrated under reduced pressure to yield a white solid, 71.3 mg (54% yield). $^1$H NMR (DMSO-d6, 400 MHz): δ=1.20 (t, J=7.07 Hz, 6H), 2.77 (d, J=4.55 Hz, 3H), 3.16-3.25 (m, 2H), 3.79 (s, 3H), 3.95-4.04 (m, 4H), 7.01 (d, J=5.05 Hz, 1H), 7.10-7.17 (m, 1H), 7.42 (t, J=7.58 Hz, 1H), 7.70 (d, J=7.58 Hz, 2H), 8.40 (br. s., 1H), 8.44 (s, 1H), 8.67 (s, 1H), 8.73 (d, J=3.79 Hz, 1H), 11.41 (s, 1H). MS (ES+): m/z 586.19 [MH+] (TOF, polar).

Compound 130A: Diethyl (4-amino-2-fluoro-5-methoxybenzyl)phosphonate

The title compound was prepared according to the procedure for Compound 102A using Compound 130B. $^1$H NMR (CDCl$_3$, 400 MHz): δ=1.25-1.30 (m, 6H), 3.06-3.14 (m, 2H), 3.84 (s, 3H), 4.01-4.09 (m, 4H), 6.56 (d, J=10.36 Hz, 1H), 6.80 (dd, J=6.57, 2.27 Hz, 1H). MS (ES+): m/z 292.11 [MH+] (TOF, polar).

Compound 130B: Diethyl (2-fluoro-5-methoxy-4-nitrobenzyl)phosphonate

A mixture of 1-(chloromethyl)-2-fluoro-5-methoxy-4-nitrobenzene (Compound 130C, 1.578 g, 7.186 mmol) and triethyl phosphite (1.43 g, 8.62 mmol) was heated at 100° C. for 16 h in a sealed tube. After concentrating the reaction mixture under reduced pressure, the crude product was purified by silica gel chromatography on an ISCO combi-flash system using DCM/MeOH as eluent (100:0→95:5) to give an orange oil, 800 mg (35% yield). $^1$H NMR (CDCl$_3$, 400 MHz): δ=1.30 (t, J=7.07 Hz, 6H), 3.20-3.27 (m, 2H), 3.97 (s, 3H), 4.11 (dd, J=8.08, 7.07 Hz, 4H), 7.17 (dd, J=5.94, 2.65 Hz, 1H), 7.67 (dd, J=8.72, 0.88 Hz, 1H). MS (ES+): m/z 322.09 [MH+] (TOF, polar).

Compound 130C: 1-(chloromethyl)-2-fluoro-5-methoxy-4-nitrobenzene

A solution of (2-fluoro-5-methoxy-4-nitrophenyl)methanol (Compound 130D, 1.45 g, 7.21 mmol) in anhydrous DCM (17.0 mL) was charged with Thionyl chloride (1.055 mL, 14.5 mmol). and stirred while refluxing for 16 h. The reaction mixture was concentrated under reduced pressure to yield a brown solid. This material was used without any further purification. $^1$H NMR (CDCl$_3$, 400 MHz): δ=3.99 (s, 3H), 4.65 (d, J=1.01 Hz, 2H), 7.19 (d, J=5.81 Hz, 1H), 7.65 (d, J=8.84 Hz, 1H).

Compound 130D: (2-fluoro-5-methoxy-4-nitrophenyl)methanol

A solution of 2-fluoro-5-methoxy-4-nitrobenzoic acid (Compound 130E, 1.60 g, 7.44 mmol) in THF (23.6 mL) is slowly charged with sodium borohydride (0.633 g, 16.8 mmol) and stirred for 5 minutes. A solution of boron trifluoride, ethyl ether complex (0.895 mL, 7.26 mmol) in THF (7.85 mL) is added to the reaction mixture. The resulting solution is heated at reflux for 4 h. The reaction mixture was cooled to 0° C., then quenched with ice (15 mL) and diluted with ether (25 mL) and 2 N NaOH (10 mL). The ether layer was washed with brine (15 mL), dried over $Na_2SO_4$, filtered and concentrated under reduced pressure to yield an off-white solid, 1.45 g (97% yield). This material was used without any further purification. $^1$H NMR (CDCl$_3$, 400 MHz): δ=3.99 (s, 3H), 4.86 (s, 2H), 7.29 (d, J=5.81 Hz, 1H), 7.64 (d, J=9.09 Hz, 1H). MS (ES$^+$): m/z 202.05 [MH$^+$] (TOF, polar).

Compound 130E:
2-fluoro-5-methoxy-4-nitrobenzoic acid

A solution of 2,5-difluoro-4-nitrobenzoic acid (1.88 g, 9.26 mmol) in MeOH (18.8 mL) was charged with potassium hydroxide (1.55 g, 27.7 mmol) in two batches. The reaction mixture was stirred at 80° C. for 1 hour. The reaction mixture was concentrated under reduced pressure and then acidified with HCl. The resulting precipitate was filtered, washed with water and dried to give the product as a light yellow powder, 1.61 g (81% yield). This material was used in successive reaction without any further purification. $^1$H NMR (DMSO-d6, 400 MHz): δ=3.92 (s, 3H), 7.47 (d, J=5.56 Hz, 1H), 7.83 (d, J=9.09 Hz, 1H). MS (ES$^+$): m/z 214.01 [MH$^-$] (TOF, polar).

Compound 131A:
8-Amino-2-methylisoquinolin-1(2H)-one

A solution of 8-amino-5-bromo-2-methylisoquinolin-1 (2H)-one (Compound 123A, 2.83 g, 10.0 mmol) in a mixture of methanol (120 mL) and acetic acid (5 mL) was hydrogenated over 5% Pd/C (500 mg) under pressure for 24 h. Another batch of 5% Pd/C (400 mg) was added to the reaction mixture and the hydrogenation was continued for a further 24 h. TLC (5% MeOH in $CH_2Cl_2$) showed the reaction was complete. The catalyst was filtered off and the filtrate was evaporated to dryness to give a residue, which was purified by column chromatography on silica gel (5% MeOH in $CH_2Cl_2$) to afford the title compound as a solid (0.40 g, 23%). $^1$H NMR (CDCl$_3$, 300 MHz): δ=3.50 (s, 3H), 6.32 (d, J=7.5 Hz, 1H), 6.48 (br, 2H), 6.54 (d, J=7.8 Hz, 1H), 6.67 (d, J=7.8 Hz, 1H), 6.91 (d, J=7.5 Hz, 1H), 7.29 (d, J=7.8 Hz, 1H).

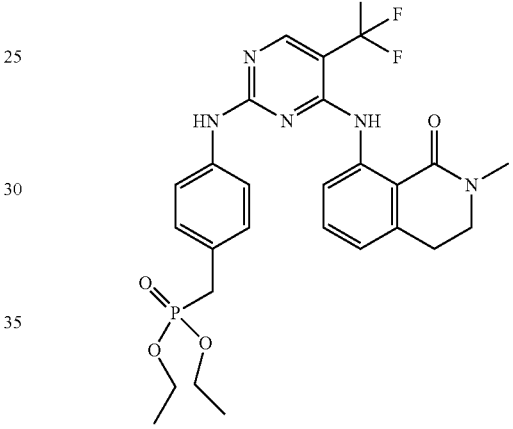

Example 132

Diethyl[4-({4-[(2-methyl-1-oxo-1,2,3,4-tetrahydroisoquinolin-8-yl)amino]-5-(trifluoromethyl)pyrimidin-2-yl}amino)benzyl]phosphonate The title product was prepared according to the procedure for Example 102 using diethyl (4-{[4-chloro-5-(trifluoromethyl)pyrimidin-2-yl]amino}benzyl)phosphonate (52.9 mg, 0.125 mmol) and 8-amino-2-methyl-3,4-dihydroisoquinolin-1(2H)-one (Compound 132A, 25 mg, 0.14 mmol). The crude material was adsorbed onto a pre-filled solid loading cartridge and purified using the Teledyne/ISCO Combiflash system, eluting with 0-5% MeOH:$CH_2Cl_2$. The desired fractions were pooled together and concentrated in vacuo, giving the title material as a white solid, 42.0 mg (59%). $^1$H NMR (400 MHz, DMSO-d$_6$) δ ppm 12.55 (br s, 1H), 9.82 (br s, 1H), 8.44 (s, 1H), 8.56 (br s, 1H), 7.58 (d, J=7.8 Hz, 2H), 7.40 (t, J=8.0 Hz, 1H), 7.19 (dd, J=8.6, 2.3 Hz, 2H), 6.97 (d, J=7.3 Hz, 1H), 3.95 (qd, J=7.4, 7.2 Hz, 4H), 3.56 (t, J=6.7 Hz, 2H), 3.18 (d, J=21.2 Hz, 2H), 3.06 (s, 3H), 2.97 (t, J=6.6 Hz, 2H), 1.18 (t, J=7.1 Hz, 6H). MS (ES$^+$): m/z 564.16 (100) [MH$^+$]. HPLC: $t_R$=3.50 min (ZQ3, polar_5 min).

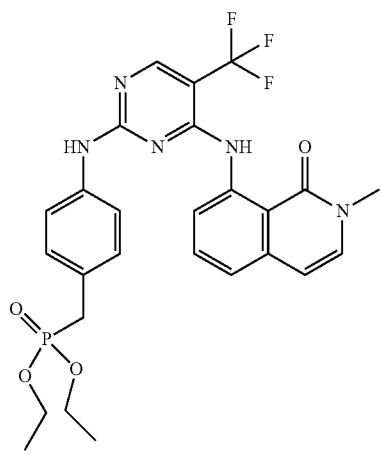 [SMILES: CCOP(=O)(Cc1ccc(Nc2ncc(C(F)(F)F)c(Nc3cccc4ccn(C)c(=O)c34)n2)cc1)OCC]

Example 131

Diethyl[4-({4-[(2-methyl-1-oxo-1,2-dihydroisoquinolin-8-yl)amino]-5-(trifluoromethyl)pyrimidin-2-yl}amino)benzyl]phosphonate The title product was prepared according to the procedure for Example 102 using diethyl (4-{[4-chloro-5-(trifluoromethyl)pyrimidin-2-yl]amino}benzyl)phosphonate (203.1 mg, 0.4793 mmol) and 8-amino-2-methylisoquinolin-1(2H)-one (Compound 131A, 100.0 mg, 0.5740 mmol). The crude product was purified using the Teledyne/ISCO Combiflash system, eluting with 0-5% MeOH:$CH_2Cl_2$. The desired fractions were pooled together and concentrated in vacuo, yielding the title material as a yellow solid, 225.9 mg (82%). $^1$H NMR (400 MHz, DMSO-d$_6$) δ ppm 13.23 (br s, 1H), 9.88 (s, 1H), 8.87 (br s, 1H), 8.48 (s, 1H), 7.55-7.68 (m, 3H), 7.53 (d, J=7.1 Hz, 1H), 7.31 (d, J=7.1 Hz, 1H), 7.24 (dd, J=8.6, 2.3 Hz, 2H), 6.70 (d, J=7.3 Hz, 1H), 3.91-4.01 (m, 4H), 3.53 (s, 3H), 3.20 (d, J=21.2 Hz, 2H), 1.18 (t, J=6.9 Hz, 6H). MS (ES$^+$): m/z 562.11 (100) [MH$^+$]. HPLC: $t_R$=3.58 min (ZQ3, polar_5 min).

Compound 132A: 8-amino-2-methyl-3,4-dihydroisoquinolin-1(2H)-one

A solution of 8-amino-2-methylisoquinolin-1(2H)-one (Compound 131A, 100 mg, 0.54 mmol) in acetic acid (10 mL) was hydrogenated over PtO$_2$ (24 mg) at room temperature for 16 h. TLC (5% MeOH in CH$_2$Cl$_2$) showed the reaction was complete. The catalyst was filtered off through Celite and the filtrate was evaporated to dryness to give a residue, which was dissolved in EtOAc (20 mL), washed with aq. sat. NaHCO$_3$ (20 mL), water (10 mL), dried and evaporated, residue was purified by column chromatography on silica gel (5% MeOH in CH$_2$Cl$_2$) to give the desired product (25 mg, 25%). $^1$H NMR (CDCl$_3$, 300 MHz): δ=2.96 (t, J=6.6 Hz, 2H), 2.98 (s, 3H), 3.55 (t, J=6.9 Hz, 2H), 6.18 (br, 2H), 6.45 (d, J=6.9 Hz, 1H), 6.58 (d, J=7.5 Hz, 1H), 7.15 (t, J=7.5 Hz, 1H).

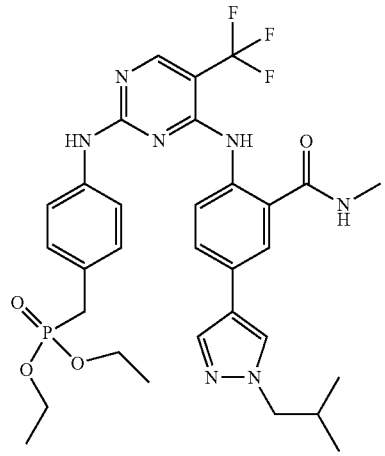

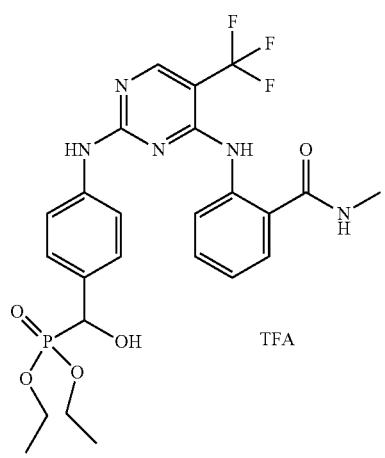 [SMILES: CCOP(=O)(OCC)C(O)c1ccc(Nc2ncc(C(F)(F)F)c(Nc3ccccc3C(=O)NC)n2)cc1]

Example 133

Diethyl[hydroxy(4-{[4-{[2-(methylcarbamoyl)phenyl]amino}-5-(trifluoromethyl)pyrimidin-2-yl]amino}phenyl)methyl]phosphonate trifluoroacetate The title compound was prepared using the procedure from Example 102 with 2-{[2-chloro-5-(trifluoromethyl)pyrimidin-4-yl]amino}-N-methylbenzamide (Compound 104A, 40.0 mg, 0.12 mmol) and diethyl[(4-aminophenyl)(hydroxy)methyl]phosphonate (Compound 115A, 37.6 mg, 0.15 mmol). The reaction mixture was purified by MDP. The desired product was obtained as 40 mg of a white solid (TFA salt, 60% yield). $^1$H NMR (CD$_3$OD, 400 MHz): δ=1.24-1.31 (m, 6H), 2.89 (s, 3H), 4.01-4.16 (m, 4H), 5.03 (d, J=12.8 Hz, 1H), 7.26 (dt, J=1.2, 7.6 Hz, 1H), 7.45-7.55 (m, 6H), 7.68 (dd, J=1.6, 7.6 Hz, 1H), 8.35 (s, 1H). MS (ES$^+$): m/z 554.13 [MH$^+$]. HPLC: t$_R$=3.05 min (OpenLynx, polar_5 min).

Example 134

Diethyl (4-{[4-({2-(methylcarbamoyl)-4-[1-(2-methylpropyl)-1H-pyrazol-4-yl]phenyl}amino)-5-(trifluoromethyl)pyrimidin-2-yl]amino}benzyl)phosphonate The title compound was prepared using the procedure from Example 97 with Diethyl (4-{[4-{[4-bromo-2-(methylcarbamoyl)phenyl]amino}-5-(trifluoromethyl)pyrimidin-2-yl]amino}benzyl)phosphonate (Example 106) and the commercially available 1-isobutyl-4-(4,4,5,5-tetramethyl-1,3,2-dioxaborolan-2-yl)-1H-pyrazole. MS (ES+): m/z 666.20 (100) [MH$^+$]; HPLC: t$_R$=3.60 min (ZQ3, polar_5 min).

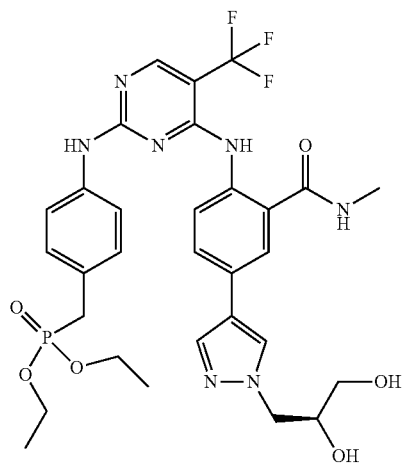 [SMILES: CCOP(=O)(Cc1ccc(Nc2ncc(C(F)(F)F)c(Nc3ccc(-c4cnn(C[C@H](O)CO)c4)cc3C(=O)NC)n2)cc1)OCC]

Example 135

Diethyl (4-{[4-{[4-{1-[(2S)-2,3-dihydroxypropyl]-1H-pyrazol-4-yl}-2-(methylcarbamoyl)phenyl]amino}-5-(trifluoromethyl)pyrimidin-2-yl]amino}benzyl)phosphonate The title compound was prepared using the procedure from Example 97 with Diethyl (4-{[4-{[4-bromo-2-(methylcarbamoyl)phenyl]amino}-5-(trifluoromethyl)pyrimidin-2-yl]amino}benzyl)phosphonate (Example 106) and 1-{[(4S)-2,2-dimethyl-1,3-dioxolan-4-yl]methyl}-4-(4,4,5,5-tetramethyl-1,3,2-dioxaborolan-2-yl)-1H-pyrazole (Compound 101A). After Suzuki reaction and SPE pre-purification, the dried material was dissolved in DCM and 1.0 M HCl in ether was added. The mixture was stirred at room temperature for half an hour. The crude was purified by MDP. MS (ES+): m/z 678.38 (100) [MH+] HPLC: $t_R$=0.87 min (UPLC, purity).

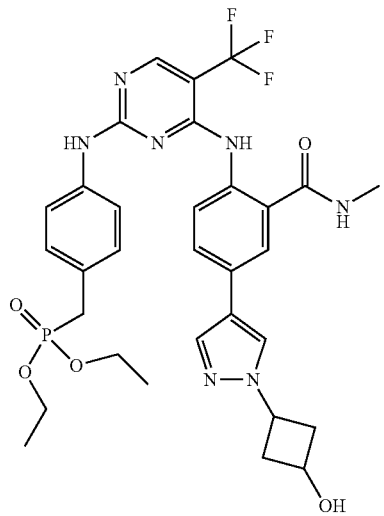 [SMILES: CCOP(=O)(Cc1ccc(Nc2ncc(C(F)(F)F)c(Nc3ccc(-c4cnn(C5CC(O)C5)c4)cc3C(=O)NC)n2)cc1)OCC]

Example 136

Diethyl (4-{[4-({4-[1-(3-hydroxycyclobutyl)-1H-pyrazol-4-yl]-2-(methylcarbamoyl)phenyl}amino)-5-(trifluoromethyl)pyrimidin-2-yl]amino}benzyl)phosphonate The title compound was prepared using the procedure from Example 97 with Diethyl (4-{[4-{[4-bromo-2-(methylcarbamoyl)phenyl]amino}-5-(trifluoromethyl)pyrimidin-2-yl]amino}benzyl)phosphonate (Example 106) and 1-[3-(tert-butyl-dimethyl-silanyloxy)-cyclobutyl]-4-(4,4,5,5-tetramethyl-[1,3,2]dioxaborolan-2-yl)-1H-pyrazole (Compound 100A). After Suzuki reaction and SPE pre-purification, dried material was dissolved in DCM and 1.0 M HCl in ether was added. The mixture was stirred at room temperature for half an hour. The crude was sent to MDP for purification. MS (ES+): m/z 674.34 (100) [MH+]; HPLC: $t_R$=0.94 min (UPLC, purity).

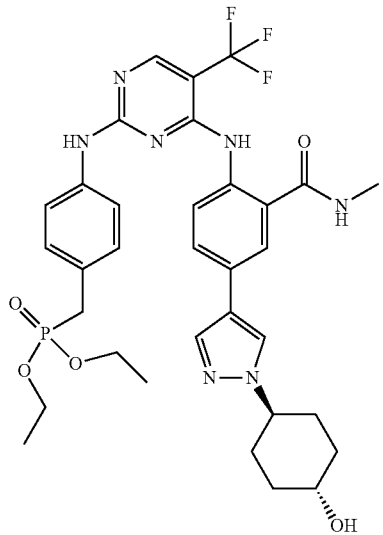 [SMILES: CCOP(=O)(Cc1ccc(Nc2ncc(C(F)(F)F)c(Nc3ccc(-c4cnn([C@H]5CC[C@H](O)CC5)c4)cc3C(=O)NC)n2)cc1)OCC]

Example 137

Diethyl (4-{[4-({4-[1-(trans-4-hydroxycyclohexyl)-1H-pyrazol-4-yl]-2-(methylcarbamoyl)phenyl}amino)-5-(trifluoromethyl)pyrimidin-2-yl]amino}benzyl)phosphonate The title compound was prepared using the procedure from Example 97 with Diethyl (4-{[4-{[4-bromo-2-(methylcarbamoyl)phenyl]amino}-5-(trifluoromethyl)pyrimidin-2-yl]amino}benzyl)phosphonate (Example 106) and 1-[4-(tert-butyl-dimethyl-silanyloxy)-cyclohexyl]-4-(4,4,5,5-tetramethyl-[1,3,2]dioxaborolan-2-yl)-1H-pyrazole (Compound 137A). After Suzuki reaction and SPE pre-purification, dried material was dissolved in DCM and 1.0 M HCl in ether was added. The mixture was stirred at room temperature for half an hour. The crude was sent to MDP for purification. MS (ES+): m/z 702.34 (100) [MH+]; HPLC: $t_R$=0.96 min (UPLC, purity).

137A: 1-(trans-4-{[tert-Butyl(dimethyl)silyl]oxy}cyclohexyl)-4-(4,4,5,5-tetramethyl-1,3,2-dioxaborolan-2-yl)-1H-pyrazole To a stirred THF (30.00 mL) solution of 1-[4-(tert-butyl-dimethyl-silanyloxy)-cyclohexyl]-4-iodo-1H-pyrazole (Compound 137B, 1.1400 g, 2.8053 mmol) was added 2.00 M of isopropylmagnesium chloride in THF (2.31 mL, 4.63 mmol) dropwise under an atmosphere of Nitrogen in 5 min at 0° C. The reaction mixture was stirred at 0° C. for another hour. 2-Methoxy-4,4,5,5-tetramethyl-1,3,2-dioxaborolane (0.9577 mL, 5.610 mmol) was added at 0° C. and then the mixture was stirred at room temperature for another hour. The mixture was treated with saturated NH$_4$Cl (10 ml), extracted with EtOAc (20 ml×3). The extracts were washed with water (10 ml), brine (15 ml), dried over Na$_2$SO$_4$. Solvent was removed under reduced pressure to give a residue which was purified by flash chromatography (10% EtOAc/hexane). MS (ES+): m/z=407.18 [MH+]. HPLC: $t_R$=3.21 min (polar_5 min, ZQ3).

Compound 137B: 1-[4-(tert-Butyl-dimethyl-silanyloxy)-cyclohexyl]-4-iodo-1H-pyrazole A mixture of trans-4-(4-Iodo-pyrazol-1-yl)-cyclohexanol (Compound 137 D, 1.00 g, 3.42 mmol), tert-butyldimethylsilyl chloride (1.03 g, 6.85 mmol), 4-dimethylaminopyridine (80 mg, 0.7 mmol), 1H-imidazole (699 mg, 10.3 mmol) and DCM (20 mL, 300 mmol) was stirred room temperature for 20 min. The material was transferred to a separatory funnel, extracting with DCM and sat. NaHCO$_3$. The organic layer was dry-loaded onto silica gel for column chromatography, eluting with 3% EtOAc/hexanes. The fractions containing the pure product were concentrated in vacuo to afford the title compound as clear oil. $^1$H NMR (400 MHz, DMSO-d6): δ=0.05 (s, 6H), 0.86 (s, 9H), 1.33-1.47 (m, 2H), 1.70-1.91 (m, 4H), 1.96 (d, J=11.9 Hz, 2H), 3.58-3.75 (m, 1H), 4.11-4.21 (m, 1H), 7.49 (s, 1H), 7.92 (s, 1H). MS (ES+): m/z=407.05 [MH$^+$]. HPLC: t$_R$=3.22 min (polar__5 min, ZQ3).

Compounds 137C and 137D: cis- and trans-4-(4-Iodopyrazol-1-yl)cyclohexanol

Sodium borohydride (0.29 g, 7.6 mmol) was added to a solution of 4-(4-iodopyrazol-1-yl)cyclohexanone (Compound 137E, 4.5 g, 15.5 mmol) in EtOH (20 mL) at RT under an atmosphere of nitrogen. The mixture was stirred at RT for 2 h, after which, the solvent evaporated and the residue was taken up in water and extracted with EtOAc (3×60 mL). The combined organic extracts were dried over Na$_2$SO$_4$, filtered, and concentrated in vacuo to give an off-white solid. This material was purified by column chromatography on silica gel by eluting with 40% EtOAc/hexanes. The first (less polar) spot obtained was identified as cis isomer and the second (more polar) spot obtained was identified as trans isomer. Cis-isomer: $^1$H NMR (300 MHz, CDCl$_3$): δ=1.63-1.74 (m, 4H), 1.87-1.96 (m, 4H), 2.09-2.19 (m, 2H), 4.07-4.20 (m, 2H), 7.50 (s, 2H). Trans-isomer: colorless solid, mp. 82-86° C. $^1$H NMR (400 MHz, CDCl$_3$): δ=1.42-1.51 (m, 2H), 1.79 (brs, 1H), 1.77-1.99 (m, 2H), 2.09-2.22 (m, 4H), 3.74 (br. tt, J=10.8, 4.0 Hz, 1H), 4.13 (tt, J=11.6, 3.8 Hz, 1H), 7.44 (d, J=0.4 Hz, 1H), 7.50 (d, J=0.4 Hz, 1H). MS (ES+): m/z=293.11 [MH$^+$]. HPLC: t$_R$=2.58 min (polar__5 min, ZQ3).

Compound 137E: 4-(4-Iodopyrazol-1-yl)cyclohexanone

A mixture of 1-(1,4-dioxaspiro[4.5]dec-8-yl)-4-iodo-1H-pyrazole (Compound 137F, 3.0 g, 8.9 mmol), pyridinium p-toluenesulfonate (4.5 g, 17.9 mmol), acetone (100 mL) and H$_2$O (100 mL) was heated at 60° C. overnight. Work-up: Solvent was evaporated and the residue was extracted with EtOAc (3×60 mL). The combined extracts were washed with water (3×50 mL), brine (50 mL), dried over Na$_2$SO$_4$, filtered, and concentrated in vacuo to give the title compound as white solid. It was used in the next step without further purification. $^1$H NMR (400 MHz, CDCl$_3$): δ=2.23-2.63 (m, 8H), 4.57-4.64 (m, 1H), 7.51 (s, 1H), 7.54 (s, 1H). MS (ES+): m/z=291.09 (100). HPLC: t$_R$=2.79 min (polar__5 min, ZQ3).

Compound 137F: 1-(1,4-Dioxaspiro[4.5]dec-8-yl)-4-iodo-1H-pyrazole

A mixture of 1,4-dioxaspiro[4.5]dec-8-yl 4-methylbenzenesulfonate (prepared according to U.S. Pat. No. 4,360,531) (2.0 g, 6.4 mmol), 4-iodopyrazole (1.36 g, 7.0 mmol), K$_2$CO$_3$ (1.06 g, 7.7 mmol), and 18-crown-6 (0.2 g, 0.7 mmol) in DMF (5 mL) was heated under nitrogen at 50° C. for 16 h. Water (50 mL) was added to the reaction mixture, which was then extracted with EtOAc (3×40 mL). The combined EtOAc extracts were washed with water (30 mL), dried over Na$_2$SO$_4$, filtered, and concentrated in vacuo. The residue was purified by column chromatography on silica gel using EtOAc/CH$_2$Cl$_2$ (1:9) to give the title compound. $^1$H NMR (CDCl$_3$, 400 MHz): δ =1.67-1.76 (m, 2H), 1.84-1.91 (m, 2H), 1.99-2.17 (m, 4H), 3.95-3.99 (m, 4H), 4.18-4.27 (m, 1H). MS (ES+): m/z=334.96 (100) [MH$^+$]. HPLC: t$_R$=3.26 min (polar__5 min, ZQ3).

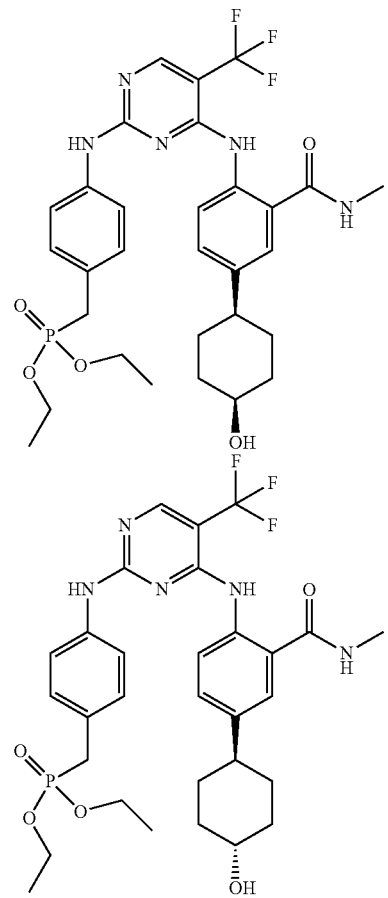

Examples 138 and 139

Diethyl (4-{[4-{[4-(cis-4-hydroxycyclohexyl)-2-(methylcarbamoyl)phenyl]amino}-5-(trifluoromethyl)pyrimidin-2-yl]amino}benzyl)phosphonate and
Diethyl (4-{[4-{[4-(trans-4-hydroxycyclohexyl)-2-(methylcarbamoyl)phenyl]amino}-5-(trifluoromethyl)pyrimidin-2-yl]amino}benzyl)phosphonate The title compound was prepared using the procedure from Example 102 with diethyl (4-{[4-chloro-5-(trifluoromethyl)pyrimidin-2-yl]amino}benzyl)phosphonate (136 mg, 0.322 mmol) and 2-amino-5-(4-hydroxycyclohexyl)-N-methylbenzamide (Compound 139A, 80.0 mg, 0.322 mmol) The reaction mixture was poured into water and extracted twice with EtOAc. The combined organic layers were washed with brine, dried over Na$_2$SO$_4$, filtered, concentrated and purified on an Isco Combiflash (0-5% MeOH/DCM) to isolate both the cis and the trans isomers. The minor (cis) isomer eluted first: 22.5 mg $^1$H NMR (400 MHz, DMSO-d6) δ 1.18 (t, J=6.95 Hz, 6H), 1.49-1.62 (m, 4H), 1.72-1.82 (m, 2H), 1.86-1.99 (m, 2H), 2.78 (d, J=4.55 Hz, 3H), 3.08-3.22 (m, 2H), 3.90-4.00 (m, 4H), 7.15 (dd, J=8.59, 2.02 Hz, 2H), 7.34 (dd, J=8.59, 1.77 Hz, 1H), 7.58 (br. s., 3H), 8.36 (br. s., 1H), 8.41 (s, 1H), 8.75 (d, J=4.55 Hz, 1H), 9.78 (br. s., 1H), 11.23 (br. s., 1H). MS (ES+): m/z=636.12 (100) [M+1]. HPLC: $t_R$=3.34 min (ZQ3, polar_5 min). Trans isomer, 90.4 mg: $^1$H NMR (400 MHz, DMSO-d6) δ 1.18 (t, J=7.07 Hz, 6H), 1.27-1.38 (m, 2H), 1.55 (dtd, J=12.95, 12.73, 2.78 Hz, 2H), 1.82 (d, J=11.87 Hz, 2H), 1.95 (dd, J=12.63, 3.28 Hz, 2H), 2.78 (d, J=4.55 Hz, 3H), 3.09-3.22 (m, 2H), 3.95 (qd, J=7.45, 7.20 Hz, 4H), 7.16 (dd, J=8.59, 2.27 Hz, 2H), 7.34 (dd, J=8.59, 2.02 Hz, 1H), 7.56 (br. s., 1H), 7.57 (d, J=2.02 Hz, 2H), 8.36 (br. s., 1H), 8.41 (s, 1H), 8.69 (d, J=4.80 Hz, 1H), 9.78 (br. s., 1H), 11.26 (br. s., 1H). MS (ES+): m/z=636.12 (100) [M+1]. HPLC: $t_R$=3.23 min (ZQ3, polar_5 min).

Compound 139A:
2-amino-5-(4-hydroxycyclohexyl)-N-methylbenzamide

A solution of 2-amino-5-(1,4-dioxaspiro[4.5]dec-8-yl)-N-methylbenzamide (Compound 139B, 333 mg, 1.15 mmol) in THF (10 mL, 200 mmol) was treated with aqueous 3N HCl (2 mL) and allowed to stir at rt for 3.5 hours. The mixture was cooled to 0° C. and basified with dropwise addition of 50% aq. NaOH to pH-10 and then was diluted with EtOAc (30 mL). The organic layer was separated, washed with brine (2×10 mL), dried over anhydrous sodium sulfate. The solvents were evaporated under reduced pressure and the crude ketone was purified on the ISCO Combiflash eluting with 80-100% EtOAc in hexane then 5% DCM/MeOH to isolate the ketone intermediate as 235 mg of a white solid. MS (ES+): m/z=247.07 (100) [M+1]. LCMS: $t_R$=2.29 min (ZQ3, polar_5 min). A solution of 2-amino-N-methyl-5-(4-oxocyclohexyl)benzamide in MeOH (7 mL, 200 mmol) was cooled to 0° C. and treated with sodium borohydride (43 mg, 1.1 mmol). The mixture was stirred at 0° C. for 1 hour then quenched with sat. aq. NH$_4$Cl (1 mL). The crude residue obtained from concentrating the reaction mixture in vacuo was taken up in 1 mL H$_2$O and EtOAc (30 m). The layers were separated. The aqueous layer was saturated with salt and washed again with ~20 mL of EtOAc. The combined organic layers were washed with brine, dried over anhydrous sodium sulfate, filtered, and concentrated. The crude solid was taken up in DCM/MeOH, treated with silica and concentrated. This silica was loaded into an sample column and purified on an ISCO Combiflash (0-5% Then 10% MeOH/DCM) to isolate 201 mg of the desired product as an 80:20 mixture of cis/trans isomers. Major product (trans): MS (ES+): m/z=249.07 (100) {M+1}; HPLC: $t_R$=2.10 min (ZQ3, polar_5 min). Minor product (cis): MS (ES+): m/z=249.10 (100) [M+1]; HPLC: $t_R$=2.28 minutes (ZQ3, polar_5 min). The mixture was used in the next step.

Compound 139B: 2-amino-5-(1,4-dioxaspiro[4.5]dec-8-yl)-N-methylbenzamide

10% Pd—C (50% H$_2$O w/w) (264 mg, 0.124 mmol) was added to a solution of 2-amino-5-(1,4-dioxaspiro[4.5]dec-7-en-8-yl)-N-methylbenzamide (Compound 139C, 357 mg, 1.24 mmol) in EtOH (30 mL, 500 mmol). The reaction mixture was subjected to three cycles of evacuation and N$_2$ purging. After a fourth evacuation, the mixture was flushed with H$_2$ and allowed to stirred under hydrogen overnight. The catalyst was removed by filtration through a pad of celite, and the filtrate was evaporated under reduced pressure to give the title compound as 333 mg of a pinkish solid. $^1$H NMR (400 MHz, DMSO-d6) δ 1.50-1.78 (m, 8H), 2.34-2.44 (m, 1H), 2.71 (d, J=4.55 Hz, 3H), 3.88 (t, J=2.40 Hz, 4H), 6.20 (s, 2H), 6.60 (d, J=8.34 Hz, 1H), 6.98 (dd, J=8.46, 1.89 Hz, 1H), 7.29 (d, J=2.02 Hz, 1H), 8.16 (d, J=4.55 Hz, 1H). MS (ES+): m/z=291.08 (100) [M+1]. HPLC: $t_R$=2.60 min (ZQ3, polar_5 min).

Compound 139C: 2-amino-5-(1,4-dioxaspiro[4.5] dec-7-en-8-yl)-N-methylbenzamide

2-Amino-5-bromo-N-methyl-benzamide (Compound 106A, 645.0 mg, 2.816 mmol), 1,4-dioxaspiro[4.5]dec-7-ene-8-boronic acid pinacol ester (899.2 mg, 3.379 mmol) and [1,1'-Bis(diphenylphosphino)ferrocene]dichloropalladium (II), complex with dichloromethane (1:1) (229.9 mg, 0.2816 mmol) were added to a 20 mL microwave tube and taken up in 1,4-Dioxane (8 mL, 100 mmol). This mixture was treated with a solution of potassium carbonate (1167 mg, 8.447 mmol) in H$_2$O (3 mL, 200 mmol). After sparging the mixture with N$_2$ for 1 minute, the tube was sealed and irradiated in the Biotage microwave reactor for 30 minutes at 100° C. The mixture was poured into water and extracted twice with EtOAc. The combined organic layers were washed with brine, dried over Na$_2$SO$_4$, filtered and concentrated to a black goo. This was taken up in DCM, treated with silica and concentrated to a plug. This plug was loaded into a sample cartridge and purified on an ISCO Combiflash unit (0-40%-70% EtOAc/Hexane) to isolate the desired product as 359 mg of a white solid. $^1$H NMR (400 MHz, DMSO-d6) δ1.78 (t, J=6.44 Hz, 2H), 2.33 (br. s., 2H), 2.50-2.51 (m, J=1.80 Hz, 2H), 2.72 (d, J=4.55 Hz, 3H), 3.91 (s, 4H), 5.85 (t, J=3.92 Hz, 1H), 6.41 (s, 2H), 6.63 (d, J=8.59 Hz, 1H), 7.23 (dd, J=8.59, 2.02 Hz, 1H), 7.48 (d, J=2.27 Hz, 1H), 8.23 (d, J=4.29 Hz, 1H). MS (ES+): m/z=289.06 (100) [M+1]. HPLC: $t_R$=2.62 min (ZQ3, polar_5 min).

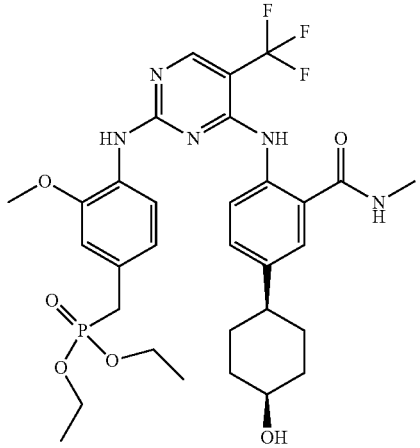

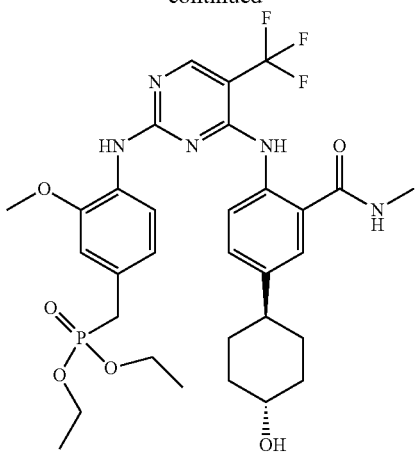

Examples 140 and 141

Diethyl (4-{[4-{[4-(cis-4-hydroxycyclohexyl)-2-(methylcarbamoyl)phenyl]amino}-5-(trifluoromethyl)pyrimidin-2-yl]amino}-3-methoxybenzyl)phosphonate and Diethyl (4-{[4-{[4-(trans-4-hydroxycyclohexyl)-2-(methylcarbamoyl)phenyl]amino}-5-(trifluoromethyl)pyrimidin-2-yl]amino}-3-methoxybenzyl)phosphonate These compounds were prepared analogously to Examples 138 and 139 using diethyl (4-{[4-chloro-5-(trifluoromethyl)pyrimidin-2-yl]amino}-3-methoxybenzyl)phosphonate and 2-amino-5-(4-hydroxycyclohexyl)-N-methylbenzamide (Compound 139A). These compounds were isolated via normal phase chromatography on an ISCO Combiflash unit (0-5% MeOH/DCM). The cis isomer was the first to elute under these conditions. Cis: isomer: $^1$H NMR (400 MHz, DMSO-d6) δ 11.34 (s, 1H), 8.72 (d, J=4.29 Hz, 1H), 8.64 (s, 1H), 8.35 (s, 1H), 8.31 (br. s., 1H), 7.59 (d, J=8.08 Hz, 1H), 7.54 (s, 1H), 7.25 (d, J=7.83 Hz, 1H), 7.01 (s, 1H), 6.82 (d, J=8.08 Hz, 1H), 4.38 (d, J=3.79 Hz, 1H), 3.98 (quin, J=7.33 Hz, 4H), 3.90 (br. s., 1H), 3.77 (s, 3H), 3.23 (d, J=21.40 Hz, 2H), 2.77 (d, J=4.55 Hz, 3H), 1.83-1.96 (m, 2H), 1.76 (d, J=11.37 Hz, 2H), 1.47-1.62 (m, 4H), 1.19 (t, J=6.95 Hz, 6H). M @ 2.5 (1H) obscured by DMSO. MS (ES+): m/z=666.14 (100) [M+1]. HPLC: $t_R$=3.44 min (ZQ3, polar_5 min). Trans isomer: was taken up in enough EtOH to ensure dissolution. To this was added 93 µL of a 0.5M solution of MeSO$_3$H in EtOH. This mixture was well stirred, concentrated under reduced pressure and dried overnight in vacuo to isolate the desired product as the methanesulfonic acid salt (35.4 mg). $^1$H NMR (400 MHz, DMSO-d6) δ11.54 (s, 1H), 8.86 (br. s., 1H), 8.69 (d, J=4.55 Hz, 1H), 8.37 (s, 1H), 8.27 (br. s., 1H), 7.52-7.57 (m, 2H), 7.26 (dd, J=1.01, 8.84 Hz, 1H), 7.03 (s, 1H), 6.84 (td, J=2.02, 8.08 Hz, 1H), 3.94-4.04 (m, 4H), 3.77 (s, 3H), 3.42-3.53 (m, 1H), 3.25 (d, J=21.50 Hz, 2H), 2.77 (d, J=4.55 Hz, 2H), 2.40-2.47 (m, 1H), 2.31 (s, 3H), 1.94 (dd, J=2.65, 12.25 Hz, 2H), 1.78 (d, J=13.14 Hz, 2H), 1.54 (dq, J=2.40, 12.84 Hz, 2H), 1.26-1.36 (m, 2H), 1.30 (br. s., 2H), 1.16-1.23 (m, 2H), 1.20 (t, J=7.07 Hz, 6H). MS (ES+): m/z=666.14 (100) [M+1]. HPLC: $t_R$=3.34 min (ZQ3, polar_5 min)

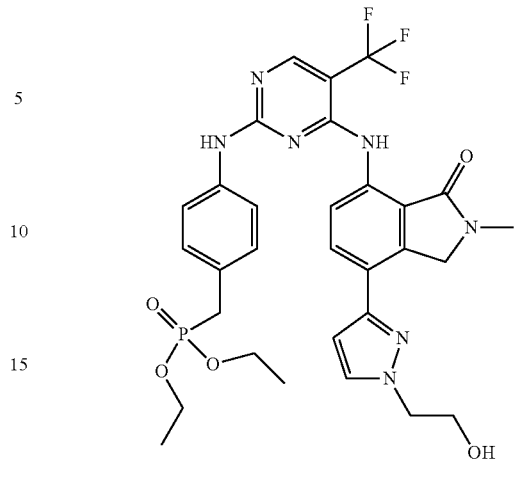

Example 142

Diethyl (4-{[4-({7-[1-(2-hydroxyethyl)-1H-pyrazol-3-yl]-2-methyl-3-oxo-2,3-dihydro-1H-isoindol-4-yl}amino)-5-(trifluoromethyl)pyrimidin-2-yl]amino}benzyl)phosphonate The title compound was prepared according to the procedure for Compound 97A diethyl[4-({4-[(7-bromo-2-methyl-3-oxo-2,3-dihydro-1H-isoindol-4-yl)amino]-5-(trifluoromethyl)pyrimidin-2-yl}amino)benzyl]phosphonate (30.0 mg, 0.0477 mmol) and [1-(2-{[tert-butyl(dimethyl)silyl]oxy}ethyl)-1H-pyrazol-3-yl]boronic acid (Compound 142A, 46.7 mg, 0.173 mmol). The afforded intermediate, diethyl (4-{[4-({7-[1-(2-{[tert-butyl(dimethyl)silyl]oxy}ethyl)-1H-pyrazol-3-yl]-2-methyl-3-oxo-2,3-dihydro-1H-isoindol-4-yl}amino)-5-(trifluoromethyl)pyrimidin-2-yl]amino}benzyl)phosphonate, was purified using an ISCO Combiflash system (eluting with 0-100% EtOAc:CH$_2$Cl$_2$). The product thus obtained was dissolved in CH$_2$Cl$_2$ (2 mL), treated with 4.0 M of HCl in dioxane (0.5 mL) and stirred at rt for 2 h. The solid was filtered off and rinsed with a mixture of CH$_2$Cl$_2$/heptane, giving the title material as an off-white solid, 24.6 mg (77%). $^1$H NMR (400 MHz, DMSO-d$_6$) δ ppm 10.89 (s, 1H), 10.03 (br s, 1H), 8.89 (br s, 1H), 8.49 (s, 1H), 7.91 (d, J=8.6 Hz, 1H), 7.81 (d, J=2.3 Hz, 1H), 7.57 (br s, 2H), 7.30 (br d, J=6.6 Hz, 2H), 6.93 (br s, 1H), 4.72 (s, 2H), 4.21 (t, J=5.6 Hz, 2H), 3.97 (quin, J=7.4 Hz, 4H), 3.81 (t, J=5.7 Hz, 2H), 3.25 (d, J=21.5 Hz, 2H), 3.13 (s, 3H), 1.16 (t, J=7.1 Hz, 6H). MS (ES$^+$): m/z 660.22 (100) [MH$^+$]. HPLC: $t_R$=2.72 min (ZQ3, nonpolar_5 min).

Compound 142A: [1-(2-{[tert-butyl(dimethyl)silyl]oxy}ethyl)-1H-pyrazol-3-yl]boronic acid In a sealed tube, a suspension of 3-(4,4,5,5-tetramethyl-1,3,2-dioxaborolane)-pyrazole (100.0 mg, 0.5154 mmol), tert-butyl-(2-iodoethoxy)-dimethylsilane (196 mg, 0.685 mmol), and Cs$_2$CO$_3$ (271 mg, 0.832 mmol) in DMF (3 mL) was stirred at 100° C. for 16 h. The sample was suspended between EtOAc and water and the layers were separated. The organic layer was washed with brine, dried over anhydrous Na$_2$SO$_4$, filtered, and concentrated in vacuo, giving the title material as the boronic acid, as a yellow oil (203.4 mg). MS (ES$^+$): m/z 270.18/271.13/272.15 (19/79/15) [MH$^+$]. HPLC: $t_R$=3.33 min (CAD, ZQ3, polar_5 min).

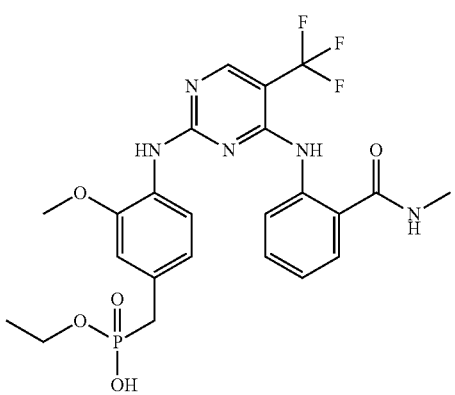 [SMILES: CCOP(=O)(O)Cc1ccc(Nc2ncc(C(F)(F)F)c(Nc3ccccc3C(=O)NC)n2)c(OC)c1]

Example 143

Ethyl hydrogen (3-methoxy-4-{[4-{[2-(methylcarbamoyl)phenyl]amino}-5-(trifluoromethyl)pyrimidin-2-yl]amino}benzyl)phosphonate A solution of diethyl (3-methoxy-4-{[4-{[2-(methylcarbamoyl)phenyl]amino}-5-(trifluoromethyl)pyrimidin-2-yl]amino}benzyl)phosphonate (Example 53, 44.3 mg, 0.0781 mmol) in 37% HCl (1 mL) was heated at 80° C. for a total of 3.5 h. The reaction was concentrated in vacuo. The residue was dissolved in DMSO and submitted for mass-directed purification (under basic conditions; ammonium bicarbonate buffer, pH 9). The fractions containing product were combined and concentrated in vacuo, giving the title material as a white solid, 11.6 mg (27%). $^1$H NMR (400 MHz, MeOD) δ ppm: 8.33 (d, J=8.3 Hz, 1H), 8.29 (s, 1H), 7.85 (d, J=8.1 Hz, 1H), 7.62 (dd, J=7.8, 1.3 Hz, 1H), 7.49 (ddd, J=8.5, 7.4, 1.5 Hz, 1H), 7.18 (td, J=7.6, 1.0 Hz, 1H), 7.05 (t, J=1.8 Hz, 1H), 6.79 (ddd, J=8.1, 2.0, 1.8 Hz, 1H), 3.89 (s, 3H), 3.79-3.88 (m, 2H), 2.96 (d, J=20.2 Hz, 2H), 2.89 (s, 3H), 1.19 (t, J=6.9 Hz, 3H). MS (ES$^+$): m/z 540.14 (100) [MH$^+$]. HPLC: $t_R$=2.63 min (ZQ3, polar_5 min).

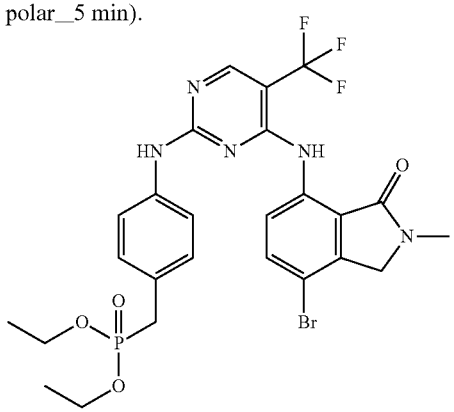

Example 144

Diethyl[4-({4-[(7-bromo-2-methyl-3-oxo-2,3-dihydro-1H-isoindol-4-yl)amino]-5-(trifluoromethyl)pyrimidin-2-yl}amino)benzyl]phosphonate The title compound was prepared according to the procedure for Example 102 using diethyl (4-{[4-chloro-5-(trifluoromethyl)pyrimidin-2-yl]amino}benzyl)phosphonate (50.0 mg, 0.118 mmol) and 7-amino-4-bromo-2-methyl-2,3-dihydro-1H-isoindol-1-one (34.14 mg, 0.1416 mmol). The reaction mixture was concentrated under reduced pressure to yield a yellow oil which was purified on an ISCO Combiflash system using (DCM/MeOH 100:0→95:5) as eluent to isolate 28.1 mg of the title compound (38%). $^1$H NMR (400 MHz, DMSO-d6) δ ppm 1.19 (t, J=7.07 Hz, 6H), 3.09 (s, 3H), 3.18-3.27 (m, 2H), 3.92-4.03 (m, 4H), 4.43 (s, 2H), 7.23-7.33 (m, 8H), 7.55 (br. s., 5H), 7.63 (d, J=8.84 Hz, 4H), 8.50 (s, 4H), 9.95 (s, 4H), 10.54 (br. s., 3H). MS (ES$^+$): m/z 627.95/629.93 (91/100) [MH$^+$]. HPLC: $t_R$=3.72 min (ZQ3, polar_5 min).

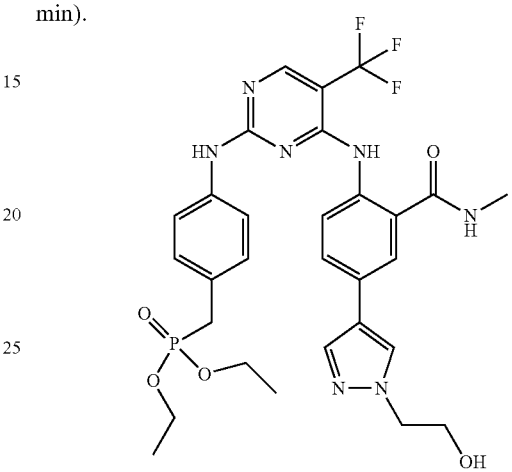

Example 145

Diethyl (4-{[4-({4-[1-(2-hydroxyethyl)-1H-pyrazol-4-yl]-2-(methylcarbamoyl)phenyl}amino)-5-(trifluoromethyl)pyrimidin-2-yl]amino}benzyl)phosphonate The title compound was prepared using the procedure from Example 97 with Diethyl (4-{[4-{[4-bromo-2-(methylcarbamoyl)phenyl]amino}-5-(trifluoromethyl)pyrimidin-2-yl]amino}benzyl)phosphonate (Example 106) and the commercially available 1-(hydroxyethyl)-1H-pyriazole-4-boronic acid pinacol ester 1-[2-(tetrahydro-pyran-2-yloxy)-ethyl]-4-(4,4,5,5-tetramethyl-[1,3,2]dioxaborolan-2-yl)-1H-pyrazole. The crude product was purified by MDP. MS (ES+): m/z 648.25 (100) [MH$^+$]; HPLC: $t_R$=0.91 min (UPLC, purity).

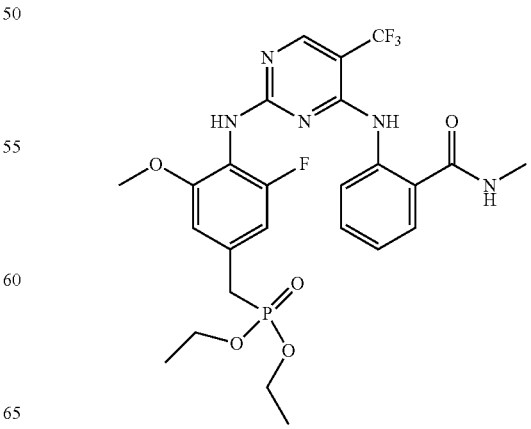

Example 146

Diethyl (3-fluoro-5-methoxy-4-{[4-{[2-(methylcarbamoyl)phenyl]amino}-5-(trifluoromethyl)pyrimidin-2-yl]amino}benzyl)phosphonate The title compound was prepared using the procedure from Example 102 (Diethyl (4-{[4-{[4-fluoro-2-(methylcarbamoyl)phenyl]amino}-5-(trifluoromethyl)pyrimidin-2-yl]amino}-3-methoxybenzyl)phosphonate) with 2-{[2-chloro-5-(trifluoromethyl)pyrimidin-4-yl]amino}-N-methylbenzamide (Compound 104A) and Diethyl (4-amino-3-fluoro-5-methoxybenzyl)phosphonate (Compound 146A). $^1$H NMR (CD$_3$OD, 400 MHz): δ=1.30 (t, J=7.07 Hz, 6H), 2.90 (s, 3H), 3.33-3.40 (m, 2H), 3.85 (s, 3H), 4.06-4.18 (m, 4H), 6.88 (dt, J=10.11, 2.02 Hz, 1H), 6.95 (s, 1H), 7.17 (br. s., 1H), 7.37 (br. s., 1H), 7.64 (d, J=6.82 Hz, 1H), 8.29 (br. s., 2H). MS (ES$^+$): m/z 586.21 [MH$^+$] (TOF, polar).

Compound 146A: Diethyl (4-amino-3-fluoro-5-methoxybenzyl)phosphonate

The title compound was prepared using the procedure from Compound 102A (2-Amino-5-fluoro-N-methylbenzamide) with Diethyl (3-fluoro-5-methoxy-4-nitrobenzyl)phosphonate (Compound 146B). $^1$H NMR (CDCl$_3$, 400 MHz): δ=1.27 (t, J=7.07 Hz, 6H), 2.99-3.08 (m, 2H), 3.87 (s, 3H), 4.00-4.06 (m, 4H), 6.59 (s, 1H), 6.63 (dt, J=10.74, 2.21 Hz, 1H). MS (ES$^+$): m/z 292.06 [MH$^+$] (TOF, polar).

Compound 146B: Diethyl (3-fluoro-5-methoxy-4-nitrobenzyl)phosphonate

The title compound was prepared using the procedure from Compound 104C (Diethyl (3-chloro-4-nitrobenzyl)phosphonate) with 5-(chloromethyl)-1-fluoro-3-methoxy-2-nitrobenzene (Compound 146C). $^1$H NMR (CDCl$_3$, 400 MHz): δ=1.31 (t, J=7.07 Hz, 6H), 3.11-3.18 (m, 2H), 3.94 (s, 3H), 4.07-4.13 (m, 4H), 6.77 (dt, J=9.79, 1.93 Hz, 1H), 6.82 (s, 1H).

Compound 146C: 5-(chloromethyl)-1-fluoro-3-methoxy-2-nitrobenzene

The title compound was prepared using the procedure from Compound 130C (1-(chloromethyl)-2-fluoro-5-methoxy-4-nitrobenzene) with (3-fluoro-5-methoxy-4-nitrophenyl)methanol (Compound 146D). $^1$H NMR (CDCl$_3$, 400 MHz): δ=3.96 (s, 3H), 4.55 (s, 2H), 6.87-6.90 (m, 2H).

Compound 146D: (3-fluoro-5-methoxy-4-nitrophenyl)methanol

The title compound was prepared using the procedure from Compound 130E (2-fluoro-5-methoxy-4-nitrobenzoic acid) with 3-fluoro-5-methoxy-4-nitrobenzoic acid (Compound 146E). $^1$H NMR (CDCl$_3$, 400 MHz): δ=3.95 (s, 3H), 4.76 (s, 2H), 6.81-6.86 (m, 1H), 6.88 (s, 1H). MS (ES$^+$): m/z 202.05 [MH$^+$] (TOF, polar).

Compound 146E: 3-fluoro-5-methoxy-4-nitrobenzoic acid

A suspension of 3-fluoro-5-methoxy-4-nitrobenzonitrile (Compound 146F, 1.15 g, 5.86 mmol) in sulfuric acid (2.4 mL) and H$_2$O (2.4 mL) was heated at 100° C. for 16 hours with stirring. The reaction mixture was allowed to cool to room temperature during which time a precipitate formed. The solid was filtered and washed with water. The solid was dried in the vacuum oven at 50° C. to yield the product as a white solid, 1.097 g (87% yield). MS (ES$^+$): m/z 214.01 [MH$^-$] (TOF, polar).

Compound 146F: 3-fluoro-5-methoxy-4-nitrobenzonitrile

Into a microwave vial was added 5-bromo-1-fluoro-3-methoxy-2-nitrobenzene (1.75 g, 7.00 mmol), Pd(PPh$_3$)$_4$ (1.132 g, 0.9798 mmol), and zinc cyanide (0.8222 g, 7.002 mmol). The vial was sealed, and then DMF (28 mL) was added. The vial was evacuated and purged with N$_2$ gas (3 times). The reaction mixture was irradiated on the microwave for 3-5 minutes at 150° C. The reaction mixture was quenched with water (30 mL) and then extracted with EtOAc (60 mL). The organic layer was washed with water (30 mL), brine (2×20 mL), dried over Na$_2$SO$_4$, filtered and concentrated under reduced pressure to yield a yellow oil. The crude material was purified by silica gel chromatography on an ISCO combi-flash Rf system using Heptane/EtOAc (100:0→55:45) as eluent to yield the desired product as a light yellow solid 1.15 g (84% yield). $^1$H NMR (CDCl$_3$, 400 MHz): δ=4.01 (s, 3H), 7.14 (t, J=1.52 Hz, 1H), 7.19 (dd, J=8.21, 1.39 Hz, 1H).

Compound 146G: 5-bromo-1-fluoro-3-methoxy-2-nitrobenzene

A solution of 5-bromo-1,3-difluoro-2-nitrobenzene (Compound 146H, 2.00 g, 8.40 mmol) in MeOH (15.0 mL) was added potassium hydroxide (504 mg, 8.98 mmol). The reaction was stirred at 90° C. for 1 hour. The reaction mixture was concentrated under reduced pressure. The residue was diluted with EtOAc (15 mL), washed with water (10 mL), washed with brine (10 mL), dried over Na$_2$SO$_4$, filtered and concentrated under reduced pressure to yield a yellow solid. The crude material was purified by silica gel chromatography on an ISCO combi-flash Rf system using Heptane/EtOAc (100:0→70:30) as eluent to yield the desired product as a light yellow solid 1.75 g (83% yield). $^1$H NMR (CDCl$_3$, 400 MHz): δ=3.95 (s, 3H), 7.01 (s, 1H), 7.05 (dd, J=8.59, 1.77 Hz, 1H).

Compound 146H: 5-bromo-1,3-difluoro-2-nitrobenzene

A solution of 4-bromo-2,6-difluoroaniline (4.75 g, 22.8 mmol) in TFA (50.2 mL) and AcOH (50.2 mL) was charged with sodium perborate tetrahydrate (16.0 g, 104 mmol). The reaction was warmed to 60° C. and heated for 24 h. The reaction was quenched with water (10 mL) and extracted with EtOAc (15 mL). The organic layer was washed with brine (10 mL) and dried over anhydrous Na$_2$SO$_4$. The organic layer was concentrated under reduced pressure to yield a yellow solid. The material was purified by silica gel chromatography on an ISCO combi-flash Rf system using Heptane/EtOAc (100:0→90:10) as eluent. The fractions containing product were combined and concentrated under reduced pressure to yield a white solid, 2.28 g (42% yield). $^1$H NMR (CDCl$_3$, 400 MHz): δ=7.31-7.35 (m, 2H).

Example 147

Diethyl (2-fluoro-3-methoxy-4-{[4-{[2-(methylcarbamoyl)phenyl]amino}-5-(trifluoromethyl)pyrimidin-2-yl]amino}benzyl)phosphonate

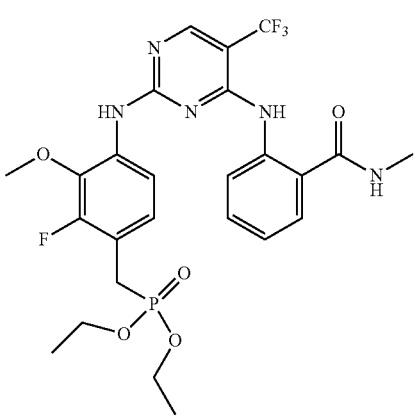

The title compound was prepared according to the procedure from Example 102 using 2-{[2-chloro-5-(trifluoromethyl)pyrimidin-4-yl]amino}-N-methylbenzamide (Compound 104A) and Diethyl (4-amino-2-fluoro-3-methoxybenzyl)phosphonate (Compound 147A). $^1$H NMR (CD$_3$OD, 400 MHz): δ=1.26-1.36 (m, 6H), 1.44 (t, J=6.95 Hz, 3H), 3.32-3.39 (m, 2H), 4.04-4.15 (m, 4H), 4.22 (q, J=7.07 Hz, 2H), 7.00 (dd, J=8.34, 1.77 Hz, 1H), 7.21 (d, J=1.77 Hz, 1H), 7.75 (d, J=8.34 Hz, 1H). MS (ES$^+$): m/z 586.14 [MH$^+$] (TOF, polar).

Compound 147A: Diethyl (4-amino-2-fluoro-3-methoxybenzyl)phosphonate

The title compound was prepared using the procedure from Compound 102A (2-Amino-5-fluoro-N-methylbenzamide) with Diethyl (2-fluoro-3-methoxy-4-nitrobenzyl)phosphonate (Compound 147B). $^1$H NMR (CDCl$_3$, 400 MHz): δ=1.29 (t, J=6.95 Hz, 6H), 3.13-3.21 (m, 2H), 3.93 (d, J=1.52 Hz, 3H), 4.04-4.12 (m, 4H), 6.55 (d, J=8.34 Hz, 1H), 6.83 (td, J=7.96, 2.78 Hz, 1H). MS (ES$^+$): m/z 292.11 [MH$^+$] (TOF, polar).

Compound 147B: Diethyl (2-fluoro-3-methoxy-4-nitrobenzyl)phosphonate

The title compound was prepared using the procedure from Compound 104C (Diethyl (3-chloro-4-nitrobenzyl)phosphonate) with 1-(chloromethyl)-2-fluoro-3-methoxy-4-nitrobenzene (Compound 147C). $^1$H NMR (CDCl$_3$, 400 MHz): δ=1.28-1.32 (m, 6H), 3.19-3.31 (m, 2H), 7.14-7.22 (m, 1H), 7.54-7.61 (m, 1H). MS (ES$^+$): m/z 322.08 [MH$^+$] (TOF, polar).

Compound 147C: 1-(chloromethyl)-2-fluoro-3-methoxy-4-nitrobenzene

The title compound was prepared using the procedure from Compound 130C (1-(chloromethyl)-2-fluoro-5-methoxy-4-nitrobenzene) with (2-fluoro-3-methoxy-4-nitrophenyl)methanol (Compound 147D). $^1$H NMR (CDCl$_3$, 400 MHz): δ=4.10 (d, J=1.77 Hz, 3H), 4.64 (d, J=1.52 Hz, 2H), 7.62 (dd, J=8.59, 1.77 Hz, 1H). MS (ES$^+$): m/z 220.00 [MH$^+$] (TOF, polar).

Compound 147D: (2-fluoro-3-methoxy-4-nitrophenyl)methanol

The title compound was prepared using the procedure from Compound 130D ((2-fluoro-5-methoxy-4-nitrophenyl)methanol) with 2-fluoro-3-methoxy-4-nitrobenzoic acid (Compound 147E). $^1$H NMR (CDCl$_3$, 400 MHz): δ=4.08 (d, J=1.77 Hz, 3H), 4.85 (s, 2H), 7.29-7.35 (m, 1H), 7.64 (dd, J=8.46, 1.89 Hz, 1H).

Compound 147E: 2-fluoro-3-methoxy-4-nitrobenzoic acid

A suspension of 2-fluoro-3-methoxy-4-nitrobenzonitrile (0.700 g, 3.57 mmol) in HCl (1.5 mL) and H$_2$O (1.5 mL) was heated at 100° C. for 16 minutes with stirring. The precipitate was filtered and washed with water. The solid was allowed to dry in the vacuum oven at 50° C. overnight to yield the product as a white solid, 736 mg (96% yield). This material was used in successive reactions without any further purification. $^1$H NMR (CDCl$_3$, 400 MHz): δ=4.13 (d, J=1.52 Hz, 3H), 7.61 (dd, J=8.72, 1.89 Hz, 1H), 7.83 (dd, J=8.72, 6.44 Hz, 1H). MS (ES$^+$): m/z 213.99 [MH$^-$] (TOF, polar).

Compound 147F: 2-fluoro-3-methoxy-4-nitrobenzonitrile

The title compound was prepared according to the procedure for 3-fluoro-5-methoxy-4-nitrobenzonitrile (Compound 146F) using 1-Bromo-2-fluoro-3-methoxy-4-nitrobenzene (Compound 147G). $^1$H NMR (CDCl$_3$, 400 MHz): δ=4.15 (d, J=2.27 Hz, 3H), 7.45 (dd, J=8.59, 5.56 Hz, 1H), 7.64 (dd, J=8.59, 1.77 Hz, 1H).

Compound 147G: 1-Bromo-2-fluoro-3-methoxy-4-nitrobenzene

The title compound was prepared according to the procedure for 5-bromo-1,3-difluoro-2-nitrobenzene (Compound 146H) using 4-Bromo-3-fluoro-2-methoxyaniline (Compound 147H). $^1$H NMR (CDCl$_3$, 400 MHz): δ=4.10 (d, J=1.77 Hz, 3H), 7.37-7.43 (m, 1H), 7.53 (dd, J=8.97, 1.89 Hz, 1H).

Compound 147H: 4-Bromo-3-fluoro-2-methoxyaniline

To a solution of 2-methoxy-3-fluoroaniline (Compound 147I, 7.70 g, 54.6 mmol) in AcOH (45.0 mL) was added a solution of bromine (6.98 g, 43.6 mmol) in AcOH (45.0 mL) dropwise. The reaction mixture was stirred at rt for 30 minutes. The resulting solid was filtered and washed with acetic acid to give the HBr salt of the desired product. The solid was dissolved in water (15 mL), basified by addition of KOH, and extracted with EtOAc (20 mL). The organic layer was dried over Na$_2$SO$_4$ and concentrated under reduced pressure to give a white solid. The crude material was purified by silica gel chromatography on an ISCO combi-flash Rf system using Heptane/EtOAc (100:0→70:30) as eluent to yield the desired product as a white solid, 6.536 mg (54% yield). $^1$H NMR (CDCl$_3$, 400 MHz): δ=3.93 (d, J=1.52 Hz, 3H), 6.42 (dd, J=8.84, 1.77 Hz, 1H), 7.01 (dd, J=8.72, 6.95 Hz, 1H). MS (ES+): m/z 221.98 [MH+] (TOF, polar).

Compound 147I: 2-methoxy-3-fluoroaniline

The title compound was prepared according to the procedure for Compound 102A (2-Amino-5-fluoro-N-methylbenzamide) with 1-fluoro-2-methoxy-3-nitrobenzene (Compound 147J). $^1$H NMR (CDCl$_3$, 400 MHz): δ=3.92 (d, J=1.52 Hz, 3H), 6.44-6.53 (m, 2H), 6.80 (td, J=8.15, 5.68 Hz, 1H). MS (ES+): m/z 142.07 [MH+] (TOF, polar).

Compound 147J: 1-fluoro-2-methoxy-3-nitrobenzene

A solution of 2-fluoro-6-nitrophenol (10.0 g, 63.6 mmol) in DMF (25.0 mL) was charged with methyl iodide (5.94 mL, 95.5 mmol) and potassium carbonate (13.2 g, 95.5 mmol). The reaction mixture was stirred at rt for 16 h. The reaction was quenched with water (30 mL) and extracted with EtOAc (30 mL). The organic layer was washed with water (25 mL), washed with Brine (25 mL), dried over anhydrous Na$_2$SO$_4$, filtered, and concentrated under reduced pressure to yield a brown oil, 11.0 g (101% yield). $^1$H NMR (CDCl$_3$, 400 MHz): δ=4.08 (d, J=2.02 Hz, 3H), 7.14 (td, J=8.34, 4.80 Hz, 1H), 7.35 (ddd, J=10.74, 8.34, 1.64 Hz, 1H), 7.58 (dt, J=8.27, 1.55 Hz, 1H).

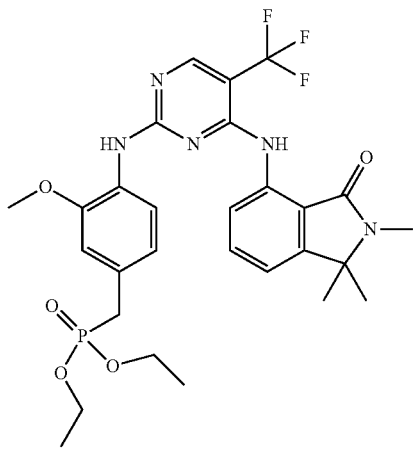

Example 148

Diethyl[3-methoxy-4-({5-(trifluoromethyl)-4-[(1,1,2-trimethyl-3-oxo-2,3-dihydro-1H-isoindol-4-yl)amino]pyrimidin-2-yl}amino)benzyl]phosphonate The title compound was prepared according to the procedure from Example 102 using diethyl (4-{[4-chloro-5-(trifluoromethyl)pyrimidin-2-yl]amino}-3-methoxybenzyl)phosphonate and 7-Amino-2,3,3-trimethyl-2,3-dihydro-1H-isoindol-1-one (Compound 148A). $^1$H NMR (400 MHz, DMSO-d6) δ ppm: 9.00 (br s, 1H), 8.33 (s, 1H), 7.92 (s, 1H), 7.38-7.45 (m, 1H), 7.32 (br s, 1H), 7.07-7.16 (m, 2H), 6.84 (s, 1H), 6.31 (br s, 1H), 3.91 (quin, J=7.3 Hz, 4H), 3.77 (s, 3H), 3.13 (s, 3H), 3.06 (d, J=21.2 Hz, 2H), 1.27 (s, 6H), 1.16 (t, J=7.1 Hz, 6H). MS (ES+): m/z 608.24 [MH+] HPLC: t$_R$=1.31 min (UPLC, analytical).

Compound 148A: 7-Amino-2,3,3-trimethyl-2,3-dihydro-1H-isoindol-1-one 20 mg of 5% Pd/C was cautiously added to a solution of 2,3,3-trimethyl-7-nitroisoindolin-1-one (Compound 148B, 0.15 g, 0.68 mmol) in ethanol (5 mL), and stirred under hydrogen atmosphere at room temperature overnight. The reaction mixture was and concentrated to remove ethanol to provide 80 mg of pure the title compound (62%). $^1$H NMR (CDCl$_3$, 500 MHz): δ1.36 (s, 6H), 3.58 (s, 3H), 3.60 (brs, 2H), 6.58 (d, J=8.0 Hz, 1H), 6.69 (d, J=7.0 Hz, 1H), 6.84 (dd, J=7.0, 8.0 Hz, 1H).

Compound 148B: 2,3,3-Trimethyl-7-nitroisoindolin-1-one

A solution of 3,3-dimethyl-7-nitroisoindolin-1-one (Compound 148C, 100 mg, 0.48 mmol) in THF (5 mL), was treated with 60% NaH (58 mg, 1.44 mmol) and stirred for 15 minutes. Methanol (0.078 mL, 1.92 mmol) and iodomethane (0.12 mL, 1.92 mmol) were added to this solution and stirred at 50° C. overnight. Cold water (3 mL) was added, the reaction mixture was concentrated to remove THF and extracted with EtOAc (3×5 mL). The combined organic layer washed with brine, dried (Na$_2$SO$_4$) and concentrated to provide 70 mg of the title compound (66%). $^1$H NMR (CDCl$_3$, 600 MHz): δ1.45 (s, 6H), 3.56 (s, 3H), 7.13 (dd, J=7.8, 84 Hz, 1H), 7.40 (d, J=7.8 Hz, 1H), 8.02 (d, J=8.4 Hz, 1H).

Compound 148C: 3,3-Dimethyl-7-nitroisoindolin-1-one

A solution of methyl 2-(2-cyanopropan-2-yl)-6-nitrobenzoate (Compound 148D, 1 g, 4.03 mmol) was stirred for 24 hrs at room temperature in 10 mL of 20% ethanolic KOH (35.64 mmol). In a separate flask, bromine (0.5 mL, 9.7 mmol) was added to a solution of NaOH (1.9 g, 47.5 mmol) in H$_2$O (40 mL) to generate NaOBr. 20 mL of this solution was slowly added to the first solution at room temperature and stirred overnight. The remaining NaOBr solution was then added and stirring continued for another 24 hrs. This reaction was quenched with saturated solution of sodium sulfite (10 mL) and stirred for 20 minutes. The solution was then acidified with potassium hydrogen sulfate solution and extracted with EtOAc (3×25 mL). The combined organic layers were washed with brine, dried (Na$_2$SO$_4$), concentrated and chromatographed (20% EtOAc in hexanes) to provide the title compound as 0.1 g of a yellowish solid (12%). $^1$H NMR (CDCl$_3$, 600 MHz): δ1.44 (s, 6H), 7.13 (dd, J=7.2, 8.4 Hz, 1H), 7.45 (d, J=7.2 Hz, 1H), 8.03 (d, J=8.4 Hz, 1H), 9.0 (brs, 1H).

Compound 148C: Methyl 2-(2-cyanopropan-2-yl)-6-nitrobenzoate

Iodomethane (1.44 mL, 22.5 mmol) and 13.62 mL of a 1 M solution of t-BuOK were added to a solution of methyl 2-(cyanomethyl)-6-nitrobenzoate (Compound 148D, 1 g, 4.5 mmol) in THF (10 mL) at 0° C. This mixture was allowed to stir overnight at room temperature, after which, it was quenched with 1M HCl (20 mL) and extracted with EtOAc (3×20 mL). The combined organic layers were washed with brine, dried (Na$_2$SO$_4$) and concentrated to provide the title compound as 1 g of an oily liquid (89%). $^1$H NMR (CDCl$_3$, 400 MHz): δ1.89 (s, 6H), 3.95 (s, 3H), 7.65 (dd, J=7.2, 8.0 Hz, 1H), 7.83 (d, J=8 Hz, 1H), 8.05 (d, J=7.2 Hz, 1H).

Compound 148C: Methyl 2-(cyanomethyl)-6-nitrobenzoate

A solution of KCN (474 mg, 7.2 mmol) in water (1 mL) was slowly added to a solution of methyl 2-(bromomethyl)-6-nitrobenzoate (1 g, 3.6 mmol) in methanol (20 mL). This mixture was allowed to stir for 4 h at 50° C. The reaction mixture was concentrated to remove methanol, diluted with water (20 mL) and extracted with EtOAc (2×20 mL). The combined organic layers were washed with brine, dried (Na$_2$SO$_4$), concentrated and purified by flash column chromatography (25% EtOAc in hexanes) to give the title compound as 0.5 g of an oily liquid (62%). $^1$H NMR (CDCl$_3$, 600 MHz): δ 3.9 (s, 2H), 3.97 (s, 3H), 7.65 (t, J=7.8 Hz, 1H), 7.85 (d, J=7.8 Hz, 1H), 8.09 (d, J=7.8 Hz, 1H).

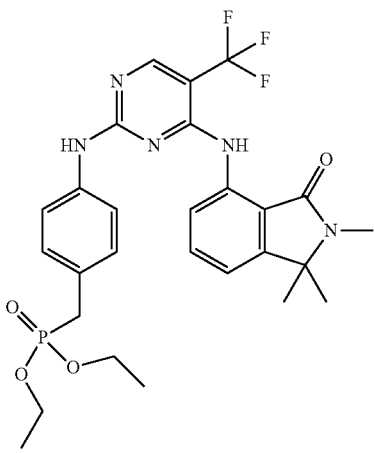 [SMILES: CCOP(=O)(Cc1ccc(Nc2ncc(C(F)(F)F)c(Nc3cccc4c3C(=O)N(C)C4(C)C)n2)cc1)OCC]

Example 149

Diethyl[4-({5-(trifluoromethyl)-4-[(1,1,2-trimethyl-3-oxo-2,3-dihydro-1H-isoindol-4-yl)amino]pyrimidin-2-yl}amino)benzyl]phosphonate The title compound was prepared according to the procedure from Example 102 using diethyl (4-{[4-chloro-5-(trifluoromethyl)pyrimidin-2-yl]amino}benzyl)phosphonate and 7-Amino-2,3,3-trimethyl-2,3-dihydro-1H-isoindol-1-one (Compound 148A). $^1$H NMR (400 MHz, DMSO-d6) δ ppm: 9.71 (br s, 1H), 8.94 (br s, 1H), 8.35 (s, 1H), 7.43 (dd, J=6.2, 1.9 Hz, 1H), 7.06-7.30 (m, 4H), 6.80 (br s, 2H), 3.80-3.95 (m, 4H), 3.13 (s, 3H), 3.01 (d, J=21.5 Hz, 2H), 1.27 (s, 6H), 1.14 (t, J=7.1 Hz, 6H). MS (ES$^+$): m/z 578.16 [MH$^+$] HPLC: t$_R$=3.27 min (ZQ3, polar_5 min).

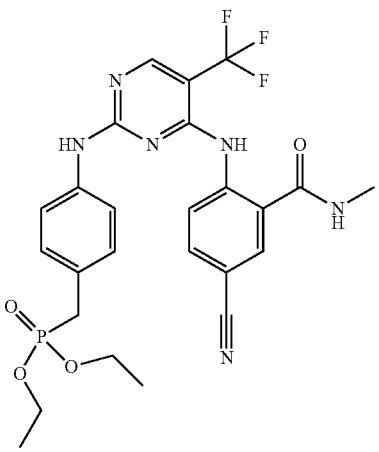 [SMILES: CCOP(=O)(Cc1ccc(Nc2ncc(C(F)(F)F)c(Nc3ccc(C#N)cc3C(=O)NC)n2)cc1)OCC]

Example 150

Diethyl (4-{[4-{[4-cyano-2-(methylcarbamoyl)phenyl]amino}-5-(trifluoromethyl)pyrimidin-2-yl]amino}benzyl)phosphonate The title compound was prepared using the procedure from Example 102 (Diethyl (4-{[4-{[4-fluoro-2-(methylcarbamoyl)phenyl]amino}-5-(trifluoromethyl)pyrimidin-2-yl]amino}-3-benzyl)phosphonate) with diethyl (4-{[4-chloro-5-(trifluoromethyl)pyrimidin-2-yl]amino}benzyl)phosphonate (10.0 mg, 0.0236 mmol) and 2-amino-5-cyano-N-methylbenzamide (Compound 150A, 8.3 mg, 0.0472 mmol). The crude mixture was purified by MDP to obtain the title compound as white solid (2.9 mg, 22% yield). $^1$H NMR (400 MHz, CD$_3$OD) δ=1.28 (t, J=7.1 Hz, 6H), 2.92 (s, 3H), 3.26 (d, J=21.5 Hz, 2H), 4.07 (qd, J=7.3, 7.1 Hz, 4H), 7.28 (dd, J=8.8, 2.5 Hz, 2H), 7.56 (d, J=6.3 Hz, 2H), 7.76 (d, J=8.6 Hz, 1H), 8.04 (d, J=1.8 Hz, 1H), 8.42 (s, 1H), 8.88 (br. s., 1H). MS (ES+): m/z 563.17 (100) [MH$^+$]; HPLC: t$_R$=1.04 min (UPLC, purity).

Compound 150A: 2-Amino-5-cyano-N-methylbenzamide

A mixture of 2-Amino-5-bromo-N-methylbenzamide (100.0 mg, 0.4365 mmol), zinc cyanide (51.26 mg, 0.4365 mmol), Pd(PPh$_3$)$_4$ (75.67 mg, 0.06548 mmol) in DMF (1.5 mL) was flushed with nitrogen and irradiated in a microwave reactor at 150° C. for 5 minutes. The reaction mixture was poured into water and extracted by ethyl acetate. The combined organic layers were washed with water and brine, concentrated in vacuo and purified on an ISCO Combiflash unit to isolate the desired product (37.0 mg, 48% yield).

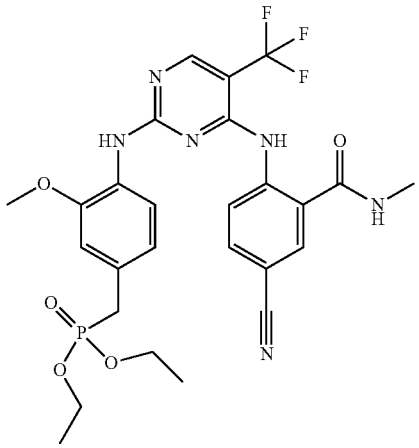

Example 151

Diethyl (4-{[4-{[4-cyano-2-(methylcarbamoyl)phenyl]amino}-5-(trifluoromethyl)pyrimidin-2-yl]amino}-3-methoxybenzyl)phosphonate The title compound was prepared using the procedure from Example 102 (Diethyl (4-{[4-{[4-fluoro-2-(methylcarbamoyl)-phenyl]amino}-5-(trifluoromethyl)pyrimidin-2-yl]amino}-3-methoxybenzyl)phosphonate) using (4-{[4-chloro-5-(trifluoromethyl)pyrimidin-2-yl]amino}-3-methoxybenzyl)phosphonate and 2-amino-5-cyano-N- methylbenzamide (Compound 150A). MS (ES+): m/z 593.19 (100) [MH⁺]; HPLC: t_R=1.08 min (UPLC, purity).

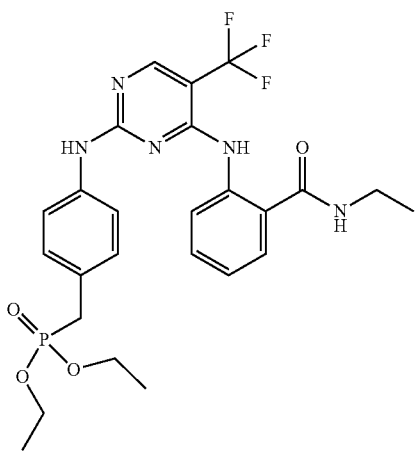 [SMILES: CCNC(=O)c1ccccc1Nc1nc(Nc2ccc(CP(=O)(OCC)OCC)cc2)ncc1C(F)(F)F]

Example 152

Diethyl (4-{[4-{[2-(ethylcarbamoyl)phenyl]amino}-5-(trifluoromethyl)pyrimidin-2-yl]amino}benzyl)phosphonate The title compound was prepared according to the procedure from Example 102 (Diethyl (4-{[4-{[4-fluoro-2-(methylcarbamoyl)-phenyl]amino}-5-(trifluoromethyl)pyrimidin-2-yl]amino}-3-methoxybenzyl)phosphonate) using diethyl (4-{[4-chloro-5-(trifluoromethyl)pyrimidin-2-yl]amino}benzyl)phosphonate and the commercially available 2-amino-N-ethylbenzamide. MS (ES+): m/z 552.51 (100) [MH⁺] HPLC: t_R=1.05 min (UPLC, purity).

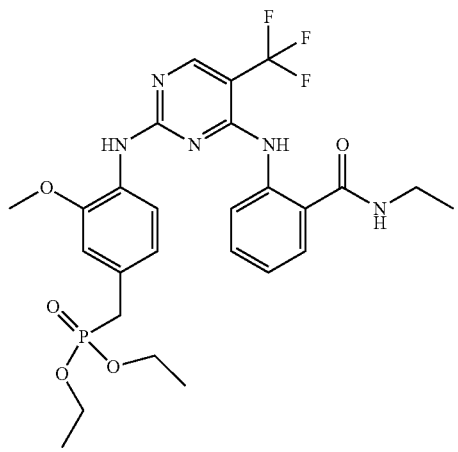 [SMILES: CCNC(=O)c1ccccc1Nc1nc(Nc2ccc(CP(=O)(OCC)OCC)cc2OC)ncc1C(F)(F)F]

Example 153

Diethyl (4-{[4-{[2-(ethylcarbamoyl)phenyl]amino}-5-(trifluoromethyl)pyrimidin-2-yl]amino}-3-methoxybenzyl)phosphonate The title compound was prepared according to the procedure from Example 102 (Diethyl (4-{[4-{[4-fluoro-2-(methylcarbamoyl)-phenyl]amino}-5-(trifluoromethyl)pyrimidin-2-yl]amino}-3-methoxybenzyl)phosphonate) using diethyl (4-{[4-chloro-5-(trifluoromethyl)pyrimidin-2-yl]amino}-3-methoxybenzyl)phosphonate and the commercially available 2-amino-N-ethylbenzamide. MS (ES+): m/z 582.25 (100) [MH⁺]; HPLC: t_R=1.09 min (UPLC, purity).

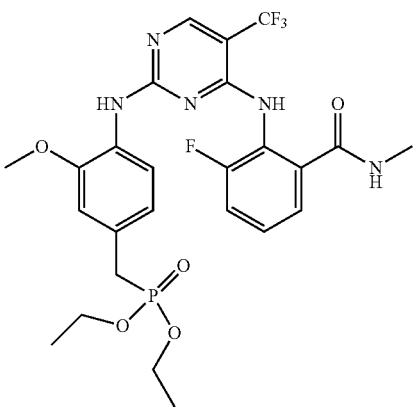

Example 154

Diethyl (4-{[4-{[2-fluoro-6-(methylcarbamoyl)phenyl]amino}-5-(trifluoromethyl)pyrimidin-2-yl]amino}-3-methoxybenzyl)phosphonate The title compound was prepared according to the procedure from Example 102 (Diethyl (4-{[4-{[4-fluoro-2-(methylcarbamoyl)-phenyl]amino}-5-(trifluoromethyl)pyrimidin-2-yl]amino}-3-methoxybenzyl)phosphonate) using diethyl (4-{[4-chloro-5-(trifluoromethyl)pyrimidin-2-yl]amino}-3-methoxybenzyl)phosphonate and the commercially available 2-amino-3-fluoro-N-methylbenzamide. ¹H NMR (CDCl₃, 400 MHz): δ=1.26 (t, J=7.07 Hz, 6H), 2.92 (d, J=4.80 Hz, 3H), 3.03-3.12 (m, 2H), 3.86 (s, 3H), 3.95-4.07 (m, 4H), 6.21 (q, J=4.97 Hz, 1H), 6.57 (d, J=9.09 Hz, 1H), 6.81 (t, J=1.89 Hz, 1H), 7.28-7.36 (m, 3H), 7.73 (br. s., 1H), 7.85 (br. s., 1H), 8.34 (s, 1H), 8.89 (br. s., 1H). MS (ES⁺): m/z 586.14 [MH⁺] (TOF, polar).

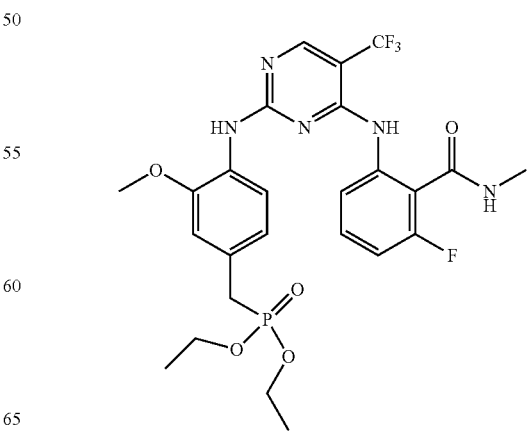

Example 155 diethyl (4-{[4-{[3-fluoro-2-(methylcarbamoyl)phenyl]amino}-5-(trifluoromethyl)pyrimidin-2-yl]amino}-3-methoxybenzyl)phosphonate The title compound was prepared according to the procedure from Example 102 (Diethyl (4-{[4-{[4-fluoro-2-(methylcarbamoyl)-phenyl]amino}-5-(trifluoromethyl)pyrimidin-2-yl]amino}-3-methoxybenzyl)phosphonate) using diethyl (4-{[4-chloro-5-(trifluoromethyl)pyrimidin-2-yl]amino}-3-methoxybenzyl)phosphonate and 2-amino-6-fluoro-N-methylbenzamide (Compound 155A). $^1$H NMR (DMSO-d6, 400 MHz): δ=1.19 (t, J=7.07 Hz, 6H), 2.76 (d, J=4.80 Hz, 3H), 3.19-3.27 (m, 2H), 3.76 (s, 3H), 3.93-4.02 (m, 4H), 6.78-6.83 (m, 1H), 6.97-7.03 (m, 2H), 7.38 (d, J=7.07 Hz, 1H), 7.49 (d, J=6.82 Hz, 1H), 8.00 (br. s., 1H), 8.38 (s, 1H), 8.62 (d, J=3.79 Hz, 1H), 8.80 (br. s., 1H), 9.78 (s, 1H). MS (ES$^+$): m/z 586.14 [MH$^+$] (TOF, polar).

Compound 155A: 2-amino-6-fluoro-N-methylbenzamide

The title compound was prepared according to the procedure for Compound 102A (2-Amino-5-fluoro-N-methylbenzamide) using 2-fluoro-N-methyl-6-nitrobenzamide (Compound 155B). $^1$H NMR (CDCl$_3$, 400 MHz): δ=2.99 (dd, J=4.80, 1.26 Hz, 3H), 6.35 (ddd, J=12.88, 8.08, 1.01 Hz, 1H), 6.44-6.49 (m, 1H), 7.09 (td, J=8.21, 6.57 Hz, 1H). MS (ES$^+$): m/z 169.08 [MH$^+$] (TOF, polar).

Compound 155B: 2-fluoro-N-methyl-6-nitrobenzamide

The title compound was prepared according to the procedure for Compound 102B (5-fluoro-N-methyl-2-nitrobenzamide) using 2-fluoro-6-nitrobenzoic acid. $^1$H NMR (CDCl$_3$, 400 MHz): δ=3.09 (d, J=5.05 Hz, 3H), 7.45 (td, J=8.34, 1.01 Hz, 1H), 7.56 (td, J=8.27, 5.43 Hz, 1H), 7.94 (dt, J=8.08, 1.01 Hz, 1H). MS (ES$^+$): m/z 199.05 [MH$^+$] (TOF, polar).

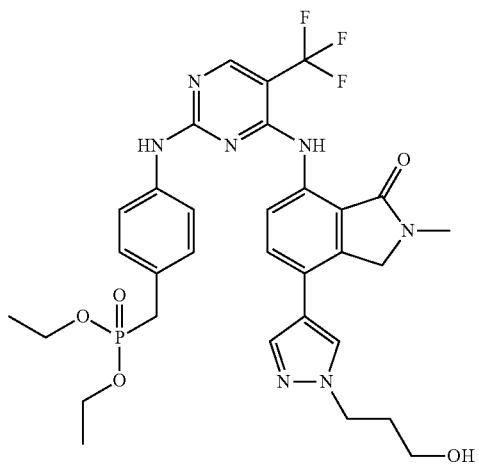 [SMILES: CCOP(=O)(Cc1ccc(Nc2ncc(C(F)(F)F)c(Nc3ccc(-c4cnn(CCCO)c4)c4c3C(=O)N(C)C4)n2)cc1)OCC]

Example 156

Diethyl (4-{[4-({7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}benzyl)phosphonate The title compound was prepared according to the procedure for Example 97 using diethyl[4-({4-[(7-bromo-2-methyl-3-oxo-2,3-dihydro-1H-isoindol-4-yl)amino]-5-(trifluoromethyl)pyrimidin-2-yl}amino)benzyl]phosphonate and 3-[4-(4,4,5,5-tetramethyl-1,3,2-dioxaborolan-2-yl)-1H-pyrazol-1-yl]propan-1-ol (WO2008/001076). $^1$H NMR (400 MHz, DMSO-d6) δ ppm: 10.74 (br s, 1H), 9.93 (s, 1H), 8.47 (s, 1H), 8.40-9.11 (m, 1H), 8.24 (s, 1H), 7.96 (s, 1H), 7.77 (d, J=8.6 Hz, 1H), 7.46-7.62 (m, 2H), 7.30 (d, J=6.8 Hz, 2H), 4.64 (s, 2H), 4.22 (t, J=7.1 Hz, 2H), 3.97 (quin, J=7.2 Hz, 4H), 3.43 (q, J=6.1 Hz, 2H), 3.26 (d, J=22.0 Hz, 2H), 3.12 (s, 3H), 1.97 (qd, J=6.7, 6.6 Hz, 2H), 1.16 (t, J=6.9 Hz, 6H). MS (ES$^+$): m/z 674.22 [MH$^+$]. HPLC: t$_R$=1.39 min (UPLC TOF, polar_3 min).

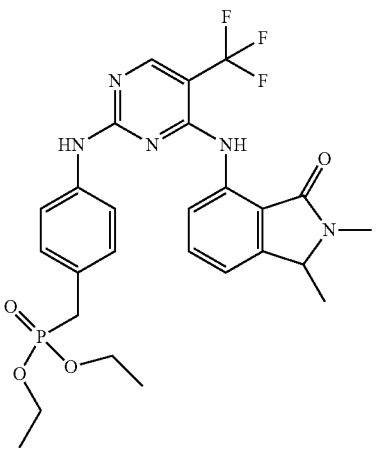 [SMILES: CCOP(=O)(Cc1ccc(Nc2ncc(C(F)(F)F)c(Nc3cccc4c3C(=O)N(C)C4C)n2)cc1)OCC]

Example 157

Diethyl[4-({4-[(1,2-dimethyl-3-oxo-2,3-dihydro-1H-isoindol-4-yl)amino]-5-(trifluoromethyl)pyrimidin-2-yl}amino)benzyl]phosphonate The title compound was prepared according to the procedure from Example 102 using diethyl (4-{[4-chloro-5-(trifluoromethyl)pyrimidin-2-yl]amino}benzyl)phosphonate (179.0 mg, 0.4224 mmol) and 7-amino-2,3-dimethyl-2,3-dihydro-1H-isoindol-1-one (Compound 157A, 83.7 mg, 0.475 mmol). The reaction mixture was poured into a separatory funnel containing saturated NaHCO$_3$ and was extracted with EtOAc. The combined organic layers were washed with brine, dried over anhydrous Na$_2$SO$_4$, filtered, and concentrated in vacuo. The crude was purified using a Teledyne/ISCO Combiflash system, eluting first with 40-100% EtOAc:Heptane and then 0-15% MeOH:CH$_2$Cl$_2$. The product was purified again by MDP (under basic conditions; ammonium bicarbonate buffer (pH 9)) to afford the title product as an off-white solid (158.3 mg, 65%). $^1$H NMR (400 MHz, DMSO-d$_6$) δ ppm 10.61 (br s, 1H), 9.93 (s, 1H), 8.71 (br s, 1H), 8.48 (s, 1H), 7.38-7.80 (m, 3H), 7.15-7.33 (m, 3H), 4.59 (q, J=6.6 Hz, 1H), 3.90-4.02 (m, 4H), 3.22 (d, J=21.5 Hz, 2H), 3.01 (s, 3H), 1.43 (d, J=6.6 Hz, 3H), 1.18 (t, J=6.9 Hz, 6H). MS (ES$^+$): m/z 564.17 (100) [MH$^+$]. HPLC: t$_R$=1.56 min (TOF, polar_3 min).

Compound 157A:
7-Amino-2,3-dimethyl-2,3-dihydro-1H-isoindol-1-one

A mixture of 3-hydroxy-2,3-dimethyl-7-nitro-2,3-dihydro-1H-isoindol-1-one (Compound 157B, 500 mg), AcOH (12 mL), and 5% Pd/C (60 mg) was hydrogenated for 14 h under 1 atm hydrogen atmosphere. The catalyst was filtered off and the filtrate was concentrated, residue was purified by column chromatography to afford 200 mg of the title compound (yield: 50%). $^1$H NMR (CDCl$_3$, 300 MHz): δ=1.43 (d, J=6.8 Hz, 3H), 3.04 (s, 3H), 4.33 (q, J=6.3 Hz, 1H), 5.20 (s, br, 2H), 6.55 (d, J=8.1 Hz, 1H), 7.21-7.26 (m, 2H).

Compound 157B: 3-Hydroxy-2,3-dimethyl-7-nitro-2,3-dihydro-1H-isoindol-1-one

A mixture of methyl 2-acetyl-6-nitrobenzoate (2 g, 8.96 mmol) and 33% methylamine in ethanol (10 mL) was stirred at reflux for 14 h. The solvents were removed under reduced pressure to afford 1.7 g of the desired product (yield: 85%). $^1$H NMR (CDCl$_3$, 300 MHz): δ=1.80 (s, 3H), 3.05 (s, 3H), 7.78 (m, 2H), 7.95 (m, 1H).

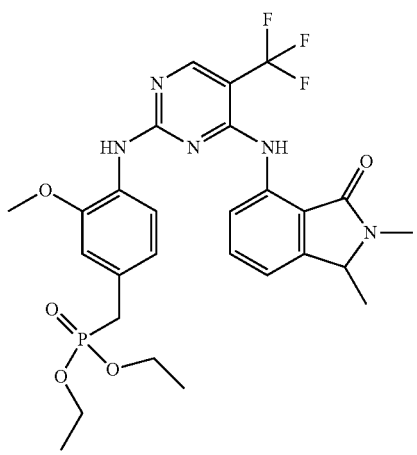

Example 158

Diethyl[4-({4-[(1,2-dimethyl-3-oxo-2,3-dihydro-1H-isoindol-4-yl)amino]-5-(trifluoromethyl)pyrimidin-2-yl}amino)-3-methoxybenzyl]phosphonate The title compound was prepared according to the procedure from Example 102 using diethyl (4-{[4-chloro-5-(trifluoromethyl)pyrimidin-2-yl]amino}-3-methoxybenzyl)phosphonate (230.1 mg, 0.5071 mmol) and 7-amino-2,3-dimethyl-2,3-dihydro-1H-isoindol-1-one (Compound 157A, 95.1 mg, 0.540 mmol) in TFE (5 mL). The reaction mixture poured into a separatory funnel containing saturated NaHCO$_3$ and extracted with EtOAc. The combined organic layers were washed with brine, dried over anhydrous Na$_2$SO$_4$, filtered, and concentrated in vacuo. The crude was adsorbed onto a pre-filled solid loading cartridge [RediSepRf 2.5 gram] and purified using an ISCO Combiflash unit [RediSepRf 4 gram silica], eluting first with 40-100% EtOAc:Heptane and then 0-15% MeOH:CH$_2$Cl$_2$. The product was purified again by MDP [under basic conditions; ammonium bicarbonate buffer (pH 9)] to afford title product as a white solid (103.1 mg, 34%). $^1$H NMR (400 MHz, DMSO-d$_6$) δ ppm 10.57 (s, 1H), 9.13 (s, 1H), 8.39 (s, 1H), 7.64-8.90 (m, 1H), 7.41 (br s, 2H), 7.18 (d, J=7.3 Hz, 1H), 7.05 (s, 1H), 6.91 (d, J=7.8 Hz, 1H), 4.55 (q, J=6.5 Hz, 1H), 3.91-4.06 (m, 4H), 3.74 (s, 3H), 3.29 (d, J=22.5 Hz, 2H), 2.99 (s, 3H), 1.40 (d, J=6.6 Hz, 3H), 1.20 (t, J=7.1 Hz, 6H). MS (ES$^+$): m/z 594.17 (100) [MH$^+$]. HPLC: t$_R$=1.59 min (TOF, polar_3 min).

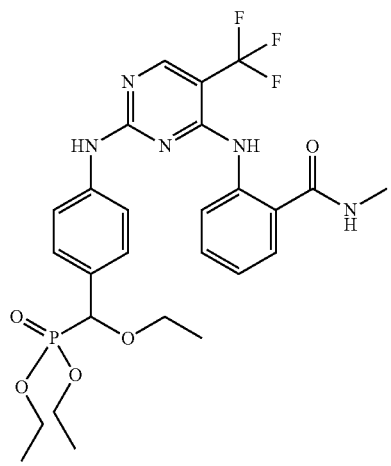 [SMILES: CCOC(c1ccc(Nc2ncc(C(F)(F)F)c(Nc3ccccc3C(=O)NC)n2)cc1)P(=O)(OCC)OCC]

Example 159

Diethyl[ethoxy(4-{[4-{[2-(methylcarbamoyl)phenyl]amino}-5-(trifluoromethyl)pyrimidin-2-yl]amino}phenyl)methyl]phosphonate Under N$_2$, a solution of 2-{[2-chloro-5-(trifluoromethyl)pyrimidin-4-yl]amino}-N-methylbenzamide (40.0 mg, 0.12 mmol) and diethyl[(4-aminophenyl)(hydroxy)methyl]-phosphonate (37.6 mg, 0.15 mmol) in a mixture of TFA (28 uL, 0.36 mmol) and EtOH (0.5 mL) was stirred at 105° C. for 45 min in a Biotage microwave reactor. The solvents were removed under reduced pressure and to the residue was added sat. NaHCO$_3$ (aq) (2 mL) and DCM (5 mL). Layers were separated and the aqueous layer was extracted with DCM (3×5 mL). The combined organic phases were dried over MgSO$_4$, concentrated, and purified by silica gel chromatography (5% 7 N NH$_3$ in MeOH in DCM) to afford the desired product as a white-colored solid (8.4 mg, yield: 12%). $^1$H NMR (CD$_3$OD, 400 MHz): δ=1.22 (dt, J=0.8, 7.6 Hz, 6H), 1.30 (t, J=7.2 Hz, 3H), 2.90 (s, 3H), 3.47-3.57 (m, 2H), 3.95-4.15 (m, 4H), 4.72 (d, J=16.0 Hz, 1H), 7.18 (dt, J=1.2, 7.6 Hz, 1H), 7.35 (dd, J=2.0, 8.4 Hz, 2H), 7.49 (dd, J=1.6, 8.8 Hz, 1H), 7.63-7.65 (m, 3H), 8.34 (s, 1H), 8.45 (m, 1H). MS (ES$^+$): m/z 582.17 [MH$^+$] HPLC: t$_R$=3.44 min (OpenLynx, polar_5 min).

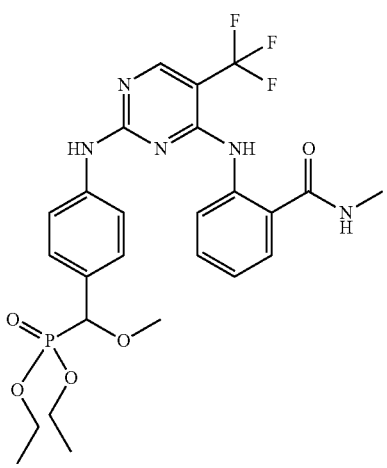 [SMILES: CCOP(=O)(OCC)C(OC)c1ccc(Nc2ncc(C(F)(F)F)c(Nc3ccccc3C(=O)NC)n2)cc1]

Example 160

Diethyl[methoxy(4-{[4-{[2-(methylcarbamoyl)phenyl]amino}-5-(trifluoromethyl)pyrimidin-2-yl]amino}phenyl)methyl]phosphonate Under $N_2$, a solution of 2-{[2-chloro-5-(trifluoromethyl)pyrimidin-4-yl]amino}-N-methylbenzamide (40.0 mg, 0.12 mmol) and diethyl[(4-aminophenyl)(hydroxy)methyl]-phosphonate (37.6 mg, 0.15 mmol) in a mixture of TFA (28 uL, 0.36 mmol) and MeOH (0.5 mL) was stirred at 105° C. for 45 min in a Biotage microwave reactor. LC-MS showed that the reaction was complete. The solvents were removed under reduced pressure and to the residue was added sat. $NaHCO_3$ (aq) (2 mL) and DCM (5 mL). Layers were separated and the aqueous layer was extracted with DCM (3×5 mL). The combined organic phases were dried over $MgSO_4$, concentrated, and purified by silica gel chromatography (5% 7 N $NH_3$ in MeOH in DCM) to afford the desired product as a white-colored solid (18.5 mg, yield: 27%). $^1$H NMR ($CD_3OD$, 400 MHz): δ=1.21 (dt, J=0.8, 7.2 Hz, 3H), 1.30 (t, J=7.2 Hz, 3H), 2.90 (s, 3H), 3.35 (s, 3H), 3.93-4.14 (m, 4H), 4.61 (d, J=15.2 Hz, 1H), 7.18 (dt, J=1.2, 7.6 Hz, 1H), 7.34 (dd, J=2.0, 8.4 Hz, 2H), 7.49 (dd, J=1.6, 8.4 Hz, 1H), 7.62-7.66 (m, 3H), 8.34 (s, 1H), 8.46 (m, 1H). MS (ES$^+$): m/z 568.11 [MH$^+$]. HPLC: $t_R$=3.31 min (OpenLynx, polar_5_min).

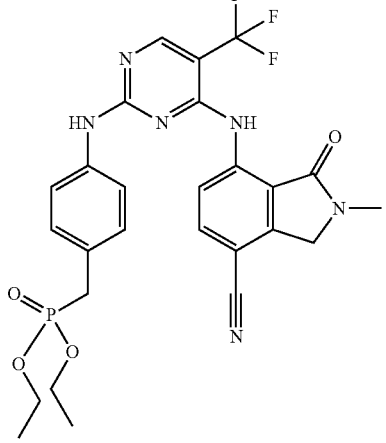

Example 161

Diethyl[4-({4-[(7-cyano-2-methyl-3-oxo-2,3-dihydro-1H-isoindol-4-yl)amino]-5-(trifluoromethyl)pyrimidin-2-yl}amino)benzyl]phosphonate A mixture of diethyl[4-({4-[(7-bromo-2-methyl-3-oxo-2,3-dihydro-1H-isoindol-4-yl)amino]-5-(trifluoromethyl)pyrimidin-2-yl}amino)benzyl]phosphonate (20.0 mg, 0.0318 mmol), zinc cyanide (3.74 mg, 0.0318 mmol), Pd(PPh$_3$)$_4$ (5.52 mg, 0.00477 mmol) in DMF (0.5 mL) was evacuated and purged with $N_2$ three times. The mixture was irradiated in a microwave reactor at 150° C. for 5 minutes. The crude mixture was passed though a Thiol-SPE cartridge to remove Pd and subsequently purified by MDP. The title compound was obtained as white solid (13.5 mg, 74% yield). $^1$H NMR (400 MHz, CDCl$_3$) δ=1.29 (t, J=7.1 Hz, 6H), 3.20 (d, J=21.5 Hz, 2H), 3.24 (s, 3H), 4.09 (quin, J=7.3 Hz, 4H), 4.54 (s, 2H), 7.31-7.39 (m, 2H), 7.49 (d, J=8.1 Hz, 2H), 7.56 (br. s., 1H), 7.70 (d, J=8.8 Hz, 1H), 8.44 (s, 1H), 8.70 (d, J=8.3 Hz, 1H), 10.85 (s, 1H). MS (ES+): m/z 575.21 (100) [MH$^+$] HPLC: $t_R$=1.08 min (UPLC, purity).

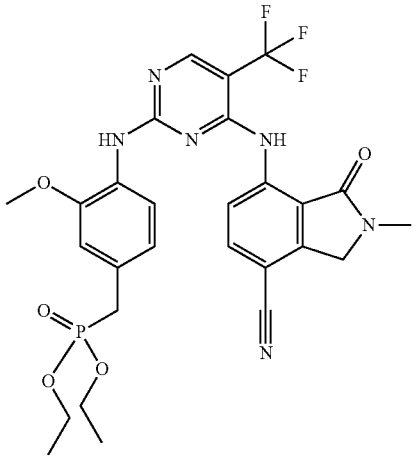

Example 162

Diethyl[4-({4-[(7-cyano-2-methyl-3-oxo-2,3-dihydro-1H-isoindol-4-yl)amino]-5-(trifluoromethyl)pyrimidin-2-yl}amino)-3-methoxybenzyl]phosphonate The title compound was prepared according to the procedure for Diethyl[4-({4-[(7-cyano-2-methyl-3-oxo-2,3-dihydro-1H-isoindol-4-yl)amino]-5-(trifluoromethyl)pyrimidin-2-yl}amino)benzyl]phosphonate (Example 161) using [4-({4-[(7-bromo-2-methyl-3-oxo-2,3-dihydro-1 H-isoindol-4-yl)amino]-5-(trifluoromethyl)pyrimidin-2-yl}amino)-3-methoxybenzyl]phosphonate. MS (ES+): m/z 605.19 (100) [MH$^+$] HPLC: $t_R$=1.09 min (UPLC, purity).

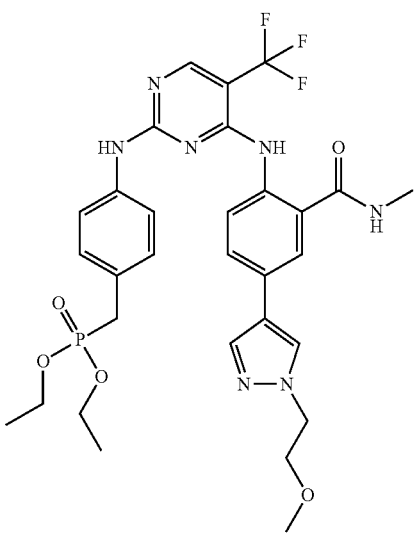 [SMILES: CCOP(=O)(Cc1ccc(Nc2ncc(C(F)(F)F)c(Nc3ccc(-c4cnn(CCOC)c4)cc3C(=O)NC)n2)cc1)OCC]

Example 163

Diethyl (4-{[4-({4-[1-(2-methoxyethyl)-1H-pyrazol-4-yl]-2-(methylcarbamoyl)phenyl}amino)-5-(trifluoromethyl)pyrimidin-2-yl]amino}benzyl)phosphonate The title compound was prepared according to the procedure for Diethyl (4-{[4-({7-[1-(2-methoxyethyl)-1H-pyrazol-4-yl]-2-methyl-3-oxo-2,3-dihydro-1H-isoindol-4-yl}amino)-5-(trifluoromethyl)pyrimidin-2-yl]amino}benzyl)phosphonate (Example 97) using Diethyl (4-{[4-{[4-bromo-2-(methylcarbamoyl)phenyl]amino}-5-(trifluoromethyl)pyrimidin-2-yl]amino}benzyl)phosphonate (Example 106) and 1-(2-methoxyethyl)-4-(4,4,5,5-tetramethyl-1,3,2-dioxaborolan-2-yl)-1H-pyrazole. MS (ES+): m/z 662.36 (100) [MH+] HPLC: $t_R$=1.00 min (UPLC, purity).

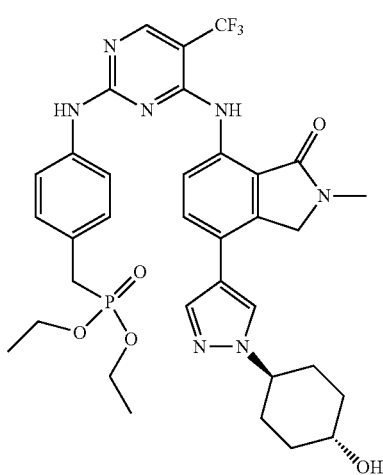 [SMILES: CCOP(=O)(Cc1ccc(Nc2ncc(C(F)(F)F)c(Nc3ccc(-c4cnn([C@H]5CC[C@H](O)CC5)c4)c4c3C(=O)N(C)C4)n2)cc1)OCC]

Example 164

Diethyl (4-{[4-({7-[1-(trans-4-hydroxycyclohexyl)-1H-pyrazol-4-yl]-2-methyl-3-oxo-2,3-dihydro-1H-isoindol-4-yl}amino)-5-(trifluoromethyl)pyrimidin-2-yl]amino}benzyl) phosphonate The title compound was prepared according to the procedure of Example 97 using diethyl[4-({4-[(7-bromo-2-methyl-3-oxo-2,3-dihydro-1H-isoindol-4-yl)amino]-5-(trifluoromethyl)pyrimidin-2-yl}amino)benzyl]phosphonate and (tert-butyl-dimethyl-silanyloxy)-cyclohexyl]-4-(4,4,5,5-tetramethyl-[1,3,2]dioxaborolan-2-yl)-1H-pyrazole (Compound 137A). After the Suzuki reaction, the crude material was pre-purified using an SPE cartridge. The subsequently dried material was dissolved in DCM and 1.0 M HCl in ether was added. The mixture was stirred at room temperature for half an hour. The crude, deprotected material was purified by MDP. MS (ES+): m/z 714.42 (100) [MH+]; HPLC: $t_R$=1.01 min (UPLC, purity).

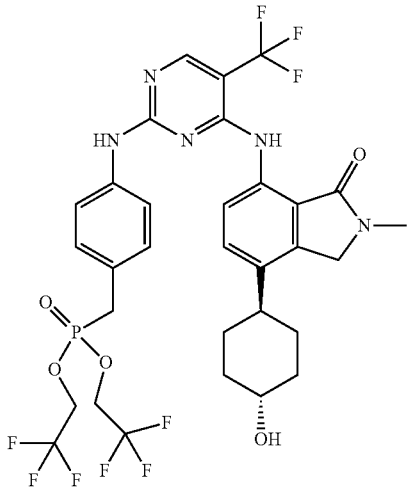 [SMILES: CN1Cc2c(c(Nc3nc(Nc4ccc(CP(=O)(OCC(F)(F)F)OCC(F)(F)F)cc4)ncc3C(F)(F)F)ccc2[C@H]2CC[C@H](O)CC2)C1=O]

Example 165

Bis(2,2,2-trifluoroethyl) (4-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}benzyl)phosphonate The title compound was prepared according to the procedure from Example 102 using bis(2,2,2-trifluoroethyl) (4-{[4-chloro-5-(trifluoromethyl)pyrimidin-2-yl]amino}benzyl) phosphonate (Compound 165A, 35.7 mg, 0.0671 mmol) and 7-amino-4-(4-hydroxycyclohexyl)-2-methyl-2,3-dihydro-1H-isoindol-1-one (18.5 mg, 0.0711 mmol). The crude material was first purified on a Teledyne/ISCO system eluting with 50-100% EtOAc:Heptane followed by MDP (under acidic conditions; formic acid). The desired fractions were collected and concentrated in vacuo, giving the title material as an off-white solid, 24.3 mg (47%, 0.0315 mmol). $^1$H NMR (400 MHz, DMSO-$d_6$) δ ppm 10.59 (br s, 1H), 9.93 (s, 1H), 8.47 (s, 1H), 8.15-9.25 (m, 1H), 7.63 (d, J=6.1 Hz, 2H), 7.34 (d, J=8.6 Hz, 1H), 7.26 (dd, J=8.6, 2.5 Hz, 2H), 4.58-4.72 (m, 5H), 4.53 (s, 2H), 3.43-3.61 (m, 3H), 3.08 (s, 3H), 1.94 (dd, J=11.7, 2.1 Hz, 2H), 1.77 (d, J=11.6 Hz, 2H), 1.56 (dtd, J=12.9, 12.7, 2.1

Hz, 2H), 1.21-1.37 (m, 2H). MS (ES+): m/z 756.16 (100) [MH+]. HPLC: $t_R$=4.14 min (ZQ3, polar_5 min).

Compound 165A: Bis(2,2,2-trifluoroethyl) (4-{[4-chloro-5-(trifluoromethyl)pyrimidin-2-yl]amino}benzyl)phosphonate The title compound was prepared according to the procedure for diethyl (4-{[4-chloro-5-(trifluoromethyl)pyrimidin-2-yl]amino}benzyl)phosphonate using (4-Aminobenzyl) phosphonic acid bis-(2,2,2-trifluoroethyl) ester (Compound 165B) and 2,4-dichloro-5-(trifluoromethyl)pyrimidine. The desired product was isolated using MDP (ammonium bicarbonate basic buffer pH 9). $^1$H NMR (400 MHz, DMSO-d$_6$) δ ppm 10.69 (s, 1H), 8.81 (s, 1H), 7.65 (d, J=8.1 Hz, 2H), 7.26 (dd, J=8.7, 2.7 Hz, 2H), 4.56-4.72 (m, 4H), 3.51 (d, J=22.2 Hz, 2H). MS (ES+): m/z 532.01/534.02 (100/64) [MH+]. HPLC: $t_R$=1.70 min (TOF, polar_3 min).

Compound 165B: (4-Aminobenzyl)phosphonic acid bis-(2,2,2-trifluoroethyl) ester

The title compound was prepared according to the procedures for Compounds 114E-114A starting with the commercially available diethyl (4-nitrobenzyl)phosphonate. $^1$H NMR (DMSO-d$_6$, 400 MHz): δ=3.27 (d, J=21.2 Hz, 2H), 4.45-4.65 (m, 4H), 5.20-5.40 (br, 2H), 6.51 (d, J=8.0 Hz, 2H), 6.85-6.95 (m, 2H).

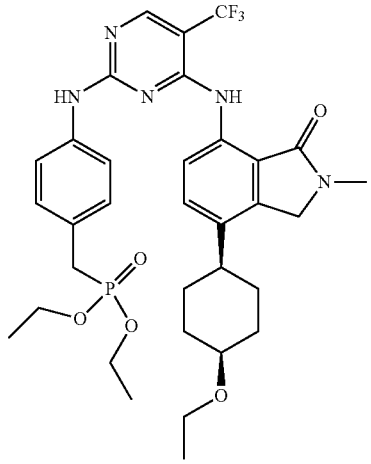 [SMILES: CCOP(=O)(Cc1ccc(Nc2ncc(C(F)(F)F)c(Nc3ccc([C@H]4CC[C@@H](OCC)CC4)c4c3C(=O)N(C)C4)n2)cc1)OCC]

Example 166

Diethyl (4-{[4-{[7-(cis-4-ethoxycyclohexyl)-2-methyl-3-oxo-2,3-dihydro-1H-isoindol-4-yl]amino}-5-(trifluoromethyl)pyrimidin-2-yl]amino}benzyl)phosphonate The title product was prepared according to the procedure for Example 102 using diethyl (4-{[4-chloro-5-(trifluoromethyl)pyrimidin-2-yl]amino}benzyl)phosphonate (40.0 mg, 0.0944 mmol) and 7-amino-4-(cis-4-ethoxycyclohexyl)-2-methyl-2,3-dihydro-1H-isoindol-1-one (Compound 166A, 32.67 mg, 0.1133 mmol). The reaction mixture was concentrated under reduced pressure to yield a yellow oil. The material was purified by silica gel chromatography on the combi-flash Rf system using 1:1 EtOAc-DCM/MeOH (100:0→95:5) as eluent. The fractions containing product were combined and concentrated under reduced pressure to yield a white solid, 44.3 mg (69% yield). $^1$H NMR (DMSO-d6, 400 MHz): δ=1.13-1.22 (m, 9H), 1.46-1.59 (m, 4H), 1.70-1.84 (m, 2H), 1.91-2.01 (m, 2H), 2.56-2.68 (m, 1H), 3.08 (s, 3H), 3.16-3.24 (m, 2H), 3.45 (q, J=6.91 Hz, 2H), 3.61 (br. s., 1H), 3.91-4.01 (m, 4H), 4.53 (s, 2H), 7.25 (dd, J=8.59, 2.27 Hz, 2H), 7.30 (d, J=7.58 Hz, 1H), 7.60 (d, J=4.55 Hz, 2H), 8.46 (s, 1H), 8.51-8.88 (m, 1H), 9.87 (br. s., 1H), 10.58 (br. s., 1H). MS (ES+): m/z 676.30 [MH+] (TOF, polar).

Compound 166A

7-Amino-4-(cis-4-ethoxycyclohexyl)-2-methyl-2,3-dihydro-1H-isoindol-1-one and

Compound 166B: 7-Amino-4-(trans-4-ethoxycyclohexyl)-2-methyl-2,3-dihydro-isoindol-1-one Palladium on charcoal (10%) (50 mg) was cautiously added to a hydrogenation flask containing a solution of 4-(4-ethoxycyclohex-1-enyl)-2-methyl-7-nitro-2,3-dihydro-isoindol-1-one (Compound 166C, 300 mg, 0.78 mmol) in ethanol (30 mL) and this mixture was hydrogenated at 40 psi for 24 hrs. The mixture was filtered and concentrated to a residue which was purified by flash column chromatography (MeOH:DCM 0.5:99.5) to separate the cis and trans isomers. Compound 166A, the cis isomer eluted first: 90 mg: $^1$H NMR (CDCl3, 500 MHz): 1.22 (t, 3H, J=7.5 Hz), 1.41-1.6 (m, 2H), 1.82 (q, 2H), 2.1 (m, 2H) 2.40 (m, 1H) 3.15 (s, 3H), 3.45 (q, 2H, J=7.5 Hz), 3.62 (s, 1H), 4.36 (s, 2H), 5.08 (s, 2H), 6.6 (d, 1H, J=8 Hz), 7.18 (d, 1H, J=8 Hz). Compound 166B, the trans isomer, eluted after: 50 mg: $^1$H NMR (CDCl3, 500 MHz): 1.22 (t, 3H, J=7.5 Hz), 1.28 (q, 2H), 1.38 (q, 2H), 1.82 (d, 2H) 2.2 (d, 2H) 2.40 (m, 1H) 3.18 (s, 3H), 3.38 (m, 1H), 3.6 (q, 2H, J=7.5 Hz), 4.38 (s, 2H), 5.1 (s, 2H), 6.6 (d, 1H, J=8 Hz), 7.18 (d, 1H, J=8 Hz).

Compound 166C: 4-(4-Ethoxycyclohex-1-enyl)-2-methyl-7-nitro-2,3-dihydro-isoindol-1-one Dioxane (20 mL) and water (5 mL) were taken in a three necked RB flask equipped with a nitrogen inlet and a thermometer. The solvents were deoxygenated for 15 min using nitrogen gas. Trifluoro-methanesulfonic acid 4-ethoxy-cyclohex-1-enyl ester (Compound 166D, 300 mg, 1.1 mmol), 2-methyl-7-nitro-4-(4,4,5,5-tetramethyl-[1,3,2]dioxaborolan-2-yl)-2,3-dihydro-isoindol-1-one (Compound 205E, 630 mg, 1.64 mmol), tetrakis triphenyl phosphine palladium catalyst (114 mg, 0.01 mmol) and cesium carbonate (889 mg, 2.7 mmol) were added. The reaction mixture was heated to 60° C. for 3 hrs. The solvents were evaporated and the residue was purified over silica gel column using (methanol:methylene chloride: 1:99). Yield: 300 mg (86%). $^1$H NMR (CDCl3, 400 MHz): δ1.2 (t, 3H, J=7 Hz), 1.8-2.4 (m, 6H), 3.15 (s, 3H), 3.50-3.64 (m, 3H), 4.36 (s, 2H), 5.79 (m, 1H), 7.4 (d, 1H, J=8.1 Hz), 7.63 (d, 1H, J=8.1 Hz).

Compound 166D: Trifluoro-methanesulfonic acid 4-ethoxy-cyclohex-1-enyl ester

4-Ethoxy cyclohexanone (Compound 166E, 0.8 gm, 5.6 mmol) and 2,2,6-di-tert-butyl pyridine (2.1 gm, 11.26 mmol) were taken up in dichloromethane (20 mL) and cooled to 0° C. Triflic anhydride (1.58 gm (5.6 mmol) was added dropwise to the cold solution which was allowed to stir at RT for 24 hrs. The solvent was removed in vacuo and the residue was triturated with ether and filtered. The filtrate was concentrated under reduced pressure and purified by flash column chromatography (hexanes:ethyl acetate 9:1). Yield: 300 mg (20%). $^1$H NMR (CDCl3, 400 MHz): δ1.2 (t, 3H, J=7.5 Hz), 1.8-2.0 (m, 2H), 2.18-2.45 (m, 4H), 3.45-3.6 (m, 3H), 5.62 (m, 1H).

Compound 166E: 4-Ethoxy cyclohexanone

A mixture of 8-Ethoxy-1,4-dioxa-spiro[4.5]decane (Compound 166F, 2 gm, 10.7 mmol) and pyridinium p-toluene sulfonate (5.4 gm, 21.5 mmol) was taken up in a 1:1 mixture of acetone and water (150 mL) and stirred at 50° C. overnight. The acetone was subsequently removed under reduced pressure and the aqueous solution was extracted with ethyl acetate. The organic layer was washed with water, dried ($Na_2SO_4$), and evaporated to give the crude material which was used in the next step without further purification. Yield: 0.8 gm (53%). $^1$H NMR (CDCl3, 500 MHz): δ 1.24 (t, J=7.1 Hz, 3H), 1.95 (m, 2H), 2.05 (m, 2H), 2.24 (m, 2H), 2.6 (m, 2H), 3.6 (q, J=7.1 Hz 2H), 3.7 (m, 1H).

Compound 166F:
8-Ethoxy-1,4-dioxa-spiro[4.5]decane

Sodium hydride (506 mg, 12.65 mmol) was added to a solution of 1,4-Dioxa-spiro[4.5]decan-8-ol (2 gm, 12.65 mmol) in dry THF (20 mL) at 0° C. After 15 minutes, ethyl iodide (2 gm, 12.65 mmol) was added and the mixture was allowed to stir at RT overnight. After removing the THF under reduced pressure, the mixture was poured into ice cold water and extracted into ethyl acetate. The crude product was purified by flash column chromatography (EtOAc:Hexane 5:95) to isolate the title compound (1.3 gm, 55%). $^1$H NMR (CDCl$_3$, 500 MHz): δ 1.2 (t, 3H, J=7), 1.45-1.92 (m, 8H), 3.4 (m, 1H), 3.45 (m, 2H), 3.98 (m, 4H).

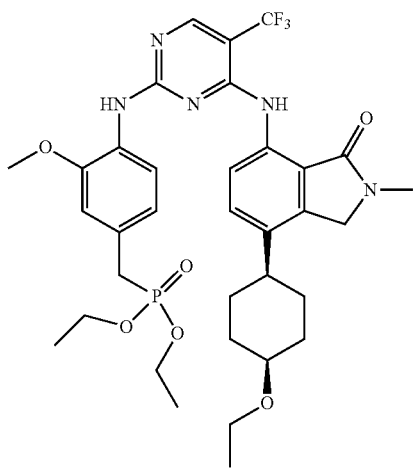

Example 167

Diethyl (4-{[4-{[7-(cis-4-ethoxycyclohexyl)-2-methyl-3-oxo-2,3-dihydro-1H-isoindol-4-yl]amino}-5-(trifluoromethyl)pyrimidin-2-yl]amino}-3-methoxybenzyl)phosphonate The title compound was prepared according to the procedure for Example 102 using diethyl (4-{[4-chloro-5-(trifluoromethyl)pyrimidin-2-yl]amino}-3-methoxybenzyl)phosphonate and 7-amino-4-(cis-4-ethoxycyclohexyl)-2-methyl-2,3-dihydro-1H-isoindol-1-one (Compound 166A). $^1$H NMR (DMSO-d6, 400 MHz): δ=1.15-1.22 (m, 9H), 1.44-1.56 (m, 4H), 1.69-1.82 (m, 2H), 1.95 (d, J=11.62 Hz, 2H), 2.53-2.63 (m, 1H), 3.07 (s, 3H), 3.22-3.30 (m, 2H), 3.45 (q, J=6.99 Hz, 2H), 3.60 (br. s., 1H), 3.75 (s, 3H), 3.94-4.04 (m, 4H), 4.49 (s, 2H), 6.91 (d, J=7.58 Hz, 1H), 7.06 (s, 1H), 7.18 (br. s., 1H), 7.49 (br. s., 1H), 8.22-8.48 (m, 2H), 9.00 (br. s., 1H), 10.56 (s, 1H). MS (ES$^+$): m/z 706.30 [MH$^+$] (TOF, polar).

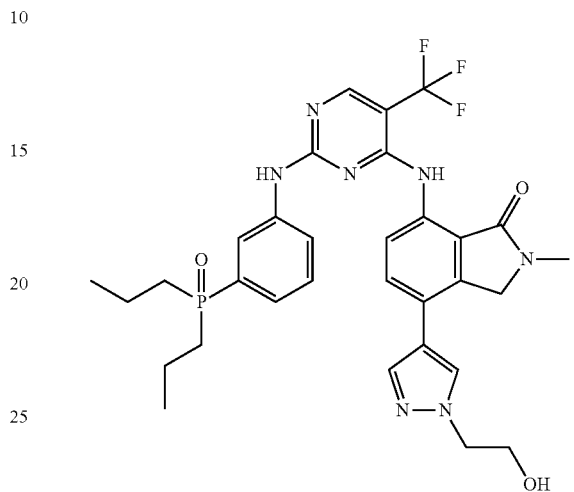

Example 168

7-{[2-{[3-(Dipropylphosphoryl)phenyl]amino}-5-(trifluoromethyl)pyrimidin-4-yl]amino}-4-[1-(3-hydroxyethyl)-1H-pyrazol-4-yl]-2-methyl-2,3-dihydro-1H-isoindol-1-one The title compound was prepared according to the procedure for Example 102 using 4-chloro-N-[3-(dipropylphosphoryl)phenyl]-5-(trifluoromethyl)pyrimidin-2-amine (Compound 168B, 50.0 mg, 0.123 mmol) and 7-amino-2-methyl-4-{1-[2-(tetrahydro-2H-pyran-2-yloxy)ethyl]-1H-pyrazol-4-yl}-2,3-dihydro-1H-isoindol-1-one (Compound 168A, 43.9 mg, 0.123 mmol). The desired product was re-crystallized in EtOH after column chromatography. $^1$H NMR (400 MHz, DMSO-d6) δ 0.90 (t, J=7.20 Hz, 6H), 1.33 (br. s., 2H), 1.48 (br. s., 2H), 1.76-2.01 (m, 4H), 3.13 (s, 3H), 3.79 (q, J=5.73 Hz, 2H), 4.21 (t, J=5.56 Hz, 2H), 4.65 (s, 2H), 4.96 (t, J=5.31 Hz, 1H), 7.39 (t, J=8.34 Hz, 1H), 7.52 (t, J=8.59 Hz, 1H), 7.68 (d, J=8.34 Hz, 1H), 7.85-7.97 (m, 2H), 8.07 (br. s., 1H), 8.15 (s, 1H), 8.51 (s, 1H), 8.80 (br. s., 1H), 10.12 (s, 1H), 10.78 (br. s., 1H). MS (ES+): m/z=642.16 [MH+]. HPLC: tR=3.61 min (ZQ3, polar_5 min)

Compound 168A: 7-Amino-2-methyl-4-{1-[2-(tetrahydro-2H-pyran-2-yloxy)ethyl]-1H-pyrazol-4-yl}-2,3-dihydro-1H-isoindol-1-one A mixture of [A] 7-amino-4-bromo-2-methyl-2,3-dihydro-1H-isoindol-1-one (1.0 g, 4.1 mmol), and 1-[2-(Tetrahydro-pyran-2-yloxy)-ethyl]-4-(4,4,5,5-tetramethyl-[1,3,2]dioxaborolan-2-yl)-1H-pyrazole [US 2007265272] (1.6 g, 5.0 mmol) and [1,1'-Bis(diphenylphosphino)ferrocene]dichloropalladium(II), complex with dichloromethane (1:1) (0.17 g, 0.21 mmol) in a microwave tube was taken up in 1,4-Dioxane (12 mL). The mixture was treated with a solution of Potassium carbonate (1.7 g, 12 mmol) in H2O (3.0 mL, 170 mmol), flushed with N2, sealed and irradiated in the CEM for 30 minutes at 100° C. Another 1 g of boronic ester was added as well as another 0.05 eq of catalyst. The mixture was sparged with N$_2$, sealed and irradiated for 45 min. This was worked up and purified. $^1$H NMR (400 MHz, DMSO-d6) δ 1.36-1.50 (m, 4H), 1.57 (td, J=9.22, 3.03 Hz, 1H), 1.63-1.71 (m, 1H), 3.03 (s, 3H), 3.35-3.41 (m, 1H), 3.57 (ddd, J=11.31, 8.40, 3.03 Hz, 1H), 3.75 (dt, J=10.80, 5.34 Hz, 1H), 3.91-3.99 (m, 1H), 4.27-4.33 (m, 2H), 4.44 (s, 2H), 4.55 (t, J=3.28 Hz, 1H), 6.06 (s, 2H), 6.62 (d, J=8.34 Hz, 1H), 7.43 (d, J=8.34 Hz, 1H), 7.74 (d, J=0.51 Hz, 1H), 7.95 (d, J=0.51 Hz, 1H).

Compound 168B: 4-chloro-N-[3-(dipropylphosphoryl)phenyl]-5-(trifluoromethyl)pyrimidin-2-amine The title compound was prepared according to the procedure for diethyl (4-{[4-chloro-5-(trifluoromethyl)pyrimidin-2-yl]amino}benzyl)phosphonate using 3-(dipropylphosphoryl) aniline (Compound 168C) and 2,4-dichloro-5-trifluoromethylpyrimidine. $^1$H NMR (400 MHz, CHLOROFORM-d) δ 1.00 (td, J=7.26, 0.88 Hz, 6H), 1.47-1.58 (m, 2H), 1.64-1.77 (m, 2H), 1.82-1.94 (m, 2H), 1.97-2.10 (m, 2H), 7.33-7.40 (m, 1H), 7.51 (td, J=7.83, 3.28 Hz, 1H), 8.00 (d, J=8.34 Hz, 1H), 8.08 (d, J=12.13 Hz, 1H), 8.60 (s, 1H). MS (ES+): m/z=405.97 (100) [MH+]. HPLC: t$_R$=3.47 min (polar_5 min).

Compound 168C: 3-(Dipropylphosphoryl)aniline

A solution of (3-nitrophenyl)(dipropyl)phosphane oxide (0.801 g, 3.14 mmol) in MeOH (3 mL) was charged with Palladium 10% wt on activated carbon (0.17 g, 0.16 mmol) and subjected to 3 cycles of evacuation and N$_2$ purging. After a fourth evacuation the flask was purged with H$_2$. The reaction was stirred at rt over night. The reaction mixture was filtered through a pad of celite and the filtrate was concentrated and purified via column chromatography to afford 329 mg of the desired product. $^1$H NMR (400 MHz, DMSO-d6) δ 0.90 (t, J=7.33 Hz, 6H), 1.21-1.36 (m, 2H), 1.36-1.52 (m, 2H), 1.67-1.91 (m, 4H), 5.30 (s, 2H), 6.67 (dt, J=8.02, 1.17 Hz, 1H), 6.72-6.79 (m, 1H), 6.88-6.95 (m, 1H), 7.11 (td, J=7.71, 3.54 Hz, 1H).

Compound 168D: (3-Nitrophenyl)(dipropyl)phosphane oxide

A solution of m-iodonitrobenzene (1.98 g, 7.95 mmol) and di-N-propylphosphine oxide (Compound 168E, 1.12 g, 8.35 mmol) in 1,4-Dioxane (13 mL) was charged with bis(dibenzylideneacetone)palladium (0.0728 g, 0.0795 mmol), Xantphos (0.138 g, 0.238 mmol) and Cesium Carbonate (3.63 g, 11.1 mmol) in a sealed tube. The vessel was flushed with nitrogen for 2 min, sealed, and stirred at 90° C. for 4 h. The reaction mixture was partitioned between EtOAc and water and separated. The aqueous was extracted with EtOAc (3×) and the combined organic fractions were washed with brine, dried over sodium sulfate, filtered, and concentrated. The compound was purified on an Isco Combiflash (50-70% EtOAc/Hexane, then 5% MeOH/DCM) to afford 0.799 g of the title compound. $^1$H NMR (400 MHz, DMSO-d6) d 0.89 (t, J=7.07 Hz, 6H), 1.21-1.34 (m, 2H), 1.40-1.53 (m, 2H), 1.89-2.07 (m, 4H), 7.82 (td, J=7.89, 2.40 Hz, 1H), 8.17 (ddt, J=9.63, 7.55, 1.14 Hz, 1H), 8.36-8.42 (m, 1H), 8.48-8.54 (m, 1H).

Compound 168E: Di-N-propylphosphine oxide

A solution of 2.0 M propylmagnesium chloride in Et$_2$O (15.000 mL, 30.000 mmol) was diluted with 6 mL of anhydrous THF and cooled to 0° C. This mixture was treated, drop-wise, with diethyl phosphite (1.2870 mL, 9.9998 mmol) and allowed to stir for 2 h, slowly warming to rt. A solution of Potassium carbonate (1.3820 g, 9.9998 mmol) in H2O (2.0 mL) was carefully added. The reaction mixture bubbled vigorously. When gas evolution had subsided EtOH (10.0 mL) was added and the mixture was filtered. The filtrate was concentrated in-vacuo and dried O/N under hi-vac. This mixture was re-dissolved in DCM and filtered through celite. The filtrate was a clear solution which upon concentration and further drying gave 1.12 g of the desired product as a clear oil. $^1$H NMR (400 MHz, DMSO-d6) d ppm 0.99 (t, J=7.3 Hz, 6H), 1.45-1.63 (m, 4H), 1.66-1.81 (m, 4H), 6.73 (d, J=443.0 Hz, 1H).

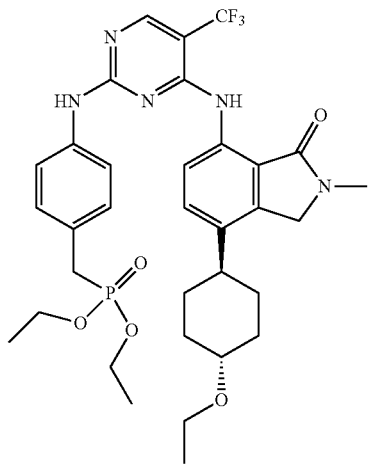 [SMILES: CCOP(=O)(Cc1ccc(Nc2ncc(C(F)(F)F)c(Nc3ccc([C@H]4CC[C@H](OCC)CC4)c4c3C(=O)N(C)C4)n2)cc1)OCC]

Example 169

Diethyl (4-{[4-{[7-(trans-4-ethoxycyclohexyl)-2-methyl-3-oxo-2,3-dihydro-1H-isoindol-4-yl]amino}-5-(trifluoromethyl)pyrimidin-2-yl]amino}benzyl) phosphonate The title product was prepared according to the procedure for Example 102 using diethyl(4-{[4-chloro-5-(trifluoromethyl)pyrimidin-2-yl]amino}benzyl)phosphonate (40.0 mg, 0.0944 mmol) and 7-amino-4-(trans-4-ethoxycyclohexyl)-2-methyl-2,3-dihydro-1H-isoindol-1-one (Compound 166B). $^1$H NMR (DMSO-d6, 400 MHz): δ=1.11 (t, J=6.95 Hz, 3H), 1.18 (t, J=6.95 Hz, 6H), 1.21-1.33 (m, 2H), 1.54-1.68 (m, 2H), 1.80 (d, J=12.63 Hz, 2H), 2.09 (dd, J=12.63, 3.28 Hz, 2H), 3.08 (s, 3H), 3.18-3.27 (m, 2H), 3.49 (q, J=6.99 Hz, 2H), 3.91-4.01 (m, 4H), 4.52 (s, 2H), 7.26 (dd, J=8.72, 1.89 Hz, 2H), 7.40 (d, J=8.59 Hz, 1H), 7.56 (br. s., 2H), 8.45 (s, 1H), 8.67 (s, 1H), 9.89 (s, 1H), 10.58 (br. s., 1H). MS (ES$^+$): m/z=676.25 [MH$^+$] (TOF, polar).

Example 170

Diethyl (4-{[4-{[7-(trans-4-ethoxycyclohexyl)-2-methyl-3-oxo-2,3-dihydro-1H-isoindol-4-yl]amino}-5-(trifluoromethyl)pyrimidin-2-yl]amino}-3-methoxybenzyl)phosphonate

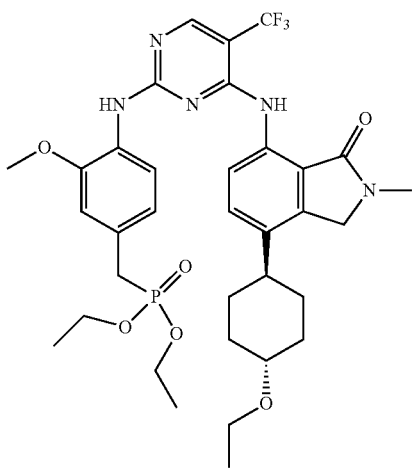

The title product was prepared according to the procedure for Example 102 using diethyl(4-{[4-chloro-5-(trifluoromethyl)pyrimidin-2-yl]amino}-3-methoxybenzyl)phosphonate (40.0 mg, 0.0944 mmol) and 7-amino-4-(trans-4-ethoxycyclohexyl)-2-methyl-2,3-dihydro-1H-isoindol-1-one (Compound 166B). $^1$H NMR (CDCl$_3$, 400 MHz): δ=1.19-1.32 (m, 9H), 1.34-1.46 (m, 2H), 1.58-1.69 (m, 2H), 1.92 (d, J=12.88 Hz, 2H), 2.23 (d, J=10.11 Hz, 2H), 2.51 (t, J=12.00 Hz, 1H), 3.14-3.21 (m, 2H), 3.22 (s, 3H), 3.31-3.43 (m, 1H), 3.59 (q, J=6.99 Hz, 2H), 3.93 (s, 3H), 3.99-4.12 (m, 4H), 4.40 (s, 2H), 6.89 (d, J=8.08 Hz, 1H), 6.94 (s, 1H), 7.34 (d, J=8.59 Hz, 1H), 7.70 (br. s., 1H), 8.28 (d, J=7.58 Hz, 1H), 8.39 (br. s., 1H), 8.62 (d, J=8.59 Hz, 1H), 10.54 (br. s., 1H). MS (ES$^+$): m/z 706.26 [MH$^+$] (TOF, polar).

Example 171

7-{[2-{[3-(Dipropylphosphoryl)phenyl]amino}-5-(trifluoromethyl)pyrimidin-4-yl]amino}-4-(trans-4-hydroxycyclohexyl)-2-methyl-2,3-dihydro-1H-isoindol-1-one The title product was prepared according to the procedure for Example 102 using 4-chloro-N-[3-(dipropylphosphoryl)phenyl]-5-(trifluoromethyl)pyrimidin-2-amine (Compound 168B) and 7-amino-4-(trans-4-hydroxycyclohexyl)-2-methyl-2,3-dihydro-1H-isoindol-1-one. $^1$H NMR (400 MHz, DMSO-d6) δ 0.93 (t, J=7.33 Hz, 6H), 1.24-1.40 (m, 4H), 1.42-1.58 (m, 4H), 1.79 (d, J=12.88 Hz, 2H), 1.82-1.89 (m, 2H), 1.89-1.98 (m, 4H), 3.08 (s, 3H), 3.42-3.54 (m, 1H), 4.54 (s, 2H), 4.64 (br. s., 1H), 7.26 (br. s., 1H), 7.63-7.72 (m, 2H), 7.79 (d, J=6.57 Hz, 2H), 8.52 (s, 1H), 8.62 (br. s., 1H), 10.14 (s, 1H), 10.59 (br. s., 1H). MS (ES+): m/z=630.27 [MH+]. HPLC: t$_R$=3.17 min (ZQ3, polar_5 min).

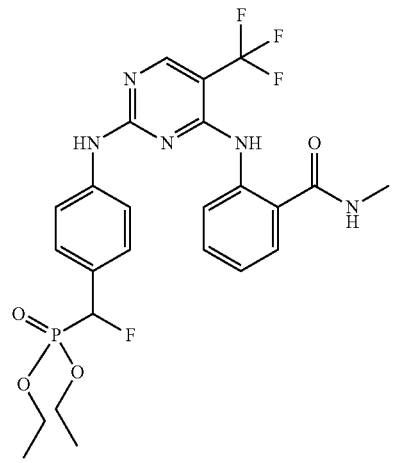

Example 172

Diethyl[fluoro(4-{[4-{[2-(methylcarbamoyl)phenyl]amino}-5-(trifluoromethyl)pyrimidin-2-yl]amino}phenyl)methyl]phosphonate A solution of diethyl[hydroxy(4-{[4-{[2-(methylcarbamoyl)phenyl]amino}-5-(trifluoromethyl)pyrimidin-2-yl]amino}phenyl)methyl]phosphonate (Example 133, 8.00 mg, 0.014 mmol) and DAST (7 mg, 0.043 mmol) in DCM (3 mL) was stirred at 0° C. for 1 h. The was treated with sat. NaHCO$_3$ (aq) (3 mL). The layers were separated and the aqueous layer was extracted with DCM (3×5 mL). The organic layers were combined, dried over MgSO$_4$, filtered, concentrated, and residue was purified by prep TLC (5% 7 N ammonia in MeOH in DCM) to give 1.5 mg of the desired product (yield: 19%). $^1$H NMR (CD$_3$OD, 400 MHz): δ=1.24 (t, J=7.6 Hz, 3H), 1.32 (t, J=7.2 Hz, 3H), 2.90 (s, 3H), 4.00-4.17 (m, 4H), 5.82 (dd, J=7.2, 44.0 Hz, 1H), 7.20 (dt, J=1.2, 8.4 Hz, 1H), 7.39 (d, J=8.4 Hz, 2H), 7.50 (dt, J=2.0, 8.8 Hz, 1H), 7.64 (dd, J=1.2, 8.0 Hz, 1H), 7.69 (d, J=8.0 Hz, 2H), 8.36 (s, 1H), 8.43 (d, J=7.2 Hz, 1H). MS (ES$^+$): m/z 556.14 [MH$^+$]. HPLC: t$_R$=1.50 min (UPLC TOF, polar_3 min).

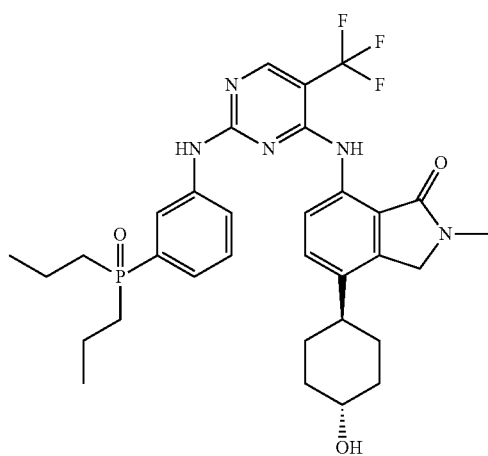 [SMILES: CCCP(=O)(CCC)c1cccc(Nc2ncc(C(F)(F)F)c(Nc3ccc([C@H]4CC[C@H](O)CC4)c4c3C(=O)N(C)C4)n2)c1]

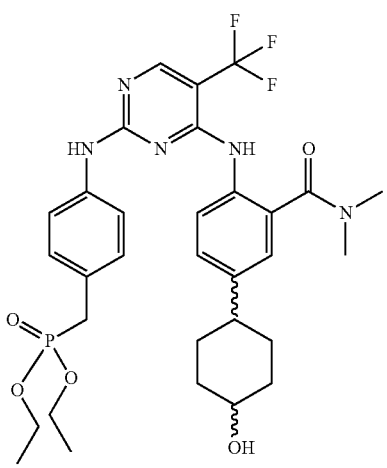 [SMILES: CCOP(=O)(Cc1ccc(Nc2ncc(C(F)(F)F)c(Nc3ccc(C4CCC(O)CC4)cc3C(=O)N(C)C)n2)cc1)OCC]

Example 173

Diethyl(4-{[4-{[2-(dimethylcarbamoyl)-4-(trans-4-hydroxycyclohexyl)phenyl]amino}-5-(trifluoromethyl)pyrimidin-2-yl]amino}benzyl)phosphonate The title product was prepared according to the procedure for Example 102 using diethyl(4-{[4-chloro-5-(trifluoromethyl)pyrimidin-2-yl]amino}benzyl) phosphonate (20 mg, 0.46 mmol) and 2-amino-5-(4-hydroxycyclohexyl)-N,N-dimethylbenzamide (Compound 173A, 120 mg, 0.46 mmol). $^1$H NMR (400 MHz, DMSO-d$_6$) δ 8.81 (s, 1H), 8.37 (s, 1H), 7.51 (br. s., 1H), 7.33 (dd, J=2.02, 8.34 Hz, 1H), 7.25 (d, J=2.02 Hz, 1H), 7.07 (br. s., 1H), 3.92 (dq, J=7.07, 7.33 Hz, 4H), 3.06-3.15 (m, 2H), 2.83-2.96 (m, 6H), 1.81-1.94 (m, 1H), 1.71-1.80 (m, 1H), 1.57 (br. s., 2H), 1.16 (t, J=7.07 Hz, 6H); MS (ES$^+$): m/z: 650.2354 [MH$^+$]. HPLC: t$_R$=1.42 min (UPLC TOF MS: polar_3 min).

Compound 173A: 2-amino-5-(4-hydroxycyclohexyl)-N,N-dimethylbenzamide

A solution of 2-amino-5-(4-{[tert-butyl(dimethyl)silyl]oxy}cyclohexyl)-N,N-dimethylbenzamide (Compound 173B, 0.320 g, 0.850 mmol) in THF (2 mL) was charged with 1.0 M of tetra-n-butylammonium fluoride in THF (8.50 mL) and stirred at rt over night. The reaction mixture was partitioned between EtOAc and water and separated. The aqueous was extracted with EtOAc (3×) and the combined organic fractions were washed with brine, dried over sodium sulfate, filtered, and concentrated. The compound was purified on an Isco Combiflash unit eluting with 75 to 100% EtOAc in heptane to afford the title compound. $^1$H NMR (400 MHz, DMSO-d$_6$) δ 6.91-6.97 (m, 1H), 6.80-6.85 (m, 1H), 6.59-6.64 (m, 1H), 4.94 (s, 2H), 4.30 (d, J=3.79 Hz, 1H), 2.91 (s, 6H), 2.24-2.39 (m, 1H), 1.62-1.80 (m, 4H), 1.34-1.54 (m, 4H), 1.20-1.32 (m, 1H); MS (ES$^+$): m/z: 263.15 [MH$^+$]. HPLC: t$_R$=2.84 min (Micromass ZQ3: polar_3 min).

Compound 173B: 2-amino-5-(4-{[tert-butyl(dimethyl)silyl]oxy}cyclohexyl)-N,N-dimethylbenzamide To a solution of 2-amino-5-(4-{[tert-butyl(dimethyl)silyl]oxy}cyclohex-1-en-1-yl)-N,N-dimethylbenzamide (Example 173, 0.320 g, 0.854 mmol) in EtOH (20 mL) was added palladium 10% wt on activated carbon (0.091 g, 0.085 mmol). The reaction mixture was evacuated and purged with hydrogen (3×) and stirred over night at rt. The reaction mixture was filtered through a pad of celite and concentrated in vacuo to afford the title compound. $^1$H NMR (400 MHz, DMSO-d$_6$) δ 6.92 (dd, J=2.15, 8.21 Hz, 1H), 6.79 (d, J=2.02 Hz, 1H), 6.63 (d, J=8.34 Hz, 1H), 2.91 (br. s., 6H), 2.29-2.41 (m, 1H), 1.62-1.79 (m, 4H), 1.43-1.59 (m, 4H), 0.83-0.93 (m, 9H); MS (ES$^+$): m/z: 377.2605 [MH$^+$]. HPLC: t$_R$=2.04 min (UPLC TOF MS: polar_3 min).

Compound 173C: 2-amino-5-(4-{[tert-butyl(dimethyl)silyl]oxy}cyclohex-1-en-1-yl)-N,N-dimethylbenzamide A solution of 2-amino-N,N-dimethyl-5-(4,4,5,5-tetramethyl-1,3,2-dioxaborolan-2-yl)benzamide (Compound 173D: 0.500 g, 1.72 mmol) and trifluoro-methanesulfonic acid 4-(tert-butyl-dimethyl-silanyloxy)-cyclohex-1-enyl ester (WO 2005092863, 0.745 g, 2.07 mmol) in 1,4-dioxane (4 mL) and H$_2$O (1 mL) was charged with [1,1'-bis(diphenylphosphino)ferrocene]dichloropalladium(II), complex with dichloromethane (1:1) (0.063 g, 0.086 mmol) and potassium carbonate (0.71 g, 5.2 mmol) in a microwave vial. The reaction mixture was evacuated and purged with nitrogen (3×) and irradiated in the microwave for 30 min at 100° C. The reaction mixture was partitioned between EtOAc and water and separated. The aqueous was extracted with EtOAc (3×) and the combined organic fractions were washed with brine, dried over sodium sulfate, filtered, and concentrated. The compound was purified on an Isco Combiflash eluting with 50 to 100% EtOAc in heptane to afford the title compound. $^1$H NMR (400 MHz, DMSO-d$_6$) δ 7.17 (dd, J=2.27, 8.59 Hz, 1H), 7.00 (d, J=2.27 Hz, 1H), 6.64 (d, J=8.59 Hz, 1H), 5.83 (d, J=2.02 Hz, 1H), 5.16 (s, 2H), 3.89-3.98 (m, 1H), 2.91 (br. s., 6H), 2.32-2.44 (m, 2H), 2.00-2.09 (m, 1H), 1.85 (d, J=10.86 Hz, 1H), 1.55-1.67 (m, 1H), 0.87 (s, 12H), 0.06 (d, J=2.27 Hz, 6H); MS (ES$^±$): m/z: 375.2372 [MH$^+$]. HPLC: t$_R$=1.96 min (UPLC TOF MS: polar_3 min).

Compound 173D: 2-amino-N,N-dimethyl-5-(4,4,5,5-tetramethyl-1,3,2-dioxaborolan-2-yl)benzamide A solution of 2-amino-5-bromo-N,N dimethyl benzimide (Compound 106A, 1.0 g, 4.1 mmol) and bis(pinacolato)diboron (2.1 g, 8.2 mmol) in DMF (10 mL) were charged with AcOK (0.81 g, 8.2 mmol) and [1,1'-bis(diphenylphosphino)ferrocene]dichloropalladium(II), complex with dichloromethane (1:1) (0.15 g, 0.20 mmol). The reaction mixture was evacuated and purged with nitrogen (3×) and heated at 100° C. over night. The reaction mixture was partitioned between EtOAc and water and separated. The aqueous was extracted with EtOAc (3×) and the combined organic fractions were washed with brine, dried over sodium sulfate, filtered, and concentrated. The compound was purified on an Isco Combiflash unit eluting with 0 to 5% MeOH in DCM to afford the title compound. $^1$H NMR (400 MHz, DMSO-d$_6$) δ 7.35 (dd, J=1.52, 8.08 Hz, 1H), 7.27 (d, J=1.26 Hz, 1H), 6.65 (d, J=8.08 Hz, 1H), 5.57 (s, 2H), 1.24 (s, 12H), 1.16 (s, 6H); MS (ES$^+$): m/z: 291.1895 [MH$^+$]. HPLC: t$_R$=1.31 min (UPLC TOF MS: polar_3 min).

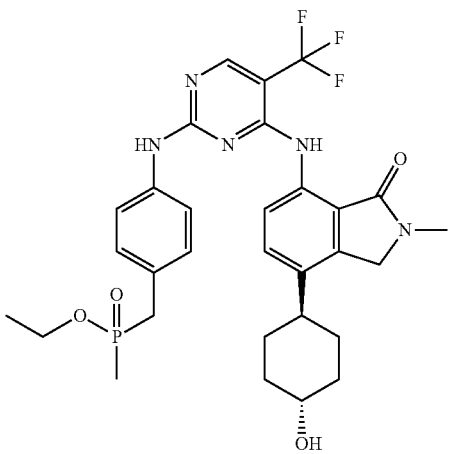 [SMILES: CCOP(C)(=O)Cc1ccc(Nc2ncc(C(F)(F)F)c(Nc3ccc([C@H]4CC[C@H](O)CC4)c4c3C(=O)N(C)C4)n2)cc1]

Example 174

Ethyl(4-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}benzyl)methylphosphinate:
The title product was prepared according to the procedure for Example 102 using [4-(4-chloro-5-trifluoromethylpyrimidin-2-ylamino)benzyl]methyl phosphinic acid ethyl ester (Compound 174A, 53 mg, 0.14 mmol) and 7-amino-4-(trans-4-hydroxycyclohexyl)-2-methyl-2,3-dihydro-1H-isoindol-1-one (35 mg, 0.13 mmol). $^1$H NMR (400 MHz, DMSO-d$_6$) δ 10.57 (br. s., 1H), 9.89 (s, 1H), 8.45 (s, 1H), 7.33 (d, J=8.34 Hz, 1H), 7.26 (d, J=6.57 Hz, 3H), 4.62 (d, J=4.55 Hz, 1H), 4.52 (s, 2H), 3.96 (dddt, J=3.16, 7.01, 7.23, 7.34 Hz, 2H), 3.45-3.55 (m, 1H), 3.18 (d, J=17.43 Hz, 2H), 3.08 (s, 3H), 1.93 (d, J=9.85 Hz, 2H), 1.76 (d, J=12.13 Hz, 2H), 1.50-1.63 (m, 2H), 1.34 (d, J=13.89 Hz, 3H), 1.21 (t, J=7.07 Hz, 3H); MS (ES$^+$): m/z: 618.2039 [MH$^+$]. HPLC: t$_R$=1.34 min (UPLC TOF MS: polar_3 min).

Compound 174A: [4-(4-Chloro-5-trifluoromethylpyrimidin-2-ylamino)benzyl]methylphosphinic acid ethyl ester The title compound was prepared according to the procedure for diethyl (4-{[4-chloro-5-(trifluoromethyl)pyrimidin-2-yl]amino}benzyl)phosphonate using ethyl(4-aminobenzyl)methylphosphinate (Compound 174B, 1.08 g, 5.07 mmol) and 2,4-dichloro-5-trifluoromethylpyrimidine. (1.0 g, 4.6 mmol). The compound was purified on an Isco Combiflash eluting with 0 to 10% MeOH in EtOAc. The compound was re-crystallized in EtOAc (~20 mL) to afford 1.1 g, 61% yield, of the title compound. $^1$H NMR (400 MHz, DMSO-d$_6$) δ 10.64 (s, 1H), 8.79 (d, J=0.51 Hz, 1H), 7.62 (d, J=8.34 Hz, 2H), 7.25 (dd, J=2.27, 8.59 Hz, 2H), 3.86-4.01 (m, 2H), 3.15 (d, J=17.68 Hz, 2H), 1.31 (d, J=13.64 Hz, 3H), 1.19 (t, J=6.95 Hz, 3H); MS (ES$^+$): m/z: 396.0708 [MH$^+$]. HPLC: t$_R$=1.41 min (UPLC TOF MS: polar_3 min).

Compound 174B: Ethyl(4-aminobenzyl)methylphosphinate

A solution of ethyl methyl(4-nitrobenzyl)phosphinate (Compound 174C, 2.4 g, 9.9 mmol) in MeOH (10 mL) was charged with palladium 10% wt on activated carbon and evacuated and purged with hydrogen (3×). The reaction was stirred at rt for 16 h. The reaction mixture was filtered through a pad of celite and concentrated in vacuo to afford 2.0 g, 95% yield, of the title compound. $^1$H NMR (400 MHz, chloroform-d) δ ppm 1.29 (t, J=7.1 Hz, 3H), 1.34 (d, J=13.6 Hz, 3H), 3.04 (d, J=17.4 Hz, 2H), 3.97-4.12 (m, 2H), 6.65 (d, J=7.8 Hz, 2H), 7.04 (dd, J=8.6, 2.5 Hz, 2H). MS (ES$^+$): m/z: 214.0976 [MH$^+$]. HPLC: t$_R$=0.76 min (TOF MS: polar_3 min).

Compound 174C: Ethyl methyl(4-nitrobenzyl)phosphinate

A solution of p-nitrobenzylbromide (2.4 g, 11 mmol) in diethoxymethylphosphine (2.0 g, 15 mmol) was stirred at 140° C. for 16 h under nitrogen in a sealed tube. The reaction mixture was concentrated in vacuo and the residue was purified by column chromatography on silica eluting with 25% EtOAc in hexane to afford 2.4 g, 87% yield, of the title compound. $^1$H NMR (400 MHz, chloroform-d) δ ppm 1.29 (t, J=7.1 Hz, 3H), 1.44 (d, J=13.9 Hz, 3H), 3.25 (d, J=17.7 Hz, 2H), 3.96-4.18 (m, 2H), 7.47 (dd, J=9.0, 2.4 Hz, 2H), 8.20 (d, J=8.1 Hz, 2H). MS (ES$^+$): m/z: 244.0745 [MH$^+$]. HPLC: t$_R$=1.13 min (TOF MS: polar_3 min)

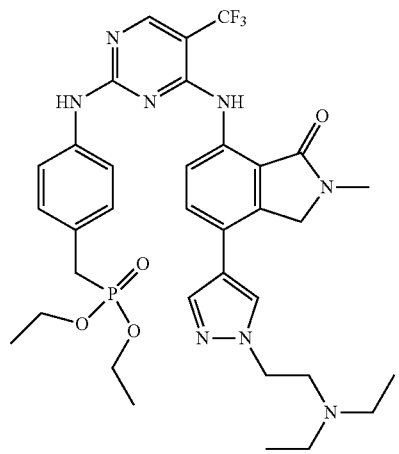 [SMILES: CCOP(=O)(Cc1ccc(Nc2ncc(C(F)(F)F)c(Nc3ccc(-c4cnn(CCN(CC)CC)c4)c4c3C(=O)N(C)C4)n2)cc1)OCC]

Example 175

Diethyl[4-({4-[(7-{1-[2-(diethylamino)ethyl]-1H-pyrazol-4-yl}-2-methyl-3-oxo-2,3-dihydro-1H-isoindol-4-yl)amino]-5-(trifluoromethyl)pyrimidin-2-yl}amino)benzyl]phosphonate The title compound was prepared according to the procedure of Example 97 using diethyl[4-({4-[(7-bromo-2-methyl-3-oxo-2,3-dihydro-1H-isoindol-4-yl)amino]-5-(trifluoromethyl)pyrimidin-2-yl}amino)benzyl]phosphonate and N,N-diethyl-2-[4-(4,4,5,5-tetramethyl-1,3,2-dioxaborolan-2-yl)-1H-pyrazol-1-yl]ethanamine (Compound 175A). MS (ES+): m/z 715.47 (100) [MH$^+$]; HPLC: t$_R$=0.75 min (UPLC, purity).

Compound 175A: N,N-diethyl-2-[4-(4,4,5,5-tetramethyl-1,3,2-dioxaborolan-2-yl)-1H-pyrazol-1-yl]ethanamine To a solution of 4-(4,4,5,5-tetramethyl-[1,3,2]dioxaborolan-2-yl)-1H-pyrazole (500 mg, 2.5 mmol) in DMF (10 mL) was added (2-chloroethyl)diethylamine (Compound 175B, 0.6 g, 4 mmol) and K$_2$CO$_3$ (1.38 g, 10 mmol). The reaction mixture was stirred at 140° C. for 1.5 h in a microwave reactor, then concentrated, residue was purified by HPLC to afford 100 mg of the title compound (yield: 12%). ¹H NMR (DMSO-d₆, 400 MHz): δ=1.1-1.2 (m, 9H), 1.25 (s, 12H), 2.72 (s, 0.5H), 2.75 (s, 1H), 3.00-3.10 (s, 4H), 3.1-3.2 (m, 2H), 3.44 (s, 3H), 4.58-4.59 (br, 3H), 7.74 (s, 1H), 7.82 (s, 0.5H), 8.05 (s, 0.5H), 8.09 (s, 1H).

Compound 175B: (2-Chloroethyl)diethylamine

A mixture of 2-diethylaminoethanol (1.17 g, 10 mmol) and SOCl₂ (100 mL) was heated at reflux for 5 h. The excess SOCl₂ was removed under vacuum to give the desired product, which was used directly in the next step.

Example 177

Diethyl(4-{[4-({2-[(4-methylpiperazin-1-yl)carbonyl]phenyl}amino)-5-(trifluoromethyl)pyrimidin-2-yl]amino}benzyl)phosphonate The title product was prepared according to the procedure for Example 102 using diethyl(4-{[4-chloro-5-(trifluoromethyl)pyrimidin-2-yl]amino}benzyl)phosphonate and the commercially available (2-aminophenyl)-(4-methylpiperazin-1-yl)methanone. MS (ES+): m/z 607.37 (100) [MH⁺]; HPLC: t_R=0.66 min (UPLC, purity).

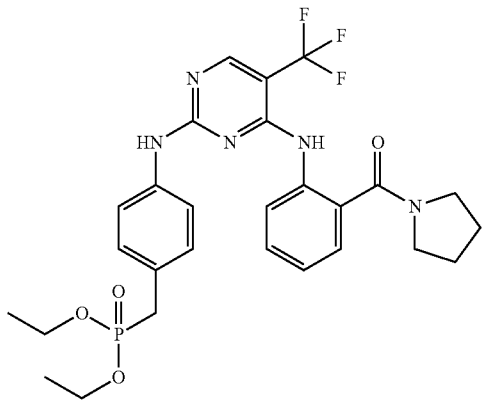 [SMILES: CCOP(=O)(Cc1ccc(Nc2ncc(C(F)(F)F)c(Nc3ccccc3C(=O)N3CCCC3)n2)cc1)OCC]

Example 176

Diethyl(4-{[4-{[2-(pyrrolidin-1-ylcarbonyl)phenyl]amino}-5-(trifluoromethyl)pyrimidin-2-yl]amino}benzyl)phosphonate The title product was prepared according to the procedure for Example 102 using diethyl(4-{[4-chloro-5-(trifluoromethyl)pyrimidin-2-yl]amino}benzyl)phosphonate and the commercially available 2-(pyrrolidin-1-ylcarbonyl)aniline. MS (ES+): m/z 578.34 (100) [MH⁺]; HPLC: t_R=1.02 min (UPLC, purity).

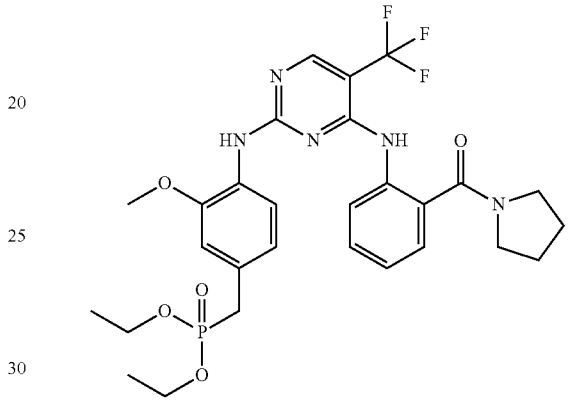

Example 178

Diethyl(3-methoxy-4-{[4-{[2-(pyrrolidin-1-ylcarbonyl)phenyl]amino}-5-(trifluoromethyl)pyrimidin-2-yl]amino}benzyl)phosphonate The title product was prepared according to the procedure for Example 102 using diethyl(4-{[4-chloro-5-(trifluoromethyl)pyrimidin-2-yl]amino}-3-methoxybenzyl)phosphonate and the commercially available 2-(pyrrolidin-1-ylcarbonyl)aniline. MS (ES+): m/z 608.35 (100) [MH⁺]; HPLC: t_R=1.07 min (UPLC, purity).

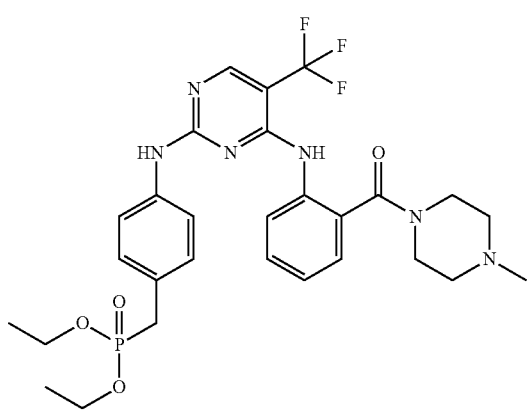 [SMILES: CCOP(=O)(Cc1ccc(Nc2ncc(C(F)(F)F)c(Nc3ccccc3C(=O)N3CCN(C)CC3)n2)cc1)OCC]

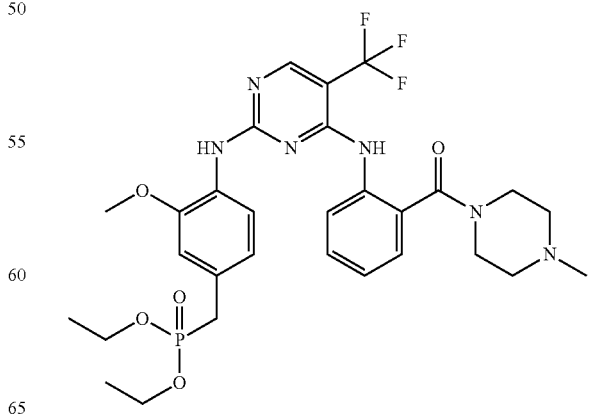

Example 179

Diethyl(3-methoxy-4-{[4-({2-[(4-methylpiperazin-1-yl)carbonyl]phenyl]amino}-5-(trifluoromethyl)pyrimidin-2-yl]amino}benzyl)phosphonate The title product was prepared according to the procedure for Example 102 using diethyl(4-{[4-chloro-5-(trifluoromethyl)pyrimidin-2-yl]amino}-3-methoxybenzyl)phosphonate and the commercially available (2-aminophenyl)-(4-methylpiperazin-1-yl)-methanone. MS (ES+): m/z 637.40 (100) [MH$^+$]; HPLC: $t_R$=0.69 min (UPLC, purity).

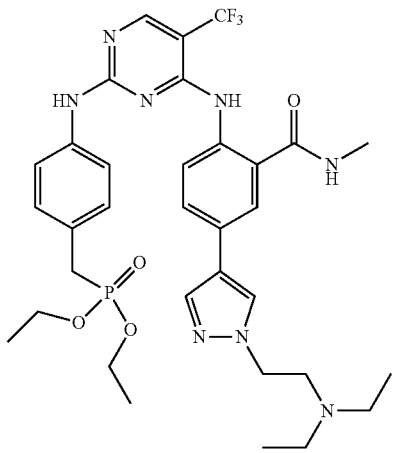 [SMILES: CCOP(=O)(Cc1ccc(Nc2ncc(C(F)(F)F)c(Nc3ccc(-c4cnn(CCN(CC)CC)c4)cc3C(=O)NC)n2)cc1)OCC]

Example 180

Diethyl(4-{[4-{[4-{1-[2-(diethylamino)ethyl]-1H-pyrazol-4-yl}-2-(methylcarbamoyl)phenyl]amino}-5-(trifluoromethyl)pyrimidin-2-yl]amino}benzyl) phosphonate The title compound was prepared according to the procedure of Example 97 using Diethyl(4-{[4-{[4-bromo-2-(methylcarbamoyl)phenyl]amino}-5-(trifluoromethyl)pyrimidin-2-yl]amino}benzyl)phosphonate (Example 106) and N,N-diethyl-2-[4-(4,4,5,5-tetramethyl-1,3,2-dioxaborolan-2-yl)-1H-pyrazol-1-yl]ethanamine (Compound 175A). MS (ES+): m/z 703.45 (100) [MH$^+$]; HPLC: $t_R$=0.73 min (UPLC, purity).

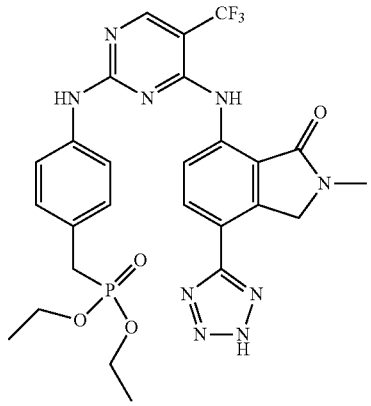 [SMILES: CCOP(=O)(Cc1ccc(Nc2ncc(C(F)(F)F)c(Nc3ccc(-c4nn[nH]n4)c4c3C(=O)N(C)C4)n2)cc1)OCC]

Example 181

Diethyl(4-{[4-{[2-methyl-3-oxo-7-(2H-tetrazol-5-yl)-2,3-dihydro-1H-isoindol-4-yl]amino}-5-(trifluoromethyl)pyrimidin-2-yl]amino}benzyl)phosphonate The title product was prepared according to the procedure for Example 102 using diethyl(4-{[4-chloro-5-(trifluoromethyl)pyrimidin-2-yl]amino}benzyl)phosphonate and 7-amino-2-methyl-4-(2H-tetrazol-5-yl)-2,3-dihydro-1H-isoindol-1-one (Compound 181A).

MS (ES+): m/z 618.33 (100) [MH$^+$]; HPLC: $t_R$=1.13 min (UPLC, purity).

Compound 181A: 7-amino-2-methyl-4-(2H-tetrazol-5-yl)-2,3-dihydro-1H-isoindol-1-one A mixture of 7-Amino-2-methyl-1-oxo-2,3-dihydro-1H-isoindole-4-carbonitrile (Compound 181B, 25.0 mg, 0.134 mmol), sodium azide (104 mg, 1.60 mmol) and ammonium chloride (85.7 mg, 1.60 mmol) in DMF (6 mL) were mixed and heated in microwave at 120° C. for 9 hours. The crude mixture was filtered and directly purified by MDP to obtain the title compound (12.0 mg, 39% yield). MS (ES+): m/z 231.23 (100) [MH$^+$]; HPLC: $t_R$=0.59 min (UPLC, analytical).

Compound 181B: 7-Amino-2-methyl-1-oxo-2,3-dihydro-1H-isoindole-4-carbonitrile

A mixture of 7-Amino-4-bromo-2-methyl-2,3-dihydro-1H-isoindol-1-one (100.0 mg, 0.4148 mmol), zinc cyanide (48.71 mg, 0.4148 mmol) and Pd(PPh$_3$)$_4$ (71.90 mg, 0.06222 mmol) in DMF (1.5 mL, 19 mmol) was evacuated and purged with N$_2$ three times. The mixture was heated in microwave at 150° C. for 5 minutes. The crude mixture was diluted with ethyl acetate and washed with water and brine. The organic layer was evaporated and purified on an ISCO Combiflash unit to isolate the title compound (50.0 mg, 64% yield). MS (ES+): m/z 188.14 (100) [MH$^+$]; HPLC: $t_R$=1.00 min (UPLC, analytical).

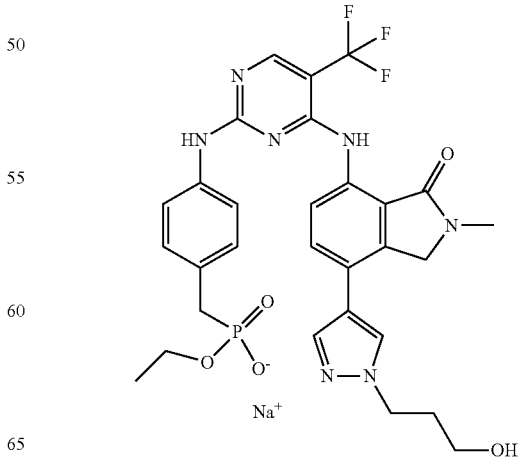

Example 182

Sodium ethyl(4-{[4-({7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}benzyl)phosphonate A mixture of Example 156 (172 mg, 0.255 mmol) in MEK (6 mL) was treated with of NaI (165 mg, 1.102 mmol) and irradiated on the microwave at 120° C. for 6 hours. The cooled reaction mixture was filtered, the solids were washed with ice cold acetone and dried in vacuo to afford the title compound as alight brown solid. $^1$H NMR (400 MHz, DMSO-d6) δ ppm 10.64 (br s, 1H), 9.72 (s, 1H), 9.19 (br s, 1H), 8.47 (br s, 1H), 8.40 (s, 1H), 8.19 (br s, 1H), 7.75 (br s, 1H), 7.28 (br s, 4H), 6.34 (br s, 1H), 4.63 (s, 2H), 4.20 (t, J=6.2 Hz, 2H), 3.60 (quin, J=7.1 Hz, 2H), 3.42-3.51 (m, 2H), 3.11 (s, 3H), 2.73 (d, J=19.5 Hz, 2H), 1.94 (quin, J=6.1 Hz, 2H), 0.94 (t, J=6.9 Hz, 3H). MS (ES+): m/z 646.20 (100) [MH$^+$]; HPLC: $t_R$=1.12 min (UPLC TOF, polar_3 min).

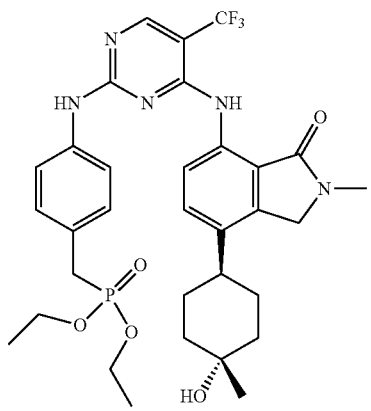 [SMILES: CCOP(=O)(Cc1ccc(Nc2ncc(C(F)(F)F)c(Nc3ccc([C@H]4CC[C@](C)(O)CC4)c4c3C(=O)N(C)C4)n2)cc1)OCC]

Example 183

Diethyl(4-{[4-{[7-(trans-4-hydroxy-4-methylcyclohexyl)-2-methyl-3-oxo-2,3-dihydro-1H-isoindol-4-yl]amino}-5-(trifluoromethyl)pyrimidin-2-yl]amino}benzyl)phosphonate The title product was prepared according to the procedure for Example 102 using diethyl(4-{[4-chloro-5-(trifluoromethyl)pyrimidin-2-yl]amino}benzyl)phosphonate and 7-amino-4-(trans-4-hydroxy-4-methylcyclohexyl)-2-methyl-2,3-dihydro-1H-isoindol-1-one (Compound 183B). $^1$H NMR (DMSO-d6, 400 MHz): δ=1.13-1.20 (m, 9H), 1.43 (td, J=13.26, 3.54 Hz, 2H), 1.53 (d, J=11.12 Hz, 2H), 1.65 (d, J=12.63 Hz, 2H), 1.89 (qd, J=12.80, 2.78 Hz, 2H), 3.08 (s, 3H), 3.17-3.25 (m, 2H), 3.92-4.01 (m, 4H), 4.51 (s, 2H), 6.97 (s, 1H), 7.10 (s, 1H), 7.23 (s, 1H), 7.25 (dd, J=8.46, 2.15 Hz, 2H), 7.38 (d, J=8.34 Hz, 1H), 7.59 (d, J=4.80 Hz, 2H), 8.46 (s, 1H), 8.66 (br. s., 1H), 9.89 (s, 1H), 10.58 (br. s., 1H). MS (ES$^+$): m/z 662.28 [MH$^+$] (TOF, polar).

Compounds 183A and 183B: 7-amino-4-(cis-4-hydroxy-4-methylcyclohexyl)-2-methyl-2,3-dihydro-1H-isoindol-1-one and 7-amino-4-(trans-4-hydroxy-4-methylcyclohexyl)-2-methyl-2,3-dihydro-1H-isoindol-1-one A solution of 7-amino-2-methyl-4-(4-oxocyclohexyl)-2,3-dihydro-1H-isoindol-1-one (68.5 mg, 0.265 mmol) in THF (4.5 mL) was cooled at 0° C. and then slowly charged with 3.0 M of methylmagnesium bromide in Et$_2$O (0.526 mL, 1.58 mmol). The reaction mixture was stirred at 0° C. for 45 min and then allowed to warm to rt with stirring for 48 h. The reaction mixture was quenched with aqueous NH$_4$Cl (10 mL) and extracted with EtOAc (15 mL). The organic layer was washed with brine (10 mL), dried over Na$_2$SO$_4$, and concentrated under reduced pressure to yield a yellow solid. The material was purified by silica gel chromatography on the combi-flash Rf system using 1:1 EtOAc-DCM/MeOH (100:0→95:5) as eluent. The first product to elute was the cis-alcohol (Compound 182A): (14.8 mg, 20% yield) $^1$H NMR (CDCl$_3$, 400 MHz): δ=1.30 (s, 3H), 1.47-1.58 (m, 2H), 1.63 (d, J=12.38 Hz, 2H), 1.73-1.95 (m, 4H), 2.40 (tt, J=12.22, 3.19 Hz, 1H), 3.16 (s, 3H), 4.34 (s, 2H), 6.87 (d, J=8.08 Hz, 1H), 7.25 (s, 1H). MS (ES$^+$): m/z 275.16 [MH$^+$] (TOF, polar). The trans-alcohol (Compound 182B) eluted after: 11.8 mg (16% yield). $^1$H NMR (CDCl$_3$, 400 MHz): δ=1.27 (d, J=3.28 Hz, 1H), 1.36 (s, 3H), 1.55-1.66 (m, 4H), 1.74-1.87 (m, 4H), 3.15 (s, 3H), 4.31 (s, 2H), 6.65 (d, J=8.34 Hz, 1H), 7.14 (d, J=8.34 Hz, 1H). MS (ES$^+$): m/z 275.16 [MH$^+$] (TOF, polar).

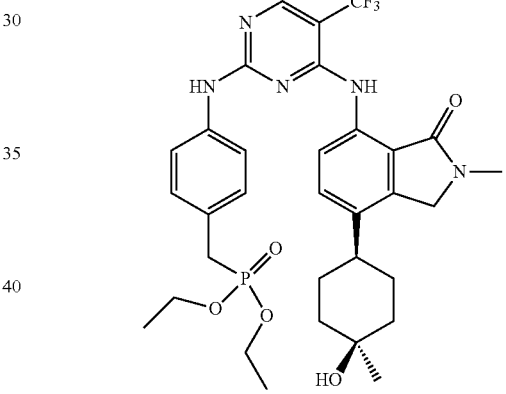

Example 184

Diethyl(4-{[4-{[7-(cis-4-hydroxy-4-methylcyclohexyl)-2-methyl-3-oxo-2,3-dihydro-1H-isoindol-4-yl]amino}-5-(trifluoromethyl)pyrimidin-2-yl]amino}benzyl)phosphonate The title product was prepared according to the procedure for Example 102 using diethyl(4-{[4-chloro-5-(trifluoromethyl)pyrimidin-2-yl]amino}benzyl)phosphonate and 7-amino-4-(cis-4-hydroxy-4-methylcyclohexyl)-2-methyl-2,3-dihydro-1H-isoindol-1-one (Compound 182A). $^1$H NMR (DMSO-d6, 400 MHz): δ=1.16 (t, J=6.95 Hz, 6H), 1.25 (s, 3H), 1.46-1.73 (m, 8H), 3.08 (s, 3H), 3.17-3.26 (m, 2H), 3.90-3.99 (m, 4H), 4.52 (s, 2H), 6.97 (s, 1H), 7.10 (s, 1H), 7.22 (s, 1H), 7.25-7.31 (m, 2H), 7.43 (d, J=8.59 Hz, 1H), 7.54 (br. s., 2H), 8.45 (s, 1H), 8.58 (br. s., 1H), 9.89 (s, 1H), 10.60 (s, 1H). MS (ES$^+$): m/z 662.27 [MH$^+$] (TOF, polar).

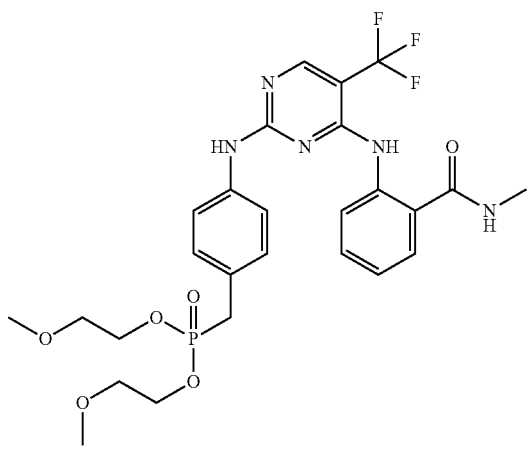

Example 185

Bis(2-methoxyethyl)(4-{[4-{[2-(methylcarbamoyl)phenyl]amino}-5-(trifluoromethyl)pyrimidin-2-yl]amino}benzyl)phosphonate The title product was prepared according to the procedure for Example 102 using 2-{[2-chloro-5-(trifluoromethyl)pyrimidin-4-yl]amino}-N-methylbenzamide (Compound 104A, 0.050 g, 0.15 mmol) and bis(2-methoxyethyl)(4-aminobenzyl)phosphonate (Compound 185A, 0.0917 g, 0.302 mmol) to afford the title compound. $^1$H NMR (400 MHz, DMSO-$d_6$) δ 8.75 (d, J=4.80 Hz, 1H), 8.44 (s, 1H), 7.69-7.74 (m, 1H), 7.57 (d, J=7.58 Hz, 2H), 7.50 (t, J=7.96 Hz, 1H), 7.13-7.21 (m, 3H), 3.94-4.05 (m, 4H), 3.46 (t, J=4.55 Hz, 4H), 3.21-3.26 (m, 6H), 3.18 (s, 2H), 2.78 (d, J=4.55 Hz, 3H); MS (ES$^+$): m/z: 598.1695 [MH$^+$]. HPLC: $t_R$=1.32 min (UPLC TOF MS: polar_3 min).

Compound 185A:
Bis(2-methoxyethyl)(4-aminobenzyl)phosphonate

A mixture of bis(2-methoxyethyl)(4-nitrobenzyl)phosphonate (Compound 185B, 6.0 g, 18 mmol) and 5% Pd/C (0.8 g) in EtOH (150 mL) was hydrogenated under 40 psi hydrogen pressure at 40° C. for 6 h. The reaction mixture was filtered and the filtrate was concentrated to give the desired product (5.3 g, 97%). $^1$H NMR (CDCl$_3$, 400 MHz): δ=3.04 (d, J=21.2 Hz, 2H), 3.28 (s, 6H), 3.42-3.46 (m, 4H), 3.97-4.03 (m, 4H), 6.55 (d, J=8.4 Hz, 2H), 6.99-7.02 (m, 2H).

Compound 185B:
Bis(2-methoxyethyl)(4-nitrobenzyl)phosphonate

At 0° C., to a solution of 2-methoxyethanol (7.60 g, 100 mmol) and TEA (10 g, 100 mmol) in THF (60 mL) was added a solution of 4-nitrobenzylphosphonic dichloride (see Compound 165B, 10 g, 40 mmol) in THF (60 mL) dropwise. The reaction mixture was warmed to room temperature and stirred at 70° C. for 12 h. Solvent was removed and residue was purified by column chromatography to give 6.0 g of the desired product (yield: 46%).

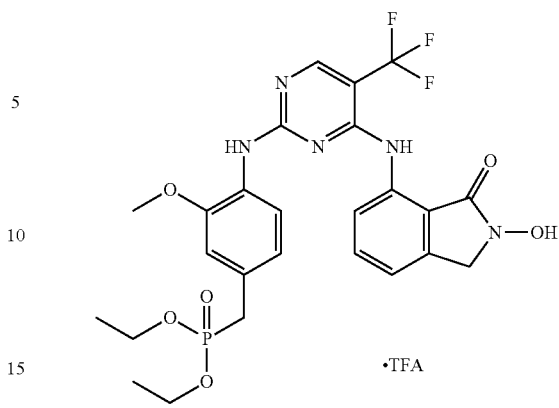

Example 186

Diethyl[4-({4-[(2-hydroxy-3-oxo-2,3-dihydro-1H-isoindol-4-yl)amino]-5-(trifluoromethyl)pyrimidin-2-yl}amino)-3-methoxybenzyl]phosphonate trifluoroacetate The title product was prepared according to the procedure for Example 102 using diethyl(4-{[4-chloro-5-(trifluoromethyl)pyrimidin-2-yl]amino}-3-methoxybenzyl)phosphonate (50.0 mg, 0.11 mmol) and 7-amino-2-hydroxy-2,3-dihydro-1H-isoindol-1-one (Compound 186A, 21.70 mg, 0.13 mmol). The reaction mixture purified by MDP to isolate the desired product (4.6 mg, yield: 7%) as a TFA salt. $^1$H NMR (CD$_3$OD, 400 MHz): δ=1.29 (t, J=7.2 Hz, 6H), 3.33 (d, J=21.2 Hz, 2H), 3.89 (s, 3H), 4.06-4.13 (m, 4H), 4.63 (s, 2H), 4.96 (dt, J=2.8, 8.4 Hz, 1H), 7.10 (t, J=2.0 Hz, 1H), 7.24 (d, J=7.6 Hz, 1H), 7.36 (dd, J=0.8, 8.0 Hz, 0.5H), 7.52 (m, 1H), 7.66 (d, J=8.0 Hz, 1H), 8.32 (d, J=8.0 Hz, 0.5H), 8.37 (s, 1H). MS (ES$^+$): m/z 582.17 [MH$^+$]. HPLC: $t_R$=3.64 min (OpenLynx, polar_5 min).

Compound 186A:
7-Amino-2-hydroxy-2,3-dihydro-1H-isoindol-1-one

To a solution of 7-nitro-2-benzyloxy-2,3-dihydro-1H-isoindol-1-one (Compound 186B, 2.3 g, 1.2 mmol) in methanol (30 mL) in a Parr hydrogenation flask was added 200 mg of 5% Pd/C. The mixture was hydrogenated under 40 psi hydrogen pressure at room temperature overnight. The reaction mixture was filtered through a glass filter paper and the filtrate was concentrated to afford 1.2 g of the pure product (90%). $^1$H NMR (CDCl$_3$, 600 MHz): δ=4.57 (s, 2H), 5.04 (br, 2H), 6.57 (d, J=7.8 Hz, 1H) 6.65 (d, J=7.5 Hz, 1H), 7.25 (dd, J=7.5, 7.8 Hz, 1H), 10.2 (s, br, 1H).

Compound 186B:
7-Nitro-2-benzyloxy-2,3-dihydro-1H-isoindol-1-one

A solution of benzyloxyamine hydrochloride (7.8 g, 48.87 mmol) in water (20 mL) was basified with sodium carbonate (6.0 g, 48.87 mmol) to get free amine. This mixture was then added to a solution of methyl 2-bromomethyl-6-nitrobenzoate (4.46 g, 16.29 mmol) in THF. The resulting mixture was stirred at 60° C. overnight, concentrated to remove THF and extracted with ethyl acetate (2×50 mL). The combined organic layer was washed with brine, dried (Na$_2$SO$_4$) and concentrated to give 3.2 g of the desired product as an off-white solid (70%). $^1$H NMR (CDCl$_3$, 600 MHz): δ=4.24 (s, 2H), 5.2 (s, 2H), 7.3-7.9 (m, 8H).

product as a yellowish solid (79%). $^1$H NMR (CDCl$_3$, 600 MHz): δ=3.98 (s, 3H), 4.64 (s, 2H), 7.60-7.90 (m, 3H).

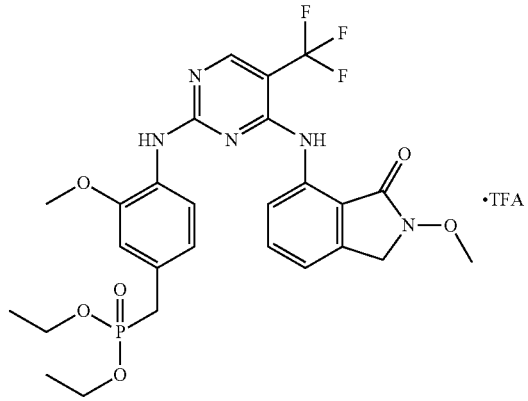 [SMILES: CCOP(=O)(Cc1ccc(Nc2ncc(C(F)(F)F)c(Nc3cccc4c3C(=O)N(OC)C4)n2)c(OC)c1)OCC]

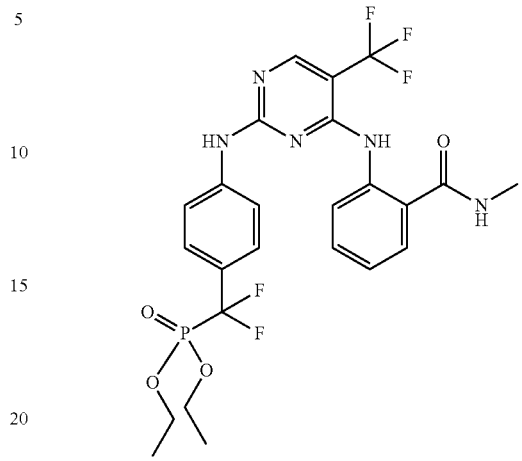

Example 187

Diethyl[3-methoxy-4-({4-[(2-methoxy-3-oxo-2,3-dihydro-1H-isoindol-4-yl)amino]-5-(trifluoromethyl)pyrimidin-2-yl}amino)benzyl]phosphonate trifluoroacetate The title product was prepared according to the procedure for Example 102 using diethyl(4-{[4-chloro-5-(trifluoromethyl)pyrimidin-2-yl]amino}-3-methoxybenzyl)phosphonate (50.0 mg, 0.11 mmol) and 7-amino-2-methoxy-2,3-dihydro-1H-isoindol-1-one (Compound 187A, 23.56 mg, 0.13 mmol). After purification by MDP 29.4 mg of the desired product was obtained as a TFA salt. (45%) $^1$H NMR (CD$_3$OD, 400 MHz): δ=1.30 (t, J=7.2 Hz, 6H), 3.34 (d, J=21.2 Hz, 2H), 3.88 (s, 3H), 3.91 (s, 3H), 4.07-4.14 (m, 4H), 4.68 (s, 2H), 6.95 (dt, J=2.0, 8.0 Hz, 1H), 7.11 (t, J=2.4 Hz, 1H), 7.27 (dd, J=0.4, 7.6 Hz, 1H), 7.53 (t, J=8.0 Hz, 1H), 7.59 (d, J=7.6 Hz, 1H), 8.38 (s, 1H). MS (ES$^+$): m/z 596.16 [MH$^+$]. HPLC: $t_R$=4.01 min (OpenLynx, polar_5 min).

Compound 187A

7-Amino-2-methoxy-2,3-dihydro-1H-isoindol-1-one

A solution of 7-nitro-2-methoxy-2,3-dihydro-1H-isoindol-1-one (Compound 187B, 0.25 g, 1.2 mmol) in ethanol (5 mL) was hydrogenated over 5% Pd/C (30 mg) overnight at room temperature. The catalyst was filtered off by a glass filter paper and the filtrate was concentrated to give 0.18 g of the pure product (yield: 85%). $^1$H NMR (CDCl$_3$, 600 MHz): δ=3.93 (s, 3H), 4.48 (s, 2H), 6.56 (d, J=8.5 Hz, 1H) 6.63 (d, J=7.0 Hz, 1H), 7.24 (dd, J=7.5, 8.5 Hz, 1H).

Compound 187B: 7-Nitro-2-methoxy-2,3-dihydro-1H-isoindol-1-one

A solution of methoxylamine hydrochloride (0.76 g, 9.12 mmol) in water (5 mL) was basified with sodium carbonate (0.96 g, 9.12 mmol) to get free amine. This mixture was then added to a solution of methyl 2-bromomethyl-6-nitrobenzoate (0.25 g, 0.91 mmol) in THF. The reaction mixture was stirred at 60° C. overnight, concentrated to remove THF, the residue was extracted with ethyl acetate (2×10 mL). The combined organic layer was washed with brine, dried (Na$_2$SO$_4$) and concentrated to give 0.15 g of the desired

Example 188

Diethyl[difluoro(4-{[4-{[2-(methylcarbamoyl)phenyl]amino}-5-(trifluoromethyl)-pyrimidin-2-yl]amino}phenyl)methyl]phosphonate The title product was prepared according to the procedure for Example 102 2-{[2-chloro-5-(trifluoromethyl)pyrimidin-4-yl]amino}-N-methylbenzamide (Compound 104A, 40.0 mg, 0.12 mmol) and diethyl[(4-aminophenyl)(difluoro)methyl]-phosphonate (Compound 188A, 40.5 mg, 0.15 mmol). The crude product was purified by silica gel chromatography (5% 7 N NH$_3$ in MeOH in DCM) to afford the desired product as a white solid (4.1 mg, yield: 6%). $^1$H NMR (CD$_3$OD, 400 MHz): δ=1.32 (t, J=7.2 Hz, 6H), 2.90 (s, 3H), 4.14-4.25 (m, 4H), 7.22 (t, J=8.4 Hz, 1H), 7.45 (d, J=8.4 Hz, 2H), 7.51 (dt, J=1.2, 7.2 Hz, 1H), 7.66 (dd, J=1.2, 7.6 Hz, 1H), 7.79 (d, J=8.8 Hz, 2), 8.39 (s, 1H), 8.47 (d, J=8.4 Hz, 1H). MS (ES$^+$): m/z 574.12 [MH$^+$]. HPLC: $t_R$=4.13 min (OpenLynx, polar_5 min).

Compound 188A: Diethyl[(4-aminophenyl)(difluoro)methyl]-phosphonate

Diethyl[(4-nitrophenyl)(difluoro)methyl]phosphonate (Compound 188B, 267 mg) was hydrogenated in the presence of 10% Pd/C (30 mg) in MeOH (10 mL) under 1 atmosphere for 4 h. The catalyst was filtered off, the filtrate was concentrated, and the residue was purified by silica gel chromatography (2% MeOH in DCM) to afford 201 mg of the desired product (yield: 83%). $^1$H NMR (CDCl$_3$, 400 MHz): δ=1.35 (t, J=7.6 Hz, 6H), 4.08 (s, br, 2), 4.31 (q, J=7.6 Hz, 4H), 6.64 (d, J=8.8 Hz, 2H), 7.86 (d, J=8.0 Hz, 2H).

Compound 188B: Diethyl[(4-nitrophenyl)(difluoro)methyl]phosphonate

Under N$_2$, a mixture of bromodifluoromethyl diethylphosphonate (0.427 g, 1.6 mmol) and Cd powder (180 mg, 1.6 mmol) in DMF (0.5 mL) was stirred at room temperature for 2 h. Most of Cd disappeared. 4-Iodo-1-nitrobenzene (249 mg, 1.00 mmol) and CuCl (115 mg, 1.16 mmol) were then added. The mixture was again stirred at room temperature for 3 h.

Ether (20 mL) was added to the reaction mixture and the precipitated solids were filtered off and washed with 10 mL of ether. The combined ether layers were washed with NH$_4$Cl (aq), dried over MgSO$_4$, and evaporated to give the title product (267 mg, yield: 86%). $^1$H NMR (CD$_3$OD, 400 MHz): δ=1.33 (t, J=7.2 Hz, 6H), 4.20-4.28 (m, 4H), 7.86 (d, J=8.4 Hz, 2H), 8.39 (d, J=8.4 Hz, 2H). MS (ES$^+$): m/z 310.06 [MH$^+$]. HPLC: t$_R$=3.92 min (ZQ3, polar_5 min).

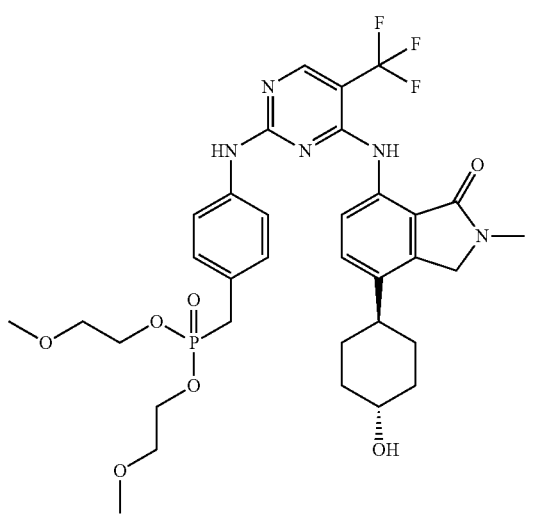

Example 189

Bis(2-methoxyethyl)(4-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}benzyl)phosphonate The title product was prepared according to the procedure for Example 102 using bis(2-methoxyethyl)(4-{[4-chloro-5-(trifluoromethyl)pyrimidin-2-yl]amino}benzyl)phosphonate (Compound 189A, 39.5 mg, 0.0816 mmol) and 7-amino-4-(4-hydroxycyclohexyl)-2-methyl-2,3-dihydro-1H-isoindol-1-one (24.7 mg, 0.0949 mmol). The reaction mixture concentrated and purified by MDP [under basic conditions; ammonium bicarbonate basic buffer (pH 9)]. The title compound was obtained as a white solid, 36.2 mg (61%). $^1$H NMR (400 MHz, DMSO-d$_6$) δ 10.58 (br s, 1H), 9.89 (s, 1H), 8.46 (s, 1H), 8.65 (br s, 1H), 7.57 (br s, 2H), 7.38 (d, J=8.8 Hz, 1H), 7.26 (dd, J=8.6, 2.0 Hz, 2H), 4.56-4.65 (m, 1H), 4.52 (s, 2H), 3.94-4.09 (m, 4H), 3.49-3.55 (m, 1H), 3.44-3.49 (m, 4H), 3.27 (d, J=13.4 Hz, 2H), 3.24 (s, 6H), 3.08 (s, 3H), 1.93 (d, J=9.9 Hz, 2H), 1.70-1.80 (m, 2H), 1.47-1.66 (m, 2H), 1.22-1.38 (m, 2H). MS (ES$^+$): m/z 708.26 (100) [MH$^+$]. HPLC: t$_R$=3.61 min (ZQ3, polar_5 min).

Compound 189A: Bis(2-methoxyethyl)(4-{[4-chloro-5-(trifluoromethyl)pyrimidin-2-yl]amino}benzyl) phosphonate The title compound was prepared according to the procedure for diethyl(4-{[4-chloro-5-(trifluoromethyl)pyrimidin-2-yl]amino}benzyl)phosphonate using Bis(2-methoxyethyl)(4-aminobenzyl)phosphonate (Compound 185A) and 2,4-dichloro-5-trifluoromethyl pyrimidine. The crude product was purified by MDP (ammonium bicarbonate basic buffer pH 9). $^1$H NMR (400 MHz, DMSO-d$_6$) δ ppm 10.65 (s, 1H), 8.80 (s, 1H), 7.61 (d, J=8.1 Hz, 2H), 7.26 (dd, J=8.7, 2.4 Hz, 2H), 3.95-4.06 (m, 4H), 3.46 (dd, J=5.4, 3.9 Hz, 4H), 3.17-3.29 (m, 8H). MS (ES$^+$): m/z 484.07/486.09 (100/95) [MH$^+$]. HPLC: t$_R$=1.43 min (TOF, polar_3 min).

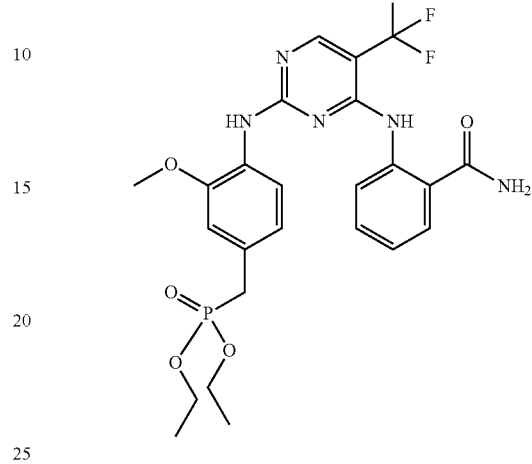

Example 190

Diethyl[4-({4-[(2-carbamoylphenyl)amino]-5-(trifluoromethyl)pyrimidin-2-yl}amino)-3-methoxybenzyl]phosphonate The title compound was prepared according to the procedure for Example 102 using diethyl (4-{[4-chloro-5-(trifluoromethyl)pyrimidin-2-yl]amino}-3-methoxybenzyl)phosphonate and the commercially available 2-aminobenzamide. $^1$H NMR (400 MHz, DMSO-d6) δ 1.19 (t, J=7.07 Hz, 6H), 3.25 (d, J=21.50 Hz, 2H), 3.76 (s, 3H), 3.93-4.03 (m, 4H), 6.85 (dt, J=8.08, 2.15 Hz, 1H), 7.02 (s, 1H), 7.06 (t, J=7.83 Hz, 1H), 7.38 (t, J=8.21 Hz, 1H), 7.52 (d, J=8.34 Hz, 1H), 7.75 (dd, J=7.96, 1.39 Hz, 1H), 7.77 (br. s., 1H), 8.27 (br. s., 1H), 8.36 (s, 1H), 8.47 (br. s., 1H), 8.80 (s, 1H), 11.82 (s, 1H). MS (ES$^+$): m/z 406.04 (100) [MH$^+$]. HPLC: t$_R$=4.01 min (ZQ3, polar_5 min).

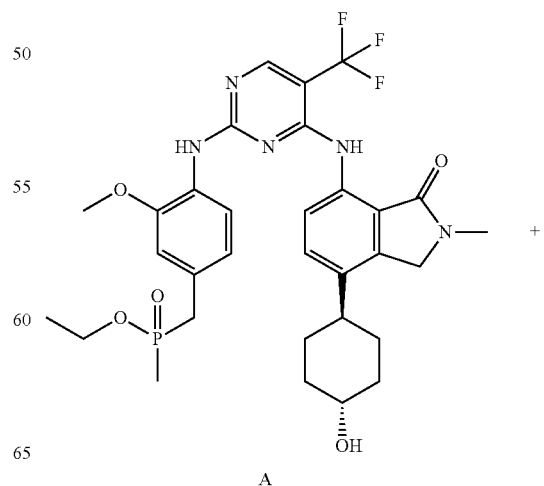

A

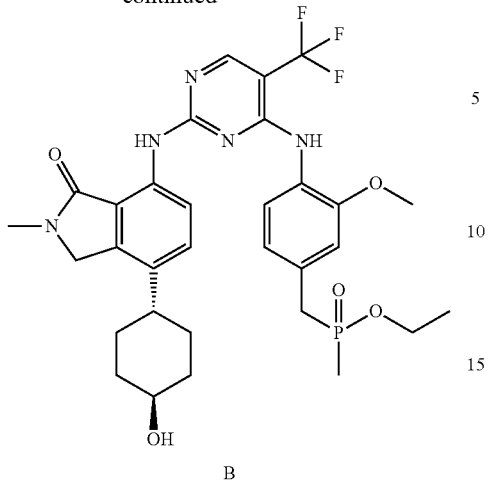

B

Example 191

(A) Ethyl(4-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}-3-methoxybenzyl)methylphosphinate and Compound 192: (B) Ethyl(4-{[2-{[7-(trans-4-hydroxycyclohexyl)-2-methyl-3-oxo-2,3-dihydro-1H-isoindol-4-yl]amino}-5-(trifluoromethyl)pyrimidin-4-yl]amino}-3-methoxybenzyl)methylphosphinate The title compounds were prepared according to the procedure for Example 102 using ethyl (4-{[4-chloro-5-(trifluoromethyl)pyrimidin-2-yl]amino}-3-methoxybenzyl)methylphosphinate (0.120 g, 0.283 mmol) and 7-amino-4-(trans-4-hydroxycyclohexyl)-2-methyl-2,3-dihydro-1H-isoindol-1-one (0.0811 g, 0.312 mmol). The reaction mixture was purified my MDP and the pure fractions were combined, neutralized with 1M NaOH and extracted with EtOAc (3x). The combined organic layers were washed with brine, dried of sodium sulfate, and concentrated to afford the title compounds. Example 191 (A) eluted first: $^1$H NMR (400 MHz, DMSO-$d_6$) δ 10.55 (s, 1H), 9.05 (br. s., 1H), 8.37 (s, 1H), 7.25 (d, J=7.58 Hz, 1H), 7.07 (s, 1H), 6.91 (d, J=8.08 Hz, 1H), 4.60 (d, J=4.29 Hz, 1H), 4.49 (s, 2H), 4.01 (dq, J=7.07, 7.24 Hz, 2H), 3.75 (s, 3H), 3.43-3.56 (m, 1H), 3.06 (s, 3H), 1.92 (d, J=9.60 Hz, 2H), 1.71 (d, J=10.61 Hz, 2H), 1.57 (q, J=13.05 Hz, 2H), 1.36 (d, J=13.89 Hz, 3H), 1.23 (t, J=7.07 Hz, 3H); MS (ES$^+$): m/z: 648.32 [MH$^+$]. HPLC: $t_R$=3.64 min (ZQ3: polar_5 min). Compound 192 (B) eluted second: $^1$H NMR (400 MHz, DMSO-$d_6$) δ 10.21 (s, 1H), 8.37 (s, 1H), 7.20 (d, J=8.34 Hz, 1H), 7.12 (s, 1H), 6.93-7.01 (m, 1H), 4.60 (d, J=4.55 Hz, 1H), 4.45 (s, 2H), 4.03 (dq, J=7.07, 7.33 Hz, 2H), 3.72 (s, 3H), 3.42-3.54 (m, 1H), 3.28 (d, J=4.04 Hz, 1H), 3.05 (s, 3H), 2.41 (t, J=11.87 Hz, 1H), 1.92 (d, J=10.11 Hz, 2H), 1.64-1.73 (m, 2H), 1.56 (q, J=12.72 Hz, 2H), 1.38 (d, J=13.89 Hz, 3H); MS (ES$^+$): m/z: 648.31 [MH$^+$]. HPLC: $t_R$=3.80 min (Micromass ZQ3: polar_5 min).

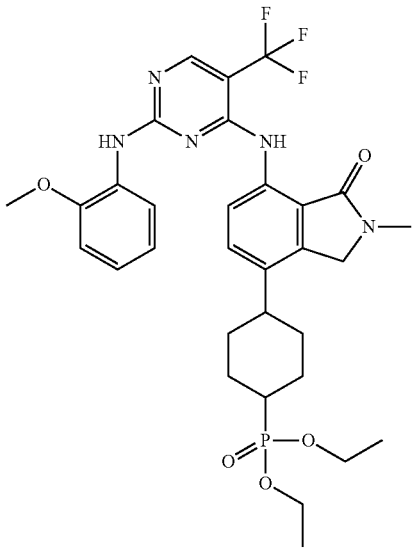

Example 193

Diethyl{4-[7-({2-[(2-methoxyphenyl)amino]-5-(trifluoromethyl)pyrimidin-4-yl}amino)-2-methyl-1-oxo-2,3-dihydro-1H-isoindol-4-yl]cyclohexyl}phosphonate The title compound was prepared according to the procedure for Example 102 using 4-chloro-N-(2-methoxyphenyl)-5-(trifluoromethyl)pyrimidin-2-amine (7.2 mg, 0.024 mmol) and diethyl [4-(7-amino-2-methyl-1-oxo-2,3-dihydro-1H-isoindol-4-yl)cyclohexyl]phosphonate (Compound 193A, 9.0 mg, 0.024 mmol). The reaction mixture was purified by MDP (basic buffer) to give a white solid. The material was further purified by silica gel chromatography (ISCO Combi-flash system, eluting with 0-8% MeOH/DCM), affording the title compound as a white solid, 5 mg. (4:1 mixture, cis and trans unassigned). $^1$H NMR (CDCl$_3$): 1.40 (t, J=7.1 Hz, 6H), 1.11 (t, J=7.6 Hz, 3H), 1.70-1.84 (m, 4H), 2.09-2.28 (m, 5H), 2.58 (m, 1H), 3.23 (s, 3H), 3.94, 3.95 (2xs, 3H), 4.14-4.23 (m, 4H), 4.39, 4.43 (2xs, 2H), 6.95-7.02 (m, 2H), 7.10 (m, 1H), 7.35 (d, J=8.6 Hz, 1H), 7.93 (m, 1H), 8.26 (m, 1H), 8.38 (s, 1H), 8.58 (d, J=8.3 Hz, 1H), 10.64 (s, 1H). MS (ES+): m/z=648.33 [MH$^+$]. HPLC: $t_R$=4.53 min (ZQ3, polar_5 min).

Compound 193A: Diethyl[4-(7-amino-2-methyl-1-oxo-2,3-dihydro-1H-isoindol-yl)cyclohexyl]phosphonate A mixture of added diethyl[4-(2-methyl-7-nitro-1-oxo-2,3-dihydro-1H-isoindol-4-yl)cyclohexa-1,3-dien-1-yl]phosphonate (Compound 193B) and 10% Pd—C (40 mg) in EtOH (10 mL) was stirred under 1 atmosphere of hydrogen at rt overnight. The catalyst was removed by filtration through a pad of celite. The solvent was evaporated under reduced pressure and the residue was purified by silica gel chromatography (ISCO Combi-flash system), affording a mixture of desired product and the partially reduced by-product (10 mg). This mixture was used in next step without further purification. MS (ES+): m/z=381.16 [MH$^+$]. HPLC: $t_R$=3.38 min (ZQ3, polar_5 min).

Compound 193B: Diethyl[4-(2-methyl-7-nitro-1-oxo-2,3-dihydro-1H-isoindol-4-yl)cyclohexa-1,3-dien-1-yl]phosphonate To a solution of diethyl[1-hydroxy-4-(2-methyl-7-nitro-1-oxo-2,3-dihydro-1H-isoindol-4-yl)cyclohex-3-en-1-yl]phosphonate (Compound 193C, 42 mg, 0.099 mmol) in PhMe (2 mL) and DCM (2 mL) was added phosphorus pentachloride (21 mg, 0.099 mmol). The mixture was stirred at rt for 2 h, after which, another 1 eq. of PCl$_5$ was added, and the mixture was stirred at rt for 3 h. The mixture was diluted with DCM (30 mL), washed with sat. aq. NaHCO$_3$ (10 mL), brine (10 mL), and dried over anhydrous sodium sulfate. Evaporation afforded the diene, which was used in the next step without further purification. MS (ES+): m/z=407.08 [MH$^+$]. HPLC: t$_R$=3.44 min (ZQ3, polar_5 min).

Compound 193C: diethyl[1-hydroxy-4-(2-methyl-7-nitro-1-oxo-2,3-dihydro-1H-isoindol-4-yl)cyclohex-3-en-1-yl]phosphonate 2-methyl-7-nitro-4-(4-oxocyclohex-1-en-1-yl)-2,3-dihydro-1H-isoindol-1-one (Compound 193D) was dissolved in DCM (10 mL), then triethyl phosphite (520 mg, 3.1 mmol) and 1N HCl/Et$_2$O (3.1 mmol, 3.1 mL) were added at 0° C. under nitrogen. The resulting mixture was slowly warmed to rt and stirred at rt overnight. The solvent was evaporated, and the residue was purified by silica gel chromatography (ISCO Combi-flash system, eluting with 0-10% MeOH/DCM) to give the title compound as a yellow solid, 470 mg, 71% yield (over two steps). $^1$H NMR (CDCl$_3$): 1.39 (t, J=7.1 Hz, 6H), 2.02 (m, 1H), 2.20 (m, 1H), 2.30-2.47 (m, 2H), 2.65-2.83 (m, 2H), 3.20 (s, 3H), 4.21-4.29 (m, 4H), 4.42, 4.48 (AB, J$_{AB}$=18.0 Hz, 2H), 5.86 (m, 1H), 7.48 (d, J=8.3 Hz, 1H), 7.71 (d, J=7.3 Hz, 1H). MS (ES+): m/z=425.12 [MH$^+$]. HPLC: t$_R$=3.19 min (ZQ3, polar_5 min).

Compound 193D: 2-methyl-7-nitro-4-(4-oxocyclohex-1-en-1-yl)-2,3-dihydro-1H-isoindol-1-one 4-(1,4-dioxaspiro[4.5]dec-7-en-8-yl)-2-methyl-7-nitro-2,3-dihydro-1H-isoindol-1-one (Compound 193E, 515 mg, 1.56 mmol) was dissolved in THF (10 mL) and aq. 3N HCl (3 mL). The resulting mixture was stirred at rt for 4 h. The mixture was diluted with EtOAc (40 mL), washed with brine (2×10 mL), and dried over anhydrous sodium sulfate. Evaporation afforded a yellow oil, which was used to next step without further purification. MS (ES+): m/z=287.10 [MH$^+$]. HPLC: t$_R$=3.13 min (ZQ3, polar_5 min).

Compound 193E: 4-(1,4-dioxaspiro[4.5]dec-7-en-8-yl)-2-methyl-7-nitro-2,3-dihydro-1H-isoindol-1-one The title product was prepared according to the procedure for 7-amino-4-(1,4-dioxaspiro[4,5]dec-7-ene-8-yl-2-methyl-2,3-dihydro-1H-isoindol-1-one using 4-bromo-2-methyl-7-nitro-2,3-dihydro-1H-isoindol-1-one and 1,4-dioxaspiro[4,5]dec-7-ene-8-boronic acid pinacol ester.

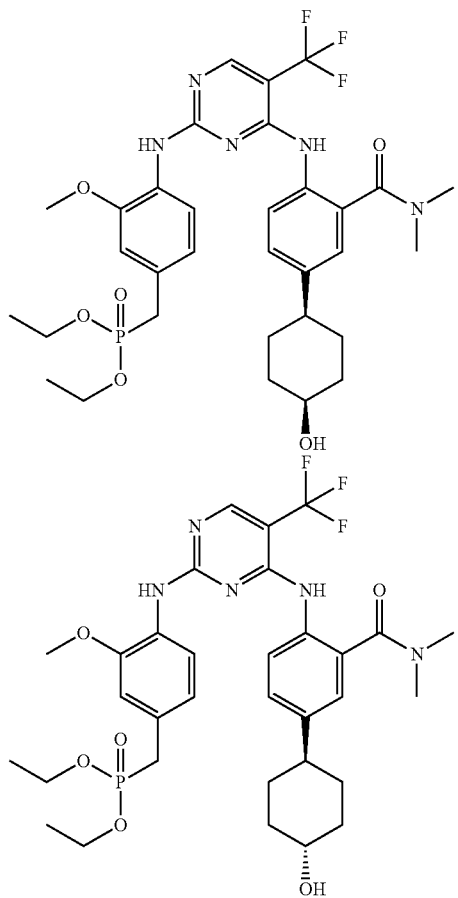

Example 194

(A) Diethyl(4-{[4-{[2-(dimethylcarbamoyl)-4-(cis-4-hydroxycyclohexyl)phenyl]amino}-5-(trifluoromethyl)pyrimidin-2-yl]amino}-3-methoxybenzyl) phosphonate and Example 195

(B) diethyl(4-{[4-{[2-(dimethylcarbamoyl)-4-(trans-4-hydroxycyclohexyl)phenyl]amino}-5-(trifluoromethyl) pyrimidin-2-yl]amino}-3-methoxybenzyl) phosphonate The title compounds were prepared according to the procedure for Example 102 using diethyl (4-{[4-chloro-5-(trifluoromethyl)pyrimidin-2-yl]amino}-3-methoxybenzyl) phosphonate (0.20 g, 0.45 mmol) and 2-amino-5-(4-hydroxycyclohexyl)-N,N-dimethylbenzamide (Compound 173A, 0.130 g, 0.496 mmol). The reaction mixture was partitioned between EtOAc and water and separated. The aqueous was extracted with EtOAc (3×) and the combined organic fractions were washed with brine, dried over sodium sulfate, filtered, and concentrated. The compound was purified on an Isco Combiflash unit eluting with 0 to 5% MeOH in DCM to afford the individual trans and cis isomers. Cis: $^1$H NMR (400 MHz, DMSO-d$_6$) δ 8.85 (s, 1H), 8.43 (s, 1H), 8.32 (s, 1H), 7.86 (d, J=8.34 Hz, 1H), 7.60 (d, J=7.83 Hz, 1H), 7.26 (dd, J=1.77, 8.59 Hz, 1H), 7.22 (d, J=2.02 Hz, 1H), 6.96 (t, J=1.89 Hz, 1H), 6.73 (d, J=7.83 Hz, 1H), 3.92-4.01 (m, 4H), 3.89 (br. s., 1H), 3.77 (s, 3H), 3.13-3.23 (m, 2H), 2.91 (d, J=15.16 Hz, 6H), 2.56 (t, J=11.87 Hz, 1H), 1.79-1.92 (m, 2H), 1.70-1.78 (m, 2H), 1.49-1.61 (m, 4H), 1.18 (t, J=7.07 Hz, 6H); MS (ES⁺): m/z: 681.2723 [MH⁺]. HPLC: $t_R$=1.45 min (UPLC TOF MS: polar_3 min). Trans: ¹H NMR (400 MHz, DMSO-d₆) δ 8.84 (s, 1H), 8.44 (s, 1H), 8.32 (s, 1H), 7.85 (d, J=8.84 Hz, 1H), 7.58 (d, J=8.08 Hz, 1H), 7.26 (dd, J=2.02, 8.34 Hz, 1H), 7.22 (d, J=2.02 Hz, 1H), 6.96 (s, 1H), 6.73 (d, J=7.83 Hz, 1H), 4.57 (d, J=4.55 Hz, 1H), 3.91-4.01 (m, 4H), 3.76 (s, 3H), 3.40-3.54 (m, 1H), 3.14-3.23 (m, 2H), 2.91 (d, J=18.95 Hz, 6H), 1.93 (d, J=9.35 Hz, 2H), 1.79 (d, J=12.38 Hz, 2H), 1.45-1.58 (m, 2H), 1.22-1.35 (m, 2H), 1.19 (t, J=7.07 Hz, 6H); MS (ES⁺): m/z: 680.2332 [MH⁺]. HPLC: $t_R$=1.40 min (UPLC TOF MS: polar_3 min).

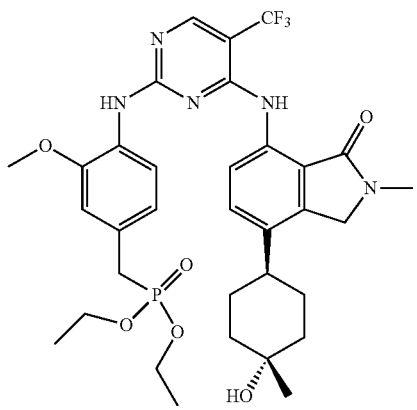

Example 196

Diethyl(4-{[4-{[7-(trans-4-hydroxy-4-methylcyclohexyl)-2-methyl-3-oxo-2,3-dihydro-1H-isoindol-4-yl]amino}-5-(trifluoromethyl)pyrimidin-2-yl]amino}-3-methoxybenzyl)phosphonate The title product was prepared according to the procedure for Example 102 using diethyl(4-{[4-chloro-5-(trifluoromethyl)pyrimidin-2-yl]amino}-3-methoxybenzyl)phosphonate and 7-amino-4-(trans-4-hydroxy-4-methylcyclohexyl)-2-methyl-2,3-dihydro-1H-isoindol-1-one (Compound 183B). ¹H NMR (DMSO-d6, 400 MHz): δ=1.16-1.20 (m, 6H), 1.27 (s, 3H), 1.46-1.57 (m, 2H), 1.64 (br. s., 6H), 2.46 (br. s., 1H), 3.07 (s, 3H), 3.25-3.34 (m, 2H), 3.74 (s, 3H), 3.94-4.03 (m, 4H), 4.49 (s, 2H), 6.94 (d, J=7.83 Hz, 1H), 7.08 (s, 1H), 7.37 (d, J=8.59 Hz, 1H), 8.38 (s, 1H), 9.10 (br. s., 1H), 10.60 (s, 1H). MS (ES⁺): m/z 692.29 [MH⁺] (TOF, polar).

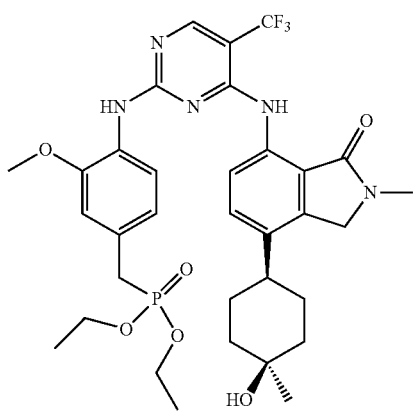

Example 197

Diethyl(4-{[4-{[7-(cis-4-hydroxy-4-methylcyclohexyl)-2-methyl-3-oxo-2,3-dihydro-1H-isoindol-4-yl]amino}-5-(trifluoromethyl)pyrimidin-2-yl]amino}-3-methoxybenzyl)phosphonate The title product was prepared according to the procedure for Example 102 using diethyl(4-{[4-chloro-5-(trifluoromethyl)pyrimidin-2-yl]amino}-3-methoxybenzyl)phosphonate and 7-amino-4-(cis-4-hydroxy-4-methylcyclohexyl)-2-methyl-2,3-dihydro-1H-isoindol-1-one (Compound 183A). ¹H NMR (DMSO-d6, 400 MHz): δ=1.15 (s, 3H), 1.20 (t, J=7.07 Hz, 6H), 1.37-1.55 (m, 4H), 1.64 (d, J=12.13 Hz, 2H), 1.81-1.96 (m, 2H), 2.40-2.48 (m, 1H), 3.07 (s, 3H), 3.23-3.34 (m, 2H), 3.76 (s, 3H), 3.96-4.06 (m, 4H), 4.49 (s, 2H), 6.92 (d, J=8.08 Hz, 1H), 7.07 (s, 1H), 7.31 (d, J=7.83 Hz, 1H), 8.38 (s, 1H), 9.06 (br. s., 1H), 10.58 (s, 1H). MS (ES⁺): m/z 692.29 [MH⁺] (TOF, polar).

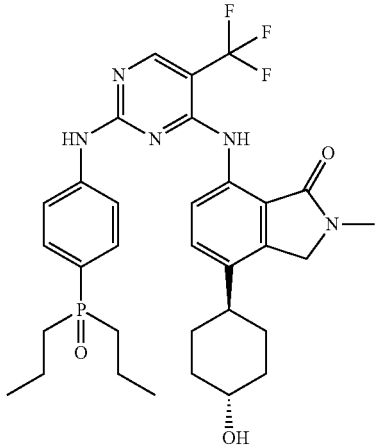 [SMILES: CCCP(=O)(CCC)c1ccc(Nc2ncc(C(F)(F)F)c(Nc3ccc([C@H]4CC[C@H](O)CC4)c4c3C(=O)N(C)C4)n2)cc1]

Example 198

7-{[2-{[4-(Dipropylphosphoryl)phenyl]amino}-5-(trifluoromethyl)pyrimidin-4-yl]amino}-4-(trans-4-hydroxycyclohexyl)-2-methyl-2,3-dihydro-1H-isoindol-1-one The title compound was prepared according to the procedure for Example 102 using 4-chloro-N-[4-(dipropylphosphoryl)phenyl]-5-(trifluoromethyl)pyrimidin-2-amine Compound 198A, (75.0 mg, 0.185 mmol) and 7-amino-4-(trans-4-hydroxycyclohexyl)-2-methyl-2,3-dihydro-1H-isoindol-1-one (48.1 mg, 0.185 mmol). The reaction mixture was concentrated in vacuo purified on an ISCO Combiflash unit (0-5% MeOH/DCM) to isolate the desired product as 66 mg of a white solid. ¹H NMR (400 MHz, DMSO-d6) d 0.93 (t, J=7.33 Hz, 6H), 1.24-1.40 (m, 4H), 1.42-1.58 (m, 4H), 1.79 (d, J=12.88 Hz, 2H), 1.82-1.89 (m, 2H), 1.89-1.98 (m, 4H), 3.08 (s, 3H), 3.42-3.54 (m, 1H), 4.54 (s, 2H), 4.64 (br. s., 1H), 7.26 (br. s., 1H), 7.63-7.72 (m, 2H), 7.79 (d, J=6.57 Hz, 2H), 8.52 (s, 1H), 8.62 (br. s., 1H), 10.14 (s, 1H), 10.59 (br. s., 1H). MS (ES+): m/z=630.27 [MH+]. HPLC: $t_R$=3.17 min (ZQ3, polar_5 min)

Compound 198A: 4-chloro-N-[4-(dipropylphosphoryl)phenyl]-5-(trifluoromethyl)pyrimidin-2-amine The title compound was prepared according to the procedure for diethyl(4-{[4-chloro-5-(trifluoromethyl)pyrimidin-2-yl]amino}benzyl)phosphonate using 2,4-Dichloro-5-trifluoromethylpyrimidine (101.6 mg, 0.4681 mmol) and 4-(dipropylphosphoryl)aniline (Compound 198B: 116 mg, 0.515 mmol). This was purified on an ISCO Combiflash unit (0-5% MeOH/DCM) to isolate 75 mg of the desired product as a white solid. $^1$H NMR (400 MHz, DMSO-d6) δ ppm 0.90 (t, J=7.3 Hz, 6H), 1.30 (br. s., 2H), 1.46 (br. s., 2H), 1.76-2.00 (m, 4H), 7.69 (dd, J=10.1, 8.6 Hz, 2H), 7.84 (dd, J=8.7, 1.9 Hz, 2H), 8.87 (s, 1H), 10.89 (s, 1H). MS (ES+): m/z=406.04 (100) 408.01 (35) [MH+]. HPLC: $t_R$=4.01 min (ZQ3, polar_5 min)

Compound 198B: 4-(diethylphosphoryl)aniline

The title compound was prepared according to the procedures leading to 3-(dipropylphosphoryl)aniline (Compound 168C) starting with the commercially available diethyl phosphine oxide and 4-iodonitrobenzene. $^1$H NMR (400 MHz, CHLOROFORM-d) δ 7.47 (dd, J=8.46, 10.48 Hz, 2H), 6.74 (dd, J=2.27, 8.59 Hz, 2H), 3.97 (br. s., 2H), 1.76-2.02 (m, 4H), 1.11 (td, J=7.71, 16.67 Hz, 6H); MS (ES+): m/z: 198.0939 [MH+]. HPLC: tR=0.83 min (UPLC TOF MS: polar_3 min).

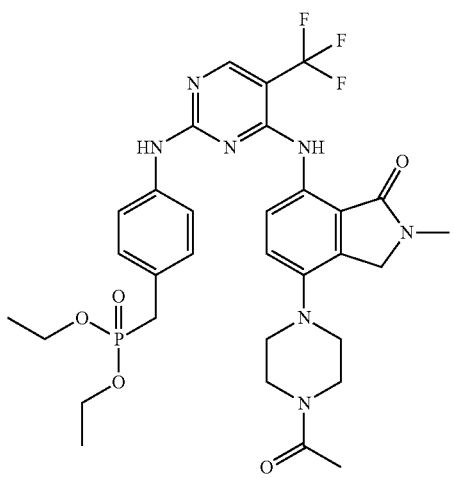 [SMILES: CCOP(=O)(Cc1ccc(Nc2ncc(C(F)(F)F)c(Nc3ccc(N4CCN(C(C)=O)CC4)c4c3C(=O)N(C)C4)n2)cc1)OCC]

Example 199

Diethyl(4-{[4-{[7-(4-acetylpiperazin-1-yl)-2-methyl-3-oxo-2,3-dihydro-1H-isoindol-4-yl]amino}-5-(trifluoromethyl)pyrimidin-2-yl]amino}benzyl)phosphonate A mixture of Diethyl[4-({4-[(7-bromo-2-methyl-3-oxo-2,3-dihydro-1H-isoindol-4-yl)amino]-5-(trifluoromethyl)pyrimidin-2-yl}amino)benzyl]phosphonate (50.0 mg, 0.0796 mmol), 1-acetylpiperazine (0.510 g, 3.98 mmol), bis(dibenzylideneacetone)palladium(0) (9.15 mg, 0.0159 mmol), and Cs$_2$CO$_3$ (77.8 mg, 0.239 mmol) in 1,4-dioxane (5 mL) was evacuated and purged with N$_2$ three times and stirred at 100° C. overnight. The crude mixture was passed through a Thiol-SPE cartridge to remove Pd and subsequently purified by MDP to isolate the title compound (10.5 mg, 20% yield). $^1$H NMR (400 MHz, CD$_3$OD) δ=1.28 (t, J=7.1 Hz, 6H), 2.17 (s, 3H), 3.04-3.10 (m, 2H), 3.11-3.15 (m, 2H), 3.19 (s, 3H), 3.23 (d, J=21.5 Hz, 2H), 3.68-3.73 (m, 2H), 3.73-3.79 (m, 2H), 4.02-4.14 (m, 4H), 4.54 (s, 2H), 7.15 (d, J=8.8 Hz, 1H), 7.38 (dd, J=8.6, 2.5 Hz, 2H), 7.53 (d, J=8.1 Hz, 2H), 8.34 (s, 1H), 8.52 (br. s., 1H).

MS (ES+): m/z 676.35 (100) [MH+]; HPLC: tR=0.97 min (UPLC, purity).

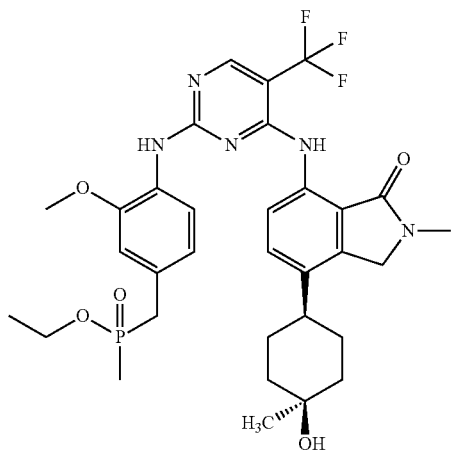 [SMILES: CCOP(C)(=O)Cc1ccc(Nc2ncc(C(F)(F)F)c(Nc3ccc([C@H]4CC[C@@](C)(O)CC4)c4c3C(=O)N(C)C4)n2)c(OC)c1]

Example 200

Ethyl(4-{[4-{[7-(cis-4-hydroxy-4-methylcyclohexyl)-2-methyl-3-oxo-2,3-dihydro-1H-isoindol-4-yl]amino}-5-(trifluoromethyl)pyrimidin-2-yl]amino}-3-methoxybenzyl)methylphosphinate A solution of ethyl(4-{[4-chloro-5-(trifluoromethyl)pyrimidin-2-yl]amino}-3-methoxybenzyl)methylphosphinate (44.8 mg, 0.106 mmol) and 7-amino-4-(cis-4-hydroxy-4-methylcyclohexyl)-2-methyl-2,3-dihydro-1H-isoindol-1-one (Compound 183A, 29.0 mg, 0.106 mmol) in a sealable microwave tube was treated with TFA (24.4 uL, 0.317 mmol), sealed and irradiated on the CEM for 15 minutes at 95° C. The reaction mixture was poured into water and extracted twice with EtOAc. The combined organic layers were washed with brine, dried over Na$_2$SO$_4$, filtered and concentrated. The crude material was purified on an ISCO Combiflash unit (0-5% MeOH/DCM) to give ~20 mg of a material that is a 3.5:1 mixture of regioisomers. This material was boiled/hot triturated in EtOAc to isolate the major regioisomer (presumed to be the cis regioisomer). $^1$H NMR (400 MHz, DMSO-d6) δ 10.55 (br. s., 1H), 9.04 (br. s., 1H), 8.37 (s, 1H), 7.44 (br. s., 1H), 7.29 (d, J=7.33 Hz, 1H), 7.06 (br. s., 1H), 6.92 (d, J=7.70 Hz, 1H), 4.47 (s, 2H), 4.25 (br. s., 1H), 4.00 (td, J=7.33, 14.66 Hz, 2H), 3.74 (s, 3H), 3.25 (d, J=17.96 Hz, 2H), 3.06 (s, 3H), 2.37-2.47 (m, 1H), 1.80-1.95 (m, 2H), 1.63 (d, J=12.10 Hz, 2H), 1.44-1.53 (m, 2H), 1.40 (d, J=13.56 Hz, 5H), 1.22 (t, J=6.97 Hz, 3H), 1.14 (s, 3H). MS (ES+): m/z=662.27 (100) [MH+]. HPLC: $t_R$=3.39 (ZQ3, nonpolar_5 min)

185

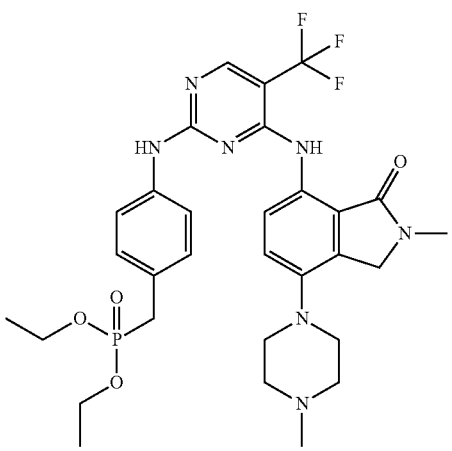 [SMILES: CCOP(=O)(Cc1ccc(Nc2ncc(C(F)(F)F)c(Nc3ccc(N4CCN(C)CC4)c4c3C(=O)N(C)C4)n2)cc1)OCC]

Example 201

Diethyl(4-{[4-{[2-methyl-7-(4-methylpiperazin-1-yl)-3-oxo-2,3-dihydro-1H-isoindol-4-yl]amino}-5-(trifluoromethyl)pyrimidin-2-yl]amino}benzyl)phosphonate The title compound was prepared according to the procedure for Diethyl(4-{[4-{[7-(4-acetylpiperazin-1-yl)-2-methyl-3-oxo-2,3-dihydro-1H-isoindol-4-yl]amino}-5-(trifluoromethyl)pyrimidin-2-yl]amino}benzyl)phosphonate (Example 199) using Diethyl[4-({4-[(7-bromo-2-methyl-3-oxo-2,3-dihydro-1H-isoindol-4-yl)amino]-5-(trifluoromethyl)pyrimidin-2-yl}amino)benzyl]phosphonate and the commerically available N-methylpiperazine. MS (ES+): m/z 648.35 (100) [MH$^+$]; HPLC: $t_R$=0.70 min (UPLC, purity).

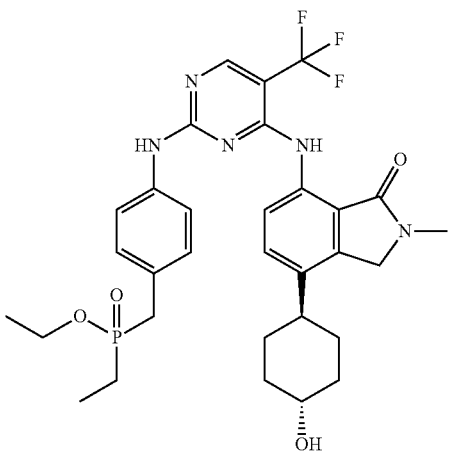 [SMILES: CCOP(=O)(CC)Cc1ccc(Nc2ncc(C(F)(F)F)c(Nc3ccc([C@H]4CC[C@H](O)CC4)c4c3C(=O)N(C)C4)n2)cc1]

Example 202

Ethyl ethyl(4-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}benzyl)phosphinate The title compound was prepared according to the procedure for Example 102 using ethyl(4-{[4-chloro-5-(trifluoromethyl)pyrimidin-2-yl]amino}benzyl)ethylphosphinate (Compound 202A, 0.075 g, 0.18 mmol) and 7-amino-4-(trans-4-hydroxycyclohexyl)-2-methyl-2,3-dihydro-1H-isoindol-1-one (0.0527 g, 0.202 mmol). The compound was purified by MDP to afford the title compound. $^1$H NMR (400 MHz, DMSO-d$_6$) δ 10.58 (br. s., 1H), 9.89 (s, 1H), 8.45 (s, 1H), 7.36 (d, J=8.59 Hz, 1H), 7.26 (d, J=6.57 Hz, 2H), 4.52 (s, 2H), 3.87-4.00 (m, 2H), 3.18 (dd, J=4.55, 16.93 Hz, 2H), 3.08 (s, 3H), 1.93 (d, J=9.35 Hz, 2H), 1.76 (d, J=12.38 Hz, 2H), 1.51-1.68 (m, 4H), 1.23-1.36 (m, 2H), 1.19 (t, J=7.07 Hz, 3H), 1.00 (td, J=7.71, 17.68 Hz, 3H); MS (ES$^+$): m/z: 632.2089 [MH$^+$]. HPLC: $t_R$=1.35 min (UPLC TOF MS: polar_3 min).

Compound 202A: Ethyl(4-{[4-chloro-5-(trifluoromethyl)pyrimidin-2-yl]amino}benzyl)ethylphosphinate The title compound was prepared according to the procedure for diethyl(4-{[4-chloro-5-(trifluoromethyl)pyrimidin-2-yl]amino}benzyl)phosphonate using 2,4-dichloro-5-trifluoromethylpyrimidine (0.150 g, 0.691 mmol) and ethyl(4-aminobenzyl)ethylphosphinate (Compound 202B, 0.173 g, 0.760 mmol). After a standard extractive work-up, the compound was purified on an Isco Combiflash unit eluting with 80 to 100% EtOAc in heptane afford a mixture of the title compound and the regioisomer. MS (ES$^+$): m/z: 410.0876 [MH$^+$]. HPLC: $t_R$=1.46 min (UPLC TOF MS: polar_3 min).

Compound 202B: Ethyl(4-aminobenzyl)ethylphosphinate

A solution of ethyl ethyl(4-nitrobenzyl)phosphinate (Compound 202C, 0.98 g, 3.8 mmol) in MeOH (4 mL) was charged with Palladium 10% wt on activated carbon (0.20 g, 0.19 mmol) and evacuated and purged with hydrogen (3×). The reaction was stirred at rt over night. The reaction mixture was filtered through a pad of celite and the filtrate was concentrated in vacuo to afford 0.848 g, 98% yield, of the title compound. $^1$H NMR (400 MHz, DMSO-d$_6$) δ 6.90 (dd, J=2.15, 8.46 Hz, 2H), 6.48 (d, J=8.08 Hz, 2H), 3.80-3.93 (m, 2H), 2.93 (dd, J=3.66, 16.29 Hz, 2H), 1.17 (t, J=7.07 Hz, 3H), 1.05 (t, J=6.95 Hz, 2H), 0.88-1.00 (m, 4H); MS (ES$^+$): m/z: 229.1305 [MH$^+$]. HPLC: $t_R$=0.83 min (UPLC TOF MS: polar_3 min).

Compound 202C: Ethyl ethyl(4-nitrobenzyl)phosphinate

A solution of dichloroethylphosphine (2.5 g, 19 mmol) in THF (11 mL) was slowly charged with sodium ethoxide (2.86 g, 42.0 mmol) at 0° C. and stirred for 15 min. The reaction mixture was charged with p-nitrobenzylbromide (4.1 g, 19 mmol) in a sealed tube and stirred at 100° C. over night. The reaction mixture was concentrated in vacuo and the residue was purified on an Isco Combiflash unit eluting with 0 to 5% MeOH in DCM to afford the title compound. $^1$H NMR (400 MHz, DMSO-d$_6$) δ 8.19 (d, J=8.34 Hz, 2H), 7.55 (dd, J=2.02, 8.84 Hz, 2H), 3.83-4.04 (m, 2H), 3.41 (d, J=16.93 Hz, 2H), 1.58-1.73 (m, 2H), 1.16 (t, J=7.07 Hz, 3H), 0.94-1.06 (m, 3H).

Example 203

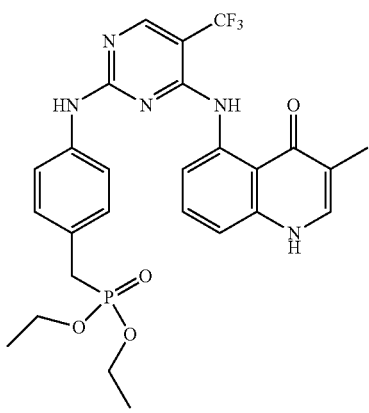 [SMILES: CCOP(=O)(Cc1ccc(Nc2ncc(C(F)(F)F)c(Nc3cccc4[nH]cc(C)c(=O)c34)n2)cc1)OCC]

Diethyl[4-({4-[(3-methyl-4-oxo-1,4-dihydroquinolin-5-yl)amino]-5-(trifluoromethyl)pyrimidin-2-yl}amino)benzyl]phosphonate The title compound was prepared according to the procedure for Example 102 using diethyl(4-{[4-chloro-5-(trifluoromethyl)pyrimidin-2-yl]amino}benzyl)phosphonate and 5-amino-3-methylquinolin-4(1H)-one (Compound 203A). $^1$H NMR (DMSO-d6, 400 MHz): δ=1.18 (t, J=7.07 Hz, 6H), 2.00 (s, 3H), 3.15-3.25 (m, 2H), 3.96 (qd, J=7.37, 7.20 Hz, 4H), 7.16 (d, J=7.83 Hz, 1H), 7.24 (dd, J=8.59, 2.27 Hz, 2H), 7.51 (t, J=7.96 Hz, 1H), 7.61 (d, J=6.82 Hz, 2H), 7.97 (d, J=5.81 Hz, 1H), 8.45 (s, 1H), 8.71 (br. s., 1H), 9.84 (s, 1H), 12.01 (d, J=6.06 Hz, 1H), 14.42 (br. s., 1H). MS (ES$^+$): m/z 562.13 [MH$^+$] (TOF, polar).

Compound 203A:
5-amino-3-methylquinolin-4(1H)-one

The title compound was prepared according to procedure for 2-Amino-5-fluoro-N-methylbenzamide (Compound 102A) using 3-methyl-5-nitroquinolin-4(1H)-one (Eur J Med Chem. 1992, 37, 547-570). $^1$H NMR (DMSO-d6, 400 MHz): δ=1.87 (d, J=0.76 Hz, 3H), 6.21 (dd, J=7.83, 1.01 Hz, 1H), 6.40 (dd, J=8.08, 1.01 Hz, 1H), 7.12 (t, J=8.08 Hz, 1H), 7.62 (dd, J=5.94, 0.88 Hz, 1H), 11.19 (d, J=5.05 Hz, 1H). MS (ES$^+$): m/z 175.07 [MH$^+$] (TOF, polar).

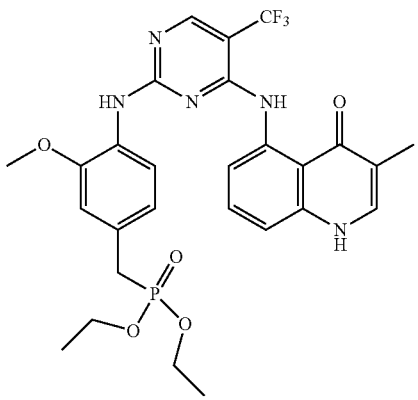

Example 204

Diethyl[3-methoxy-4-({4-[(3-methyl-4-oxo-1,4-dihydroquinolin-5-yl)amino]-5-(trifluoromethyl)pyrimidin-2-yl}amino)benzyl]phosphonate The title compound was prepared according to the procedure for Example 102 using diethyl (4-{[4-chloro-5-(trifluoromethyl)pyrimidin-2-yl]amino}-3-methoxybenzyl)phosphonate and 5-amino-3-methylquinolin-4(1H)-one (Compound 203A). $^1$H NMR (DMSO-d6, 400 MHz): δ=1.20 (t, J=7.07 Hz, 6H), 1.98 (s, 3H), 3.24-3.31 (m, 2H), 3.75 (s, 3H), 3.94-4.04 (m, 4H), 6.90 (d, J=7.83 Hz, 1H), 7.04 (s, 1H), 7.08 (d, J=8.34 Hz, 1H), 7.34-7.44 (m, 1H), 7.50 (d, J=7.83 Hz, 1H), 7.94 (s, 1H), 8.37 (s, 1H), 8.48 (br. s., 1H), 8.91 (s, 1H), 11.86 (br. s., 1H), 14.41 (s, 1H). MS (ES$^+$): m/z 592.14 [MH$^+$] (TOF, polar).

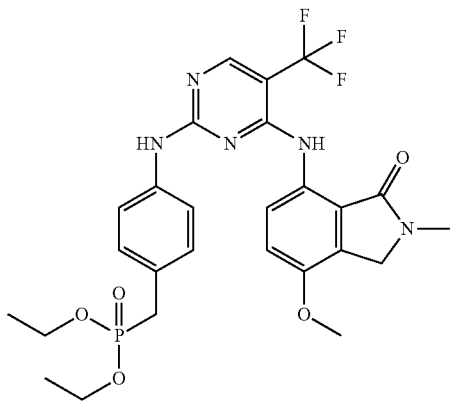 [SMILES: CCOP(=O)(Cc1ccc(Nc2ncc(C(F)(F)F)c(Nc3ccc(OC)c4c3C(=O)N(C)C4)n2)cc1)OCC]

Example 205

Diethyl[4-({4-[(7-methoxy-2-methyl-3-oxo-2,3-dihydro-1H-isoindol-4-yl)amino]-5-(trifluoromethyl)pyrimidin-2-yl}amino)benzyl]phosphonate The title compound was prepared according to the procedure for Example 102 using diethyl (4-{[4-chloro-5-(trifluoromethyl)pyrimidin-2-yl]amino}benzyl)phosphonate and 7-Amino-4-methoxy-2-methyl-2,3-dihydro-1H-isoindol-1-one (Compound 205A). MS (ES+): m/z 581.20 (100) [MH$^+$] HPLC: t$_R$=1.08 min (UPLC, purity).

Compound 205A: 7-Amino-4-methoxy-2-methyl-2,3-dihydro-1H-isoindol-1-one

Pd/C (7.67 mg, 0.0720 mmol) was added to a solution of 4-methoxy-2-methyl-7-nitro-2,3-dihydro-1H-isoindol-1-one in MeOH (2 mL) and EtOAc (2 mL) and the mixture was hydrogenated at stp overnight. The solution was filtered and the title compound was not further purified. MS (ES+): m/z 193.14 (100) [MH$^+$]; HPLC: t$_R$=0.65 min (UPLC, analytical).

Compound 205B: 4-Methoxy-2-methyl-7-nitro-2,3-dihydro-1H-isoindol-1-one

A mixture of 4-Hydroxy-2-methyl-7-nitro-2,3-dihydro-1H-isoindol-1-one (Compound 205C, 50.0 mg, 0.240 mmol), potassium carbonate (49.8 mg, 0.360 mmol) in DMF (2 mL, 20 mmol) was treated with methyl iodide (22.4 µL, 0.360 mmol) and allowed to stir at room temperature overnight. The reaction was poured into EtOAc and washed with water and brine and the crude material was purified using an ISCO Combiflash unit (MeOH in DCM: 0-1%) to obtain the title product as a solid. (27 mg, 50% yield). $^1$H NMR (400 MHz, CD$_3$OD) δ=3.17 (s, 3H), 4.02 (s, 3H), 4.44 (s, 2H), 7.27 (d, J=8.8 Hz, 1H), 7.94 (d, J=8.8 Hz, 1H). MS (ES+): m/z 223.19 (100) [MH$^+$]; HPLC: t$_R$=0.76 min (UPLC, analytical).

Compound 205C: 4-hydroxy-2-methyl-7-nitro-2,3-dihydro-1H-isoindol-1-one

Potassium trifluoro(2-methyl-7-nitro-1-oxo-2,3-dihydro-1H-isoindol-4-yl)borate (Compound 205D, 100.0 mg, 0.3355 mmol) was treated with 9 M hydrogen peroxide in H$_2$O (30 mL, 270 mmol) and 2.0 M of sodium hydroxide in H$_2$O (6 mL, 12 mmol) in 3 portions over 7 days (at RT). The mixture was diluted with EtOAc and water, after which, the water layer was acidifed to pH 1-2. The product precipitated and was collected by filtration. The EtOAc layer was concentrated and found to contain the product as well. The combined product was not further purified. MS (ES+): m/z 209.12 (100) [MH$^+$]; HPLC: t$_R$=0.61 min (UPLC, analytical).

Compound 205D: Potassium trifluoro(2-methyl-7-nitro-1-oxo-2,3-dihydro-1H-isoindol-4-yl)borate To a solution of 2-methyl-7-nitro-4-(4,4,5,5-tetramethyl-[1,3,2]dioxaborolan-2-yl)-2,3-dihydro-isoindol-1-one (Compound 205E, 2.0 g, 6.29 mmol) in methanol (25 mL) was added potassium hydrogen fluoride in water (4.5 M, 9.0 mL, 40.5 mmol). The resulting mixture was stirred for 2 h at room temperature. Solids formed were collected by filtration, washed with hot acetone (25 mL) and dried in air to afford 1.75 g of the title compound (yield: 94%). $^1$H NMR (D$_2$O, 300 MHz): δ=2.94 (s, 3H), 4.30 (s, 2H), 7.50 (m, 2H).

Compound 205E: 2-methyl-7-nitro-4-(4,4,5,5-tetramethyl-[1,3,2]dioxaborolan-2-yl)-2,3-dihydro-isoindol-1-one Pd$_2$(dba)$_3$ (2.02 g, 2.21 mmol) and tricyclohexylphosphine (2.48 g, 8.85 mmol) were stirred for 30 minutes in a nitrogen degassed solution of dioxane (375 mL). To this was added 4-bromo-2-methyl-7-nitro-2,3-dihydro-isoindol-1-one (20.0 g, 73.8 mmol), bis(pinacolato)diboron (24.4 g, 96 mmol) and KOAc (11.58 g, 118.1 mmol) and the mixture was heated to reflux for 6 h. After cooling to RT the precipitated was removed by filtration. The filtrate was evaporated to dryness and the residue was triturated with diisopropyl ether (100 mL) and filtered to give 2-methyl-7-nitro-4-(4,4,5,5-tetramethyl-[1,3,2]dioxaborolan-2-yl)-2,3-dihydro-isoindol-1-one as a yellow solid (16.0 g, 68%). $^1$H NMR (CDCl$_3$, 500 MHz) δ 1.34 (s, 12H), 3.24 (s, 3H), 4.58 (s, 2H), 7.68 (d, J=7.5 Hz, 1H), 8.06 (d, J=7.5 Hz, 1H).

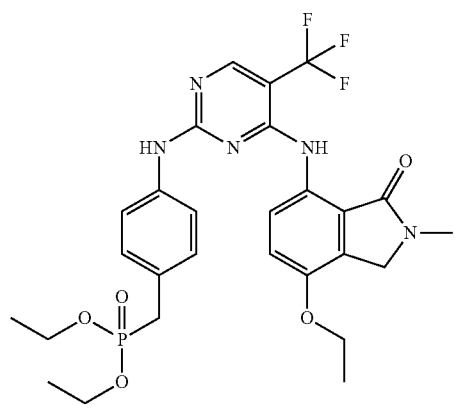 [SMILES: CCOc1ccc(Nc2nc(Nc3ccc(CP(=O)(OCC)OCC)cc3)ncc2C(F)(F)F)c2c1CN(C)C2=O]

Example 206

Diethyl[4-({4-[(7-ethoxy-2-methyl-3-oxo-2,3-dihydro-1H-isoindol-4-yl)amino]-5-(trifluoromethyl)pyrimidin-2-yl}amino)benzyl]phosphonate The title compound was prepared according to the procedure for Example 102 using diethyl (4-{[4-chloro-5-(trifluoromethyl)pyrimidin-2-yl]amino}benzyl)phosphonate and 7-Amino-4-ethoxy-2-methyl-2,3-dihydro-1H-isoindol-1-one (Compound 206A). MS (ES+): m/z 594.25 (100) [MH$^+$]; HPLC: t$_R$=1.14 min (UPLC, purity).

Compound 206A: 7-Amino-4-ethoxy-2-methyl-2,3-dihydro-1H-isoindol-1-one

The title compound was prepare according to the procedure for 7-Amino-4-methoxy-2-methyl-2,3-dihydro-1H-isoindol-1-one (Compound 205A) using 4-Ethoxy-2-methyl-7-nitro-2,3-dihydro-1H-isoindol-1-one (Compound 206B). MS (ES+): m/z 207.16 (100) [MH$^+$]; HPLC: t$_R$=0.78 min (UPLC, analytical).

Compound 206B: 4-Ethoxy-2-methyl-7-nitro-2,3-dihydro-1H-isoindol-1-one

The title compound was prepare according to the procedure for 4-Methoxy-2-methyl-7-nitro-2,3-dihydro-1H-isoindol-1-one (Compound 205B) using 4-Hydroxy-2-methyl-7-nitro-2,3-dihydro-1H-isoindol-1-one and iodoethane (Compound 205C, 28.8 uL, 0.360 mmol). $^1$H NMR (400 MHz, CD$_3$OD) δ=1.47 (t, J=7.1 Hz, 3H), 3.17 (s, 3H), 4.27 (q, J=6.9 Hz, 2H), 4.43 (s, 2H), 7.23 (d, J=8.8 Hz, 1H), 7.90 (d, J=8.8 Hz, 1H). MS (ES+): m/z 251.21 (100) [MH$^+$]; HPLC: t$_R$=1.06 min (UPLC, Analytical).

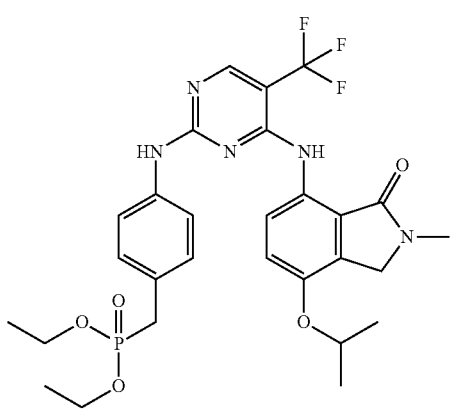 [SMILES: CCOP(=O)(Cc1ccc(Nc2ncc(C(F)(F)F)c(Nc3ccc(OC(C)C)c4c3C(=O)N(C)C4)n2)cc1)OCC]

Example 207

Diethyl(4-{[4-{[2-methyl-3-oxo-7-(propan-2-yloxy)-2,3-dihydro-1H-isoindol-4-yl]amino}-5-(trifluoromethyl)pyrimidin-2-yl]amino}benzyl)phosphonate The title compound was prepared according to the procedure for Example 102 using diethyl (4-{[4-chloro-5-(trifluoromethyl)pyrimidin-2-yl]amino}benzyl)phosphonate and 7-Amino-2-methyl-4-(propan-2-yloxy)-2,3-dihydro-1H-isoindol-1-one (Compound 207A). MS (ES+): m/z 608.27 (100) [MH$^+$]; HPLC: t$_R$=1.18 min (UPLC, purity).

Compound 207A: 7-Amino-2-methyl-4-(propan-2-yloxy)-2,3-dihydro-1H-isoindol-1-one The title compound was prepare according to the procedure for 7-Amino-4-methoxy-2-methyl-2,3-dihydro-1H-isoindol-1-one (Compound 205A) using 2-Methyl-7-nitro-4-(propan-2-yloxy)-2,3-dihydro-1H-isoindol-1-one (Compound 207B). MS (ES+): m/z 222.21 (100) [MH$^+$]; HPLC: t$_R$=0.93 min (UPLC, analytical).

Compound 207B: 2-Methyl-7-nitro-4-(propan-2-yloxy)-2,3-dihydro-1H-isoindol-1-one The title compound was prepare according to the procedure for 4-Methoxy-2-methyl-7-nitro-2,3-dihydro-1H-isoindol-1-one (Compound 205B) using 4-Hydroxy-2-methyl-7-nitro-2,3-dihydro-1H-isoindol-1-one and 4-Hydroxy-2-methyl-7-nitro-2,3-dihydro-1H-isoindol-1-one (Compound 205C, 50.0 mg, 0.240 mmol) and isopropyl iodide. $^1$H NMR (400 MHz, CD$_3$OD) δ=1.40 (d, J=6.1 Hz, 6H), 3.15 (s, 3H), 4.37 (s, 2H), 4.80-4.87 (m, 1H), 7.22 (d, J=8.8 Hz, 1H), 7.86 (d, J=8.8 Hz, 1H). MS (ES+): m/z 237.18 (100) [MH$^+$]; HPLC: t$_R$=0.94 min (UPLC, Analytical).

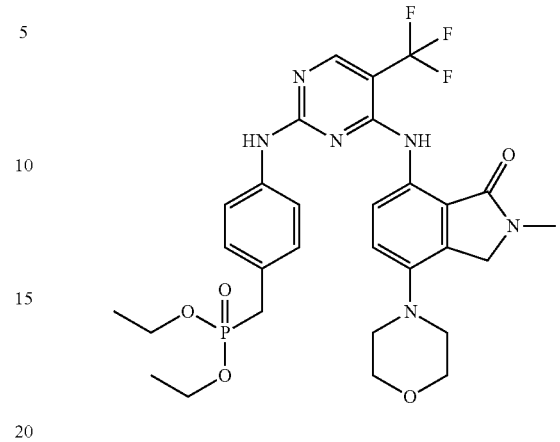

Example 208

Diethyl(4-{[4-{[2-methyl-7-(morpholin-4-yl)-3-oxo-2,3-dihydro-1H-isoindol-4-yl]amino}-5-(trifluoromethyl)pyrimidin-2-yl]amino}benzyl)phosphonate The title compound was prepared according to the procedure for Example 102 using diethyl (4-{[4-chloro-5-(trifluoromethyl)pyrimidin-2-yl]amino}benzyl)phosphonate and 7-Amino-2-methyl-4-(morpholin-4-yl)-2,3-dihydro-1H-isoindol-1-one (Compound 208A). MS (ES+): m/z 636.24 (100) [MH$^+$]; HPLC: t$_R$=1.05 min (UPLC, purity).

Compound 208A: 7-Amino-2-methyl-4-(morpholin-4-yl)-2,3-dihydro-1H-isoindol-1-one The title compound was prepared according to the procedure for 7-Amino-4-methoxy-2-methyl-2,3-dihydro-1H-isoindol-1-one (Compound 205A) using 2-Methyl-4-(morpholin-4-yl)-7-nitro-2,3-dihydro-1H-isoindol-1-one (Compound 208B). MS (ES+): m/z 248.23 (100) [MH$^+$]; HPLC: t$_R$=0.62 min (UPLC, analytical).

Compound 208B: 2-Methyl-4-(morpholin-4-yl)-7-nitro-2,3-dihydro-1H-isoindol-1-one A mixture of 4-Bromo-2-methyl-7-nitro-2,3-dihydro-1H-isoindol-1-one (100.0 mg, 0.3689 mmol), morpholine (321.7 uL, 3.689 mmol), DIPEA (642.6 uL, 3.689 mmol) in DMF (4 mL) were mixed in sealed tube under an atmosphere of argon and heated at 90° C. for 4 days. The crude material was purified by MDP directly under basic conditions the desired product. MS (ES+): m/z 278.24 (100) [MH$^+$]; HPLC: t$_R$=0.81 min (UPLC, analytical).

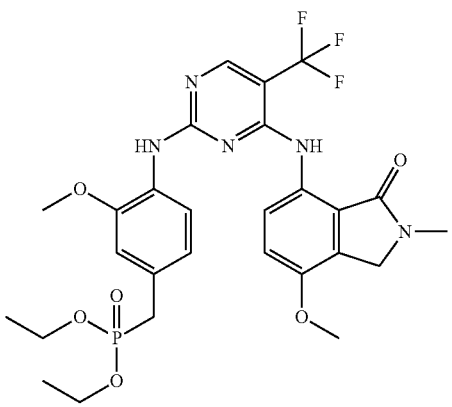 [SMILES: CCOP(=O)(Cc1ccc(Nc2ncc(C(F)(F)F)c(Nc3ccc(OC)c4c3C(=O)N(C)C4)n2)c(OC)c1)OCC]

Example 209

Diethyl[3-methoxy-4-({4-[(7-methoxy-2-methyl-3-oxo-2,3-dihydro-1H-isoindol-4-yl)amino]-5-(trifluoromethyl)pyrimidin-2-yl}amino)benzyl]phosphonate The title compound was prepared according to the procedure for Example 102 using diethyl (4-{[4-chloro-5-(trifluoromethyl)pyrimidin-2-yl]amino}-3-methoxybenzyl)phosphonate and 7-Amino-4-methoxy-2-methyl-2,3-dihydro-1H-isoindol-1-one (Compound 205A). MS (ES+): m/z 610.25 (100) [MH$^+$]; HPLC: $t_R$=1.10 min (UPLC, purity).

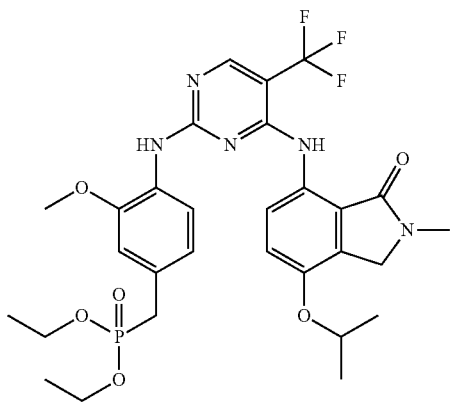

Example 211

Diethyl(3-methoxy-4-{[4-{[2-methyl-3-oxo-7-(propan-2-yloxy)-2,3-dihydro-1H-isoindol-4-yl]amino}-5-(trifluoromethyl)pyrimidin-2-yl]amino}benzyl)phosphonate. The title compound was prepared according to the procedure for Example 102 using diethyl(4-{[4-chloro-5-(trifluoromethyl)pyrimidin-2-yl]amino}-3-methoxybenzyl)phosphonate and 7-Amino-2-methyl-4-(propan-2-yloxy)-2,3-dihydro-1H-isoindol-1-one (Compound 207A). MS (ES+): m/z 638.26 (100) [MH$^+$]; HPLC: $t_R$=1.21 min (UPLC, purity).

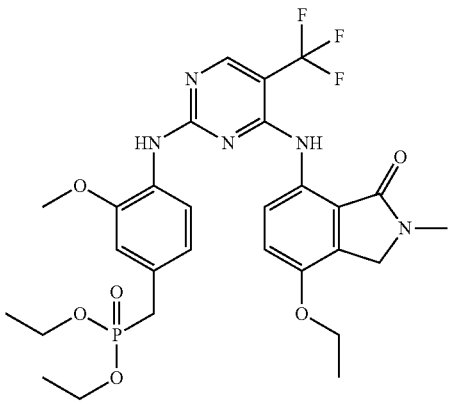 [SMILES: CCOc1ccc(Nc2nc(Nc3ccc(CP(=O)(OCC)OCC)cc3OC)ncc2C(F)(F)F)c2c1CN(C)C2=O]

Example 210

Diethyl[4-({4-[(7-ethoxy-2-methyl-3-oxo-2,3-dihydro-1H-isoindol-4-yl)amino]-5-(trifluoromethyl)pyrimidin-2-yl}amino)-3-methoxybenzyl]phosphonate The title compound was prepared according to the procedure for Example 102 using diethyl (4-{[4-chloro-5-(trifluoromethyl)pyrimidin-2-yl]amino}-3-methoxybenzyl)phosphonate and 7-Amino-4-ethoxy-2-methyl-2,3-dihydro-1H-isoindol-1-one (Compound 206A). MS (ES+): m/z 624.28 (100) [MH$^+$]; HPLC: $t_R$=1.16 min (UPLC, purity).

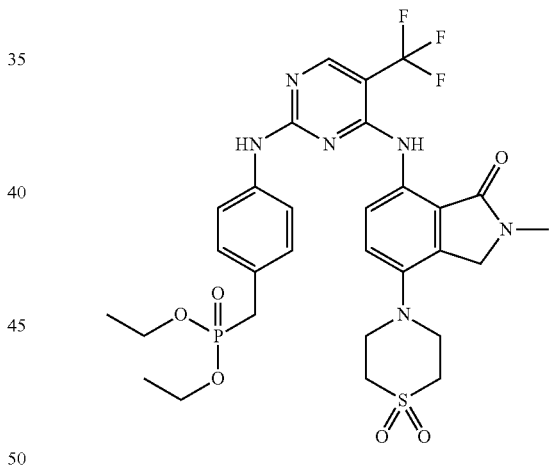

Example 212

Diethyl(4-{[4-{[7-(1,1-dioxidothiomorpholin-4-yl)-2-methyl-3-oxo-2,3-dihydro-1H-isoindol-4-yl]amino}-5-(trifluoromethyl)pyrimidin-2-yl]amino}benzyl)phosphonate The title compound was prepared according to the procedure for Example 199 using Diethyl [4-({4-[(7-bromo-2-methyl-3-oxo-2,3-dihydro-1H-isoindol-4-yl)amino]-5(trifluoromethyl)pyrimidin-2-yl}amino)benzyl]phosphonate and thiomorpholine-1,1-dioxide and replacing Cs$_2$CO$_3$, with K$_3$PO$_4$. MS (ES+): m/z 683.25 (100) [MH$^+$]; HPLC: $t_R$=0.98 min (UPLC, purity).

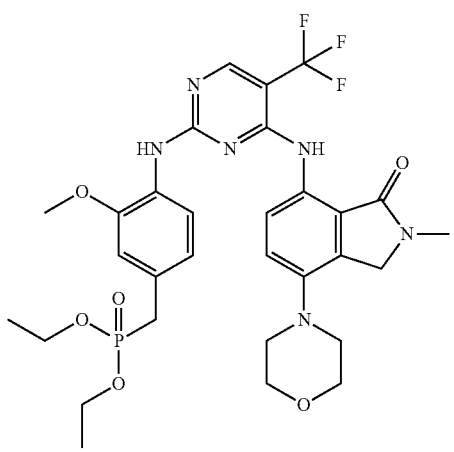 [SMILES: CCOP(=O)(Cc1ccc(Nc2ncc(C(F)(F)F)c(Nc3ccc(N4CCOCC4)c4c3C(=O)N(C)C4)n2)c(OC)c1)OCC]

Example 215

Diethyl(3-methoxy-4-{[4-{[2-methyl-7-(morpholin-4-yl)-3-oxo-2,3-dihydro-1H-isoindol-4-yl]amino}-5-(trifluoromethyl)pyrimidin-2-yl]amino}benzyl)phosphonate The title compound was prepared according to the procedure for Example 102 using diethyl(4-{[4-chloro-5-(trifluoromethyl)pyrimidin-2-yl]amino}-3-methoxybenzyl)phosphonate and 7-Amino-2-methyl-4-(morpholin-4-yl)-2,3-dihydro-1H-isoindol-1-one (Compound 208A). MS (ES+): m/z 665.33 (100) [MH$^+$]; HPLC: t$_R$=1.07 min (UPLC, purity).

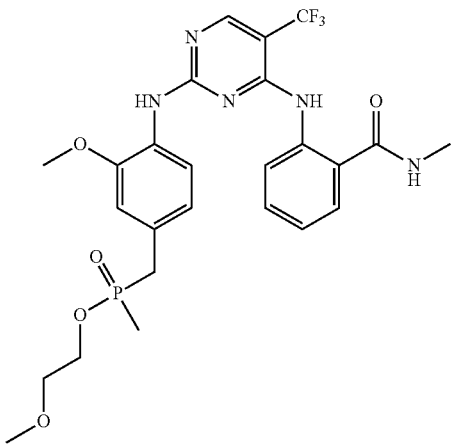

Example 216

2-Methoxyethyl(3-methoxy-4-{[4-{[2-(methylcarbamoyl)phenyl]amino}-5-(trifluoromethyl)pyrimidin-2-yl]amino}benzyl)methylphosphinate The title compound was prepared according to the procedure for Example 102 using 2-methoxyethyl(4-amino-3-methoxybenzyl)methylphosphinate and 2-{[2-chloro-5-(trifluoromethyl)pyrimidin-4-yl]amino}-N-methylbenzamide (Compound 104A). $^1$H NMR (DMSO-d6, 400 MHz): δ=1.33 (d, J=14.15 Hz, 3H), 2.76 (d, J=4.55 Hz, 3H), 3.21 (d, J=17.94 Hz, 2H), 3.26 (s, 3H), 3.48-3.52 (m, 2H), 3.77 (s, 3H), 4.03 (ddt, J=6.19, 4.48, 3.13, 3.13 Hz, 2H), 6.81-6.87 (m, 1H), 7.02 (s, 1H), 7.07 (t, J=7.45 Hz, 1H), 7.28 (t, J=8.08 Hz, 1H), 7.51 (d, J=7.33 Hz, 1H), 7.64-7.70 (m, 1H), 8.37 (s, 1H), 8.72 (d, J=4.29 Hz, 1H), 8.79 (br. s., 1H), 11.43 (s, 1H). MS (ES$^+$): m/z 568.15 [MH$^+$] (TOF, polar).

Compound 216A: 2-Methoxyethyl(4-amino-3-methoxybenzyl)methylphosphinate

The title compound was prepared according the procedure for 2-Amino-5-fluoro-N-methylbenzamide (Compound 102A) using 2-methoxyethyl(3-methoxy-4-nitrobenzyl)methylphosphinate (Compound 216B). $^1$H NMR (CDCl$_3$, 400 MHz): δ=1.39 (d, J=13.64 Hz, 3H), 3.10 (d, J=17.43 Hz, 2H), 3.39 (s, 3H), 3.54-3.59 (m, 2H), 3.87 (s, 3H), 4.09-4.14 (m, 2H), 6.66-6.71 (m, 1H), 6.76-6.79 (m, 1H), 6.80 (t, J=1.89 Hz, 1H). MS (ES$^+$): m/z 274.11 [MH$^+$] (TOF, polar).

Compound 216B: 2-Methoxyethyl(3-methoxy-4-nitrobenzyl)methylphosphinate

A mixture of (3-methoxy-4-nitrobenzyl)methylphosphinic acid (Compound 216C: 0.250 g, 1.02 mmol) and 1-bromo-2-methoxy ethane (0.287 mL, 3.06 mmol) in DMF (3.0 mL) was charged with potassium carbonate (0.169 g, 1.22 mmol) and n-Bu$_4$NI (0.188 g, 0.510 mmol). The reaction mixture was allowed to heat at 50° C. for 16 hours with stirring. The reaction mixture was quenched with water (10 mL) and extracted with EtOAc (15 mL). The organic layer was washed with water (10 mL), washed with brine (10 mL), dried over Na$_2$SO$_4$, filtered, concentrated under reduced pressure to yield a yellow oil. The crude material was purified by silica gel chromatography on the combi-flash Rf system using 1:1 EtOAc-DCM/MeOH (100:0→90:10) as eluent. The fractions containing product were combined and concentrated under reduced pressure to yield a yellow oil, 0.140 g (45% yield). $^1$H NMR (CDCl$_3$, 400 MHz): δ=1.47 (d, J=13.89 Hz, 3H), 3.24 (dd, J=17.43, 3.79 Hz, 2H), 3.39 (s, 3H), 3.51-3.62 (m, 2H), 3.98 (s, 3H), 4.14 (ddd, J=8.27, 4.42, 4.23 Hz, 2H), 6.93 (dt, J=8.34, 1.89 Hz, 1H), 7.12 (t, J=1.77 Hz, 1H), 7.85 (dd, J=8.21, 0.63 Hz, 1H). MS (ES$^+$): m/z 304.08 [MH$^+$] (TOF, polar).

Compound 216C: (3-Methoxy-4-nitrobenzyl)methylphosphinic acid

A solution of ethyl(3-methoxy-4-nitrobenzyl)methylphosphinate (Compound 216D, 0.500 g, 1.83 mmol) in 37% HCl (5.00 mL) was stirred at 100° C. for 6 hours. The reaction mixture was concentrated under reduced pressure to yield the desired product as a yellow foam, 457.2 mg (102% yield). This material was used in successive reactions without any further purification. $^1$H NMR (CDCl$_3$, 400 MHz): δ=1.41 (d, J=13.89 Hz, 3H), 3.13 (d, J=16.42 Hz, 2H), 3.97 (s, 3H), 6.89 (d, J=8.08 Hz, 1H), 7.02 (s, 1H), 7.82 (d, J=8.34 Hz, 1H). MS (ES$^+$): m/z 246.05 [MH$^+$] (TOF, polar).

Compound 216D: Ethyl(3-methoxy-4-nitrobenzyl)methylphosphinate

A mixture of 4-(bromomethyl)-2-methoxy-1-nitrobenzene (1.50 g, 6.10 mmol) and diethoxymethylphosphine (1.00 g, 7.34 mmol) were heated at 100° C. for 16 h in a sealed tube. The reaction mixture was concentrated under reduced pressure to yield a dark yellow oil. The crude material was purified by silica gel chromatography on an ISCO combi-flash Rf system using 1:1 DCM-EtOAc/MeOH (100:0→95:5) as eluent. The fractions containing product were combined and concentrated under reduced pressure to yield a yellow solid, 0.622 g (37% yield). $^1$H NMR (CDCl$_3$, 400 MHz): δ=1.32 (t, J=7.07 Hz, 3H), 1.45 (d, J=13.89 Hz, 3H), 3.20 (dd, J=17.31, 5.94 Hz, 2H), 3.98 (s, 3H), 4.01-4.12 (m, 2H), 6.92 (ddd, J=8.21, 2.02, 1.89 Hz, 1H), 7.09 (t, J=1.89 Hz, 1H), 7.85 (d, J=8.34 Hz, 1H). MS (ES$^+$): m/z 274.07 [MH$^+$] (TOF, polar).

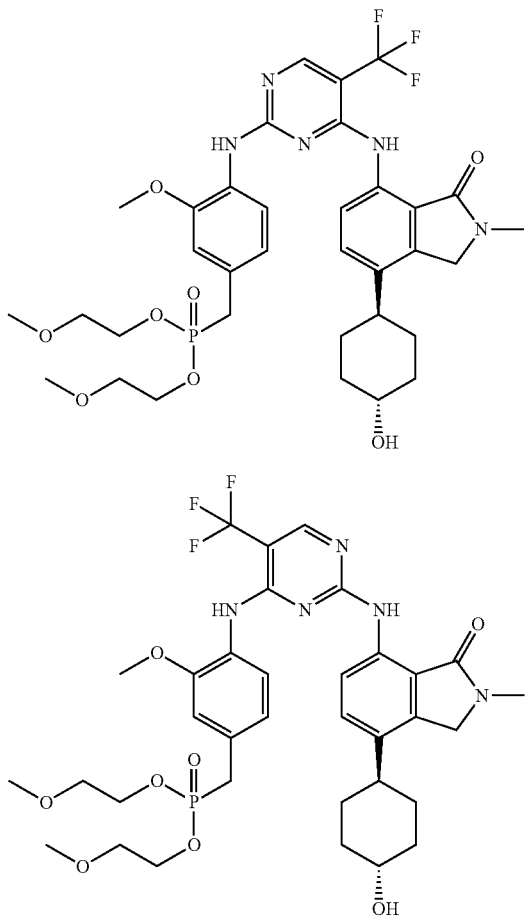

Example 217

(A) Bis(2-methoxyethyl) (4-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}-3-methoxybenzyl)phosphonate and Compound 218: (B) Bis(2-methoxyethyl)(4-{[2-{[7-(trans-4-hydroxycyclohexyl)-2-methyl-3-oxo-2,3-dihydro-1H-isoindol-4-yl]amino}-5-(trifluoromethyl)pyrimidin-4-yl]amino}-3-methoxybenzyl)phosphonate The title compounds were prepared according to the procedure for compound 102 using bis(2-methoxyethyl)(4-{[4-chloro-5-(trifluoromethyl)pyrimidin-2-yl]amino}-3-methoxybenzyl)phosphonate (Example 217A/B, 107 mg, 0.208 mmol) and 7-amino-4-(4-hydroxycyclohexyl)-2-methyl-2,3-dihydro-1H-isoindol-1-one (73.2 mg, 0.281 mmol). The reaction mixture was concentrated in vacuo and purified on a Teledyne/ISCO Combiflash system, eluting with 0-15% 7N NH$_3$(MeOH):EtOAc. The collected material was still not pure and was purified again by MDP (under acidic conditions; formic acid), which successfully separated the two regioisomers.

Example 217 (A) was the first to elute by LCMS (t$_R$=1.36 min) and was isolated as a white solid (49.5 mg, 32%). $^1$H NMR (400 MHz, DMSO-d$_6$) δ ppm 10.56 (s, 1H), 9.05 (br s, 1H), 8.37 (s, 1H), 8.27-8.43 (m, 1H), 7.44 (br s, 1H), 7.30 (d, J=8.6 Hz, 1H), 7.06 (s, 1H), 6.92 (d, J=7.8 Hz, 1H), 4.49 (s, 2H), 4.01-4.09 (m, 4H), 3.75 (s, 3H), 3.46-3.49 (m, 4H), 3.33 (d, J=21.7 Hz, 2H), 3.24 (s, 6H), 3.06 (s, 3H), 2.38-2.47 (m, 1H), 1.92 (dd, J=12.0, 2.1 Hz, 2H), 1.66-1.76 (m, 2H), 1.60 (q, J=11.8 Hz, 2H), 1.21-1.34 (m, 2H). MS (ES$^+$): m/z 738.22 (100) [MH$^+$] HPLC: t$_R$=1.36 min (TOF, polar__3 min). [Methine cyclohexanol shift and alcohol proton overlap with H$_2$O shift (or DMSO) in $^1$H NMR.]

Compound 218 (B) was second to elute by LCMS (t$_R$=1.43 min) and was isolated as an off-white solid (41.0 mg, 26%). $^1$H NMR (400 MHz, DMSO-d$_6$) δ ppm 10.20 (s, 1H), 8.47 (br s, 1H), 8.37 (s, 1H), 7.78 (br s, 1H), 7.39 (br s, 1H), 7.25 (d, J=8.3 Hz, 1H), 7.12 (s, 1H), 6.98 (dt, J=8.1, 2.0 Hz, 1H), 4.58 (d, J=3.8 Hz, 1H), 4.45 (s, 2H), 4.01-4.13 (m, 4H), 3.72 (s, 3H), 3.47-3.51 (m, 4H), 3.41 (d, J=22.2 Hz, 2H), 3.25 (s, 6H), 3.04 (s, 3H), 2.35-2.46 (m, 1H), 1.91 (d, J=9.3 Hz, 2H), 1.52-1.74 (m, 4H), 1.17-1.33 (m, 2H). MS (ES$^+$): m/z 738.28 (100) [MH$^+$]. HPLC: t$_R$=1.43 min (TOF, polar__3 min). [Methine cyclohexanol shift overlaps with either DMSO and water shifts in $^1$H NMR.]

Examples 217A and 217B

Bis(2-methoxyethyl)(4-{[4-chloro-5-(trifluoromethyl)pyrimidin-2-yl]amino}-3-methoxybenzyl) phosphonate [A] and bis(2-methoxyethyl)(4-{[2-chloro-5-(trifluoromethyl)pyrimidin-4-yl]amino}-3-methoxybenzyl)phosphonate [B]

The title compound was prepared according to the procedure for diethyl(4-{[4-chloro-5-(trifluoromethyl)pyrimidin-2-yl]amino}benzyl)phosphonate using Bis(2-methoxyethyl)(4-amino-3-methoxybenzyl)phosphonate (Compound 217C) and 2,4-dichloro-5-trifluoromethylpyrimidine. [A] and [B] were carried onto subsequent steps as a mixture.

Compound 217C: Bis(2-methoxyethyl)(4-amino-3-methoxybenzyl)phosphonate

A mixture of bis(2-methoxyethyl)(4-nitro-3-methoxybenzyl)phosphonate (Compound 217D, 4.5 g, 12.4 mmol) and 5% Pd/C (2 g, wet) in MeOH (100 mL) was hydrogenated under 50 psi hydrogen pressure at 50° C. for 18 h. The reaction mixture was filtered and the filtrate was concentrated to give the desired product (4 g, 97%). $^1$H NMR (DMSO-d$_6$, 400 MHz): δ=3.11 (d, J=21.2 Hz, 2H), 3.34 (s, 6H), 3.49 (m, 4H), 3.81 (s, 3H), 4.05 (m, 4H), 6.12 (d, J=8.4 Hz, 2H), 6.20 (dd, J=8.4 Hz, 1H), 6.78 (s, 1H).

Compound 217D: Bis(2-methoxyethyl)(3-methoxy-4-nitrobenzyl)phosphonate

At 0° C., to a solution of 2-methoxyethanol (6 g, 78.9 mmol) and TEA (14 g, 120 mmol) was added a solution of 3-methoxy-4-nitrobenzylphosphonic dichloride (Compound 114C, 20 g) in THF (100 mL) dropwise. The reaction mixture was warmed to room temperature and stirred at 70° C. for 18 h. Solvent was removed and residue was purified by column chromatography to give 4.5 g of the desired product (yield: 44%).

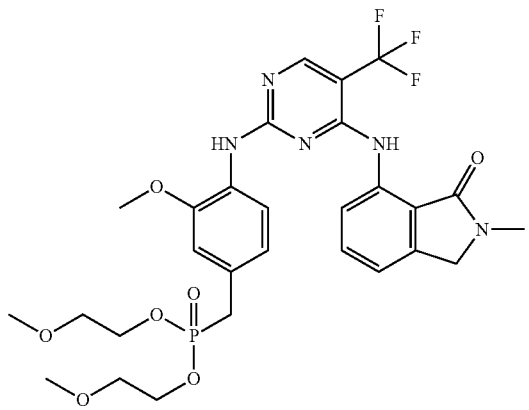

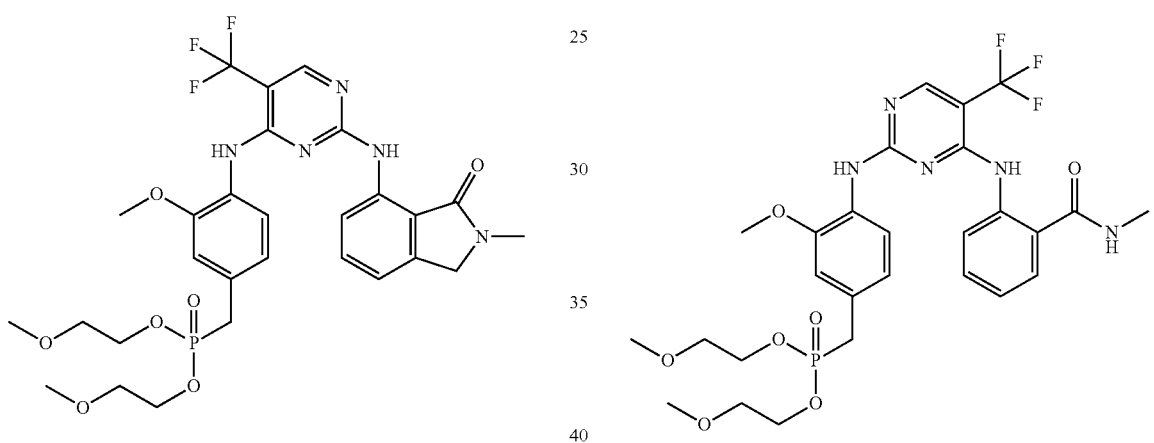

Example 219

(A) Bis(2-methoxyethyl)[3-methoxy-4-({4-[(2-methyl-3-oxo-2,3-dihydro-1H-isoindol-4-yl)amino]-5-(trifluoromethyl)pyrimidin-2-yl}amino)benzyl]phosphonate and Compound 220: (B) Bis(2-methoxyethyl)[3-methoxy-4-({2-[(2-methyl-3-oxo-2,3-dihydro-1H-isoindol-4-yl)amino]-5-(trifluoromethyl)pyrimidin-4-yl}amino)benzyl]phosphonate The title compounds were prepared according to the procedure for compound 102 using bis(2-methoxyethyl)(4-{[4-chloro-5-(trifluoromethyl)pyrimidin-2-yl]amino}-3-methoxybenzyl)phosphonate (217A/B, 107 mg, 0.208 mmol) and 7-amino-2-methyl-2,3-dihydro-1H-isoindol-1-one (56.2 mg, 0.346 mmol). The reaction mixture concentrated in vacuo and purified first on a Teledyne/ISCO Combiflash system eluting with 0-15% 7N NH$_3$(MeOH):EtOAc followed by MDP (under acidic conditions; formic acid), which successfully separated the two regioisomers. Example 219 (A) was the first to elute (LCMS (t$_R$=1.39 min). affording a white solid (48.4 mg, 36%). $^1$H NMR (400 MHz, DMSO-d$_6$) δ ppm 10.57 (s, 1H), 9.13 (s, 1H), 8.39 (s, 1H), 8.33 (br s, 1H), 7.41 (dd, J=6.8, 6.3 Hz, 2H), 7.15 (d, J=7.3 Hz, 1H), 7.06 (s, 1H), 6.91 (d, J=7.8 Hz, 1H), 4.45 (s, 2H), 3.99-4.11 (m, 4H), 3.74 (s, 3H), 3.44-3.52 (m, 4H), 3.33 (d, J=21.5 Hz, 2H), 3.25 (s, 6H), 3.06 (s, 3H). MS (ES$^+$): m/z 640.15 (100) [MH$^+$]. HPLC: t$_R$=1.39 min (TOF, polar_3 min). Compound 220 (B) was the second to elute by LCMS (t$_R$=1.49 min) affording an off-white solid, (43.4 mg, 32%). $^1$H NMR (400 MHz, DMSO-d$_6$) δ ppm 10.21 (s, 1H), 8.53 (br s, 1H), 8.39 (s, 1H), 7.84 (br s, 1H), 7.39 (d, J=5.6 Hz, 1H), 7.31 (t, J=7.8 Hz, 1H), 7.12 (t, J=1.9 Hz, 1H), 7.04 (d, J=7.6 Hz, 1H), 6.97 (dt, J=7.9, 2.1 Hz, 1H), 4.41 (s, 2H), 4.02-4.10 (m, 4H), 3.71 (s, 3H), 3.45-3.52 (m, 4H), 3.38 (d, J=22.0 Hz, 2H), 3.25 (s, 6H), 3.04 (s, 3H). MS (ES$^+$): m/z 640.16 (100) [MH$^+$]. HPLC: t$_R$=1.49 min (TOF, polar_3 min).

Example 221

Bis(2-methoxyethyl)(3-methoxy-4-{[4-{[2-(methylcarbamoyl)phenyl]amino}-5-(trifluoromethyl)pyrimidin-2-yl]amino}benzyl)phosphonate The title compound was prepared according to Example 102 using 2-{[2-chloro-5-(trifluoromethyl)pyrimidin-4-yl]amino}-N-methylbenzamide (Compound 104A, 50.0 mg, 0.15 mmol) and bis(2-methoxyethyl)(4-amino-3-methoxybenzyl)phosphonate (Compound 217C, 55.4 mg, 0.17 mmol). 58.1 mg (61%) of the desired product obtained after purification. $^1$H NMR (400 MHz, MeOD) δ ppm 8.24-8.35 (m, 2H), 7.95 (d, J=8.08 Hz, 1H), 7.62 (dd, J=7.83, 1.52 Hz, 1H), 7.46 (ddd, J=8.53, 7.39, 1.52 Hz, 1H), 7.16 (td, J=7.58, 1.01 Hz, 1H), 6.96 (t, J=2.02 Hz, 1H), 6.72-6.80 (m, 1H), 4.05-4.16 (m, 4H), 3.87 (s, 3H), 3.50-3.57 (m, 4H), 3.33 (s, 6H), 3.20-3.29 (m, 2H), 2.89 (s, 3H). MS (ES$^+$): m/z 628.16/629.20 (100/98) [MH$^+$]. HPLC: t$_R$=1.39 min (Micromass TOF: polar_3 min).

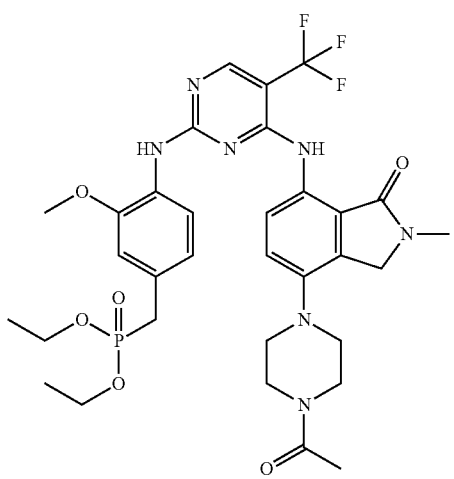 [SMILES: CCOP(=O)(Cc1ccc(Nc2ncc(C(F)(F)F)c(Nc3ccc(N4CCN(C(C)=O)CC4)c4c3C(=O)N(C)C4)n2)c(OC)c1)OCC]

Example 223

Diethyl(4-{[4-{[7-(4-acetylpiperazin-1-yl)-2-methyl-3-oxo-2,3-dihydro-1H-isoindol-4-yl]amino}-5-(trifluoromethyl)pyrimidin-2-yl]amino}-3-methoxybenzyl)phosphonate The title compound was prepared according to the procedure for Example 199 using Diethyl[4-({4-[(7-bromo-2-methyl-3-oxo-2,3-dihydro-1H-isoindol-4-yl)amino]-5-(trifluoromethyl)pyrimidin-2-yl}amino)-3-methoxybenzyl]phosphonate and 1-acetylpiperazine. MS (ES+): m/z 706.38 (100) [MH+]; HPLC: $t_R$=0.99 min (UPLC, purity).

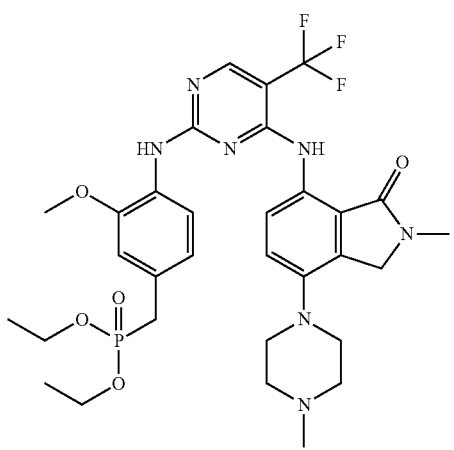 [SMILES: CCOP(=O)(Cc1ccc(Nc2ncc(C(F)(F)F)c(Nc3ccc(N4CCN(C)CC4)c4c3C(=O)N(C)C4)n2)c(OC)c1)OCC]

Example 224

Diethyl(3-methoxy-4-{[4-{[2-methyl-7-(4-methylpiperazin-1-yl)-3-oxo-2,3-dihydro-1H-isoindol-4-yl]amino}-5-(trifluoromethyl)pyrimidin-2-yl]amino}benzyl)phosphonate The title compound was prepared according to the procedure for Example 199 using Diethyl [4-({4-[(7-bromo-2-methyl-3-oxo-2,3-dihydro-1H-isoindol-4-yl)amino]-5-(trifluoromethyl)pyrimidin-2-yl}amino)-3-methoxybenzyl] phosphonate and N-methylpiperazine. MS (ES+): m/z 678.34 (100) [MH+]; HPLC: $t_R$=0.71 min (UPLC, purity).

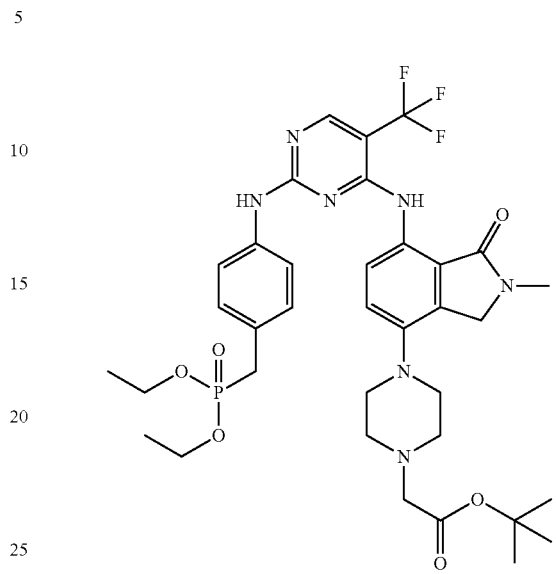

Example 225 tert-Butyl[4-(7-{[2-({4-[(diethoxyphosphoryl)methyl]phenyl}amino)-5-(trifluoromethyl)pyrimidin-4-yl]amino}-2-methyl-1-oxo-2,3-dihydro-1H-isoindol-4-yl)piperazin-1-yl]acetate The title compound was prepared according to the procedure for Example 199 using Diethyl[4-({4-[(7-bromo-2-methyl-3-oxo-2,3-dihydro-1H-isoindol-4-yl)amino]-5-(trifluoromethyl)pyrimidin-2-yl}amino)benzyl]phosphonate and piperazine-1-acetic acid tert-butyl ester. MS (ES+): m/z 748.41 (100) [MH+]; HPLC: $t_R$=0.85 min (UPLC, purity).

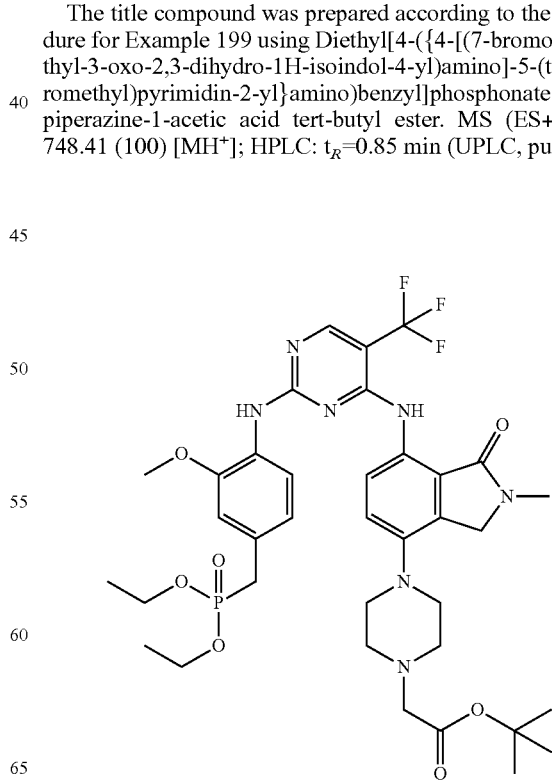

Example 226 tert-Butyl[4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)piperazin-1-yl]acetate The title compound was prepared according to the procedure for Example 199 using Diethyl[4-({4-[(7-bromo-2-methyl-3-oxo-2,3-dihydro-1H-isoindol-4-yl)amino]-5-(trifluoromethyl)pyrimidin-2-yl}amino)-3-methoxybenzyl]phosphonate and piperazine-1-acetic acid tert-butyl ester. MS (ES+): m/z 778.42 (100) [MH$^+$]; HPLC: t$_R$=0.86 min (UPLC, purity).

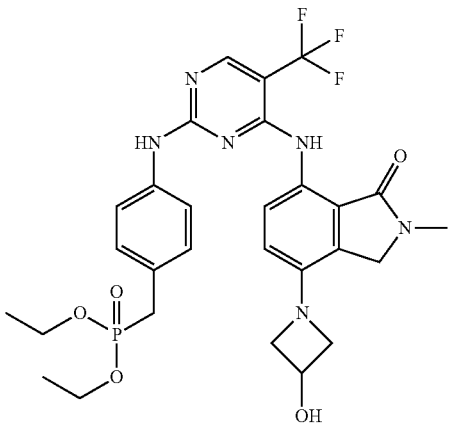 [SMILES: CCOP(=O)(Cc1ccc(Nc2ncc(C(F)(F)F)c(Nc3ccc(N4CC(O)C4)c4c3C(=O)N(C)C4)n2)cc1)OCC]

Example 227

Diethyl(4-{[4-{[7-(3-hydroxyazetidin-1-yl)-2-methyl-3-oxo-2,3-dihydro-1H-isoindol-4-yl]amino}-5-(trifluoromethyl)pyrimidin-2-yl]amino}benzyl)phosphonate The title compound was prepared according to the procedure for Example 199 using Diethyl[4-({4-[(7-bromo-2-methyl-3-oxo-2,3-dihydro-1H-isoindol-4-yl)amino]-5-(trifluoromethyl)pyrimidin-2-yl}amino)benzyl]phosphonate and 3-hydroxyazetidine. MS (ES+): m/z 621.25 (100) [MH$^+$]; HPLC: t$_R$=0.89 min (UPLC, purity).

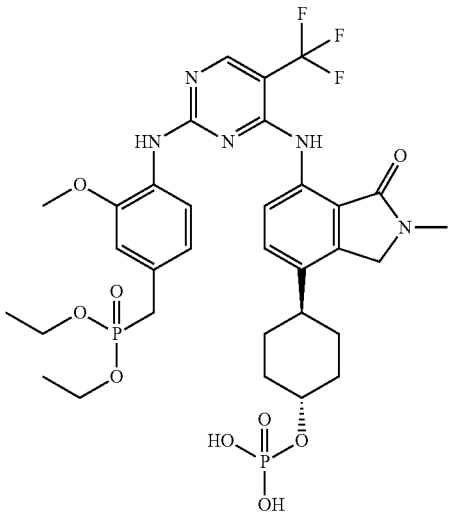 [SMILES: CCOP(=O)(Cc1ccc(Nc2ncc(C(F)(F)F)c(Nc3ccc([C@H]4CC[C@H](OP(=O)(O)O)CC4)c4c3C(=O)N(C)C4)n2)c(OC)c1)OCC]

Example 228

Diethyl(3-methoxy-4-{[4-({2-methyl-3-oxo-7-[trans-4-(phosphonooxy)cyclohexyl]-2,3-dihydro-1H-isoindol-4-yl}amino)-5-(trifluoromethyl)pyrimidin-2-yl]amino}benzyl)phosphonate To a solution of diethyl[4-({4-[(7-{trans-4-[(di-tert-butoxyphosphoryl)oxy]cyclohexyl}-2-methyl-3-oxo-2,3-dihydro-1H-isoindol-4-yl)amino]-5-(trifluoromethyl)pyrimidin-2-yl}amino)-3-methoxybenzyl]phosphonate (Compound 228A, 38.5 mg, 0.044 mmol) in THF (2 mL) was added TFA (1 mL). The reaction mixture was stirred at rt for 1 h. Solvents were then removed in vacuo and the residue was purified by MDP (formic acid conditions) to obtain 31.9 mg of the desired product (yield: 95%). $^1$H NMR (DMSO-d$_6$, 400 MHz): δ=1.19 (t, J=7.6 Hz, 6H), 1.41-1.46 (m, 2H), 1.66-1.76 (m, 4H), 2.12-2.15 (m, 2H), 2.49 (m, 1H), 3.04 (s, 3H), 3.29 (d, J=21.20 Hz, 2H), 3.73 (s, 3H), 3.96-4.03 (m, 4H), 4.12 (m, 1H), 4.47 (s, 2H), 6.89 (d, J=7.6 Hz, 1H), 7.05 (s, 1H), 7.36 (d, J=8.8 Hz, 1H), 7.43 (s, br, 1H), 8.36 (d, J=0.8 Hz, 1H), 8.98 (s, 1H), 10.54 (s, 1H). MS (ES$^+$): m/z 758.21 [MH$^+$]. HPLC: t$_R$=1.27 min (UPLC TOF, polar_3 min).

Compound 228A: diethyl[4-({4-[(7-{trans-4-[(di-tert-butoxyphosphoryl)oxy]cyclohexyl}-2-methyl-3-oxo-2,3-dihydro-1H-isoindol-4-yl)amino]-5-(trifluoromethyl)pyrimidin-2-yl}amino)-3-methoxybenzyl]phosphonate A solution of diethyl(4-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}-3-methoxybenzyl)phosphonate (100.0 mg, 0.15 mmol), di(tert-butyl)N,N-diethylphosphoramidite (367.9 mg, 1.48 mmol), and 1H-tetrazole (113.7 mg, 1.62 mmol) in DCM (5 mL) was stirred at rt for 18 h. The mixture was then cooled to −78° C. and mCPBA (43.65 mg, 0.18 mmol) was added. The resulting mixture was allowed to warm to rt during 1 h, and stirred for another 14 h. The mixture was concentrated in vacuo and the residue was purified by silica gel chromatography (5% 7 N ammonia in MeOH in DCM) to afford 38.5 mg of the desired product. $^1$H NMR (CDCl$_3$, 400 MHz): δ=1.27 (t, J=7.2 Hz, 6H), 1.51 (s, 18H), 1.60-1.71 (m, 4H), 1.90-1.93 (m, 2H), 2.30-2.32 (m, 2H), 2.52 (dt, J=2.4, 7.2 Hz, 1H), 3.18 (d, J=21.60 Hz, 2H), 3.22 (s, 3H), 3.93 (s, 3H), 4.00-4.09 (m, 4H), 4.38 (s, 2H), 6.88 (dt, J=2.0, 8.4 Hz, 1H), 6.95 (t, J=2.0 Hz, 1H), 7.32 (d, J=8.8 Hz, 1H), 7.65 (s, 1H), 8.28 (d, J=7.6 Hz, 1H), 8.39 (s, 1H), 8.64 (d, J=8.8 Hz, 1H), 10.51 (s, 1H). MS (ES$^+$): m/z 870.39 [MH$^+$]. HPLC: t$_R$=4.67 min (ZQ3, polar_5 min).

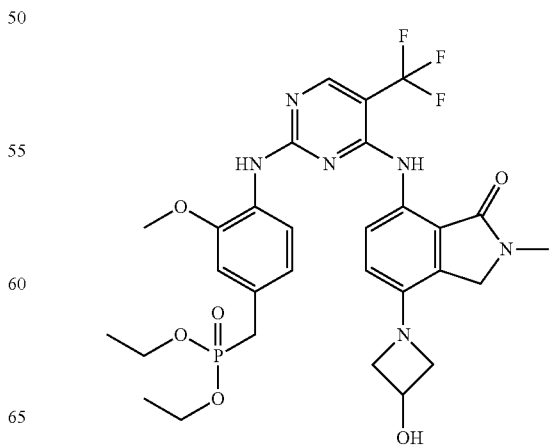

Example 229

Diethyl(4-{[4-{[7-(3-hydroxyazetidin-1-yl)-2-methyl-3-oxo-2,3-dihydro-1H-isoindol-4-yl]amino}-5-(trifluoromethyl)pyrimidin-2-yl]amino}-3-methoxybenzyl)phosphonate The title compound was prepared according to the procedure for Example 199 using Diethyl[4-({4-[(7-bromo-2-methyl-3-oxo-2,3-dihydro-1H-isoindol-4-yl)amino]-5-(trifluoromethyl)pyrimidin-2-yl}amino)-3-methoxybenzyl]phosphonate and 3-hydroxyazetidine. MS (ES+): m/z 651.24 (100) [MH$^+$]; HPLC: t$_R$=0.91 min (UPLC, purity).

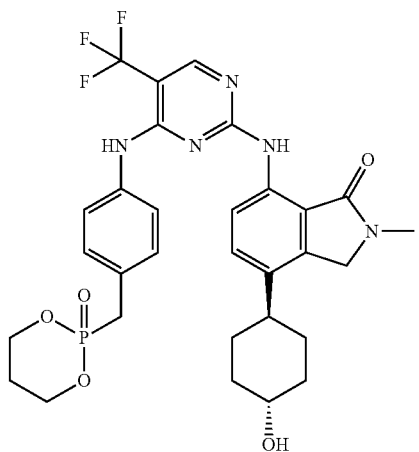

(A)

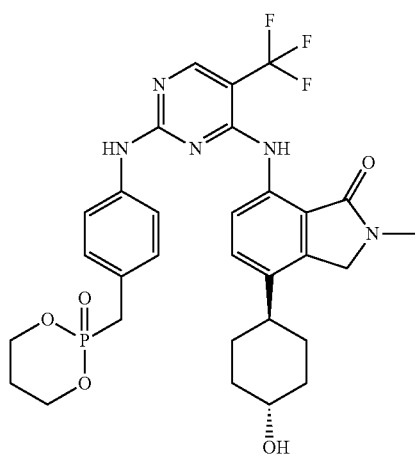

(B)

Compound 230: (A above) 4-(trans-4-hydroxycyclohexyl)-2-methyl-7-{[4-({4-[(2-oxido-1,3,2-dioxaphosphinan-2-yl)methyl]phenyl}amino)-5-(trifluoromethyl)pyrimidin-2-yl]amino}-2,3-dihydro-1H-isoindol-1-one

Example 230

(B above) 4-(trans-4-hydroxycyclohexyl)-2-methyl-7-{[2-({4-[(2-oxido-1,3,2-dioxaphosphinan-2-yl)methyl]phenyl}amino)-5-(trifluoromethyl)pyrimidin-4-yl]amino}-2,3-dihydro-1H-isoindol-1-one The title compounds were prepared according to the procedure for compound 102 using 4-chloro-N-{4-[(2-oxido-1,3,2-dioxaphosphinan-2-yl)methyl]phenyl}-5-(trifluoromethyl)pyrimidin-2-amine (Compound 230A, 22.8 mg, 0.0559 mmol) and 7-amino-4-(4-hydroxycyclohexyl)-2-methyl-2,3-dihydro-1H-isoindol-1-one (22.0 mg, 0.0845 mmol). The crude material was purified using a Teledyne/ISCO Combiflash system, eluting with 0-15% 7N NH$_3$(MeOH):EtOAc. The collected material was a mixture of regioisomers and was purified again by Supercritical Fluid Chromatography (SFC).

Compound 230 (A) eluted first, as the more non-polar compound (t$_R$=1.29 min) and was isolated as 9.4 mg of a white solid, (26%). $^1$H NMR (400 MHz, DMSO-d$_6$) δ ppm 10.12 (br s, 1H), 8.93 (br s, 1H), 8.31 (br s, 1H), 7.97 (br s, 1H), 7.34 (br s, 4H), 7.20 (d, J=8.3 Hz, 1H), 4.48-4.60 (m, 3H), 4.44 (s, 2H), 4.29-4.41 (m, 2H), 3.42-3.54 (m, 3H), 3.04 (s, 3H), 2.34-2.44 (m, 1H), 2.01-2.14 (m, 1H), 1.87-1.96 (m, J=9.6 Hz, 2H), 1.82 (dd, J=14.5, 2.4 Hz, 1H), 1.51-1.70 (m, 4H), 1.19-1.32 (m, 2H). MS (ES$^+$): m/z 632.18 (100) [MH$^+$]. HPLC: t$_R$=1.29 min (TOF, polar_3 min).

Example 230 (B) eluted after, as the more polar compound (t$_R$=1.27 min) and was isolated as 11.7 mg a white solid, (33%). $^1$H NMR (400 MHz, DMSO-d$_6$) δ ppm 10.57 (br s, 1H), 9.87 (br s, 1H), 8.55 (br s, 1H), 8.45 (s, 1H), 7.55 (d, J=2.3 Hz, 2H), 7.33 (d, J=7.8 Hz, 1H), 7.28 (d, J=7.1 Hz, 2H), 4.56-4.86 (m, 1H), 4.41-4.56 (m, 4H), 4.27-4.40 (m, 2H), 3.46-3.55 (m, 1H), 3.36-3.44 (m, 2H), 3.08 (s, 3H), 2.07 (ddd, J=14.6, 10.5, 10.3 Hz, 1H), 1.93 (d, J=10.1 Hz, 2H), 1.67-1.84 (m, 3H), 1.51-1.64 (m, 2H), 1.21-1.36 (m, 2H). MS (ES$^+$): m/z 632.18 (100) [MH$^+$]. HPLC: t$_R$=1.27 min (TOF, polar_3 min).

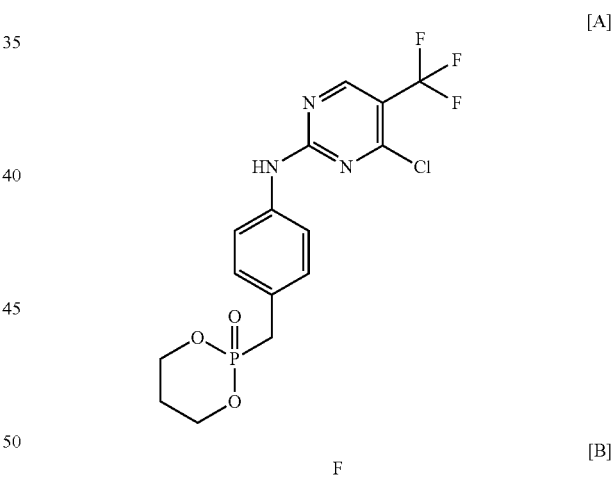

[A]

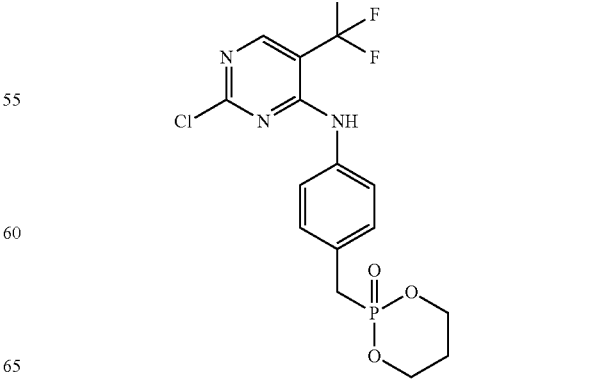

[B]

Compound 230A: 4-chloro-N-{4-[(2-oxido-1,3,2-dioxaphosphinan-2-yl)methyl]phenyl}-5-(trifluoromethyl)pyrimidin-2-amine and Compound 230B: 2-chloro-N-{4-[(2-oxido-1,3,2-dioxaphosphinan-2-yl)methyl]phenyl}-5-(trifluoromethyl)pyrimidin-4-amine [B]

The title compound was prepared according to the procedure for diethyl(4-{[4-chloro-5-(trifluoromethyl)pyrimidin-2-yl]amino}benzyl)phosphonate using 4-[(2-oxido-1,3,2-dioxaphosphinan-2-yl)methyl]aniline (Compound 230C) and 2,4-dichloro-5-trifluoromethylpyrimidine.

Compound 230C: 4-[(2-oxido-1,3,2-dioxaphosphinan-2-yl)methyl]aniline

To a solution of 2-(4-nitrobenzyl)-1,3,2-dioxaphosphinane 2-oxide (Compound 230D, 70 mg, 0.27 mmol) in anhydrous THF was added 10% Pd/C (10 mg). The resulting mixture was heated at 50° C. under 50 psi H$_2$ atmosphere for 6 h. Catalyst was filtered off and the filtrate was concentrated to give the desired product (50 mg, yield: 80%). $^1$H NMR (CD$_3$OD, 400 MHz): δ=1.72-1.76 (m, 1H), 1.98-2.02 (m, 1H), 3.19 (d, J=20.4 Hz, 2H), 4.28-4.40 (m, 4H), 6.68 (d, J=8.0 Hz, 2H), 7.03 (d, J=8.4 Hz, 2H).

Compound 230D: 2-(4-Nitrobenzyl)-1,3,2-dioxaphosphinane 2-oxide

Crude (4-Nitrobenzyl)phosphonic dichloride (Compound 230E) above was dissolved in anhydrous THF (20 mL). To this solution was added TEA (840 mg, 7.5 mmol) and 1,3-propane-diol (190 mg, 2.5 mmol) at 0° C. The resulting mixture was stirred at room temperature overnight, concentrated and the residue was purified by column chromatography to give the target product (70 mg). $^1$H NMR (CD$_3$OD, 400 MHz): δ=2.85 (d, J=20.0 Hz, 2H), 3.28-3.30 (m, 2H), 3.55-3.58 (m, 2H), 3.75-7.78 (m, 2H), 6.64 (d, J=8.4 Hz, 2H), 7.07 (d, J=8.4 Hz, 2H).

Compound 230E: (4-Nitrobenzyl)phosphonic dichloride

A solution of (4-nitrobenzyl)phosphonic acid (500 mg, 2.3 mmol) in thionyl chloride (20 mL) was refluxed overnight. The excess amount of thionyl chloride was removed under reduced pressure to leave a residue, which was used in the next step without purification.

Example 231

Diethyl(3-methoxy-4-{[4-{[2-(methylcarbamoyl)pyridin-3-yl]amino}-5-(trifluoromethyl)pyrimidin-2-yl]amino}benzyl)phosphonate Diethyl(4-{[4-chloro-5-(trifluoromethyl)pyrimidin-2-yl]amino}-3-methoxybenzyl)phosphonate (30.0 mg, 0.0661 mmol) and 3-amino-N-methylpyridine-2-carboxamide (Compound 231C, 15.0 mg, 0.0992 mmol) were taken up in TFE (2.7 mL, 37 mmol) and treated with TFA (15.3 uL, 0.198 mmol). This mixture was irradiated on the CEM for 120 min at 100° C. Rxn mixture was poured into water and extracted twice with EtOAc. The combined organic layers were dried over Na$_2$SO$_4$, filtered, concentrated and purified on an ISCO CombiFlash system (eluting with 0-4% MeOH/DCM) to isolate, after concentrating the relevant fractions and drying in vacuo, the desired product as 20.8 mg of a white solid. $^1$H NMR (400 MHz, DMSO-d6) δ1.19 (t, J=7.07 Hz, 6H), 2.81 (d, J=4.80 Hz, 3H), 3.28 (d, J=20.50 Hz, 2H), 3.74 (s, 3H), 3.94-4.04 (m, 4H), 6.90 (dt, J=8.15, 1.99 Hz, 1H), 7.05 (s, 1H), 7.33-7.51 (m, 2H), 8.21 (d, J=3.54 Hz, 1H), 8.41 (s, 1H), 9.08 (br. s., 1H), 9.11 (q, J=4.21 Hz, 1H), 12.45 (s, 1H). MS (ES+): m/z=569.10 (100) [M+1]. HPLC: tR=1.52 min (UPLC TOF, polar_3 min).

Compound 231A: 3-Amino-N-methylpyridine-2-carboxamide

A solution of 3-aminopicolinic acid (0.3 g, 2 mmol) in DMF (2.0 mL, 26 mmol) was cooled to 0° C., treated with DIPEA (7.57 mL, 43.4 mmol), methylamine hydrochloride (1.47 g, 21.7 mmol) and TBTU (0.837 g, 2.61 mmol). The flask was sealed and the mixture was allowed to come up to RT stirring for 3 hours. The reaction mixture was poured into water and extracted with EtOAc three times. The combined organic layers were dried over Na2SO4, filtered and concentrated to an oil which was passed through an ion exchange column (SCX). The MeOH/NH3 washes were combined to isolate 108 mg of a brown oil which crystallized upon standing. $^1$H NMR (400 MHz, DMSO-d6) d 2.76 (d, J=4.80 Hz, 3H), 6.81 (br. s., 2H), 7.13 (dd, J=8.30, 1.50 Hz, 1H), 7.22 (dd, J=8.30, 4.30 Hz, 1H), 7.77 (dd, J=4.17, 1.39 Hz, 1H), 8.52 (d, J=3.79 Hz, 1H). MS (ES+): m/z=152.04 [MH+].

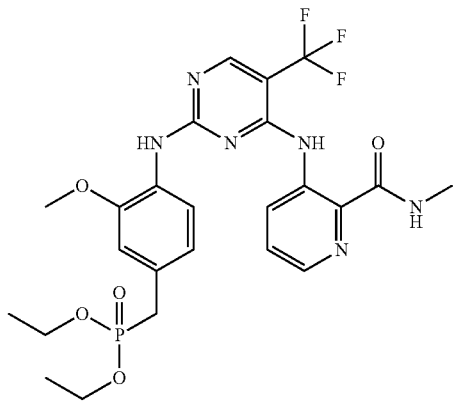 [SMILES: CCOP(=O)(Cc1ccc(Nc2ncc(C(F)(F)F)c(Nc3cccnc3C(=O)NC)n2)c(OC)c1)OCC]

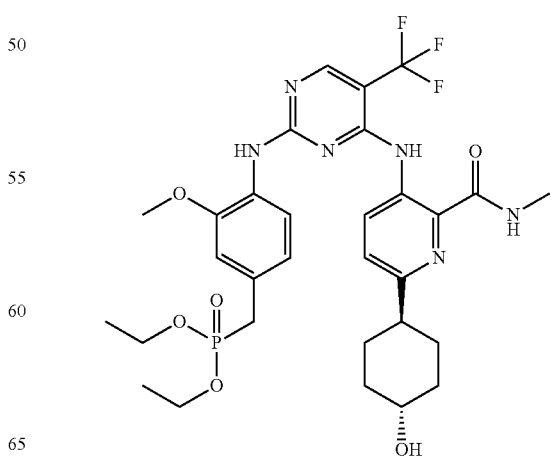

Example 232

Diethyl(4-{[4-{[6-(trans-4-hydroxycyclohexyl)-2-(methylcarbamoyl)pyridin-3-yl]amino}-5-(trifluoromethyl)pyrimidin-2-yl]amino}-3-methoxybenzyl) phosphonate The title compound was prepared according to the procedure for Example 231 using diethyl(4-{[4-chloro-5-(trifluoromethyl)pyrimidin-2-yl]amino}-3-methoxybenzyl)phosphonate (44.9 mg, 0.0989 mmol) and 3-amino-6-(trans-4-hydroxycyclohexyl)-N-methylpyridine-2-carboxamide (Example 232A, 37 mg, 0.15 mmol). The reaction mixture was poured into water and extracted twice with EtOAc. The combined organic layers were dried over $Na_2SO_4$, filtered, concentrated and purified on an ISCO CombiFlash system (eluting with 0-4% MeOH/DCM) to isolate, after concentrating the relevant fractions and drying in vacuo, the desired product as 44.5 mg of a white solid. $^1$H NMR (400 MHz, DMSO-d6) d 1.20 (t, J=7.07 Hz, 6H), 1.23-1.33 (m, 2H), 1.59-1.72 (m, 2H), 1.77-1.86 (m, 2H), 1.94 (dd, J=13.01, 3.66 Hz, 2H), 2.56-2.67 (m, 1H), 2.83 (d, J=4.80 Hz, 3H), 3.28 (d, J=17.94 Hz, 2H), 3.45-3.55 (m, 1H), 3.74 (s, 3H), 3.94-4.04 (m, 4H), 4.57 (d, J=4.29 Hz, 1H), 6.89 (ddd, J=8.02, 2.27, 2.08 Hz, 1H), 7.05 (s, 1H), 7.35 (d, J=8.84 Hz, 1H), 7.41 (br. s., 1H), 8.38 (s, 1H), 8.88-8.95 (m, 1H), 9.01 (br. s., 1H), 12.33 (s, 1H). HRMS (ES+): m/z=667.2100 (100) [M+1]. HPLC: tR=1.50 min (ZQ2, polar_3 min).

Compound 232A: 3-amino-6-(trans-4-hydroxycyclohexyl)-N-methylpyridine-2-carboxamide A solution of 3-amino-N-methyl-6-(4-oxocyclohexyl)pyridine-2-carboxamide (Compound 232B, 53 mg, 0.21 mmol) in MeOH (3 mL, 70 mmol) was cooled to 0° C. and treated with sodium borohydride (8.1 mg, 0.21 mmol). The mixture was stirred at 0° C. for 20 minutes. The reaction was quenched with sat. aq. $NH_4Cl$ (1 mL) and concentrated. The residue was taken up in 1 mL $H_2O$ and EtOAc (30 m). The layers were separated. The aqueous layer was saturated with salt and washed again with ~20 mL of EtOAc. The combined organic layers were washed with brine, dried over anhydrous sodium sulfate, filtered, and concentrated. The crude solid was taken up in DCM, treated with silica and concentrated. This silica was loaded into a sample column and purified on an ISCO Combiflash unit (0-7% MeOH/DCM) to isolate the product as a mixture of predominantly trans isomer. $^1$H NMR (400 MHz, CHLOROFORM-d) δ 1.37-1.57 (m, 4H), 1.92-2.01 (m, 2H), 2.07-2.16 (m, 2H), 2.55 (tt, J=11.87, 3.54 Hz, 1H), 2.99 (d, J=5.05 Hz, 3H), 3.63-3.77 (m, 1H), 5.81 (br. s., 2H), 6.95 (d, J=8.40 Hz, 1H), 7.04 (d, J=8.40 Hz, 1H), 8.11 (br. s., 1H).

Compound 232B: 3-amino-N-methyl-6-(4-oxocyclohexyl)pyridine-2-carboxamide

A mixture of 3-Amino-6-(1,4-dioxaspiro[4.5]dec-8-yl)-N-methylpyridine-2-carboxamide (Compound 232C, 0.160 g, 0.549 mmol) in AcOH (1.0 mL, 18 mmol) and $H_2O$ (0.2 mL, 10 mmol) was warmed to 75° C. for 2.5 hours, after which, the reaction was cooled and concentrated in vacuo. The residue was taken up in water and basified with a saturated aqueous solution of $K_2CO_3$. This mixture was extracted three times with DCM and the combined organic layers were dried over $Na_2SO_4$, filtered and concentrated to a brown tar. This was taken up in DCM, treated with silica and concentrated and loaded into a sample cartridge. The product was isolated after purification on an ISCO Combiflash unit (eluting with 0-4% MeOH/DCM) as 53 mg of a white crystalline solid. $^1$H NMR (400 MHz, DMSO-d6) δ 1.97-2.13 (m, 4H), 2.26 (dt, J=14.40, 2.02 Hz, 2H), 2.52-2.59 (m, 2H), 2.77 (d, J=5.05 Hz, 3H), 3.05 (tdd, J=11.43, 3.79, 3.66 Hz, 1H), 6.65 (s, 2H), 7.09 (d, J=8.30 Hz, 1H), 7.20 (d, J=8.30 Hz, 1H), 8.42 (d, J=4.80 Hz, 1H). MS (ES+): m/z=247.87 (90) [M+1]. HPLC: tR=2.95 min (ZQ3, polar_5 min).

Compound 232C: 3-Amino-6-(1,4-dioxaspiro[4.5]dec-8-yl)-N-methylpyridine-2-carboxamide A solution of 3-amino-6-(1,4-dioxaspiro[4.5]dec-8-yl)pyridine-2-carboxylic acid (Compound 232D, 0.229 g, 0.823 mmol) in DMF (2.0 mL, 26 mmol) was cooled to 0° C. treated with DIPEA (2.87 mL, 16.4 mmol), methylamine hydrochloride (0.556 g, 8.23 mmol) and TBTU (0.396 g, 1.23 mmol). The flask was sealed and the mixture was allowed to come up to RT and stir overnight. The DMF and DIPEA were removed in vacuo and the residue was taken up in water and extracted multiple times with EtOAc and DCM. The combined organic layers were dried over $Na_2SO_4$, filtered and concentrated to a yellow oil. This was purified on an ISCO Combiflash unit using 0-4% MeOH/DCM to isolate 145 mg of an oil. $^1$H NMR (400 MHz, DMSO-d6) δ 1.51-1.87 (m, 8H), 2.54-2.64 (m, 1H), 2.79 (d, J=4.80 Hz, 3H), 3.88 (s, 4H), 6.62 (s, 2H), 7.05-7.10 (m, 1H), 7.11-7.16 (m, 1H), 8.29 (d, J=4.55 Hz, 1H). MS (ES+): m/z=292.01 (100) [M+1]. HPLC: tR=3.31 min (ZQ3, polar_5 min).

Compound 232D: 3-amino-6-(1,4-dioxaspiro[4.5]dec-8-yl)pyridine-2-carboxylic acid Ethyl 3-amino-6-(1,4-dioxaspiro[4.5]dec-8-yl)pyridine-2-carboxylate (Compound 232E, 228 mg, 0.744 mmol) was taken up in THF (1.0 mL) and MeOH (1.0 mL, 25 mmol). This was treated with a solution of Lithium hydroxide, monohydrate (156 mg, 3.72 mmol) in $H_2O$ (1.0 mL) and allowed to stir at rt for 4 hours. The THF was removed in vacuo and treated, dropwise with 1N HCl until a pH of ~5 was achieved. This aqueous solution was extracted with EtOAc (3×50 mL) and saturated with salt and stirred with ~100 mL DCM. The combined organic layers were dried over $Na_2SO_4$, filtered and concentrated to a crude yellow oil which was used without further purification. MS (ES+): m/z=278.86 [MH+]. HPLC: $t_R$=2.39 min (ZQ3, polar_5 min).

Compound 232E: Ethyl 3-amino-6-(1,4-dioxaspiro[4.5]dec-8-yl)pyridine-2-carboxylate 10% Pd/C (345 mg, 0.0812 mmol) was added to a solution of ethyl 3-amino-6-(1,4-dioxaspiro[4.5]dec-7-en-8-yl)pyridine-2-carboxylate (Compound 232F, 247 mg, 0.812 mmol) in EtOH (5.0 mL). The flask containing this mixture was subjected to 3 cycles of evacuation and $N_2$ purging. After the 4th evacuation the flask was purged with $H_2$ and allowed to stir for 24 hours. The reaction mixture was filtered through celite, the filter cake was washed with MeOH and DCM. The combined filtrate was concentrated to 228 mg of a yellow solid. $^1$H NMR (400 MHz, DMSO-d6) δ 1.30 (t, J=7.07 Hz, 3H), 1.59 (dd, J=12.51, 5.43 Hz, 2H), 1.63-1.70 (m, 2H), 1.70-1.79 (m, 4H), 2.59 (tt, J=11.15, 3.51 Hz, 1H), 3.87 (s, 4H), 4.28 (q, J=7.07 Hz, 2H), 6.50 (s, 2H), 7.17 (s, 2H). MS (ES+): m/z=306.91 (100) [M+1]. HPLC: tR=3.19 min (ZQ3, polar_5 min).

Compound 232F: Ethyl 3-amino-6-(1,4-dioxaspiro[4.5]dec-7-en-8-yl)pyridine-2-carboxylate (1) A mixture of 3-amino-6-bromopyridine-2-carboxylic acid ethyl ester-(Compound 232G, 0.31 g, 1.3 mmol), 1,4-dioxaspiro[4,5]dec-7-ene-8-boronic acid pinacol ester (0.406 g, 1.52 mmol) and [1,1'-Bis(diphenylphosphino)ferrocene]dichloropalladium(11), complex with dichloromethane (1:1) (0.10 g, 0.12 mmol) in a 35 mL sealable microwave tube was taken up in 1,4-Dioxane (4.9 mL). This mixture was treated with a solution of Potassium carbonate (0.52 g, 3.8 mmol) in H$_2$O (1 mL), flushed with nitrogen, sealed and irradiated in a microwave reactor for 30 minutes at 100° C. The mixture was poured into water and extracted twice with EtOAc. The combined organic layers were washed with brine, dried over Na$_2$SO$_4$ filtered and concentrated to a brown residue. This was taken up in DCM, treated with silica and concentrated. The resulting silica plug was loaded on to a sample cartridge and purified on an ISCO Combiflash system (0-50% EtOAc/Heptane) to isolate the desired product as 247 mg of an oil which crystallized upon standing. $^1$H NMR (400 MHz, DMSO-d6) d 1.30 (t, J=7.20 Hz, 3H), 1.77 (t, J=6.44 Hz, 2H), 2.32-2.40 (m, 2H), 2.60 (td, J=6.44, 1.52 Hz, 2H), 3.91 (s, 4H), 4.28 (q, J=7.07 Hz, 2H), 6.25 (t, J=4.04 Hz, 1H), 6.65 (s, 2H), 7.17 (d, J=8.84 Hz, 1H), 7.52 (d, J=8.84 Hz, 1H). MS (ES+): m/z=305.12 (100) [M+1]. HPLC: tR=3.50 min (ZQ3, polar__5 min).

Compound 232G: 3-Amino-6-bromopyridine-2-carboxylic acid ethyl ester

A suspension of ethyl 3-aminopicolinate (Compound 232H, 4.15 g, 25.0 mmol) in H$_2$O (30.0 mL) was treated with enough sulfuric acid to enable dissolution (~1 mL). 2 mL of the total 10.7 mL of HOAC to be used in this reaction was added in order to make the rxn mixture mostly homogeneous. The vigorously stirring mixture was then treated with a solution of Bromine (1.29 mL, 25.0 mmol) in the remaining AcOH (10.7 mL). This Br$_2$/HOAc solution was added dropwise. A ppt formed upon addition. This was allowed to stir for 15 min as the reaction mixture became a yellow-orange suspension. The mixture was filtered to collect the yellow ppt. The filtrate was neutralized with saturated aq K$_2$CO$_3$ forming more ppt. This was also collected and combined with the yellow ppt. This was dried on the filter and left O/N in the dark. 5.15 g of a yellow solid was isolated. This was recrystallized in EtOH to isolate 4.236 g of pale orange crystals. The mother liquor was concentrated, taken up in DCM/MeOH, treated with silica and re-concentrated. This was loaded into a sample cartridge and purified on an ISCO Combiflash system eluting with 0-5% MeOH/DCM. After concentrating the fractions, the desired product was isolated as 579 mg of a yellow solid. Combined yield 79%. 1H NMR (400 MHz, DMSO-d6) d 1.30 (t, J=7.07 Hz, 3H), 4.29 (q, J=7.07 Hz, 2H), 6.90 (br. s., 2H), 7.21 (d, J=8.59 Hz, 1H), 7.44 (d, J=8.84 Hz, 1H). MS (ES+): m/z=244.94 (100), 246.92 (100) [M+1, Br isotopes]. HPLC: tR=3.45 min (ZQ3, polar__5 min) Material from column: 579 mg, HNMR clean and identical to crystals. 1H NMR (400 MHz, DMSO-d6) d 1.30 (t, J=7.20 Hz, 3H), 4.29 (q, J=7.07 Hz, 2H), 6.90 (s, 2H), 7.21 (d, J=8.59 Hz, 1H), 7.44 (d, J=8.59 Hz, 1H) These products were combined.

Compound 232H: Ethyl 3-aminopicolinate

A solution of 3-aminopicolinic acid (5.00 g, 36.2 mmol) in EtOH (70 mL) and concentrated sulfuric acid (6.0 mL, 110 mmol) was heated to 100° C. and stirred for 5 days. The cooled mixture was concentrated to ~20 mL and poured over ice. This mixture was treated with aqueous ammonia (NH4OH, conc) until pH>7. This was extracted twice with 100 mL EtOAc. The basified aqueous layer was saturated with salt and extracted again with 2×100 mL EtOAc. The combined organic layers were washed with brine, dried over Na$_2$SO$_4$, filtered and concentrated to 4.15 g of an off white solid (69%). $^1$H NMR (400 MHz, DMSO-d6) δ 1.30 (t, J=7.07 Hz, 3H), 4.27 (q, J=7.07 Hz, 2H), 6.67 (br. s., 2H), 7.17-7.22 (m, 1H), 7.24-7.29 (m, 1H), 7.84 (dd, J=4.04, 1.52 Hz, 1H). MS (ES+): m/z=167.06 (100) [M+1]. HPLC: t$_R$=2.76 min (ZQ3, vvpolar__5 min).

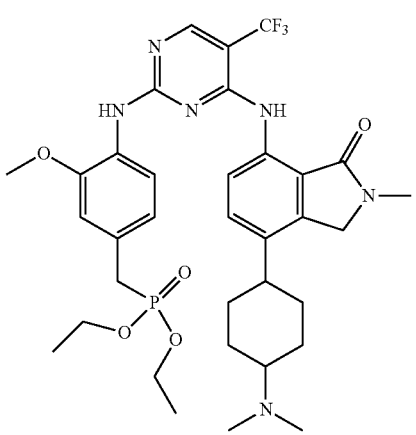

Example 233

Diethyl(4-{[4-({7-[4-(dimethylamino)cyclohexyl]-2-methyl-3-oxo-2,3-dihydro-1H-isoindol-4-yl}amino)-5-(trifluoromethyl)pyrimidin-2-yl]amino}-3-methoxybenzyl)phosphonate The title compound was prepared according to the procedure for Example 102 using diethyl (4-{[4-chloro-5-(trifluoromethyl)pyrimidin-2-yl]amino}-3-methoxybenzyl)phosphonate and 7-amino-4-[4-(dimethylamino)cyclohexyl]-2-methyl-2,3-dihydro-1H-isoindol-1-one (Compound 233A). $^1$H NMR (CD$_3$OD, 400 MHz): δ=1.30 (t, J=7.07 Hz, 6H), 1.75-1.85 (m, 2H), 1.85-2.02 (m, 4H), 2.39 (d, J=14.15 Hz, 2H), 2.77-2.88 (m, 1H), 3.04 (s, 6H), 3.18 (s, 3H), 3.38-3.50 (m, 3H), 3.86 (s, 3H), 4.07-4.20 (m, 4H), 4.51 (s, 2H), 7.01-7.07 (m, 1H), 7.12 (t, J=2.15 Hz, 1H), 7.62 (d, J=8.59 Hz, 2H), 8.32-8.42 (m, 2H). MS (ES$^+$): m/z 705.26 [MH$^+$] (TOF, polar).

Compound 233A: 7-amino-4-[4-(dimethylamino)cyclohexyl]-2-methyl-2,3-dihydro-1H-isoindol-1-one A solution of 7-amino-2-methyl-4-(4-oxocyclohexyl)-2,3-dihydro-1H-isoindol-1-one (100.0 mg, 0.3871 mmol) in 1,2-Dichloroethane (2.0 mL) was charged with 2.0 M of dimethylamine in THF (0.2903 mL, 0.5807 mmol) and sodium triacetoxyborohydride (164.1 mg, 0.7743 mmol). The reaction mixture was stirred at rt for 24 hours. The reaction mixture was quenched with NaHCO$_3$ (10 mL) and extracted with EtOAc (20 mL). The organic layer was washed with brine (10 mL), dried over Na$_2$SO$_4$, filtered and concentrated under reduced pressure to yield a light yellow oil. The crude material was purified by silica gel chromatography on the combiflash Rf system using DCM/7M $NH_3$ in MeOH (100:0→90:10) as eluent. The fractions containing product were combined and concentrated under reduced pressure to yield a light yellow solid, 64.7 mg (58% yield). $^1$H NMR (CDCl$_3$, 400 MHz): δ=1.53 (d, J=11.12 Hz, 4H), 1.91 (d, J=11.12 Hz, 2H), 2.08 (d, J=14.65 Hz, 2H), 2.31 (br. s., 6H), 2.45 (br. s., 1H), 2.48-2.58 (m, 1H), 3.14 (s, 3H), 4.30 (s, 2H), 5.07 (br. s., 2H), 6.57 (d, J=8.34 Hz, 1H), 7.26 (br. s., 1H). MS (ES$^+$): m/z 288.21 [MH$^+$] (TOF, polar).

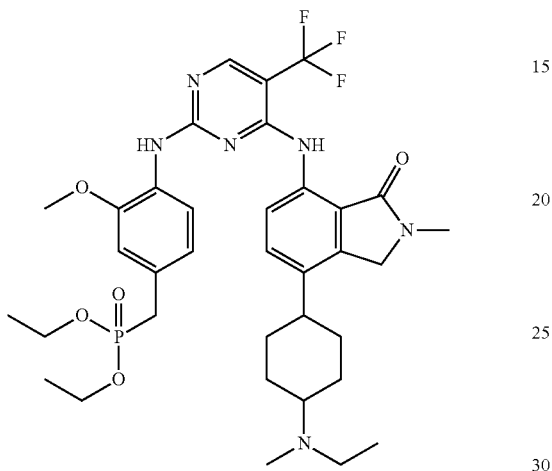

Example 236

Diethyl[4-({4-[(7-{4-[ethyl(methyl)amino]cyclohexyl}-2-methyl-3-oxo-2,3-dihydro-1H-isoindol-4-yl)amino]-5-(trifluoromethyl)pyrimidin-2-yl}amino)-3-methoxybenzyl]phosphonate This compound was prepared according to the procedure for Example 102 using diethyl(4-{[4-chloro-5-(trifluoromethyl)pyrimidin-2-yl]amino}-3-methoxybenzyl)phosphonate and 7-amino-4-{4-[ethyl(methyl)amino]cyclohexyl}-2-methyl-2,3-dihydro-1H-isoindol-1-one (Compound 236A). $^1$H NMR (400 MHz, MeOD) δ ppm 1.28 (t, J=7.07 Hz, 6H) 1.39 (t, J=7.33 Hz, 3H) 1.70-1.86 (m, 4H) 2.04 (br. s., 2H) 2.19 (d, J=7.83 Hz, 2H), 2.71 (br. s., 1H) 2.86 (s, 3H) 3.17-3.19 (m, 3H) 3.33 (s, 1H) 3.34-3.37 (m, 2H) 3.39 (s, 1H) 3.43-3.52 (m, 1H) 3.89 (s, 3H) 4.05-4.14 (m, 4H) 4.55 (s, 2H) 7.01 (dt, J=8.02, 2.31 Hz, 1H), 7.15 (t, J=2.02 Hz, 1H) 7.42 (d, J=8.34 Hz, 1H) 7.57 (d, J=8.08 Hz, 1H) 8.36 (br. s., 1H). MS (ES+): m/z 719.25/720.29 (100/20) [MH+]. HPLC: t$_R$=1.17 min (UPLC TOF: polar_3 min).

Compound 236A: 7-amino-4-{4-[ethyl(methyl)amino]cyclohexyl}-2-methyl-2,3-dihydro-1H-isoindol-1-one The title product was prepared according to the procedure for Compound 233A using 7-amino-2-methyl-4-(4-oxocyclohexyl)-2,3-dihydro-1H-isoindol-1-one and ethyl-methylamine. Used without purification in the next step.

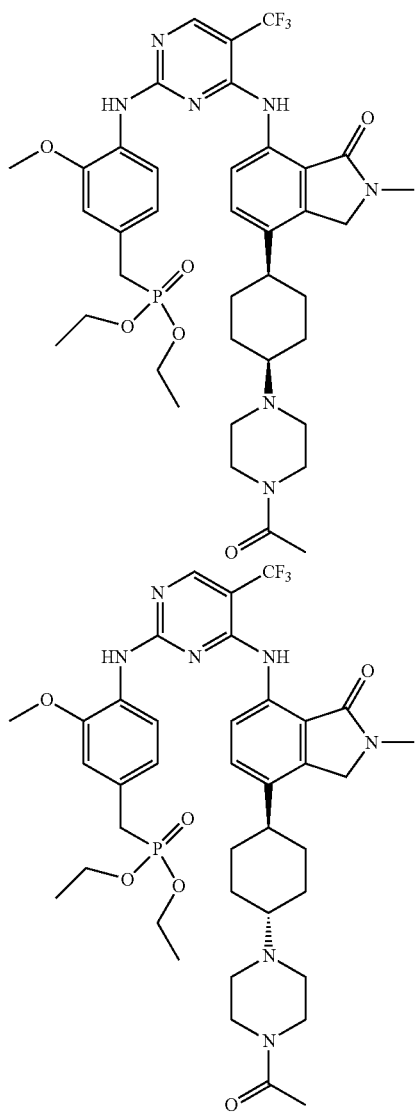

Example 237

Diethyl(4-{[4-({7-[cis-4-(4-acetylpiperazin-1-yl)cyclohexyl]-2-methyl-3-oxo-2,3-dihydro-1H-isoindol-4-yl}amino)-5-(trifluoromethyl)pyrimidin-2-yl]amino}-3-methoxybenzyl)phosphonate and Example 238 diethyl(4-{[4-({7-[trans-4-(4-acetylpiperazin-1-yl)cyclohexyl]-2-methyl-3-oxo-2,3-dihydro-1H-isoindol-4-yl}amino)-5-(trifluoromethyl)pyrimidin-2-yl]amino}-3-methoxybenzyl)phosphonate The title compounds were prepared according to the procedure for Example 102 using diethyl(4-{[4-chloro-5-(trifluoromethyl)pyrimidin-2-yl]amino}-3-methoxybenzyl)phosphonate and 4-[4-(4-acetyl piperazin-1-yl)cyclohexyl]-7-amino-2-methyl-2,3-dihydro-1H-isoindol-1-one (Compound 237A). The reaction mixture was purified by MDP. Example 237 was first peak to elute. $^1$H NMR (CDCl$_3$, 400 MHz): δ=1.28 (t, J=6.95 Hz, 6H), 1.50-1.73 (m, 7H), 2.02 (s, 2H), 2.12 (s, 3H), 2.50 (br. s., 2H), 2.62 (br. s., 3H), 3.13-3.21 (m, 2H), 3.22 (s, 3H), 3.42-3.75 (m, 4H), 3.93 (s, 3H), 3.99-4.10 (m, 4H), 4.38 (s, 2H), 6.90 (dt, J=8.08, 2.15 Hz, 1H), 6.94 (t, J=2.02 Hz, 1H), 7.34 (d, J=8.84 Hz, 1H), 7.63 (s, 1H), 8.28 (d, J=7.58 Hz, 1H), 8.40 (s, 1H), 8.64 (d, J=8.59 Hz, 1H), 10.51 (s, 1H). MS (ES$^+$): m/z 788.31 [MH$^+$] (TOF, polar). Example 238 eluted afterwards: $^1$H NMR (CDCl$_3$, 400 MHz): δ=1.28 (t, J=7.07 Hz, 6H), 1.87 (d, J=4.04 Hz, 2H), 1.91-2.03 (m, 2H), 2.12-2.25 (m, 7H), 2.84 (br. s., 2H), 3.21 (s, 3H), 3.23-3.33 (m, 4H), 3.86 (s, 3H), 3.93 (br. s., 2H), 4.04 (qdd, J=7.31, 7.31, 7.31, 7.14, 1.77 Hz, 4H), 4.38 (s, 2H), 6.94-7.00 (m, 2H), 7.36 (d, J=7.83 Hz, 1H), 7.71 (br. s., 1H), 8.23 (br. s., 2H), 11.20 (br. s., 1H). MS (ES$^+$): m/z 788.31 [MH$^+$] (TOF, polar).

Compound 237A: 4-[4-(4-acetylpiperazin-1-yl)cyclohexyl]-7-amino-2-methyl-2,3-dihydro-1H-isoindol-1-one The title product was prepared according to the procedure for Compound 233A using 7-amino-2-methyl-4-(4-oxocyclohexyl)-2,3-dihydro-1H-isoindol-1-one and 1-acetylpiperazine. $^1$H NMR (CDCl$_3$, 400 MHz): δ=1.80-1.98 (m, 3H), 2.01-2.14 (m, 6H), 2.25 (d, J=19.20 Hz, 1H), 2.42-2.62 (m, 5H), 3.12-3.17 (m, 3H), 3.45-3.70 (m, 4H), 4.28-4.33 (m, 2H), 5.10 (br. s., 2H), 6.58 (d, J=8.08 Hz, 1H), 7.17 (d, J=8.34 Hz, 1H). MS (ES$^+$): m/z 371.26 [MH$^+$] (TOF, polar).

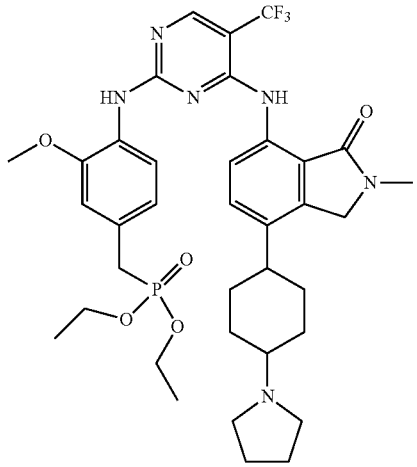

Example 242

Diethyl(4-{[5-chloro-4-({2-methyl-3-oxo-7-[4-(pyrrolidin-1-yl)cyclohexyl]-2,3-dihydro-1H-isoindol-4-yl}amino)pyrimidin-2-yl]amino}-3-methoxybenzyl)phosphonate The title product was prepared according to the procedure for Example 102 using diethyl(4-{[4-chloro-5-(trifluoromethyl)pyrimidin-2-yl]amino}-3-methoxybenzyl)phosphonate and 7-amino-2-methyl-4-[4-(pyrrolidin-1-yl)cyclohexyl]-2,3-dihydro-1H-isoindol-1-one (Compound 242A). $^1$H NMR (400 MHz, CHLOROFORM-d) δ ppm 1.27 (t, J=6.95 Hz, 6H), 1.58-1.71 (m, 2H), 1.98-2.08 (m, 4H), 2.13 (br. s., 4H), 2.29 (d, J=9.85 Hz, 3H), 2.57-2.67 (m, 2H), 2.93-3.06 (m, 2H), 3.15-3.22 (m, 2H), 3.23 (s, 3H), 3.93 (s, 3H), 3.99-4.10 (m, 4H), 4.37 (s, 2H), 6.87-6.92 (m, 1H), 6.93 (t, J=2.02 Hz, 1H), 7.30 (d, J=8.84 Hz, 1H), 7.68 (s, 1H), 8.25 (d, J=8.34 Hz, 1H), 8.39 (s, 2H), 8.63 (d, J=8.59 Hz, 1H), 10.53 (s, 1H). MS (ES$^+$): m/z 731.32 [MH$^+$]; HPLC: t$_R$=1.22 min (UPLC TOF, polar_3 min).

Compound 242A: 7-amino-2-methyl-4-[4-(pyrrolidin-1-yl)cyclohexyl]-2,3-dihydro-1H-isoindol-1-one The title product was prepared according to the procedure for Compound 233A using 7-amino-2-methyl-4-(4-oxocyclohexyl)-2,3-dihydro-1H-isoindol-1-one and pyrrolidine. Product used crude in the next step.

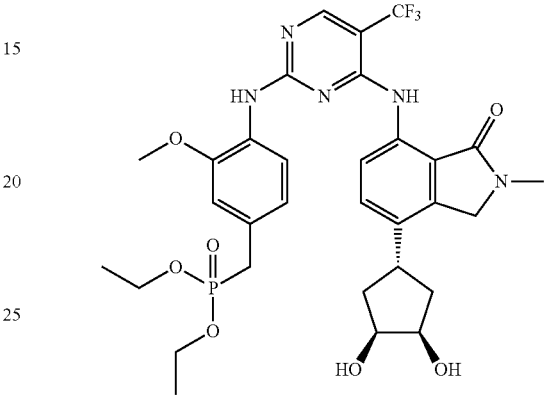

Example 243

Diethyl(4-{[4-({7-[-3,4-dihydroxycyclopentyl]-2-methyl-3-oxo-2,3-dihydro-1H-isoindol-4-yl}amino)-5-(trifluoromethyl)pyrimidin-2-yl]amino}-3-methoxybenzyl)phosphonate The title compound was prepared according to the procedure for Example 102 using diethyl (4-{[4-chloro-5-(trifluoromethyl)pyrimidin-2-yl]amino}-3-methoxybenzyl)phosphonate (43 mg, 0.095 mmol) and 7-amino-4-(3,4-dihydroxycyclopentyl)-2-methyl-2,3-dihydro-1H-isoindol-1-one trifluoroacetate (salt) (Compound 243A, 36 mg, 0.096 mmol). The reaction mixture was diluted with EtOAc (30 mL), washed with sat. aq. NaHCO$_3$ (2×10 mL), brine (10 mL), and dried over anhydrous sodium sulfate. The solvents were evaporated under reduced pressure, and the residue was purified by silica gel chromatography (ISCO Combi-flash system, eluting with 0-10% MeOH:DCM) to give the title compound as a white solid, 34 mg, 52% yield. $^1$H NMR (CDCl$_3$): 1.26 (t, J=7.1 Hz, 6H), 1.95-2.01 (m, 2H), 2.23-2.29 (m, 2H), 3.17 (d, J=21.7 Hz, 2H), 3.21 (s, 3H), 3.53 (m, 1H), 3.91 (s, 3H), 3.97-4.07 (m, 4H), 4.35 (s, 2H), 4.39-4.43 (m, 2H), 6.84 (s, 1H), 6.94 (m, 1H), 7.32 (d, J=8.8 Hz, 1H), 7.67 (s, 1H), 8.26 (d, J=8.1 Hz, 1H), 8.38 (s, 1H), 8.54 (d, J=8.6 Hz, 1H), 10.31 (s, 1H). MS (ES+): m/z=680.14 [MH$^+$]. HPLC: t$_R$=3.60 min (ZQ3, polar_5 min).

Compound 243A: 7-Amino-4-(3,4-dihydroxycyclopentyl)-2-methyl-2,3-dihydro-1H-isoindol-1-one trifluoroacetate To a solution of tert-butyl[7-(3,4-dihydroxycyclopentyl)-2-methyl-3-oxo-2,3-dihydro-1H-isoindol-4-yl]carbamate (Compound 243B, 36 mg, 0.099 mmol) in DCM (2 mL) was added TFA (1 mL). The resulting mixture was stirred at rt for 30 min, then evaporated under reduced pressure to give the desired product. This TFA salt was directly used in next step. MS (ES+): m/z=263.09 [MH+]. HPLC: $t_R$=0.78 min (ZQ3, polar_5 min).

Compound 243B: tert-Butyl[7-(3,4-dihydroxycyclopentyl)-2-methyl-3-oxo-2,3-dihydro-1H-isoindol-4-yl]carbamate To a solution of tert-butyl[7-(cyclopent-3-en-1-yl)-2-methyl-3-oxo-2,3-dihydro-1H-isoindol-4-yl]carbamate (Compound 243C: 33 mg, 0.10 mmol) in t-BuOH (1 mL) and H$_2$O (1 mL) were added N-methylmorpholine N-oxide (14 mg, 0.12 mmol) and potassium osmate dihydrate (0.37 mg, 0.0010 mmol). The resulting mixture was stirred at rt overnight. The mixture was diluted with EtOAc (30 mL), washed with brine (10 mL), and dried over anhydrous sodium sulfate. The solvents were evaporated under reduced pressure to give the title compound as a white solid, 36 mg, 99% yield. $^1$H NMR (CDCl$_3$): 1.52 (s, 9H), 1.90-1.94 (m, 2H), 2.14-2.19 (m, 2H), 2.34 (br s, 2H), 3.17 (s, 3H), 3.56 (m, 1H), 4.33 (s, 2H), 4.39 (m, 2H), 7.26 (d, J=8.6 Hz, 1H), 8.14 (d, J=8.6 Hz, 1H), 9.50 (br s, 1H). MS (ES+): m/z=363.16 [MH+]. HPLC: $t_R$=3.44 min (ZQ3, polar_5 min).

Compound 243C: tert-Butyl[7-(cyclopent-3-en-1-yl)-2-methyl-3-oxo-2,3-dihydro-1H-isoindol-4-yl]carbamate To a solution of tert-butyl[7-(hepta-1,6-dien-4-yl)-2-methyl-3-oxo-2,3-dihydro-1H-isoindol-4-yl]carbamate (Compound 243D, 180 mg, 0.50 mmol) in DCM (10 mL) was added (benzylidene)bis(tricyclohexylphosphine)ruthenium (IV)dichloride (21 mg, 0.025 mmol). The resulting mixture was stirred at rt under nitrogen. The solvent was evaporated under reduced pressure, and the residue was purified by silica gel chromatography (ISCO Combi-flash system, eluting with 10-30% EtOAc/Heptane) to give the title compound as a white solid, 150 mg, 90% yield. $^1$H NMR (CDCl$_3$): 1.54 (s, 9H), 2.43-2.48 (m, 2H), 2.81-2.86 (m, 2H), 3.18 (s, 3H), 3.45 (m, 1H), 4.32 (s, 2H), 5.80-5.84 (m, 2H), 7.35 (d, J=8.6 Hz, 1H), 8.12 (d, J=8.6 Hz, 1H), 9.53 (br s, 1H). MS (ES+): m/z=329.13 [MH+]. HPLC: $t_R$=4.65 min (ZQ3, polar_5 min).

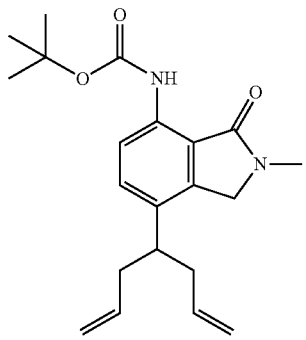 [SMILES: C=CCC(CC=C)c1ccc(NC(=O)OC(C)(C)C)c2c1CN(C)C2=O]

Compound 243D: tert-Butyl[7-(hepta-1,6-dien-4-yl)-2-methyl-3-oxo-2,3-dihydro-1H-isoindol-4-yl]carbamate To a solution of 1-{7-[(tert-butoxycarbonyl)amino]-2-methyl-1-oxo-2,3-dihydro-1H-isoindol-4-yl}but-3-en-1-yl acetate (Compound 243E, 895 mg, 2.39 mmol) in DCM (30 mL) were added indium tribromide (85 mg, 0.24 mmol), followed by the addition of allyltrimethylsilane (550 mg, 4.8 mmol) in DCM (0.5 mL). The resulting mixture was refluxed under nitrogen overnight. The solvent was evaporated and the residue was purified by silica gel chromatography (ISCO Combi-flash system, eluting with 10-50% EtOAc/Heptane) to give the desired product as a white solid, 180 mg. The unreacted starting material was recovered and resubjected to the reaction using 2.0 eq. allyltrimethylsilane and 0.2 eq. InBr$_3$. The mixture was refluxed overnight. The solvent was evaporated and the residue was purified by silica gel chromatography (ISCO Combi-flash system, eluting with 10-50% EtOAc/Heptane) to give the desired product as a white solid, 125 mg. Totally 305 mg, 36% yield. $^1$H NMR (CDCl$_3$): 1.53 (s, 9H), 2.34-2.47 (m, 4H), 2.67 (m, 1H), 3.16 (s, 3H), 4.27 (s, 2H), 4.92-4.99 (m, 4H), 5.55-5.64 (m, 2H), 7.29 (d, J=8.6 Hz, 1H), 8.16 (d, J=8.6 Hz, 1H), 9.52 (br s, 1H). MS (ES+): m/z=379.13 [MNa+]. HPLC: $t_R$=4.83 min (ZQ3, polar_5 min).

Compound 243E: 1-{7-[(tent-butoxycarbonyl)amino]-2-methyl-1-oxo-2,3-dihydro-1H-isoindol-4-yl}but-3-en-1-yl acetate To a solution of tert-butyl(7-formyl-2-methyl-3-oxo-2,3-dihydro-1H-isoindol-4-yl)carbamate (Compound 243F, 105 mg, 0.362 mmol) in THF (5 mL) was added Allyl-MgBr (0.72 mmol, 0.72 mL, 1M in Et$_2$O solution) at −78° C. under nitrogen. The resulting mixture was stirred at −78° C. for 1 h, then quenched with aq. NH$_4$Cl (2 mL) and warmed to rt. The mixture was diluted with EtOAc (30 mL), washed with brine (2×10 mL), and dried over anhydrous sodium sulfate. Evaporation of the solvents under reduced pressure to gave the desired alcohol tert-butyl[7-(1-hydroxybut-3-en-1-yl)-2-methyl-3-oxo-2,3-dihydro-1H-isoindol-4-yl]carbamate. This crude alcohol was taken up in DCM (3 mL) and pyridine (0.292 mL, 3.62 mmol) and treated with acetic anhydride (73.8 mg, 0.723 mmol). The mixture was stirred at rt overnight. Another 5 eq. acetic anhydride was added, and the mixture was stirred at rt for another day. The mixture was diluted with EtOAc (30 mL), washed with 1N HCl (2×10 mL), sat. aq. NaHCO$_3$ (2×10 mL), brine (10 mL), and dried over anhydrous sodium sulfate. The crude material was purified by silica gel chromatography (ISCO Combi-flash system, eluting with 20-50% EtOAc/Heptane) to give the title compound as a white solid. 110 mg, 81% yield over two steps. $^1$H NMR (CDCl$_3$): 1.52 (s, 9H), 2.06 (s, 3H), 2.57 (m, 1H), 2.71 (m, 1H), 3.17 (s, 3H), 4.35 (d, J=17.2 Hz, 1H), 4.54 (d, J=17.2 Hz, 1H), 5.05-5.11 (m, 2H), 5.62 (m, 1H), 5.72 (t, J=7.3 Hz, 1H), 7.43 (d, J=8.8 Hz, 1H), 8.19 (d, J=8.6 Hz, 1H), 9.60 (br s, 1H). MS (ES+): m/z=397.13 [MNa+]. HPLC: $t_R$=4.40 min (ZQ3, polar_5 min).

Compound 243F: tert-butyl(7-formyl-2-methyl-3-oxo-2,3-dihydro-1H-isoindol-4-yl)carbamate To a mixture of tert-butyl{2-methyl-3-oxo-7-[(E)-2-phenylethenyl]-2,3-dihydro-1H-isoindol-4-yl}carbamate (Compound 109D, 1.05 g, 2.88 mmol), potassium ferricyanide(III) (2.84 g, 8.64 mmol), potassium carbonate (1.19 g, 8.64 mmol), (DHQD)$_2$PHAL (22.4 mg, 0.0288 mmol) in t-BuOH (30 mL) and H$_2$O (30 mL) was added potassium osmate, dihydrate (10.6 mg, 0.0288 mmol). The resulting mixture was stirred at rt overnight. Sodium sulfite (2.18 g, 17.3 mmol) was added, and the reaction mixture was stirred at rt for 1 h. The mixture was diluted with EtOAc (100 mL), washed with brine (30 mL), and dried over anhydrous sodium sulfate. Evaporation under reduced pressure afforded the diol as a light-yellow solid, which was used to next step without further purification.

To a solution of the above crude diol in THF (20 mL) and H$_2$O (6 mL) was added sodium metaperiodate (0.924 g, 4.32 mmol). The resulting mixture was stirred at rt for 4 h. The mixture was diluted with EtOAc (100 mL), washed with brine (20 mL), and dried over anhydrous sodium sulfate. The residue was purified by silica gel chromatography (ISCO Combiflash system, eluting with 20-50% EtOAc/Heptane) affording the title compound as a white solid, 795 mg, 95% yield over 2 steps. $^1$H NMR (CDCl$_3$): 1.55 (s, 9H), 3.20 (s, 3H), 4.70 (s, 2H), 7.89 (d, J=8.6 Hz, 1H), 8.37 (d, J=8.6 Hz, 1H), 9.93 (br s, 1H), 9.99 (s, 1H). MS (ES+): m/z=235.06 [MH$^+$−56]. HPLC: t$_R$=4.04 min (ZQ3, polar_5 min).

Compound 244A: Diethyl(4-{[4-chloro-5-(trifluoromethyl)pyrimidin-2-yl]amino}-3-ethoxybenzyl)phosphonate The title compound was prepared according to the procedure for diethyl(4-{[4-chloro-5-(trifluoromethyl)pyrimidin-2-yl]amino}benzyl)phosphonate using diethyl(4-amino-3-ethoxybenzyl)phosphonate and 2,4-dichloro-5-trifluoromethylpyrimidine. The crude material was purified on an ISCO CombiFlash®Rf 4X Organic Purification System eluting with 1:1 EtOAc-DCM/MeOH (100:0→95:5)] affording a mixture of both regioisomers. The product was further purified by MDP to afford 514 mg (30%) of the desired regioisomer. $^1$H NMR (400 MHz, MeOD) δ 8.62 (s, 1H), 8.02 (d, J=8.08 Hz, 1H), 7.03 (t, J=2.15 Hz, 1H), 6.92 (td, J=2.34, 8.21 Hz, 1H), 4.04-4.22 (m, 6H), 3.28 (s, 1H), 3.23 (s, 1H), 1.41 (t, J=6.95 Hz, 3H), 1.27 (t, J=7.07 Hz, 7H). MS (ES$^+$): m/z 468.07/470.09 (100/90) [MH$^+$]. HPLC: t$_R$=1.66 min (Micromass TOF: polar_3 min).

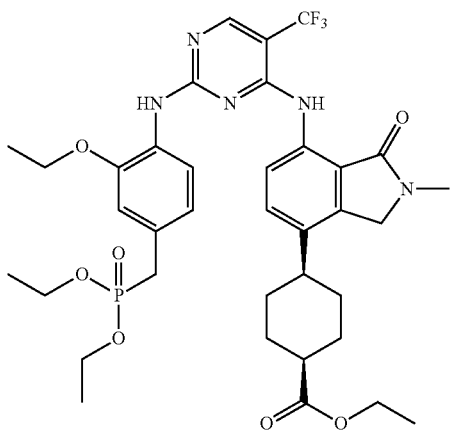 [SMILES: CCOc1cc(CP(=O)(OCC)OCC)ccc1Nc1ncc(C(F)(F)F)c(Nc2ccc([C@H]3CC[C@@H](C(=O)OCC)CC3)c3c2C(=O)N(C)C3)n1]

Example 244

Ethyl cis-4-(7-{[2-({4-[(diethoxyphosphoryl)methyl]-2-ethoxyphenyl}amino)-5-(trifluoromethyl)pyrimidin-4-yl]amino}-2-methyl-1-oxo-2,3-dihydro-1H-isoindol-4-yl)cyclohexanecarboxylate The title compound was prepared according to the procedure for Example 102 using diethyl (4-{[4-chloro-5-(trifluoromethyl)pyrimidin-2-yl]amino}-3-ethoxybenzyl)phosphonate (Compound 244A 123.2 mg, 0.26 mmol) and ethyl cis-4-(7-amino-2-methyl-1-oxo-2,3-dihydro-1H-isoindol-4-yl)cyclohexanecarboxylate (100.0 mg, 0.32 mmol). The reaction mixture was concentrated in vacuo and purified by on an ISCO CombiFlash®Rf System eluting with: 0→5% MeOH in DCM] to afford 143.3 mg (73%) of the desired product. $^1$H NMR (400 MHz, MeOD) δ ppm 8.44 (d, J=10.36 Hz, 1H), 8.35 (s, 1H), 7.89 (d, J=8.34 Hz, 1H), 7.24 (d, J=8.59 Hz, 1H), 7.06 (t, J=2.15 Hz, 1H), 6.92 (dt, J=8.21, 2.21 Hz, 1H), 4.52 (s, 2H), 4.26 (q, J=7.16 Hz, 2H), 4.05-4.19 (m, 6H), 3.29 (s, 2H), 3.19 (s, 3H), 2.79 (br. s., 1H), 2.63-2.73 (m, 1H), 2.30 (d, J=7.33 Hz, 2H), 1.76 (d, J=6.06 Hz, 6H), 1.42 (t, J=6.95 Hz, 3H), 1.27-1.38 (m, 9H). MS (ES+): m/z 749.30/750.31 (100/25) [MH$^+$] HPLC: t$_R$=1.82 min (Micromass TOF: polar_3 min).

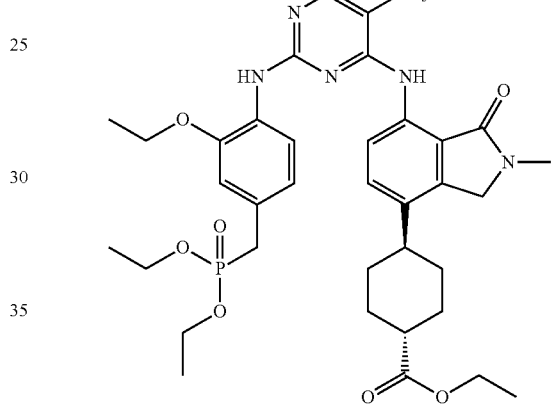

Example 245

Ethyl trans-4-(7-{[2-({4-[(diethoxyphosphoryl)methyl]-2-ethoxyphenyl}amino)-5-(trifluoromethyl)pyrimidin-4-yl]amino}-2-methyl-1-oxo-2,3-dihydro-1H-isoindol-4-yl)cyclohexanecarboxylate The title compound was prepared according to the procedure for Example 102 using of diethyl (4-{[4-chloro-5-(trifluoromethyl)pyrimidin-2-yl]amino}-3-ethoxybenzyl)phosphonate (Compound 244A, 29.84 mg, 0.064 mmol) and ethyl trans-4-(7-amino-2-methyl-1-oxo-2,3-dihydro-1H-isoindol-4-yl)cyclohexanecarboxylate (22.2 mg, 0.070 mmol). 31.2 mg (65%) of the desired product was isolated after work-up/chromatography. $^1$H NMR (400 MHz, MeOD) δ ppm 8.48 (d, J=7.83 Hz, 1H), 8.35 (s, 1H), 7.87 (d, J=8.08 Hz, 1H), 7.38 (d, J=8.84 Hz, 1H), 7.05 (s, 1H), 6.94 (dt, J=8.08, 2.27 Hz, 1H), 4.52 (s, 2H), 4.04-4.22 (m, 8H), 3.28 (s, 2H), 3.19 (s, 3H), 2.63 (t, J=11.62 Hz, 1H), 2.42-2.54 (m, 1H), 2.13 (d, J=14.15 Hz, 2H), 1.90-1.99 (m, 2H), 1.54-1.77 (m, 4H), 1.41 (t, J=6.95 Hz, 3H), 1.24-1.33 (m, 9H). MS (ES$^+$): m/z 748.26/749.29 (100/98) [MH$^+$]. HPLC: t$_R$=1.80 min (Micromass TOF: polar_3 min).

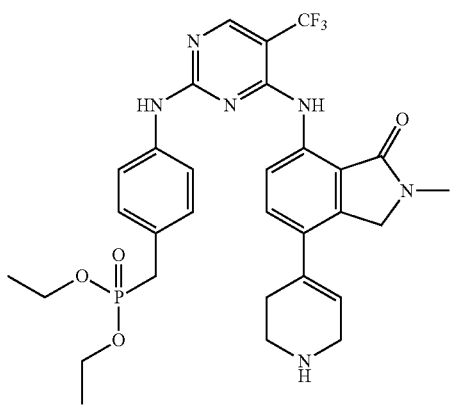 [SMILES: CCOP(=O)(Cc1ccc(Nc2ncc(C(F)(F)F)c(Nc3ccc(C4=CCNCC4)c4c3C(=O)N(C)C4)n2)cc1)OCC]

Example 246

Diethyl(4-{[4-{[2-methyl-3-oxo-7-(1,2,3,6-tetrahydropyridin-4-yl)-2,3-dihydro-1H-isoindol-4-yl]amino}-5-(trifluoromethyl)pyrimidin-2-yl]amino}benzyl)phosphonate To tert-butyl 4-(7-{[2-({4-[(diethoxyphosphoryl)methyl]phenyl}amino)-5-(trifluoromethyl)pyrimidin-4-yl]amino}-2-methyl-1-oxo-2,3-dihydro-1H-isoindol-4-yl)-3,6-dihydropyridine-1(2H)-carboxylate (Compound 246A, 180 mg, 0.25 mmol) was added methylene chloride (1 mL) and trifluoroacetic acid (1 mL). The mixture was stirred at room temperature for 1 hour, after which, the reaction mixture was concentrated and purified by MDP. $^1$H NMR (400 MHz, methanol-d4) δ=1.27 (t, J=6.9 Hz, 6H), 2.77-2.85 (m, 2H), 3.19 (s, 3H), 3.29 (d, J=21.5 Hz, 2H), 3.50 (t, J=6.1 Hz, 2H), 3.88-3.94 (m, 2H), 4.01-4.17 (m, 4H), 4.59 (s, 2H), 6.02 (dt, J=3.3, 1.7 Hz, 1H), 7.35 (dd, J=8.5, 2.4 Hz, 2H), 7.50 (d, J=8.8 Hz, 1H), 7.57 (d, J=8.1 Hz, 2H), 8.35-8.43 (m, 1H), 8.72 (br. s., 1H). MS (ES$^+$): m/z 631.23 (100) [MH$^+$]; HPLC: t$_R$=0.68 min (UPLC, purity).

Compound 246A: tert-Butyl 4-(7-{[2-({4-[(diethoxyphosphoryl)methyl]phenyl}amino)-5-(trifluoromethyl)pyrimidin-4-yl]amino}-2-methyl-1-oxo-2,3-dihydro-1H-isoindol-4-yl)-3,6-dihydropyridine-1(2H)-carboxylate Diethyl[4-({4-[(7-bromo-2-methyl-3-oxo-2,3-dihydro-1H-isoindol-4-yl)amino]-5-(trifluoromethyl)pyrimidin-2-yl}amino)benzyl]phosphonate (200.0 mg, 0.3183 mmol), 4-(4,4,5,5-tetramethyl-[1,3,2]dioxaborolan-2-yl)-3,6-dihydro-2H-pyridine-1-carboxylic acid tert-butyl ester (Tetrahedron Letters, 2000, 44, pp 3705-3708, 147.6 mg, 0.4774 mmol), potassium carbonate (132.0 mg, 0.9548 mmol) [1,1-bis(diphenylphosphino)ferrocene]dichloropalladium(II), complex with dichloromethane (1:1) (26.0 mg, 0.03183 mmol), 1,4-dioxane (1.0 mL) and water (0.25 mL) were mixed and heated in microwave at 100° C. for 30 minutes. The crude mixture was worked up with ethyl acetate, water and brine. Column chromatography was used to purify the title compound (0-3% methanol in methylene chloride). MS (ES$^+$): m/z 731.33 (100) [MH$^+$]; HPLC: t$_R$=1.53 min (UPLC, Analytical).

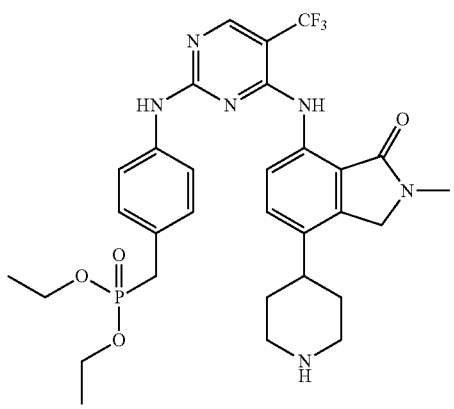 [SMILES: CCOP(=O)(Cc1ccc(Nc2ncc(C(F)(F)F)c(Nc3ccc(C4CCNCC4)c4c3C(=O)N(C)C4)n2)cc1)OCC]

Example 247

Diethyl(4-{[4-{[2-methyl-3-oxo-7-(piperidin-4-yl)-2,3-dihydro-1H-isoindol-4-yl]amino}-5-(trifluoromethyl)pyrimidin-2-yl]amino}benzyl)phosphonate A mixture of diethyl(4-{[4-{[2-methyl-3-oxo-7-(1,2,3,6-tetrahydropyridin-4-yl)-2,3-dihydro-1H-isoindol-4-yl]amino}-5-(trifluoromethyl)pyrimidin-2-yl]amino}benzyl) phosphonate (Example 246, 30.0 mg, 0.0476 mmol) and platinum dioxide (32.4 mg, 0.143 mmol) in ethyl acetate (2 mL) was stirred under 1 atmosphere of hydrogen at room temperature overnight. The crude mixture was purified by MDP to obtain the title compound as a trifluoroacetic acid salt (2.7 mg, 9.0% yield). $^1$H NMR (400 MHz, methanol-d4) δ=1.26 (t, J=7.1 Hz, 6H), 1.95-2.14 (m, 4H), 2.99 (td, J=10.5, 5.4 Hz, 1H), 3.20 (s, 5H), 3.29 (d, J=21.5 Hz, 2H), 3.55 (d, J=12.9 Hz, 2H), 3.97-4.13 (m, 4H), 4.55 (s, 2H), 7.34 (dd, J=8.6, 2.5 Hz, 2H), 7.42 (d, J=8.8 Hz, 1H), 7.58 (d, J=8.1 Hz, 2H), 8.33-8.41 (m, 1H), 8.71 (br. s., 1H). MS (ES$^+$): m/z 633.20 (100) [MH$^+$]; HPLC: t$_R$=0.70 min (UPLC, purity).

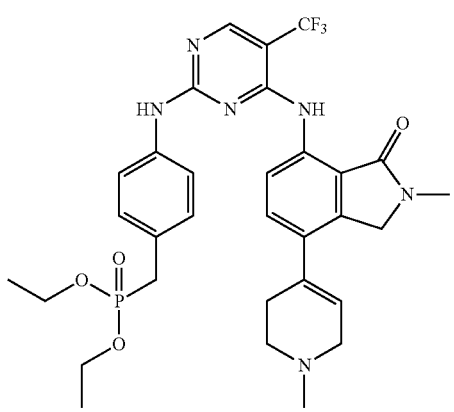 [SMILES: CCOP(=O)(Cc1ccc(Nc2ncc(C(F)(F)F)c(Nc3ccc(C4=CCN(C)CC4)c4c3C(=O)N(C)C4)n2)cc1)OCC]

Example 248

Diethyl(4-{[4-{[2-methyl-7-(1-methyl-1,2,3,6-tetrahydropyridin-4-yl)-3-oxo-2,3-dihydro-1H-isoindol-4-yl]amino}-5-(trifluoromethyl)pyrimidin-2-yl]amino}benzyl)phosphonate Diethyl(4-{[4-{[2-methyl-3-oxo-7-(1,2,3,6-tetrahydropyridin-4-yl)-2,3-dihydro-1H-isoindol-4-yl]amino}-5-(trifluoromethyl)pyrimidin-2-yl]amino}benzyl)phosphonate (Example 246, 20.0 mg, 0.0317 mmol), formic acid (5 uL, 0.1 mmol) and formaldehyde (3.0 uL, 0.11 mmol) were mixed in methanol (1.0 mL) at room temperature for 30 minutes. Sodium cyanoborohydride (20.0 mg, 0.318 mmol) was added and the mixture was stirred at room temperature overnight. The crude mixture was purified by MDP to obtain the title compound as a trifluoroacetic acid salt (7.3 mg, 35.7% yield). $^1$H NMR (400 MHz, methanol-d4) δ=1.27 (t, J=7.1 Hz, 6H), 2.87 (br. s., 1H), 2.93 (br. s., 1H), 3.05 (s, 3H), 3.19 (s, 3H), 3.29 (d, J=21.5 Hz, 2H), 3.36-3.46 (m, 1H), 3.73 (br. s., 1H), 3.80-3.90 (m, 1H), 4.00-4.16 (m, 5H), 4.59 (s, 2H), 5.95-6.04 (m, 1H), 7.34 (dd, J=8.6, 2.5 Hz, 2H), 7.50 (d, J=8.6 Hz, 1H), 7.58 (d, J=8.1 Hz, 2H), 8.36-8.43 (m, 1H), 8.75 (br. s., 1H). MS (ES$^+$): m/z 645.23 (100) [MH$^+$]; HPLC: $t_R$=0.69 min (UPLC, purity).

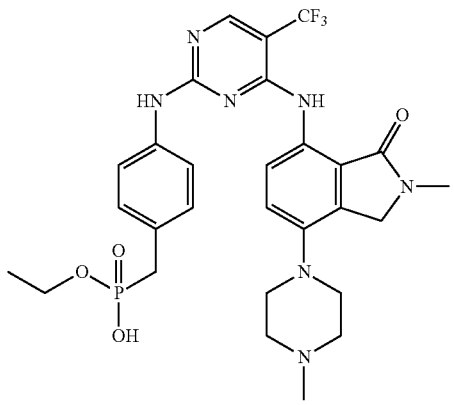 [SMILES: CCOP(=O)(O)Cc1ccc(Nc2ncc(C(F)(F)F)c(Nc3ccc(N4CCN(C)CC4)c4c3C(=O)N(C)C4)n2)cc1]

Example 249

Ethyl hydrogen(4-{[4-{[2-methyl-7-(4-methylpiperazin-1-yl)-3-oxo-2,3-dihydro-1H-isoindol-4-yl]amino}-5-(trifluoromethyl)pyrimidin-2-yl]amino}benzyl)phosphonate The title compound was prepared according to the procedure for Example 254 using Diethyl [4-({4-[(7-bromo-2-methyl-3-oxo-2,3-dihydro-1H-isoindol-4-yl)amino]-5-(trifluoromethyl)pyrimidin-2-yl}amino)benzyl]phosphonate and N-methylpiperazine. MS (ES$^+$): m/z 620.28 (100) [MH$^+$]; HPLC: $t_R$=0.61 min (UPLC, purity).

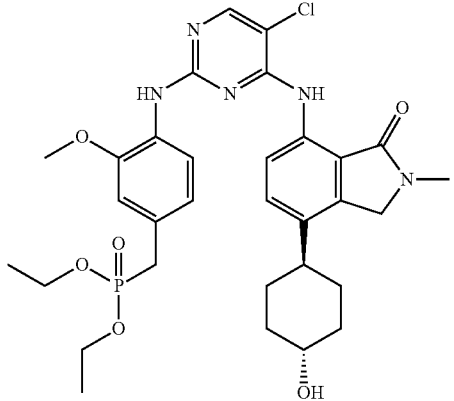 [SMILES: CCOP(=O)(Cc1ccc(Nc2ncc(Cl)c(Nc3ccc([C@H]4CC[C@H](O)CC4)c4c3C(=O)N(C)C4)n2)c(OC)c1)OCC]

Example 250

Diethyl{4-[(5-chloro-4-{[7-(trans-4-hydroxycyclohexyl)-2-methyl-3-oxo-2,3-dihydro-1H-isoindol-4-yl]amino}pyrimidin-2-yl)amino]-3-methoxybenzyl}phosphonate A solution of diethyl(4-amino-3-methoxybenzyl)phosphonate (75.1 mg, 0.275 mmol) and 7-[(2,5-dichloropyrimidin-4-yl)amino]-4-(trans-4-hydroxycyclohexyl)-2-methyl-2,3-dihydro-1H-isoindol-1-one (49.7 mg, 0.122 mmol) in TFE (4 mL) was charged with TFA (65.3 mg, 0.573 mmol) and irradiated under microwave heating [Biotage, 105° C.] for 2 h. The reaction mixture was transferred to a round bottom flask and concentrated in vacuo. The crude was adsorbed onto a pre-filled solid loading cartridge (RediSepRf 2.5 g) and purified using the Teledyne/ISCO system (RediSepRf 24 g silica), eluting first with 40-100% EtOAc:Heptane and then 0-5% 7N NH$_3$(MeOH):EtOAc. Additional purification was performed using mass-directed purification (under acidic conditions; TFA). The desired fractions were combined and concentrated in vacuo. The material was passed through an SPE cartridge [Phenomenex Strata SCX, 1 gram/6 mL size], eluting first with MeOH and then a 1:1 7N NH$_3$ (MeOH):MeOH mixture, which gave the title material as a yellow solid, 29.6 mg (37%). $^1$H NMR (400 MHz, MeOD) δ ppm 8.52 (d, J=8.6 Hz, 1H), 8.07 (s, 1H), 7.99 (d, J=8.3 Hz, 1H), 7.38 (d, J=8.8 Hz, 1H), 7.02 (t, J=2.0 Hz, 1H), 6.93 (dt, J=8.3, 2.3 Hz, 1H), 4.50 (s, 2H), 4.01-4.14 (m, 4H), 3.92 (s, 3H), 3.67 (tt, J=10.9, 4.4 Hz, 1H), 3.28 (d, J=19.7 Hz, 2H), 3.17 (s, 3H), 2.57 (tt, J=12.0, 3.3 Hz, 1H), 2.09 (dd, J=12.0, 2.7 Hz, 2H), 1.89 (d, J=12.6 Hz, 2H), 1.67 (dtd, J=13.2, 12.9, 2.8 Hz, 2H), 1.38-1.52 (m, 2H), 1.29 (t, J=7.1 Hz, 6H). [Three exchangeable protons are absent due to solvent.] MS (ES$^+$): m/z 644.21/646.23 (100/81) [MH$^+$]. HPLC: $t_R$=1.39 min (TOF, polar_3 min).

Compound 250A: 7-[(2,5-Dichloropyrimidin-4-yl)amino]-4-(trans-4-hydroxycyclohexyl)-2-methyl-2,3-dihydro-1H-isoindol-1-one A solution of 2,4,5-trichloropyrimidine (550.5 mg, 3.001 mmol) and 7-amino-4-(trans-4-hydroxycyclohexyl)-2-methyl-2,3-dihydro-1H-isoindol-1-one (166.6 mg, 0.6400 mmol) in DMA (8 mL) was charged with DIPEA (1 mL, 6 mmol) and then heated to 100° C. overnight. The reaction mixture was cooled to ambient temperature, diluted with EtOAc, and poured into water. The material was extracted thrice with EtOAc and the combined organic layers were washed with brine, dried over anhydrous Na$_2$SO$_4$, filtered, and concentrated in vacuo. The crude material was adsorbed onto a pre-filled solid loading cartridge [RediSepRf 25 gram] and purified using the Teledyne/ISCO system [RediSepRf 12 gram silica], eluting first with 0-100% EtOAc:CH$_2$Cl$_2$ and then 0-5% MeOH:CH$_2$Cl$_2$. The desired fractions were pooled together and concentrated in vacuo, giving the title material as a brown solid, 173.0 mg. $^1$H NMR (400 MHz, DMSO-d$_6$) δ ppm 11.07 (s, 1H), 8.52 (s, 1H), 8.43 (d, J=8.6 Hz, 1H), 7.52 (d, J=8.6 Hz, 1H), 4.60 (d, J=4.5 Hz, 1H), 4.57 (s, 2H), 3.48 (ddd, J=15.0, 6.4, 4.4 Hz, 1H), 3.10 (s, 3H), 1.93 (br s, 2H), 1.77 (br d, J=12.4 Hz, 2H), 1.55 (dtd, J=13.0, 12.7, 2.5 Hz, 2H), 1.22-1.37 (m, 3H). MS (ES$^+$): m/z 407.10/409.10 (100/72) [MH$^+$]. HPLC: $t_R$=1.40 min (TOF, polar_3 min).

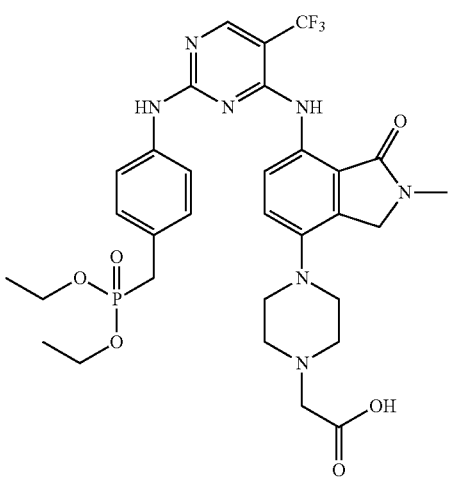 [SMILES: CCOP(=O)(Cc1ccc(Nc2ncc(C(F)(F)F)c(Nc3ccc(N4CCN(CC(=O)O)CC4)c4c3C(=O)N(C)C4)n2)cc1)OCC]

Example 251

[4-(7-{[2-({4-[(Diethoxyphosphoryl)methyl]phenyl}amino)-5-(trifluoromethyl)pyrimidin-4-yl]amino}-2-methyl-1-oxo-2,3-dihydro-1H-isoindol-4-yl)piperazin-1-yl]acetic acid A mixture of diethyl[4-({4-[(7-bromo-2-methyl-3-oxo-2,3-dihydro-1H-isoindol-4-yl)amino]-5-(trifluoromethyl)pyrimidin-2-yl}amino)benzyl]phosphonate (200.0 mg, 0.3183 mmol), piperazine-1-acetic acid tert-butyl ester (382 mg, 1.91 mmol), bis(dibenzylideneacetone)palladium (58.29 mg, 0.06366 mmol), 2,2'-bis-diphenylphosphanyl-[1,1']binaphthalenyl (118.9 mg, 0.1910 mmol), $Cs_2CO_3$ (0.3111 g, 0.9548 mmol) in 1,4-dioxane (20 mL) was evacuated and purged with nitrogen three times. The mixture was stirred at 100° C. for 2 days. The crude mixture was purified by MDP. The purified ester was taken up in methylene chloride (1.2 mL) and trifluoroacetic acid (0.6 mL) and the mixture was stirred at room temperature for 3 hours. The crude product was purified by MDP to obtain the title compound as a trifluoroacetic acid salt. $^1$H NMR (400 MHz, methanol-d4) δ=1.27 (t, J=7.1 Hz, 6H), 3.19 (s, 3H), 3.29 (d, J=21.5 Hz, 2H), 3.41 (br. s., 4H), 3.60 (br. s., 4H), 4.07 (qd, J=7.2, 6.9 Hz, 4H), 4.17 (s, 2H), 4.51 (s, 2H), 7.26 (d, J=9.1 Hz, 1H), 7.34 (d, J=6.6 Hz, 2H), 7.57 (d, J=7.8 Hz, 2H), 8.36 (s, 1H), 8.69 (br. s., 1H). MS (ES$^+$): m/z 692.27 (100) [MH$^+$]; HPLC: $t_R$=0.78 min (UPLC, purity).

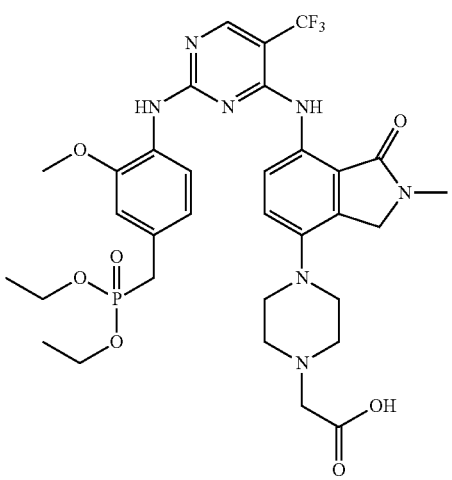 [SMILES: CCOP(=O)(Cc1ccc(Nc2ncc(C(F)(F)F)c(Nc3ccc(N4CCN(CC(=O)O)CC4)c4c3C(=O)N(C)C4)n2)c(OC)c1)OCC]

Example 252

[4-(7-{[2-({4-[(Diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)piperazin-1-yl]acetic acid (OSIP 759590AE1/6822-29-2)

The title compound was prepared according to the procedure for Example 251 using diethyl [4-({4-[(7-bromo-2-methyl-3-oxo-2,3-dihydro-1H-isoindol-4-yl)amino]-5-(trifluoromethyl)pyrimidin-2-yl}amino)-3-methoxybenzyl]phosphonate and piperazine-1-acetic acid tert-butyl ester. MS (ES$^+$): m/z 722.28 (100) [MH$^+$]; HPLC: $t_R$=0.80 min (UPLC, purity).

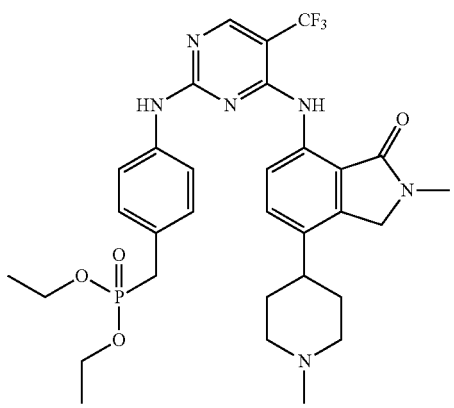

Example 253

Diethyl(4-{[4-{[2-methyl-7-(1-methylpiperidin-4-yl)-3-oxo-2,3-dihydro-1H-isoindol-4-yl]amino}-5-(trifluoromethyl)pyrimidin-2-yl]amino}benzyl)phosphonate The title compound was prepared according to the procedure for Example 247 using diethyl (4-{[4-{[2-methyl-1,2,3,6-tetrahydropyridin-4-yl)-3-oxo-2,3-dihydro-1H-isoindol-4-yl]amino}-5-(trifluoromethyl)pyrimidin-2-yl]amino}benzyl)phosphonate (Example 248, 24 mg, 0.037 mmol). After purification MDP, the title compound was isolated as its trifluoroacetic acid salt (12.0 mg, 50% yield). $^1$H NMR (400 MHz, methanol-d4) δ=1.26 (t, J=7.1 Hz, 6H), 2.01-2.19 (m, 4H), 2.96 (s, 4H), 3.11-3.25 (m, 5H), 3.29 (d, J=21.5 Hz, 2H), 3.62-3.72 (m, 2H), 3.98-4.13 (m, 4H), 4.55 (s, 2H), 7.34 (dd, J=8.5, 2.4 Hz, 2H), 7.40 (d, J=8.8 Hz, 1H), 7.58 (d, J=8.3 Hz, 2H), 8.38 (s, 1H), 8.70 (br. s., 1H). MS (ES$^+$): m/z 647.27 (100) [MH$^+$]; HPLC: $t_R$=0.70 min (UPLC, purity).

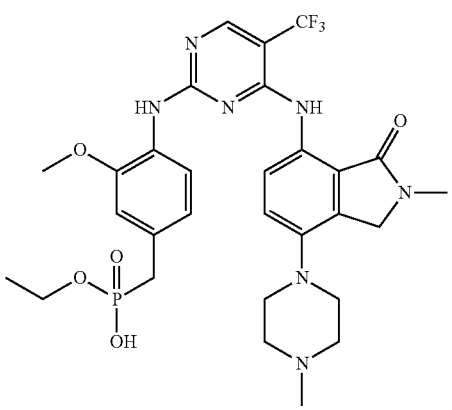 [SMILES: CCOP(=O)(O)Cc1ccc(Nc2ncc(C(F)(F)F)c(Nc3ccc(N4CCN(C)CC4)c4c3C(=O)N(C)C4)n2)c(OC)c1]

Example 254

Ethyl hydrogen(3-methoxy-4-{[4-{[2-methyl-7-(4-methylpiperazin-1-yl)-3-oxo-2,3-dihydro-1H-isoindol-4-yl]amino}-5-(trifluoromethyl)pyrimidin-2-yl]amino}benzyl)phosphonate A mixture of diethyl[4-({4-[(7-bromo-2-methyl-3-oxo-2,3-dihydro-1H-isoindol-4-yl)amino]-5-(trifluoromethyl)pyrimidin-2-yl}amino)-3-methoxybenzyl]phosphonate (200.0 mg, 0.3038 mmol), 1-methylpiperazine (202 uL, 1.82 mmol), bis(dibenzylideneacetone)palladium(0) (34.9 mg, 0.0608 mmol), Cs$_2$CO$_3$ (297 mg, 0.911 mmol) in 1,4-dioxane (20 mL) was evacuated and purged with nitrogen three times and allowed to stir at 100° C. overnight. The reaction mixture was passed through a Thiol-SPE cartridge to remove Pd and the crude material was purified by MDP. The resulting material, diethyl(3-methoxy-4-{[4-{[2-methyl-7-(4-methylpiperazin-1-yl)-3-oxo-2,3-dihydro-1H-isoindol-4-yl]amino}-5-(trifluoromethyl)pyrimidin-2-yl]amino}benzyl)phosphonate, was taken up in conc. HCl (2.0 mL) and heated at 80° C. for 2 hours. The crude material was again purified by MDP to obtain the title compound (2.3 mg, 1.2% yield). $^1$H NMR (400 MHz, methanol-d4) δ=1.26 (t, J=6.9 Hz, 3H), 2.99 (s, 3H), 3.17 (s, 3H), 3.18 (d, J=20.7 Hz, 2H), 3.24-3.29 (m, 2H), 3.33-3.36 (m, 2H), 3.38-3.46 (m, 2H), 3.58 (br. s., 2H), 3.88 (s, 3H), 4.03 (quin, J=7.1 Hz, 2H), 4.48 (s, 2H), 7.00 (d, J=8.1 Hz, 1H), 7.10 (s, 1H), 7.21 (d, J=8.8 Hz, 1H), 7.60 (d, J=7.6 Hz, 1H), 8.32 (s, 1H), 8.39 (br. s., 1H). MS (ES$^+$): m/z 650.29 (100) [MH$^+$]; HPLC: t$_R$=0.63 min (UPLC, purity).

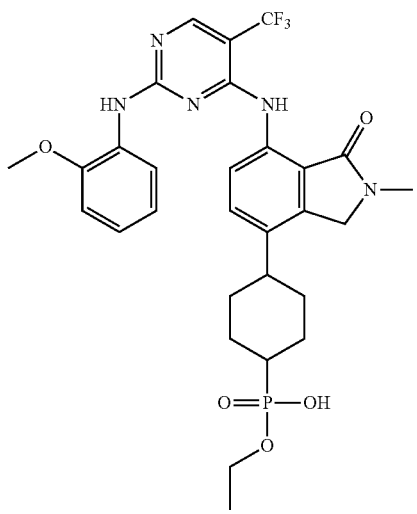

Example 255

Ethyl hydrogen{4-[7-({2-[(2-methoxyphenyl)amino]-5-(trifluoromethyl)pyrimidin-4-yl}amino)-2-methyl-1-oxo-2,3-dihydro-1H-isoindol-4-yl]cyclohexyl}phosphonate trifluoroacetate A solution of diethyl{4-[7-({2-[(2-methoxyphenyl)amino]-5-(trifluoromethyl)pyrimidin-4-yl}amino)-2-methyl-1-oxo-2,3-dihydro-1H-isoindol-4-yl]cyclohexyl}phosphonate (Example 193, 20.0 mg, 0.0309 mmol) and sodium iodide (27.5 mg, 0.183 mmol) in 2-butanone (2 mL) was subjected to microwave heating [Biotage, 120° C.] for 6 h. A solid had precipitated, which was filtered off and washed several times with ice cold acetone. The material was submitted for mass-directed purification (under acidic conditions; TFA). The desired fractions were combined and concentrated in vacuo, giving the title material as a pale yellow solid, as a mixture of cis and trans isomers, 8.4 mg. $^1$H NMR (400 MHz, MeOD) δ ppm 8.35 (br s, 2H), 7.68-7.82 (m, 1H), 7.21-7.40 (m, 2H), 7.14 (d, J=8.1 Hz, 1H), 6.95-7.09 (m, 1H), 4.51 (s, 2H), 4.05-4.21 (m, 2H), 3.88 (s, 3H), 3.18 (s, 3H), 2.58-2.76 (m, 1H), 2.02-2.33 (m, 4H), 1.77-2.00 (m, 2H), 1.55-1.74 (m, 2H), 1.26-1.43 (m, 4H). MS (ES$^+$): m/z 620.18 (100) [MH$^+$]. HPLC: t$_R$=1.51 min (TOF, polar_3 min). **[NMR is only a rough estimate of where peaks should fall; integration is off as the material is a mixture of cis and trans isomers.]

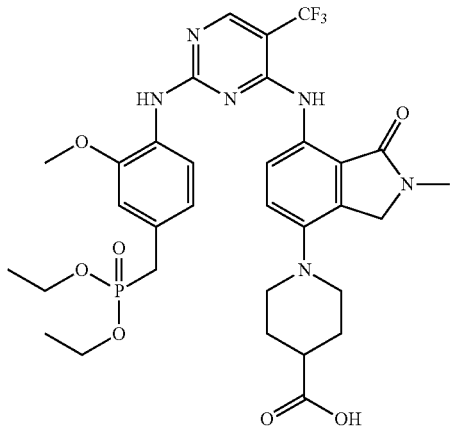 [SMILES: CCOP(=O)(Cc1ccc(Nc2ncc(C(F)(F)F)c(Nc3ccc(N4CCC(C(=O)O)CC4)c4c3C(=O)N(C)C4)n2)c(OC)c1)OCC]

Example 256

1-(7-{[2-({4-[(Diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)piperidine-4-carboxylic acid A mixture of diethyl(4-{[4-chloro-5-(trifluoromethyl)pyrimidin-2-yl]amino}-3-methoxybenzyl)phosphonate (30.0 mg, 0.0661 mmol), methyl 1-(7-amino-2-methyl-1-oxo-2,3-dihydro-1H-isoindol-4-yl)piperidine-4-carboxylate (Compound 256A, 20.0 mg, 0.0659 mmol), trifluoroacetic acid (15.2 uL, 0.198 mmol) and trifluoroethanol (1.0 mL, 14 mmol) was irradiated in microwave reactor at 105° C. for 30 minutes. The crude mixture was concentrated to dryness, taken up in THF (0.1 mL), methanol (0.1 mL) and treated with a solution of lithium hydroxide monohydrate (27.7 mg, 0.659 mmol) in water (0.1 mL). The mixture was stirred at room temperature overnight. The crude was purified by MDP to obtain the title compound as a trifluoroacetic acid salt (7.2 mg, 15.5% yield). $^1$H NMR (400 MHz, DMSO-d6) δ=1.29 (t, J=7.1 Hz, 6H), 1.83-1.97 (m, 2H), 2.03-2.14 (m, 2H), 2.46-2.57 (m, 1H), 2.93 (t, J=10.5 Hz, 2H), 3.18 (s, 3H), 3.34 (d, J*=18.7 Hz, 2H), 3.40 (d, J=12.1 Hz, 2H), 3.90 (s, 3H), 4.10 (quin, J=7.3 Hz, 4H), 4.52 (s, 2H), 6.94-7.01 (m, 1H), 7.09-7.17 (m, 2H), 7.67 (d, J=8.1 Hz, 1H), 8.27-8.47 (m, 2H). MS (ES$^+$): m/z 707.19 (100) [MH$^+$]; HPLC: $t_R$=1.01 min (UPLC, purity).

Compound 256A: Methyl 1-(7-amino-2-methyl-1-oxo-2,3-dihydro-1H-isoindol-4-yl)piperidin-4-carboxylate A mixture of methyl 1-(2-methyl-7-nitro-1-oxo-2,3-dihydro-1H-isoindol-4-yl)piperidine-4-carboxylate (Compound 256B, 33 mg, 0.099 mmol) and palladium/C in methanol (1.0 mL) was stirred under 1 atmosphere of hydrogen at room temperature overnight. The reaction mixture was filtered through celite, concentrated in vacuo and used directly in next step without further purification (20 mg, 72% yield). MS (ES$^+$): m/z 304.20 (100) [MH$^+$]; HPLC: $t_R$=0.58 min (UPLC, Analytical).

Compound 256B: Methyl 1-(2-methyl-7-nitro-1-oxo-2,3-dihydro-1H-isoindol-4-yl)piperidine-4-carboxylate 4-Bromo-2-methyl-7-nitro-2,3-dihydro-1H-isoindol-1-one (320.0 mg, 1.180 mmol), methyl isonipecotate (1.595 mL, 11.80 mmol), DIPEA (2.056 mL, 11.80 mmol) and DMF (5 mL) were mixed and heated in sealed tube at 90° C. for 3 days. The crude mixture was purified by MDP under basic conditions to obtain the title compound (33 mg, 8.4% yield). MS (ES$^+$): m/z 334.16 (100) [MH$^+$]; HPLC: $t_R$=0.80 min (UPLC, Analytical).

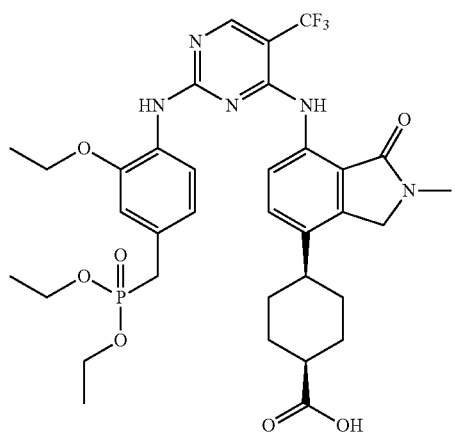 [SMILES: CCOc1cc(CP(=O)(OCC)OCC)ccc1Nc1ncc(C(F)(F)F)c(Nc2ccc([C@H]3CC[C@@H](C(=O)O)CC3)c3c2C(=O)N(C)C3)n1]

Example 257 cis-4-(7-{[2-({4-[(Diethoxyphosphoryl)methyl]-2-ethoxyphenyl}amino)-5-(trifluoromethyl)pyrimidin-4-yl]amino}-2-methyl-1-oxo-2,3-dihydro-1H-isoindol-4-yl)cyclohexanecarboxylic acid Ethyl cis-4-(7-{[2-({4-[(diethoxyphosphoryl)methyl]-2-ethoxyphenyl}amino)-5-(trifluoromethyl)pyrimidin-4-yl]amino}-2-methyl-1-oxo-2,3-dihydro-1H-isoindol-4-yl)cyclohexanecarboxylate (Example 244, 72.0 mg, 0.096 mmol) was taken up in THF (0.13 mL, 1.60 mmol) and MeOH (0.13 mL, 3.20 mmol). This was treated with a solution of lithium hydroxide, monohydrate (20.2 mg, 0.48 mmol) in H$_2$O (0.13 mL, 7.2 mmol) and was allowed to stir at rt for 30 hrs. The reaction was concentrated in vacuo to a solid and was purified by CombiFlash®Rf 4X Organic Purification System [24 g RediSep® Normal-phase GOLD Silica Flash Column, dried loaded, elution gradient: 0→5% MeOH in DCM] to afford 68.6 mg (99%) of the desired product. $^1$H NMR (400 MHz, MeOD) δ ppm 8.43 (d, J=9.09 Hz, 1H), 8.34 (s, 1H), 7.88 (d, J=8.34 Hz, 1H), 7.26 (d, J=8.84 Hz, 1H), 7.03 (t, J=2.02 Hz, 1H), 6.90 (dt, J=8.21, 2.21 Hz, 1H), 4.51 (s, 2H), 4.03-4.17 (m, 6H), 3.27 (s, 2H), 3.18 (s, 3H), 2.74 (br. s., 1H), 2.61-2.70 (m, 1H), 2.30 (d, J=12.38 Hz, 2H), 1.66-1.82 (m, 6H), 1.41 (t, J=6.95 Hz, 3H), 1.28 (t, J=7.07 Hz, 6H). MS (ES$^+$): m/z 720.22/721.26 (100/98) [MH$^+$]. HPLC: $t_R$=1.62 min (Micromass TOF: polar_3 min).

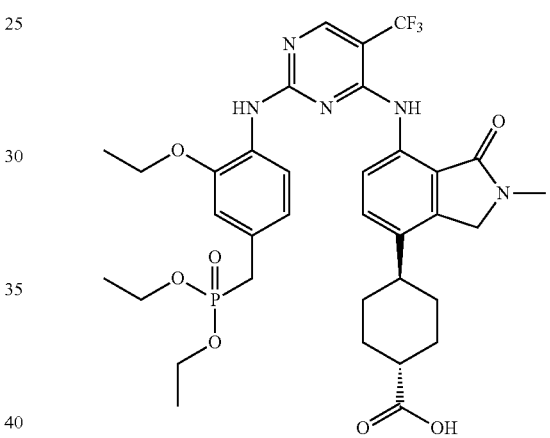

Example 258

Trans-4-(7-{[2-({4-[(diethoxyphosphoryl)methyl]-2-ethoxyphenyl}amino)-5-(trifluoromethyl)pyrimidin-4-yl]amino}-2-methyl-1-oxo-2,3-dihydro-1H-isoindol-4-yl)cyclohexanecarboxylic acid Ethyl trans-4-(7-{[2-({4-[(diethoxyphosphoryl)methyl]-2-ethoxyphenyl}amino)-5-(trifluoromethyl)pyrimidin-4-yl]amino}-2-methyl-1-oxo-2,3-dihydro-1H-isoindol-4-yl)cyclohexanecarboxylate (Example 245, 23.4 mg, 0.031 mmol) was taken up in THF (0.042 mL, 0.52 mmol) and MeOH (0.042 mL, 1.0 mmol). This was treated with a solution of lithium hydroxide, monohydrate (6.57 mg, 0.16 mmol) in H$_2$O (0.042 mL, 2.30 mmol) and allowed to stir at rt for 30 hrs. The reaction was concentrated in vacuo to a solid and was purified by CombiFlash®Rf 4X Organic Purification System [24 g RediSep® Normal-phase GOLD Silica Flash Column, dried loaded, elution gradient: 0→5% MeOH in DCM] to afford 22.3 mg (99%) of the desired product. $^1$H NMR (400 MHz, MeOD) δ ppm 4.54 (s, 1H), 4.05-4.21 (m, 6H), 3.29 (s, 2H), 3.20 (s, 3H), 2.60-2.69 (m, 1H), 2.38-2.48 (m, 1H), 2.15 (d, J=11.87 Hz, 2H), 1.91-1.98 (m, 2H), 1.56-1.77 (m, 4H), 1.43 (t, J=6.95 Hz, 3H), 1.30 (t, 6H). MS (ES+): m/z 720.22/721.25 (100/98) [MH+]. HPLC: $t_R$=1.54 min (Micromass TOF: polar_3 min)

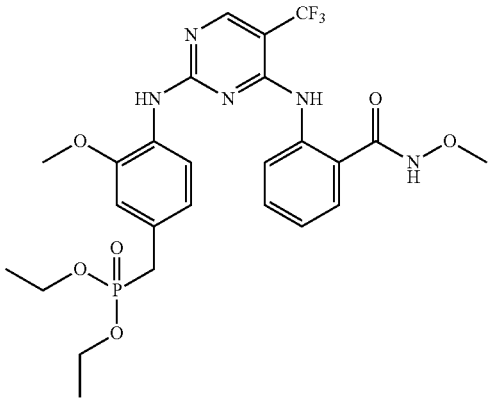 [SMILES: CCOP(=O)(Cc1ccc(Nc2ncc(C(F)(F)F)c(Nc3ccccc3C(=O)NOC)n2)c(OC)c1)OCC]

Example 259

Diethyl(3-methoxy-4-{[4-{[2-(methoxycarbamoyl)phenyl]amino}-5-(trifluoromethyl)pyrimidin-2-yl]amino}benzyl)phosphonate The title compound was prepared according to the procedure for Example 102 using diethyl (4-{[4-chloro-5-(trifluoromethyl)pyrimidin-2-yl]amino}-3-methoxybenzyl)phosphonate (0.060 g, 0.13 mmol) and 2-amino-N-methoxybenzamide (Compound 259A, 0.0242 g, 0.145 mmol). The crude material was purified on an Isco Combiflash unit using 0→5% MeOH in DCM as eluent to afford 55.7 mg of the title compound (72%). $^1$H NMR (400 MHz, DMSO-d6) δ 11.95 (s, 1H), 10.70 (br. s., 1H), 8.79 (br. s., 1H), 8.38 (s, 1H), 7.48-7.57 (m, 2H), 7.42 (t, J=7.71 Hz, 1H), 7.09 (t, J=7.33 Hz, 1H), 7.01 (s, 1H), 6.83 (td, J=2.02, 8.08 Hz, 1H), 3.91-4.04 (m, 4H), 3.76 (s, 3H), 3.70 (s, 3H), 3.18-3.28 (m, 2H), 1.19 (t, J=7.07 Hz, 6H); MS (ES+): m/z: 585.1915 [MH+]. HPLC: $t_R$=1.41 min (UPLC TOF MS: polar_3 min).

Compound 259A: 2-Amino-N-methoxybenzamide

A mixture of isatoic anhydride (5.0 g, 31 mmol) and methoxylamine hydrochloride (3.8 g, 46 mmol) in EtOH (100 mL) and H$_2$O (10 mL) was charged with Triethylamine (6.4 mL, 46 mmol) and stirred at reflux for 4 h. The reaction mixture was concentrated in vacuo and partitioned between EtOAc and water and separated. The aqueous layer was extracted with EtOAc (3×) and the combined organic fractions were washed with brine, dried over sodium sulfate, filtered, and concentrated. The obtained solid was washed with ether and hexanes to afford 4.5 g, 88% yield, of the title compound as a brown solid. $^1$H NMR (400 MHz, DMSO-d6) δ 11.40 (br. s., 1H), 7.30 (dd, J=1.14, 7.96 Hz, 1H), 7.09-7.19 (m, 1H), 6.70 (dd, J=0.76, 8.34 Hz, 1H), 6.45-6.52 (m, 1H), 6.30 (br. s., 2H), 3.67 (s, 3H); MS (ES+): m/z: 167.0783 [MH+]. HPLC: $t_R$=0.83 min (UPLC TOF: polar_3 min).

Example 260

Diethyl[(5-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}pyridin-2-yl)methyl]phosphonate and Compound 261: Diethyl[(5-{[2-{[7-(trans-4-hydroxycyclohexyl)-2-methyl-3-oxo-2,3-dihydro-1H-isoindol-4-yl]amino}-5-(trifluoromethyl)pyrimidin-4-yl]amino}pyridin-2-yl)methyl]phosphonate

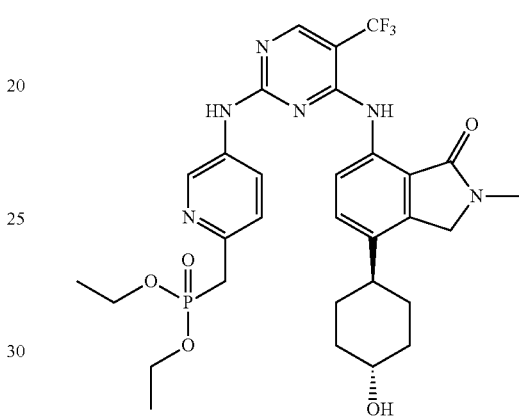

+

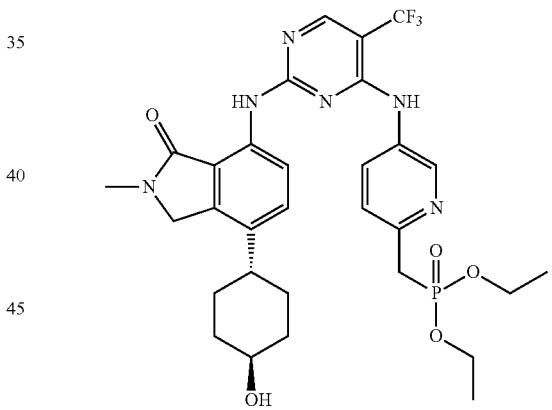

A solution of 2,4-dichloro-5-trifluoromethylpyrimidine (59 mg, 0.27 mmol), diethyl[(5-aminopyridin-2-yl)methyl]phosphonate hydrochloride (Compound 260A, 76.6 mg, 0.27 mmol), and DIPEA (0.14 mL, 0.82 mmol) in THF (0.5 mL) was stirred at 60° C. for 2 h, after which, the solvents were removed in vacuo. The residue was treated with 7-amino-4-(trans-4-hydroxycyclohexyl)-2-methyl-2,3-dihydro-1H-isoindol-1-one (71.1 mg, 0.27 mmol), TFA (0.063 mL, 0.82 mmol, TFE (0.8 mL). The resulting mixture was irradiated in a microwave reactor at 100° C. for 45 min. Solvents were removed in vacuo and the residue was dissolved in DCM (5 mL) and neutralized with sat. NaHCO$_3$ (aq.) (5 mL). The organic phase was separated, aqueous phase extracted with DCM (2×5 mL). The organic phases were combined, dried over MgSO$_4$, filtered, concentrated, and residue was purified by prep TLC (5% 7 N ammonia in MeOH in DCM) to give 1.3 mg of diethyl[(5-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}-pyridin-2-yl)methyl]phosphonate (Example 260) as the more polar spot on TLC (yield: 0.73%) and 3.8 mg of diethyl[(5-{[2-{[7-(trans-4-hydroxycyclohexyl)-2-methyl-3-oxo-2,3-dihydro-1H-isoindol-4-yl]amino}-5-(trifluoromethyl)pyrimidin-4-yl]amino}pyridin-2-yl)methyl]phosphonate (Compound 261) as the less polar spot on TLC (yield: 2.1%).

For Example 260: $^1$H NMR (CDCl$_3$, 400 MHz): δ=1.29 (t, J=7.2 Hz, 6H), 1.46 (m, 2H), 1.60 (m, 2H), 1.89 (m, 2H), 2.15 (m, 2H), 2.49 (m, 1H), 3.22 (s, 3H), 3.44 (d, J=22.0 Hz, 2H), 3.75 (m, 1H), 4.06-4.14 (m, 4H), 4.39 (s, 2H), 7.17 (s, 1H), 7.34 (d, J=8.4 Hz, 1H), 7.40 (dd, J=2.4, 8.4 Hz, 1H), 8.17 (d, J=7.6 Hz, 1H), 8.39 (s, 1H), 8.51 (d, J=7.6 Hz, 1H), 8.60 (d, J=2.4 Hz, 1H), 10.61 (s, 1H). MS (ES$^+$): m/z 649.17 [MH$^+$]. HPLC: t$_R$=3.18 min (OpenLynx, polar_5 min).

For Compound 261: $^1$H NMR (CDCl$_3$, 400 MHz): δ=1.30 (t, J=6.8 Hz, 6H), 1.58-1.67 (m, 4H), 1.87 (m, 2H), 2.14 (m, 2H), 2.46 (m, 1H), 3.19 (s, 3H), 3.47 (d, J=22.0 Hz, 2H), 3.75 (m, 1H), 4.08-4.15 (m, 4H), 4.35 (s, 2H), 6.82 (s, 1H), 7.28 (d, J=8.8 Hz, 1H), 7.48 (dd, J=2.4, 8.4 Hz, 1H), 8.12 (m, 1H), 8.30 (s, br, 1H), 8.42 (s, 1H), 8.56 (d, J=2.4 Hz, 1H), 10.33 (s, 1H). MS (ES$^+$): m/z 649.17 [MH$^+$]. HPLC: t$_R$=3.24 min (OpenLynx, polar_5 min).

Compound 260A:
Diethyl[(5-aminopyridin-2-yl)methyl]phosphonate hydrochloride

To a solution of diethyl({5-[bis(tert-butoxycarbonyl)amino]pyridin-2-yl}methyl)phosphonate (Compound 260B, 2.5 g, 5.6 mmol) in dry EtOAc (150 mL) was added HCl in EtOAc solution dropwise. The reaction mixture was stirred at room temperature for 1 h. The solids were collected by filtration, dried to give 2.1 g of the desired product as a white solid. $^1$H NMR (DMSO-d$_6$, 400 MHz): δ=1.16 (t, J=7.2 Hz, 6H), 3.64 (d, J=22.0 Hz 2H), 3.97-4.04 (m, 4H), 7.50 (dd, J=2.0, 8.8 Hz, 1H), 7.64 (dd, J=2.0, 8.8 Hz, 1H), 7.95 (d, J=2.4 Hz, 1H).

Compound 260B: Diethyl({5-[bis(tert-butoxycarbonyl)amino]pyridin-2-yl}methyl)phosphonate To a solution of di-tert-butyl[6-(bromomethyl)pyridin-3-yl]imidodicarbonate (Compound 260C, 3.0 g, 7.7 mmol) in dry xylene (100 mL) was added a triethyl phosphite (6.0 g, 36 mmol). The reaction mixture was stirred at 140° C. for 4 h, then concentrated. The residue was purified by column chromatography to give the desired compound (2.5 g, yield: 92%) as a liquid. $^1$H NMR (CDCl$_3$, 400 MHz): δ=1.34 (t, J=7.6 Hz, 6H), 1.39 (s, 18H), 3.43 (d, J=22.0 Hz 2H), 4.09-4.18 (m, 4H), 7.43 (dd, J=2.0, 8.0 Hz, 1H), 7.67 (s, 1H), 8.33 (d, J=8.0 Hz, 1H).

Compound 260C: Di-tert-butyl[6-(bromomethyl)pyridin-3-yl]imidodicarbonate

A mixture of di-tert-butyl (6-methylpyridin-3-yl)imidodicarbonate (Compound 260D, 15 g, 49 mmol), NBS (8.2 g, 49 mmol) and AIBN (1.0 g) in CCl$_4$ (200 mL) was stirred at 100° C. overnight. TLC showed the reaction was complete. The reaction mixture was concentrated and residue was purified by column chromatography to afford the desired compound (5.0 g, yield: 26%) as a yellow solid. $^1$H NMR (CDCl$_3$, 400 MHz): δ=1.41 (s, 18H), 4.53 (s, 2H), 7.44 (dd, J=2.4, 8.0 Hz, 1H), 7.67 (d, J=8.4 Hz, 1H), 8.33 (dd, J=2.4, 8.0 Hz, 1H).

Compound 260D: Di-tert-butyl(6-methylpyridin-3-yl)imidodicarbonate

To a solution of 6-methylpyridin-3-ylamine (20 g, 0.18 mol) in DCM (500 mL) was added triethylamine (60 mL) and (Boc)$_2$O (100 g) followed by DMAP (8 g, 66 mmol) in portions. The resulting mixture was stirred at room temperature for 36 h. The mixture was washed with water (400 mL) and aqueous phase was extracted with DCM (2×500 mL). The combined organic layers were dried over MgSO$_4$, concentrated, and purified by column chromatography to afford the desired compound (10 g, 35%) as a solid. $^1$H NMR (CDCl$_3$, 400 MHz): δ=1.41 (s, 18H), 2.55 (s, 3H), 7.14 (d, J=8.0 Hz, 1H), 7.34 (dd, J=2.4, 8.0 Hz, 1H), 8.27 (d, J=2.4 Hz, 1H).

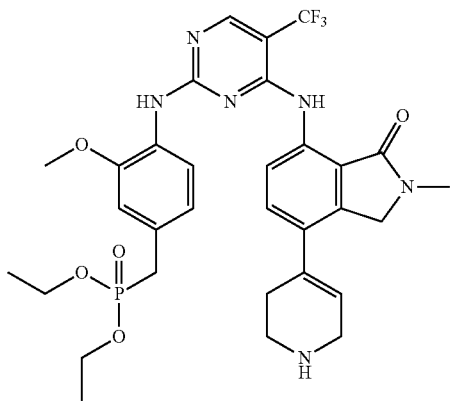 [SMILES: CCOP(=O)(Cc1ccc(Nc2ncc(C(F)(F)F)c(Nc3ccc(C4=CCNCC4)c4c3C(=O)N(C)C4)n2)c(OC)c1)OCC]

Example 262

Diethyl(3-methoxy-4-{[4-{[2-methyl-3-oxo-7-(1,2,3,6-tetrahydropyridin-4-yl)-2,3-dihydro-1H-isoindol-4-yl]amino}-5-(trifluoromethyl)pyrimidin-2-yl]amino}benzyl)phosphonate The title compound was prepared according to the procedure for Example 246 using tert-butyl 4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)-3,6-dihydropyridine-1(2H)-carboxylate (Compound 262A). MS (ES$^+$): m/z 661.33 (100) [MH$^+$]; HPLC: t$_R$=0.71 min (UPLC, purity).

Compound 262A: tert-Butyl 4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)-3,6-dihydropyridine-1(2H)-carboxylate The title compound was prepared according to the procedure for Compound 246A using diethyl[4-({4-[(7-bromo-2-methyl-3-oxo-2,3-dihydro-1H-isoindol-4-yl)amino]-5-(trifluoromethyl)pyrimidin-2-yl}amino)-3-methoxybenzyl]phosphonate and 4-(4,4,5,5-tetramethyl-[1,3,2]

dioxaborolan-2-yl)-3,6-dihydro-2H-pyridine-1-carboxylic acid tert-butyl ester (Tetrahedron Letters, 2000, 44, pp 3705-3708). MS (ES+): m/z 761.33 (100) [MH+]; HPLC: $t_R$=1.56 min (UPLC, analytical).

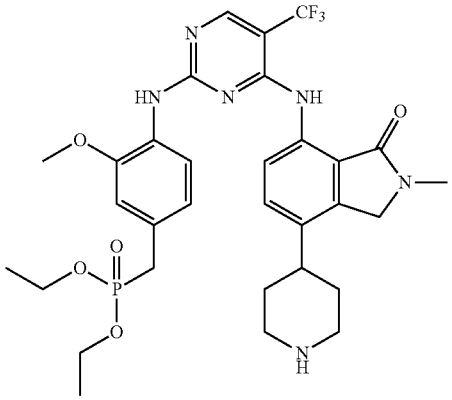 [SMILES: CCOP(=O)(Cc1ccc(Nc2ncc(C(F)(F)F)c(Nc3ccc(C4CCNCC4)c4c3C(=O)N(C)C4)n2)c(OC)c1)OCC]

Example 263

Diethyl (3-methoxy-4-{[4-{[2-methyl-3-oxo-7-(piperidin-4-yl)-2,3-dihydro-1H-isoindol-4-yl]amino}-5-(trifluoromethyl)pyrimidin-2-yl]amino}benzyl)phosphonate The title compound was prepared according to the procedure for Example 247 using Example 262. MS (ES+): m/z 663.33 (100) [MH+]; HPLC: $t_R$=0.73 min (UPLC, purity).

Example 264

Diethyl (3-methoxy-4-{[4-{[2-methyl-7-(1-methyl-1,2,3,6-tetrahydropyridin-4-yl)-3-oxo-2,3-dihydro-1H-isoindol-4-yl]amino}-5-(trifluoromethyl)pyrimidin-2-yl]amino}benzyl)phosphonate The title compound was prepared according to the procedure for Example 248 using Example 262. MS (ES+): m/z 675.32 (100) [MH+]; HPLC: $t_R$=0.72 min (UPLC, purity).

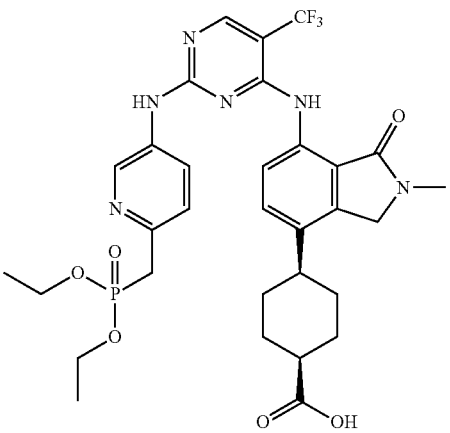 [SMILES: CCOP(=O)(Cc1ccc(Nc2ncc(C(F)(F)F)c(Nc3ccc([C@H]4CC[C@@H](C(=O)O)CC4)c4c3C(=O)N(C)C4)n2)cn1)OCC]

Example 267 cis-4-(7-{[2-({6-[(Diethoxyphosphoryl)methyl]pyridin-3-yl}amino)-5-(trifluoromethyl)pyrimidin-4-yl]amino}-2-methyl-1-oxo-2,3-dihydro-1H-isoindol-4-yl)cyclohexanecarboxylic acid A solution of 2,4-dichloro-5-trifluoromethylpyrimidine (59 mg, 0.27 mmol), diethyl[(5-aminopyridin-2-yl)methyl] phosphonate hydrochloride (Compound 260A, 76.6 mg, 0.27 mmol), and DIPEA (0.14 mL, 0.82 mmol) in THF (0.5 mL) was stirred at 60° C. for 2 h, after which, the solvents were removed in vacuo. To the residue was added ethyl cis-4-(7-amino-2-methyl-1-oxo-2,3-dihydro-1H-isoindol-4-yl)cyclohexanecarboxylate (86.38 mg, 0.273 mmol), TFA (0.063 mL, 0.82 mmol), and TFE (0.8 mL). The resulting mixture was irradiated in microwave reactor at 100° C. for 45 min. Solvents were once again removed in vacuo, and the residue was dissolved in DCM (5 mL) and neutralized with sat. $NaHCO_3$ (aq.) (5 mL). The organic phase was separated, aqueous phase extracted with DCM (2×5 mL). The organic phases were combined, dried over $MgSO_4$, filtered, concentrated, and residue purified by preparative TLC (5% 7 N ammonia in MeOH in DCM) to give 25 mg of a mixture of products ethyl cis-4-(7-{[2-({6-[(diethoxyphosphoryl)methyl]pyridin-3-yl}amino)-5-(trifluoromethyl)pyrimidin-4-yl]amino}-2-methyl-1-oxo-2,3-dihydro-1H-isoindol-4-yl)cyclohexanecarboxylate and ethyl cis-4-(7-{[4-({6-[(diethoxyphosphoryl)methyl]pyridin-3-yl}amino)-5-(trifluoromethyl)pyrimidin-2-yl]amino}-2-methyl-1-oxo-2,3-dihydro-1H-isoindol-4-yl)cyclohexanecarboxylate, which were hydrolyzed as follows: To the mixture was added $LiOH.H_2O$ (14.9 mg, 0.355 mmol, 10 eq), MeOH (0.5 mL), and THF (0.5 mL). The resulting mixture was stirred at rt for 5 h. Solvents were removed and the residue was purified by preparative TLC (5% MeOH in DCM) to give 2.5 mg of the title compound cis-4-(7-{[2-({6-[(diethoxyphosphoryl)methyl]pyridin-3-yl}amino)-5-(trifluoromethyl)pyrimidin-4-yl]amino}-2-methyl-1-oxo-2,3-dihydro-1H-isoindol-4-yl)cyclohexanecarboxylic acid (yield: 1.4%). $^1$H NMR ($CD_3OD$, 400 MHz): δ=1.30 (t, J=7.6 Hz, 6H), 1.69-1.76 (m, 6H), 2.28 (m, 2H), 2.61 (m, 1H), 2.73 (m, 1H), 3.15 (s, 3H), 3.58 (d, J=22.0 Hz, 2H), 4.12-4.20 (m, 4H), 4.44 (s, 2H), 7.13 (d, J=8.8 Hz, 1H), 7.55 (dd, J=2.4, 8.4 Hz, 1H), 7.95-7.98 (m, 2H), 8.37 (d, J=0.4 Hz, 1H), 8.59 (d, J=2.8 Hz, 1H). MS (ES+): m/z 677.20 [MH+]. HPLC: $t_R$=1.34 min (UPLC TOF, polar_3 min).

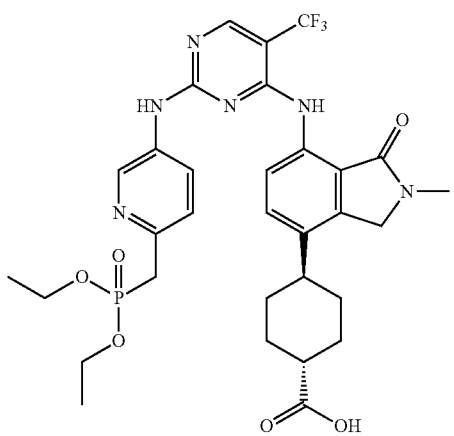 [SMILES: CCOP(=O)(Cc1ccc(Nc2ncc(C(F)(F)F)c(Nc3ccc([C@H]4CC[C@H](C(=O)O)CC4)c4c3C(=O)N(C)C4)n2)cn1)OCC]

Example 268 trans-4-(7-{[2-({6-[(diethoxyphosphoryl)methyl]pyridin-3-yl}amino)-5-(trifluoromethyl)pyrimidin-4-yl]amino}-2-methyl-1-oxo-2,3-dihydro-1H-isoindol-4-yl)cyclohexanecarboxylic acid A solution of 2,4-dichloro-5-trifluoromethylpyrimidine (59 mg, 0.27 mmol), diethyl[(5-aminopyridin-2-yl)methyl]phosphonate hydrochloride (76.6 mg, 0.273 mmol), and DIPEA (0.43 mL, 0.82 mmol) in THF (0.5 mL) was stirred at 60° C. for 2 h. LC-MS indicated the completion of reaction. Solvents were removed and to the residue was added ethyl trans-4-(7-amino-2-methyl-1-oxo-2,3-dihydro-1H-isoindol-4-yl)cyclohexanecarboxylate (86.38 mg, 0.273 mmol), TFA (0.063 mL, 0.82 mmol), and TFE (0.8 mL). The resulting mixture was microwaved on a Biotage microwave at 100° C. for 45 min. Solvents were removed in vacuo, and the residue was dissolved in DCM (5 mL) and neutralized with sat NaHCO$_3$ (aq) (5 mL). The organic phase was separated; aqueous phase extracted with DCM (2×5 mL). The organic phases were combined, dried over MgSO$_4$, filtered, concentrated, and residue was purified by prep TLC (5% 7 N ammonia in MeOH in DCM) to give 19 mg of a mixture of ethyl trans-4-(7-{[2-({6-[(diethoxyphosphoryl)methyl]pyridin-3-yl}amino)-5-(trifluoromethyl)pyrimidin-2-yl]amino}-2-methyl-1-oxo-2,3-dihydro-1H-isoindol-4-yl)cyclohexanecarboxylate and cis-4-(7-{[4-({6-[(diethoxyphosphoryl)methyl]pyridin-3-yl}amino)-5-(trifluoromethyl)pyrimidin-2-yl]amino}-2-methyl-1-oxo-2,3-dihydro-1H-isoindol-4-yl)cyclohexanecarboxylate, which was hydrolyzed as follows: To the mixture was added LiOH.H$_2$O (11.3 mg, 0.27 mmol), MeOH (0.5 mL), and THF (0.5 mL). The resulting mixture was stirred at rt for 5 h. Solvents were removed and the residue was purified by prep TLC (5% MeOH in DCM) to afford 4 mg of the title compound (yield: 2.2%). $^1$H NMR (CD$_3$OD, 400 MHz): δ=1.30 (t, J=7.6 Hz, 6H), 1.56-1.69 (m, 4H), 1.88 (m, 2H), 2.12 (m, 2H), 2.40 (m, 1H), 2.55 (m, 1H), 3.15 (s, 3H), 3.58 (d, J=22.0 Hz, 2H), 4.15-4.19 (m, 4H), 4.45 (s, 2H), 7.30 (d, J=8.4 Hz, 1H), 7.57 (dd, J=2.8, 8.8 Hz, 1H), 7.98 (dd, J=3.0, 8.4 Hz, 1H), 8.03 (s, br, 1H), 8.37 (s, 1H), 8.59 (d, J=2.4 Hz, 1H). MS (ES$^+$): m/z 677.25 [MH$^+$]. HPLC: t$_R$=1.32 min (UPLC TOF, polar_3 min).

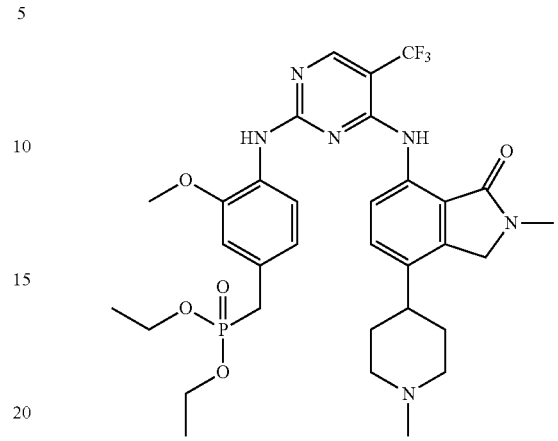

Example 269

Diethyl (3-methoxy-4-{[4-{[2-methyl-7-(1-methylpiperidin-4-yl)-3-oxo-2,3-dihydro-1H-isoindol-4-yl]amino}-5-(trifluoromethyl)pyrimidin-2-yl]amino}benzyl)phosphonate The title compound was prepared according to the procedure for Example 247 using Example 264. MS (ES$^+$): m/z 677.29 (100) [MH$^+$]; HPLC: t$_R$=0.73 min (UPLC, purity).

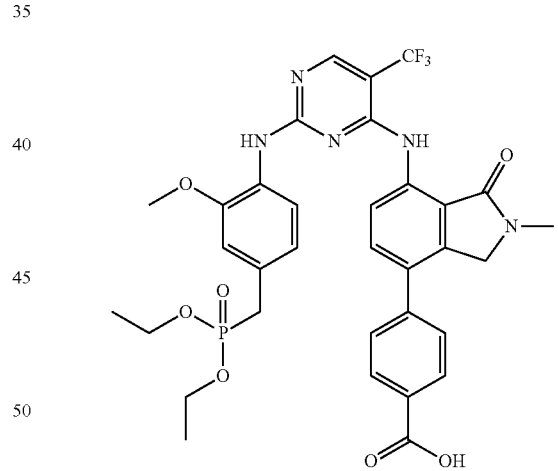

Example 270

4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)benzoic acid Diethyl[4-({4-[(7-bromo-2-methyl-3-oxo-2,3-dihydro-1H-isoindol-4-yl)amino]-5-(trifluoromethyl)pyrimidin-2-yl}amino)-3-methoxybenzyl]phosphonate (20.0 mg, 0.0304 mmol), 4-(Dihydroxyboryl)benzoic acid (10.1 mg, 0.0608 mmol), potassium carbonate (12.6 mg, 0.0911 mmol), [1,1'- bis(diphenylphosphino)ferrocene]dichloropalladium(II), complex with dichloromethane (1:1) (2.48 mg, 0.00304 mmol), 1,4-dioxane (0.6 mL) and water (0.15 mL) were mixed and heated in microwave at 100° C. for 30 minutes. The crude mixture was passed through Thiol-SPE cartridge to remove Pd and was subsequently purified by MDP to obtain the title compound (5.7 mg, 27% yield). $^1$H NMR (400 MHz, DMSO-d6) δ=1.13 (t, J=7.1 Hz, 6H), 3.08 (s, 3H), 3.34 (d, J=21.5 Hz, 2H), 3.75 (s, 3H), 3.85-4.02 (m, 4H), 4.67 (s, 2H), 6.94 (d, J=8.1 Hz, 1H), 7.08 (br. s., 1H), 7.43 (br. s., 1H), 7.58 (d, J=8.6 Hz, 1H), 7.75 (m, J=8.3 Hz, 2H), 8.02 (m, J=8.6 Hz, 2H), 8.42 (s, 1H), 9.20 (s, 1H), 13.05 (s, 1H). MS (ES$^+$): m/z 700.25 (100) [MH$^+$]; HPLC: $t_R$=1.07 min (UPLC, purity).

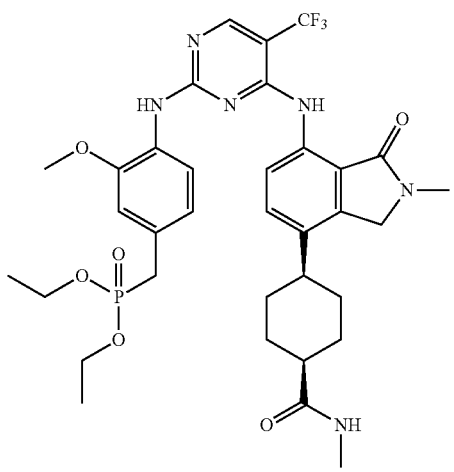 [SMILES: CCOP(=O)(Cc1ccc(Nc2ncc(C(F)(F)F)c(Nc3ccc([C@H]4CC[C@@H](C(=O)NC)CC4)c4c3C(=O)N(C)C4)n2)c(OC)c1)OCC]

Example 271

Diethyl (3-methoxy-4-{[4-({2-methyl-7-[cis-4-(methylcarbamoyl)cyclohexyl]-3-oxo-2,3-dihydro-1H-isoindol-4-yl}amino)-5-(trifluoromethyl)pyrimidin-2-yl]amino}benzyl)phosphonate cis-4-(7-{[2-({4-[(Diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexanecarboxylic acid (10.0 mg, 0.0142 mmol), TBTU (9.1 mg, 0.0283 mmol) and DMF (0.8 mL) were mixed and the mixture was stirred at room temperature for 30 minutes. Methylammonium chloride (9.6 mg, 0.142 mmol) and DIPEA (24.7 μL, 0.142 mmol) were added and the mixture was stirred at room temperature for 2 hours. The crude was purified by MDP to obtain the title compound (4.4 mg, 43% yield). $^1$H NMR (400 MHz, methanol-d4) δ=1.29 (t, J=7.1 Hz, 6H), 1.67-1.81 (m, 4H), 1.87-2.01 (m, 2H), 2.15 (d, J=12.4 Hz, 2H), 2.60 (br. s., 1H), 2.71 (t, J=11.2 Hz, 1H), 2.79 (s, 3H), 3.18 (s, 3H), 3.37 (d, J=21.7 Hz, 2H), 3.90 (s, 3H), 4.10 (quin, J=7.3 Hz, 4H), 4.53 (s, 2H), 6.99 (d, J=7.8 Hz, 1H), 7.13 (s, 1H), 7.34 (br. s., 1H), 7.67 (d, J=8.1 Hz, 1H), 8.33 (br. s., 2H). MS (ES$^+$): m/z 719.36 (100) [MH$^+$]; HPLC: $t_R$=1.04 min (UPLC, purity).

The following compounds were prepare in analogous manner using cis-4-(7-{[2-({4-[(Diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexanecarboxylic acid and the appropriate amine.

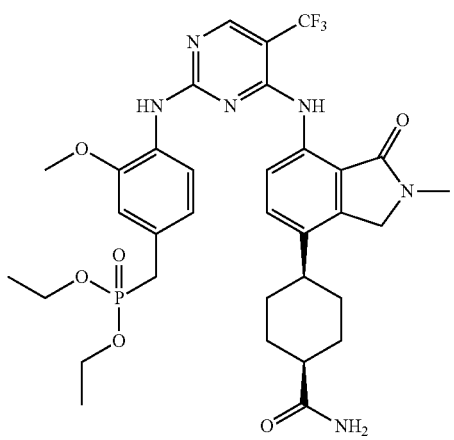 [SMILES: CCOP(=O)(Cc1ccc(Nc2ncc(C(F)(F)F)c(Nc3ccc([C@H]4CC[C@@H](C(N)=O)CC4)c4c3C(=O)N(C)C4)n2)c(OC)c1)OCC]

Example 272

Diethyl (4-{[4-{[7-(cis-4-carbamoylcyclohexyl)-2-methyl-3-oxo-2,3-dihydro-1H-isoindol-4-yl]amino}-5-(trifluoromethyl)pyrimidin-2-yl]amino}-3-methoxybenzyl)phosphonate MS (ES$^+$): m/z 705.31 (100) [MH$^+$]; HPLC: $t_R$=1.00 min (UPLC, purity).

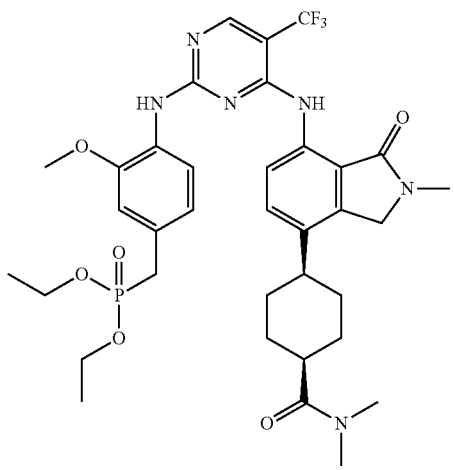 [SMILES: CCOP(=O)(Cc1ccc(Nc2ncc(C(F)(F)F)c(Nc3ccc([C@H]4CC[C@@H](C(=O)N(C)C)CC4)c4c3C(=O)N(C)C4)n2)c(OC)c1)OCC]

Example 273

Diethyl (4-{[4-({7-[cis-4-(dimethylcarbamoyl)cyclo-hexyl]-2-methyl-3-oxo-2,3-dihydro-1H-isoindol-4-yl}amino)-5-(trifluoromethyl)pyrimidin-2-yl]amino}-3-methoxybenzyl)phosphonate MS (ES$^+$): m/z 733.36 (100) [MH$^+$]; HPLC: $t_R$=1.13 min (UPLC, purity).

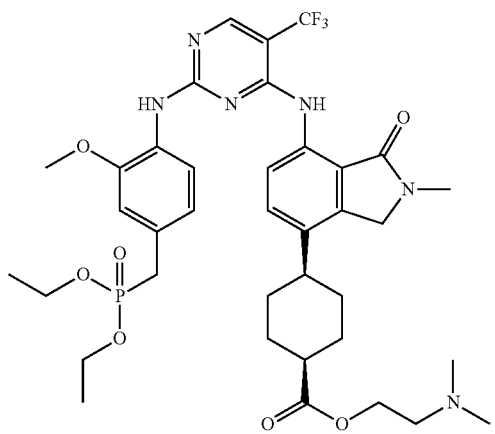 [SMILES: CCOP(=O)(Cc1ccc(Nc2ncc(C(F)(F)F)c(Nc3ccc([C@H]4CC[C@@H](C(=O)OCCN(C)C)CC4)c4c3C(=O)N(C)C4)n2)c(OC)c1)OCC]

Example 274

2-(Dimethylamino)ethyl cis-4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexanecarboxylate $^1$H NMR (400 MHz, methanol-d4) δ=1.29 (t, J=7.1 Hz, 6H), 1.76 (d, J=6.1 Hz, 6H), 2.24-2.39 (m, 8H), 2.70 (t, J=5.6 Hz, 3H), 2.83 (br. s., 1H), 3.18 (s, 3H), 3.32 (d, J=22.7 Hz, 2H), 3.90 (s, 3H), 4.09 (quin, J=7.3 Hz, 4H), 4.31 (t, J=5.7 Hz, 2H), 4.51 (s, 2H), 6.92 (d, J=8.1 Hz, 1H), 7.06 (s, 1H), 7.26 (d, J=8.1 Hz, 1H), 7.88 (d, J=7.6 Hz, 1H), 8.34 (s, 1H), 8.46 (br. s., 1H). MS (ES$^+$): m/z 777.32 (100) [MH$^+$]; HPLC: $t_R$=0.79 min (UPLC, purity).

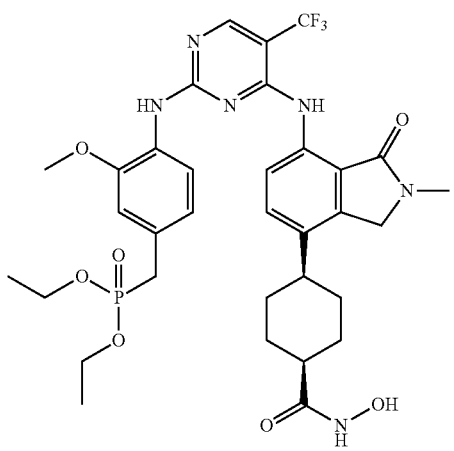 [SMILES: CCOP(=O)(Cc1ccc(Nc2ncc(C(F)(F)F)c(Nc3ccc([C@H]4CC[C@@H](C(=O)NO)CC4)c4c3C(=O)N(C)C4)n2)c(OC)c1)OCC]

Example 275

Diethyl (4-{[4-({7-[cis-4-(hydroxycarbamoyl)cyclohexyl]-2-methyl-3-oxo-2,3-dihydro-1H-isoindol-4-yl}amino)-5-(trifluoromethyl)pyrimidin-2-yl]amino}-3-methoxybenzyl)phosphonate To 50% 1-propylphosphonic acid cyclic anhydride in DMF (9.9 µL, 0.017 mmol) were added additional DMF (0.5 mL), DIPEA (9.9 µL, 0.0567 mmol) and cis-4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexanecarboxylic acid (10.0 mg, 0.0142 mmol). The mixture was stirred at room temperature for 30 minutes. Hydroxylamine hydrochloride (2.0 mg, 0.0283 mmol) was added and the mixture was stirred at room temperature overnight. The crude mixture was purified by MDP to obtain the title compound (5.2 mg, 51% yield). $^1$H NMR (400 MHz, methanol-d4) d ppm 1.29 (t, J=7.1 Hz, 6H), 1.68-1.82 (m, 4H), 2.00-2.16 (m, 4H), 2.52 (br. s., 1H), 2.73 (t, J=11.1 Hz, 1H), 3.19 (s, 3H), 3.38 (d, J=21.7 Hz, 2H), 3.90 (s, 3H), 4.11 (qd, J=7.3, 7.1 Hz, 4H), 4.55 (s, 2H), 6.95-7.04 (m, 1H), 7.14 (s, 1H), 7.39 (br. s., 1H), 7.65 (d, J=8.1 Hz, 1H), 8.33 (br. s., 2H). MS (ES$^+$): m/z 721.19 (100) [MH$^+$]; HPLC: $t_R$=0.97 min (UPLC, purity).

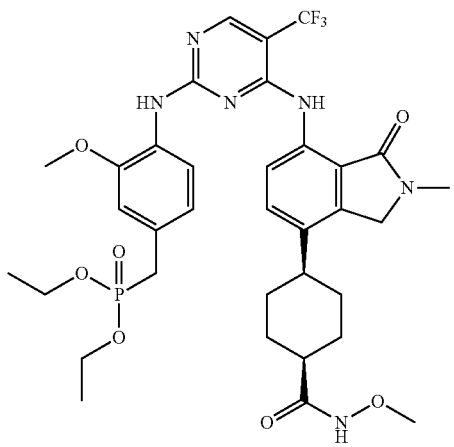 [SMILES: CCOP(=O)(Cc1ccc(Nc2ncc(C(F)(F)F)c(Nc3ccc([C@H]4CC[C@@H](C(=O)NOC)CC4)c4c3C(=O)N(C)C4)n2)c(OC)c1)OCC]

Example 276

Diethyl (3-methoxy-4-{[4-({7-[cis-4-(methoxycarbamoyl)cyclohexyl]-2-methyl-3-oxo-2,3-dihydro-1H-isoindol-4-yl}amino)-5-(trifluoromethyl)pyrimidin-2-yl]amino}benzyl)phosphonate The title compound was prepared in according to the procedure for Example 275 replacing Hydroxylamine hydrochloride with methoxylamine hydrochloride. MS (ES$^+$): m/z 735.36 (100) [MH$^+$]; HPLC: $t_R$=1.03 min (UPLC, purity).

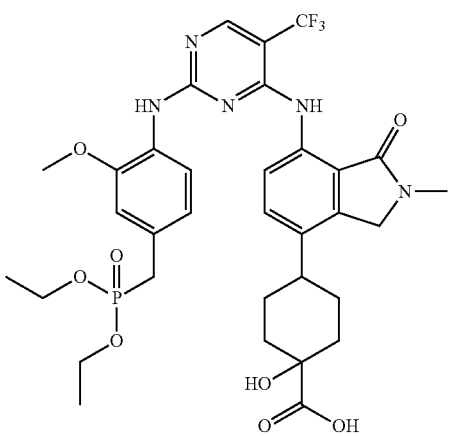 [SMILES: CCOP(=O)(Cc1ccc(Nc2ncc(C(F)(F)F)c(Nc3ccc(C4CCC(O)(C(=O)O)CC4)c4c3C(=O)N(C)C4)n2)c(OC)c1)OCC]

Example 278

4-(7-{2-[4-(Diethoxy-phosphorylmethyl)-2-methoxy-phenylamino]-5-trifluoromethyl-pyrimidin-4-ylamino}-2-methyl-1-oxo-2,3-dihydro-1H-isoindol-4-yl)-1-hydroxy-cyclohexanecarboxylic acid A solution of diethyl (4-{[4-chloro-5-(trifluoromethyl)pyrimidin-2-yl]amino}-3-methoxybenzyl)phosphonate (105 mg, 0.23 mmol) and methyl 4-(7-amino-2-methyl-1-oxo-2,3-dihydro-1H-isoindol-4-yl)-1-{[tert-butyl(dimethyl)silyl]oxy}cyclohexanecarboxylate (Compound 278A, 110 mg, 0.26 mmol) in TFE (3 mL) was charged with TFA (75 mg, 0.66 mmol) and irradiated on the microwave at 100° C. for 30 min. The reaction mixture was diluted with EtOAc (30 mL), washed with sat. aq. NaHCO₃ (2×10 mL), brine (10 mL), and dried over anhydrous sodium sulfate. The solvents were evaporated under reduced pressure, and the crude material was used in next step without further purification. The above material was dissolved in THF (6 mL), then TBAF (2.0 mL, 2.0 mmol, 1M solution in THF) was added. The resulting mixture was stirred at rt overnight. The reaction mixture was diluted with EtOAc (30 mL), washed with water (10 mL), brine (10 mL), and dried over anhydrous sodium sulfate. The solvents were evaporated under reduced pressure, and the crude material was used in the hydrolysis without further purification. The above crude ester was dissolved in THF (2 mL), MeOH (2 mL) and H₂O (2 mL), then lithium hydroxide monohydrate (48.5 mg, 1.16 mmol) was added. The resulting mixture was stirred at rt for 1 h. The mixture was acidified with aq. 1M HCl to pH=3, then extracted with EtOAc (3×10 mL), the combined organic phases were washed with brine (10 mL), and dried over anhydrous sodium sulfate. The solvents were evaporated under reduced pressure and the residue was purified by silica gel chromatography (ISCO system: MeOH/DCM=0-10%) to give the title compound as a white solid, 62 mg, 36% yield over three steps. LC-MS and ¹H NMR showed that it was a single isomer. ¹H NMR (DMSO-d₆): 1.20 (t, J=7.0 Hz, 6H), 1.55-1.65 (m, 2H), 1.74-1.99 (m, 6H), 2.58 (m, 1H), 3.07 (s, 3H), 3.24 (d, J=21.2 Hz, 2H), 3.76 (s, 3H), 3.95-4.04 (m, 4H), 4.51 (s, 2H), 4.99 (s, 1H), 6.90 (d, J=7.8 Hz, 1H), 7.05 (s, 1H), 7.26 (m, 1H), 7.51 (m, 1H), 8.38 (s, 1H), 8.98 (s, 1H), 10.57 (s, 1H), 12.38 (s, 1H). MS (ES+): m/z=722.17 [MH⁺]. HPLC: $t_R$=3.43 min (ZQ3, polar_5 min).

Compound 278A: 4-(7-Amino-2-methyl-1-oxo-2,3-dihydro-1H-isoindol-4-yl)-1-(tert-butyl-dimethyl-silanyloxy)-cyclohexanecarboxylic acid methyl ester To a mixture of {[tert-butyl(dimethyl)silyl]oxy}propanedinitrile (390 mg, 2.0 mmol) [which was prepared according to literature: Nemoto, H.; Li, X.; Ma, R.; Suzuki, I.; Shibuya, M. *Tetrahedron Lett*. 2003, 44, 73-75] and 7-amino-2-methyl-4-(4-oxocyclohexyl)-2,3-dihydro-1H-isoindol-1-one (258 mg, 1.0 mmol) in MeOH (10 mL) was added 4-dimethylaminopyridine (12 mg, 0.10 mmol). The resulting mixture was stirred at rt for 30 min. The solvent was evaporated under reduced pressure, and the residue was suspended in DCM (10 mL), the light-yellow solid was filtered off, the filtrate was concentrated and purified by silica gel chromatography (ISCO system: EtOAc:Heptane=30-90%) to give the title compound as a light-yellow solid, 160 mg, 37% yield. ¹H NMR (CDCl₃): 0.12 (s, 6H), 0.98 (s, 9H), 1.63-1.66 (m, 2H), 1.82-2.00 (m, 6H), 2.44 (m, 1H), 3.14 (s, 3H), 3.74 (s, 3H), 4.31 (s, 2H), 6.66 (d, J=8.1 Hz, 1H), 7.13 (d, J=8.1 Hz, 1H). MS (ES+): m/z=433.17 [MH⁺]. HPLC: $t_R$=4.35 min (ZQ3, nonpolar_5 min).

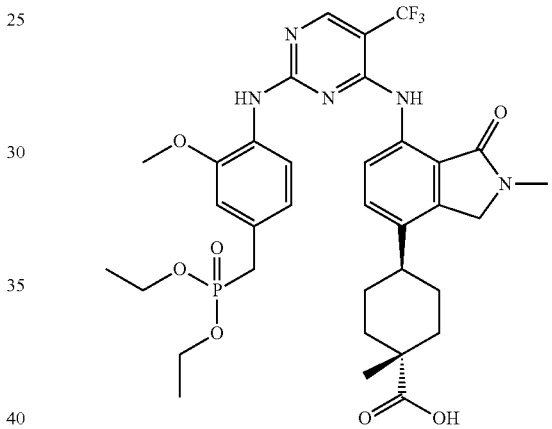

Example 282 trans-4-(7-{[2-({4-[(Diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)-1-methylcyclohexanecarboxylic acid The title compound was prepared according to the procedure for Example 102 using trans-4-(7-amino-2-methyl-1-oxo-2,3-dihydro-1H-isoindol-4-yl)-1-methylcyclohexanecarboxylic acid (Compound 282A, 90 mg, 0.28 mmol) and diethyl (4-{[4-chloro-5-(trifluoromethyl)pyrimidin-2-yl]amino}-3-methoxybenzyl)phosphonate (126 mg, 0.28 mmol). The reaction mixture was concentrated and purified by column chromatography (99:1, methanol/dichloromethane) to give the title compound, which was recrystallized in isopropanol to afford 11 mg (yield: 6%) of pure product. ¹H NMR (CDCl₃, 300 MHz): δ=1.26 (t, J=7.2 Hz, 6H), 1.42 (s, 3H), 1.77-1.81 (m, 4H), 1.90-1.92 (m, 4H), 2.50-2.52 (m, 1H), 3.18 (d, J=21 Hz, 2H), 3.22 (s, 3H), 3.92 (s, 3H), 4.0-4.08 (m, 4H), 4.38 (s, 2H), 6.91 (d, J=7.8 Hz, 1H), 6.94 (s, 1H), 7.39 (d, J=7.8 Hz, 1H), 7.80 (bs, 1H), 8.22 (bs, 1H), 8.38 (s, 1H), 8.60 (d, J=8.4 Hz, 1H), 10.55 (s, 1H). MS (ES⁺): m/z 720.24 [MH⁺]. HPLC: $t_R$=1.48 min (UPLC TOF, polar_3 min).

Compound 282A: trans-4-(7-Amino-2-methyl-1-oxo-2,3-dihydro-1H-isoindol-4-yl)-1-methylcyclohexane carboxylic acid To a solution of LiOH.H$_2$O (252 mg, 6 mmol) in THF/EtOH/water (1/1/1, 3 mL) was added the above mixture of ethyl cis-4-(7-amino-2-methyl-1-oxo-2,3-dihydro-1H-isoindol-4-yl)-1-methylcyclohexanecarboxylate (Compound 282B) and ethyl trans-4-(7-amino-2-methyl-1-oxo-2,3-dihydro-1H-isoindol-4-yl)-1-methylcyclohexanecarboxylate (Compound 282C) (198 mg, 0.6 mmol). The reaction mixture was heated under reflux for 8 h, then concentrated. The residue was taken into water and extracted with ethyl acetate. The organic layer was dried (Na$_2$SO$_4$) and concentrated to give the unreacted ethyl cis-4-(7-amino-2-methyl-1-oxo-2,3-dihydro-1H-isoindol-4-yl)-1-methylcyclohexanecarboxylate (Compound 282B, 100 mg). The aqueous layer was acidified with acetic acid and extracted with dichloromethane (3×20 mL). The combined dichloromethane layer was dried (Na$_2$SO$_4$) and concentrated to give 70 mg of the title compound. $^1$H NMR (CDCl$_3$, 300 MHz): δ=1.20-1.46 (m, 4H), 1.67-1.70 (m, 2H), 1.84-1.87 (m, 2H), 2.09 (s, 3H), 2.39 (m, 1H), 3.13 (s, 3H), 4.27 (s, 2H), 6.57 (d, J=8.0 Hz, 1H), 7.12 (d, J=8.0 Hz, 1H).

Compound 282B Ethyl cis-4-(7-amino-2-methyl-1-oxo-2,3-dihydro-1H-isoindol-4-yl)-1-methylcyclohexanecarboxylate and

Compound 282C: Ethyl trans-4-(7-amino-2-methyl-1-oxo-2,3-dihydro-1H-isoindol-4-yl)-1-methylcyclohexanecarboxylate A solution of ethyl 1-methyl-4-(2-methyl-7-nitro-1-oxo-2,3-dihydro-1H-isoindol-4-yl)cyclohex-3-ene-1-carboxylate (Compound 282D, 278 mg, 0.78 mmol) in dichloromethane/methanol mixture (20 mL/6 mL) was hydrogenated over 10% Pd on charcoal (50 mg) under 50 psi pressure for 48 h. The reaction mixture was filtered, concentrated, and the crude residue was used in next step without purification.

Compound 282D: Ethyl 1-methyl-4-(2-methyl-7-nitro-1-oxo-2,3-dihydro-1H-isoindol-4-yl)cyclohex-3-ene-1-carboxylate A mixture of dioxane and water (15 mL, 4:1) was degassed for 30 min. 2-Methyl-7-nitro-4-(4,4,5,5-tetramethyl-1,3,2-dioxaborolan-2-yl)-2,3-dihydro-1H-isoindol-1-one (373 mg, 1.19 mmol), ethyl 1-methyl-4-{[(trifluoromethyl)sulfonyl]oxy}cyclohex-3-ene-1-carboxylate (Compound 282E, 300 mg, 0.92 mmol), Pd (PPh$_3$)$_4$ (106 mg, 0.092 mmol), and cesium carbonate (747 mg, 2.3 mmol) were then added. The reaction mixture was heated at 70° C. for 2 h. After cooled to room temperature, the mixture was filtered and concentrated to dryness, the residue was purified by column chromatography (SiO$_2$, 5% ethyl acetate/dichloromethane) to give 278 mg (yield: 77%) of the desired compound. $^1$H NMR (CDCl$_3$, 300 MHz): δ=1.26 (t, J=6.9 Hz, 3H), 1.76-1.78 (m, 1H), 2.07-2.22 (m, 3H), 2.40 (m, 1H), 2.80-2.42 (m, 1H), 3.21 (s, 3H), 4.15 (q, J=6.9 Hz, 2H), 5.92 (s, 1H), 7.44 (d, J=8.5 Hz, 1H), 7.70 (d, J=8.5 Hz, 1H).

Compound 282E: Ethyl 1-methyl-4-{[(trifluoromethyl)sulfonyl]oxy}cyclohex-3-ene-1-carboxylate To a cold solution of ethyl 1-methyl-4-oxo-cyclohexanecarboxylate (Compound 282F, 1.2 g, 6.52 mmol) and 2,6-di-tert-butylpyridine (2.27 g, 11.08 mmol) in dichloromethane (40 mL) was added triflic anhydride (1.2 mL, 7.17 mmol) over a period of 20 min. The resulting mixture was allowed to warm to room temperature and stirred for 16 h. The reaction mixture was concentrated to dryness and the residue was treated with ether. The solid (salt of 2,6-di-tert-butylpyridine) was filtered off and the filtrate was concentrated, residue was purified by column chromatography (SiO$_2$, 5% ethyl acetate/hexanes) to give 300 mg (yield: 14%) of the desired product. $^1$H NMR (CDCl$_3$, 600 MHz): δ=1.25 (t, J=6.9 Hz, 3H), 1.72-1.76 (m, 1H), 2.06-2.09 (m, 2H), 2.13-2.17 (m, 1H), 2.36-2.42 (m, 2H), 2.71-2.75 (m, 1H), 3.20 (s, 3H), 4.13-4.16 (q, J=6.9 Hz, 2H), 5.71 (s, 1H).

Compound 282F: Ethyl 1-methyl-4-oxo-cyclohexanecarboxylate

8-Methyl-1,4-dioxa-spiro[4.5]decane-8-carboxylic acid ethyl ester (Compound 282G) was dissolved in THF (20 mL) and 3N aq. HCl (30 mL). The resulting mixture was stirred at rt overnight. The mixture was diluted with EtOAc (50 mL), washed with brine (20 mL), and dried over anhydrous sodium sulfate. $^1$H NMR (CDCl$_3$): 1.28 (t, J=7.1 Hz, 3H), 1.29 (s, 3H), 1.63-1.70 (m, 2H), 2.30-2.74 (m, 6H), 3.94 (s, 4H), 4.19 (q, J=7.1 Hz, 2H).

Compound 282G: 8-Methyl-1,4-dioxa-spiro[4.5]decane-8-carboxylic acid ethyl ester To a solution of LDA (7.0 mL, 14 mmol, 2M solution in THF/ethylbenzene) in THF (10 mL) was added a solution of 1,4-dioxa-spiro[4.5]decane-8-carboxylic acid ethyl ester (Compound 282H, 2.14 g, 9.99 mmol) in THF (5 mL) at −78° C. under nitrogen. The resulting mixture was stirred at this temperature for 30 min, then a solution of methyl iodide (1.98 g, 14.0 mmol) in THF (5 mL) was added. The resulting mixture was slowly warmed to rt overnight. The reaction was quenched with sat. aq. NH$_4$Cl (20 mL) and diluted with EtOAc (50 mL). The organic layer was washed with brine (30 mL), and dried over anhydrous sodium sulfate. The solvents were evaporated under reduced pressure to give the desired compound as a light-yellow oil, 2.30 g, 100% yield. The material was used in next step without further purification. $^1$H NMR (CDCl$_3$): 1.20 (s, 3H), 1.26 (t, J=7.1 Hz, 3H), 1.52-1.68 (m, 6H), 2.12-2.17 (m, 2H), 3.94 (s, 4H), 4.15 (q, J=7.1 Hz, 2H).

Compound 282H: 1,4-Dioxa-spiro[4.5]decane-8-carboxylic acid ethyl ester (2, 6930-8)

A mixture of 4-ethoxycarbonyl-cyclohexanone (11.0 g, 64.6 mmol), 1,2-ethanediol (6.02 g, 96.9 mmol), and p-TsOH.H$_2$O (620 mg, 3.2 mmol) in toluene (60 mL) was refluxed using a Dean-Stark to collect water overnight. The mixture was cooled to rt, then quenched with sat. aq. NaHCO$_3$ (30 mL) and diluted with EtOAc (100 mL). The organic layer was washed with brine (30 mL), and dried over anhydrous sodium sulfate. The solvents were evaporated under reduced pressure to give the title compound as a light-yellow oil. 13.8 g, 100% yield. The material was used in next step without further purification. $^1$H NMR (CDCl$_3$): 1.25 (t, J=7.1 Hz, 3H), 1.52-1.60 (m, 2H), 1.76-1.83 (m, 4H), 1.92-1.97 (m, 2H), 2.34 (m, 1H), 3.95 (s, 4H), 4.13 (q, J=7.1 Hz, 2H).

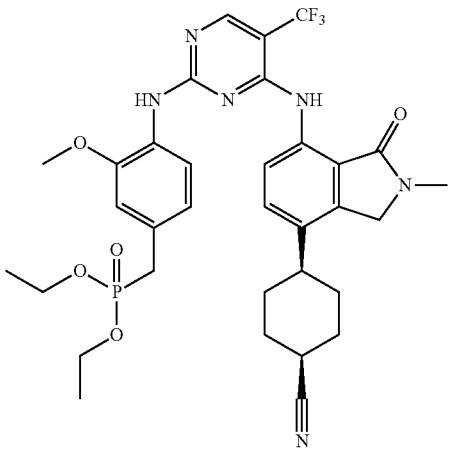 [SMILES: CCOP(=O)(Cc1ccc(Nc2ncc(C(F)(F)F)c(Nc3ccc([C@H]4CC[C@@H](C#N)CC4)c4c3C(=O)N(C)C4)n2)c(OC)c1)OCC]

Example 283

Diethyl (4-{[4-{[7-(cis-4-cyanocyclohexyl)-2-methyl-3-oxo-2,3-dihydro-1H-isoindol-4-yl]amino}-5-(trifluoromethyl)pyrimidin-2-yl]amino}-3-methoxybenzyl)phosphonate In 25 mL Schlenk tube, trans-4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexyl methanesulfonate (Compound 283A, 130.0 mg, 0.17 mmol) was dissolved in DMF (13.0 mL, 168 mmol) and was added degassed (3×) with argon. The reaction was heated at 100° C. under an atmosphere of argon for 7 hrs. The reaction was dissolved in EtOAc and washed with water (2×) and brine (1×) respectfully. The organic layer was collected and concentrated in vacuo to a solid and was purified by CombiFlash®Rf 4X Organic Purification System [dried loaded on 12 g silica load cartridge, 40 g RediSep® Normal-phase GOLD Silica Flash Column, elution gradient: 0→4% MeOH in DCM] to afford 37.4 mg (31.7%) of the desired product. $^1$H NMR (400 MHz, MeOD) δ 8.49 (br. s., 1H), 8.33 (s, 1H), 7.85 (d, J=7.58 Hz, 1H), 7.33 (d, J=8.59 Hz, 1H), 7.03-7.09 (m, 1H), 6.93 (td, J=2.27, 8.08 Hz, 1H), 4.51 (s, 2H), 4.08 (quin, J=7.26 Hz, 4H), 3.90 (s, 3H), 3.33 (s, 1H), 3.27 (s, 1H), 3.17 (s, 4H), 2.68 (d, J=5.56 Hz, 1H), 2.10 (d, J=10.36 Hz, 2H), 1.75-1.93 (m, 6H), 1.28 (t, J=7.07 Hz, 6H). MS (ES$^+$): m/z 687.17/688.20 (100/70) [MH$^+$]. HPLC: $t_R$=1.54 min (Micromass TOF: polar__3 min).

Compound 283A: Trans-4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexyl methanesulfonate To a stirring solution of diethyl (4-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}-3-methoxybenzyl)phosphonate (0.45 g, 0.66 m mol) in DCM (1.68 mL), cooled to 0° C., was slowly added triethylamine (0.185 mL, 1.33 mol) followed by methanesulfonyl chloride (0.13 mL, 1.66 mmol) and 4-dimethylaminopyridine (0.81 mg, 6.60 μmol). The mixture was stirred at rt overnight. After 16 hrs, a precipitate formed. The organic layer was re-dissolved in DCM and washed with water (2×), dried over sodium sulfated, filtered and concentrated in vacuo to a solid. The crude product was purified by CombiFlash®Rf 4X Organic Purification System [dried loaded, 3×12 g RediSep® Normal-phase GOLD Silica Flash Column, elution gradient: 0→4% 7N NH$_3$ (MeOH) in DCM] to afford 220 mg (44%) of the desired product. $^1$H NMR (400 MHz, MeOD) δ 8.48 (br. s., 1H), 8.33 (s, 1H), 7.82 (d, J=8.08 Hz, 1H), 7.40 (d, J=8.59 Hz, 1H), 7.06 (d, J=2.02 Hz, 1H), 6.96 (d, J=7.58 Hz, 1H), 4.74-4.80 (m, 1H), 4.51 (s, 2H), 4.09 (quin, J=7.20 Hz, 4H), 3.89 (s, 3H), 3.34 (s, 1H), 3.29 (br. s., 2H), 3.18 (s, 3H), 3.10 (s, 3H), 2.64 (br. s., 1H), 2.29 (d, J=11.37 Hz, 2H), 1.69-2.00 (m, 6H), 1.28 (t, J=7.07 Hz, 6H). MS (ES$^+$): m/z 756.19/757.23 (100/90) [MH$^+$]. HPLC: $t_R$=1.53 min (Micromass TOF: polar__3 min).

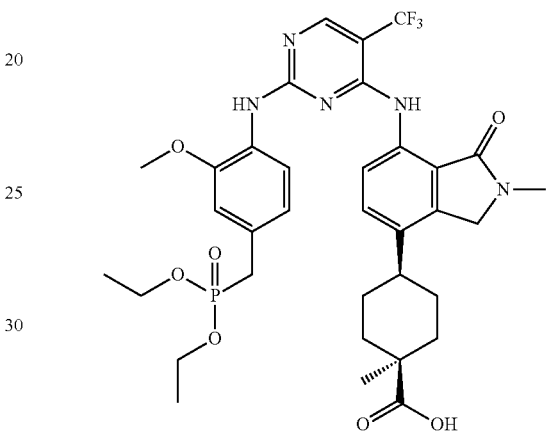

Example 284 cis-4-(7-{[2-({4-[(Diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)-1-methylcyclohexanecarboxylic acid The title compound was prepared according to the procedure for Example 102 using cis-4-(7-amino-2-methyl-1-oxo-2,3-dihydro-1H-isoindol-4-yl)-1-methylcyclohexanecarboxylic acid (Compound 284A, 42 mg, 0.13 mmol) and diethyl (4-{[4-chloro-5-(trifluoromethyl)pyrimidin-2-yl]amino}-3-methoxybenzyl)phosphonate (58 mg, 0.131 mmol). The reaction mixture was concentrated and purified by column chromatography (99:1, methanol/dichloromethane) to give the title compound, which was recrystallized in isopropanol to afford 25 mg (27%) of pure product. $^1$H NMR (CDCl$_3$, 300 MHz): δ=1.27-1.32 (m, 11H), 1.78-1.85 (m, 4H), 2.30 (d, J=12.6 Hz, 2H), 2.58 (m, 1H), 3.20 (s, 3H), 3.33 (d, J=22 Hz, 2H), 3.87 (s, 3H), 4.09-4.13 (m, 4H), 4.37 (s, 2H), 6.78 (s, 1H), 6.91 (d, J=8.4 Hz, 1H), 7.31 (d, J=8.4 Hz, 1H), 7.80 (bs, 1H), 8.07 (d, J=5.4 Hz, 1H), 8.34-8.36 (m, 2H), 10.15 (s, 1H). MS (ES$^+$): m/z 720.26 [MH$^+$]. HPLC: $t_R$=1.48 min (UPLC TOF, polar__3 min).

Compound 284A: cis-4-(7-Amino-2-methyl-1-oxo-2,3-dihydro-1H-isoindol-4-yl)-1-methylcyclohexanecarboxylic acid To a solution of aq. KOH (2 mL, 2 mmol) in dioxane/EtOH/water (1/1/1, 3 mL) was added ethyl cis-4-(7-amino-2-methyl-1-oxo-2,3-dihydro-1H-isoindol-4-yl)-1-methylcyclohexanecarboxylate (Compound 282B, 100 mg, 0.30 mmol). The reaction mixture was heated under reflux for 6 h, then concentrated and the residue was acidified (pH=5) using acetic acid. The mixture was extracted using dichloromethane (3×10 mL), the combined dichloromethane layers were dried (Na$_2$SO$_4$) and concentrated to give 42 mg of the title compound. $^1$H NMR (CDCl$_3$, 300 MHz): δ=1.28-1.30 (m, 2H), 1.59-1.62 (m, 2H), 1.72-1.73 (m, 2H), 2.10 (s, 3H), 2.32-2.34 (m, 3H), 3.13 (s, 3H), 4.27 (s, 2H), 6.54 (d, J=8.4 Hz, 1H), 7.07 (d, J=8.4 Hz, 1H).

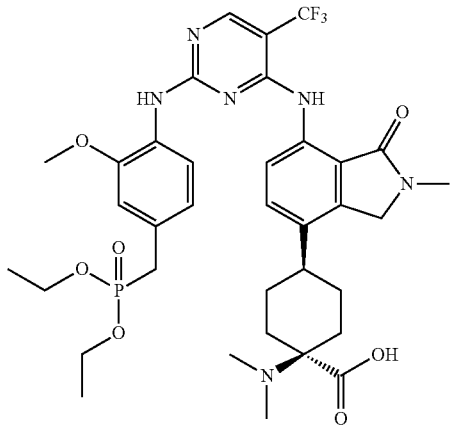 [SMILES: CCOP(=O)(Cc1ccc(Nc2ncc(C(F)(F)F)c(Nc3ccc([C@H]4CC[C@@](C(=O)O)(N(C)C)CC4)c4c3C(=O)N(C)C4)n2)c(OC)c1)OCC]

Example 285 cis-4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)-1-(dimethylamino)cyclohexanecarboxylic acid The title compound was prepared according to the procedure for Example 102 using diethyl (4-{[4-chloro-5-(trifluoromethyl)pyrimidin-2-yl]amino}-3-methoxybenzyl)phosphonate (50.0 mg, 0.105 mmol) and 4-(7-amino-2-methyl-1-oxo-2,3-dihydro-1H-isoindol-4-yl)-1-(dimethylamino) cyclohexanecarboxylic acid (Compound 285A, 38.2 mg, 0.115 mmol). The reaction mixture was concentrated and purified on an ISCO CombiFlash unit eluting with 0-5%-10%-20% MeOH in DCM to isolate the desired product as a 96:04 mixture of isomers. The cis isomer is most likely predominating (see Tetrahedron Letters 2006, 62, 10000-10004 and references cited therein). $^1$H NMR (400 MHz, METHANOL-d4) δ 8.41 (d, J=8.84 Hz, 1H), 8.34 (s, 1H), 7.66 (d, J=8.08 Hz, 1H), 7.61 (d, J=8.59 Hz, 1H), 7.08 (s, 1H), 7.01 (td, J=2.34, 7.96 Hz, 1H), 4.50 (s, 2H), 4.04-4.17 (m, 4H), 3.86 (s, 3H), 3.41 (d, J=21.40 Hz, 2H), 3.18 (s, 3H), 3.16 (s, 6H), 2.75-2.82 (m, 1H), 2.46 (d, J=14.40 Hz, 2H), 2.20-2.31 (m, 2H), 1.83-1.92 (m, 4H), 1.28 (t, J=6.95 Hz, 6H). MS (ES+): m/z=749.3107 [MH+]. HPLC: $t_R$=1.23 min (UPLC, polar_5 min).

Compound 285A: 4-(7-amino-2-methyl-1-oxo-2,3-dihydro-1H-isoindol-4-yl)-1-(dimethylamino)cyclohexanecarboxylic acid Sodium 1-amino-4-{7-[(tert-butoxycarbonyl)amino]-2-methyl-1-oxo-2,3-dihydro-1H-isoindol-4yl}cyclohexanecarboxylate (Compound 285B, 50.0 mg, -0.118 mmol) was taken up in MeOH (1.0 mL, 25 mmol) and over the course of about 5 days was treated repeatedly with formaldehyde (52.5 uL, 0.705 mmol) and Formic acid (26.6 uL, 0.705 mmol) followed by several hours of stirring and then sodium cyanoborohydride (73.8 mg, 1.18 mmol) addition. The reaction was eventually driven to completion after which, the reaction mixture became a suspension. This was filtered and the solid washed a little MeOH. The MeOH filtrate was concentrated to yield a waxy white material which was triturated with DCM and filtered. The DCM filtrate was concentrated to a clear oil and dried in vacuo. $^1$H NMR (400 MHz, CHLOROFORM-d) d 9.52 (s, 1H), 8.10-8.15 (m, 1H), 7.42 (d, J=8.59 Hz, 1H), 4.36 (s, 2H), 3.18 (s, 3H), 2.93 (s, 6H), 2.82 (dd, J=4.67, 8.72 Hz, 1H), 2.23 (t, J=4.55 Hz, 4H), 1.97-2.07 (m, 2H), 1.83-1.94 (m, 2H), 1.50 (s, 9H). MS (ES+): m/z=432.2303 [MH+]. HPLC: $t_R$=1.12 min (UPLC TOF, polar_3 min). The crude product was taken up in DCM and treated with TFA, stirred for 15 min. The reaction mixture was concentrated to an oil and used without further purification and characterization.

Compound 285B: Sodium 1-amino-4-{7-[(tert-butoxycarbonyl)amino]-2-methyl-1-oxo-2,3-dihydro-1H-isoindol-4-yl}cyclohexanecarboxylate Di-tert-butyl 8-{7-[(tert-butoxycarbonyl)amino]-2-methyl-1-oxo-2,3-dihydro-1H-isoindol-4-yl}-2,4-dioxo-1,3-diazaspiro[4.5]decane-1,3-dicarboxylate (Compound 285C, 0.904 g, 1.44 mmol) was taken up in DME (20 mL, 200 mmol) and warmed to effect dissolution. After the rxn mixture had cooled to rt, 1.0 M of Sodium hydroxide in water (13 mL, 13 mmol) was added. A white ppt began forming within minutes. After 60 minutes the DME was removed in vacuo and reaction mixture was filtered to collect the ppt which was washed with water then acetone. After drying, 451.7 mg of a white solid was isolated. $^1$H NMR (400 MHz, DMSO-d6) δ 9.55 (br. s., 1H), 7.94 (d, J=9.09 Hz, 1H), 7.39 (d, J=7.33 Hz, 1H), 4.50 (s, 2H), 3.05 (s, 3H), 2.45 (br. s., 1H), 1.60-1.97 (m, 6H), 1.48 (s, 9H), 1.35 (br. s., 2H). MS (ES+): m/z=304.1487 (M-BOC).

Compound 285C: Di-tert-butyl 8-{7-[(tert-butoxycarbonyl)amino]-2-methyl-1-oxo-2,3-dihydro-1H-isoindol-4-yl}-2,4-dioxo-1,3-diazaspiro[4.5]decane-1,3-dicarboxylate Di-tert-Butyldicarbonate (3640 mg, 16.7 mmol) was added, in one portion, to a suspension of 8-(7-amino-2-methyl-1-oxo-2,3-dihydro-1H-isoindol-4-yl)-1,3-diazaspiro [4.5]decane-2,4-dione (Compound 285D, 1059 mg, 3.225 mmol) in DME (25 mL, 240 mmol). This was cooled to 0° C. and treated with a solution of 4-Dimethylaminopyridine (7.09 mg, 0.0580 mmol) in ~1 mL DME followed by Triethylamine (454 uL, 3.26 mmol). The cooling bath was removed and the mixture was stirred overnight. The reaction mixture was concentrated in vacuo, taken up in DCM and washed successively with 1M HCl, saturated NaHCO$_3$ solution, and brine. The organic layer was dried over Na$_2$SO$_4$, filtered and concentrated to a yellow solid. This was redissolved in DCM, treated with silica and concentrated. This was loaded on to a sample cartridge and purified on tan ISCO CombiFlash unit, eluting with 0-50% EtOAc/Heptane. The pure fractions were concentrated to give 904 mg of a white solid. $^1$H NMR (400 MHz, CHLOROFORM-d) δ 9.54 (s, 1H), 8.17 (d, J=8.59 Hz, 1H), 7.55 (d, J=8.59 Hz, 1H), 4.36 (s, 2H), 3.17 (s, 3H), 2.87-2.95 (m, 1H), 2.57 (ddd, J=4.93, 8.46, 13.89 Hz, 2H), 2.13-2.23 (m, 2H), 2.03-2.13 (m, 2H), 1.92-2.02 (m, 2H), 1.61 (s, 9H), 1.58 (s, 9H), 1.53 (s, 9H).

Compound 285D: 8-(7-amino-2-methyl-1-oxo-2,3-dihydro-1H-isoindol-4-yl)-1,3-diazaspiro[4.5]decane-2,4-dione A suspension of 7-amino-2-methyl-4-(4-oxocyclohexyl)-2,3-dihydro-1H-isoindol-1-one (1000.0 mg, 3.8712 mmol) and ammonium carbonate (818 mg, 8.52 mmol) in MeOH (15 mL, 370 mmol) was treated with a solution of Potassium cyanide (529 mg, 8.13 mmol) in $H_2O$ (10 mL). This mixture, which began turning white, was heated to 80° C. for 16 hours. In the morning the reaction mixture was a thick white slurry. This was transferred to a round bottom flask and concentrated to a solid which was suspended in water and collected via filtration. The filter cake washed with water two more times and once with acetone. The solid was dried under vacuum for several hours to afford the title product as 1.059 g of a pale beige solid. $^1$HNMR (400 MHz, DMSO-d6) δ 10.57 (br. s., 1H), 8.65 (s, 1H), 7.23 (d, J=8.34 Hz, 1H), 6.54 (d, J=8.34 Hz, 1H), 5.85 (s, 2H), 4.36 (s, 2H), 2.99 (s, 3H), 2.40-2.48 (m, 1H), 1.54-1.86 (m, 8H). MS (ES+): m/z=329.1119 [MH+]. HPLC: $t_R$=0.96 min (UPLC TOF, polar_3 min).

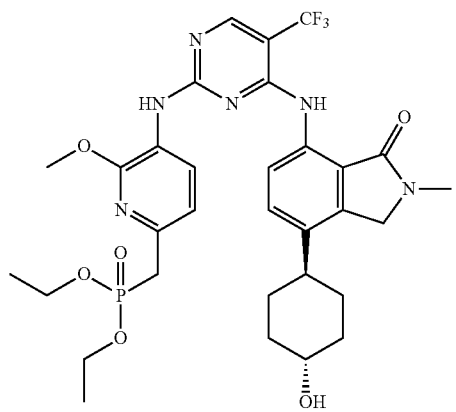

Example 286

Diethyl[(5-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}-6-methoxypyridin-2-yl)methyl]phosphonate The title compound was prepared according to the procedure for Example 102 using diethyl [(5-{[4-chloro-5-(trifluoromethyl)pyrimidin-2-yl]amino}-6-methoxypyridin-2-yl)methyl]phosphonate (Compound 286A, 100 mg, 0.22 mmol) and 7-amino-4-(trans-4-hydroxycyclohexyl)-2-methyl-2,3-dihydro-1H-isoindol-1-one (115 mg, 0.44 mmol). The crude material was purified by MDP to obtain the title compound (82 mg, 55% yield). $^1$H NMR (400 MHz, methanol-d4) δ=1.31 (t, J=6.9 Hz, 6H), 1.38-1.53 (m, 2H), 1.62-1.77 (m, 2H), 1.84-1.93 (m, 2H), 2.04-2.14 (m, 2H), 2.53-2.64 (m, 1H), 3.17 (s, 3H), 3.44 (d, J=21.7 Hz, 2H), 3.62-3.72 (m, 1H), 4.01 (s, 3H), 4.10-4.21 (m, 4H), 4.51 (s, 2H), 6.99 (dd, J=8.1, 2.8 Hz, 1H), 7.39 (d, J=8.6 Hz, 1H), 8.15 (d, J=7.3 Hz, 1H), 8.37 (s, 2H). MS (ES$^+$): m/z 679.31 (100) [MH$^+$]; HPLC: $t_R$=1.06 min (UPLC, purity).

Compound 286A: Diethyl[(5-{[4-chloro-5-(trifluoromethyl)pyrimidin-2-yl]amino}-6-methoxy pyridin-2-yl)methyl]phosphonate The title compound was prepared according to the procedure for diethyl (4-{[4-chloro-5-(trifluoromethyl)pyrimidin-2-yl]amino}benzyl)phosphonate using 2,4-dichloro-5-trifluoromethylpyrimidine and diethyl[(5-amino-6-methoxypyridin-2-yl)methyl]phosphonate (Compound 286B). The crude material was purified by column chromatography (methylene chloride:$CH_3CN$=0-20%) to obtain a mixture of 2 regioisomers with a ratio of roughly 4:1 (the major one is the desired title compound [364 mg, 61% yield]). $^1$H NMR (400 MHz, DMSO-d6) δ=1.22 (t, J=6.9 Hz, 6H), 3.35 (d, J=21.7 Hz, 2H), 3.87 (s, 3H), 4.00-4.07 (m, 4H), 6.98 (dd, J=7.8, 2.8 Hz, 1H), 7.83 (d, J=7.6 Hz, 1H), 8.72 (s, 1H), 9.90 (s, 1H). MS (ES$^+$): m/z 455.21 (100), 457.15 (33) [MH$^+$]; HPLC: $t_R$=1.41 min (UPLC, Analytical).

Compound 286B: Diethyl[(5-amino-6-methoxypyridin-2-yl)methyl]phosphonate

A mixture of diethyl[(6-methoxy-5-nitropyridin-2-yl)methyl]phosphonate (Compound 286C, 750 mg, 2.465 mmol) and Pd/C (0.247 mmol) in 3 mL methanol was stirred under 1 atmosphere of hydrogen at room temperature overnight. The crude mixture was filtered through celite and the product (630 mg, 93% yield) was used directly in next step. $^1$H NMR (DMSO-d6) δ=6.82 (d, J=7.6 Hz, 1H), 6.66 (dd, J=7.7, 2.8 Hz, 1H), 4.81 (s, 2H), 3.97 (quin, J=7.3 Hz, 4H), 3.84 (s, 3H), 3.13 (d, J=21.2 Hz, 2H), 1.18 (t, J=7.1 Hz, 6H). MS (ES$^+$): m/z 275.19 (100) [MH$^+$]; HPLC: $t_R$=0.81 min (UPLC, Analytical).

Compound 286C: Diethyl[(6-methoxy-5-nitropyridin-2-yl)methyl]phosphonate

A solution of 2-methoxy-3-nitropyridine (6.92 g, 44.9 mmol) and diethyl chloromethylphosphonate (7.00 mL, 44.9 mmol) in 40 mL DMSO was added drop wise to a stirred mixture of potassium tert-butoxide (15.1 g, 134.6 mmol) and 40 mL DMSO. The mixture was stirred at room temperature for 30 minutes, after which, it was poured into a 1N HCl/ice mixture and extracted with methylene chloride. The combined organic layers were washed with water, brine, dried over anhydrous sodium sulfate, filtered, concentrated and purified by column chromatography (DCM:EtOAc 1:1). The slower eluting regioisomer was collected and confirmed to be the desired product (750 mg, 5.5% yield). MS (ES$^+$): m/z 305.16 (100) [MH$^-$]; HPLC: $t_R$=1.16 min (UPLC, Analytical).

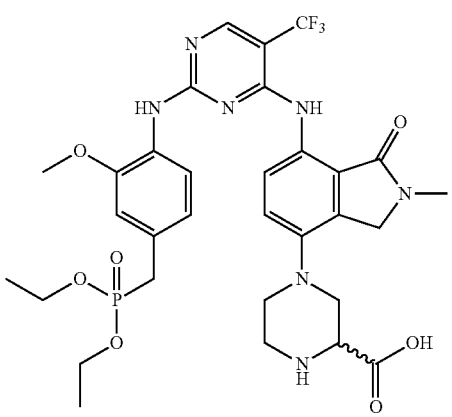 [SMILES: CCOP(=O)(Cc1ccc(Nc2ncc(C(F)(F)F)c(Nc3ccc(N4CCNC(C(=O)O)C4)c4c3C(=O)N(C)C4)n2)c(OC)c1)OCC]

Example 287

4-(7-{[2-({4-[(Diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)piperazine-2-carboxylic acid Diethyl (4-{[4-chloro-5-(trifluoromethyl)pyrimidin-2-yl]amino}-3-methoxybenzyl)phosphonate (18 mg, 0.039 mmol), methyl 4-(7-amino-2-methyl-1-oxo-2,3-dihydro-1H-isoindol-4-yl)piperazine-2-carboxylate (Compound 287A, 6.0 mg, 0.020 mmol), trifluoroacetic acid (4.6 µL, 0.060 mmol) and 0.5 mL trifluoroethanol were mixed. The mixture was heated in microwave 105° C. for 30 minutes. Solvent was evaporated. To the crude solid was added, 0.1 mL THF, 0.1 mL methanol, 0.1 mL water and lithium hydroxide monohydrate (8.3 mg, 0.20 mmol). The mixture was stirred at room temperature overnight. The crude material was purified by MDP to obtain the title compound as a trifluoroacetic acid salt (1.1 mg, 7.9% yield). $^1$H NMR (400 MHz, methanol-d4) δ=1.28 (t, J=7.3 Hz, 6H), 3.18 (s, 3H), 3.21-3.24 (m, 1 H), 3.33 (d, J=21.7 Hz, 2H), 3.37-3.43 (m, 2H), 3.45-3.51 (m, 1H), 3.55-3.61 (m, 2H), 3.90 (s, 3H), 4.06-4.11 (m, 4H), 4.32-4.39 (m, 1H), 4.44-4.59 (m, 2H), 6.99 (d, J=7.8 Hz, 1H), 7.09 (s, 1H), 7.25 (d, J=8.8 Hz, 1H), 7.75 (d, J=8.3 Hz, 1H), 8.35 (s, 1H), 8.49 (br. s., 1H). MS (ES$^+$): m/z 708.26 (100) [MH$^+$]; HPLC: $t_R$=0.77 min (UPLC, purity).

Compound 287A: Methyl 4-(7-amino-2-methyl-1-oxo-2,3-dihydro-1H-isoindol-4-yl)piperazine-2-carboxylate A mixture of Di-tert-Butyl(7-bromo-2-methyl-3-oxo-2,3-dihydro-1H-isoindol-4-yl)iminodicarbonate (400 mg, 0.906 mmol), N-1-boc-2-piperazinecarboxylic methyl ester (1.00 g, 4.09 mmol), bis(tri-tert-butylphosphine)palladium (0) (46 mg, 0.09 mmol), cetyltrimethylammonium bromide (20 mg, 0.05 mmol), and 50% aqueous KOH (152 mg, 1.36 mmol) in 8 mL toluene were evacuated and purged with argon three times. The mixture was heated at 105° C. for 2 days. The reaction mixture was decanted and the solids were washed with toluene. The combined toluene washings were evaporated to afford brown oil which was taken up in methylene chloride and washed with aqueous saturated NaHCO$_3$, water and brine. The organic layer was dried over anhydrous sodium sulfate, filtered, concentrated and purified by column chromatography (methylene chloride in heptane: 0-40%) to afford 1-tert-butyl 2-methyl 4-{7-[bis(tert-butoxycarbonyl)amino]-2-methyl-1-oxo-2,3-dihydro-1H-isoindol-4-yl}piperazine-1,2-dicarboxylate. 1 mL methylene chloride and 1 mL trifluoroacetic acid were added to 1-tert-butyl 2-methyl 4-{7-[bis(tert-butoxycarbonyl)amino]-2-methyl-1-oxo-2,3-dihydro-1H-isoindol-4-yl}piperazine-1,2-dicarboxylate. The mixture was stirred at room temperature overnight. Solvent was evaporated and the material was purified by MDP purification to obtain the product as a methyl ester (6.0 mg, 2.2% yield). MS (ES$^+$): m/z 305.25 (100) [MH$^+$]; HPLC: $t_R$=0.39 min (UPLC, Analytical).

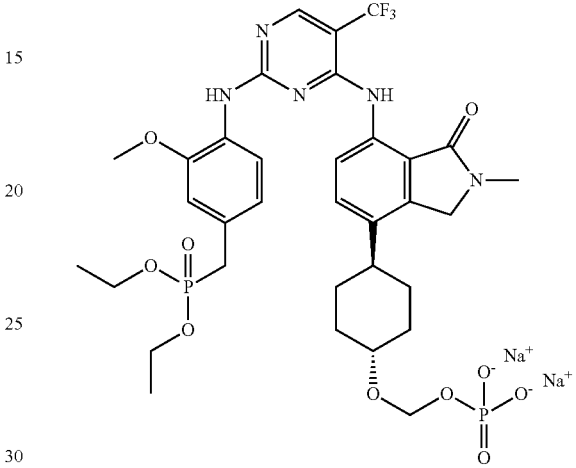

Example 288

{[trans-4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexyl]oxy}methyl phosphate To a solution containing diethyl[3-methoxy-4-({4-[(2-methyl-7-{trans-4-[(methylsulfanyl)methoxy]cyclohexyl}-3-oxo-2,3-dihydro-1H-isoindol-4-yl)amino]-5-(trifluoromethyl)pyrimidin-2-yl}amino)benzyl]phosphonate (Compound 288A, 100.0 mg, 0.11 mmol), phosphoric acid (93.4 mg, 0.95 mmol), and ground molecular sieves in THF (1.40 mL, 17.3 mmol) at 0° C. was added NIS (47 mg, 0.21 mmol), and the mixture solution was stirred at rt for 2 hr. The reaction mixture was filtered through a pad of celite and the solids were washed with methanol. The filtrate was treated with 1 M Na$_2$S$_2$O$_3$ till the solution became transparent. After which, a saturated solution of Na$_2$CO$_3$ was added to the solution till the pH=10. Solid precipitate formed and was removed by filtration. The filtrate was concentrated in vacuo and the residue was purified by CombiFlash®Rf 4X Organic Purification System [dried loaded onto celite, 40 g RediSep® Reverse-phase GOLD Silica Flash Column, elution gradient: 0→100% EtOH in Water] to afford 51 mg (60%) of the desired compound. $^1$H NMR (400 MHz, MeOD) δ 8.53 (d, J=7.33 Hz, 1H), 8.32 (s, 1H), 7.93 (d, J=8.08 Hz, 1H), 7.35 (d, J=8.59 Hz, 1H), 7.05 (s, 1H), 6.91 (td, J=2.15, 8.08 Hz, 1H), 5.12 (d, J=6.57 Hz, 2H), 4.51 (s, 2H), 4.07 (quin, J=7.33 Hz, 4H), 3.83-3.95 (m, 4H), 3.26 (s, 2H), 3.17 (s, 3H), 2.51-2.67 (m, 1H), 2.28 (d, J=9.35 Hz, 2H), 1.89 (d, J=12.13 Hz, 2H), 1.61-1.77 (m, 2H), 1.36-1.51 (m, 2H), 1.28 (t, J=7.07 Hz, 6H). MS (ES$^+$): m/z 788.22/789.25 (100/50) [MH$^+$]. HPLC: $t_R$=1.34 min (Micromass TOF: polar__3 min).

Compound 288A: Diethyl[3-methoxy-4-({4-[(2-methyl-7-{trans-4-[(methylsulfanyl)methoxy cyclohexyl}-3-oxo-2,3-dihydro-1H-isoindol-4-yl)amino]-5-(trifluoromethyl)pyrimidin-2-yl}amino)benzyl] phosphonate To a solution of diethyl (4-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}-3-methoxybenzyl)phosphonate (239 mg, 0.35 mmol) and dimethyl sulfide (0.209 mL, 2.85 mmol) in MeCN (9.56 mL, 183 mmol) and DMF (4.78 mL, 61.7 mmol) at 0° C. was added benzoyl peroxide (343 mg, 1.42 mmol) in four equal portion over 20 minutes, and the mixture was stirred at 0° C. for 1 hr and then at rt for 4 hrs. After 4 hrs, the reaction was not complete. The reaction still remained in a semi-suspension. 1 ml of DMF, 8 eq of dimethyl sulfide and 4 eq of benzoyl peroxide were added to the reaction mixture. The reaction was left to stir overnight at rt. After 16 hrs, the reaction was complete. The mixture was diluted with ethyl acetate and washed with 10% $Na_2CO_3$ (1×) and then with brine (2×). The organic phase was dried, filtered and then evaporated. The crude product was purified by CombiFlash®Rf 4X Organic Purification System [dried loaded with DCM, 12 g RediSep® Normal-phase GOLD Silica Flash Column, elution gradient: 0→5% MeOH in DCM] to afford 177 mg (68%) of the desired product. $^1$H NMR (400 MHz, MeOD) δ 8.42-8.50 (m, 1H), 8.32 (d, J=0.51 Hz, 1H), 7.82-7.89 (m, 1H), 7.35 (d, J=8.84 Hz, 1H), 7.05 (t, J=2.02 Hz, 1H), 6.93 (d, J=8.08 Hz, 1H), 4.72 (s, 2H), 4.48 (s, 2H), 4.03-4.14 (m, 4H), 3.90 (s, 3H), 3.70-3.81 (m, 1H), 3.32 (s, 1H), 3.27 (s, 1H), 3.16 (s, 3H), 2.52-2.65 (m, 1H), 2.12-2.20 (m, 5H), 1.90 (d, J=12.38 Hz, 2H), 1.61-1.76 (m, 2H), 1.42 (d, J=14.65 Hz, 2H), 1.25-1.32 (m, 6H). MS (ES$^+$): m/z 738.26/739.26 (100/35) [MH$^+$]. HPLC: $t_R$=1.56 min (Micromass TOF: polar_3 min).

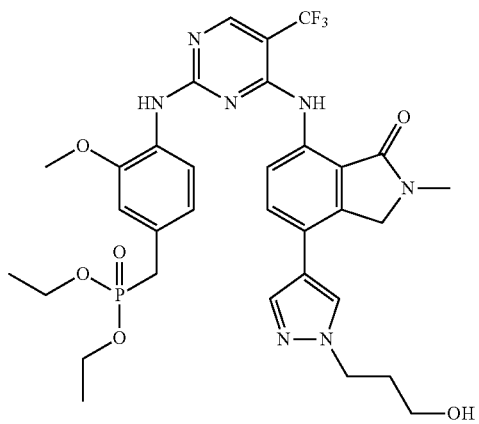 [SMILES: CCOP(=O)(Cc1ccc(Nc2ncc(C(F)(F)F)c(Nc3ccc(-c4cnn(CCCO)c4)c4c3C(=O)N(C)C4)n2)c(OC)c1)OCC]

Example 289

Diethyl (4-{[4-({7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate The title compound was prepared according to the procedure for Example 102 using diethyl (4-{[4-chloro-5-(trifluoromethyl)pyrimidin-2-yl]amino}-3-methoxybenzyl)phosphonate (897 mg, 1.98 mmol) and 7-amino-4-[1-(3-hydroxypropyl)-1H-pyrazol-4-yl]-2-methyl-2,3-dihydro-1H-isoindol-1-one (Compound 289A, 633.5 mg, 2.212 mmol). in TFE (12 mL) was charged with TFA (654.2 mg, 5.737 mmol) and irradiated by microwave heating [Biotage, 105° C.] for 1 h. The reaction mixture was transferred to a round bottom flask and concentrated in vacuo. The residue was dissolved in MeOH (unmeasured amount), cooled to 0° C., and charged with 7.0 M of $NH_3$ in MeOH (5 mL, 40 mmol). After stirring from 0° C. to rt over 1 h 45 min, the suspension was concentrated in vacuo and the crude product purified using a Teledyne/ISCO Combiflash system eluting with a solvent system of 0-10% MeOH:$CH_2Cl_2$ to afford the title material as a white solid, 1.1017 g (78%). $^1$H NMR (400 MHz, DMSO-d$_6$) δ 10.72 (s, 1H), 9.12 (s, 1H), 8.38 (s, 1H), 8.27 (s, 1H), 8.06-8.63 (m, 1H), 7.96 (s, 1H), 7.70 (d, J=8.84 Hz, 1H), 7.41 (d, J=7.07 Hz, 1H), 7.10 (br. t, J=2.00 Hz, 1H), 6.96 (br td, J=2.30, 8.00 Hz, 1H), 4.53-4.67 (m, 3H), 4.21 (t, J=7.20 Hz, 2H), 4.00 (qd, J=7.06, 8.12 Hz, 4H), 3.74 (s, 3H), 3.43 (q, J=6.06 Hz, 2H), 3.36 (d, J=19.96 Hz, 2H), 3.11 (s, 3H), 1.97 (quin, J=6.63 Hz, 2H), 1.17 (t, J=6.95 Hz, 6H). MS (ES$^+$): m/z 704.23 (100) [MH$^+$]. HPLC: $t_R$=3.73 min (ZQ3, polar_5 min).

Compound 289A: 7-Amino-4-[1-(3-hydroxypropyl)-1H-pyrazol-4-yl]-2-methyl-2,3-dihydro-1H-isoindol-1-one To a suspension of 4-[1-(3-hydroxypropyl)-1H-pyrazol-4-yl]-2-methyl-7-nitro-2,3-dihydro-1H-isoindol-1-one (Compound 289B, 920.0 mg, 2.908 mmol) in EtOH (85 mL), Pd/C (10%, 50 $H_2O$) (1.41 g, 0.662 mmol) was added and the mixture was evacuated and charged several times, first with nitrogen and then with $H_2$ gas. The suspension was stirred at rt for 2 h, after which it was filtered through a bed of Celite and rinsed thoroughly with MeOH and EtOAc. The filtrate was concentrated in vacuo and purified using a Teledyne/ISCO Combiflash system eluting with 0-5% MeOH:$CH_2Cl_2$ to afford the title material as 633.7 mg of a light brown solid, (76%,). $^1$H NMR (400 MHz, DMSO-d$_6$) δ 7.93 (d, J=0.51 Hz, 1H), 7.71 (d, J=0.76 Hz, 1H), 7.43 (d, J=8.34 Hz, 1H), 6.61 (d, J=8.34 Hz, 1H), 6.05 (s, 2H), 4.59 (t, J=5.05 Hz, 1H), 4.45 (s, 2H), 4.17 (t, J=6.95 Hz, 2H), 3.41 (q, J=6.06 Hz, 2H), 3.03 (s, 3H), 1.94 (quin, J=6.57 Hz, 2H). MS (ES$^+$): m/z 287.13 (100) [MH$^+$]. HPLC: $t_R$=0.89 min (TOF, polar_3 min).

Compound 289B: 4-[1-(3-Hydroxypropyl)-1H-pyrazol-4-yl]-2-methyl-7-nitro-2,3-dihydro-1H-isoindol-1-one A suspension of 2-methyl-7-nitro-4-(4,4,5,5-tetramethyl-1,3,2-dioxaborolan-2-yl)-2,3-dihydro-1H-isoindol-1-one (Compound 289C, 1.825 g, 5.736 mmol), 3-(4-bromo-1H-pyrazol-1-yl)propan-1-ol (1.449 g, 7.066 mmol), [1,1'-bis(diphenylphosphino)ferrocene]dichloropalladium(II), complex with dichloromethane (1:1) (509.5 mg, 0.6239 mmol), and potassium carbonate (2.397 g, 17.34 mmol) in a 4:1 ratio of dioxane (20 mL) to $H_2O$ (5 mL) was evacuated and charged with nitrogen several times. The sample was irradiated under microwave conditions [Biotage, 100° C.] for 45 min. The reaction mixture was transferred to a separatory funnel, brine was added, and the reaction was extracted with $CH_2Cl_2$. The combined organic layers were dried over anhydrous $Na_2SO_4$, filtered, and concentrated in vacuo. The crude was adsorbed onto a pre-filled solid loading cartridge [RediSepRf 25 gram] and purified using the Teledyne/ISCO system [RediSepRf 40 gram silica GOLD], slowly eluting with 0-15% MeOH:$CH_2Cl_2$. Fractions containing product were pooled together and concentrated in vacuo, yielding the title material as a yellow solid, 920.0 mg (50%, 2.850 mmol). 1H NMR (400 MHz, DMSO-d6) δ 8.35 (s, 1H), 8.05 (s, 1H), 7.99 (d, J=8.34 Hz, 1H), 7.88 (d, J=8.34 Hz, 1H), 4.72 (s, 2H), 4.63 (t, J=5.05 Hz, 1H), 4.25 (t, J=7.07 Hz, 2H), 3.43 (q, J=6.06 Hz, 2H), 3.11 (s, 3H), 1.98 (quin, J=6.63 Hz, 2H). MS (ES+): m/z 317.11 (100) [MH+]. HPLC: t_R=0.91 min (TOF, polar_3 min).

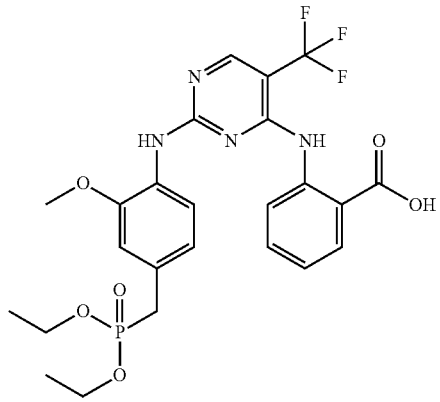 [SMILES: CCOP(=O)(Cc1ccc(Nc2ncc(C(F)(F)F)c(Nc3ccccc3C(=O)O)n2)c(OC)c1)OCC]

Example 290

2-{[2-({4-[(Diethoxyphosphoryl)methyl]-2-methoxyphenyl}amino)-5-(trifluoromethyl)pyrimidin-4-yl]amino}benzoic acid The title compound was prepared according to the procedure for example 102 using diethyl (4-{[4-chloro-5-(trifluoromethyl)pyrimidin-2-yl]amino}-3-methoxybenzyl)phosphonate (50.0 mg, 0.110 mmol) and anthranilic acid (15.1 mg, 0.110 mmol). The reaction mixture concentrated under reduced pressure and purified on an ISCO Combiflash system (DCM/MeOH 100:0→95:5) twice. $^1$H NMR (400 MHz, CHLOROFORM-d) δ 11.65 (br. s., 1H), 9.74 (s, 1H), 8.48 (d, J=8.84 Hz, 1H), 8.25 (s, 1H), 8.08 (dd, J=1.39, 7.96 Hz, 1H), 7.81 (br. s., 1H), 7.47 (t, J=7.71 Hz, 1H), 7.12 (t, J=7.58 Hz, 1H), 6.94 (s, 1H), 6.88 (dd, J=2.02, 8.08 Hz, 1H), 4.06-4.17 (m, 4H), 3.85 (s, 3H), 3.18-3.29 (m, 2H), 1.30 (t, J=7.07 Hz, 6H). MS (ES+): m/z 555.1432 (MH+). HPLC: t_R=1.47 min (UPLC TOF, polar_3 min).

Compound 299A:
5-amino-1,3-dimethylquinolin-4(1H)-one

A mixture of 1,3-dimethyl-5-nitroquinolin-4(1H)-one and 1,3-dimethyl-7-nitroquinolin-4(1H)-one Compound 299B, 2.2 g, 10 mmol) in MeOH (150 mL) was hydrogenated over 5% Pd/C (0.8 g) at 40° C. under 40 psi hydrogen pressure overnight. The catalyst was filtered off and the filtrate was concentrated and purified by HPLC to give the title compound (540 mg, 28%) as a pure regioisomer. $^1$H NMR (DMSO-d_6, 400 MHz): δ=1.92 (s, 3H), 3.69 (s, 3H), 6.63 (d, J=8.0 Hz, 1H), 6.80 (d, J=8.4 Hz, 1H), 7.40 (t, J=8.0 Hz, 1H), 7.91 (s, 1H).

Compound 299B: 1,3-Dimethyl-5-nitroquinolin-4(1H)-one and 1,3-Dimethyl-7-nitroquinolin-4(1H)-one At 0° C., to a mixture of 3-methyl-5-nitroquinolin-4(1H)-one and 3-methyl-7-nitroquinolin-4(1H)-one (*Eur. J. Med. Chem.* 1997, 32, 547, 3 g, 15 mmol) in THF (100 mL) was added NaH (3.6 g, 60 mmol), and the resulting mixture was stirred at room temperature for 30 min, then CH_3I (2.4 g, 17 mmol) was added and the stirring was continued at room temperature overnight. The reaction mixture was carefully quenched with water (20 mL) and extracted 3 times with EtOAc. The combined organic layer was concentrated and purified by column chromatography to yield: 2.2 g of the desired product (yield: 68%).

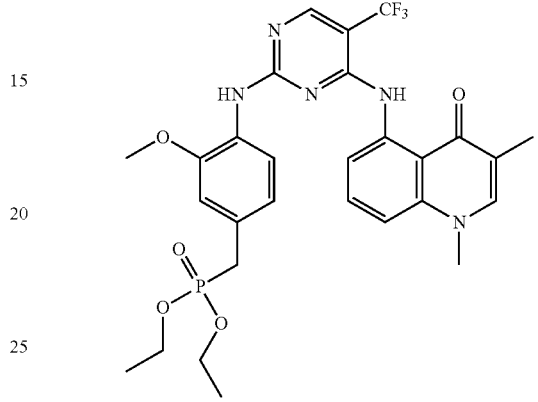

Example 300

Diethyl[4-({4-[(1,3-dimethyl-4-oxo-1,4-dihydroquinolin-5-yl)amino]-5-(trifluoromethyl)pyrimidin-2-yl}amino)-3-methoxybenzyl]phosphonate The title compound was prepared according to Compound 102A using diethyl (4-{[4-chloro-5-(trifluoromethyl)pyrimidin-2-yl]amino}-3-methoxybenzyl)phosphonate (99.5 mg, 0.219 mmol) and 5-amino-1,3-dimethylquinolin-4(1H)-one (Compound 299A, 49.2 mg, 0.261 mmol). $^1$H NMR (400 MHz, DMSO-d_6) δ ppm 14.66 (s, 1H), 8.88 (s, 1H), 8.60 (br s, 1H), 8.38 (s, 1H), 8.07 (s, 1H), 7.43-7.63 (m, 2H), 7.18 (d, J=8.6 Hz, 1H), 7.05 (s, 1H), 6.90 (d, J=7.8 Hz, 1H), 3.95-4.05 (m, 4H), 3.80 (s, 3H), 3.76 (s, 3H), 3.28 (d, J=21.5 Hz, 2H), 1.98 (s, 3H), 1.20 (t, J=6.9 Hz, 6H). MS (ES$^+$): m/z 606.16 (60) [MH$^+$]. HPLC: t_R=1.46 min (TOF, polar_3 min).

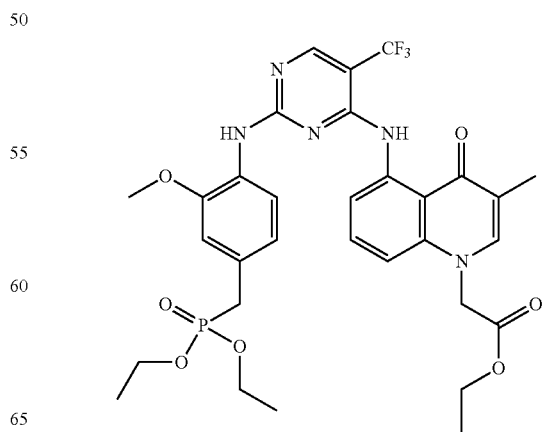

Example 301

Ethyl[5-{[2-({4-[(diethoxyphosphoryl)methyl]-2-methoxyphenyl}amino)-5-(trifluoromethyl)pyrimidin-4-yl]amino}-3-methyl-4-oxoquinolin-1(4H)-yl] acetate The title compound was prepared according to Compound 102A using diethyl (4-{[4-chloro-5-(trifluoromethyl)pyrimidin-2-yl]amino}-3-methoxybenzyl)phosphonate (50.0 mg, 0.110 mmol) and ethyl (5-amino-3-methyl-4-oxoquinolin-1 (4H)-yl)acetate (Example 301A, 31.5 mg, 0.121 mmol). $^1$H NMR (CD$_3$OD, 400 MHz): δ=1.24-1.32 (m, 9H), 2.12 (s, 3H), 3.29 (d, J=21.2 Hz, 2H), 4.05-4.16 (m, 6H), 4.84 (s, 2H), 6.91 (dt, J=2.8, 8.4 Hz, 1H), 7.04 (t, J=2.0 Hz, 1 H), 7.40 (d, J=8.8 Hz, 1H), 7.60 (t, J=8.4 Hz, 1H), 7.89 (s, 1H), 7.98 (d, J=8.0 Hz, 1H), 8.37 (s, 1H), 8.66 (d, J=7.6 Hz, 1H). MS (ES$^+$): m/z 678.17 [MH$^+$]. HPLC: $t_R$=1.50 min (UPLC TOF, polar_3 min).

Compound 301A: Ethyl (5-amino-3-methyl-4-oxo-quinolin-1(4H)-yl)acetate

A solution of (3-Methyl-5-nitro-4-oxo-4H-quinolin-1-yl)-acetic acid ethyl ester (Compound 301B, 250 mg, 0.86 mmol) in ethanol and dichloromethane (10 mL/20 mL) was cautiously treated with palladium on charcoal (10%) (30 mg) and hydrogenated at atmospheric pressure for 1 hr. The mixture was filtered and the filtrate was concentrated to a residue which upon trituration with t-butyl methyl ether gave the desired product as 150 mg of a light yellow solid (67%). $^1$H NMR of compound C (CDCl3, 300 MHz): δ 1.24 (t, 3H, J=7.5 Hz), 2.04 (s, 3H), 4.22 (q, 2H, J=7.5 Hz), 4.58 (s, 2H), 6.18 (d, J=8.4 Hz, 1H), 6.35 (d, J=8.5 Hz, 1H), 7.24 (m, 3H).

Compound 301B: (3-Methyl-5-nitro-4-oxo-4H-quinolin-1-yl)-acetic acid ethyl ester and A suspension of 3-methyl-5-nitroquinolin-4(1H)-one and 3-methyl-7-nitroquinolin-4(1H)-one (*Eur. J. Med. Chem.* 1997, 32, 547, 500 mg, 2.45 mmol,) and cesium carbonate (800 mg (2.45 mmol) in toluene (50 mL) was treated with ethyl bromoacetate (0.3 mL, 2.45 mmol) and stirred at RT for 3 days. The solid (Cesium salt of starting materials) was filtered and washed with dichloromethane. The filtrate was concentrated to give 400 mg of the crude material which was purified using flash column chromatography (DCM:MeOH, 99:1) to isolate the desired region-isomer: 100 mg $^1$H NMR (CDCl3, 300 MHz): δ 1.3 (m, 3H, J=7.2 Hz), 2.08 (s, 3H), 4.25 (q, 2H, J=7.2 Hz), 4.8 (s, 2H), 7.3 (m, 2H), 7.4 (s, 1H), 7.65 (t, J=8 Hz, 1H). The other isomer was also recovered: 70 mg.

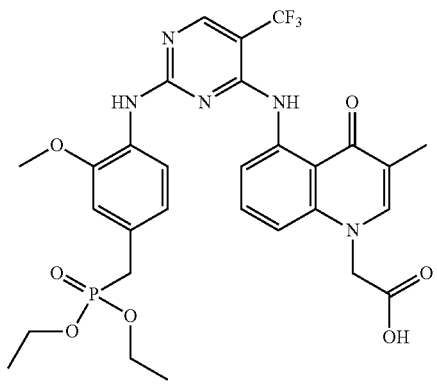 [SMILES: CCOP(=O)(Cc1ccc(Nc2ncc(C(F)(F)F)c(Nc3cccc4c3c(=O)c(C)cn4CC(=O)O)n2)c(OC)c1)OCC]

Example 302

[5-{[2-({4-[(Diethoxyphosphoryl)methyl]-2-methoxyphenyl}amino)-5-(trifluoromethyl)pyrimidin-4-yl]amino}-3-methyl-4-oxoquinolin-1(4H)-yl] acetic acid A solution of ethyl[5-{[2-({4-[(diethoxyphosphoryl)methyl]-2-methoxyphenyl}amino)-5-(trifluoromethyl)pyrimidin-4-yl]amino}-3-methyl-4-oxoquinolin-1(4H)-yl]acetate (Example 300, 41 mg, 0.061 mmol) in MeOH (0.5 mL), and THF (0.5 mL) was charged with LiOH H$_2$O (25.6 mg, 0.61 mmol). The resulting mixture was stirred at room temperature for 5 h. The reaction mixture was concentrated under reduced pressure. The material was purified by prep TLC (5% MeOH in DCM) to give 24.1 mg of the desired product (yield: 61%). $^1$H NMR (DMSO-d$_6$, 400 MHz): δ=1.20 (m, 6H), 1.99 (s, 3H), 3.24 (d, J=21.2 Hz, 2H), 3.78 (s, 3H), 3.99 (m, 2H), 6.90 (d, 1H), 7.03 (s, 1H), 7.43 (s, br, 1H), 7.61 (d, J=7.2 Hz, 1H), 7.94 (s, br, 1H). 8.36 (s, 1H), 8.51-8.56 (m, 2H). MS (ES$^+$): m/z 651.19 [MH$^+$]. HPLC: $t_R$=1.32 min (UPLC TOF, polar_3 min).

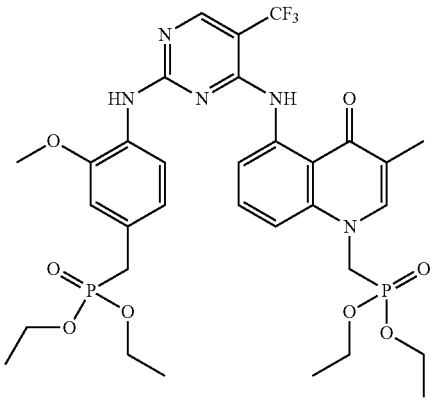 [SMILES: CCOP(=O)(Cc1ccc(Nc2ncc(C(F)(F)F)c(Nc3cccc4c3c(=O)c(C)cn4CP(=O)(OCC)OCC)n2)c(OC)c1)OCC]

Example 303

Diethyl{[5-{[2-({4-[(diethoxyphosphoryl)methyl]-2-methoxyphenyl}amino)-5-(trifluoromethyl)pyrimidin-4-yl]amino}-3-methyl-4-oxoquinolin-1(4H)-yl] methyl}phosphonate The title compound was prepared according to Compound 102A using diethyl (4-{[4-chloro-5-(trifluoromethyl)pyrimidin-2-yl]amino}-3-methoxybenzyl)phosphonate (45.4 mg, 0.100 mmol) and diethyl[(5-amino-3-methyl-4-oxoquinolin-1(4H)-yl)methyl]phosphonate hydrochloride (Compound 303A, 39.7 mg, 0.110 mmol). $^1$H NMR (CD$_3$OD, 400 MHz): δ=1.24 (t, J=7.2 Hz, 6H), 1.28 (t, J=7.2 Hz, 6H), 2.12 (s, 3H), 3.28 (d, J=21.2 Hz, 2H), 3.91 (s, 3H), 4.06-4.11 (m, 8H), 4.86 (s, 2H), 6.91 (d, J=8.4 Hz, 1H), 7.04 (m, 1H), 7.44 (d, J=8.8 Hz, 1H), 7.62 (m, 1H), 7.92 (s, 1H), 7.96 (dd, J=2.4, 8.4 Hz, 1H), 8.37 (s, 1H), 8.67 (d, J=8.0 Hz, 1H). MS (ES$^+$): m/z 742.18 [MH$^+$]. HPLC: $t_R$=1.44 min (UPLC TOF, polar_3 min).

Compound 303A: Diethyl[(5-amino-3-methyl-4-oxoquinolin-1(4H)-yl)methyl]phosphonate hydrochloride A solution of (3-Methyl-5-nitro-4-oxo-4H-quinolin-1-ylmethyl)-phosphonic acid diethyl ester (Compound 303B, 20 mg; 0.05 mmol) in methanol (5 mL) was charged with Pd/C (5 mg) and 1M HCl in ether (1 mL) under nitrogen and stirred under 1 atmosphere of hydrogen overnight at RT. The solution was filtered the filtrate concentrated to get the final compound (yield 20 mg; 99%; tlc 1:9 MeOH:DCM); $^1$H NMR (300 MHz, CDCl$_3$), δ ppm, 8.12 (s, 1H), 8.01 (d, 6 Hz, 1H,) 7.88-7.83 (m, 1H) 7.40 (d, J=9 Hz, 1H) 4.12-4.13 (m, 4H,) 3.31-3.29 (m, 2H), 2.14 (s, 3H), 1.27-1.25 (m, 6H)

Compound 303B: 3-Methyl-5-nitro-4-oxo-4H-quinolin-1-ylmethyl)-phosphonic acid diethyl ester Sodium hydride (40 mg; 1.6 mmol) was added to a solution of 3-methyl-5-nitroquinolin-4(1H)-one and 3-methyl-7-nitroquinolin-4(1H)-one (*Eur. J. Med. Chem.* 1997, 32, 547; 150 mg; 0.7 mmol) in DMF (20 mL) at 0° C. After this mixture stirred for 30 minutes diethyl iodomethylphosphonate (750 mg; 2.6 mmol) was added and solution was stirred overnight at RT. The solvent was evaporated to get crude product which was subjected to flash chromatography (1:9 MeOH:DCM) to get the title product. (20 mg; 17.8%). $^1$H NMR (300 MHz, CDCl$_3$), δ ppm, 7.66 (s, 2H), 7.49 (s, 1H) 7.25 (s, 1H) 4.45 (d, J=15 Hz, 2H) 4.05-4.12 (m, 4H), 2.06 (s, 3H), 1.27-1.23 (m, 6H).

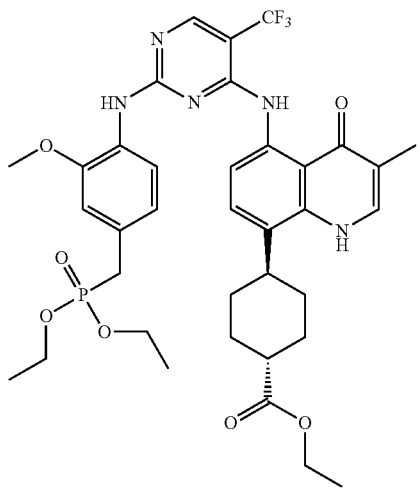

Example 304

Ethyl trans-4-(5-{[2-({4-[(diethoxyphosphoryl)methyl]-2-methoxyphenyl}amino)-5-(trifluoromethyl)pyrimidin-4-yl]amino}-3-methyl-4-oxo-1,4-dihydroquinolin-8-yl)cyclohexanecarboxylate The title compound was prepared according to Compound 102A using diethyl (4-{[4-chloro-5-(trifluoromethyl)pyrimidin-2-yl]amino}-3-methoxybenzyl)phosphonate (233.0 mg, 0.44 mmol) and ethyl trans-4-(5-amino-3-methyl-4-oxo-1,4-dihydroquinolin-8-yl)cyclohexanecarboxylate (Compound 304A, 172.0 mg, 0.52 mmol). $^1$H NMR (400 MHz, MeOD) δ ppm 1.26-1.35 (m, 9 H) 1.69-1.94 (m, 6H) 2.14 (s, 3H) 2.31 (d, J=13.64 Hz, 2H) 2.83 (br. s., 1H) 2.97-3.06 (m, 1H) 3.33 (s, 1H) 3.39 (s, 1H) 3.91 (s, 3H) 4.10 (quin, J=7.26 Hz, 4H) 4.24 (q, J=7.24 Hz, 2H) 6.93 (m, J=6.06 Hz, 1H) 7.11 (t, J=2.02 Hz, 1H) 7.35 (d, J=7.83 Hz, 1H) 7.81 (d, J=7.83 Hz, 1H) 7.87 (s, 1H) 8.31 (s, 1H) 8.49 (br. s., 1H). MS (ES$^+$): m/z: 746.20/747.19 (100/40) [MH$^+$]. HPLC: $t_R$=4.42 min (Micromass ZQ3: polar_5 min).

Compound 304A: (1) Ethyl trans-4-(5-amino-3-methyl-4-oxo-1,4-dihydroquinolin-8-yl)cyclohexanecarboxylate and Compound 304B: (2) Ethyl cis-4-(5-amino-3-methyl-4-oxo-1,4-dihydroquinolin-8-yl)cyclohexanecarboxylate A mixture of ethyl 4-(5-amino-3-methyl-4-oxo-1,4-dihydroquinolin-8-yl)cyclohex-3-ene-1-carboxylate (Compound 304C, 0.270 g, 0.83 mmol) and palladium 10% wt on activated carbon (88.0 mg, 0.083 mmol) in EtOH (2.17 mL) was evacuated and purged with hydrogen (3×) and subsequently stirred under one atmosphere of hydrogen at rt for 16 hrs. The reaction mixture was filtered and the filtrate was concentrated in vacuo to an orange oil. The product was purified by mass directed purification which resolved the cis and trans isomers. Compound 304A, the trans isomer eluted first: $^1$H NMR (400 MHz, MeOD) δ ppm 1.27 (t, J=7.07 Hz, 3H) 1.53-1.73 (m, 4H) 1.79 (d, J=4.29 Hz, 2H) 2.02 (d, J=0.76 Hz, 3H) 2.26 (d, J=13.14 Hz, 2H) 2.70-2.82 (m, 2H) 4.17 (q, J=7.07 Hz, 2H) 6.38 (d, J=8.34 Hz, 1H) 7.12 (d, J=8.34 Hz, 1H) 7.63 (s, 1H). MS (ES$^+$): m/z 329.16/329.36 (100/70) [MH$^+$]. HPLC: $t_R$=1.28 min (Micromass TOF: polar_3 min). Compound 304B, the cis isomer eluted after: $^1$H NMR (400 MHz, CDCl$_3$) δ ppm 1.25 (t, J=7.07 Hz, 3H) 1.54 (br. s., 1H) 1.70 (d, J=12.63 Hz, 1H) 1.87 (br. s., 1H) 2.02 (d, J=0.51 Hz, 1H) 2.07 (br. s., 1H) 2.35-2.45 (m, 1H) 2.69-2.81 (m, 1H) 4.12 (q, J=7.07 Hz, 1H) 6.39 (d, J=8.34 Hz, 1H) 7.20 (d, J=8.34 Hz, 1H) 7.64 (d, J=0.76 Hz, 1H). MS (ES$^+$): m/z 329.14/329.35 (100/70) [MH$^+$]. HPLC: $t_R$=1.30 min (Micromass TOF: polar_3 min).

Compound 304C: Ethyl 4-(5-amino-3-methyl-4-oxo-1,4-dihydroquinolin-8-yl)cyclohex-3-ene-1-carboxylate A solution of ethyl 4-(3-methyl-5-nitro-4-oxo-1,4-dihydroquinolin-8-yl)cyclohex-3-ene-1-carboxylate (Compound 304D, 600 mg, 1.69 mmol) in EtOH (50 mL) was charged with SnCl$_2$ (1.2 g, 5.33 mmol). The resulting mixture was stirred under reflux for 18 h. The reaction mixture was concentrated under reduced pressure. The residue was quenched with aq. NaHCO$_3$ solution (500 mL) and extracted with EtOAc (3×200 mL). The combined organic layers were dried over Na$_2$SO$_4$, filtered and concentrated under reduced pressure. The material was purified by prep TLC to afford the desired compound (270 mg, yield: 49%). $^1$H NMR (CDCl$_3$, 400 MHz): δ=1.22 (t, J=7.2 Hz, 3H), 1.99 (s, 3H), 2.03 (m, 1H), 2.11-2.13 (m, 2H), 2.19-2.21 (m, 2H), 2.34-2.39 (m, 2H), 2.78 (m, 1H), 3.42 (d, J=3.2 Hz, 1H), 4.12 (q, J=7.2 Hz, 2H), 5.71 (s, 1H), 6.20 (d, J=8.0 Hz, 1H), 6.71 (s, br, 2H), 6.93 (d, J=8.0 Hz, 1H), 7.36 (d, J=6.0 Hz, 1H), 8.91 (s, br, 1H).

Compound 304D: Ethyl 4-(3-methyl-5-nitro-4-oxo-1,4-dihydroquinolin-8-yl)cyclohex-3-ene-1-carboxylate A mixture of 8-bromo-3-methyl-5-nitroquinolin-4(1H)-one (Compound 304E, 700 mg, 2.47 mmol), ethyl 4-(4,4,5,5-tetramethyl-[1,3,2]dioxaborolan-2-yl)cyclohex-3-enecarboxylate (1.8 g, 6.43 mmol, commercially available or can be prepared according to WO2008/099221), Pd(PPh$_3$)$_4$ (20 mg), and Na$_2$CO$_3$ (1 g, 9.43 mmol) in 1,4-dioxane/H$_2$O (150 mL, 4:1) was evacuated and purged with N$_2$. The reaction mixture was stirred at 100° C. for 18 h under N$_2$. The reaction mixture was filtered and the filtrate was concentrated under reduced pressure. The material was purified by flash column chromatography to afford the desired compound (600 mg, yield: 67%). $^1$H NMR (DMSO-d$_6$, 400 MHz): δ=1.22 (t, J=7.2 Hz, 3H), 1.85 (m, 1H), 1.96 (s, 3H), 2.08 (m, 1H), 2.26 (m, 1H), 2.38-2.49 (m, 3H), 2.78 (m, 1H), 4.12 (q, J=7.2 Hz, 2H), 5.84 (s, 1H), 7.46 (d, J=8.0 Hz, 1H), 7.58 (d, J=8.0 Hz, 1H), 7.83 (d, J=6.0 Hz, 1H), 10.94 (d, J=6.0 Hz, 1H).

Compound 304E:
8-Bromo-3-methyl-5-nitroquinolin-4(1H)-one

A mixture of methyl 3-[(2-bromo-5-nitrophenyl)amino]-2-methylprop-2-enoate (Compound 304F, 10 g, 3.2 mmol) and PhOPh (6 mL) was stirred at 250° C. for 2 h. The reaction mixture was allowed to cool to room temperature. Petroleum ether (60 mL) was added to the reaction mixture and the precipitate was filtered. The material was purified by column chromatography to afford 2.8 g of the desired product (yield: 28%) as a solid. $^1$H NMR (DMSO-d$_6$, 400 MHz): δ=1.95 (s, 3H), 7.48 (d, J=8.0 Hz, 1H), 7.91 (s, 1H), 8.12 (d, J=8.0 Hz, 1H), 11.46 (s, br, 1H).

Compound 304F: Methyl 3-[(2-bromo-5-nitrophenyl)amino]-2-methylprop-2-enoate

A mixture of methyl 3,3-dimethoxy-2-methylpropionate (10 g, 46 mmol. Commercially available or can be prepared according to Org. Biomol. Chem. 2006, 4, 2945), 2-bromo-5-nitrophenylamine (12 g, 74 mmol) and p-TsOH (50 mg, 0.29 mmol) in benzene (200 mL) was stirred at reflux for 24 h. The reaction mixture was allowed to cool to room temperature. The reaction mixture was concentrated under reduced pressure. The residue was recrystallized from DCM to afford the desired product (9.8 g, yield: 67.5%) as a solid. $^1$H NMR (DMSO-d$_6$, 400 MHz): δ=1.86 (s, 3H), 3.29 (s, 3H), 7.64 (dd, J=2.4, 8.4 Hz, 1H), 7.87 (s, 1H), 7.88 (d, J=8.4 Hz, 1H), 8.24 (d, J=2.4 Hz, 1H).

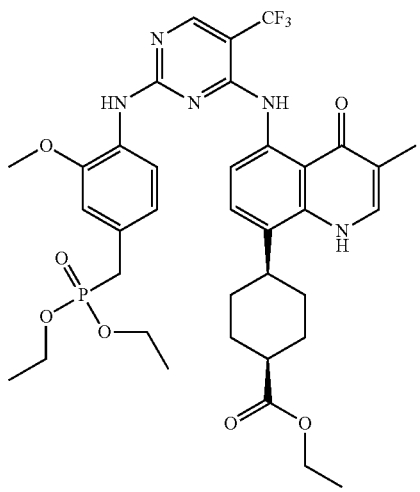

Example 305

Ethyl cis-4-(5-{[2-({4-[(diethoxyphosphoryl)methyl]-2-methoxyphenyl}amino)-5-(trifluoromethyl)pyrimidin-4-yl]amino}-3-methyl-4-oxo-1,4-dihydroquinolin-8-yl)cyclohexanecarboxylate The title compound was prepared according to Compound 102A using diethyl (4-{[4-chloro-5-(trifluoromethyl)pyrimidin-2-yl]amino}-3-methoxybenzyl)phosphonate (94.83 mg, 0.18 mmol) and ethyl cis-4-(5-amino-3-methyl-4-oxo-1,4-dihydroquinolin-8-yl)cyclohexanecarboxylate (Compound 304B, 70.0 mg, 0.213 mmol). $^1$H NMR (400 MHz, MeOD) δ ppm 8.57 (br. s., 1H), 8.32 (s, 1H), 7.82-7.88 (m, 2H), 7.48 (d, J=8.6 Hz, 1H), 7.09 (d, J=3.8 Hz, 1H), 6.96 (dt, J=8.1, 2.2 Hz, 1H), 4.16 (q, J=7.2 Hz, 2H), 4.05-4.13 (m, 4H), 3.91 (s, 3H), 3.35 (s, 1H), 3.33 (br. s., 1H), 2.92-3.03 (m, 1H), 2.51 (td, J=11.7, 3.4 Hz, 1H), 2.44-2.56 (m, 1H), 2.17 (br. s., 5H), 1.98 (d, J=10.1 Hz, 2H), 1.63-1.83 (m, 4H), 1.25-1.33 (m, 9H). MS (ES$^+$): m/z: 746.20/747.19 (100/40) [MH$^+$]. HPLC: t$_R$=4.44 min (Micromass ZQ3: polar_5 min).

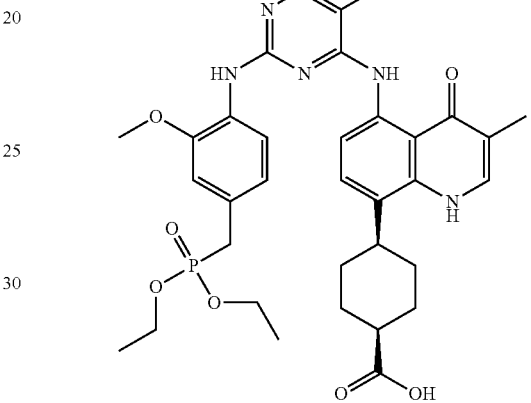

Example 306

Cis-4-(5-{[2-({4-[(diethoxyphosphoryl)methyl]-2-methoxyphenyl}amino)-5-(trifluoromethyl)pyrimidin-4-yl]amino}-3-methyl-4-oxo-1,4-dihydroquinolin-8-yl)cyclohexanecarboxylic acid A solution of ethyl cis-4-(5-{[2-({4-[(diethoxyphosphoryl)methyl]-2-methoxyphenyl}amino)-5-(trifluoromethyl)pyrimidin-4-yl]amino}-3-methyl-4-oxo-1,4-dihydroquinolin-8-yl)cyclohexanecarboxylate (Example 305, 61.7 mg, 0.083 mmol) in THF (0.11 mL) and MeOH (0.11 mL) was charged with a solution of lithium hydroxide, monohydrate (17.4 mg, 0.41 mmol) in H$_2$O (0.11 mL) and allowed to stir at rt for 30 hrs. The reaction was concentrated under reduced pressure. The material was purified on an Isco combi-flash unit using DCM/MeOH (100:0→95:5) as eluent to afford 22.3 mg (38%) of the desired product. $^1$H NMR (400 MHz, MeOD) δ ppm 1.24-1.30 (m, 6H) 1.76-1.89 (m, 6H) 2.11-2.15 (m, 3H) 2.34 (d, J=4.80 Hz, 2H) 2.73 (br. s., 1H) 2.99 (s, 1H) 3.29 (br. s., 1H) 3.34 (s, 1H) 3.89-3.94 (m, 3H) 4.02-4.13 (m, 4H) 6.87 (dt, J=8.21, 2.34 Hz, 1H) 7.03 (t, J=2.02 Hz, 1H) 7.41 (d, J=8.59 Hz, 1H) 7.84 (d, J=0.76 Hz, 1H) 8.03 (d, J=8.34 Hz, 1H) 8.33 (s, 1H) 8.49 (d, J=6.32 Hz, 1H). MS (ES$^+$): m/z 718.15/719.19 (100/98) [MH$^+$]. HPLC: t$_R$=1.47 min (Micromass TOF: polar_3 min).

265

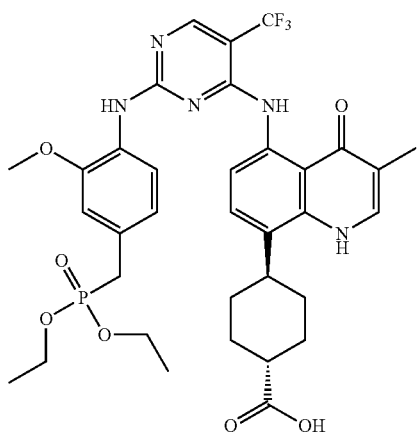

Example 307

Trans-4-(5-{[2-({4-[(diethoxyphosphoryl)methyl]-2-methoxyphenyl}amino)-5-(trifluoromethyl)pyrimidin-4-yl]amino}-3-methyl-4-oxo-1,4-dihydroquinolin-8-yl)cyclohexanecarboxylic acid A solution of Ethyl trans-4-(5-{[2-({4-[(diethoxyphosphoryl)methyl]-2-methoxyphenyl}amino)-5-(trifluoromethyl)pyrimidin-4-yl]amino}-3-methyl-4-oxo-1,4-dihydroquinolin-8-yl)cyclohexanecarboxylate (Example 304, 72.0 mg, 0.097 mmol) in THF (0.125 mL) and MeOH (0.129 mL) was charged with a solution of lithium hydroxide, monohydrate (20.2 mg, 0.48 mmol) in $H_2O$ (0.129 mL) and allowed to stir at rt for 30 hrs. The reaction was concentrated under reduced pressure. The material was purified on an Isco combi-flash unit using DCM/MeOH (100:0→95:5) as eluent to afford 45 mg (60%) of the desired product. $^1$H NMR (400 MHz, MeOD) δ ppm 1.24-1.33 (m, 6H) 1.66-1.86 (m, 4H) 1.96-2.04 (m, 2H) 2.12-2.14 (m, 3H) 2.15-2.22 (m, 2H) 3.39-3.43 (m, 1H) 3.46-3.50 (m, 1H) 3.91-3.94 (m, 3H) 4.05-4.11 (m, 4H) 6.88-6.94 (m, 1H) 7.03-7.07 (m, 1H) 7.47-7.52 (m, 1H) 7.83-7.86 (m, 1H) 8.01-8.06 (m, 1H) 8.33-8.35 (m, 1H) 8.50-8.59 (m, 1H). MS (ES$^+$): m/z 718.22/719.26 (100/98) [MH$^+$]. HPLC: $t_R$=1.43 min (Micromass TOF: polar_3 min).

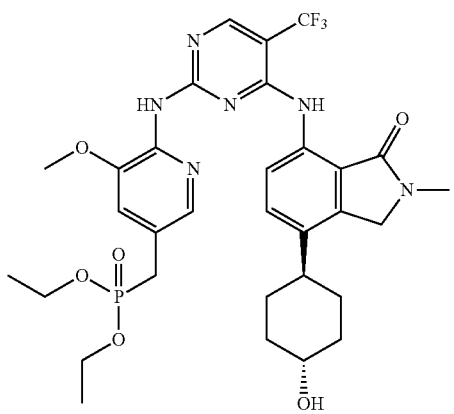 [SMILES: CCOP(=O)(Cc1cnc(Nc2ncc(C(F)(F)F)c(Nc3ccc([C@H]4CC[C@H](O)CC4)c4c3C(=O)N(C)C4)n2)c(OC)c1)OCC]

266

Example 308

Diethyl[(6-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}-5-methoxypyridin-3-yl)methyl]phosphonate To a suspension of 7-{[2-chloro-5-(trifluoromethyl)pyrimidin-4-yl]amino}-4-(trans-4-hydroxycyclohexyl)-2-methyl-2,3-dihydro-1H-isoindol-1-one (Compound 308C, 130.0 mg, 0.29 mmol), diethyl[(6-amino-5-methoxypyridin-3-yl)methyl]phosphonate (Compound 308A, 80.9 mg, 0.29 mmol), Pd(OAc)$_2$ (3.31 mg, 0.015 mmol), Xantphos (17.1 mg, 0.029 mmol), and $Cs_2CO_3$ (192.2 mg, 0.59 mmol) in dry dioxane (1.2 mL) was bubbled nitrogen for 2 min. This mixture was then irradiated at 160° C. for 40 min in a CEM microwave reactor. After cooled to room temperature, the reaction mixture was filtered and the filtrate was concentrated and purified by silica gel chromatography (1-5% MeOH in DCM) to give 1.9 mg of the title compound (yield: 1%). $^1$H NMR (CDCl$_3$, 400 MHz): δ=1.29 (t, J=7.2 Hz, 6H), 1.45 (m, 2H), 1.63 (m, 2H), 1.90 (m, 2H), 2.16 (m, 2H), 2.50 (m, 1H), 3.18 (d, J=21.2 Hz, 2H), 3.22 (s, 3H), 3.77 (m, 1H), 3.94 (s, 3H), 4.04-4.10 (m, 4H), 4.39 (s, 2H), 7.41 (d, J=8.4 Hz, 1H), 8.04 (s, 1H), 8.45 (s, 1H), 9.33 (d, J=8.0 Hz, 1H), 10.86 (s, 1H). MS (ES$^+$): m/z 679.23 [MH$^+$]. HPLC: $t_R$=1.21 min (UPLC TOF, polar_3 min).

Compound 308A: Diethyl[(6-amino-5-methoxypyridin-3-yl)methyl]phosphonate

Diethyl[(5-methoxy-6-nitropyridin-3-yl)methyl]phosphonate (Compound 308B, 102.6 mg) was hydrogenated in the presence of 10% Pd/C (20 mg) in MeOH (5 mL) under 1 atmosphere for 4 h. The catalyst was filtered off, the filtrate was concentrated, and the residue (85 mg, 92% yield) was used in the next step without purification. $^1$H NMR (CDCl$_3$, 400 MHz): δ=1.27 (dt, J=2.0, 6.8 Hz, 6H), 3.02 (d, J=20.8 Hz, 2H), 3.84 (s, 3H), 4.01-4.08 (m, 4H), 4.74 (s, 2H), 6.98 (t, J=2.0 Hz, 1H), 7.52 (t, J=2.0 Hz, 1H). MS (ES$^+$): m/z 275.10 [MH$^+$]. HPLC: $t_R$=0.77 min (UPLC TOF, polar_3 min).

Compound 308B: Diethyl[(5-methoxy-6-nitropyridin-3-yl)methyl]phosphonate

A solution of 2-nitro-3-methoxypyridine (300 mg, 1.95 mmol) and diethyl chloromethylphosphonate (363 mg, 1.95 mmol) in DMSO (4 mL) was added dropwise to vigorously stirred solution of t-BuONa (0.561 g, 5.84 mmol) in DMSO (4 mL) at room temperature. The reaction mixture turned to deep orange immediately. Stirring was continued for 30 min, then the mixture was poured into 1 M HCl (aq) (10 mL). The product was extracted into ether (3×30 mL), dried over MgSO$_4$, concentrated, and purified by silica gel chromatography (3% MeOH in DCM) to afford 102.6 mg of diethyl[(6-amino-5-methoxypyridin-3-yl)methyl]phosphonate (yield: 17%). $^1$H NMR (CD$_3$OD, 400 MHz): δ=1.30 (t, J=6.8 Hz, 6H), 3.45 (d, J=22.4 Hz, 2H), 4.00 (s, 3H), 4.09-4.17 (m, 4H), 7.79 (t, J=2.4 Hz, 1H), 7.97 (t, J=2.4 Hz, 1H). MS (ES$^+$): m/z 305.07 [MH$^+$]. HPLC: $t_R$=1.17 min (UPLC TOF, polar_3 min).

Compound 308C: 7-{[2-Chloro-5-(trifluoromethyl)pyrimidin-4-yl]amino}-4-(trans-4-hydroxycyclohexyl)-2-methyl-2,3-dihydro-1H-isoindol-1-one and 7-{[4-chloro-5-(trifluoromethyl)pyrimidin-2-yl]amino}-4-(trans-4-hydroxycyclohexyl)-2-methyl-2,3-dihydro-1H-isoindol-1-one To a suspension of 2,4-dichloro-5-trifluoromethylpyrimidine (300 mg, 1.38 mmol) and 7-amino-4-(trans-4-hydroxycyclohexyl)-2-methyl-2,3-dihydro-1H-isoindol-1-one (360 mg, 1.38 mmol) anhydrous dioxane (2 mL) was added DIPEA (0.48 mL, 2.76 mmol). The resulting mixture was stirred at 80° C. for 2 h to afford a brownish clear solution. After cooled to room temperature, the solvent was removed in vacuo and the residue was purified by silica gel chromatography (5% MeOH in DCM) to afford 380 mg of the desired products as a 64:36 ratio of two products with the minor is the desired 7-{[2-chloro-5-(trifluoromethyl)pyrimidin-4-yl] amino}-4-(trans-4-hydroxycyclohexyl)-2-methyl-2,3-dihydro-1H-isoindol-1-one (yield: 62%). $^1$H NMR (DMSO-d$_6$, 400 MHz) of the mixture: δ=1.25-1.35 (m, 2H), 1.50-1.60 (m, 2H), 1.76-1.79 (m, 2H), 1.93-1.95 (m, 2H), 2.48-2.54 (m, 1H), 3.10 (s, 1.92H), 3.46 (s, 1.08H), 3.45-3.51 (m, 1H), 4.56 (d, J=6.8 Hz, 1.28H), 4.63 (d, J=4.0 Hz, 0.72H), 7.49 (d, J=8.4 Hz, 0.64H), 7.53 (d, J=8.4 Hz, 0.36H), 8.30 (d, J=8.8 Hz, 0.64H), 8.46 (d, J=8.8 Hz, 0.36H), 8.73 (s, 0.36H), 8.91 (s, 0.64H), 10.79 (s, br, 0.64H), 11.10 (s, br, 0.36H). MS (ES$^+$) for the minor product: m/z 441.12 [MH$^+$, $^{35}$Cl], 443.13 [MH$^+$, $^{37}$Cl]. HPLC: t$_R$=1.47 min (UPLC TOF, polar__3 min). MS (ES$^+$) for the major product: m/z 441.12 [MH$^+$, $^{35}$Cl], 443.13 [MH$^+$, $^{37}$Cl]. HPLC: t$_R$=1.61 min (UPLC TOF, polar__3 min).

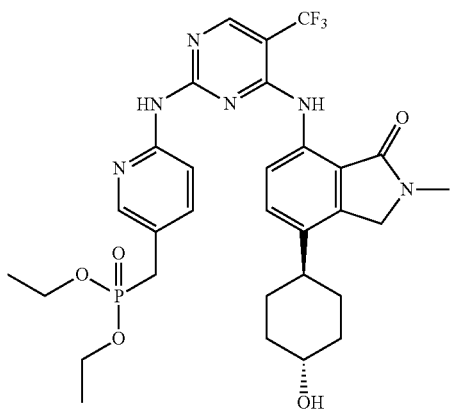 [SMILES: CCOP(=O)(Cc1ccc(Nc2ncc(C(F)(F)F)c(Nc3ccc([C@H]4CC[C@H](O)CC4)c4c3C(=O)N(C)C4)n2)nc1)OCC]

Example 309

Diethyl[(6-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}pyridin-3-yl)methyl]phosphonate To a suspension of 7-{[2-chloro-5-(trifluoromethyl)pyrimidin-4-yl]amino}-4-(trans-4-hydroxycyclohexyl)-2-methyl-2,3-dihydro-1H-isoindol-1-one (Compound 308C, 200 mg, 0.45 mmol. 36:64 mixture of regioisomers with the minor as the desired one), diethyl[(6-aminopyridin-3-yl)methyl] phosphonate (Compound 309A, 111 mg, 0.45 mmol), Pd(OAc)$_2$ (5.09 mg, 0.023 mmol), Xantphos (26.2 mg, 0.045 mmol), and Cs$_2$CO$_3$ (296 mg, 0.91 mmol) in dry dioxane (2.8 mL) was bubbled nitrogen for 2 min. This mixture was then irradiated at 160° C. for 40 min in a CEM microwave reactor. After cooled to room temperature, the reaction mixture was filtered and the filtrate was concentrated and purified by silica gel chromatography (1-5% MeOH in DCM) to give 32.6 mg of the title compound (yield: 11%), the more polar of the two regioisomers on the TLC. $^1$H NMR (CDCl$_3$, 400 MHz): δ=1.28 (t, J=7.2 Hz, 6H), 1.44 (m, 2H), 1.63 (m, 2H), 1.91 (m, 2H), 2.16 (m, 2H), 2.50 (m, 1H), 3.12 (d, J=21.2 Hz, 2H), 3.22 (s, 3H), 3.77 (m, 1H), 4.02-4.10 (m, 4H), 4.39 (s, 2H), 7.32 (d, J=8.4 Hz, 1H), 7.68 (d, J=8.4 Hz, 1H), 7.98 (s, 1H), 8.22 (s, 1H), 8.36 (d, J=8.4 Hz, 1H), 8.45 (s, 1H), 8.62 (d, J=8.4 Hz, 1H), 10.59 (s, 1H). MS (ES$^+$): m/z 649.18 [MH$^+$]. HPLC: t$_R$=3.38 min (ZQ3, polar__5 min).

Compound 309A: Diethyl[(6-aminopyridin-3-yl)methyl]phosphonate

A mixture of di-tert-butyl[5-(bromomethyl)pyridin-2-yl] imidodicarbonate (Compound 309B, 1.162 g, 3 mmol) and triethyl phosphite (0.598 g, 3.6 mmol) in dioxane (2 mL) was stirred at 110° C. for 4 h. The cooled reaction mixture (room temperature) was treated with 4 N HCl in dioxane (5 mL) and DCM (10 mL) and allowed to stir at room temperature for 6 h. Sat. NaHCO$_3$ (aq, 15 mL) was added and the mixture was extracted with DCM (3×40 mL). The combined organic phases were dried over MgSO$_4$, concentrated, and purified by silica gel chromatography (5% 7 N ammonia in MeOH in DCM) to afford 227 mg of the title compound (yield: 31%). $^1$H NMR (CDCl$_3$, 400 MHz): δ=1.29 (t, J=6.8 Hz, 6H), 2.98 (d, J=20.8 Hz, 2 H), 4.02-4.09 (m, 4H), 5.65 (s, br, 2H), 6.58 (d, J=8.8 Hz, 1H), 7.51 (dt, J=2.4, 8.8 Hz, 1H), 7.82 (t, J=2.4 Hz, 1H). MS (ES$^+$): m/z 245.09 [MH$^+$]. HPLC: t$_R$=0.70 min (UPLC TOF, polar__3 min).

Compound 309B: Di-tert-butyl[5-(bromomethyl) pyridin-2-yl]imidodicarbonate

A mixture of di-tert-butyl (5-methylpyridin-2-yl)imidodicarbonate (Compound 309C, 5.66 g, 18.4 mmol), NBS (3.92 g, 22 mmol), and benzoyl peroxide (0.444 g, 1.84 mmol) in CCl$_4$ (30 mL) was heated at 80° C. for 6 h. The mixture was cooled to room temperature, the solids were filtered off and the filtrate was concentrated. The residue was purified by silica gel chromatography (EtOAc/heptane: 1:1) to give 4.66 g of di-tert-butyl[5-(bromomethyl)pyridin-2-yl]imidodicarbonate (yield: 65%).

Compound 309C: Di-tert-butyl (5-methylpyridin-2-yl)imidodicarbonate

A mixture of 2-amino-5-methylpyridine (2 g, 18.5 mmol), di-tert-butyldicarbonate (8.88 g, 40.7 mmol), 4-dimethylaminopyridine (0.452 g, 3.7 mmol), and DIPEA (7.09 mL, 40.7 mmol) in DCM (20 mL) was stirred at room temperature for 18 h. Solvents were removed and the residue was purified by silica gel chromatography (EtOAc/heptane: 1:1) to afford 4.89 g of ~3:1 mixture of bis-Boc and mono-Boc-protected product (yield: 85%). $^1$H NMR (CDCl$_3$, 400 MHz): δ=1.44 (s, 18H), 2.35 (s, 3H), 7.10 (d, J=8.4 Hz, 1H), 7.54 (dd, J=2.4, 8.4 Hz, 1H), 8.32 (d, J=2.4 Hz, 1H).

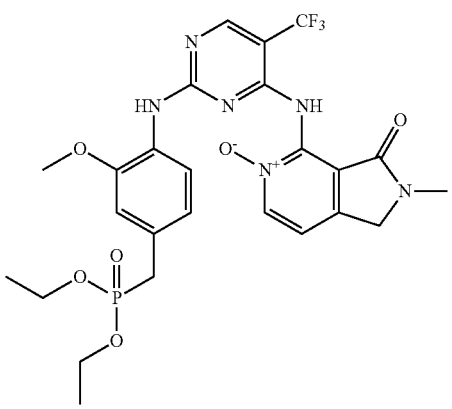 [SMILES: CCOP(=O)(Cc1ccc(Nc2ncc(C(F)(F)F)c(Nc3c4c(cc[n+]3[O-])CN(C)C4=O)n2)c(OC)c1)OCC]

Example 310

Diethyl[4-({4-[(2-methyl-5-oxido-3-oxo-2,3-dihydro-1H-pyrrolo[3,4-c]pyridin-4-yl)amino]-5-(trifluoromethyl)pyrimidin-2-yl}amino)benzyl]phosphonate The title compound was prepared according to the procedure for Example 102 using diethyl (4-{[4-chloro-5-(trifluoromethyl)pyrimidin-2-yl]amino}-3-methoxybenzyl)phosphonate (204 mg, 0.381 mmol) and 4-amino-2-methyl-1,2-dihydro-3H-pyrrolo[3,4-c]pyridin-3-one 5-oxide (Compound 310A, 68.3 mg, 0.381 mmol). The reaction mixture was concentrated under reduced pressure to yield a dark yellow oil which was purified by silica gel chromatography on the combi-flash Rf system using DCM/MeOH (100:0→90:10). The fractions containing product were combined and concentrated under reduced pressure to yield a white solid (38.4 mg, 17%). $^1$H NMR (DMSO-d6, 400 MHz): δ=8.99 (br. s., 1H), 8.47-8.55 (m, 3H), 7.47 (d, J=6.57 Hz, 1H), 7.24 (d, J=7.58 Hz, 1H), 6.85 (s, 1H), 6.56 (d, J=8.08 Hz, 1H), 4.45 (s, 2H), 3.90-3.99 (m, 4H), 3.70 (s, 3H), 3.12-3.21 (m, 2H), 2.86-2.89 (m, 3H), 1.17 (t, J=7.07 Hz, 6H). MS (ES$^+$): m/z 597.10 [MH$^+$] (TOF, polar).

Compound 310A: 4-Amino-2-methyl-1,2-dihydro-3H-pyrrolo[3,4-c]pyridin-3-one 5-oxide A mixture of 4-amino-2-methyl-1,2-dihydro-3H-pyrrolo[3,4-c]pyridin-3-one (Compound 310B, 62.5 mg, 0.383 mmol) and m-Chloroperbenzoic acid (145 mg, 0.843 mmol) in Acetone (10.0 mL) was stirred at rt for 90 minutes. The reaction mixture was concentrated under reduced pressure to an off white solid. The crude material was purified by silica gel chromatography on the combi-flash Rf system using DCM/7 N NH$_3$ in MeOH (100:0→90:10) as eluent. The fractions containing product were combined and concentrated under reduced pressure to yield a white solid (68.3 mg, 99.5%). $^1$H NMR (DMSO-d6, 400 MHz): δ=8.19 (d, J=6.57 Hz, 1H), 7.02 (br. s., 2H), 6.82 (d, J=6.57 Hz, 1H), 4.41 (s, 2H), 3.01 (s, 3H). MS (ES$^+$): m/z 180.07 [MH$^+$] (TOF, polar).

Compound 310C: 4-amino-2-methyl-1,2-dihydro-3H-pyrrolo[3,4-c]pyridin-3-one

A solution of 4-[(2,4-dimethoxybenzyl)amino]-2-methyl-1,2-dihydro-3H-pyrrolo[3,4-c]pyridin-3-one one (1.8 g, 5.7 mmol) in 37% HCl (7.0 mL) was stirred at rt for 16 hours. The reaction mixture was neutralized with NaOH and extracted with EtOAc (15 mL). The organic layer was washed with water (10 mL), washed with brine (10 mL), dried over Na$_2$SO$_4$, filtered, and concentrated under reduced pressure to yield a red solid. The crude material was purified by silica gel chromatography on the combi-flash Rf system using DCM/MeOH (100:0→95:5) as eluent. The fractions containing product were combined and concentrated under reduced pressure to yield an orange solid, (319 mg, 34%). $^1$H NMR (DMSO-d6, 400 MHz): δ=2.99 (s, 3H), 4.37 (s, 2H), 6.54 (br. s., 2H), 6.73 (d, J=5.05 Hz, 1H), 8.04 (d, J=5.05 Hz, 1H). MS (ES$^+$): m/z 164.07 [MH$^+$] (TOF, polar).

Compound 310D: 4-[(2,4-dimethoxybenzyl)amino]-2-methyl-1,2-dihydro-3H-pyrrolo[3,4-c]pyridin-3-one A solution of 4-chloro-2-methyl-1,2-dihydro-3H-pyrrolo[3,4-c]pyridin-3-one (Compound 310E, 1.5 g, 8.2 mmol) in N-Methylpyrrolidinone (20 mL) was charged with 2,4-dimethoxy benzylamine (2.5 mL, 16 mmol) and irradiated in the microwave for 40 min at 160° C. The reaction mixture was quenched with water (15 mL) and extracted with EtOAc (20 mL). The aqueous layer was back-extracted with EtOAc (3×10 mL). The combined organic fractions were washed with brine, dried over sodium sulfate, filtered, and concentrated under reduced pressure to yield a red solid. The crude material was purified by silica gel chromatography on the combi-flash Rf system using Heptane/EtOAc (70:30→0:100) as eluent. The fractions containing product were combined and concentrated under reduced pressure to yield an orange solid. $^1$H NMR (DMSO-d6, 400 MHz): δ=8.10 (d, J=5.30 Hz, 1H), 7.11 (d, J=8.34 Hz, 1H), 7.01-7.07 (m, 1H), 6.72 (d, J=5.31 Hz, 1H), 6.57 (d, J=2.27 Hz, 1H), 6.44 (dd, J=2.53, 8.34 Hz, 1H), 4.53 (d, J=6.06 Hz, 2H), 4.37 (s, 2H), 3.81 (s, 3H), 3.73 (s, 3H), 2.98 (s, 3H). MS (ES$^+$): m/z 314.14 [MH$^+$] (TOF, polar).

Compound 310E: 4-chloro-2-methyl-1,2-dihydro-3H-pyrrolo[3,4-c]pyridin-3-one A solution of 4,6-dichloro-N-methyl-N-(prop-2-yn-1-yl)pyrimidine-5-carboxamide (Compound 310F, 7.6 g, 31 mmol) in Nitrobenzene (76 mL) was evacuated and purged with argon (3×). The reaction mixture was irradiated in the microwave for 1.5 minutes at 250° C. The reaction mixture was filtered through a pad of celite. The nitrobenzene solution was passed through a silica gel plug and washed with DCM to remove the nitrobenzene. The silica was then washed with DCM/MeOH solution (90:10). The filtrated was concentrated under reduced pressure to yield a red solid. The crude material was purified by silica gel chromatography on a combi-flash Rf system using DCM/MeOH (100:0→95:5) as eluent. The fractions containing product were combined and concentrated under reduced pressure to yield an orange solid (3.1598 g, 56%). $^1$H NMR (DMSO-d6, 400 MHz): δ=8.53 (d, J=5.05 Hz, 1H), 7.70 (d, J=5.05 Hz, 1H), 4.53 (s, 2H), 3.05 (s, 3H). MS (ES$^+$): m/z 183.02 [M$^+$] (TOF, polar).

Compound 310F: 4,6-dichloro-N-methyl-N-(prop-2-yn-1-yl)pyrimidine-5-carboxamide A solution of 4,6-dichloropyrimidine-5-carboxylic acid (Compound 310G, 15.0 g, 77.7 mmol) and thionyl chloride (28.3 mL, 389 mmol) was refluxed in DCM (100 mL) for 2 h. The reaction mixture was concentrated in vacuo, taken up in DMF (200 mL) and charged drop-wise with a solution of N-methyl-2-propyn-1-amine (5.4 g, 78 mmol) and triethylamine (21.7 mL, 155 mmol) in DMF at −60° C. and stirred at rt for 24 h. The reaction mixture was partitioned between EtOAc and water and separated. The aqueous layer was extracted with EtOAc (3×) and the combined organic fractions were washed with brine, dried over sodium sulfate, filtered, and concentrated. The compound was purified on an Isco Combiflash to afford 7.66 g, 40% yield, of the title compound. $^1$H NMR (DMSO-d6, 400 MHz): δ=9.04 (s, 1H), 4.37 (d, J=2.53 Hz, 2H), 3.08 (s, 1H), 2.95 (s, 3H). MS (ES$^+$): m/z 246.0039 [MH$^+$] (TOF, polar).

Compound 310G:
4,6-dichloropyrimidine-5-carboxylic acid

A solution of 4,6-dichloro-5-pyrimidinecarbaldehyde (15.0 g, 84.8 mmol) in DMF (360 mL) was charged with potassium monopersulfate (38.9 g, 254 mmol) and stirred over night at rt. The reaction mixture was filtered through a pad of celite and partitioned between EtOAc and water and separated. The aqueous was extracted with EtOAc (3×) and the combined organic fractions were washed with water (2×), brine, and dried over sodium sulfate, filtered, and concentrated to afford the title compound. $^1$H NMR (DMSO-d6, 400 MHz): δ=9.02 (s, 1H).

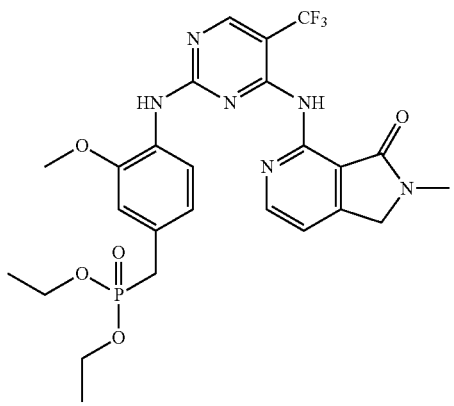 [SMILES: CCOP(=O)(Cc1ccc(Nc2ncc(C(F)(F)F)c(Nc3nccc4c3C(=O)N(C)C4)n2)c(OC)c1)OCC]

Example 311

Diethyl[4-({4-[(2-methyl-3-oxo-2,3-dihydro-1H-pyrrolo[3,4-c]pyridin-4-yl)-amino]-5-(trifluoromethyl)pyrimidin-2-yl}amino)benzyl]phosphonate A solution of diethyl[3-methoxy-4-({4-[(2-methyl-5-oxido-3-oxo-2,3-dihydro-1H-pyrrolo[3,4-c]pyridin-4-yl)amino]-5-(trifluoromethyl)pyrimidin-2-yl}amino)benzyl] phosphonate (Example 310, 35.0 mg, 0.0587 mmol) in EtOH (2.0 mL) was charged with iron (6.9 mg, 0.12 mmol) and heated to reflux. The reaction mixture was charged with 1 M of HCl in H$_2$O (0.07 mL, 0.07 mmol) and stirred at reflux for 10 minutes. Additional 1 M of HCl in H$_2$O (0.03 mL, 0.03 mmol) was added to the reaction mixture and stirred at reflux for 10 minutes. The reaction mixture was filtered through a pad of celite. The filtrate was quenched with NaHCO$_3$ (10 mL) and extracted with EtOAc (15 mL). The organic layer was washed with brine, dried over Na$_2$SO$_4$, filtered and concentrated under reduced pressure to a yellow solid. The crude material was purified by silica gel chromatography on an ISCO Combi-flash Rf system using DCM/MeOH (100:0→95:5) as eluent. The fractions containing product were combined and concentrated under reduced pressure to yield a white solid (17.0 mg, 50%). The material was re-purified by HPLC. The fractions containing product were combined and concentrated to yield a white solid (4.3 mg, 13%). $^1$H NMR (DMSO-d6, 400 MHz): δ=8.71 (br. s., 1H), 8.60 (d, J=5.05 Hz 1H), 8.54 (s, 1H), 8.47 (br. s., 1H), 8.32 (s, 1H), 7.41 (d, J=5.05 Hz, 1H), 6.95 (s, 1H), 6.85-6.92 (m, 1H), 4.57 (s, 2H), 3.90-4.01 (m, 4H), 3.84 (s, 3H), 3.21 (s, 1H), 3.06 (s, 3H), 1.19 (t, J=6.95 Hz, 6H). MS (ES$^+$): m/z 581.10 [MH$^+$] (TOF, polar).

The invention further includes the following examples:

| Ex. 312 | 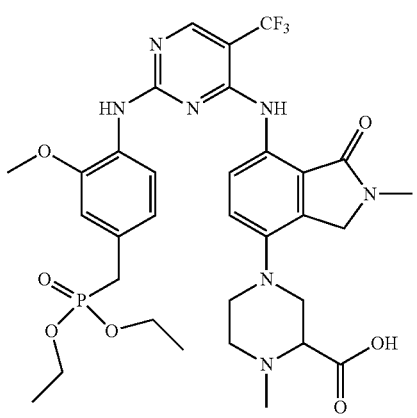 | 4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)-1-methylpiperazine-2-carboxylic acid |

| Ex. 313 | 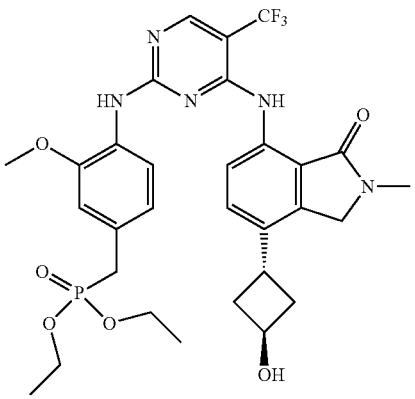 | diethyl (4-{[4-{[7-(trans-3-hydroxycyclobutyl)-2-methyl-3-oxo-2,3-dihydro-1H-isoindol-4-yl]amino}-5-(trifluoromethyl)pyrimidin-2-yl]amino}-3-methoxybenzyl)phosphonate |
| --- | --- | --- |
| Ex. 314 | 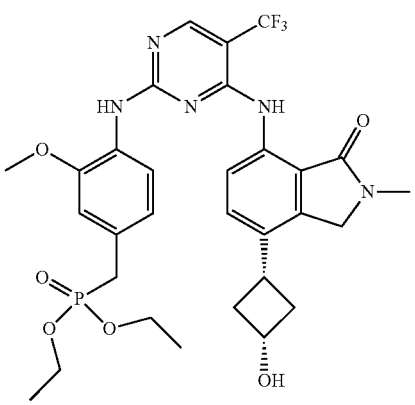 | diethyl (4-{[4-{[7-(cis-3-hydroxycyclobutyl)-2-methyl-3-oxo-2,3-dihydro-1H-isoindol-4-yl]amino}-5-(trifluoromethyl)pyrimidin-2-yl]amino}-3-methoxybenzyl)phosphonate |
| Ex. 315 | 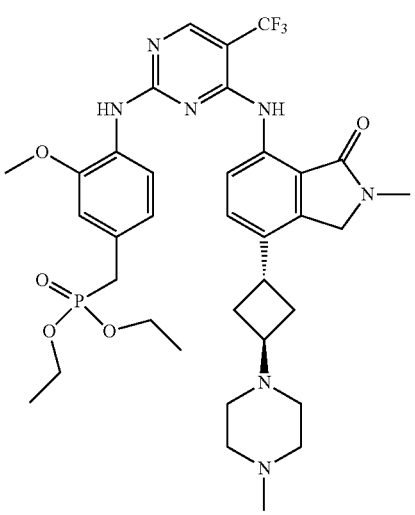 | diethyl (3-methoxy-4-{[4-({2-methyl-7-[trans-3-(4-methylpiperazin-1-yl)cyclobutyl]-3-oxo-2,3-dihydro-1H-isoindol-4-yl}amino)-5-(trifluoromethyl)pyrimidin-2-yl]amino}benzyl)phosphonate |

| | | |
|---|---|---|
| Ex. 316 | 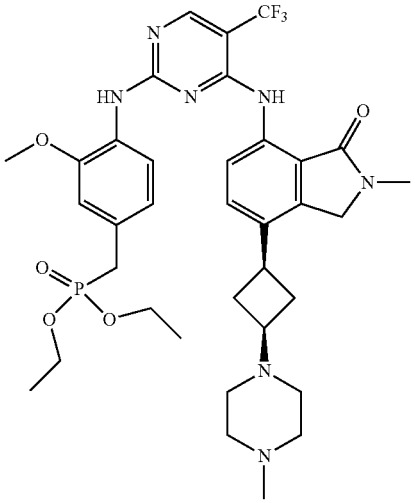 | diethyl (3-methoxy-4-{[4-({2-methyl-7-[cis-3-(4-methylpiperazin-1-yl)cyclobutyl]-3-oxo-2,3-dihydro-1H-isoindol-4-yl}amino)-5-(trifluoromethyl)pyrimidin-2-yl]amino}benzyl)phosphonate |
| Ex. 317 | 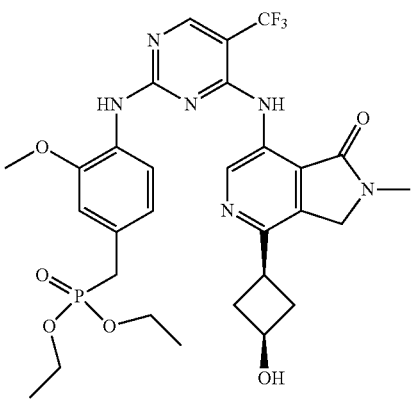 | diethyl (4-{[4-{[4-(cis-3-hydroxycyclobutyl)-2-methyl-1-oxo-2,3-dihydro-1H-pyrrolo[3,4-c]pyridin-7-yl]amino}-5-(trifluoromethyl)pyrimidin-2-yl]amino}-3-methoxybenzyl)phosphonate |
| Ex. 318 | 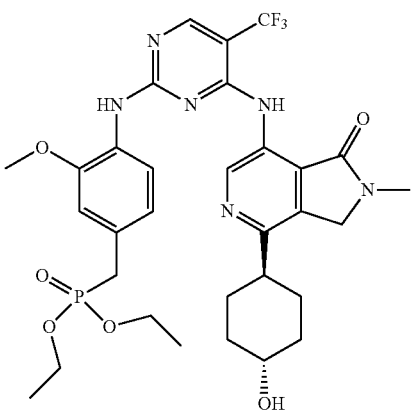 | diethyl (4-{[4-{[4-(trans-4-hydroxycyclohexyl)-2-methyl-1-oxo-2,3-dihydro-1H-pyrrolo[3,4-c]pyridin-7-yl]amino}-5-(trifluoromethyl)pyrimidin-2-yl]amino}-3-methoxybenzyl)phosphonate |

| Ex. 319 | 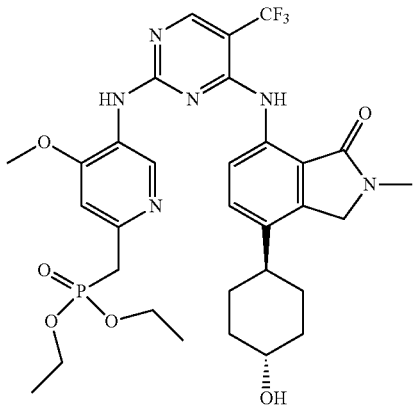 | diethyl [(5-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}-4-methoxypyridin-2-yl)methyl]phosphonate |
|---|---|---|
| Ex. 320 | Chiral 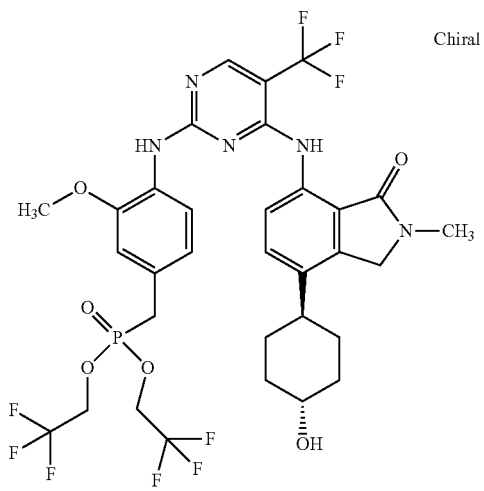 [SMILES: COc1cc(CP(=O)(OCC(F)(F)F)OCC(F)(F)F)ccc1Nc1ncc(C(F)(F)F)c(Nc2ccc([C@H]3CC[C@H](O)CC3)c3c2C(=O)N(C)C3)n1 ; "Chiral"] | Bis(2,2,2-trifluoroethyl) (4-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}-3-methoxybenzyl)phosphonate |
| Ex. 321 | 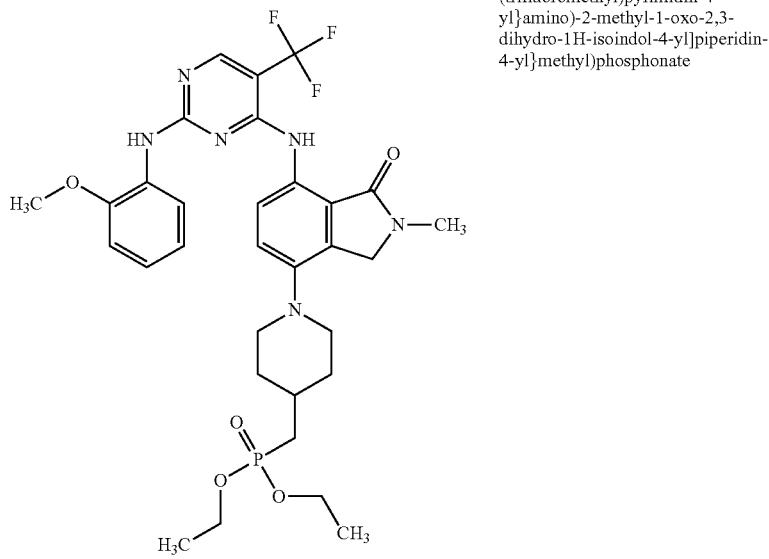 | Diethyl ({1-[7-({2-[(2-methoxyphenyl)amino]-5-(trifluoromethyl)pyrimidin-4-yl}amino)-2-methyl-1-oxo-2,3-dihydro-1H-isoindol-4-yl]piperidin-4-yl}methyl)phosphonate |

| Ex. 322 | 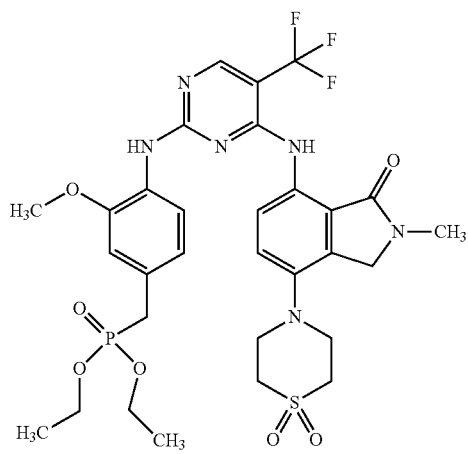 | Diethyl (4-{[4-{[7-(1,1-dioxidothiomorpholin-4-yl)-2-methyl-3-oxo-2,3-dihydro-1H-isoindol-4-yl]amino}-5-(trifluoromethyl)pyrimidin-2-yl]amino}-3-methoxybenzyl)phosphonate |
|---|---|---|
| Ex. 323 | 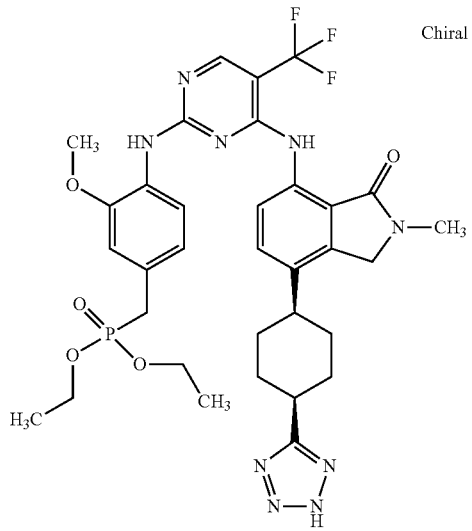 [SMILES: CCOP(=O)(Cc1ccc(Nc2ncc(C(F)(F)F)c(Nc3ccc([C@H]4CC[C@@H](c5nn[nH]n5)CC4)c4c3C(=O)N(C)C4)n2)c(OC)c1)OCC ; "Chiral"] Chiral | diethyl (3-methoxy-4-{[4-({2-methyl-3-oxo-7-[cis-4-(2H-tetrazol-5-yl)cyclohexyl]-2,3-dihydro-1H-isoindol-4-yl}amino)-5-(trifluoromethyl)pyrimidin-2-yl]amino}benzyl)phosphonate |
| Ex. 324 | 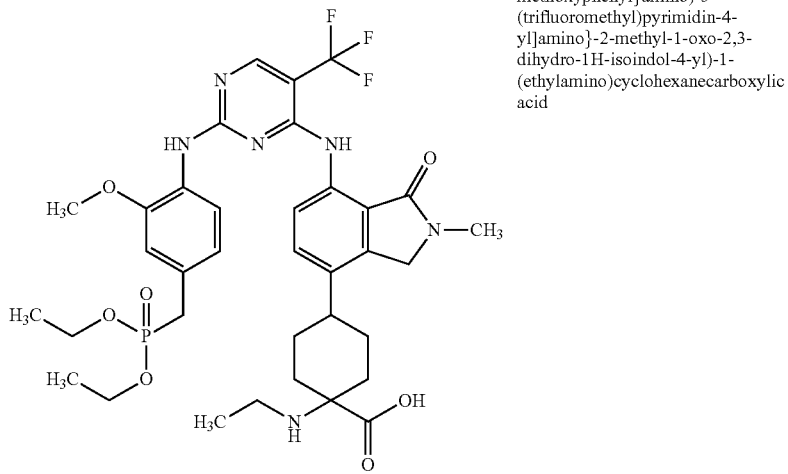 | 4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)-1-(ethylamino)cyclohexanecarboxylic acid |

| Ex. 325 | 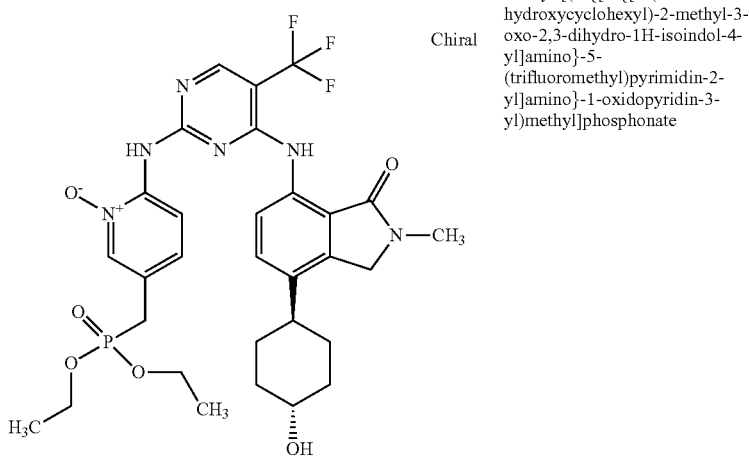 | diethyl [(6-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}-1-oxidopyridin-3-yl)methyl]phosphonate |
|---|---|---|
| Ex. 326 | 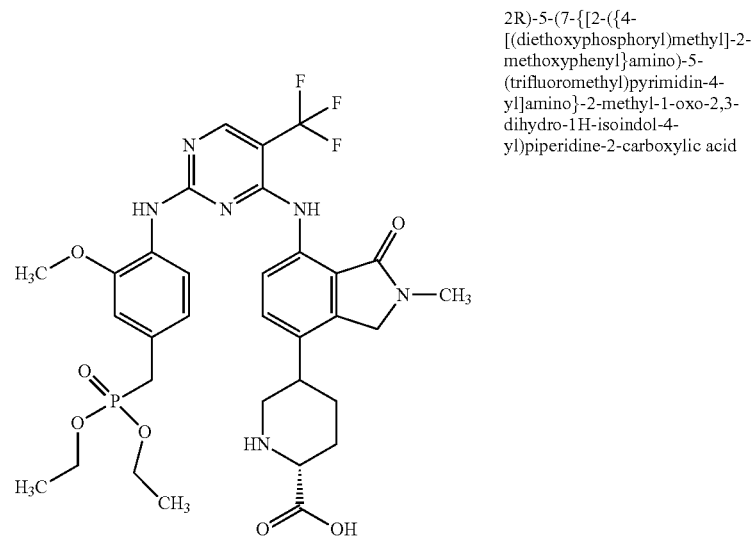 | 2R)-5-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)piperidine-2-carboxylic acid |
| Ex. 327 | 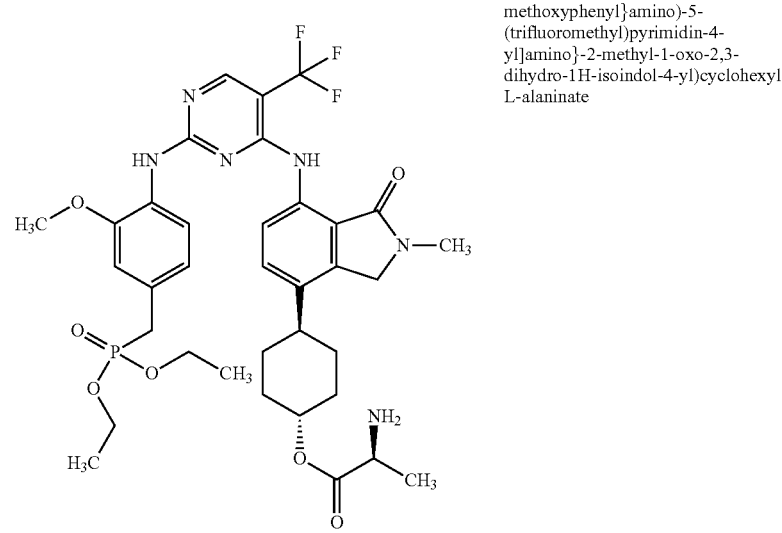 | trans-4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexyl L-alaninate |

| Ex. 328 | 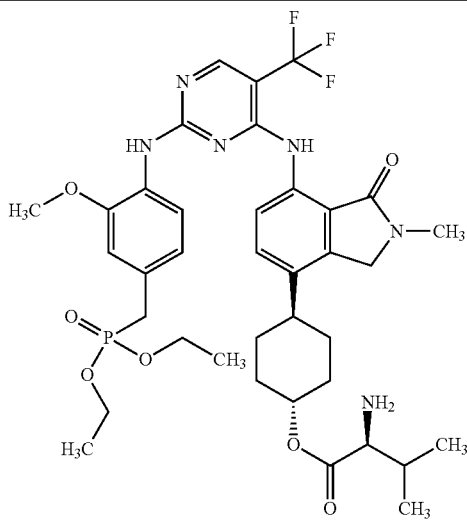 | trans-4-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)cyclohexyl L-valinate |
|---|---|---|
| Ex. 329 | 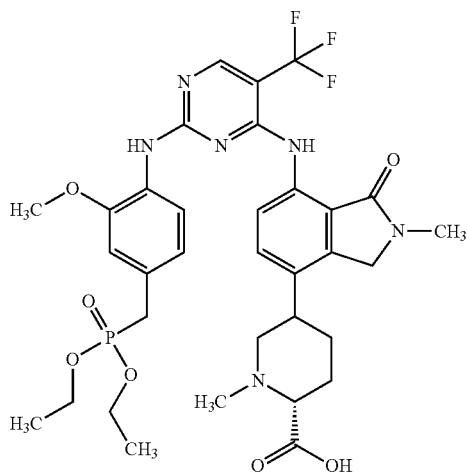 | (2R)-5-(7-{[2-({4-[(diethoxyphosphoryl)methyl]-2-methoxyphenyl}amino)-5-(trifluoromethyl)pyrimidin-4-yl]amino}-2-methyl-1-oxo-2,3-dihydro-1H-isoindol-4-yl)-1-methylpiperidine-2-carboxylic acid |

Unless otherwise noted, all materials/reagents were obtained from commercial suppliers and used without further purification. $^{1}$H NMR (400 MHz or 300 MHz) and $^{13}$C NMR (100.6 MHz) spectra were recorded on Bruker or Varian instruments at ambient temperature with TMS or the residual solvent peak as the internal standard. The line positions or multiples are given in ppm (δ) and the coupling constants (J) are given as absolute values in Hertz (Hz). The multiplicities in $^{1}$H NMR spectra are abbreviated as follows: s (singlet), d (doublet), t (triplet), q (quartet), quint (quintet), m (multiplet), $m_c$ (centered multiplet), br or broad (broadened), AA'BB'. The signal multiplicities in $^{13}$C NMR spectra were determined using the DEPT135 pulse sequence and are abbreviated as follows: +(CH or CH$_3$), -(CH$_2$), $C_{quart}$ (C). Reactions were monitored by thin layer chromatography (TLC) on silica gel 60 $F_{254}$ (0.2 mm) precoated aluminum foil and visualized using UV light. Flash chromatography was performed with silica gel (400-230 mesh). Preparatory TLC was performed on Whatman LK6F Silica Gel 60 Å A size 20×20 cm plates with a thickness of 1000 μm. Hydromatrix (=diatomaceous earth) was purchased from Varian.

Preparative HPLC purifications was performed on a Waters® Mass-Directed Purification System equipped with 2525 Binary Gradient Module, 2767 Sample Manager, a Column Fluidics Organizer (CFO), 2996 Photodiode Array Detector, a 515 pump for column regeneration, a reagent manager for the makeup flow, a 515 pump for at-column-dilution, ZQ™ single-quadrupole Mass Detector equipped with a Z-spray electrospray interface, controlled by MassLynx™ Version 4.1 with FractionLynx™ software. All purification work was completed using a parallel dual-column Luna C18(2) 21×150 mm, 5 μm LC/MS system and ARW (accelerated retention window). The mobile phases were water (0.1% TFA) and acetonitrile (0.1% TFA); all reagents used were of HPLC grade. The flow rate was 30 mL/min. After the columns, a 1:1000 LC packings flow splitter allowed transfer of a small portion of the eluent into the UV detector and, subsequently, a 10% portion into the ZQ MS.

The electrospray source was set at 3.0 kV capillary voltage, 30 V cone voltage, 110° C. source temperature, 350° C. desolvation temperature, 600 L/h desolvation gas flow, and 60 L/h cone gas flow. For the analyzer, the multiplier was set at 550 for preparative tune method. Analytical LC-MS data was collected on ZQ2, ZQ3, or UPLC-ACQUITY. ZQ2 is an Agilent 1100 HPLC equipped with a Gilson 215 Liquid Handler, Gilson 819 Injection Module, and Waters Micromass ZQ2000 for ionization. ZQ3 is an Agilent 1100 HPLC equipped with an HP Series 1100 auto injector and Waters Micromass ZQ2000 for ionization. Both systems use the Xterra MS C18, 5μ, particle size, 4.6×50 mm with a mobile phase of Acetonitrile (A) and 0.01% Formic Acid in HPLC water (B). The flow rate is 1.3 mL/min, the run time is 5 min, and the gradient profiles are 0.00 min 5% A, 3.00 min 90% A, 3.50 min 90% A, 4.00 min 5% A, 5.00 min 5% A for polar_5 min and 0.00 min 25% A, 3.00 min 99% A, 3.50 min 99% A, 4.00 min 25% A, 5.00 min 25% A for nonpolar_5 min. All Waters Micromass ZQ2000 instruments utilized electrospray ionization in positive (ES+) or negative (ES−) mode. The Waters Micromass ZQ2000 instrument from ZQ3 may also utilize atmospheric pressure chemical ionization in positive (AP+) or negative (AP−) mode. The Waters UPLC-ACQUITY system consists of an ACQUITY sample manager attached to ACQUITY SQ MS and ACQUITY PDA detectors. It uses an ACQUITY UPLC BEH® C18 2.1×50 mm 1.7 μm column with a mobile phase of 0.1% formic acid in water (A) and 0.1% formic acid in acetonitrile (B). The flow rate is 1.0 mL/min, run time is 2 min, and the gradient profile is 0.00 min 95% A, 1.50 min 1% A, 1.85 min 1% A, 2.0 min 95% A for analytical. UV detection is at 254 nm, and the MS utilizes electrospray ionization in positive mode (ES+). All melting points were determined with a Mel-Temp II apparatus and are uncorrected. Elemental analyses were obtained by Atlantic Microlab, Inc., Norcross, Ga.

Biological Properties

In some aspects of the invention, compounds of the invention are inhibitors of kinases, including FAK.

The invention includes a compound of Formula 1 or a pharmaceutically acceptable salt thereof, in any of the above recitations or examples, which exhibits inhibition of FAK in a biochemical assay (such as described herein) with an $IC_{50}$ of about 1 μM or less, or about 100 nM or less, or about 10 nM or less.

The invention includes a compound of Formula 1 or a pharmaceutically acceptable salt thereof, in any of the above recitations or examples, which exhibits inhibition of FAK in a cellular assay (such as described herein, e.g., MIA-PaCa2) with an $IC_{50}$ of about 1 μM or less, or about 100 nM or less, or about 10 nM or less.

In some aspects of the invention, compounds of the invention are selective inhibitors of FAK. In some embodiments, the compound is a selective inhibitor of FAK over other kinase targets. In some embodiments, the compound is at least about 50-fold selective for FAK over Aurora B in a cell-based assay. In some embodiments, the compound is at least about 1000-fold selective for FAK over Src and/or KDR in a cell-based assay.

The invention includes a compound of Formula 1 or a pharmaceutically acceptable salt thereof, which is sufficiently orally bioavailable for effective oral human administration. For example, the compound may have an oral bioavailability (F) of at least about 30%, 40%, or 50%.

The invention includes a compound of Formula 1 or a pharmaceutically acceptable salt thereof, which has a suitable therapeutic window for effective human administration, oral or otherwise.

The invention includes a compound of Formula 1 or a pharmaceutically acceptable salt thereof, which exhibits an oral exposure AUC(0-∞) of at least about 2 μg h/mL with 20 mg/kg oral dosing in mouse.

Biochemical HTRF (FRET) Assay Protocol

The ability of compounds to inhibit the kinase activity of recombinant FAK enzyme was determined by a HTRF (FRET) assay using Biotinylated PGT (B*PGT) as a peptide substrate. The assay determines the ability of compounds to inhibit phosphorylation of PGT by recombinant FAK enzyme in the presence of ATP at RT. The reaction is stopped after 1 h and phosphotyrosine content of Biotin*PGT is measured using anti-phosphotyrosine specific Mab label with Eu3+-cryptate (Cisbio) and XL665 labeled streptavidin (Cisbio) by Homogeneous Time-Resolved Fluorescence (HTRF) method.

The Stock Reagents Used are as Follows:
Kinase Reaction Buffer: 75 mM HEPES, pH 7.4 (Gibco); 19 mM MgCl2 (Sigma M1028); 0.938 mM MnCl2 (Sigma M1787); 1.5% Glycerol; 1.5 mM DTT (add fresh).
Enzyme Buffer: Reaction Buffer plus 0.03% BSA.
Development Buffer: 1 part 200 mM EDTA/50 mM Tris-HCl pH 7.4; 2 parts 1M KF; 0.07% BSA.
Other Reagents: Biotinylated PGT (Cisbio, Cat #61GT0BLD), 0.5 mg/mL in 50% DMSO; FAK (PTK2) enzyme (Invitrogen PV4085); Potassium Fluoride (VWR VW3456-1); ATP (10 mM stock); DTT (1M stock); 10% BSA; PT-66 Cryptate (Cisbio, Cat #61T66KLB); XL-665 conjugated Streptavidin (Cisbio Cat #611SAXLB).
Materials: 384 well white ProxiPlate (Perkin Elmer, Cat #6006280).

Assay Protocol: The compounds were serially diluted from 10 uM to 5 pM (1:5 dil, 10 points) in kinase buffer (1×) containing 3% DMSO and added 5 uL to each well of a 384-well plate except negative and positive control wells. Only DMSO was added to positive and negative control wells. For negative control wells, no ATP was added but only 5 uL of B*PGT was added. B*PGT (final conc 7.5 ng/well) and ATP (final conc 100 uM) was added in 5 uL to all wells except negative control wells. Reaction was started by adding FAK enzyme (final conc 0.2 ng/well) in 5 ul of enzyme buffer per well and incubated at RT for 1 h. Phosphotyrosine content of B*BGT was detected by adding PT66-Cryptate (1:100 dil) and XL665 conjugated streptavidin (1:100 dil) to each well in 7.5 uL development buffer and incubating for 1 h at RT. The plate was read on Victor machine Comparison of the assay signals obtained in the presence of compound with those of positive and negative controls, allows the degree of inhibition of phosphorylation of PGT to be determined over a range of compound concentrations. These inhibition values are fitted to a sigmoidal dose-response inhibition curve to determine the IC50 values (i.e. the concentration of the compound that inhibits phosphorylation of PGT by 50%).

Biochemical Omnia Assay Protocol

The Omnia Assay (Invitrogen) has been optimized for GST-tagged full-length FAK enzyme (PTK2, Invitrogen PV4085). In this assay system, Omnia Y Peptide 3 (Invitrogen KNZ3031) functions as a substrate for FAK. Phosphorylation of this SOX-containing peptide by FAK results in an increase in fluorescence at 485 nm upon excitation at 360 nm. Assays were carried out in 384-well OptiPlates (Perkin Elmer 6007290) in a total volume of 20 μL containing FAK (25 nM), Omnia Y Peptide 3 (10 μM), ATP (50 μM), and test compound (variable) in assay buffer (50 mM HEPES, pH 7.5, 5 mM $MgCl_2$, 0.15 mM $MnCl_2$, 1% glycerol, 1 mM DTT, 1 mM EGTA, 0.01% BSA) with 1% DMSO.

$IC_{50}$s for test compounds were typically determined using an 11-point three-fold serial dilution with a final assay concentration ranging from 0.17 nM to 10 μM. All compound concentrations were assayed in duplicate. Initial compound dilutions were prepared at 100× concentration in 100% DMSO from a 10 mM stock solution. Compounds were further diluted 1:25 in assay buffer resulting in a 4× concentrated solution.

In running the assay, 5 μL of the above 4× concentrated compound solution (or 4% DMSO for positive controls) was added to the assay plate followed by 5 μL of a solution containing peptide (40 μM) and ATP (200 μM) in assay buffer.

The reaction was initiated by the addition of 10 µL of FAK (50 nM) in assay buffer, or assay buffer alone for negative controls. The increase in fluorescence due to peptide phosphorylation was monitored continuously as a function of time using a Spectramax M5 plate reader (Molecular Devices) equipped with SoftMax Pro 5.2 software.

$IC_{50}$ values were determined from the slopes of the linear progress curves by non-linear curve-fitting using Graph Pad Prism 5 (GraphPad Software, Inc.). $IC_{50}$'s were determined in duplicate (n=2).

In Table 1, the following definitions apply A: <1 µM; B: 1-10 µM; C: >10 µM.

TABLE 1

| Ex. | Mean FAK Biochem Omnia IC50 (50 uM ATP) | Mean FAK Biochem FRET IC50 (100 uM ATP) |
|---|---|---|
| 1 | A | A |
| 2 | — | B |
| 3 | A | — |
| 4 | A | B |
| 5 | — | A |
| 6 | A | A |
| 7 | — | A |
| 8 to 26 | A | — |
| 27 | — | B |
| 28 to 40 | A | — |
| 41 | A | B |
| 42 | A | — |
| 43 | A | — |
| 44 | A | — |
| 45 | A | — |
| 46 | — | B |
| 47 to 143 | A | — |
| 145 to 236 | A | — |
| 237 | — | — |
| 238 to 264 | A | — |
| 267 | C | — |
| 268 | B | — |
| 269 to 289 | A | — |
| 300 to 311 | A | — |

Cell-Based Assays for Inhibition of FAK Autophosphorylation: MiaPaCa2 and U87MG

The ability of compounds to inhibit FAK autophosphorylation was determined in a cell-based capture ELISA assay using MiaPaCa2 pancreatic cancer cells (ATCC, Cat #CRL-1420) and the FAK [pY397] ELISA kit from Invitrogen (KHO0441). The assay determines the ability of compounds to block endogenous autophosphorylation of FAK stimulated by fibronectin. Cells plated on fibronectin coated 96-well plate were incubated with compounds at various concentrations in the complete growth medium for 2 h. Cell lysates were then prepared and FAK protein was captured onto a FAK antibody-coated 96-well ELISA plate. The phosphotyrosine content of FAK protein was then monitored by quantitation of degree of binding of an antibody that recognizes only the phosphorylated FAK at Y397 within the captured protein. The antibody used has a reporter enzyme (e.g. horse radish peroxidase, HRP) covalently attached, such that binding to phosphorylated FAK can be determined quantitatively by incubation with an appropriate HRP substrate.

Stock Reagents:
Cell Lysis Buffer (Biosource): 10 mM Tris-HCl, pH 7.4; 100 mM NaCl; 1 mM EDTA; 1 mM EGTA; 1 mM NaF; 20 mM $Na_4P_2O_7$; 2 mM $Na_3VO_4$; 1% Triton X-100; 10% glycerol; 0.1% SDS; 0.5% deoxycholate; 1 mM PMSF (stock is 0.3M in DMSO); Protease inhibitor cocktail (Sigma, P-2714).

Reagents Provided in Biosource FAK [pY397] Immunoassay Kit (Cat #KHO0441]: Standard diluent buffer; FAK antibody-coated wells, 96 wells per plate; Rabbit anti-FAK [pY397] detection antibody; Goat anti-rabbit IgG-Horseradish Peroxidase (HRP) concentrate (100×); HRP diluent; Wash buffer concentrate (25×); Stabilized chromogen (TMB); Stop solution; Plate covers, adhesive strips.

Assay Protocol:
Cultures of MiaPaca2 cells growing in DMEM with 10% fetal bovine serum were detached by trypsin-EDTA. The cells were then suspended in cell assay medium. Cells were then plated onto fibronectin (600 ng/well)-coated 96-well flat bottom plates at $4 \times 10^5$ cells per well in 60 uL cell growth medium and incubated overnight at 37° C. in a $CO_2$ incubator.

Compound dilutions were prepared from 10 mM DMSO stocks by dilution in cell growth medium, the final concentration of DMSO in the assay being 1%. To compound incubation wells, 60 uL of test compound was added as 2× concentration (compounds were assayed at concentrations between 10 µM to 3 nM); to positive control wells, 60 µL of cell assay medium containing 2% DMSO was added. The cells were then incubated with compounds at 37° C. for 2 h. The medium was removed by aspiration and cells were lysed by addition of 20 uL of ice-cold cell lysis buffer per well. The plates were kept on ice for 20 min and 35 uL of standard diluent was added to each well. 50 uL of cell lysate from each well was transferred to respective wells in an assay plate and 50 uL of detection antibody was added to all wells except H1-H6 which were no antibody control wells. Capture assay plates were incubated overnight in a cold room.

Following incubation of the cell lysates and detection antibodies in the ELISA plate, the wells were washed 4 times with 120 uL of wash buffer (1×), then 100 uL of diluted HRP conjugated antibody (1:100 dil in diluent) was added to each well, and the plate was incubated at RT for 30 min. The wells were then washed for 4 times with 120 uL of wash buffer (1×) and 100 uL of chromogen was added to each well and incubated in the dark at RT for 20-30 min. 10 uL of stop solution was added to each well and the absorbance measured at 450 nm.

Comparison of the assay signals obtained in the presence of compound with those of positive and negative controls (cells with no compound and no detection antibody being added), allows degree of inhibition of phospho-FAK [Y397] to be determined over a range of compound concentrations. These inhibition vales were fitted to a sigmoidal dose-response inhibition curve to determine the $IC_{50}$ values (i.e. the concentration of the compound that inhibits phosphorylation of FAK by 50%). The assay as described above was modified to determine the effect of inclusion of 50% (v/v) mouse or human plasma. In this assay, the compound plate was prepared as 2× concentration in 100 uL of 100% mouse or human plasma, and 60 uL of this was added to 60 uL of culture medium and incubated at 37° C. incubator for 2 h. The rest of the assay was carried out as described above.

The ability of compounds to inhibit FAK autophosphorylation was determined in a cell-based capture ELISA assay using U87MG glioblastoma cells (ATCC, Cat #HTB-14) and the FAK [pY397] ELISA kit from Invitrogen (KHO0441). The assay determines the ability of compounds to block endogenous autophosphorylation of FAK stimulated by fibronectin. Cells plated on fibronectin coated 96-well plate were incubated with compounds at various concentrations in the complete growth medium for 2 h. Cell lysates were then prepared and FAK protein was captured onto a FAK antibody-coated 96-well ELISA plate. The phosphotyrosine content of FAK protein was then monitored by quantitation of degree of binding of an antibody that recognizes only the phosphorylated FAK at Y397 within the captured protein. The antibody used has a reporter enzyme (e.g. horse radish peroxidase, HRP) covalently attached, such that binding to phosphorylated FAK can be determined quantitatively by incubation with an appropriate HRP substrate.

Stock Reagents:

Cell Lysis Buffer (Biosource #FNN0011): 10 mM Tris-HCl, pH 7.4; 100 mM NaCl; 1 mM EDTA; 1 mM EGTA; 1 mM NaF; 20 mM $Na_4P_2O_7$; 2 mM $Na_3VO_4$; 1% Triton X-100; 10% glycerol; 0.1% SDS; 0.5% deoxycholate; 1 mM PMSF (stock is 0.1M in ethanol, Sigma #93482); Protease inhibitor cocktail (Sigma, P-2714).

Reagents Provided in Biosource FAK [pY397] Immunoassay Kit (Cat #KHO0441]: Standard diluent buffer; FAK antibody-coated wells, 96 wells per plate; Rabbit anti-FAK [pY397] detection antibody; Goat anti-rabbit IgG-Horseradish Peroxidase (HRP) concentrate (100×); HRP diluent; Wash buffer concentrate (25×); Stabilized chromogen (TMB); Stop solution; Plate covers, adhesive strips.

Assay Protocol:

Cultures of U87MG cells growing in MEM (Earles) containing non-essential amino acids, sodium pyruvate (1 mM), L-glutamate (1%) and 10% fetal bovine serum were detached by trypsin-EDTA and suspended in cell growth medium. Cells were then plated onto fibronectin (600 ng/well)-coated 96-well flat bottom plates at $1.7 \times 10^4$ cells per well in 60 uL cell growth medium and incubated overnight at 37° C. in a $CO_2$ incubator.

Compound dilutions were prepared from 10 mM DMSO stocks by dilution in cell growth medium, the final concentration of DMSO in the assay being 0.6%. To compound incubation wells, 60 uL of test compound was added as 2× concentration (compounds were assayed at concentrations between 4 μM-1.3 nM); to positive control wells, 60 μL of cell assay medium containing 1.3% DMSO was added. The cells were then incubated with compounds at 37° C. for 2 h. The medium was removed by aspiration and cells were lysed by addition of 20 uL of ice-cold cell lysis buffer per well. The plates were kept on ice for 20 min and 50 uL of standard diluent was added to each well. 50 uL of cell lysate from each well was transferred to respective wells in an assay plate and 50 uL of detection antibody was added to all wells except H1-H6 which were no antibody control wells. Capture assay plates were incubated overnight in a cold room.

Following incubation of the cell lysates and detection antibodies in the ELISA plate, the wells were washed 4 times with 120 uL of wash buffer (1×), then 100 uL of diluted HRP conjugated antibody (1:100 dil in diluent) was added to each well, and the plate was incubated at RT for 30 min. The wells were then washed for 4 times with 120 uL of wash buffer (1×) and 100 uL of chromogen was added to each well and incubated in the dark at RT for 5-10 min. 100 uL of stop solution was added to each well and the absorbance measured at 450 nm, 0.1 s.

Comparison of the assay signals obtained in the presence of compound with those of positive and negative controls (cells with no compound and no detection antibody being added), allows degree of inhibition of phospho-FAK [Y397] to be determined over a range of compound concentrations. These inhibition vales were fitted to a sigmoidal dose-response inhibition curve to determine the $IC_{50}$ values (i.e. the concentration of the compound that inhibits phosphorylation of FAK by 50%). The assay as described above was modified to determine the effect of inclusion of 50% (v/v) mouse or human plasma. In this assay, the compound plate was prepared as 2× concentration in 100 uL of 100% mouse or human plasma, and 60 uL of this was added to 60 uL of culture medium and incubated at 37° C. incubator for 2 h. The rest of the assay was carried out as described above.

In Tables 2 and 3, the following definitions apply A: <1 μM; B: 1-10 μM; C: >10 μM.

TABLE 2

| Ex. | Mean FAK Cell Mechanistic $IC_{50}$ MIA-PaCa2 | Mean FAK Cell Mechanistic $IC_{50}$ + 50% mP MIA-PaCa2 | Mean FAK Cell Mechanistic $IC_{50}$ + 50% hP MIA-PaCa2 |
|---|---|---|---|
| 1 | A | A | A |
| 2 | — | — | — |
| 3 | C | C | C |
| 4 | B | B | B |
| 5 | A | A | A |
| 6 | B | — | — |
| 7 | A | A | A |
| 8 | A | A | A |
| 9 | A | A | A |
| 10 | A | A | A |
| 11 | A | A | A |
| 12 | B | B | B |
| 13 | A | A | A |
| 14 | A | A | A |
| 15 | A | A | A |
| 16 | A | A | A |
| 17 | A | A | A |
| 18 | A | A | A |
| 19 | A | A | A |
| 20 | A | A | A |
| 21 | A | A | A |
| 22 | A | A | A |
| 23 | A | A | A |
| 24 | A | A | A |
| 25 | — | B | — |
| 26 | A | B | A |
| 27 | B | B | B |
| 28 | A | A | A |
| 29 | A | B | B |
| 30 | B | B | B |
| 31 | A | A | A |
| 32 | A | A | A |
| 33 | — | C | — |
| 34 | — | B | — |
| 35 | — | B | — |
| 36 | — | A | — |
| 37 | — | B | — |
| 38 | — | B | — |
| 39 | — | B | — |
| 40 | B | B | B |
| 41 | B | B | B |
| 42 | B | B | B |
| 43 | B | B | B |
| 44 | C | C | C |
| 45 | A | A | A |
| 46 | A | A | A |
| 47 | — | B | — |
| 48 | — | B | — |
| 49 | A | A | A |
| 50 | — | B | — |
| 51 | — | C | — |
| 52 | A | A | A |
| 53 | A | A | A |
| 54 | — | C | — |
| 55 | — | C | — |
| 56 | A | A | A |
| 57 | — | B | — |
| 58 | — | B | — |
| 59 | — | B | — |
| 60 | A | A | A |
| 61 | A | A | B |
| 62 | A | A | B |
| 63 | A | A | A |
| 64 | A | A | A |
| 65 | A | A | A |
| 66 | — | A | — |
| 67 | A | A | A |
| 68 | A | A | B |
| 69 | A | A | A |
| 70 | A | A | A |
| 71 | A | A | A |
| 72 | — | A | — |
| 73 | — | A | — |

TABLE 2-continued

| Ex. | Mean FAK Cell Mechanistic IC$_{50}$ MIA-PaCa2 | Mean FAK Cell Mechanistic IC$_{50}$ + 50% mP MIA-PaCa2 | Mean FAK Cell Mechanistic IC$_{50}$ + 50% hP MIA-PaCa2 |
|---|---|---|---|
| 74 | — | A | — |
| 75 | A | A | A |
| 76 | A | A | B |
| 77 | A | A | A |
| 78 | A | A | — |
| 79 | A | A | A |
| 80 | A | A | A |
| 81 | A | A | A |
| 82 | A | A | A |
| 83 | — | A | — |
| 84 | — | A | — |
| 85 | — | A | — |
| 86 | — | A | — |
| 87 | — | A | — |
| 88 | — | A | — |
| 89 | — | A | — |
| 90 | — | A | — |
| 91 | — | A | — |
| 92 | — | A | — |
| 93 | — | A | — |
| 94 | — | A | — |
| 95 | — | A | — |
| 96 | — | A | — |

TABLE 3

| Ex. # | Mean FAK Cell Mechanistic IC$_{50}$ + 50% mP MIA-PaCa2 | Mean FAK Cell Mechanistic IC$_{50}$ + 50% mP U87MG |
|---|---|---|
| 97 | B | |
| 98 | A | |
| 99 | A | |
| 100 | A | |
| 101 | A | |
| 102 | A | |
| 103 | A | |
| 104 | A | |
| 105 | B | |
| 106 | A | |
| 107 | A | |
| 108 | A | |
| 109 | B | |
| 110 | A | |
| 111 | A | |
| 112 | A | |
| 113 | A | |
| 114 | A | |
| 115 | B | |
| 116 | B | |
| 117 | A | |
| 118 | B | |
| 119 | A | |
| 120 | B | |
| 121 | A | |
| 122 | A | |
| 123 | A | |
| 124 | A | |
| 125 | A | |
| 126 | A | |
| 127 | B | |
| 128 | B | |
| 129 | B | |
| 130 | A | |
| 131 | A | |
| 132 | A | |
| 133 | A | |
| 134 | B | |
| 135 | B | |
| 136 | B | |
| 137 | B | |
| 138 | A | |
| 139 | A | B |
| 140 | A | |
| 141 | A | A |
| 142 | A | |
| 143 | A | |
| 144 | A | |
| 145 | A | |
| 146 | A | |
| 147 | A | A |
| 148 | B | |
| 149 | B | |
| 150 | A | |
| 151 | A | |
| 152 | A | |
| 153 | A | |
| 154 | A | A |
| 155 | A | A |
| 156 | A | A |
| 157 | A | |
| 158 | A | A |
| 159 | A | |
| 160 | A | |
| 161 | B | |
| 162 | A | |
| 163 | A | |
| 164 | A | |
| 165 | A | |
| 166 | A | |
| 167 | A | |
| 168 | A | |
| 169 | A | |
| 170 | A | |
| 171 | A | A |
| 172 | A | |
| 173 | B | |
| 174 | A | |
| 175 | A | |
| 176 | B | |
| 177 | B | |
| 178 | B | |
| 179 | B | |
| 180 | A | |
| 181 | B | |
| 182 | B | |
| 183 | A | |
| 184 | A | |
| 185 | A | |
| 186 | A | |
| 187 | A | |
| 188 | A | |
| 189 | A | |
| 190 | A | |
| 191 | A | |
| 193 | A | |
| 194 | B | |
| 195 | B | B |
| 196 | A | |
| 197 | A | |
| 198 | A | |
| 199 | A | |
| 200 | A | |
| 201 | A | |
| 202 | A | A |
| 203 | A | |
| 204 | A | A |
| 205 | A | |
| 206 | A | |
| 207 | A | |

TABLE 3-continued

| Ex. # | Mean FAK Cell Mechanistic IC$_{50}$ + 50% mP MIA-PaCa2 | Mean FAK Cell Mechanistic IC$_{50}$ + 50% mP U87MG |
|---|---|---|
| 208 | A | |
| 209 | A | |
| 210 | A | |
| 211 | A | |
| 212 | A | |
| 215 | A | |
| 216 | A | A |
| 217 | A | |
| 219 | A | |
| 221 | A | |
| 223 | A | |
| 224 | A | |
| 225 | A | |
| 226 | A | |
| 227 | A | |
| 228 | A | |
| 229 | A | |
| 230 | A | |
| 231 | A | A |
| 232 | A | |
| 233 | A | |
| 236 | A | A |
| 237 | A | |
| 238 | A | |
| 242 | A | |
| 243 | A | |
| 244 | B | |
| 245 | B | |
| 246 | A | |
| 247 | A | |
| 248 | A | |
| 249 | B | |
| 250 | A | |
| 251 | A | |
| 252 | A | |
| 253 | A | |
| 254 | B | |
| 255 | B | |
| 256 | A | A |
| 258 | A | |
| 257 | A | |

TABLE 3-continued

| Ex. # | Mean FAK Cell Mechanistic IC$_{50}$ + 50% mP MIA-PaCa2 | Mean FAK Cell Mechanistic IC$_{50}$ + 50% mP U87MG |
|---|---|---|
| 259 | A | A |
| 260 | A | A |
| 262 | | A |
| 263 | | A |
| 264 | | A |
| 267 | | B |
| 268 | | B |
| 269 | | A |
| 270 | | B |
| 271 | | A |
| 272 | | A |
| 273 | | A |
| 274 | | A |
| 275 | | A |
| 276 | | A |
| 278 | | B |
| 282 | | A |
| 283 | | A |
| 284 | | A |
| 285 | | A |
| 286 | | A |
| 287 | | B |
| 288 | | A |
| 289 | | A |
| 290 | | B |
| 300 | | A |
| 301 | | A |
| 302 | | B |
| 303 | | A |
| 304 | | A |
| 305 | | A |
| 306 | | A |
| 307 | | B |
| 308 | | B |
| 309 | A | A |
| 310 | | B |
| 311 | | B |

Table 4 shows U87MG cellular mechanistic data for compounds in human and mouse plasma.

TABLE 4

| Structure | # | U87MG FAK Cell Mech IC50 +hP (uM) | U87MG FAK Cell Mech IC50 +mP (uM) |
|---|---|---|---|
| 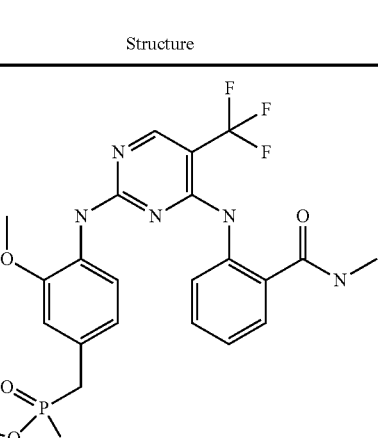 | Ex. 53 | 0.16 | 0.07 |

TABLE 4-continued

| Structure | # | U87MG FAK Cell Mech IC50 +hP (uM) | U87MG FAK Cell Mech IC50 +mP (uM) |
|---|---|---|---|
| [structure] | Cpd A | >4; >4 | 3.693904; >4; >4; >4 |
| [structure] | Cpd B | >4; >4 | 0.256967; 0.540094 |

Compositions

The invention includes pharmaceutical compositions comprising a compound or pharmaceutically acceptable salt thereof of the invention, which is formulated for a desired mode of administration with or without one or more pharmaceutically acceptable and useful carriers. The compounds can also be included in pharmaceutical compositions in combination with one or more other therapeutically active compounds.

The pharmaceutical compositions of the present invention comprise a compound of the invention (or a pharmaceutically acceptable salt thereof) as an active ingredient, optional pharmaceutically acceptable carrier(s) and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Compounds of the invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

A formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Compounds of the invention can be provided for formulation at high purity, for example at least about 90%, 95%, or 98% pure by weight.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Uses

Compounds of the invention inhibit the activity of tyrosine kinase enzymes in animals, including humans, and are useful in the treatment and/or prevention of various diseases and conditions such as hyperproliferative disorders such as cancer. In particular, compounds of the invention, and compositions thereof, are inhibitors of FAK, and are useful in treating conditions modulated, at least in part, by FAK.

In some aspects, the invention includes a method of treating cancer comprising administering to a mammal in need thereof a therapeutically effective amount of a compound or salt of the invention.

In some aspects, the invention includes a method of treating a cancer mediated at least in part by FAK comprising administering to a mammal in need thereof a therapeutically effective amount of a compound or salt of Formula 1.

In some aspects, the invention includes a method of treating or a method of manufacturing a medicament for treating a cancer, such as those above, which is mediated at least in part by FAK, comprising administering to a mammal in need thereof a therapeutically effective amount of a compound or salt of the invention.

The compounds of Formula I of the present invention are useful in the treatment of a variety of cancers, including, but not limited to, solid tumors, sarcoma, fibrosarcoma, osteoma, melanoma, retinoblastoma, rhabdomyosarcoma, glioblastoma, neuroblastoma, teratocarcinoma, hematopoietic malignancy, and malignant ascites. More specifically, the cancers include, but not limited to, lung cancer, bladder cancer, pancreatic cancer, kidney cancer, gastric cancer, breast cancer, colon cancer, prostate cancer (including bone metastases), hepatocellular carcinoma, ovarian cancer, esophageal squamous cell carcinoma, melanoma, an anaplastic large cell lymphoma, an inflammatory myofibroblastic tumor, and a glioblastoma.

In some aspects, the above methods are used to treat one or more of bladder, colorectal, nonsmall cell lung, breast, or pancreatic cancer. In some aspects, the above methods are used to treat one or more of ovarian, gastric, head and neck, prostate, hepatocellular, renal, glioma, or sarcoma cancer.

In some aspects, the invention includes a method, including the above methods, wherein the compound is used to inhibit cellular epithelial to mesenchymal transition (EMT).

In some aspects, the method further comprises administering at least on additional active agent. In some aspects, the invention includes a method of treating cancer comprising administering to a mammal in need thereof a therapeutically effective amount of a compound or salt of the invention, wherein at least one additional active anti-cancer agent is used as part of the method.

In some aspects, the invention includes a method of treating cancer mediated at least in part by FAK comprising administering to a mammal in need thereof a therapeutically effective regimen comprising a compound or salt of Formula 1 and at least one additional active agent.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

GENERAL DEFINITIONS AND ABBREVIATIONS

Except where otherwise indicated, the following general conventions and definitions apply. Unless otherwise indicated herein, language and terms are to be given their broadest reasonable interpretation as understood by the skilled artisan. Any examples given are nonlimiting.

Any section headings or subheadings herein are for the reader's convenience and/or formal compliance and are non-limiting.

A recitation of a compound herein is open to and embraces any material or composition containing the recited compound (e.g., a composition containing a racemic mixture, tautomers, epimers, stereoisomers, impure mixtures, etc.). In that a salt, solvate, or hydrate, polymorph, or other complex of a compound includes the compound itself, a recitation of a compound embraces materials containing such forms. Isotopically labeled compounds are also encompassed except where specifically excluded. For example, hydrogen is not limited to hydrogen containing zero neutrons.

The term "active agent" of the invention means a compound of the invention in any salt, polymorph, crystal, solvate, or hydrated form.

The term "pharmaceutically acceptable salt(s)" is known in the art and includes salts of acidic or basic groups which can be present in the compounds and prepared or resulting from pharmaceutically acceptable bases or acids.

The term "substituted" and substitutions contained in formulas herein refer to the replacement of one or more hydrogen radicals in a given structure with a specified radical, or, if not specified, to the replacement with any chemically feasible radical. When more than one position in a given structure can be substituted with more than one substituent selected from specified groups, the substituents can be either the same or different at every position (independently selected) unless otherwise indicated. In some cases, two positions in a given structure can be substituted with one shared substituent. It is understood that chemically impossible or highly unstable configurations are not desired or intended, as the skilled artisan would appreciate.

In descriptions and claims where subject matter (e.g., substitution at a given molecular position) is recited as being selected from a group of possibilities, the recitation is specifically intended to include any subset of the recited group. In the case of multiple variable positions or substituents, any combination of group or variable subsets is also contemplated.

Unless indicated otherwise, a substituent, diradical or other group referred to herein can be bonded through any suitable position to a referenced subject molecule. For example, the term "indolyl" includes 1-indolyl, 2-indolyl, 3-indolyl, etc.

The convention for describing the carbon content of certain moieties is "($C_{a-b}$)" or "$C_a$-$C_b$," meaning that the moiety can contain any number of from "a" to "b" carbon atoms. $C_0$alkyl means a single covalent chemical bond when it is a connecting moiety, and a hydrogen when it is a terminal moiety. Similarly, "x-y" can indicate a moiety containing from x to y atoms, e.g., $_{5-6}$heterocycloalkyl means a heterocycloalkyl having either five or six ring members. "$C_{x-y}$" may be used to define number of carbons in a group. For example, "$C_{0-12}$alkyl" means alkyl having 0-12 carbons, wherein $C_0$alkyl means a single covalent chemical bond when a linking group and means hydrogen when a terminal group.

The term "absent," as used herein to describe a structural variable (e.g., "—R— is absent") means that diradical R has no atoms, and merely represents a bond between other adjoining atoms, unless otherwise indicated.

Unless otherwise indicated (such as by a connecting "-"), the connections of compound name moieties are at the rightmost recited moiety. That is, the substituent name starts with a terminal moiety, continues with any bridging moieties, and ends with the connecting moiety. For example, "heteroarylthio$C_{1-4}$alkyl is a heteroaryl group connected through a thio sulfur to a $C_{1-4}$ alkyl, which alkyl connects to the chemical species bearing the substituent.

The term "aliphatic" means any hydrocarbon moiety, and can contain linear, branched, and cyclic parts, and can be saturated or unsaturated.

The term "alkyl" means any saturated hydrocarbon group that is straight-chain or branched. Examples of alkyl groups include methyl, ethyl, propyl, 2-propyl, n-butyl, iso-butyl, tert-butyl, pentyl, and the like.

The term "alkenyl" means any ethylenically unsaturated straight-chain or branched hydrocarbon group. Representative examples include, but are not limited to, ethenyl, 1-propenyl, 2-propenyl, 1-, 2-, or 3-butenyl, and the like.

The term "alkynyl" means any acetylenically unsaturated straight-chain or branched hydrocarbon group. Representative examples include, but are not limited to, ethynyl, 1-propynyl, 2-propynyl, 1-, 2-, or 3-butynyl, and the like.

The term "alkoxy" means —O-alkyl, —O-alkenyl, or —O-alkynyl. "Haloalkoxy" means an —O-(haloalkyl) group. Representative examples include, but are not limited to, trifluoromethoxy, tribromomethoxy, and the like.

"Haloalkyl" means an alkyl, preferably lower alkyl, that is substituted with one or more same or different halo atoms.

"Hydroxyalkyl" means an alkyl, preferably lower alkyl, that is substituted with one, two, or three hydroxy groups; e.g., hydroxymethyl, 1 or 2-hydroxyethyl, 1,2-, 1,3-, or 2,3-dihydroxypropyl, and the like.

The term "alkanoyl" means —C(O)-alkyl, —C(O)-alkenyl, or —C(O)-alkynyl.

"Alkylthio" means an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

The term "cyclic" means any ring system with or without heteroatoms (N, O, or $S(O)_{0-2}$), and which can be saturated or unsaturated. Ring systems can be bridged and can include fused rings. The size of ring systems may be described using terminology such as "$_{x-y}$cyclic," which means a cyclic ring system that can have from x to y ring atoms. For example, the term "$_{9-10}$carbocyclic" means a 5,6 or 6,6 fused bicyclic carbocyclic ring system which can be satd., unsatd. or aromatic. It also means a phenyl fused to one 5 or 6 membered satd. or unsatd. carbocyclic group. Nonlimiting examples of such groups include naphthyl, 1,2,3,4 tetrahydronaphthyl, indenyl, indanyl, and the like.

The term "carbocyclic" means a cyclic ring moiety containing only carbon atoms in the ring(s) without regard to aromaticity. A 3-10 membered carbocyclic means chemically feasible monocyclic and fused bicyclic carbocyclics having from 3 to 10 ring atoms. Similarly, a 4-6 membered carbocyclic means monocyclic carbocyclic ring moieties having 4 to 6 ring carbons, and a 9-10 membered carbocyclic means fused bicyclic carbocyclic ring moieties having 9 to 10 ring carbons.

The term "cycloalkyl" means a non-aromatic 3-12 carbon mono-cyclic, bicyclic, or polycyclic aliphatic ring moiety. Cycloalkyl can be bicycloalkyl, polycycloalkyl, bridged, or spiroalkyl. One or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like.

The term "unsaturated carbocyclic" means any cycloalkyl containing at least one double or triple bond. The term "cycloalkenyl" means a cycloalkyl having at least one double bond in the ring moiety.

The terms "bicycloalkyl" and "polycycloalkyl" mean a structure consisting of two or more cycloalkyl moieties that have two or more atoms in common. If the cycloalkyl moieties have exactly two atoms in common they are said to be "fused". Examples include, but are not limited to, bicyclo [3.1.0]hexyl, perhydronaphthyl, and the like. If the cycloalkyl moieties have more than two atoms in common they are said to be "bridged". Examples include, but are not limited to, bicyclo[2.2.1]heptyl ("norbornyl"), bicyclo[2.2.2]octyl, and the like.

The term "spiroalkyl" means a structure consisting of two cycloalkyl moieties that have exactly one atom in common. Examples include, but are not limited to, spiro[4.5]decyl, spiro[2.3]hexyl, and the like.

The term "aromatic" means a planar ring moieties containing 4n+2 pi electrons, wherein n is an integer.

The term "aryl" means an aromatic moieties containing only carbon atoms in its ring system. Non-limiting examples include phenyl, naphthyl, and anthracenyl. The terms "arylalkyl" or "arylalkyl" or "aralkyl" refer to any alkyl that forms a bridging portion with a terminal aryl.

"Aralkyl" means alkyl, preferably lower alkyl, that is substituted with an aryl group as defined above; e.g., —$CH_2$ phenyl, —$(CH_2)_2$phenyl, —$(CH_2)_3$ phenyl, $CH_3CH(CH_3)$ $CH_2$phenyl, and the like and derivatives thereof.

The term "heterocyclic" means a cyclic ring moiety containing at least one heteroatom (N, O, or $S(O)_{0-2}$), including heteroaryl, heterocycloalkyl, including unsaturated heterocyclic rings.

The term "heterocycloalkyl" means a non-aromatic monocyclic, bicyclic, or polycyclic heterocyclic ring moiety of 3 to 12 ring atoms containing at least one ring having one or more heteroatoms. The rings may also have one or more double bonds. However, the rings do not have a completely conjugated pi-electron system. Examples of heterocycloalkyl rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, N-methylpiperidine, azepane, 1,4-diazapane, azocane, [1,3]dioxane, oxazolidine, piperazine, homopiperazine, morpholine, thiomorpholine, 1,2,3,6-tetrahydropyridine and the like. Other examples of heterocycloalkyl rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocycloalkyl rings. The term "heterocycloalkyl" also includes fused ring systems and can include a carbocyclic ring that is partially or fully unsaturated, such as a benzene ring, to form benzofused heterocycloalkyl rings. For example, 3,4-dihydro-1,4-benzodioxine, tetrahydroquinoline, tetrahydroisoquinoline and the like. The term "heterocycloalkyl" also includes heterobicycloalkyl, heteropolycycloalkyl, or heterospiroalkyl, which are bicycloalkyl, polycycloalkyl, or spiroalkyl, in which one or more carbon atom(s) are replaced by one or more heteroatoms selected from O, N, and S. For example, 2-oxa-spiro[3.3]heptane, 2,7-diaza-spiro[4.5]decane, 6-oxa-2-thia-spiro[3.4]octane, octahydropyrrolo[1,2-a]pyrazine, 7-aza-bicyclo[2.2.1]heptane, 2-oxa-bicyclo [2.2.2]octane, and the like, are such heterocycloalkyls.

Examples of saturated heterocyclic groups include, but are not limited to oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, 1,4-diazepanyl Non-aryl heterocyclic groups include satd. and unsatd. systems and can include groups having only 4 atoms in their ring system. The heterocyclic groups include benzo-fused ring systems and ring systems substituted with one or more oxo moieties. Recitation of ring sulfur is understood to include the sulfide, sulfoxide or sulfone where feasible. The heterocyclic groups also include partially unsatd. or fully satd. 4-10 membered ring systems, e.g., single rings of 4 to 8 atoms in size and bicyclic ring systems, including aromatic 6-membered aryl or heteroaryl rings fused to a non-aromatic ring. Also included are 4-6 membered ring systems ("4-6 membered heterocyclic"), which include 5-6 membered heteroaryls, and include groups such as azetidinyl and piperidinyl. Heterocyclics can be heteroatom-attached where such is possible. For instance, a group derived from pyrrole can be pyrrol-1-yl (N-attached) or pyrrol-3-yl (C-attached). Other heterocyclics include imidazo(4,5-b)pyridin-3-yl and benzoimidazol-1-yl.

Examples of heterocyclic groups include pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, and the like.

The term "unsaturated heterocyclic" means a heterocycloalkyl containing at least one unsaturated bond. The term "heterobicycloalkyl" means a bicycloalkyl structure in which at least one carbon atom is replaced with a heteroatom. The term "heterospiroalkyl" means a spiroalkyl structure in which at least one carbon atom is replaced with a heteroatom.

Examples of partially unsaturated heteroalicyclic groups include, but are not limited to: 3,4-dihydro-2H-pyranyl, 5,6-dihydro-2H-pyranyl, 2H-pyranyl, 1,2,3,4-tetrahydropyridinyl, and 1,2,5,6-tetrahydropyridinyl.

The terms "heteroaryl" or "hetaryl" mean a monocyclic, bicyclic, or polycyclic aromatic heterocyclic ring moiety containing 5-12 atoms. Examples of such heteroaryl rings include, but are not limited to, furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The terms "heteroaryl" also include heteroaryl rings with fused carbocyclic ring systems that are partially or fully unsaturated, such as a benzene ring, to form a benzofused heteroaryl. For example, benzimidazole, benzoxazole, benzothiazole, benzofuran, quinoline, isoquinoline, quinoxaline, and the like. Furthermore, the terms "heteroaryl" include fused 5-6, 5-5, 6-6 ring systems, optionally possessing one nitrogen atom at a ring junction. Examples of such hetaryl rings include, but are not limited to, pyrrolopyrimidinyl, imidazo[1,2-a]pyridinyl, imidazo[2,1-b]thiazolyl, imidazo[4,5-b]pyridine, pyrrolo[2,1-f][1,2,4]triazinyl, and the like. Heteroaryl groups may be attached to other groups through their carbon atoms or the heteroatom(s), if applicable. For example, pyrrole may be connected at the nitrogen atom or at any of the carbon atoms.

Heteroaryls include, e.g., 5 and 6 membered monocyclics such as pyrazinyl and pyridinyl, and 9 and 10 membered fused bicyclic ring moieties, such as quinolinyl. Other examples of heteroaryl include quinolin-4-yl, 7-methoxy-quinolin-4-yl, pyridin-4-yl, pyridin-3-yl, and pyridin-2-yl. Other examples of heteroaryl include pyridinyl, imidazolyl, pyrimidinyl, pyrazolyl, triazolyl, pyrazinyl, tetrazolyl, furanyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. Examples of 5-6 membered heteroaryls include, thiophenyl, isoxazolyl, 1,2,3-triazolyl, 1,2,3-oxadiazolyl, 1,2,3-thiadiazolyl, 1,2,4-triazolyl, 1,3,4-oxadiazolyl, 1,3,4-thiadiazolyl, 1,2,5-oxadiazolyl, 1,2,5-thiadiazolyl, pyridyl, pyridazinyl, pyrimidinyl, pyrazinyl, 1,2,4 oxadiazinyl, 1,2,5-triazinyl, 1,3,5-triazinyl, and the like.

"Heteroaralkyl" group means alkyl, preferably lower alkyl, that is substituted with a heteroaryl group; e.g., —CH$_2$ pyridinyl, —(CH$_2$)$_2$pyrimidinyl, —(CH$_2$)$_3$imidazolyl, and the like, and derivatives thereof.

A pharmaceutically acceptable heteroaryl is one that is sufficiently stable to be attached to a compound of the invention, formulated into a pharmaceutical composition and subsequently administered to a patient in need thereof.

Examples of monocyclic heteroaryl groups include, but are not limited to: pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl tetrazolyl, pyridinyl, pyridazinyl, pyrimidinyl, pyrazinyl.

Examples of fused ring heteroaryl groups include, but are not limited to: benzoduranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, azaquinazoline, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrimido[2,3-b]pyrazinyl, pyrimido[4,5-d]pyrimidinyl.

"Arylthio" means an —S-aryl or an —S-heteroaryl group, as defined herein. Representative examples include, but are not limited to, phenylthio, pyridinylthio, furanylthio, thienylthio, pyrimidinylthio, and the like and derivatives thereof.

The term "9-10 membered heterocyclic" means a fused 5,6 or 6,6 bicyclic heterocyclic ring moiety, which can be satd., unsatd. or aromatic. The term "9-10 membered fused bicyclic heterocyclic" also means a phenyl fused to one 5 or 6 membered heterocyclic group. Examples include benzofuranyl, benzothiophenyl, indolyl, benzoxazolyl, 3H-imidazo[4,5-c]pyridin-yl, dihydrophthazinyl, 1H-imidazo[4,5-c]pyridin-1-yl, imidazo[4,5-b]pyridyl, 1,3 benzo[1,3]dioxolyl, 2H-chromanyl, isochromanyl, 5-oxo-2,3 dihydro-5H-[1,3]thiazolo[3,2-a]pyrimidyl, 1,3-benzothiazolyl, 1,4,5,6 tetrahydropyridazyl, 1,2,3,4,7,8 hexahydropteridinyl, 2-thioxo-2,3,6,9-tetrahydro-1H-purin-8-yl, 3,7-dihydro-1H-purin-8-yl, 3,4-dihydropyrimidin-1-yl, 2,3-dihydro-1,4-benzodioxinyl, benzo[1,3]dioxolyl, 2H-chromenyl, chromanyl, 3,4-dihydrophthalazinyl, 2,3-ihydro-1H-indolyl, 1,3-dihydro-2H-isoindol-2-yl, 2,4,7-trioxo-1,2,3,4,7,8-hexahydropteridin-yl, thieno[3,2-d]pyrimidinyl, 4-oxo-4,7-dihydro-3H-pyrrolo[2,3-d]pyrimidin-yl, 1,3-dimethyl-6-oxo-2-thioxo-2,3,6,9-tetrahydro-1H-purinyl, 1,2-dihydroisoquinolinyl, 2-oxo-1,3-benzoxazolyl, 2,3-dihydro-5H-1,3-thiazolo-[3,2-a]pyrimidinyl, 5,6,7,8-tetrahydro-quinazolinyl, 4-oxochromanyl, 1,3-benzothiazolyl, benzimidazolyl, benzotriazolyl, purinyl, furylpyridyl, thiophenylpyrimidyl, thiophenylpyridyl, pyrrolylpiridyl, oxazolylpyridyl, thiazolylpiridyl, 3,4-dihydropyrimidin-1-yl imidazolylpyridyl, quinoliyl, isoquinolinyl, quinazolinyl, quinoxalinyl, naphthyridinyl, pyrazolyl[3,4]pyridine, 1,2-dihydroisoquinolinyl, cinnolinyl, 2,3-dihydro-benzo[1,4]dioxin4-yl, 4,5,6,7-tetrahydro-benzo[b]-thiophenyl-2-yl, 1,8-naphthyridinyl, 1,5-napthyridinyl, 1,6-naphthyridinyl, 1,7-napthyridinyl, 3,4-dihydro-2H-1,4-benzothiazine, 4,8-dihydroxy-quinolinyl, 1-oxo-1,2-dihydro-isoquinolinyl, 4-phenyl-[1,2,3]thiadiazolyl, and the like.

"Aryloxy" means an —O-aryl or an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

One in the art understands that an "oxo" requires a second bond from the atom to which the oxo is attached. Accordingly, it is understood that oxo cannot be substituted onto an aryl or heteroaryl ring.

The term "halo" or "halogen" means fluoro, chloro, bromo, or iodo.

"Acyl" means a —C(O)R group, where R can be selected from the nonlimiting group of hydrogen or optionally substituted lower alkyl, trihalomethyl, unsubstituted cycloalkyl, aryl. "Thioacyl" or "thiocarbonyl" means a—C(S)R" group, with R as defined above.

The term "protecting group" means a suitable chemical group that can be attached to a functional group and removed at a later stage to reveal the intact functional group. Examples of suitable protecting groups for various functional groups are described in T. W. Greene and P. G. M. Wuts, Protective Groups in Organic Synthesis, 2d Ed., John Wiley and Sons (1991 and later editions); L. Fieser and M. Fieser, Fieser and Fieser's Reagents for Organic Synthesis, John Wiley and Sons (1994); and L. Paquette, ed. Encyclopedia of Reagents for Organic Synthesis, John Wiley and Sons (1995). The term "hydroxy protecting group", as used herein, unless otherwise indicated, includes Ac, CBZ, and various hydroxy protecting groups familiar to those skilled in the art including the groups referred to in Greene.

As used herein, the term "pharmaceutically acceptable salt" means those salts which retain the biological effectiveness and properties of the parent compound and do not present insurmountable safety or toxicity issues.

The term "pharmaceutical composition" means an active compound in any form suitable for effective administration to a subject, e.g., a mixture of the compound and at least one pharmaceutically acceptable carrier.

As used herein, a "physiologically/pharmaceutically acceptable carrier" means a carrier or diluent that does not cause significant irritation to an organism and does not abrogate the biological activity and properties of the administered compound.

A "pharmaceutically acceptable excipient" means an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The terms "treat," "treatment," and "treating" means reversing, alleviating, inhibiting the progress of, or partially or completely preventing the disorder or condition to which such term applies, or one or more symptoms of such disorder or condition. "Preventing" means treating before an infection occurs.

"Therapeutically effective amount" means that amount of the compound being administered which will relieve to some extent one or more of the symptoms of the disorder being treated, or result in inhibition of the progress or at least partial reversal of the condition.

The following abbreviations are used:
min. minute(s)
h hour(s)
d day(s)
RT or rt room temperature
$t_R$ retention time
L liter
mL milliliter
mmol millimole
μmol micromole
equiv. or eq. equivalents
NMR nuclear magnetic resonance
MDP(S) mass-directed HPLC purification (system)
LC/MS liquid chromatography mass spectrometry
HPLC high performance liquid chromatography
TLC thin layer chromatography
$CDCl_3$ deuterated chloroform
$CD_3OD$ or MeOD deuterated methanol
DMSO-$d_6$ deuterated dimethylsulfoxide
LDA lithium diisopropylamide
DCM dichloromethane
THF tetrahydrofuran
EtOAc ethyl acetate
MeCN acetonitrile
DMSO dimethylsulfoxide
Boc tert-butyloxycarbonyl
DME 1,2-dimethoxyethane
DMF N,N-dimethylformamide
DIPEA diisopropylethylamine
PS-DIEA polymer-supported diisopropylethylamine
PS-$PPh_3$-Pd polymer-supported Pd$(PPh_3)_4$
EDC 1-(3-dimethylaminopropyl)-3-ethylcarbodiimide
HOBt 1-hydroxybenzotriazole
DMAP 4-dimethylaminopyridine
TBTU O-(benzotriazol-1-yl)-N,N,N',N'-tetramethyluronium tetrafluoroborate
TEMPO 2,2,6,6-tetramethylpiperidine-1-oxyl
TFA trifluoroacetic acid

The invention claimed is:

1. A compound of Formula 1:

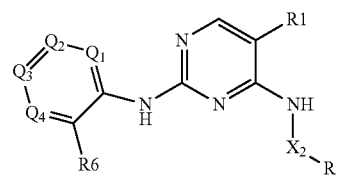

wherein:

R1 is halogen, —$CF_3$, or —CCH;

at least one of $Q_2$ to $Q_4$ is >C—$X_1$—R2;

$Q_1$ and the remaining $Q_2$ to $Q_4$ are independently >CH, >CF, >N, or >N-oxide;

$X_1$ and $X_2$ are independently —$(CR^7R^8)_{0-2}$—;

each $R^7$ and $R^8$ is independently halogen, $C_{0-3}$aliphatic, or —$OC_{0-3}$aliphatic, either of which is optionally halogen substituted, except that in the case of $X_2$, $R^7$ and $R^8$ are not halogen or —$OC_{0-3}$aliphatic;

R6 is halogen, —$OC_{0-3}$aliphatic, or $C_{0-3}$aliphatic, either optionally substituted by one or more halogen or by —$OCF_3$;

R2 is —$P(O)R^9R^{10}$;

$R^9$ and $R^{10}$ are independently $C_{0-3}$aliphatic, either of which can be taken together at any of their atoms to form a ring, wherein any of the foregoing can be further substituted by one or more halogen, $C_{0-6}$aliphatic, or $_{3-6}$cyclic;

R is

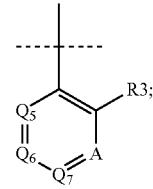

one of $Q_6$, $Q_7$, or A is >CR4;

$Q_5$ and the remaining $Q_6$ to $Q_7$ and A are independently >CH, >CF, >N, or >N-oxide;

R3 is $C_{0-6}$aliphatic, —$S(O)_2R^{11}$, —$S(O)_2NR^{11}R^{12}$, —$C(O)NR^{11}R^{12}$, —$C(O)OR^{11}$; —$NR^{11}S(O)_2R^{12}$, or —$NR^{11}R^{12}$;

$R^{11}$ and $R^{12}$ are independently $C_{0-6}$aliphatic, which can be taken together at any of their atoms to form a ring containing 1-3 heteroatoms;

or alternatively R3 and A define any optionally substituted $_{5-6}$cyclic containing one or more heteroatoms;

R4 is $_{4-6}$cyclic, —$OC_{0-6}$aliphatic, or $C_{0-6}$aliphatic, each optionally substituted, or halogen;

or a pharmaceutically acceptable salt thereof.

2. The compound or salt of claim 1, wherein:

$Q_3$ is >C—$CH_2$—$R^2$; and $R^9$ and $R^{10}$ are independently $C_{0-3}$alkoxy.

3. The compound or salt of claim 2, wherein R4 is optionally substituted cyclohexyl.

4. The compound or salt of claim 1, having the Formula 1a:

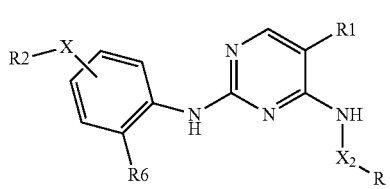

wherein:
$X_1$ and $X_2$ are independently —$(CR^7R^8)_{0-1}$—;
R is

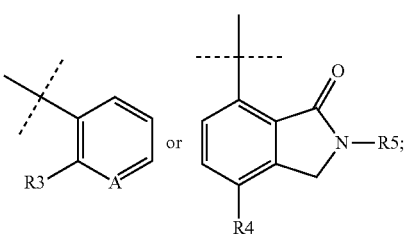

A is CH or N;
R1 is halogen, —$CF_3$, or —CCH;
R2 is —$P(O)R^9R^{10}$;
R3 is —$S(O)_2R^{11}$, —$S(O)_2NR^{11}R^{12}$, —$C(O)NR^{11}R^{12}$, —$C(O)OR^{11}$; —$NR^{11}S(O)_2R^{12}$, or —$NR^{11}R^{12}$;
R4 is -x-y-z, wherein:
  x is $_{4-6}$cyclic; y is absent or $_{4-6}$heterocyclic; and z is absent or $C_{1-3}$alkyl optionally substituted by 1-2 hydroxy or $C_{1-6}$alkoxy groups, or z is hydroxy or —C(O)O—$C_{0-3}$alkyl; or
  -x-y-z is $C_{0-6}$alkoxy, $C_{2-6}$alkenyl, $C_{2-6}$alkynyl, or $C_{0-6}$alkyl, each optionally substituted by 1-2 hydroxy groups;
R5 is $C_{0-2}$alkyl optionally substituted by 1-3 independent hydroxy or halogen groups;
R6 is halo, —$C_{0-3}$alkoxy, —$C_{0-3}$alkyl optionally substituted by halo, or —$OCF_3$;
each $R^7$ and $R^9$ is independently H or —$CH_3$;
$R^9$ and $R^{10}$ are independently hydroxy, $C_{1-6}$alkoxy, or $C_{0-6}$alkyl, any of which can be taken together at any of their atoms to form a ring, or aryl, —O-aryl, or $_{4-6}$heterocyclic, wherein any of the foregoing can be further substituted by $_{3-6}$cyclic;
$R^{11}$ and $R^{12}$ are independently $C_{0-6}$alkyl, which can be taken together at any of their atoms to form a ring containing 1-3 heteroatoms; $R^{11}$ or $R^{12}$ can independently be taken at any of their atoms with the ring to which R3 is attached to form a ring.

5. The compound or salt of claim 4, wherein:
$X_1$ and $X_2$ are independently a bond or methylene and $X_1$ is meta or para to the position of nitrogen attachment;
R is

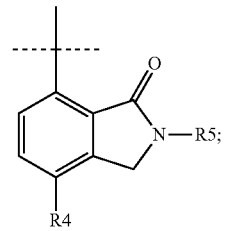

A is CH or N;
R1 is Cl, Br, or —$CF_3$;
R3 is —$N(CH_3)S(O)_2CH_3$ or —$C(O)NHCH_3$; and
R6 is H or methoxy.

6. The compound or salt of claim 5, wherein $R^9$ and $R^{10}$ are independently $C_{0-4}$alkoxy.

7. The compound or salt of claim 6, wherein $X_1$ is a methylene group positioned meta to R6.

8. The compound or salt of claim 7, wherein:
A is CH;
$X_2$ is a bond;
R1 is —$CF_3$; and
R3 is —$C(O)NHCH_3$.

9. The compound or salt of claim 1, having the formula:

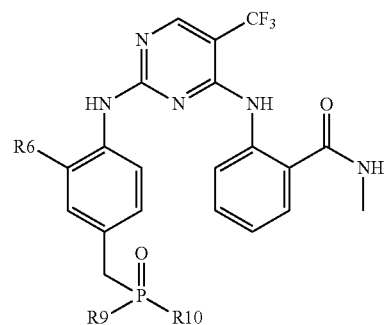

wherein R6 is H or methoxy; and
R9 and R10 are independently $C_{0-3}$alkoxy.

10. The compound or salt of claim 4, wherein:
$X_1$ and $X_2$ are independently a bond or methylene and $X_1$ is meta or para to the position of nitrogen attachment;
R is

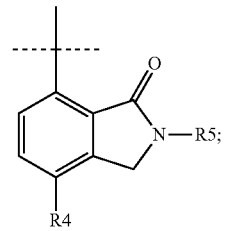

R1 is Br, Cl, or —$CF_3$;
R4 is -x-y-z, wherein
  x is $C_{4-6}$cycloalkyl, phenyl, pyrazolyl, pyrrolidinyl, piperidinyl, or piperazinyl; y is absent, piperidinyl, or piperazinyl; and z is absent, $C_{1-3}$alkyl optionally substituted by 1-2 hydroxy groups, or z is hydroxy or —C(O)O—$C_{0-3}$alkyl; or
  -x-y-z is $C_{0-6}$alkoxy, $C_{2-6}$alkenyl, $C_{2-6}$alkynyl, or $C_{0-6}$alkyl, each optionally substituted by 1-2 hydroxy;
R5 is methyl; and
R6 is H or methoxy.

11. The compound or salt of claim 10, wherein $R^9$ and $R^{10}$ are independently $C_{0-3}$alkoxy.

12. The compound or salt of claim 10, wherein R4 is $C_{4-6}$cycloalkyl which is optionally substituted by hydroxy, piperazinyl that is optionally N-methyl substituted, —C(O)O—$C_{0-3}$alkyl, or $C_{1-3}$alkyl optionally substituted by 1-2 hydroxy groups.

13. The compound or salt of claim 10, wherein:
$X_1$ is a methylene group positioned meta to R6;
$X_2$ is a bond;
R1 is —$CF_3$; and
R4 is -x-y-z, wherein
    x is $C_{4-6}$cycloalkyl, phenyl, pyrazolyl, pyrrolidinyl, piperidinyl, or piperazinyl;
    y is absent; and
    z is absent, $C_{1-3}$alkyl optionally substituted by 1-2 hydroxy groups, hydroxy, or —C(O)O—$C_{0-3}$alkyl.

14. A compound selected from any one of Examples 1-329 herein or a pharmaceutically acceptable salt thereof.

15. The compound or salt of claim 4, which is present as a material in substantially pure form.

16. The compound or salt of claim 4, which exhibits inhibition of FAK in a MIA-PaCa2 or U87MG assay with an $IC_{50}$ of about 1 µM or less.

17. The compound or salt of claim 4, which has an oral bioavailability (F) of at least about 30%.

18. The compound or salt of claim 4, which exhibits an oral exposure AUC(0-∞) of at least about 2 µg h/mL with 20 mg/kg oral dosing in mouse.

19. A pharmaceutical composition comprising the compound or salt of claim 4, formulated with or without one or more pharmaceutical carriers.

20. A method of treating a cancer mediated at least in part by FAK and selected from breast or ovarian cancer comprising administering to a mammal in need thereof a therapeutically effective amount of a compound or salt of claim 4.

21. A compound or salt of claim 1, which is: diethyl (3-methoxy-4-{[4-{[2-(methylcarbamoyl)phenyl]amino}-5-(trifluoromethyl)pyrimidin-2-yl]amino}benzyl)phosphonate.

22. A compound or salt of claim 1, which is: diethyl (4-{[4-{[7-(trans-4-hydroxycyclohexyl)-2-methyl-3-oxo-2,3-dihydro-1H-isoindol-4-yl]amino}-5-(trifluoromethyl)pyrimidin-2-yl]amino}-3-methoxybenzyl) phosphonate hydrochloride.

23. A compound or salt of claim 1, which is: diethyl (3-methoxy-4-{[4-({2-methyl-7-[trans-4-(4-methylpiperazin-1-yl)cyclohexyl]-3-oxo-2,3-dihydro-1H-isoindol-4-yl}amino)-5-(trifluoromethyl)pyrimidin-2-yl]amino}benzyl)phosphonate.

24. A compound or salt of claim 1, which is: 2-{2-[3-(Dimethylphosphinoylmethyl)phenylamino]-5-trifluoromethylpyrimidin-4-ylamino}-N-methylbenzamide.

25. A compound or salt of claim 1, which is: 2-{[2-{[4-(Dimethylphosphoryl)phenyl]amino}-5-(trifluoromethyl)pyrimidin-4-yl]amino}-N-methylbenzamide.

* * * * *